US012441730B2

(12) United States Patent
Machacek et al.

(10) Patent No.: US 12,441,730 B2
(45) Date of Patent: *Oct. 14, 2025

(54) PRMT5 INHIBITORS

(71) Applicant: Merck Sharp & Dohme LLC, Rahway, NJ (US)

(72) Inventors: Michelle Machacek, Belmont, MA (US); Michael D. Altman, Needham, MA (US); Shuhei Kawamura, Cambridge, MA (US); Michael H. Reutershan, Brighton, MA (US); David L. Sloman, Newton, MA (US); Phieng Siliphaivanh, Newton Highlands, MA (US); Sebastian E. Schneider, Boston, MA (US); Charles S. Yeung, Dedham, MA (US); David J. Witter, Ontario (CA); Craig R. Gibeau, Northborough, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 661 days.

This patent is subject to a terminal disclaimer.

(21) Appl. No.: 17/783,967

(22) PCT Filed: Dec. 14, 2020

(86) PCT No.: PCT/US2020/064759

§ 371 (c)(1),
(2) Date: Jun. 9, 2022

(87) PCT Pub. No.: WO2021/126729

PCT Pub. Date: Jun. 24, 2021

(65) Prior Publication Data

US 2023/0114091 A1 Apr. 13, 2023

Related U.S. Application Data

(60) Provisional application No. 62/949,242, filed on Dec. 17, 2019, provisional application No. 63/025,329, filed on May 15, 2020.

(51) Int. Cl.

| | |
|---|---|
| ***C07D 471/10*** | (2006.01) |
| ***A61K 31/4747*** | (2006.01) |
| ***C07D 519/00*** | (2006.01) |

(52) U.S. Cl.

CPC ......... *C07D 471/10* (2013.01); *C07D 519/00* (2013.01)

(58) Field of Classification Search

CPC .... C07D 471/10; A61K 31/4747; A61P 35/00

USPC ............................................ 546/18; 514/278

See application file for complete search history.

(56) References Cited

U.S. PATENT DOCUMENTS

| | | | |
|---|---|---|---|
| 2,789,118 | A | 4/1957 | Seymour |
| 2,990,401 | A | 6/1961 | Seymour |
| 3,048,581 | A | 8/1962 | Josef |
| 3,126,375 | A | 3/1964 | Hensel et al. |
| 3,749,712 | A | 7/1973 | Cavazza |
| 3,928,326 | A | 12/1975 | Brattsand |
| 3,929,768 | A | 12/1975 | Brattsand |
| 3,996,359 | A | 12/1976 | Brattsand |
| 4,231,938 | A | 11/1980 | Monaghan et al. |
| 4,294,926 | A | 10/1981 | Monaghan et al. |
| 4,319,039 | A | 3/1982 | Albers-schonberg |
| 4,346,227 | A | 8/1982 | Terahara et al. |
| 4,410,629 | A | 10/1983 | Terahara et al. |
| 4,444,784 | A | 4/1984 | Hoffman et al. |
| 4,537,859 | A | 8/1985 | Terahara et al. |
| 4,681,893 | A | 7/1987 | Roth |
| 4,782,084 | A | 11/1988 | Vyas et al. |
| 4,820,850 | A | 4/1989 | Verhoeven et al. |
| 4,885,314 | A | 12/1989 | Vyas et al. |
| 4,911,165 | A | 3/1990 | Lennard et al. |
| 4,916,239 | A | 4/1990 | Treiber |

(Continued)

FOREIGN PATENT DOCUMENTS

| | | |
|---|---|---|
| EP | 0604181 A1 | 6/1994 |
| EP | 0618221 A2 | 10/1994 |

(Continued)

OTHER PUBLICATIONS

Database Pubchem Compound Feb. 12, 2015 (Feb. 12, 2015), Anonymous: "SCHEMBL4841966".

(Continued)

*Primary Examiner* — Charanjit Aulakh
(74) *Attorney, Agent, or Firm* — James Corcoran; Catherine D. Fitch

(57) ABSTRACT

The present invention provides a compound of Formula (I) (I) and the pharmaceutically acceptable salts, esters, and prodrugs thereof, which are PRMT5 inhibitors. Also provided are methods of making compounds of Formula I, pharmaceutical compositions comprising compounds of Formula I, and methods of using these compounds to treat cancer, sickle cell, and hereditary persistence of foetal hemoglobin (HPFH) mutations.

(I)

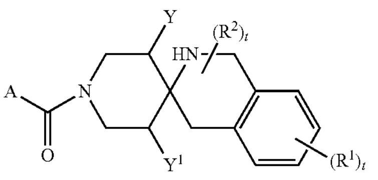

14 Claims, No Drawings

(56) References Cited

U.S. PATENT DOCUMENTS

| | | | |
|---|---|---|---|
| 4,929,437 | A | 5/1990 | Tobert |
| 5,030,447 | A | 7/1991 | Joshi et al. |
| 5,118,853 | A | 6/1992 | Lee et al. |
| 5,134,142 | A | 7/1992 | Matsuo et al. |
| 5,162,339 | A | 11/1992 | Lowe, III |
| 5,177,080 | A | 1/1993 | Angerbauer et al. |
| 5,180,589 | A | 1/1993 | Joshi et al. |
| 5,189,164 | A | 2/1993 | Kapa et al. |
| 5,232,929 | A | 8/1993 | Desai |
| 5,242,930 | A | 9/1993 | Baker |
| 5,273,995 | A | 12/1993 | Roth |
| 5,290,946 | A | 3/1994 | Lee et al. |
| 5,342,952 | A | 8/1994 | Butler et al. |
| 5,344,991 | A | 9/1994 | Reitz et al. |
| 5,354,772 | A | 10/1994 | Kathawala |
| 5,356,896 | A | 10/1994 | Kabadi et al. |
| 5,373,003 | A | 12/1994 | Lowe, III |
| 5,380,738 | A | 1/1995 | Norman et al. |
| 5,387,595 | A | 2/1995 | Mills |
| 5,393,790 | A | 2/1995 | Reitz et al. |
| 5,409,944 | A | 4/1995 | Black et al. |
| 5,420,245 | A | 5/1995 | Brown |
| 5,436,265 | A | 7/1995 | Black et al. |
| 5,459,270 | A | 10/1995 | Williams |
| 5,466,823 | A | 11/1995 | Talley et al. |
| 5,474,995 | A | 12/1995 | Ducharme et al. |
| 5,489,691 | A | 2/1996 | Butler et al. |
| 5,494,926 | A | 2/1996 | Owens |
| 5,496,833 | A | 3/1996 | Baker |
| 5,510,510 | A | 4/1996 | Patel |
| 5,523,430 | A | 6/1996 | Patel |
| 5,532,359 | A | 7/1996 | Marsters, Jr. |
| 5,536,752 | A | 7/1996 | Ducharme et al. |
| 5,550,142 | A | 8/1996 | Ducharme et al. |
| 5,571,792 | A | 11/1996 | Bolton |
| 5,589,485 | A | 12/1996 | Hochlowski |
| 5,602,098 | A | 2/1997 | Sebti |
| 5,604,260 | A | 2/1997 | Guay et al. |
| 5,633,272 | A | 5/1997 | Talley et al. |
| 5,637,699 | A | 6/1997 | Dorn |
| 5,643,958 | A | 7/1997 | Iwasawa |
| 5,661,152 | A | 8/1997 | Bishop |
| 5,698,584 | A | 12/1997 | Black et al. |
| 5,710,140 | A | 1/1998 | Ducharme et al. |
| 5,719,147 | A | 2/1998 | Dorn |
| 5,728,830 | A | 3/1998 | Kanda |
| 5,750,567 | A | 5/1998 | Baudoin |
| 5,789,647 | A | 8/1998 | Heidlas |
| 5,856,439 | A | 1/1999 | Clerc |
| 5,861,419 | A | 1/1999 | Dube et al. |
| 5,889,053 | A | 3/1999 | Baudoin |
| 5,919,786 | A | 7/1999 | Iwasawa |
| 5,932,598 | A | 8/1999 | Talley et al. |
| 5,936,097 | A | 8/1999 | Commercon |
| 6,001,843 | A | 12/1999 | Dube et al. |
| 6,020,343 | A | 2/2000 | Belley et al. |
| 6,069,134 | A | 5/2000 | Roth et al. |
| RE37,314 | E | 8/2001 | Hirai et al. |
| 6,284,781 | B1 | 9/2001 | Danishefsky et al. |
| 6,288,237 | B1 | 9/2001 | Hoefle et al. |
| 7,199,127 | B2 | 4/2007 | Jeong et al. |
| 7,454,431 | B2 | 11/2008 | Vo et al. |
| 7,589,068 | B2 | 9/2009 | Cosford et al. |
| 7,655,675 | B2 | 2/2010 | Nadin et al. |
| 9,469,615 | B2 * | 10/2016 | Boyce .................... A61P 11/06 |
| 2004/0102360 | A1 | 5/2004 | Barnett et al. |
| 2004/0116432 | A1 | 6/2004 | Carling et al. |
| 2005/0029941 | A1 | 2/2005 | Kwon |
| 2005/0043361 | A1 | 2/2005 | Colca |
| 2005/0044294 | A1 | 2/2005 | Vo |
| 2005/0075320 | A1 | 4/2005 | Nadin |
| 2005/0176776 | A1 | 8/2005 | Coleman et al. |
| 2005/0222138 | A1 | 10/2005 | Ohhata et al. |
| 2018/0155343 | A1 | 6/2018 | Almansa-rosales |
| 2020/0317686 | A1 | 10/2020 | Vandyck et al. |
| 2023/0092404 | A1 | 3/2023 | Machacek et al. |
| 2023/0108452 | A1 | 4/2023 | Machacek et al. |

FOREIGN PATENT DOCUMENTS

| | | | |
|---|---|---|---|
| EP | 0675112 | A1 | 10/1995 |
| EP | 0696593 | A2 | 2/1996 |
| WO | 1994015932 | A1 | 7/1994 |
| WO | 1994019357 | A1 | 9/1994 |
| WO | 1995008542 | A1 | 3/1995 |
| WO | 199500516 | A1 | 4/1995 |
| WO | 1995010514 | A1 | 4/1995 |
| WO | 1995010515 | A1 | 4/1995 |
| WO | 1995011917 | A1 | 5/1995 |
| WO | 1995012572 | A1 | 5/1995 |
| WO | 1995012612 | A1 | 5/1995 |
| WO | 1995024612 | A1 | 9/1995 |
| WO | 1995025086 | A1 | 9/1995 |
| WO | 1995032987 | A1 | 12/1995 |
| WO | 1995034535 | A1 | 12/1995 |
| WO | 1996000736 | A1 | 1/1996 |
| WO | 1996005168 | A1 | 2/1996 |
| WO | 1996005169 | A1 | 2/1996 |
| WO | 1996005529 | A1 | 2/1996 |
| WO | 1996006138 | A1 | 2/1996 |
| WO | 1996006193 | A1 | 2/1996 |
| WO | 1996016443 | A1 | 5/1996 |
| WO | 1996017861 | A1 | 6/1996 |
| WO | 1996021456 | A1 | 7/1996 |
| WO | 1996021701 | A2 | 7/1996 |
| WO | 1996022278 | A1 | 7/1996 |
| WO | 1996024611 | A1 | 8/1996 |
| WO | 1996024612 | A1 | 8/1996 |
| WO | 1996030017 | A1 | 10/1996 |
| WO | 1996030018 | A1 | 10/1996 |
| WO | 1996030343 | A1 | 10/1996 |
| WO | 1996030362 | A1 | 10/1996 |
| WO | 1996030363 | A1 | 10/1996 |
| WO | 1996031111 | A1 | 10/1996 |
| WO | 1996031477 | A1 | 10/1996 |
| WO | 1996031478 | A1 | 10/1996 |
| WO | 1996031501 | A1 | 10/1996 |
| WO | 1996033159 | A1 | 10/1996 |
| WO | 1996034850 | A1 | 11/1996 |
| WO | 1996034851 | A1 | 11/1996 |
| WO | 1997000252 | A1 | 1/1997 |
| WO | 1997002920 | A1 | 1/1997 |
| WO | 1997003047 | A1 | 1/1997 |
| WO | 1997003050 | A1 | 1/1997 |
| WO | 1997004785 | A1 | 2/1997 |
| WO | 1997017070 | A1 | 5/1997 |
| WO | 1997018813 | A1 | 5/1997 |
| WO | 1997021701 | A1 | 6/1997 |
| WO | 1997023478 | A1 | 7/1997 |
| WO | 1997026246 | A1 | 7/1997 |
| WO | 1997030053 | A1 | 8/1997 |
| WO | 1997038665 | A2 | 10/1997 |
| WO | 1997044350 | A1 | 11/1997 |
| WO | 1998002436 | A1 | 1/1998 |
| WO | 1998028980 | A1 | 7/1998 |
| WO | 1998029119 | A1 | 7/1998 |
| WO | 0050032 | A1 | 8/2000 |
| WO | 200044777 | A1 | 8/2000 |
| WO | 200061186 | A1 | 10/2000 |
| WO | 2001070677 | A1 | 9/2001 |
| WO | 2001090084 | A1 | 11/2001 |
| WO | 2002030912 | A1 | 4/2002 |
| WO | 2002036555 | A1 | 5/2002 |
| WO | 2002047671 | A2 | 6/2002 |
| WO | 2002081433 | A1 | 10/2002 |
| WO | 2002081435 | A1 | 10/2002 |
| WO | 2002083064 | A2 | 10/2002 |
| WO | 2002083138 | A1 | 10/2002 |
| WO | 2002083139 | A1 | 10/2002 |
| WO | 2002083140 | A1 | 10/2002 |
| WO | 2003013506 | A1 | 2/2003 |
| WO | 2003018543 | A1 | 3/2003 |
| WO | 2003039460 | A2 | 5/2003 |

(56) References Cited

FOREIGN PATENT DOCUMENTS

| | | | |
|---|---|---|---|
| WO | 2003049527 | A2 | 6/2003 |
| WO | 2003049678 | A2 | 6/2003 |
| WO | 2003049679 | A2 | 6/2003 |
| WO | 2003050064 | A2 | 6/2003 |
| WO | 2003050122 | A2 | 6/2003 |
| WO | 2003079973 | A2 | 10/2003 |
| WO | 2003084473 | A2 | 10/2003 |
| WO | 2003086279 | A2 | 10/2003 |
| WO | 2003086394 | A1 | 10/2003 |
| WO | 2003086403 | A1 | 10/2003 |
| WO | 2003086404 | A1 | 10/2003 |
| WO | 2003093251 | A1 | 11/2003 |
| WO | 2003093252 | A1 | 11/2003 |
| WO | 2003093253 | A1 | 11/2003 |
| WO | 2003093264 | A1 | 11/2003 |
| WO | 2003099211 | A2 | 12/2003 |
| WO | 2003105855 | A1 | 12/2003 |
| WO | 2003106417 | A1 | 12/2003 |
| WO | 2004031137 | A1 | 4/2004 |
| WO | 2004031138 | A1 | 4/2004 |
| WO | 2004031139 | A1 | 4/2004 |
| WO | 2004037171 | A2 | 5/2004 |
| WO | 2004039370 | A1 | 5/2004 |
| WO | 2004039774 | A2 | 5/2004 |
| WO | 2004039800 | A1 | 5/2004 |
| WO | 2004041162 | A2 | 5/2004 |
| WO | 2004058148 | A2 | 7/2004 |
| WO | 2004058700 | A2 | 7/2004 |
| WO | 2004089911 | A1 | 10/2004 |
| WO | 2004096129 | A2 | 11/2004 |
| WO | 2004096130 | A2 | 11/2004 |
| WO | 2004096131 | A2 | 11/2004 |
| WO | 2004096135 | A2 | 11/2004 |
| WO | 2004101538 | A1 | 11/2004 |
| WO | 2004101539 | A1 | 11/2004 |
| WO | 2005014553 | A1 | 2/2005 |
| WO | 2005017190 | A2 | 2/2005 |
| WO | 2005018547 | A2 | 3/2005 |
| WO | 2005018638 | A1 | 3/2005 |
| WO | 2005019205 | A1 | 3/2005 |
| WO | 2005019206 | A1 | 3/2005 |
| WO | 2005030731 | A1 | 4/2005 |
| WO | 2005100344 | A1 | 10/2005 |
| WO | 2005100356 | A1 | 10/2005 |
| WO | 2012087861 | A1 | 6/2012 |
| WO | 2017032840 | A1 | 3/2017 |
| WO | 2019094312 | A1 | 5/2019 |
| WO | 2021126732 | A1 | 6/2021 |

OTHER PUBLICATIONS

Aggarwal, Priya et al., Nuclear Cyclin D1/CDK4 Kinase Regulates CUL4 Expression and Triggers Neoplastic Growth via Activation of the PRMT5 Methyltransferase, Cancer Cell, 2010, 329-340, 18.

Ben-Av et al., Induction of Vascular Endothielial Growth Factor Expression in Synovial fibroblasts by Prostaglandin E and Interleukin-1: A Potential mechanism for Inflammatory Angiogenesis, FEBS Letters, 1995, 83-87, 372.

Benezra et al., In Vivo Angiogenic Activity of Interleukins, Arch Ophthalmol, 1990, 573-576, 108.

Blume-Jensen, Peter et al., Oncogenic kinase signalling, Nature, 2001, 355-365, 411.

Bouma et al., Thrombin Activable Fibrinolysis Inhibitor (TAFI, Plasma Procarboxypeptidedase B, Procarboxypeptidase R, Procarboxypeptidase U), Thrombosis Research, 2001, 329-354, 101.

Brower, Tumor Angiogenesis New Drugs on the Block, Nature America, 1999, 963-968, 17.

Chakraborty et al., Developmental Expression of the Cyclo-Oxygenase-1 and Cyclo-oxygenase-2 genes in the Peri-implantation Mouse Uterus and their differential regulation by the blastocyst and ovarian steroids, J. Mol Endocrinol, 1996, 107-122, 16.

Chiang, Kelly et al., PRMT5 is a Critical Regulator of Breast Cancer Stem Cell Function via Histone Methylation and FOXP1 Expression, Cell Reports, 2017, 3498-3513, 21.

Chiarugi et al., Cox-2, iNOS and p53 as play-makers of tumor angiogenesis (Review), International J. of Molecular Medicine, 1998, 715-719, 2.

Cho, Er-Chieh et al., Arginine methylation controls growth regulation by E2F-1, The EMBO Journal, 2012, 1785-1797, 31.

Clarke, Thomas L. et al., PRMT5-Dependent Methylation of the TIP60 Coactivator RUVBL1 is a Key Regulator of Homologous Recombination, Molecular Cell, 2017, 900-916, e1-e7, 65.

Diaz-Flores et al., Intense Vascular Sprouting From Rat Femoral Vein Induced by Prostaglandins E1 and E2, The Anatomical Record, 1994, 68-76, 238.

Fathallah-Shaykh et al., Gene Transfer of IFN-y into Established Brain Tumors Represses Grwoth by Antiangiogenesis, J. of Immunology, 2000, 217-222, 164.

Fernandez et al., Neovascularization Produced by Angiotensin II, Clinical Mediicne, 1985, 141-145, 105.

Gerhart, Sarah V. et al., Activation of the p53-MDM4 regulatory axis defines the antitumour response to PRMT5 inhibition through its role in regulating cellular splicing, Scientific Reports, 2018, 1-15, 8:9711.

Gralinkski et al., Effects of Troglitazone and Pioglitazone on Cytokine-Mediated Endothelial Cell Proliferation in Vitro, J. of Cardiovascular Pharmacology, 1998, 909-913, 31.

Gu et al., Effect of Novel CAAX Peptidomimetic Farnesyltransferase Inhibitor on Angiogenesis In Vitro and In Vivo, European J. of Cancer, 1999, 1394-1401, 35.

Gu, Zhongping et al., Protein Arginine Methyltransferase 5 Functions in Opposite Ways in the Cytoplasm and Nucleus of Prostate Cancer Cells, Plos One, 2012, 1-13, Issue 8 | e44033.

Hall et al., The Promise and Reality of Cancer Gene Therapy, Am. J. Hum. Genet, 1997, 785-789, 61.

Hamard, Pierre-Jacques et al., PRMT5 Regulates DNA Repair by Controlling the Alternative Splicing of Histone-Modifying Enzymes, Cell Reports, 2018, 2643-2657, 24.

Harada et al., Expression and Regulation of Vascular Endothelial Growth Factor in Osteoblasts, Clinical Ortho, 1995, 76-80, 313.

Hla et al., Human Cyclooxygenase-2 cDNA, Proc. Natl. Acad. Sci., 1992, 7384-7388, 89.

Kanduri, Meena et al., Differential genome-wide array-based methylation profiles in prognostic subsets of chronic lymphocytic leukemia, Blood, 2010, 296-305, 115(2).

Kim et al., Inhibition of Endothelial Growth Factor-Induced Angiogenesis Suppreses Tumour Growth in Vivo, Nature, 1993, 841-844, 362.

Kim, A. Y. et al., Gastric cancer by multidetector row CT: preoperative staging, Abdom Imaging, 2005, 465-472, 30.

Korte et al., Changes of the Coagulation and Fibrinolysis System n Malignancy: Their possible Impact on Future Diagnostic And Therapeutic Procedures, Clin Chem Lab Med, 2000, 679-692, 38 (8), 38.

Kufe et al., Principles of Gene Therapy, Cancer Medicine, 2000, pp. 876-889, 5th Ed.

Li et al., Adenovirus-Mediated Delivery of a uPA/uPAR Antagonist Suppresses Angiogenesis—Dependent Tumor Growth and Dissemination in Mice, Gene Therapy, 1998, 1105-1113, 5.

Majima et al., Significant Roles of Inducible Cyclooxygenase (COX)-2 in Angiogenesis in Rat Sponge Implants, Jpn. J. Pharmacol., 1997, 105-114, 75.

Miller et al., Histone Deacetylase Inhibitors, J. of Medicinal Chemistry, 2003, 5097-5116, 46.

Murata et al., Peroxisome Proliferator-Activated Receptor-y Ligands Inhibit Choroidal Neovascularization, Inestigative Ophthalmology & visual Science, 2000, 2309-2317, 41.

Murata et al., Response of Experimental Retinal Neovascularization to Thiazolidinediones, Arch Ophthamol, 2001, 709-717, 119.

Nicholas, Courtney et al., PRMT5 is upregulated in malignant and metastatic melanoma, and regulates expression of the MITF transcription factor, Cancer Res, 2012, 4 pages, 72 (8 Suppl): LB-254.

(56) References Cited

OTHER PUBLICATIONS

Pal, Sharmistha et al., Low levels of miR-92b/96 induce PRMT5 translation and H3R8/H4R3 methylation in mantle cell lymphoma, The EMBO Journal, 2007, 3558-3569, 26.
Powers, Matthew A. et al., Protein Arginine Methyltransferase 5 Accelerates Tumor Growth by Arginine Methylation of the Tumor Suppressor Programmed Cell Death 4, Cancer Res, 2011, 5579-5587, 71(16).
Pubchem, SID 230731034, Available Date: Feb. 12, 2015 [retrieved on Mar. 2, 2021]. Retrieved from the Internet URL: https://pubchem.ncbi.nlm.nih.gov/substance/230731034entire document (8 pages).
Rank, Gerhard et al., Identification of a PRMT5-dependent repressor complex linked to silencing of human fetal globin gene expression, Blood, 2010, 1585-1592, 116(9).
Seed et al., The Inhibition of Colon-26 Adenocarcinoma Development and Angiogenesis by Topical Diclofenac in 2.5% Hyaluronan, Cancer Research, 1997, 1625-1629, 57.
Tsujii et al., Cyclooxgenase Regulates Angiogenesis Induced by Colon Cancer Cells, Cell, 1998, 705-716, 93.
Wang, Li et al., Protein Arginine Methyltransferase 5 Suppresses the Transcription of the RB Family of Tumor Suppressors in Leukemia and Lymphoma Cells, Molecular and Cellular Biology, 2008, 6262-6277, vol. 28, No. 20.
Xin et al., Peroxisome Proliferator Activated Receptor y Ligands are Potent Inhibitors of Angiogenesis in Vitro and in Vivo, J. Biol Chem,, 1999, 9116-9121, 13.
Yalpani et al., Coronary Heart Disease is the most Serious Threat to life in the Western World, but Progress is Being Made in Finding Ways to Reduce the Risks of Suffering Such a Fate, Chemistry & Industry, 1996, 85-89.
Zacharski et al., Heparin and Cancer, Thromb Haemost, 1998, 10-23, 80.
Ziche et al., Role of Prostaglandin E, and Copper in Angiogenesis, JNCI, 1982, 475-482, 69.
Chen, Shih-Shih et al., Epigenetic changes during disease progressionin a murine model of human chroniclymphocytic leukemia, PNAS, 106(32), 13433-13438, 2009.
Gu, Zhongping et al., Protein arginine methyltransferase 5 is essential for growth of lung cancer cells, Biochem J, 446(2), 1-16, 2012.
Mao, Ruifeng et al., Potent, Selective, and Cell Active Protein Arginine Methyltransferase 5 (PRMT5) Inhibitor Developed by Structure-Based Virtual Screening and Hit Optimization, Journal of Medicinal Chemistry, 60, 6289-6304, 2017.
Still et al., Rapid Chromatographic Technique for Preparative Separations with Moderate Resolution, J. Org. Chem., 43, 2923-2925, 1978.

* cited by examiner

PRMT5 INHIBITORS

CROSS-REFERENCE TO RELATED APPLICATIONS

This application is a national stage entry under 35 U.S.C. § 371 of PCT/US2020/064759 filed Dec. 14, 2020, which claims priority to U.S. applications 63/025,329 filed May 15, 2020; and 62/949,242 filed Dec. 17, 2019, the contents of which are hereby incorporated by reference in their entireties.

BACKGROUND OF THE INVENTION

PRMT5 (aka JBP1, SKB1, 1BP72, SKB1his and HRMTIL5) is a Type II arginine methyltransferase, and was first identified in a two-hybrid search for proteins interacting with the Janus tyrosine kinase (Jak2) (Pollack et al., 1999). PRMT5 plays a significant role in control and modulation of gene transcription. Inter alia, PRMT5 is known to symmetrically methylate histone H3 at Arg-8 (a site distinct from that methylated by PRMT4) and histone H4 at Arg-3 (the same site methylated by PRMT1). PRMT5 has been reported to perform diverse roles including but not limited to impacting cell viability, sternness, DNA damage repair and RNA splicing (Clarke et al., Mol Cell (2017), Chiang et al., Cell Rep (2017), Gerhart et al., Sci Rep (2018)). Specifically, inhibition of PRMT5 induces alternative splicing of the negative regulator of p53, MDM4 resulting in increased expression of the short isoform of MDM4 (MDM4-S), decreased expression of the full-length isoform (MDM4-FL) and increased p53 activity (Gerhart el al Sci Rep (2018)). Most of the physiological functions of p53 are attributable to its role as a transcriptional activator, responding to agents that damage DNA. p53 status is wild type in approximately half of human cancer cases. These include 94% in cervix, 87% in blood malignancies, 85% in bones and endocrine glands, and 75% of primary breast cancer. Restoration of p53 in cancer cells harboring wild type p53, by way of inhibiting mechanisms that suppress its function leads to growth arrest and apoptosis and is regarded as a potentially effective means of tumor suppression.

In response to DNA damage caused by a variety of agents, including doxorubicin, camptothecin and UV light, and also in response to treatment with Nutlin-3, knockdown of PRMT5 results in an increase in sub-G1 population and concomitant reduction in G1 cells and, in the presence of p53, a significant increase in apoptosis. Knockdown of PRMT5 also resulted in an increased level of p21, a key p53 target gene that regulates cell cycle arrest during the p53 response and MDM2, a p53 E3 ubiquitin ligase, but not PUMA, NOXA, AlP1 & APAF1, p53 target genes linked to apoptosis.

Knockdown of PRMT5 (but not PRMT1 or CARM1/PRMT4) results in decreased p53 stabilization, decreased basal p53 levels, decreased p53 oligomerisation, and also decreased expression of elF4E a major component of translational machinery involved in ribosome binding to mRNA. Indeed, elF4E is a potent oncogene, which has been shown to promote malignant transformation in vitro and human cancer formation.

The role of PRMT5 in the DNA damage response has been explored with groups reporting a role for PRMT5 in regulating high fidelity homologous recombination mediated DNA repair in both solid (Clarke et al., Mol Cell (2017)) and hematological tumor models (Hamard et al., Cell Rep (2018)).

PRMT5 is aberrantly expressed in around half of human cancer cases, further linking this mechanism to cancers. PRMT5 overexpression has been observed in patient tissue samples and cell lines of Prostate cancer (Gu et al., 2012), Lung cancer (Zhongping et al., 2012), Melanoma cancer (Nicholas et al., 2012), Breast cancer (Powers et al., 2011), Colorectal cancer (Cho et al., 2012), Gastric cancer (Kim et al., 2005), Esophagus and Lung carcinoma (Aggarwal et al., 2010) and B-Cell lymphomas and leukemia (Wang, 2008). Moreover, elevated expression of PRMT5 in Melanoma, Breast and Colorectal cancers has been demonstrated to correlate with a poor prognosis.

Lymphoid malignancies including chronic lymphocytic leukemia (CLL) are associated with over-expression of PRMT5. PRMT5 is over-expressed (at the protein level) in the nucleus and cytosol in a number of patient derived Burkitt's lymphoma; mantle cell lymphoma (MCL); in vitro EBV-transformed lymphoma; leukemia cell lines; and B-CLL cell lines, relative to normal CD19+ B lymphocytes (Pal et al., 2007; Wang et al., 2008). Intriguingly, despite elevated levels of PRMT5 protein in these tumor cells, the levels of PRMT5 mRNA are reduced (by a factor of 2-5). Translation of PRMT5 mRNA is, however, enhanced in lymphoma cells, resulting in increased levels of PRMT5 (Pal et al., 2007; Wang et al., 2008).

In addition to genomic changes, CLL, like almost all cancers, has aberrant epigenetic abnormalities characterised by global hypomethylation and hot-spots of repressive hypermethylation of promoters including tumor suppressor genes. While the role of epigenetics in the origin and progression of CLL remains unclear, epigenetic changes appear to occur early in the disease and specific patterns of DNA methylation are associated with worse prognosis (Chen et al., 2009; Kanduri et al., 2010). Global symmetric methylation of histones H3R8 and H4R3 is increased in transformed lymphoid cell lines and MCL clinical samples (Pal et al., 2007), correlating with the overexpression of PRMT5 observed in a wide variety of lymphoid cancer cell lines and MCL clinical samples.

PRMT5 is therefore a target for the identification of novel cancer therapeutics.

Hemoglobin is a major protein in red blood cells and is essential for the transport of oxygen from the lungs to the tissues. In adult humans, the most common hemoglobin type is a tetramer called hemoglobin A, consisting of two α and two β subunits. In human infants, the hemoglobin molecule is made up of two α and two γ chains. The gamma chains are gradually replaced by β subunits as the infant grows. The developmental switch in human ß-like globin gene subtype from foetal (γ) to adult (ß) that begins at birth heralds the onset of the hemoglobinopathies ß-thalassemia or sickle cell disease (SCD). In ß-thalassemia the adult chains are not produced. In SCD, a point mutation in the coding sequence in the ß globin gene leads to the production of a protein with altered polymerisation properties. The observation that increased adult γ-globin gene expression (in the setting of hereditary persistence of foetal hemoglobin (HPFH) mutations) significantly ameliorates the clinical severity of ß-thalassemia and SCD has prompted the search for therapeutic strategies to reverse γ-globin gene silencing. To date, this has been achieved through pharmacological induction, using compounds that broadly influence epigenetic modifications, including DNA methylation and histone deacetylation. The development of more targeted therapies is dependent on the identification of the molecular mechanisms underpinning foetal globin gene silencing. These mechanisms have remained elusive, despite exhaustive study of the HPFH mutations, and considerable progress in many other aspects of globin gene regulation.

PRMT5 plays a critical role in triggering coordinated repressive epigenetic events that initiate with dimethylation of histone H4 Arginine 3 (H4R3me2s), and culminate in DNA methylation and transcriptional silencing of the γ-genes (Rank et al., 2010). Integral to the synchronous establishment of the repressive markers is the assembly of a PRMT5-dependent complex containing the DNA methyltransferase DNMT3A, and other repressor proteins (Rank et al., 2010). DNMT3A is directly recruited to bind to the PRMT5-induced H4R3me2s mark, and loss of this mark through shRNA-mediated knock-down of PRMT5, or enforced expression of a mutant form of PRMT5 lacking methyltransferase activity leads to marked upregulation of γ-gene expression, and complete abrogation of DNA methylation at the γ-promoter. Treatment of human erythroid progenitors with non-specific methyltransferase inhibitors (Adox and MTA) also resulted in upregulation of γ-gene expression (He Y, 2013). Inhibitors of PRMT5 thus have potential as therapeutics for hemoglobinopathies such as ß-thalassemia or Sickle Cell Disease (SCD).

The present inventors have developed compounds that inhibit the activity of PRMT5 and therefore may be of use in treating conditions ameliorated by the inhibition of the activity of PRMT5.

SUMMARY OF THE INVENTION

Invented are compounds of formula I (I)

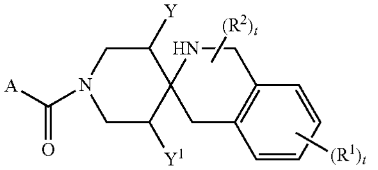

and the pharmaceutically acceptable salts, esters, and prodrugs thereof, which are PRMT5 inhibitors. Also provided are methods of making compounds of Formula I, pharmaceutical compositions comprising compounds of Formula I, and methods of using these compounds to treat cancer, sickle cell, and hereditary persistence of foetal hemoglobin (HPFH) mutations. The invention does not include:

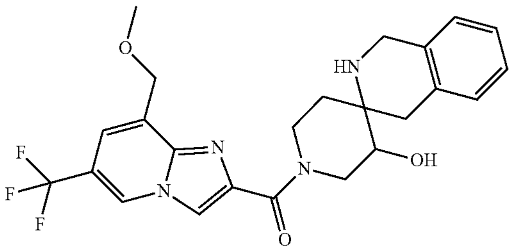

,

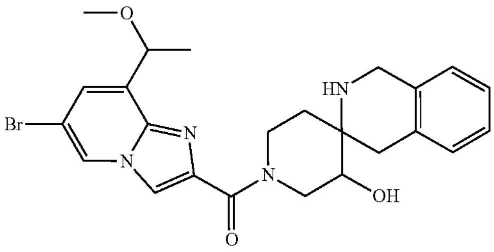

,

-continued

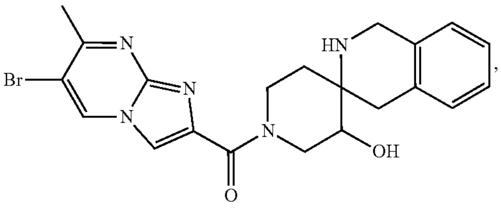

, or

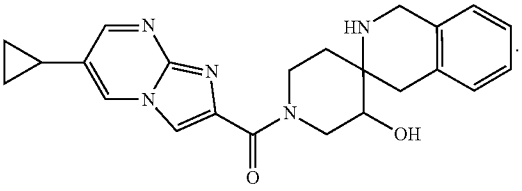

.

DETAILED DESCRIPTION OF THE INVENTION

The invention is a compound of formula I (I)

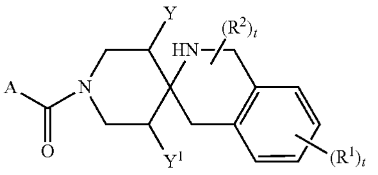

or a pharmaceutically acceptable salt thereof, wherein

Y is H or OH;

$Y^1$ is H or OH;

$R^1$ is H, halogen, or $C_{1-6}$alkyl optionally substituted with halogen;

$R^2$ is H or D;

each t is independently 0, 1, or 2;

A is (a) unsubstituted or substituted aryl;

(b) unsubstituted or substituted unsaturated 5- or 6-membered heterocycle;

(c) unsubstituted or substituted saturated 5- or 6-membered heterocycle; or (d) unsubstituted or substituted unsaturated 8-13-membered bicyclic heterocycle, wherein formula I does not include:

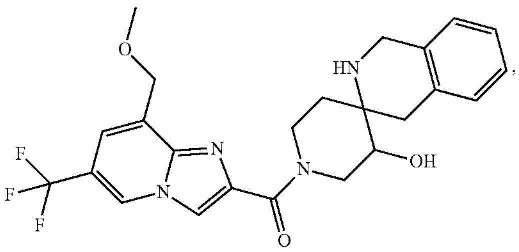

,

-continued

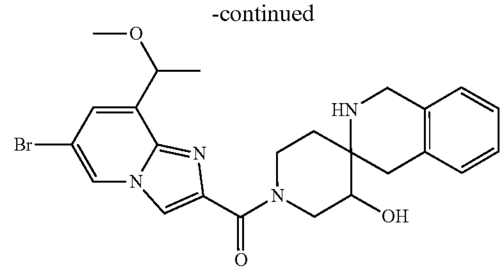

,

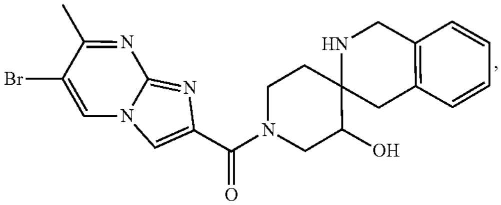

, or

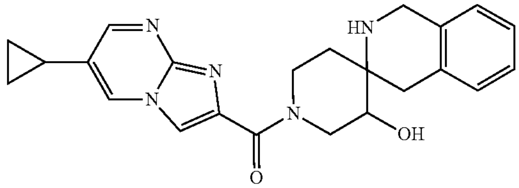

.

In an embodiment of the invention,

Y is H or OH;

$Y^1$ is H or OH;

$R^1$ is H, halogen, or $C_{1-6}$alkyl optionally substituted with halogen;

t is 0, 1, or 2;

$R^2$ is H or D;

A is (a) phenyl, optionally substituted with one or two moieties independently selected from $OC_{1-6}$alkyl, halogen, $C(O)R^5$, O-cyclopropyl, or an unsaturated heterocycle having 1-3 nitrogen atoms and 0-1 oxygen atoms wherein the unsaturated heterocycle is optionally substituted with $C_{1-6}$alkyl, wherein $R^5$ is a saturated heterocycle having 1 nitrogen atom and 1 oxygen atom;

(b) an unsaturated 6-membered heterocycle with 1-2 N atoms, wherein the heterocycle is substituted with $NHR^3$, wherein the heterocycle is additionally optionally substituted with 1 or 2 halogens, wherein $R^3$ is saturated heterocycle with 1 nitrogen atom, wherein the $R^3$ nitrogen is substituted with $C(O)C_{1-6}$ alkyl and wherein the $R^3$ heterocycle is optionally substituted with 1 or 2 halogens;

(c) an unsaturated 6-membered heterocycle with 1 N atom optionally substituted with one, two or three moieties independently selected from halogen, =O, $C_{1-6}$alkyl, $C_{3-6}$cycloalkyl, $C_{1-6}$fluoroalkyl, 5-membered unsaturated heterocycle having 3 or 4 N atoms, OH, $OC_{1-6}$alkyl, $OC_{1-6}$alkoxy, $NC_{1-6}$alkyl, or $NHR^4$, wherein $R^4$ is saturated heterocycle having 1N atom optionally substituted with one or two $C(O)C_{1-6}$alkyl and wherein the $C(O)C_{1-6}$alkyl is optionally substituted with one or two fluoro atoms;

(d)

i. an unsaturated 5-membered heterocycle with 1 or 2 Nitrogen atoms and 0-1 Oxygen atom optionally substituted with a 5-membered unsaturated heterocycle with 1 nitrogen atom and 1 oxygen atom wherein each heterocycle is independently optionally substituted with $C_{1-6}$alkyl, ii. an unsaturated 5-membered heterocycle with 2 N atoms optionally substituted with $CHF_2$, cyclopropyl, or a phenyl optionally mono-substituted, independently disubstituted, or independently trisubstituted with halogen, $C_{1-6}$alkyl, $OC_{1-6}$alkyl, or $C_{1-6}$fluoroalkyl;

(e) an unsaturated 8-11-membered bicyclic heterocycle with 1-4 nitrogen atoms, 0-1 oxygen atoms, and 0-1 sulfur atoms, unsubstituted, mono-substituted, independently disubstituted, or independently trisubstituted with i) $CR^6R^7R^8$, wherein $R^6$ is H, $C_{1-6}$alkyl, or halogen, $R^7$ is H, $C_{1-6}$alkyl, halogen or OH, and $R^8$ is H, CN, $C_{1-6}$alkyl optionally substituted with CN, halogen, OH, $OC_{1-6}$alkyl, or $C_{1-6}$haloalkyl;

ii) $C(O)NR^9R^{10}$, wherein $R^9$ is H, $C_{1-6}$alkyl, halogen, or $C_{1-6}$haloalkyl, and $R^{10}$ is H, $C_{1-6}$alkyl, $C_{1-6}$alkyl $(C_{1-6}alkyl)_{1-2}$, halogen, or $C_{1-6}$haloalkyl, iii) CN;

iv) $C_3$ to $C_6$ saturated or unsaturated carbocycle optionally mono-substituted, independently disubstituted, or independently trisubstituted with $C_{1-6}$alkyl, 1-3 halogens, or CN;

v) halogen;

vi) $C_{0-6}alkylO(CH_2)_{0-2}R^{11}$, wherein:

$R^{11}$ is H, $C_{1-6}$alkyl, $(C_{1-6}alkyl)(OC_{1-6}alkyl)$, $OC_{1-6}$alkyl, $C_{1-6}alkyl(C_{1-6}alkyl)_{1-2}$, $C_{1-6}$alkyl $(C_{1-6}alkyl)_{1-2}OH$, $C_{3-6}$heterocycle or $C_{3-6}$cycloalkyl wherein the $C_{3-6}$ heterocycle or $C_{3-6}$cycloalkyl are optionally mono-substituted, independently disubstituted, or independently trisubstituted with $C_{1-6}$alkyl, halogen, CN, or =O;

vii) =O;

viii) $C_{3-6}$heterocycle or $C_{3-6}$cycloalkyl wherein the $C_{3-6}$heterocycle or $C_{3-6}$cycloalkyl are optionally mono-substituted, independently disubstituted, or independently trisubstituted with $C_{1-6}$alkyl, $C_{1-6}$cycloalkyl, halogen, CN, or =O;

ix) $N(C_{1-6}alkyl)(C_{1-6}alkyl)(OC_{1-6}alkyl)$ or $N(C_{1-6}alkyl)(C_{1-6}alkyl)$, wherein the alkyl moiety is optionally substituted with 5-membered unsaturated ring with 2 nitrogen atoms, 0-1 oxygen atom, wherein the ring is optionally substituted with $C_{1-6}$alkyl, halogen, or $C_{1-6}$haloalkyl;

xi) $C_{3-6}$heterocycle optionally mono-substituted, independently disubstituted, or independently trisubstituted with 5-membered unsaturated ring with 2 nitrogen, xii) an unsaturated 8-11 membered bicyclic heterocycle with 1-4 nitrogen atoms, 0-1 oxygen atoms, and 0-1 sulfur atoms, unsubstituted, mono-substituted, independently disubstituted, or independently trisubstituted with $C_{1-6}$alkyl, or halogen, xiii) unsaturated 5- or 6-membered heterocycle with 1-2 nitrogen atoms, 0-1 oxygen atoms, and 0-1 sulfur atoms optionally mono-substituted or independently disubstituted with $C_{1-6}$alkyl or $OC_{1-6}$ alkyl, wherein the alkyl is optionally substituted with 1-3 halogens;

xiv) $C_{1-6}$alkyl optionally substituted with CN or halogen; or (f) unsaturated 13-membered tricyclic heterocycle with 1 oxygen, wherein the tricyclic heterocycle is optionally substituted with OH.

In an embodiment of the invention,

Y is H or OH;

$Y^1$ is H or OH;

$R^1$ is H, halogen, or $C_{1-6}$alkyl optionally substituted with halogen;

t is 1;

$R^2$ is H or D;

A is (a) phenyl, optionally substituted with one or two moieties independently selected from $OC_{1-6}$alkyl, halogen, $C(O)R^5$, O-cyclopropyl, or an unsaturated heterocycle having 1-3 nitrogen atoms and 0-1 oxygen atoms wherein the unsaturated heterocycle is optionally substituted with $C_{1-6}$alkyl, wherein $R^5$ is a saturated heterocycle having 1 nitrogen atom and 1 oxygen atom;

(b) an unsaturated 6-membered heterocycle with 1-2 N atoms, wherein the heterocycle is substituted with $NHR^3$, wherein the heterocycle is additionally optionally substituted with 1 or 2 halogens, wherein $R^3$ is saturated heterocycle with 1 nitrogen atom, wherein the $R^3$ nitrogen is substituted with $C(O)C_{1-6}$ alkyl and wherein the $R^3$ heterocycle is optionally substituted with 1 or 2 halogens;

(c) an unsaturated 6-membered heterocycle with 1 N atom optionally substituted with one, two or three moieties independently selected from halogen, =O, $C_{1-6}$alkyl, $C_{3-6}$cycloalkyl, $C_{1-6}$fluoroalkyl, 5-membered unsaturated heterocycle having 3 or 4 N atoms, OH, $OC_{1-6}$alkyl, $OC_{1-6}$alkoxy, $NC_{1-6}$alkyl, or $NHR^4$, wherein $R^4$ is saturated heterocycle having 1N atom optionally substituted with one or two $C(O)C_{1-6}$alkyl and wherein the $C(O)C_{1-6}$alkyl is optionally substituted with one or two fluoro atoms;

(d)

i. an unsaturated 5-membered heterocycle with 1 or 2 Nitrogen atoms and 0-1 Oxygen atom optionally substituted with a 5-membered unsaturated heterocycle with 1 nitrogen atom and 1 oxygen atom wherein each heterocycle is independently optionally substituted with $C_{1-6}$alkyl, ii. an unsaturated 5-membered heterocycle with 2 N atoms optionally substituted with $CHF_2$, cyclopropyl, or an phenyl optionally mono-substituted, independently disubstituted, or independently trisubstituted with halogen, $C_{1-6}$alkyl, $OC_{1-6}$alkyl, or $C_{1-6}$fluoroalkyl;

(e) an unsaturated 8-11-membered bicyclic heterocycle with 1-4 nitrogen atoms, 0-1 oxygen atoms, and 0-1 sulfur atoms, unsubstituted, mono-substituted, independently disubstituted, or independently trisubstituted with i) $CR^6R^7R^8$, wherein $R^6$ is H, $CH_3$, or F, $R^7$ is H, $CH_3$, F or OH, and $R^8$ is H, CN, $CH_3$, F, OH, $OCH_3$, $CF_3$, or $CH_2CN$;

ii) $C(O)NR^9R^{10}$, wherein $R^9$ is H, $CH_3$, F, or $CF_3$, and $R^{10}$ is H, $CH_3$, $CH_3(CH_3)_2$, F, or $CF_3$;

iii) CN;

iv) $C_3$ to $C_6$ saturated or unsaturated carbocycle optionally mono-substituted, independently disubstituted, or independently trisubstituted with $C_{1-6}$alkyl, 1-3 halogens, or CN;

v) halogen;

vi) $C_{0-6}alkylO(CH_2)_{0-2}R^{11}$, wherein:

$R^{11}$ is H, $CH_3$, $CH_2OCH_3$, $OCH_3$, $CH(CH_3)_2$, $C(CH_3)_2OH$, vii)

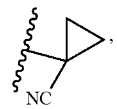, 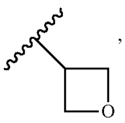, 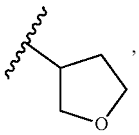, 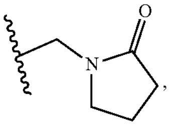, 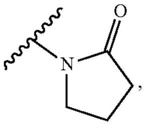, 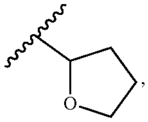, or 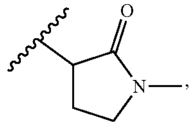,

=O;

viii)

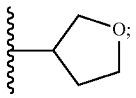;

ix)

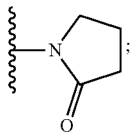;

x) $N(C_{1-6}alkyl)(C_{1-6}alkyl)(OC_{1-6}alkyl)$ or $N(C_{1-6}alkyl)(C_{1-6}alkyl)$, wherein the alkyl moiety is optionally substituted with 5-membered unsaturated ring with 2 nitrogen atoms, 0-1 oxygen atom, wherein the ring is optionally substituted with $C_{1-6}$alkyl, halogen, or $C_{1-6}$haloalkyl;

xi)

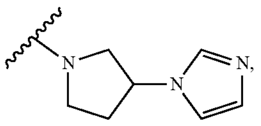, 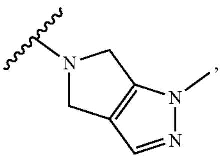, 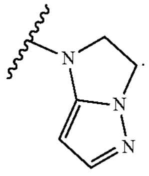, 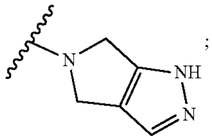;

xii)

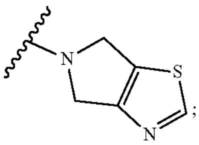; 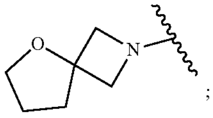;

-continued

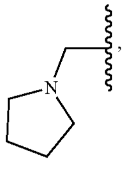,
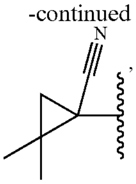, or
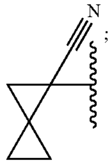;

xiii) unsaturated 5- or 6-membered heterocycle with 1-2 nitrogen atoms, 0-1 oxygen atoms, and 0-1 sulfur atoms optionally mono-substituted or independently disubstituted with $C_{1-6}$alkyl or $OC_{1-6}$alkyl, wherein the alkyl is optionally substituted with 1-3 halogens;

xiv) $C_{1-6}$alkyl optionally substituted with CN or halogen; or (f) unsaturated 13-membered tricyclic heterocycle with 1 oxygen, wherein the tricyclic heterocycle is optionally substituted with OH.

In an embodiment of the invention,

Y is H or OH;

$Y^1$ is H or OH;

A is (a) phenyl, optionally substituted with one or two moieties independently selected from $OCH_2CH_3$, Cl, O-cyclopropyl, $C(O)R^5$, or an unsaturated 5-membered heterocycle having 1-3 nitrogen atoms and 0-1 oxygen atoms wherein the unsaturated heterocycle is optionally substituted with cyclopropyl or $C_{1-6}$alkyl, wherein $R^5$ is

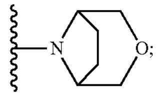;

(b) an unsaturated 6-membered heterocycle with 1 or 2 N atoms substituted with $NHR^3$, wherein the heterocycle is additionally optionally substituted with 1 or 2 halogens, wherein $R^3$ is a saturated heterocycle with 1 nitrogen atom wherein the $R^3$ nitrogen is substituted with $C(O)CH_3$, and wherein the $R^3$ heterocycle is additionally optionally independently substituted with 1 or 2 halogens;

(c) unsaturated 6-membered heterocycle with 1 N atom optionally substituted with one, two or three moieties independently selected from Cl, Br, F, =O, $CH_3$, $CF_3$, $CH_2CF_3$, $CH(CH_3)CF_3$, $OCH_2CH_2OH$, $NHCH_3$, cyclopropyl, $OCH_2CH_3$, $OCH_2CH_2CH_3$, $OCH_3$, OH, or 5-membered unsaturated heterocycle having 3 or 4 nitrogen atoms; (d)

i. unsaturated 5-membered heterocycle with 1 nitrogen atom and 1 oxygen atom substituted with 5-membered unsaturated heterocycle with 1 nitrogen atom and 1 oxygen atom wherein each heterocycle is optionally independently substituted with $CH_3$;

ii. unsaturated 5-membered heterocycle with 2 nitrogen atoms optionally substituted with $CHF_2$, cyclopropyl or an phenyl wherein the phenyl is optionally mono-substituted, independently disubstituted, or independently trisubstituted with F, $CH_3$, $OCH_3$, cyclopropyl, or $CHF_2$;

(e) unsaturated 8-11-membered bicyclic heterocycle with 1-4 nitrogen atoms, 0-1 oxygen atoms, and 0-1 sulfur atoms, unsubstituted, mono-substituted, independently disubstituted, or independently trisubstituted with Br, F, Cl, I, $CH_3$, CN, $CH(CH_3)_2$, $CH_2OH$, $C(CH_3)_2OH$, $C(O)NHCH_3$, $C(O)N(CH_3)_2$, $CF_3$, $CHF_2$, $C(CH_3)_2OCH_3$, $CH(CH_3)OCH_3$, $CH_2OCH_3$, $CH_2CH_2OCH_3$, $CH(OH)CF_3$, $CH(OH)CH_3$, $(CH_2)_2CN$, $CH_2CF_3$, $CH(CH_3)_2$, $CH_2CH_3$, cyclopropyl, cyclopropyl-$CH_3$, =O, OH, $OCH_3$, $OCH_2CH_3$, $OCH(CH_3)_2$, $O(CH_2)_2OCH_3$, $OCH_2C(CH_3)_2OH$, $N(CH_3)(CH_2)_2OCH_3$, $CH(CH_3)CN$,

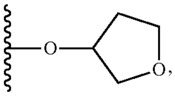,
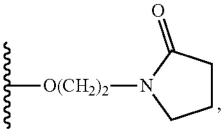,
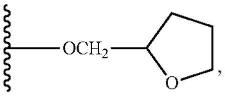,
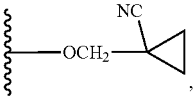,
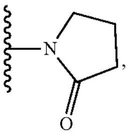,
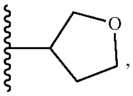,
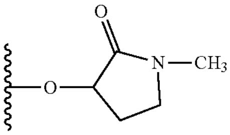,
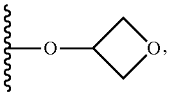,
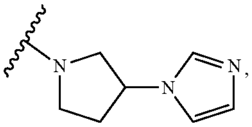,
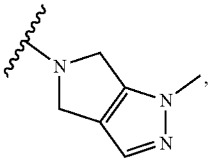,
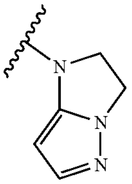,
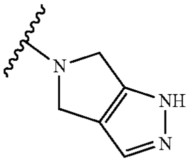,
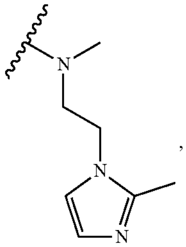,
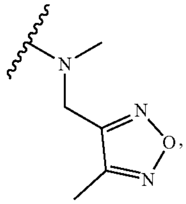,
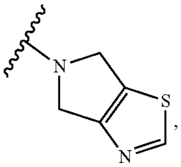,
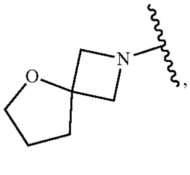,
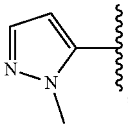,
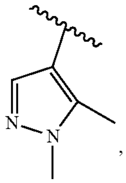, -continued

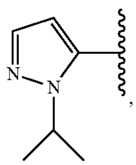,
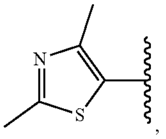,
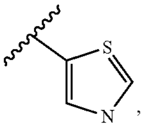,
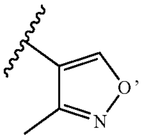,
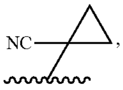,
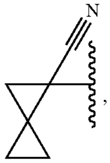,
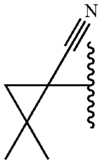,
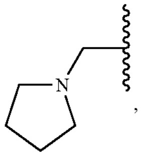,
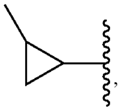,
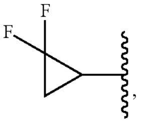,
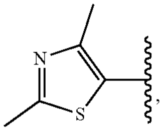,
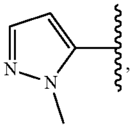,
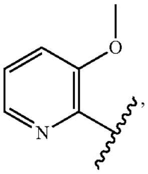,
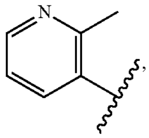, or
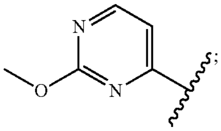;

or (f) unsaturated 13-membered tricyclic heterocycle with 1 O, wherein the tricyclic heterocycle is optionally substituted with OH.

In an embodiment of the invention,

A is (a) phenyl, optionally substituted with one or two moieties independently selected from $OCH_2CH_3$, Cl, O-cyclopropyl, $C(O)R^5$, or an unsaturated 5-membered heterocycle having 3 nitrogen atoms substituted with cyclopropyl or $CH_3$, or an unsaturated 5-membered heterocycle having 2 nitrogen atoms and 1 oxygen atom optionally substituted with cyclopropyl, wherein $R^5$ is

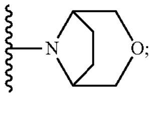 [SMILES: *N1C2CCC1COC2];

(b)

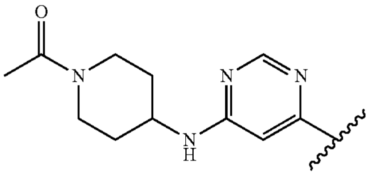 or

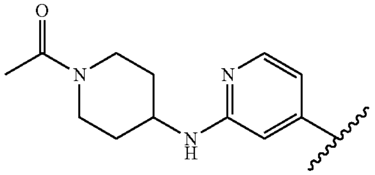

optionally substituted with 1 or 2 moieties independently selected from F or Cl;

(c)

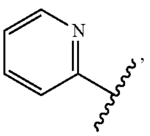, 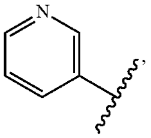, or 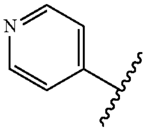

optionally substituted with 1, 2, or 3 moieties independently selected from Cl, F, Br, =O, $CH_3$, $CF_3$, $CH_2CF_3$, $CH(CH_3)CF_3$, $OCH_2CH_2OH$, $NHCH_3$, cyclopropyl, $OCH_2CH_3$, $OCH_2CH_2CH_3$, $OCH_3$, OH,

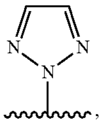, or 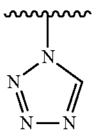;

(d)

i. 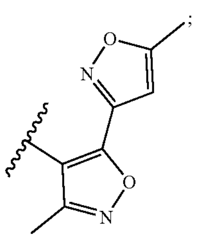; or ii. 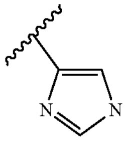

optionally substituted with $CHF_2$, cyclopropyl or an phenyl, wherein the phenyl is optionally mono-substituted, independently disubstituted, or independently trisubstituted with F, $CH_3$, $OCH_3$, cyclopropyl, or $CHF_2$;

(e) an unsaturated 8-11-membered bicyclic heterocycle with 1-4 nitrogen atoms, 0-1 oxygen atoms, and 0-1 sulfur atoms, selected from

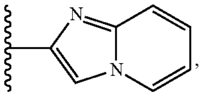,
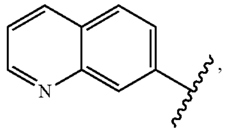,
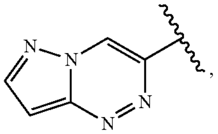,
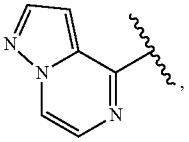,
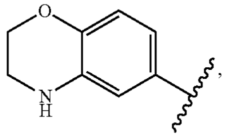,
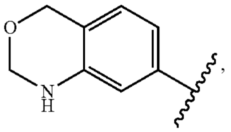,
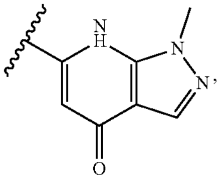,
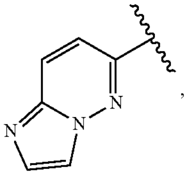,
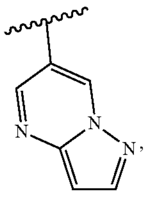,
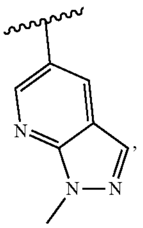,
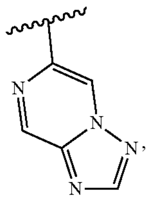,
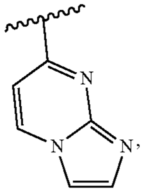,
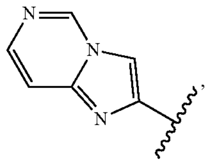,
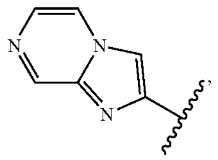,
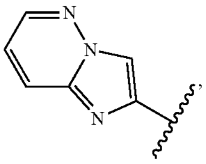,
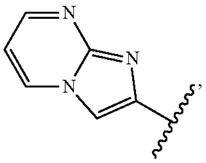,
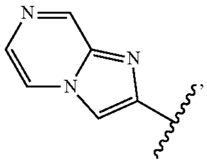,
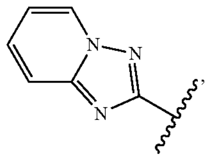,
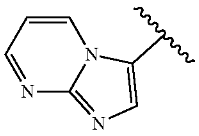,
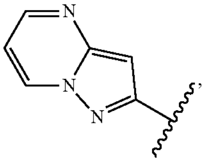,
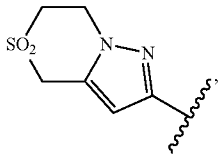, -continued

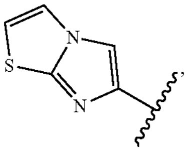,
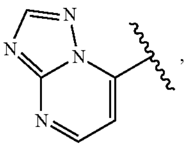,
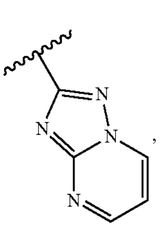,
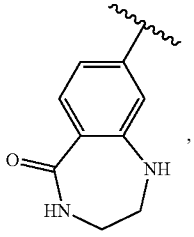,
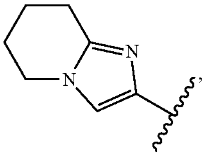,
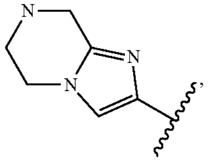,
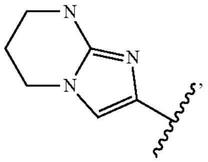,
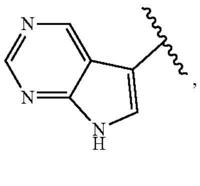,
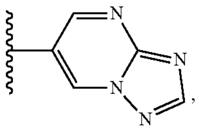, wherein the bicyclic heterocycle is unsubstituted, mono-substituted, independently disubstituted, or independently trisubstituted with Br, F, Cl, I, $CH_3$, CN, $CH(CH_3)_2$, $CH_2OH$, $C(CH_3)_2OH$, $C(O)NHCH_3$, $C(O)N(CH_3)_2$, $CF_3$, $CHF_2$, $C(CH_3)_2OCH_3$, $CH(CH_3)OCH_3$, $CH_2OCH_3$, $CH_2CH_2OCH_3$, $CH(OH)CF_3$, $CH(OH)CH_3$, $(CH_2)_2CN$, $CH_2CF_3$, $CH(CH_3)_2$, $CH_2CH_3$, cyclopropyl, cyclopropyl-$CH_3$, =O, OH, $OCH_3$, $OCH_2CH_3$, $OCH(CH_3)_2$, $O(CH_2)_2OCH_3$, $OCH_2C(CH_3)_2OH$, $N(CH_3)(CH_2)_2OCH_3$, $CH(CH_3)CN$,

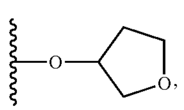,
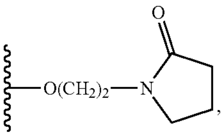,
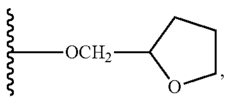,
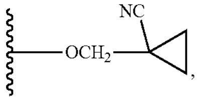,
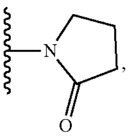,
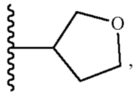,
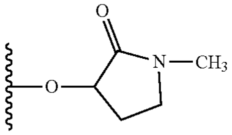, -continued
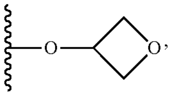,
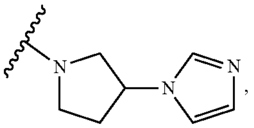,
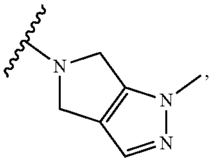,
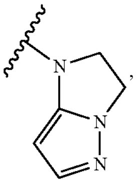,
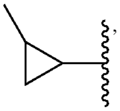,
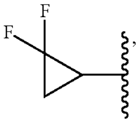,
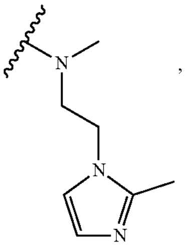,
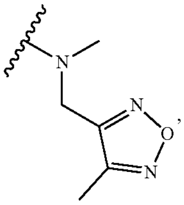,
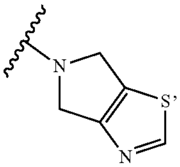,
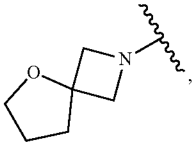,
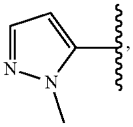,
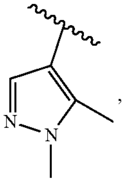,
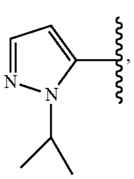,
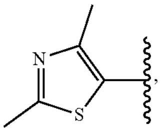,
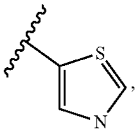,
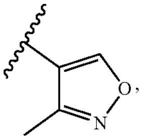,
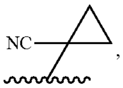,
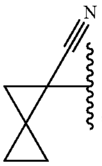,
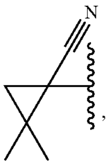,
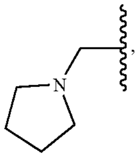,
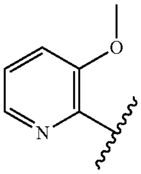,
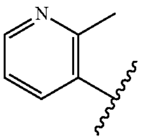, or
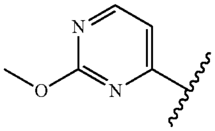;
or
(f)
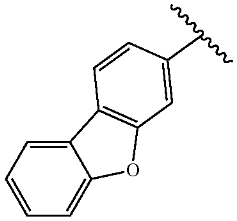 [SMILES: *c1ccc2c(c1)oc1ccccc12]
substituted with OH.
In an embodiment of the invention,
A is selected from
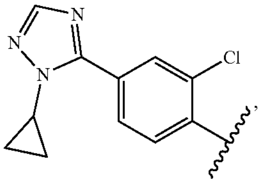,
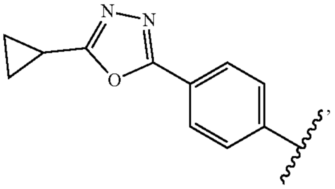,
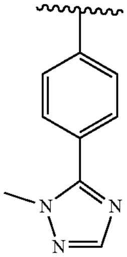,
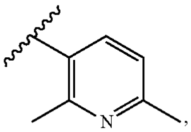,
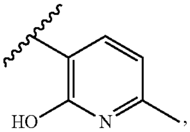,
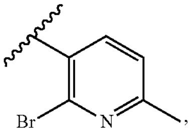,
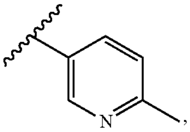,
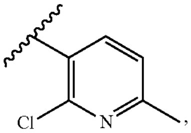,
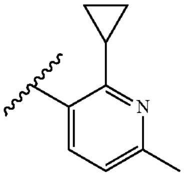
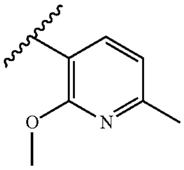
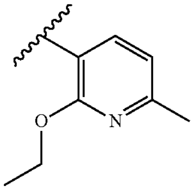
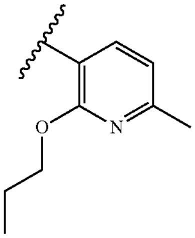

-continued
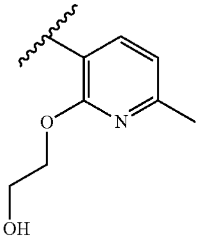
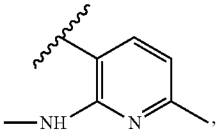,
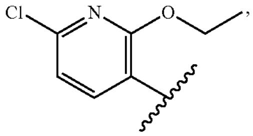,
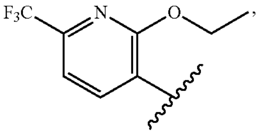,
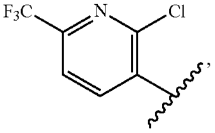,
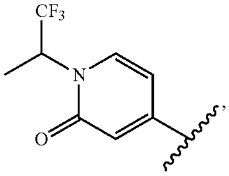,
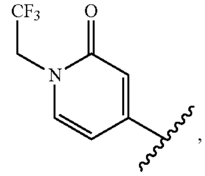,
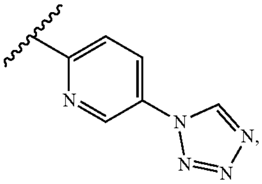,
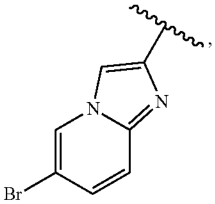,
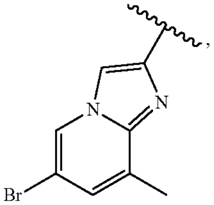,
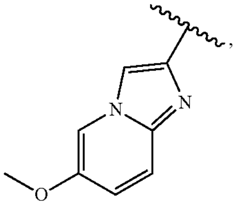,
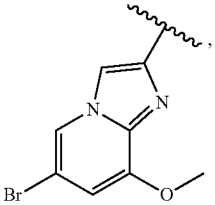,
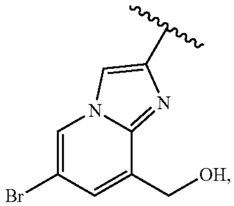,
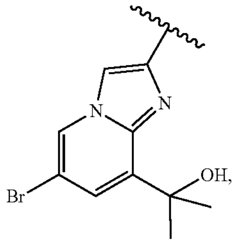,
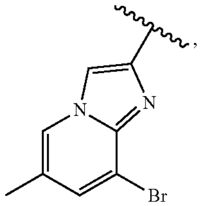,
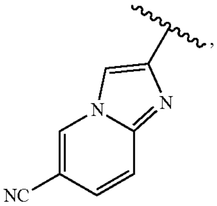,
-continued
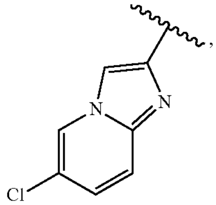,
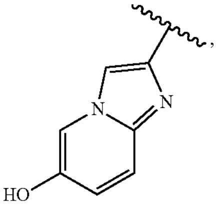,
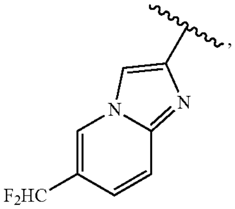,
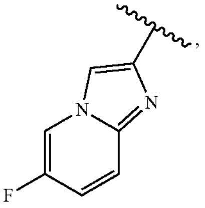,
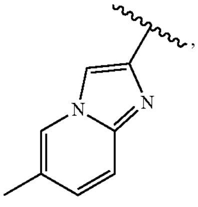,
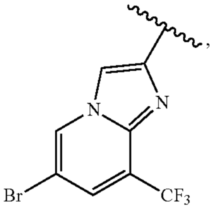
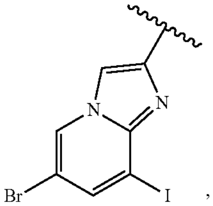,
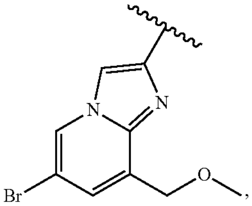,
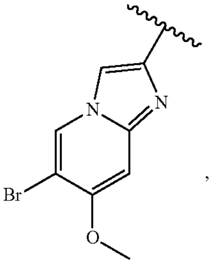,
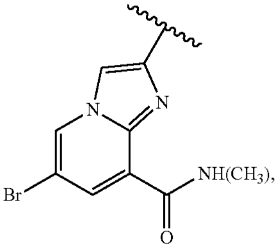,
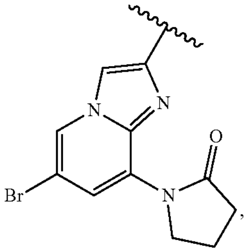,
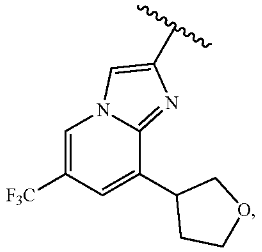,
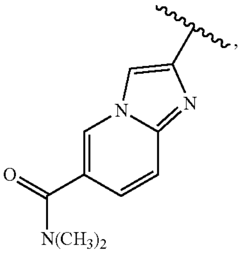,
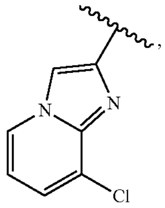, -continued
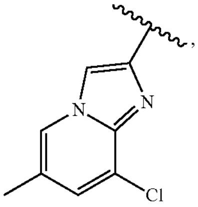,
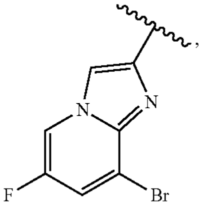,
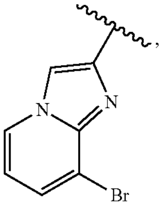,
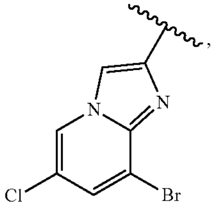,
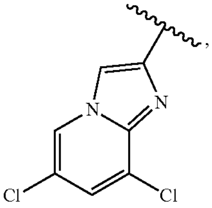,
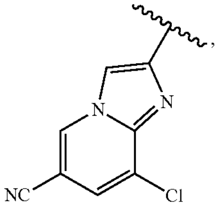,
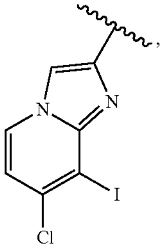,
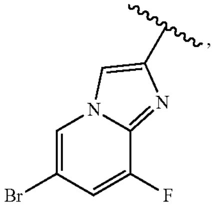,
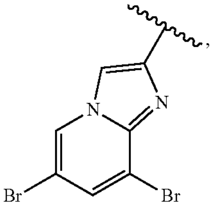,
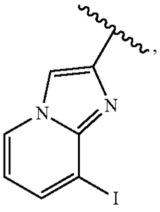,
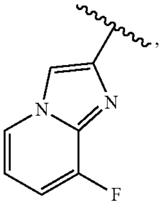,
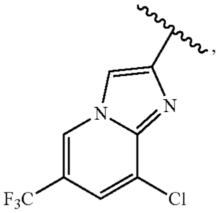,
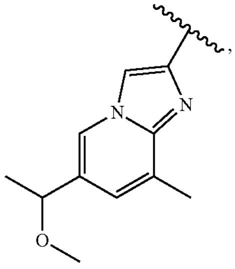,
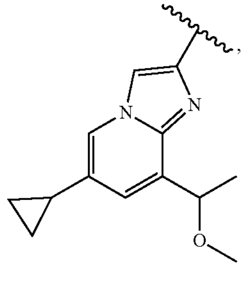,
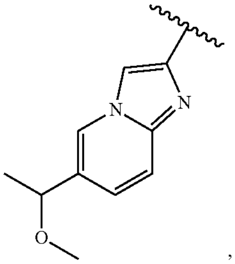,
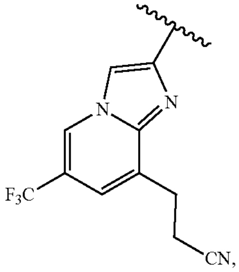,
-continued
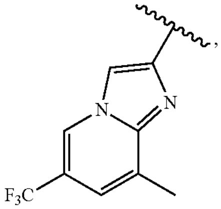,
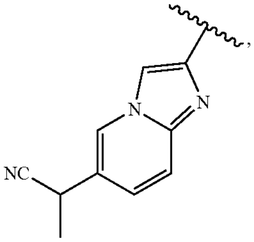,
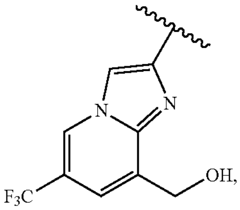,
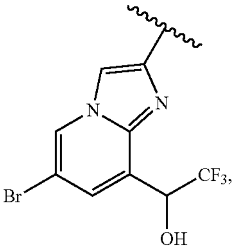,
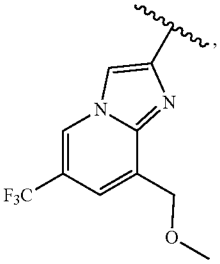,
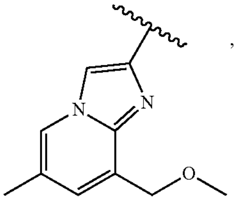,
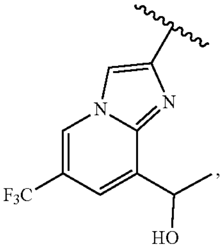,
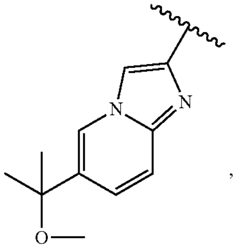,
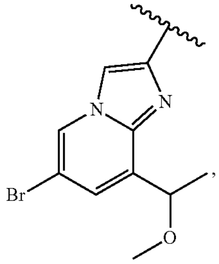,
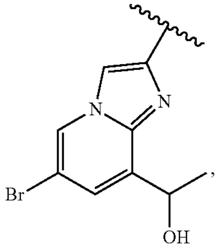,
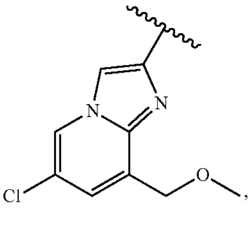,
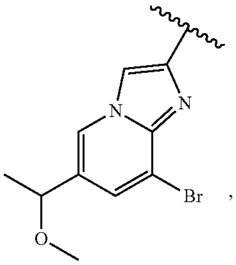, -continued
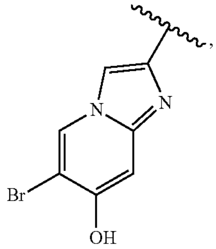
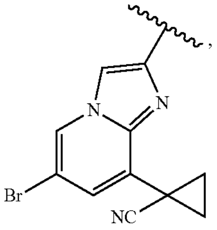
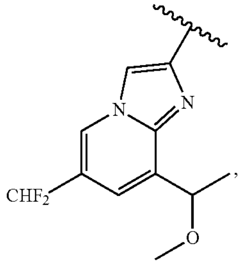
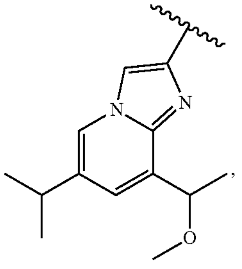
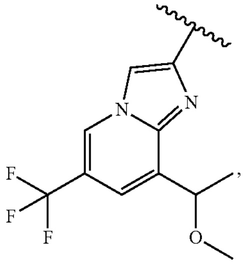
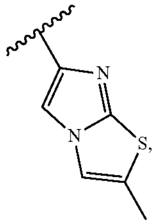
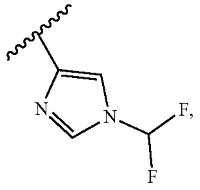
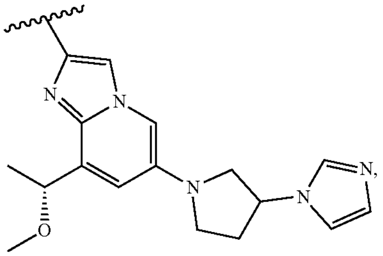
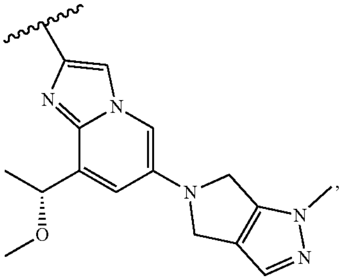
-continued
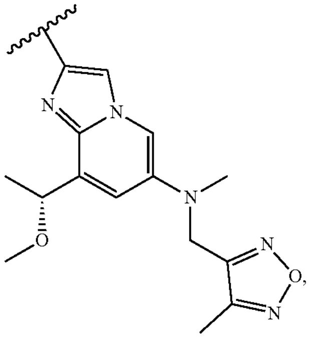
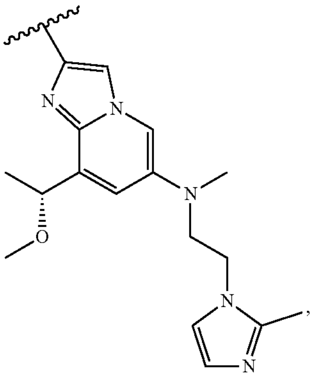
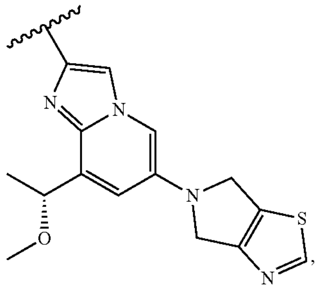
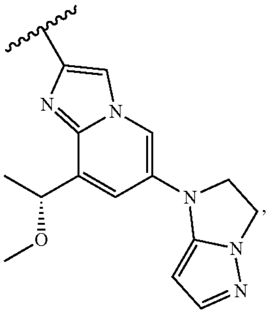
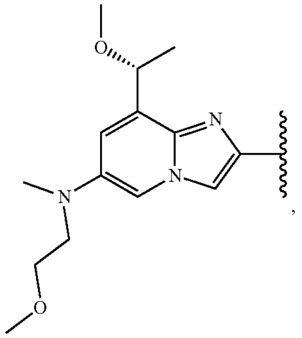
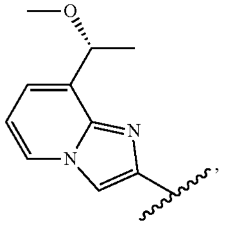

-continued
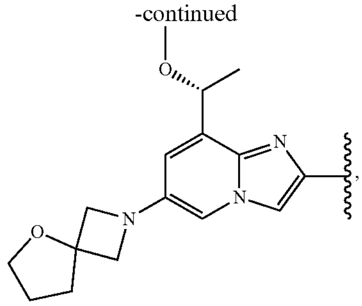,
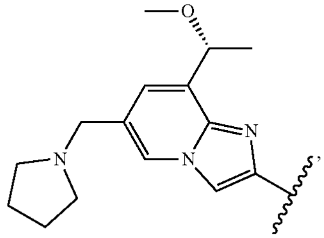,
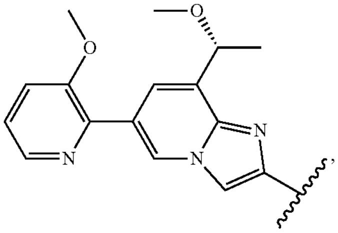,
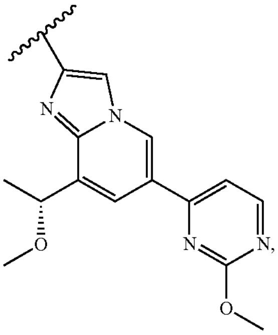,
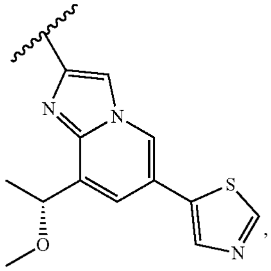,
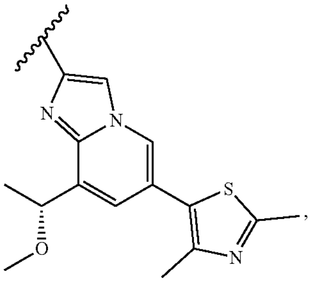,
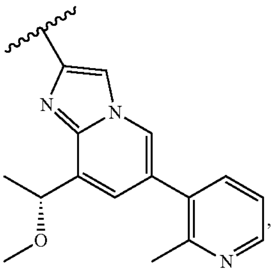,
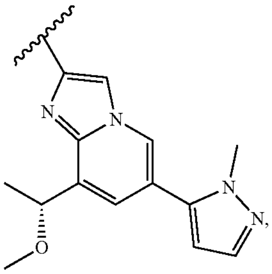,
-continued
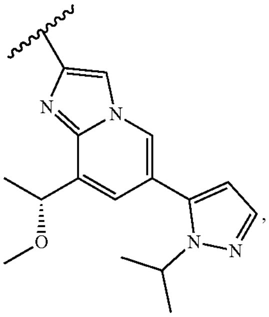,
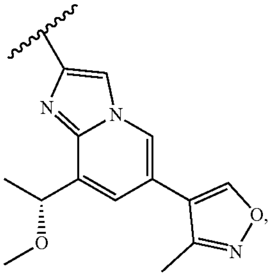,
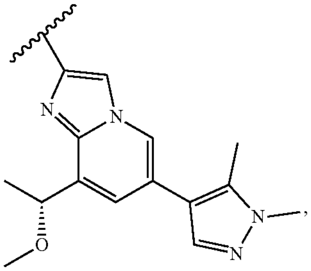,
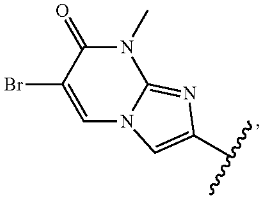,
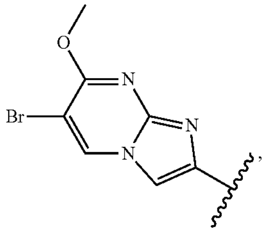,
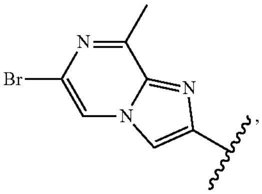,
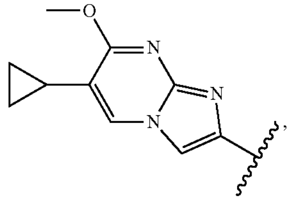,
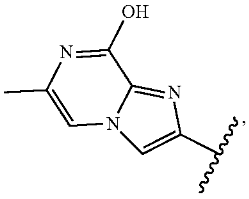,
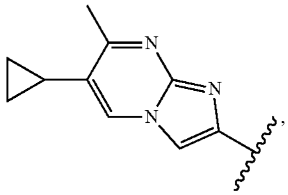,
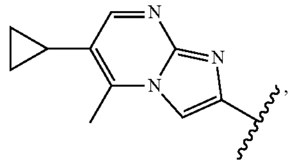,
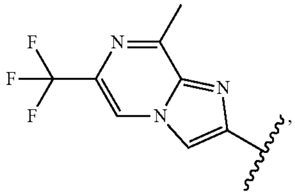, -continued
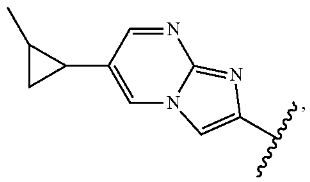
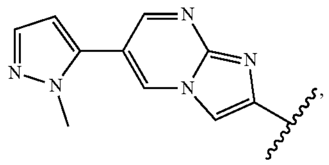
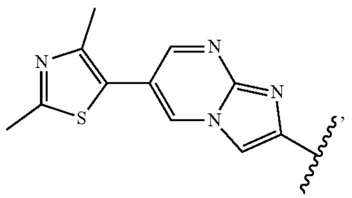
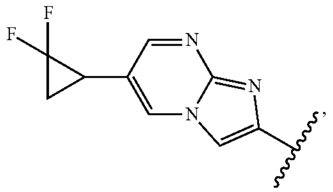
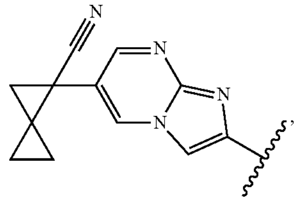
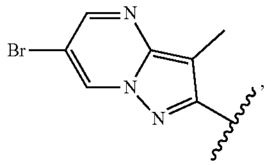
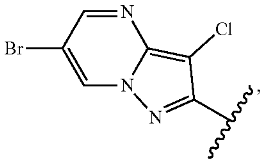
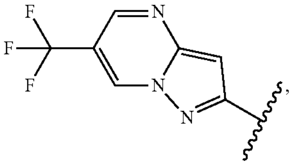
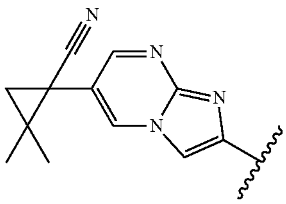
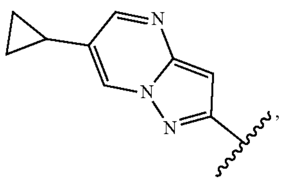
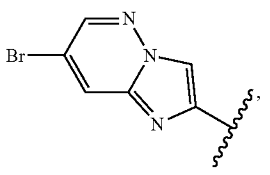
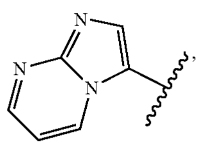
-continued
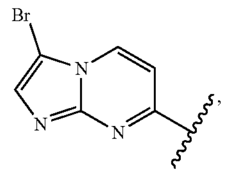
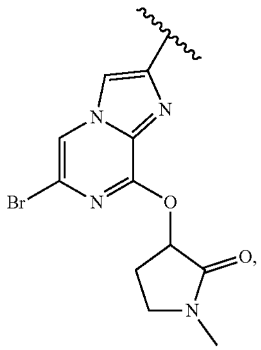
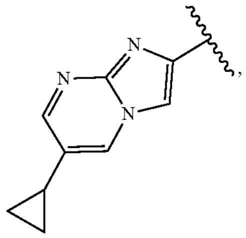
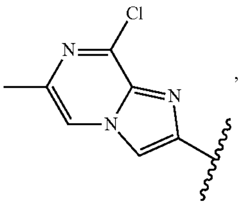
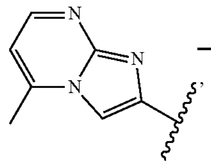
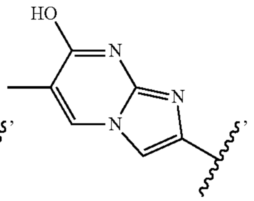
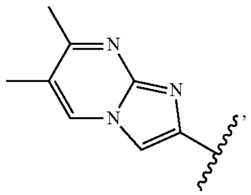
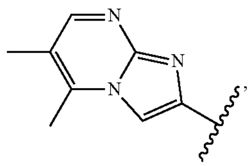
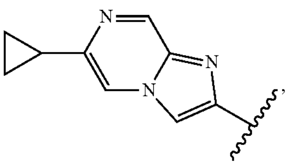
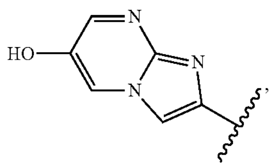
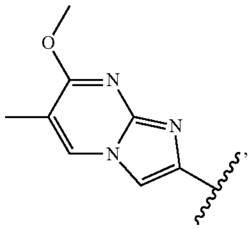
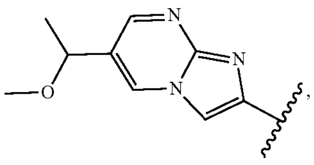
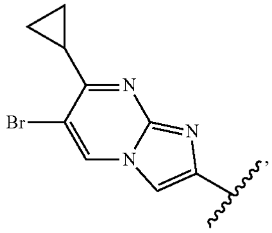
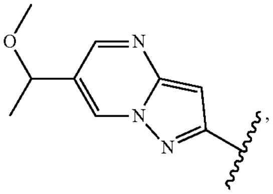

-continued
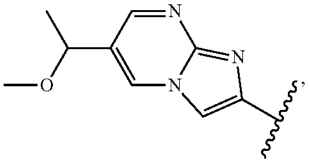,
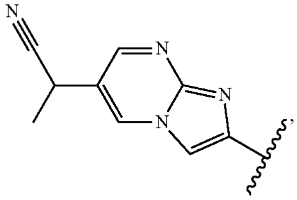, 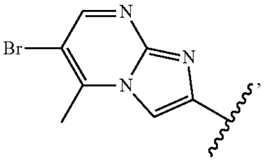,
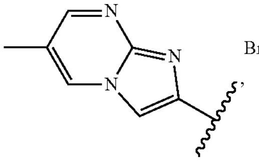, 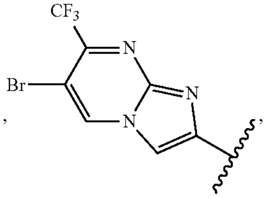,
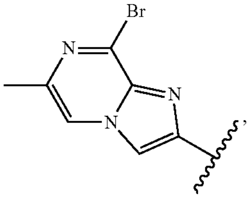, 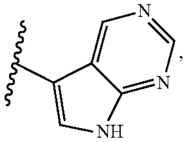,
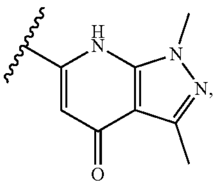, 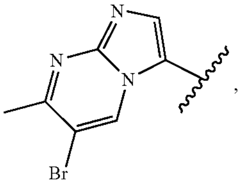,
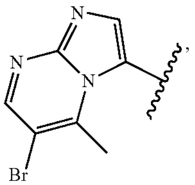, 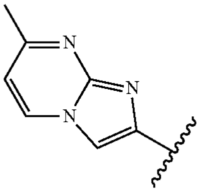,
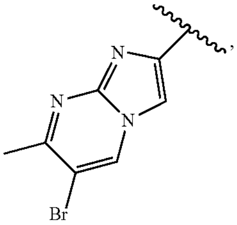, 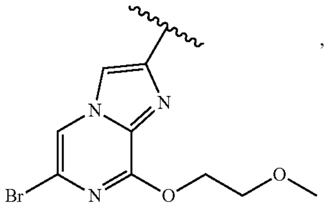,
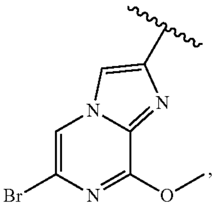, 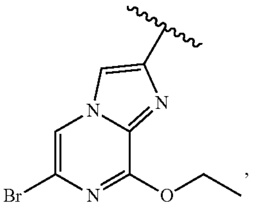,
-continued
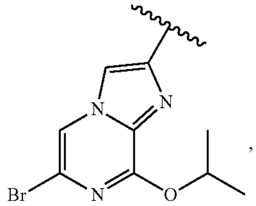, 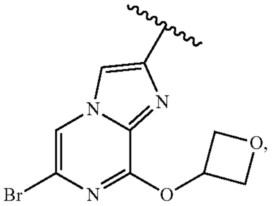,
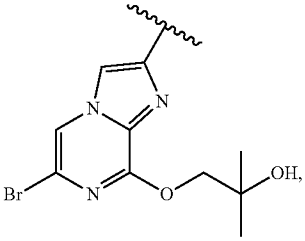, 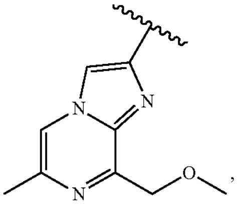,
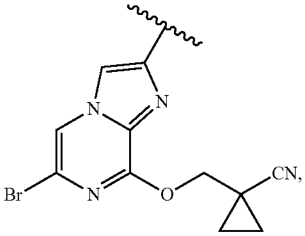, 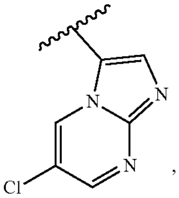,
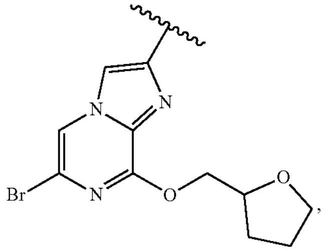,
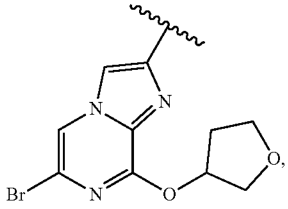, 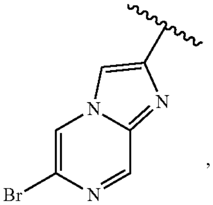,
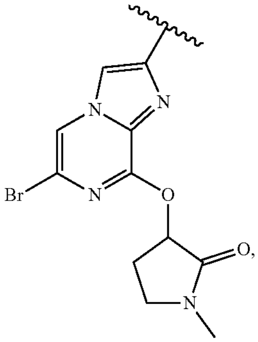,
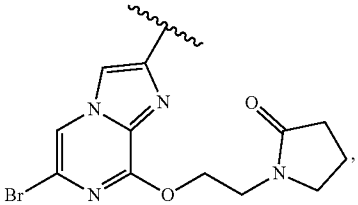, 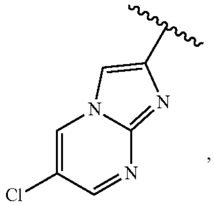, -continued
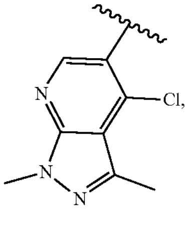
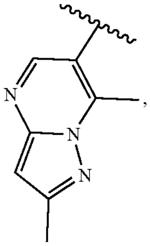
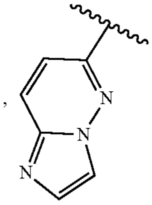
,
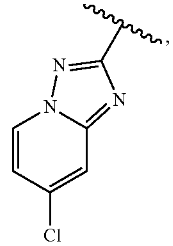
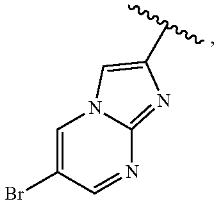
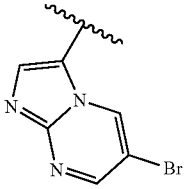
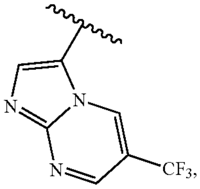
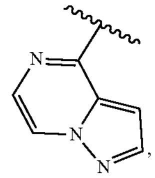
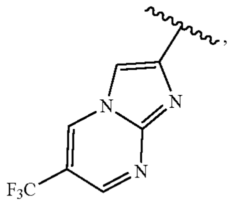
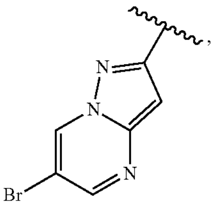
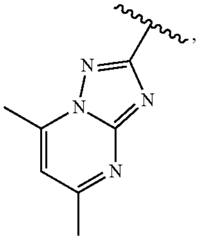
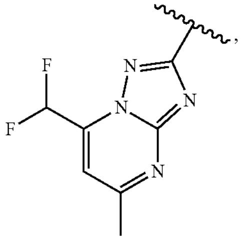
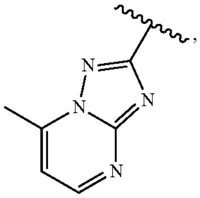
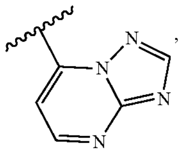
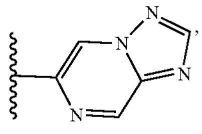
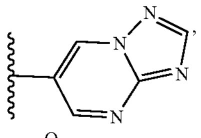
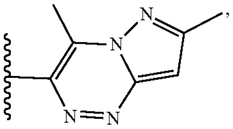
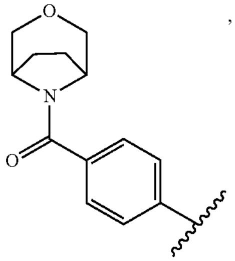
,
-continued
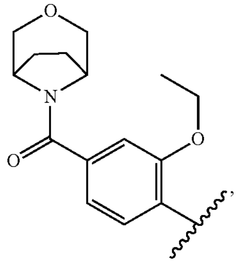
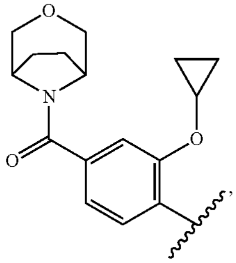
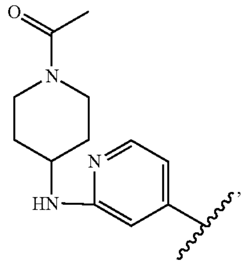
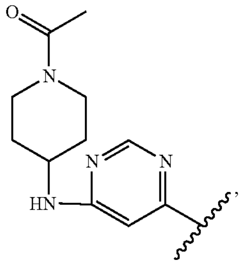
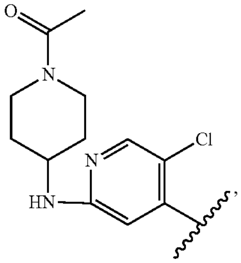
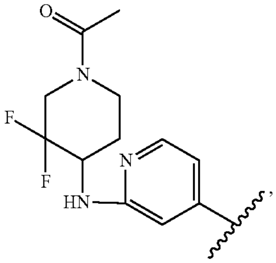
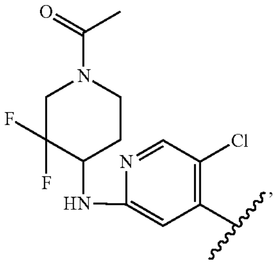
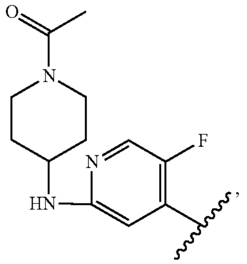
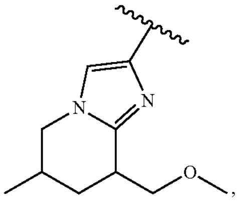
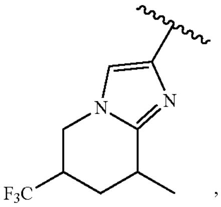
,
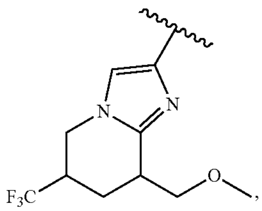
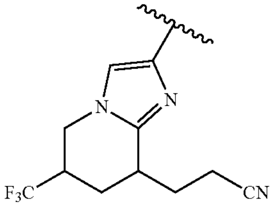
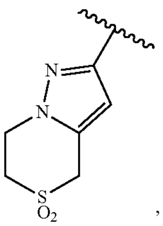
,
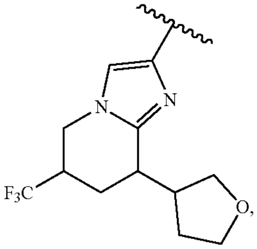

-continued

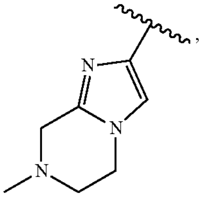

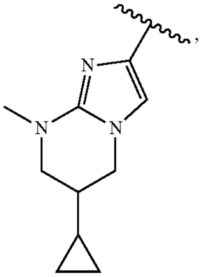

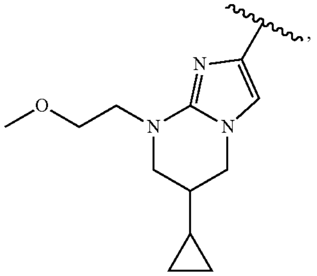

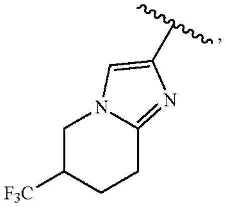

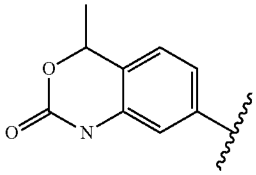

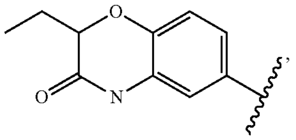

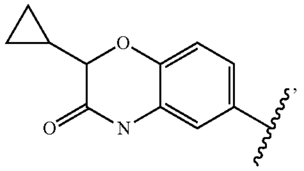

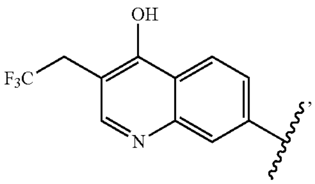

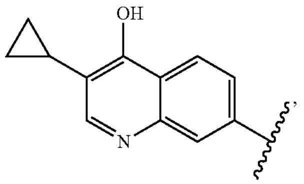

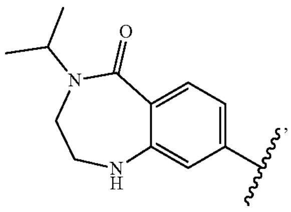

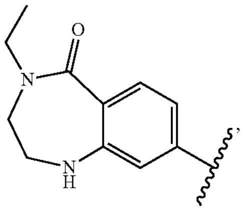

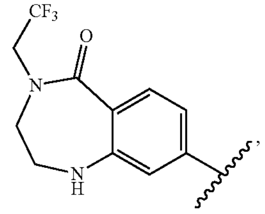

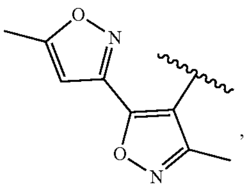

-continued

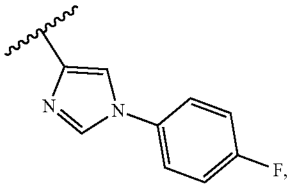

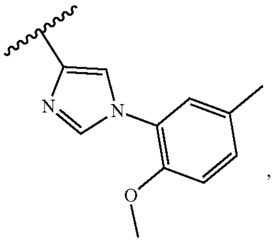

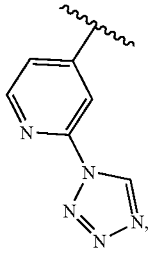

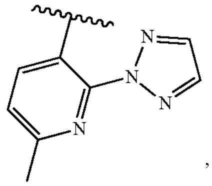

, or

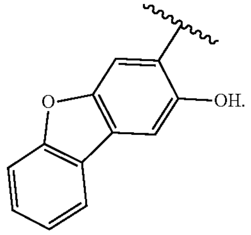

In an embodiment of the invention, Y is OH and $Y^1$ is H.

In an embodiment of the invention, Y is H and $Y^1$ is OH.

In an embodiment of the invention, Y is H and $Y^1$ is H.

An embodiment of the invention is the compound of formula (Ia);

(Ia)

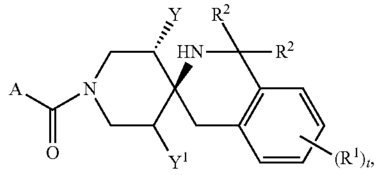

or pharmaceutically acceptable salt thereof.

An embodiment of the invention is the compound of formula (Ib);

(Ib)

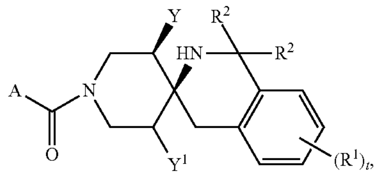

or pharmaceutically acceptable salt thereof.

An embodiment of the invention is the compound of formula (Ic);

(Ic)
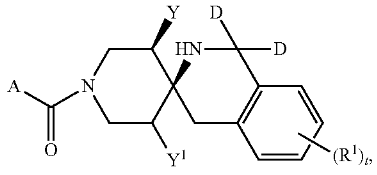
or pharmaceutically acceptable salt thereof.
An embodiment of the invention is the compound of formula (Id);
(Id)
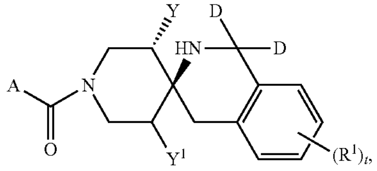
or pharmaceutically acceptable salt thereof.
In an embodiment of the invention the compound of formula I is
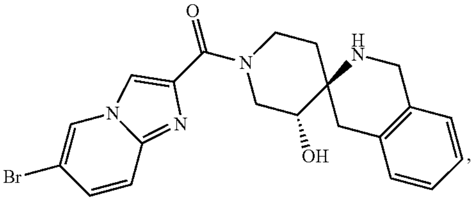
,
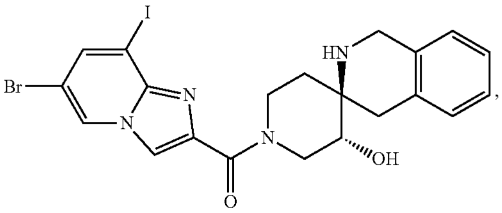
,
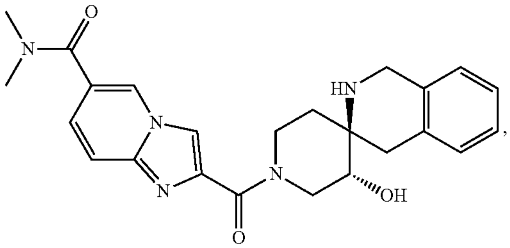
,
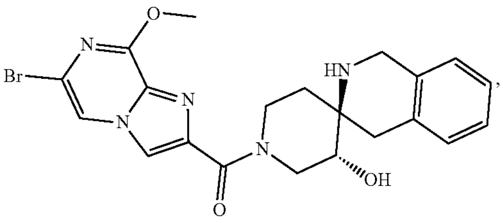
,
-continued
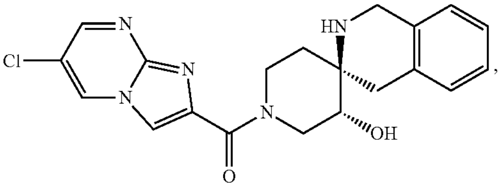
,
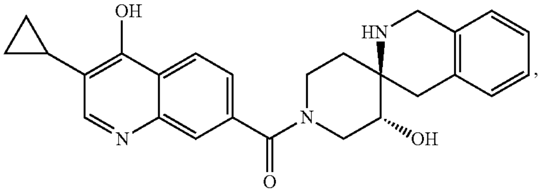
,
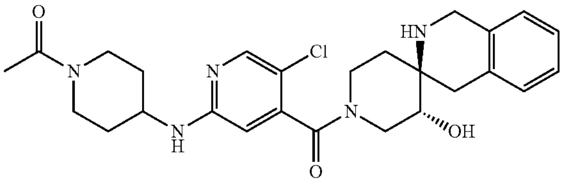
,
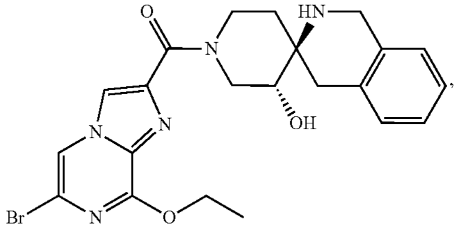
,
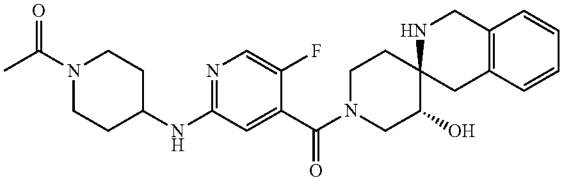
,
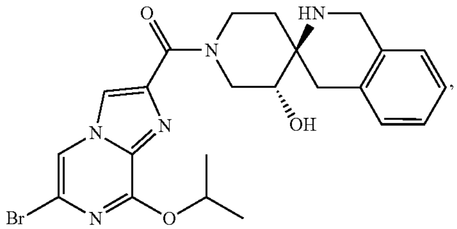
,
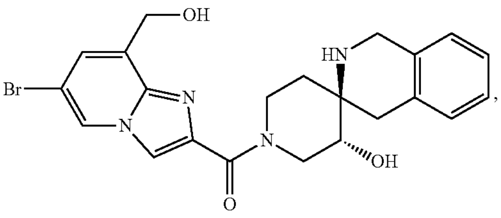
,
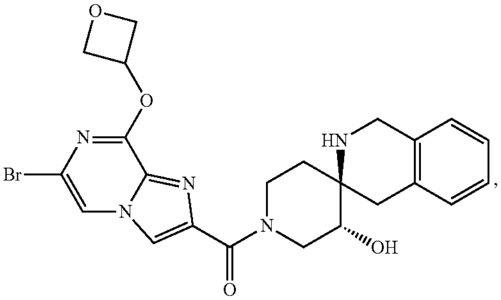
, -continued
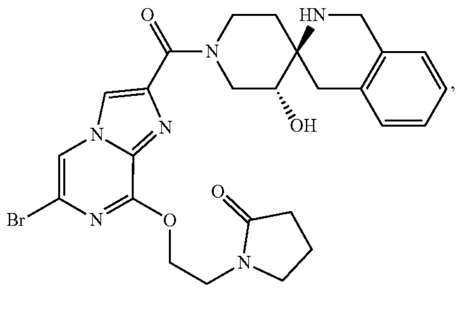
,
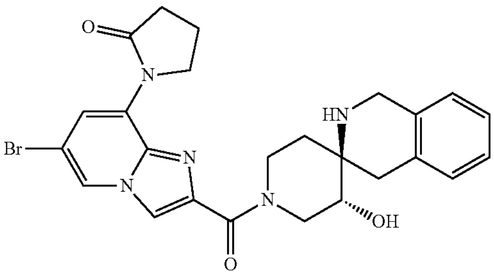
,
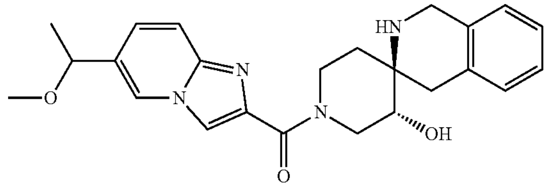
,
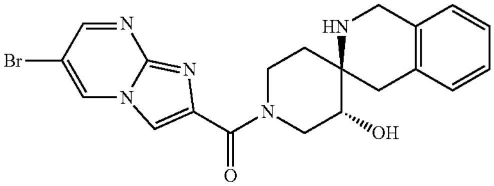
,
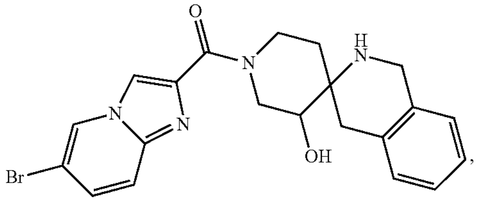
,
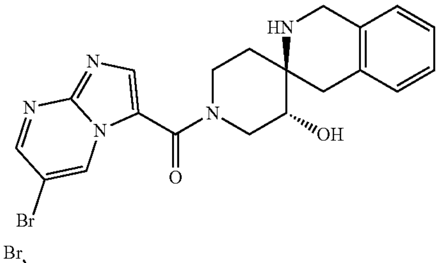
,
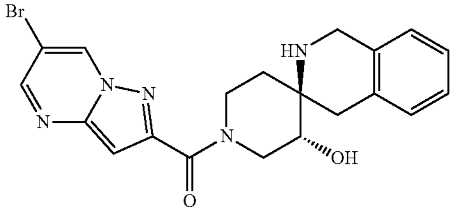
,
-continued
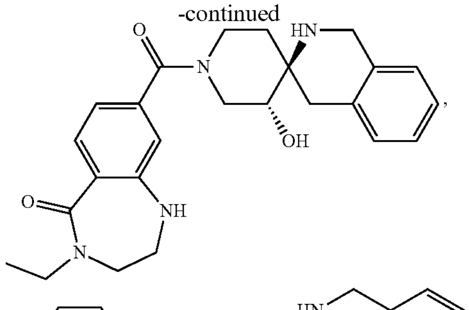
,
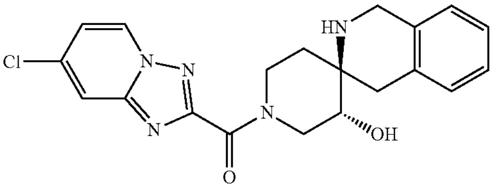
,
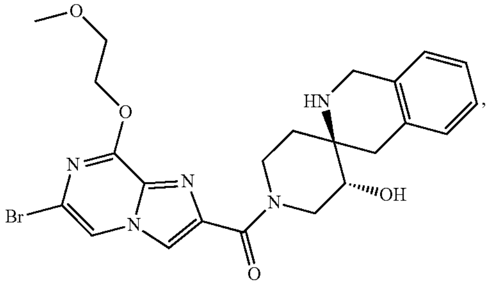
,
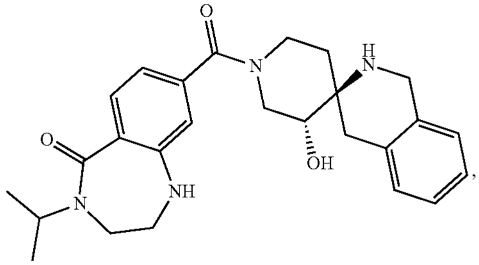
,
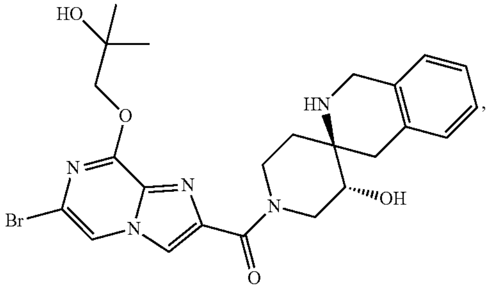
,
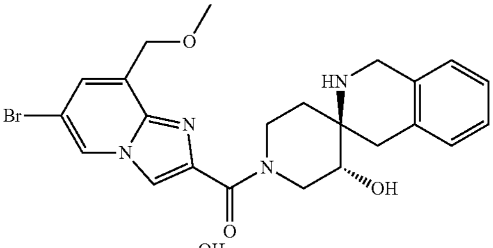
,
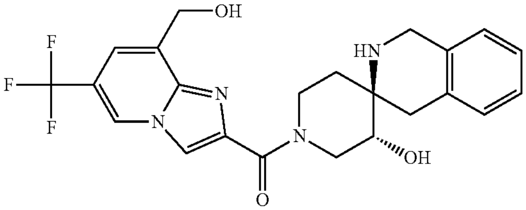
, -continued
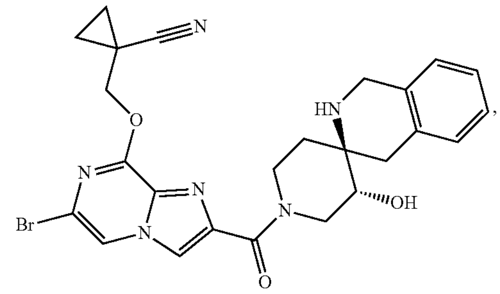
,
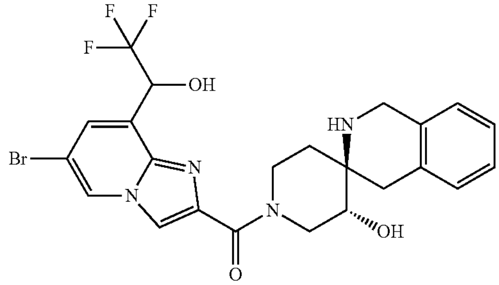
,
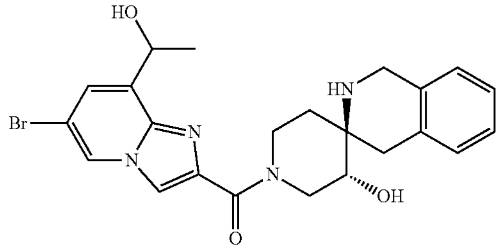
,
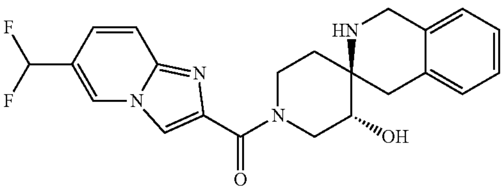
,
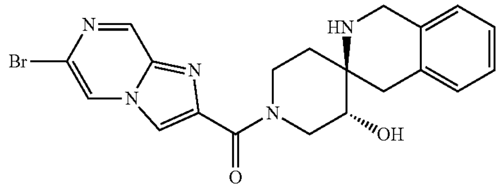
,
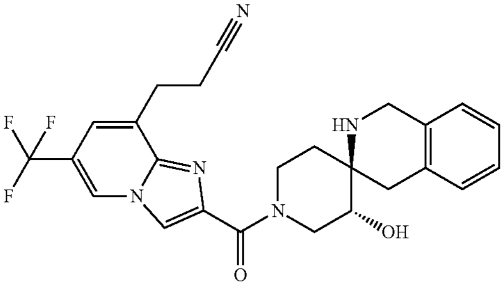
,
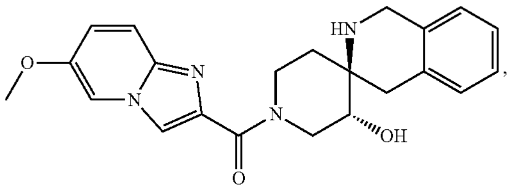
,
-continued
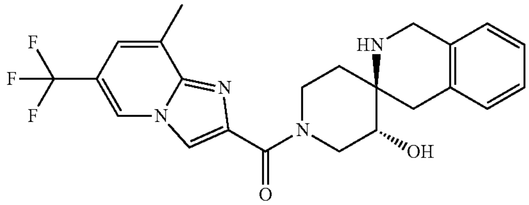
,
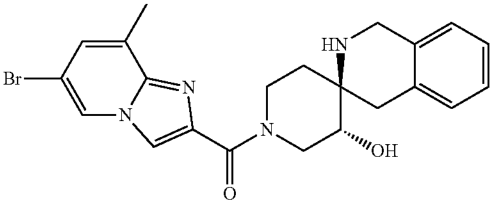
,
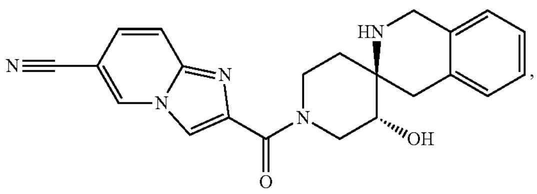
,
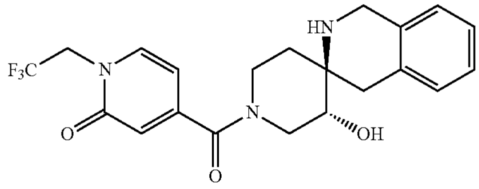
,
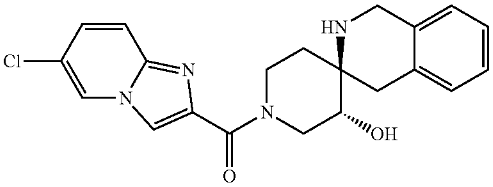
,
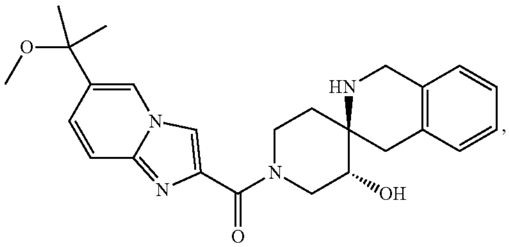
,
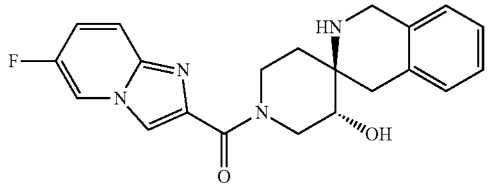
,
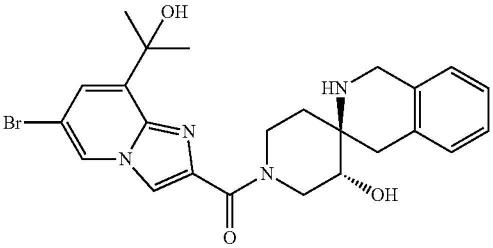
, -continued
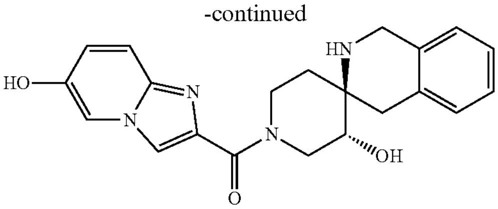,
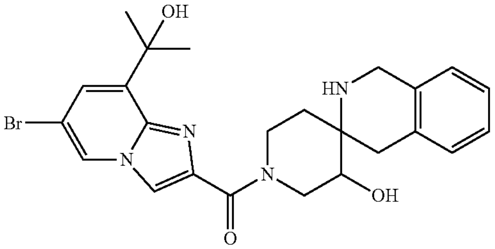,
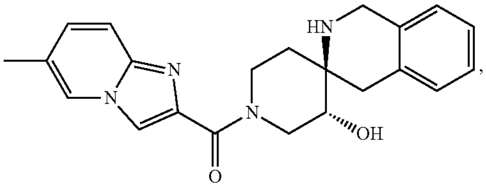,
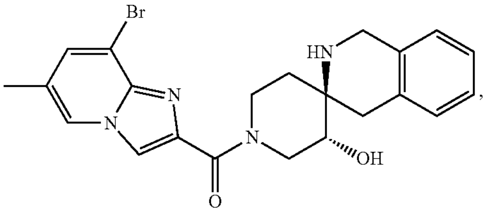,
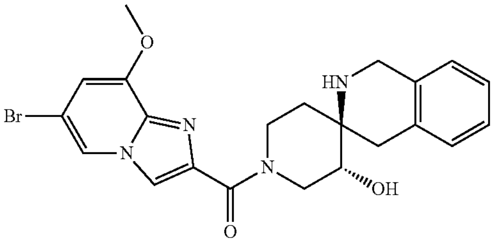,
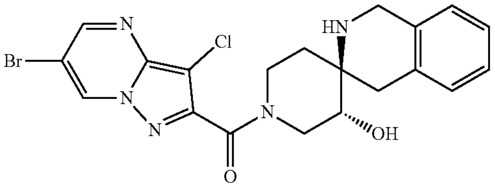,
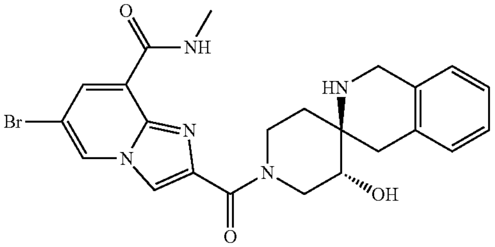,
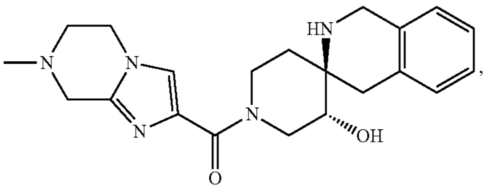,
-continued
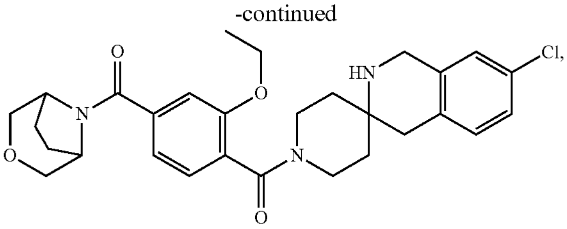,
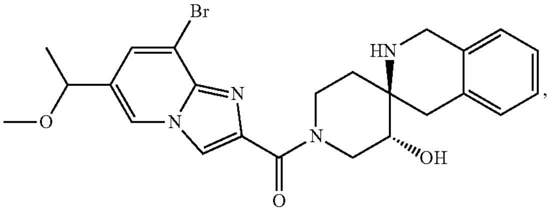,
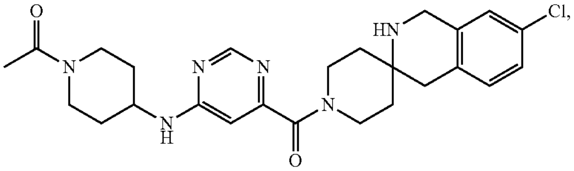,
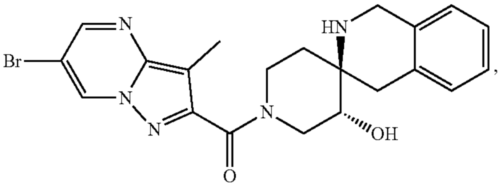,
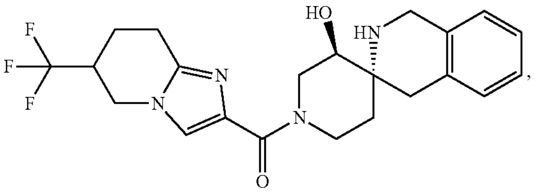,
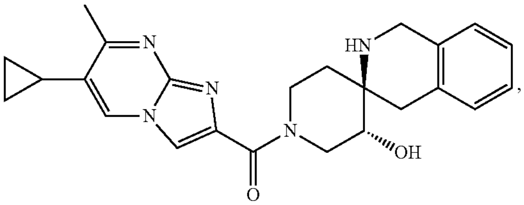,
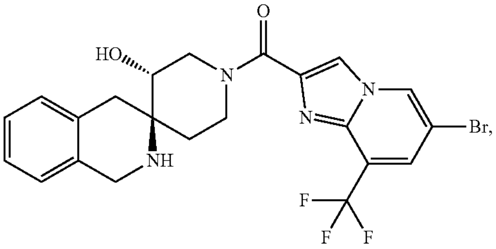,
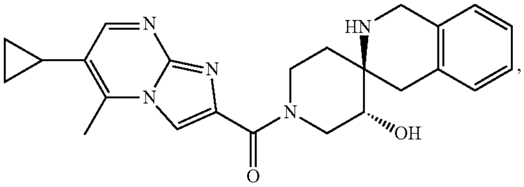, -continued
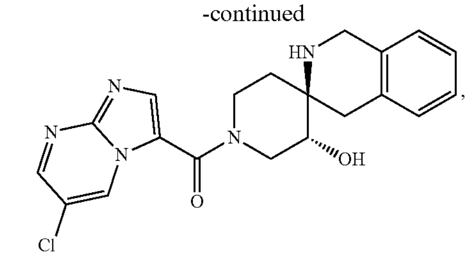
,
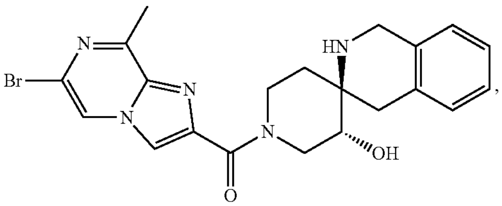
,
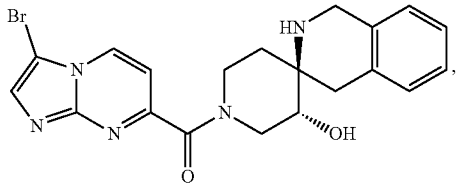
,
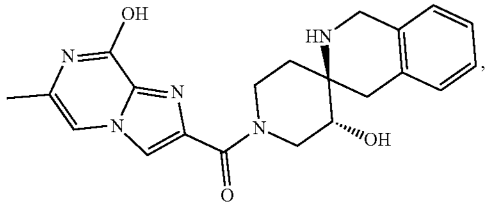
,
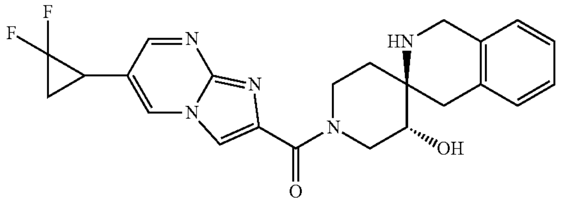
,
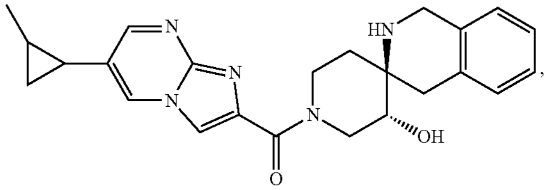
,
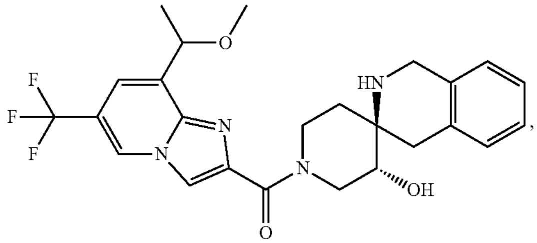
,
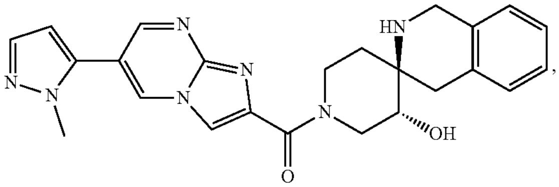
,
-continued
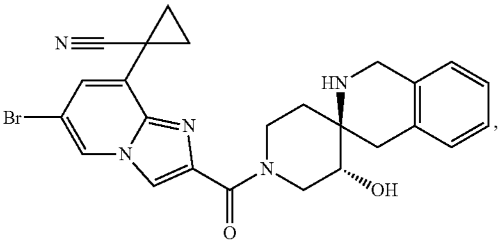
,
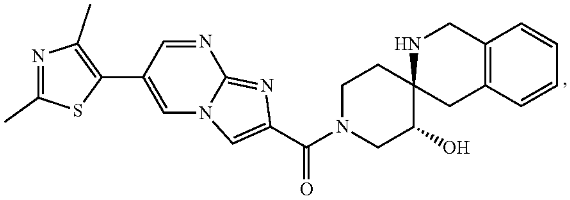
,
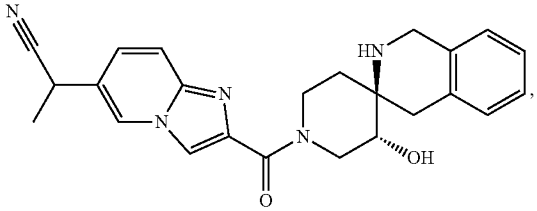
,
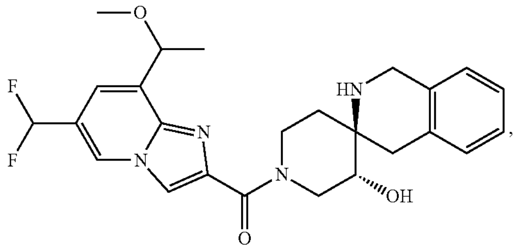
,
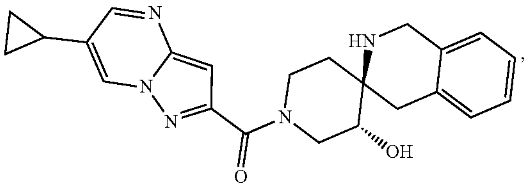
,
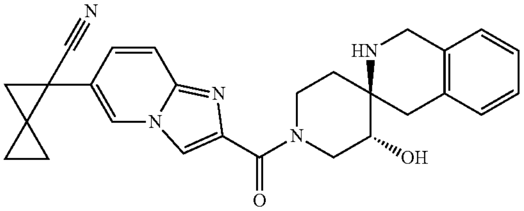
,
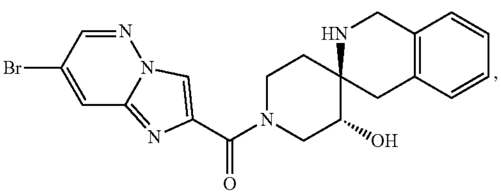
,
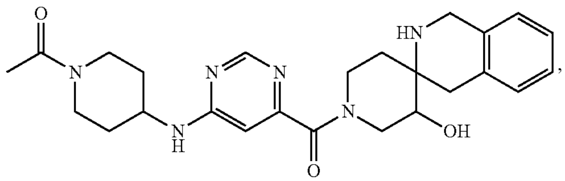
, -continued
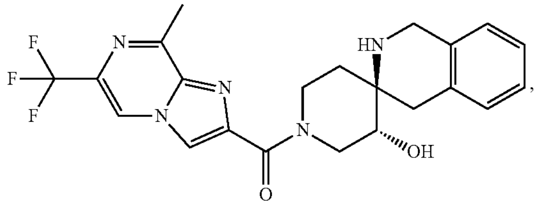,
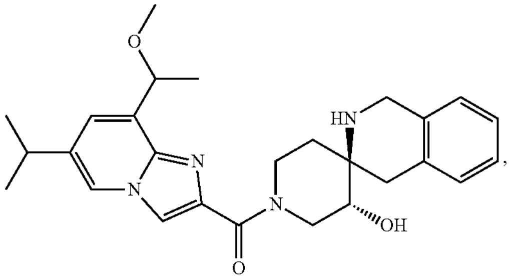,
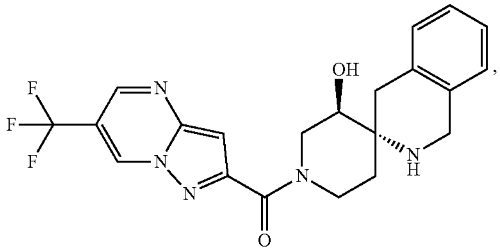,
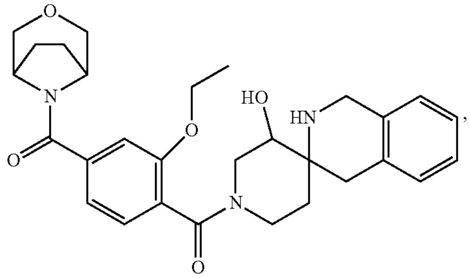,
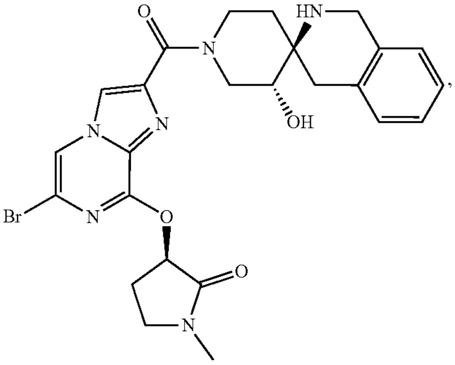,
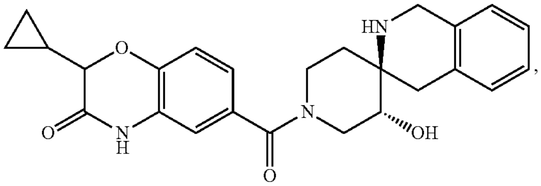,
-continued
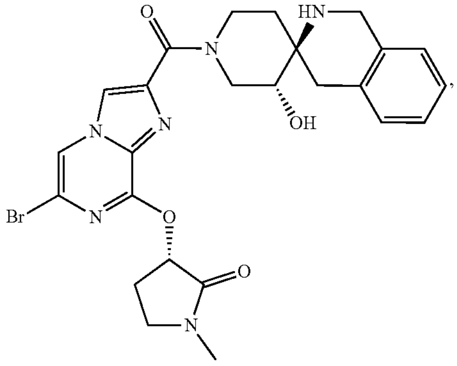,
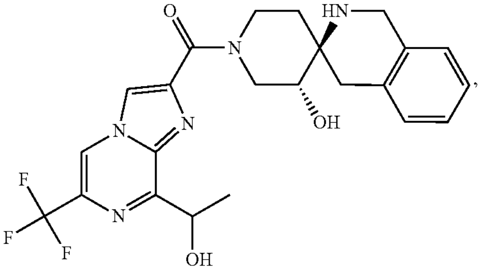,
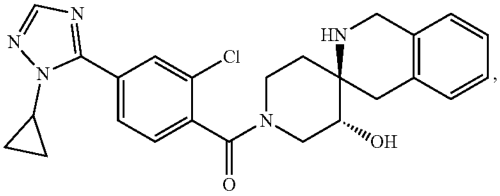,
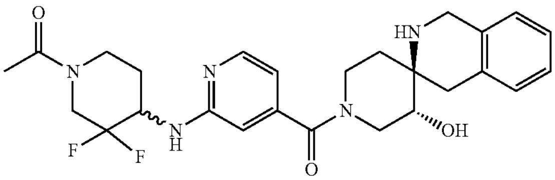,
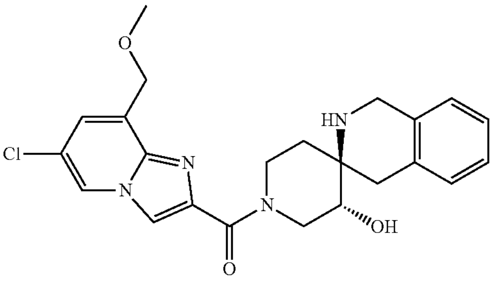,
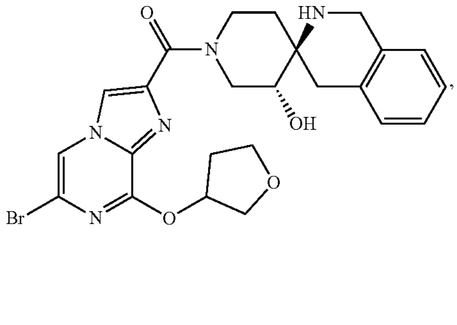, -continued
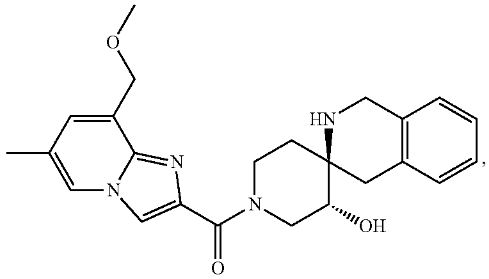
,
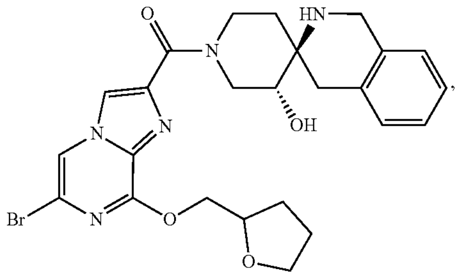
,
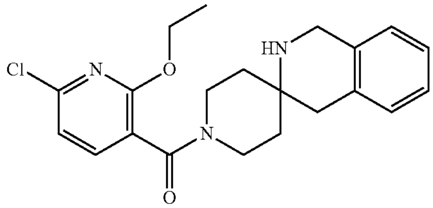
,
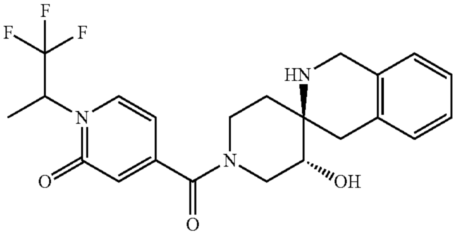
,
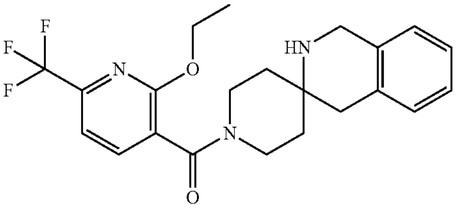
,
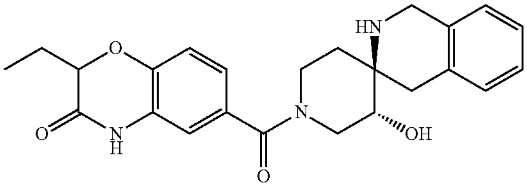
,
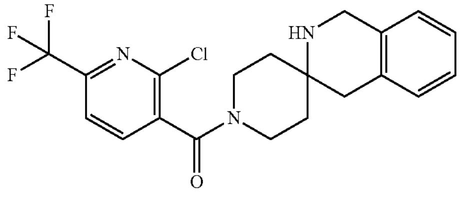
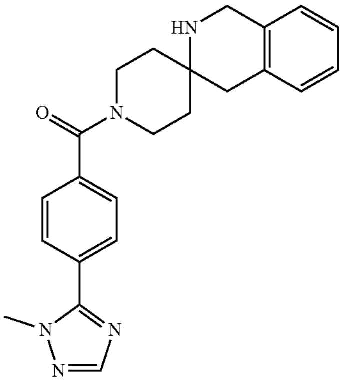
,
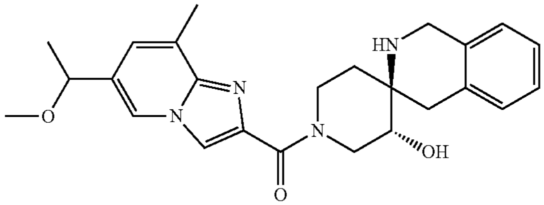
,
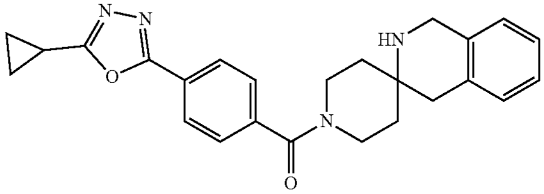
,
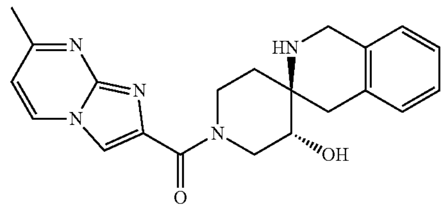
,
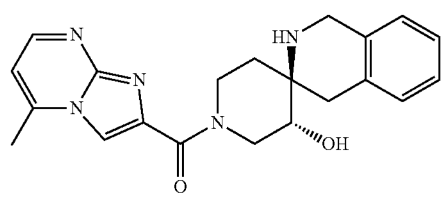
,
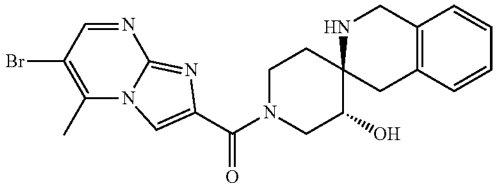
,
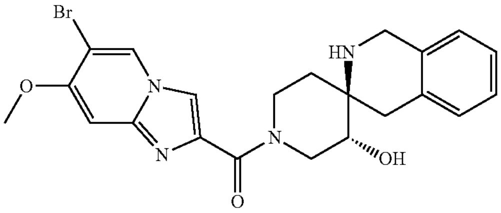
, -continued
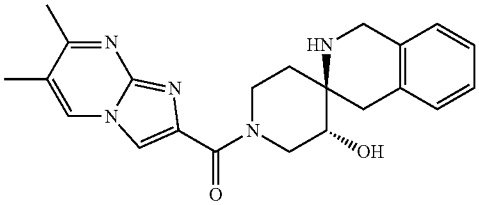
,
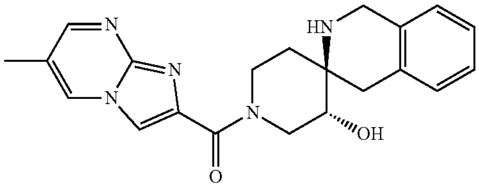
,
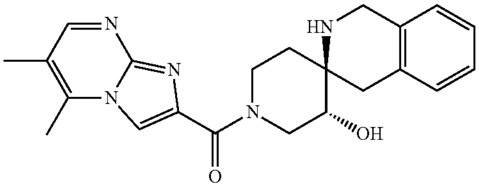
,
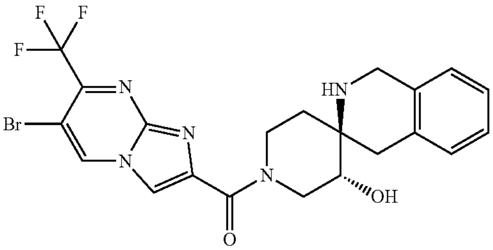
,
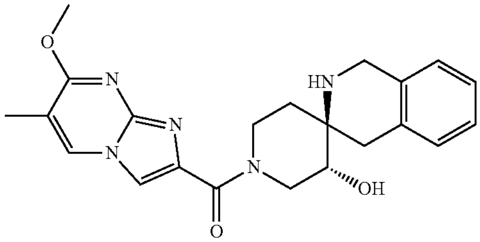
,
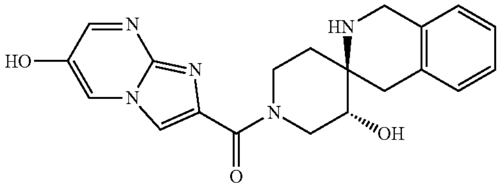
,
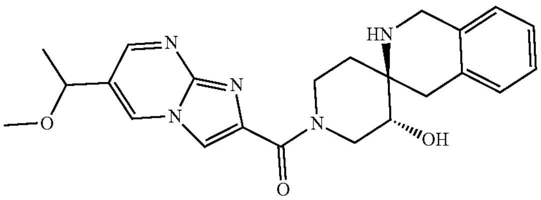
,
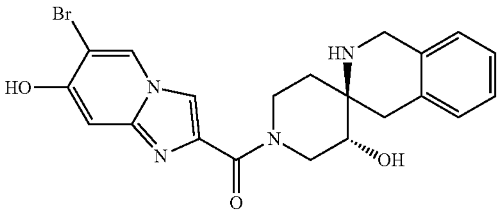
,
-continued
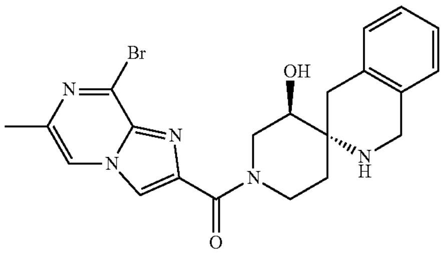
,
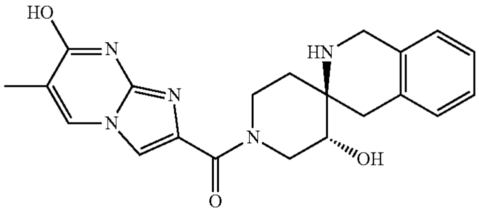
,
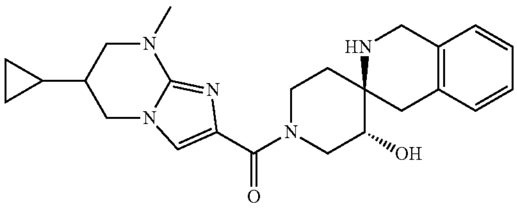
,
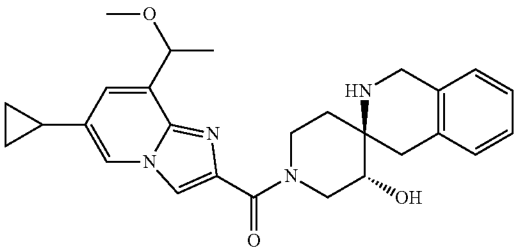
,
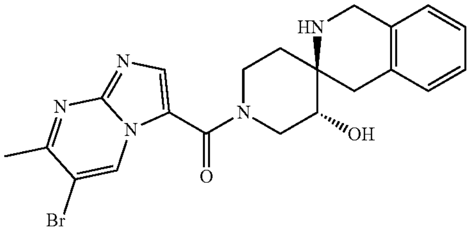
,
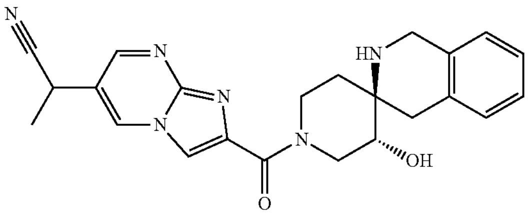
,
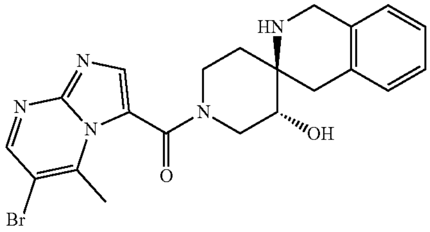
, -continued
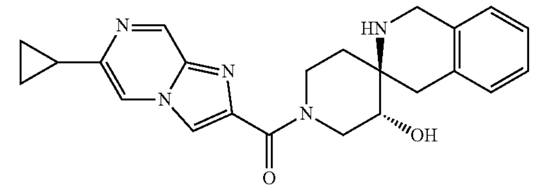
,
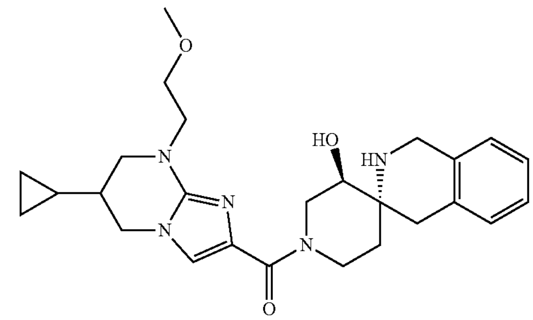
,
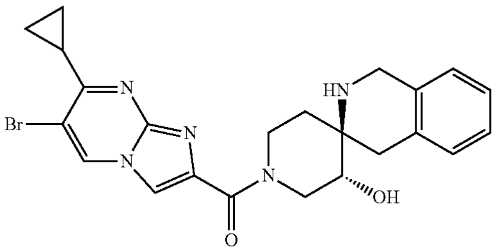
,
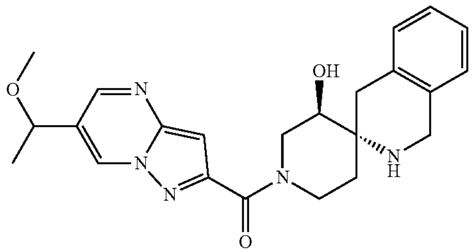
,
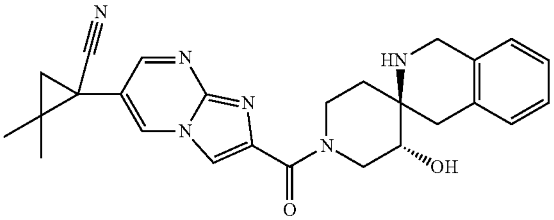
,
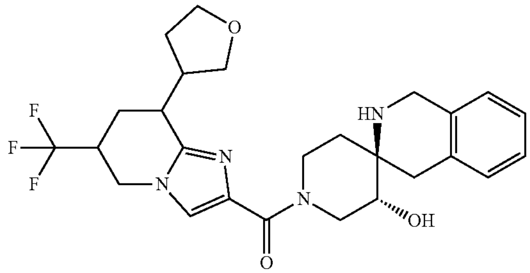
,
-continued
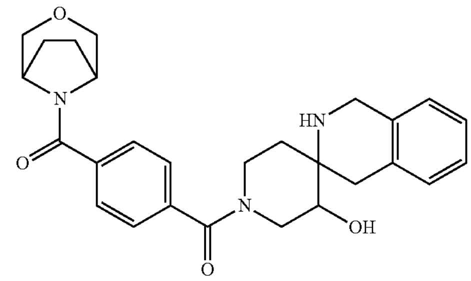
,
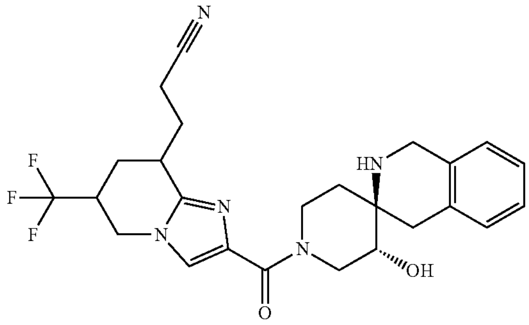
,
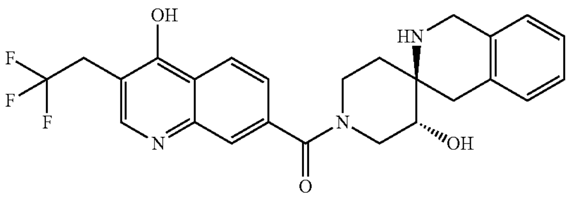
,
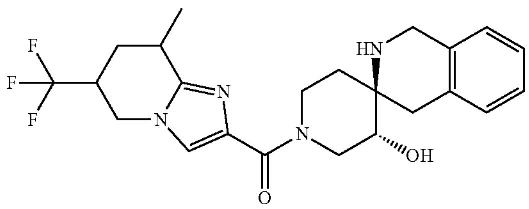
,
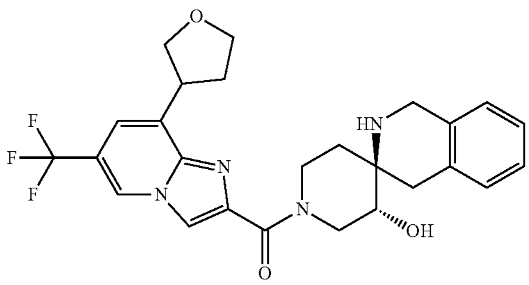
,
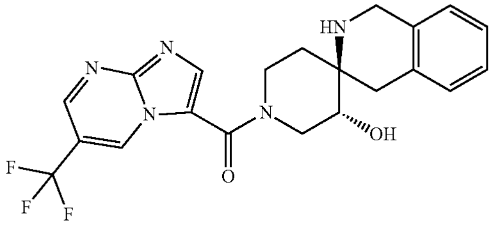
, -continued
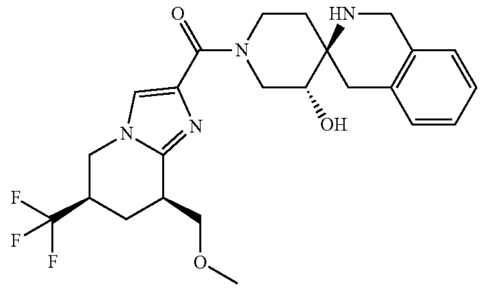
,
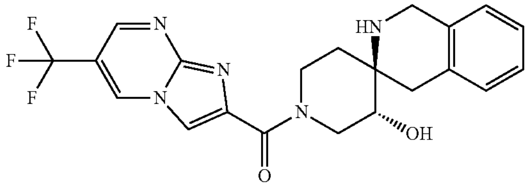
,
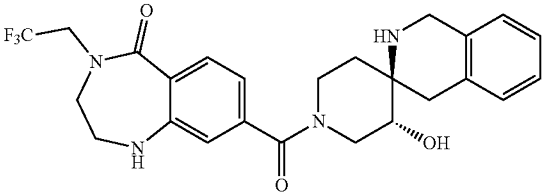
,
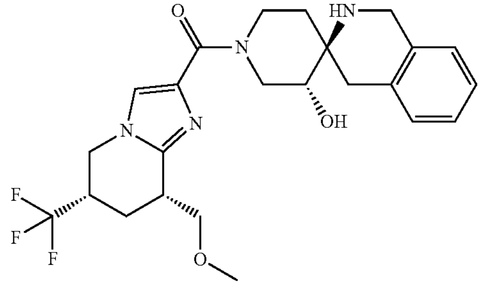
,
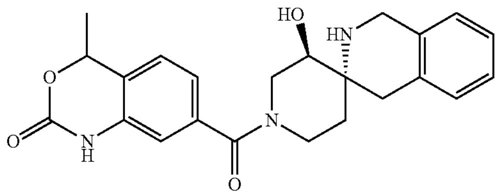
,
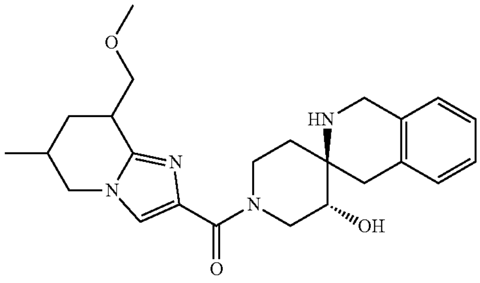
,
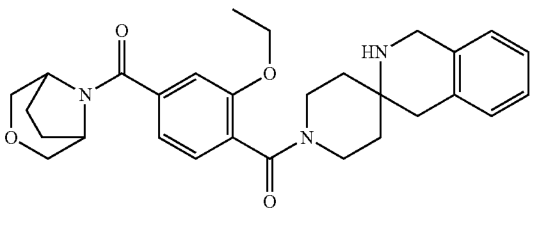
,
-continued
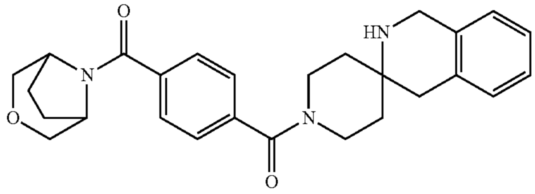
,
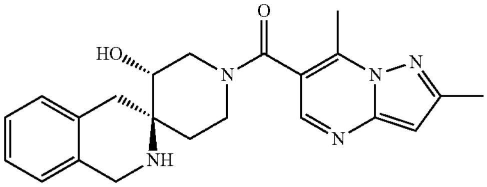
,
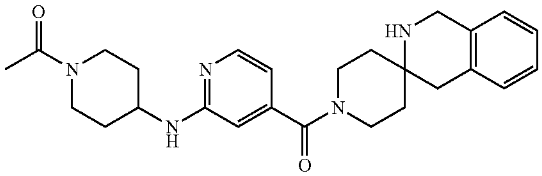
,
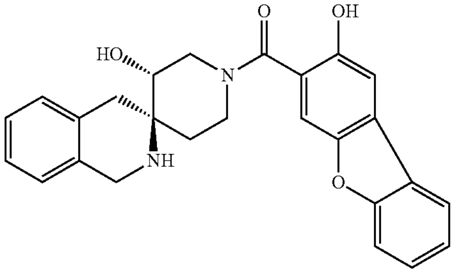
,
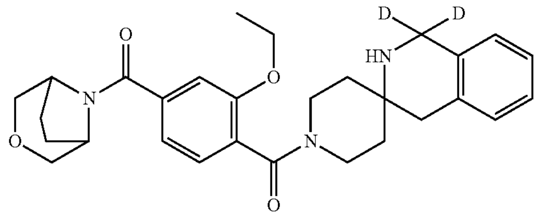
,
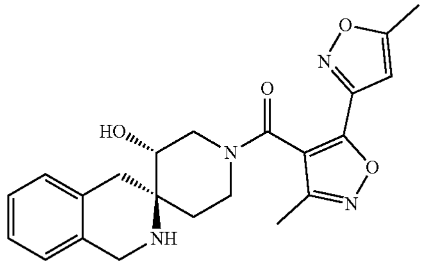
,
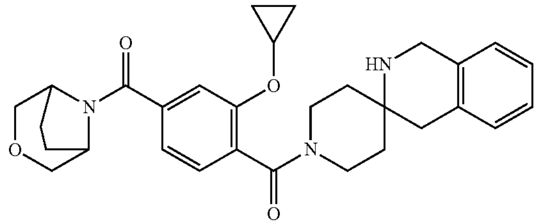
,
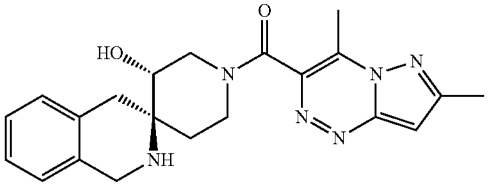
, -continued
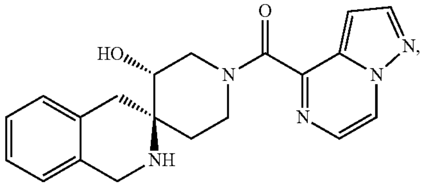
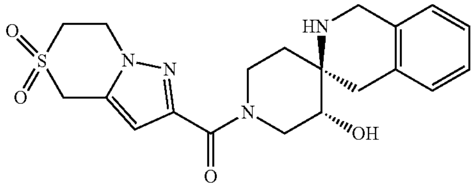
,
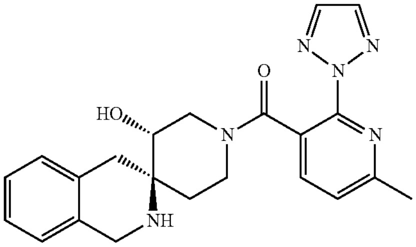
,
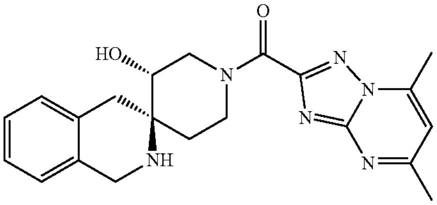
,
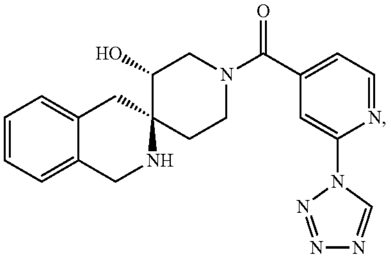
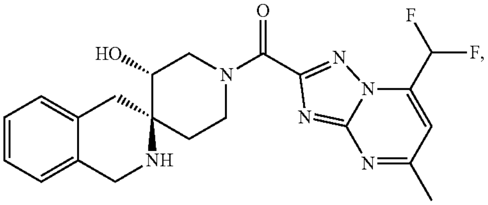
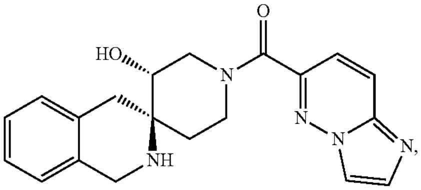
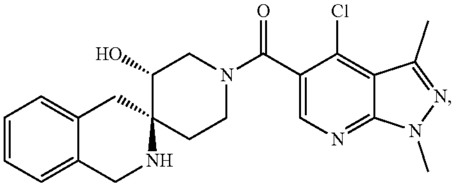
-continued
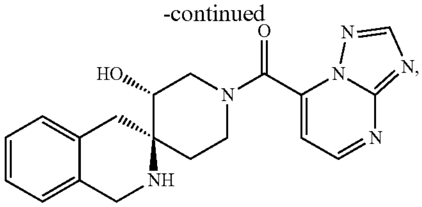
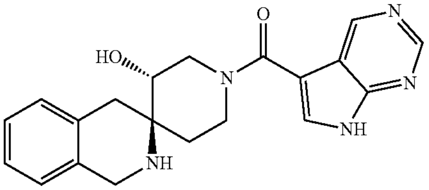
,
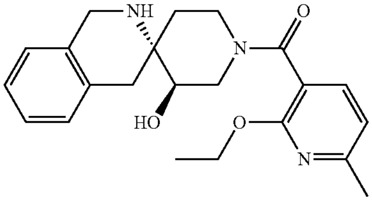
,
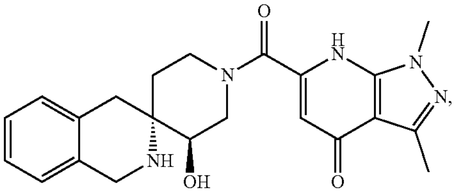
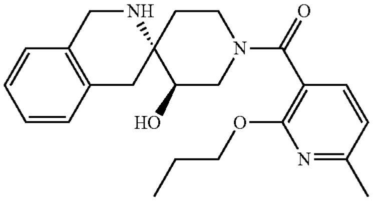
,
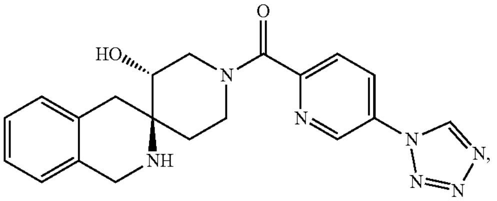
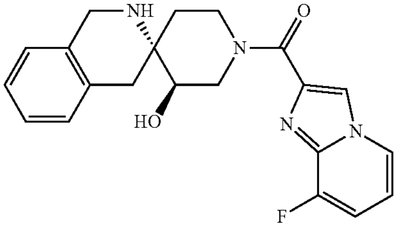
,
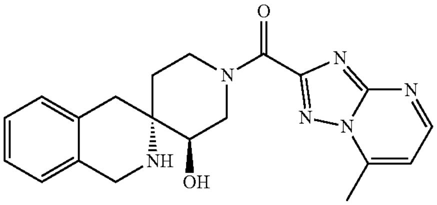
, -continued
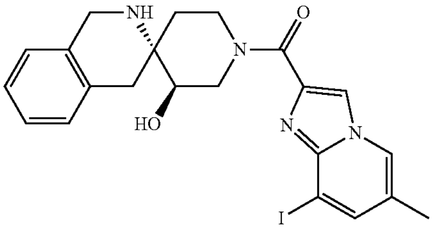
,
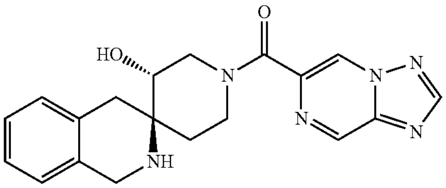
,
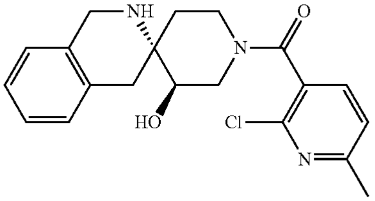
,
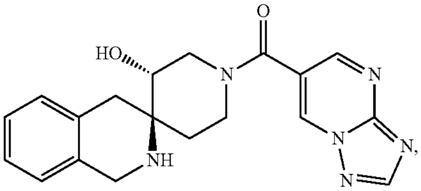
,
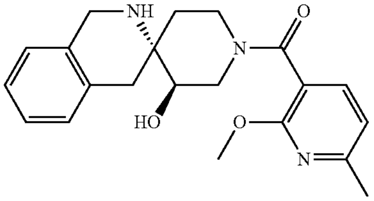
,
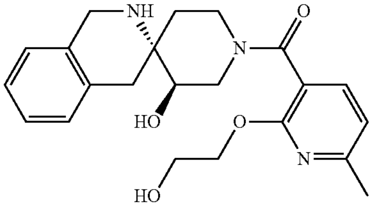
,
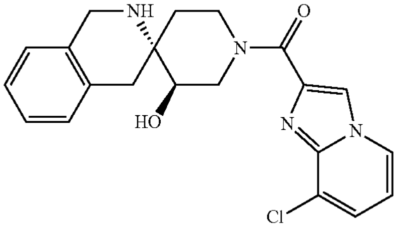
,
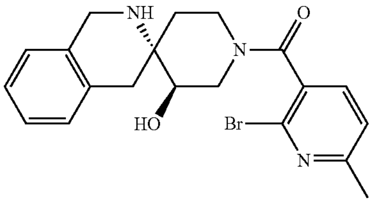
,
-continued
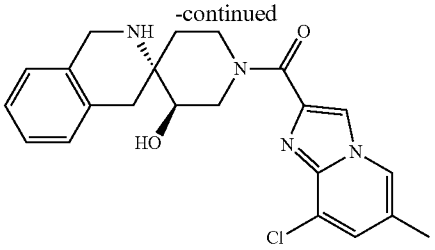
,
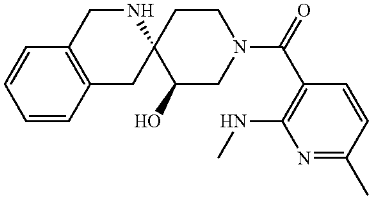
,
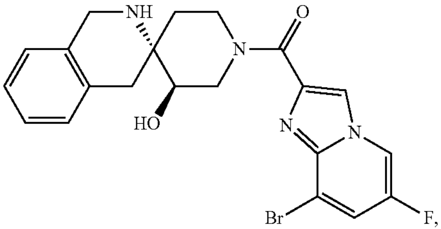
,
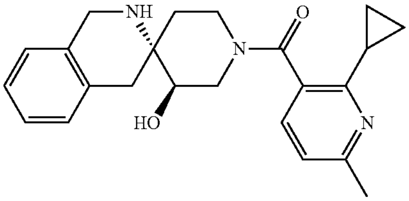
,
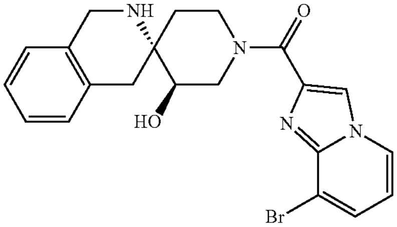
,
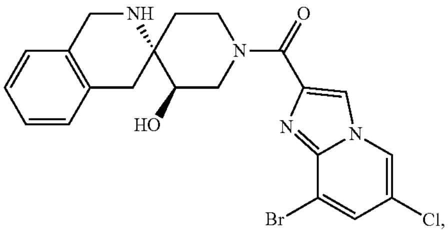
,
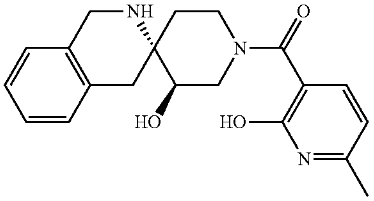
, -continued
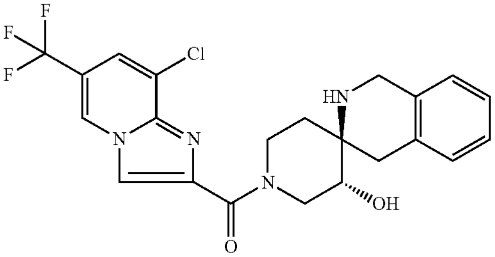
,
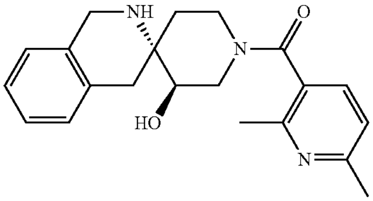
,
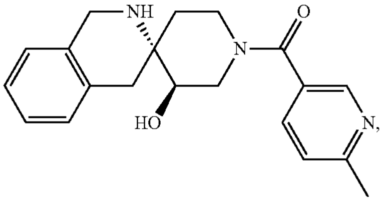
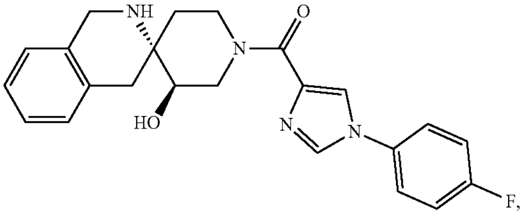
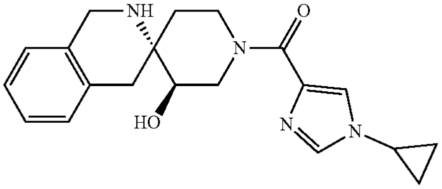
,
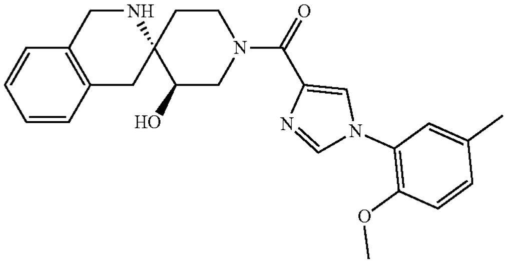
,
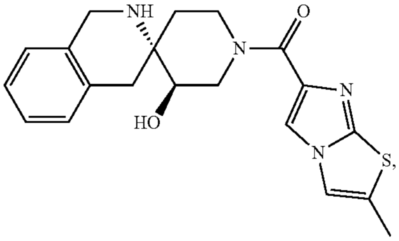
-continued
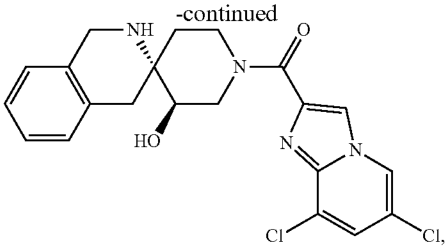
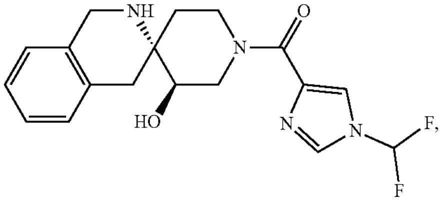
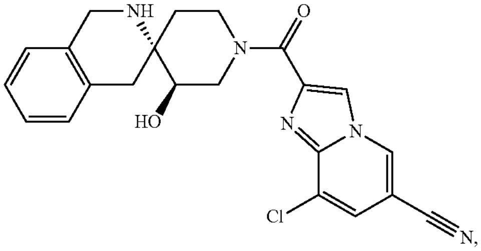
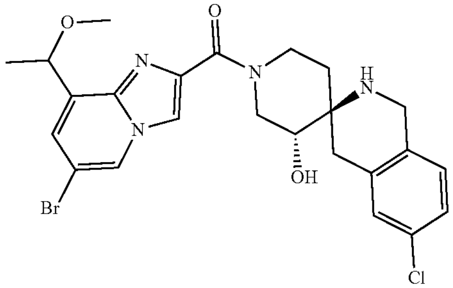
,
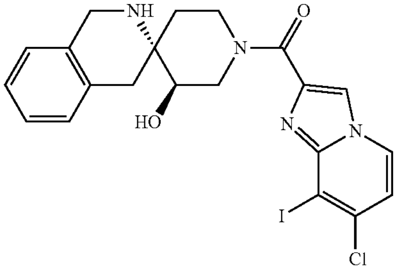
,
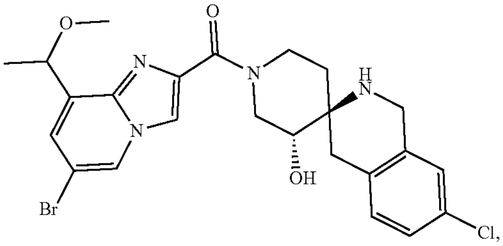
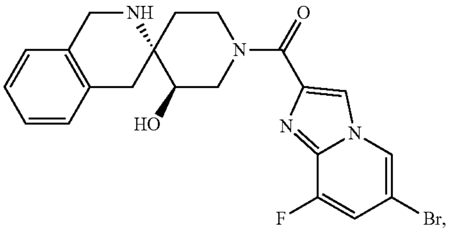

-continued
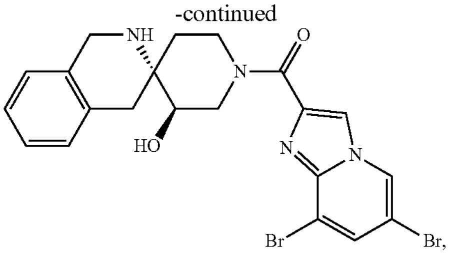
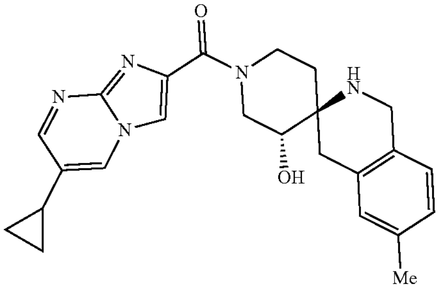
,
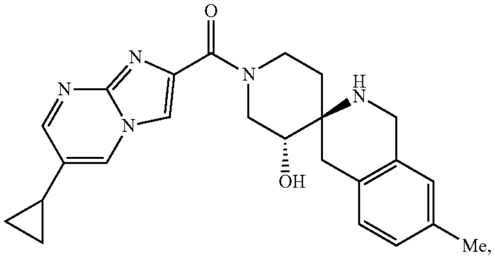
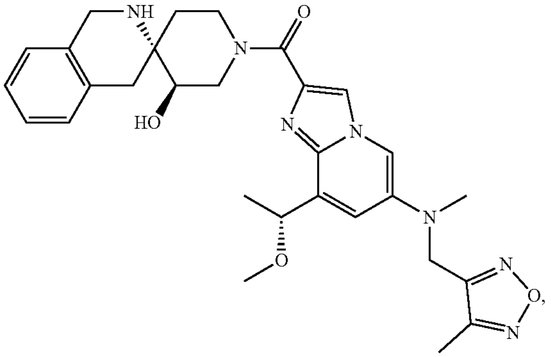
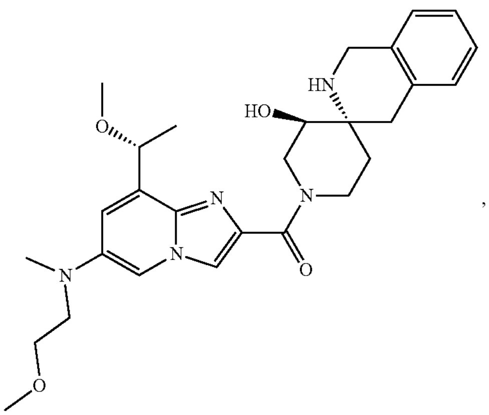
,
-continued
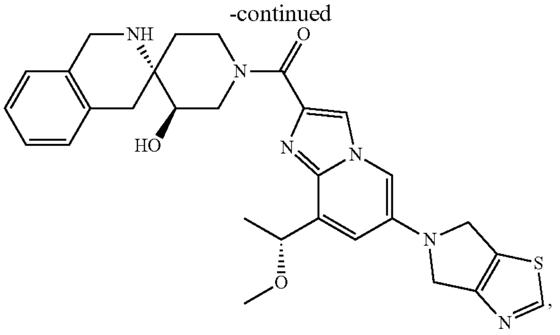
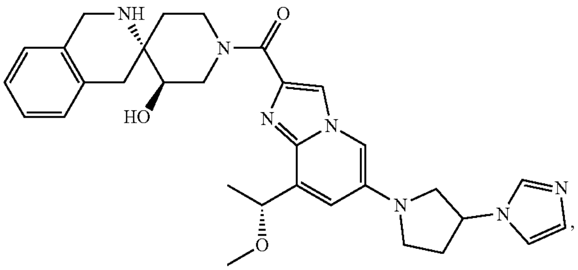
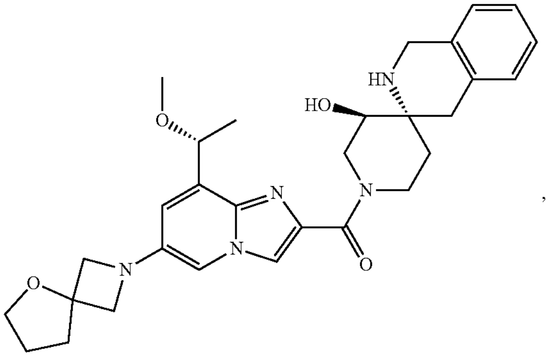
,
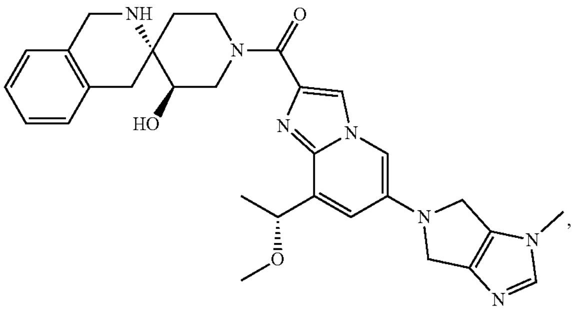
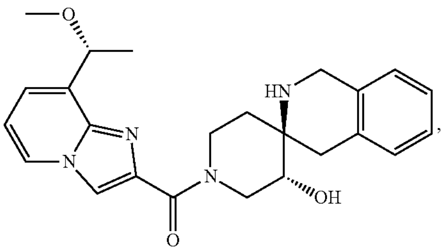

-continued
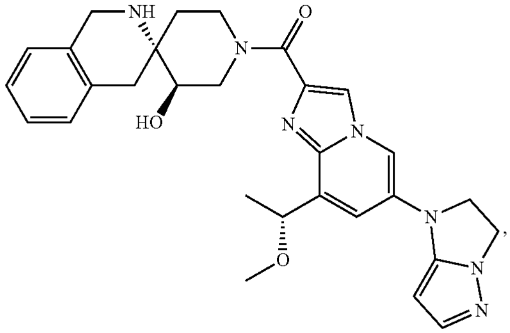
,
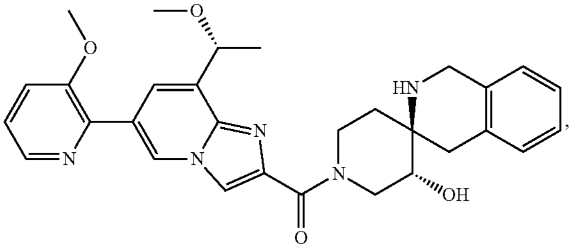
,
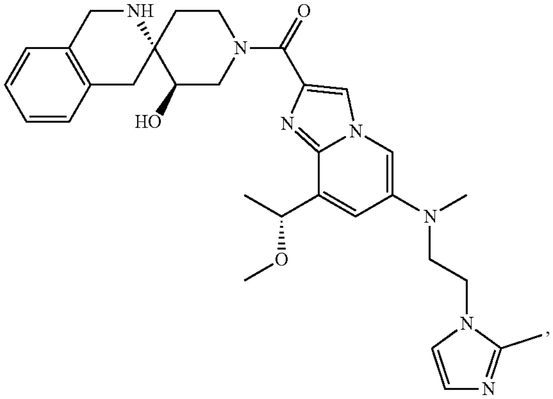
,
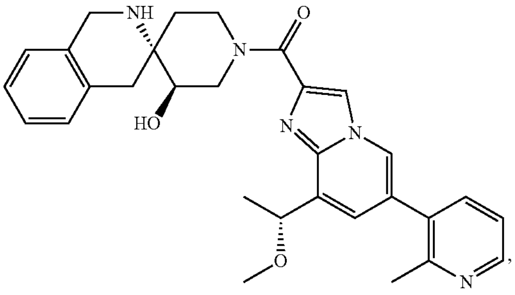
,
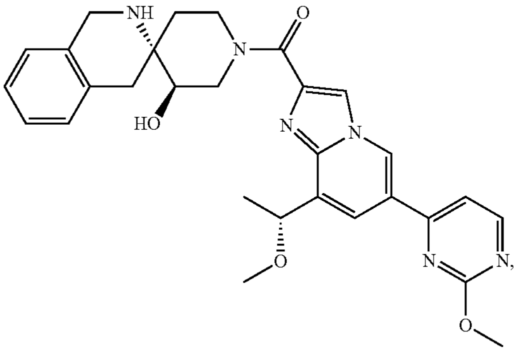
,
-continued
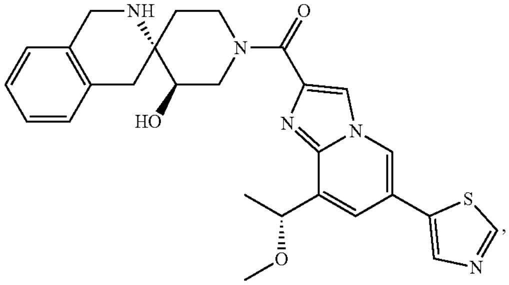
,
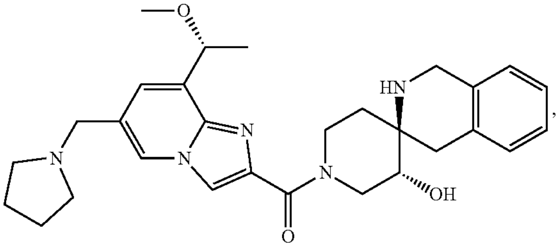
,
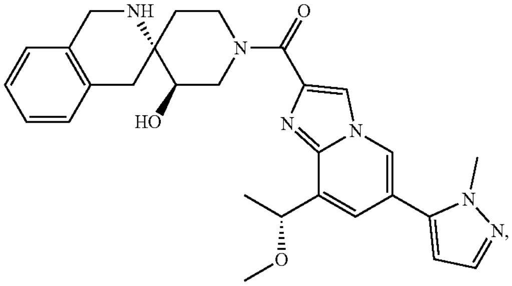
,
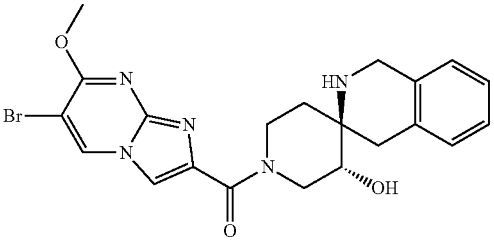
,
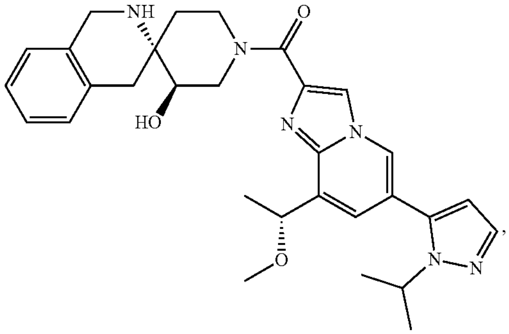
,
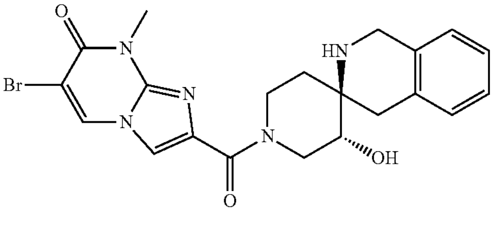
, -continued
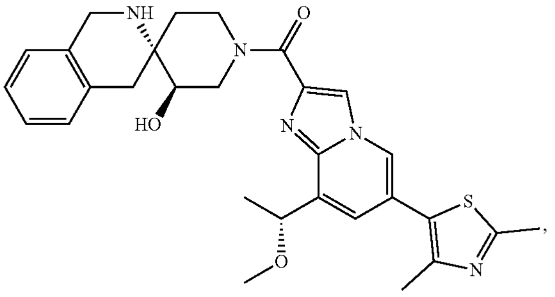
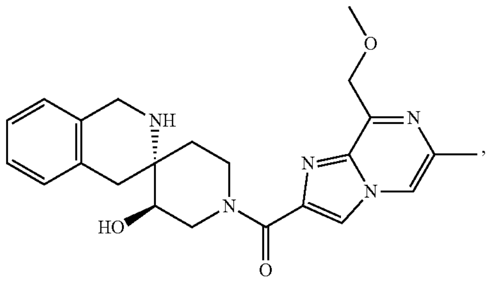
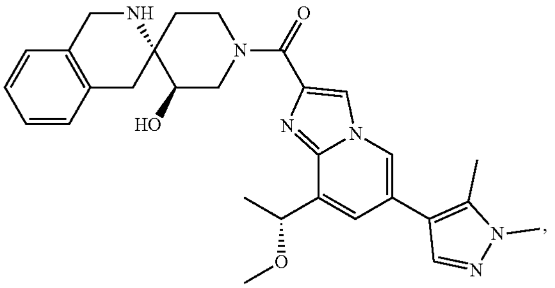
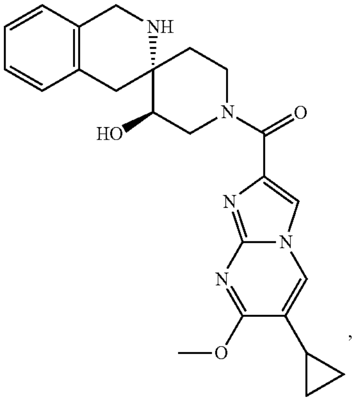
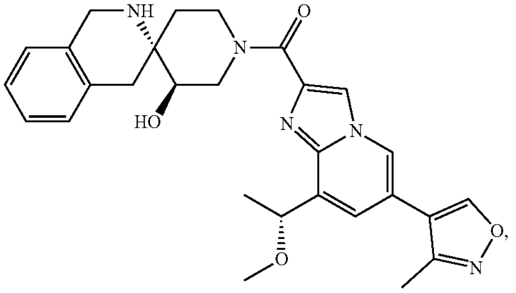
-continued
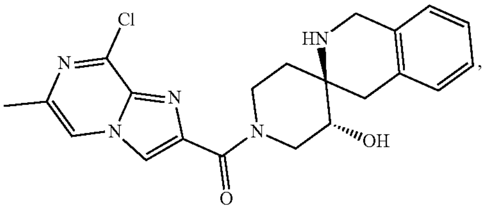
or a pharmaceutically acceptable salt thereof.
For the avoidance of any doubt, formula I, Ia, Ib, Ic, or Id, does not include:
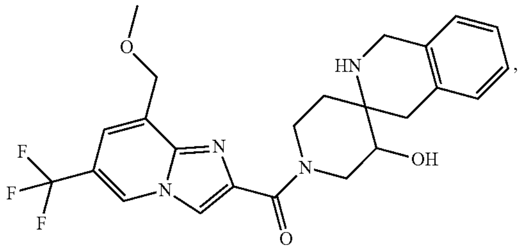
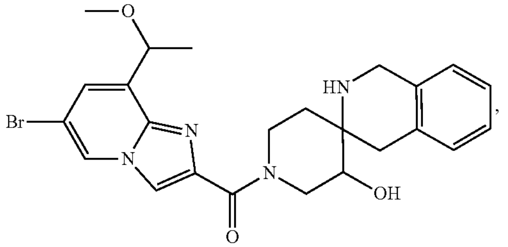
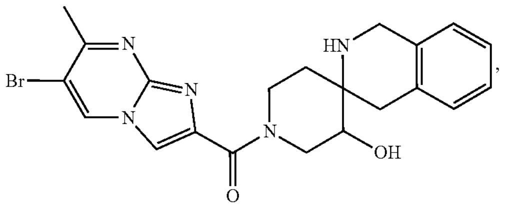
or
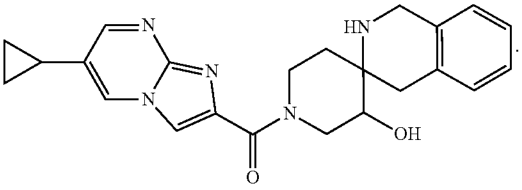
For the avoidance of any doubt, formula I, Ia, Ib, Ic, or Id, does not include:
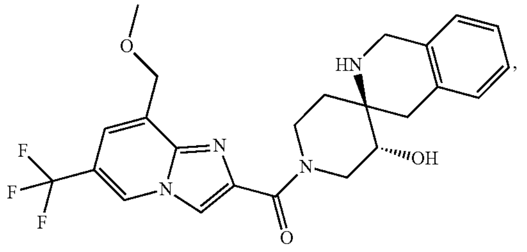

-continued

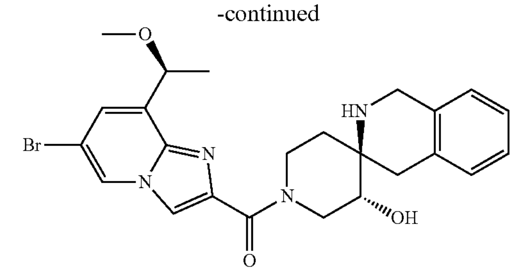

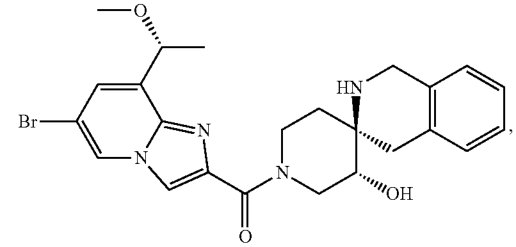

,

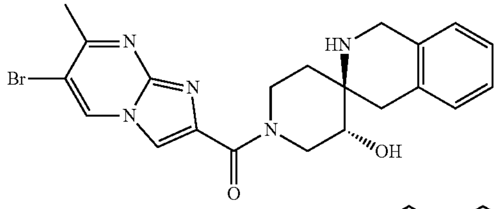

, or

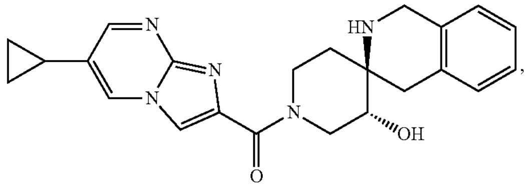

,

For the avoidance of any doubt, formula I, Ia, Ib, Ic, or Id, does not include: ((3R,3'R)-3'-hydroxy-1,4-dihydro-1'H,2H-spiro[isoquinoline-3,4'-piperidin]-1'-yl)[8-(methoxymethyl)-6-(trifluoromethyl)imidazo[1,2-a]pyridin-2-yl] methanone, (6-bromo-8-((S)-1-methoxyethyl)imidazo[1,2-a]pyridin-2-yl)((3R,3'R)-3'-hydroxy-1,4-dihydro-2H-spiro [isoquinoline-3,4'-piperidin]-1'-yl)methanone, (6-bromo-8-((R)-1-methoxyethyl)imidazo[1,2-a]pyridin-2-yl)((3R,3'R)-3'-hydroxy-1,4-dihydro-2H-spiro[isoquinoline-3,4'-piperidin]-1'-yl)methanone, (6-bromo-7-methylimidazo[1,2-a]pyrimidin-2-yl)[(3R,3'R)-3'-hydroxy-1,4-dihydro-1'H,2H-spiro[isoquinoline-3,4'-piperidin]-1'-yl]methanone, or (6-cyclopropylimidazo[1,2-a]pyrimidin-2-yl)[(3R,3'R)-3'-hydroxy-1,4-dihydro-1'H,2H-spiro[isoquinoline-3,4'-piperidin]-1'-yl]methanone.

Reference to compounds of formula I encompasses formula I, Ia, Ib, Ic, or Id, and all subembodiments thereof, in the following.

In one embodiment, the present invention is a composition for treating cancer comprising an effective amount of at least one compound of formula I, Ia, Ib, Ic, or Id, or a pharmaceutically acceptable salt thereof.

The invention also provides a pharmaceutical composition comprising an effective amount of at least one compound of Formula I, or a pharmaceutically acceptable salt thereof, and a pharmaceutically acceptable carrier.

In one embodiment, the present invention is a composition for treating cancer comprising an effective amount of at least one compound of formula I, Ia, Ib, Ic, or Id, or a pharmaceutically acceptable salt thereof, and a pharmaceutically acceptable carrier.

The invention also provides a pharmaceutical composition comprising an effective amount of at least one compound of formula I, Ia, Ib, Ic, or Id, or a pharmaceutically acceptable salt thereof, and an effective amount of at least one other pharmaceutically active ingredient (such as, for example, a chemotherapeutic agent or an anti-cancer agent), and a pharmaceutically acceptable carrier.

In one embodiment, the present invention is a composition for treating hemoglobinopathies such as ß-thalassemia or Sickle Cell Disease (SCD), comprising a compound of formula I, Ia, Ib, Ic, or Id, or a pharmaceutically acceptable salt thereof.

In one embodiment, the present invention is a composition for treating hemoglobinopathies such as ß-thalassemia or Sickle Cell Disease (SCD), comprising a compound of formula I, Ia, Ib, Ic, or Id, or a pharmaceutically acceptable salt thereof, and a pharmaceutically acceptable carrier.

In one embodiment, the present invention is a method of inhibiting PRMT5 in a patient in need thereof comprising administering to said patient an effective amount of at least one compound of formula I, Ia, Ib, Ic, or Id, or a pharmaceutically acceptable salt thereof.

In another embodiment, the present invention is a method of treating cancer comprising administering to a patient in need thereof a an effective amount of at least one compound of formula I, Ia, Ib, Ic, or Id, or a pharmaceutically acceptable salt thereof.

In another embodiment, the present invention is a method of treating cancer comprising administering to a patient in need thereof a an effective amount of at least one compound of formula I, Ia, Ib, Ic, or Id, or a pharmaceutically acceptable salt thereof, and a pharmaceutically acceptable carrier.

In another embodiment, the present invention provides a method for treating cancer in a patient in need thereof comprising administering to said patient an effective amount of at least one compound of formula I, Ia, Ib, Ic, or Id, or a pharmaceutically acceptable salt thereof, in combination with an effective amount of at least one chemotherapeutic agent.

In another embodiment, the present invention provides a method for treating cancer in a patient in need thereof comprising administering to said patient an effective amount of at least one compound of formula I, Ia, Ib, Ic, or Id, or a pharmaceutically acceptable salt thereof, in combination with an effective amount of at least one anti-cancer agent.

The methods of the invention include the administration of a pharmaceutical composition comprising at least one compound of the invention and a pharmaceutically acceptable carrier.

In another embodiment, the present invention includes a method of treating hemoglobinopathies such as ß-thalassemia or Sickle Cell Disease (SCD), comprising administering to a patient in need thereof a compound of formula I, Ia, Ib, Ic, or Id, or a pharmaceutically acceptable salt thereof.

In another embodiment, the present invention is a method of treating cancer comprising administering to a patient in need thereof a compound of formula I, Ia, Ib, Ic, or Id, or a pharmaceutically acceptable salt thereof.

In another embodiment, the present invention is a method of treating cancer comprising administering to a patient in need thereof a compound of formula I, Ia, Ib, Ic, or Id, or a pharmaceutically acceptable salt thereof, and a pharmaceutically acceptable carrier.

In another embodiment, the present invention is a method of treating hemoglobinopathies such as ß-thalassemia or Sickle Cell Disease (SCD), comprising administering to a patient in need thereof a compound of formula I, Ia, Ib, Ic, or Id, or a pharmaceutically acceptable salt thereof.

In another embodiment, the present invention is a method of treating hemoglobinopathies such as ß-thalassemia or Sickle Cell Disease (SCD), comprising administering to a patient in need thereof a compound of formula I, Ia, Ib, Ic, or Id, or a pharmaceutically acceptable salt thereof, and a pharmaceutically acceptable carrier.

In another embodiment, the present invention is a method of treating cancer comprising administering to a patient in need thereof, a composition comprising a compound of formula I, Ia, Ib, Ic, or Id, or a pharmaceutically acceptable salt thereof, and a pharmaceutically acceptable carrier.

In another embodiment, the present invention includes a method of treating hemoglobinopathies such as ß-thalassemia or Sickle Cell Disease (SCD), comprising administering to a patient in need thereof a compound of formula I, Ia, Ib, Ic, or Id, or a pharmaceutically acceptable salt thereof.

In another embodiment, the present invention includes a method of treating hemoglobinopathies such as ß-thalassemia or Sickle Cell Disease (SCD), comprising administering to a patient in need thereof a compound of formula I, Ia, Ib, Ic, or Id, or a pharmaceutically acceptable salt thereof, and a pharmaceutically acceptable carrier.

In another embodiment, the present invention is a method of treating hemoglobinopathies such as ß-thalassemia or Sickle Cell Disease (SCD), comprising administering to a patient in need thereof, a composition comprising a compound of formula I, Ia, Ib, Ic, or Id, or a pharmaceutically acceptable salt thereof, and a pharmaceutically acceptable carrier.

In another embodiment, the present invention is the use of a compound of formula I, Ia, Ib, Ic, or Id, or a pharmaceutically acceptable salt thereof, in the manufacture of a medicament for treating cancer.

In another embodiment of the present invention is the use of a compound of formula I, Ia, Ib, Ic, or Id, or a pharmaceutically acceptable salt thereof, in the manufacture of a medicament for treating hemoglobinopathies such as ß-thalassemia or Sickle Cell Disease (SCD).

In another embodiment, the present invention includes the use of compounds of formula I, Ia, Ib, Ic, or Id, or a pharmaceutically acceptable salt thereof, for the preparation of a medicament for the treatment of cancer, or hemoglobinopathies such as ß-thalassemia or Sickle Cell Disease (SCD).

Another embodiment is the use of compounds of formula I, Ia, Ib, Ic, or Id, or a pharmaceutically acceptable salt thereof, for the preparation of a medicament for the treatment of cancer. In a subembodiment, the cancer is i) cardiac cancer, ii) lung cancer, iii) gastrointestinal cancer, iv) genitourinary tract cancer, v) liver cancer, vi) bone cancer, vii) nervous system cancer, viii) gynecological cancer, ix) hematological cancer, x) skin cancer, or xi) adrenal cancer.

Another embodiment is the use of compounds of formula I, Ia, Ib, Ic, or Id, or a pharmaceutically acceptable salt thereof, for the preparation of a medicament for the treatment of hemoglobinopathies such as ß-thalassemia or Sickle Cell Disease (SCD).

In another embodiment, the present invention includes compounds of formula I, Ia, Ib, Ic, or Id, for use in the treatment of cancer or hemoglobinopathies such as ß-thalassemia or Sickle Cell Disease (SCD). In another embodiment, the present invention includes compounds of formula I, Ia, Ib, Ic, or Id, or a pharmaceutically acceptable salt thereof, for use in the treatment of cardiac cancer, lung cancer, gastrointestinal cancer, genitourinary tract cancer, liver cancer, bone cancer, nervous system cancer, gynecological cancer, hematological cancer, skin cancer, or adrenal cancer.

In one example of the invention the cancer treated is colo-rectal cancer (such as, for example, colon adenocarcinoma and colon adenoma). Thus, another example of the invention is directed to a method of treating colo-rectal cancer in a patient in need of such treatment, said method comprising administering an effective of a compound of formula I, Ia, Ib, Ic, or Id, or a pharmaceutically acceptable salt thereof, to said patient. Another example of the invention is directed to a method of treating colo-rectal cancer in a patient in need of such treatment, said method comprising administering to said patient an effective amount of a compound of formula I, Ia, Ib, Ic, or Id, or a pharmaceutically acceptable salt thereof, and an effective amount of at least one chemotherapeutic agent. Another example of the invention is directed to a method of treating colo-rectal cancer in a patient in need of such treatment, said method comprising administering to said patient an effective amount of a compound of formula I, Ia, Ib, Ic, or Id, or a pharmaceutically acceptable salt thereof, and an effective amount of at least one anti-cancer agent.

The invention also provides any of the above methods of treating cancer wherein the cancer is melanoma. Thus, another example of the invention is directed to a method of treating melanoma in a patient in need of such treatment, said method comprising administering an effective amount of a compound of formula I, Ia, Ib, Ic, or Id, or a pharmaceutically acceptable salt thereof, to said patient. Another example of the invention is directed to a method of treating melanoma in a patient in need of such treatment, said method comprising administering to said patient an effective amount of a compound of formula I, Ta, Tb, Ic, or Id, or a pharmaceutically acceptable salt thereof, and an effective amount of at least one chemotherapeutic agent. Another example of the invention is directed to a method of treating melanoma in a patient in need of such treatment, said method comprising administering to said patient an effective amount of a compound of formula I, Ia, Tb, Ic, or Id, or a pharmaceutically acceptable salt thereof, and an effective amount of at least one anti-cancer agent.

The methods of treating cancers described herein can optionally include the administration of an effective amount of radiation (i.e., the methods of treating cancers described herein optionally include the administration of radiation therapy).

The methods of treating cancer described herein include methods of treating cancer that comprise administering a therapeutically effective amount of a compound of the instant invention, or a pharmaceutically acceptable salt thereof, in combination with radiation therapy and/or in combination with a second compound selected from: an estrogen receptor modulator, an androgen receptor modulator, a retinoid receptor modulator, a cytotoxicytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein, or a pharmaceutically acceptable salt thereof.

In any of the methods of treating cancer described herein, unless stated otherwise, the methods can optionally include the administration of an effective amount of radiation therapy. For radiation therapy, γ-radiation is preferred.

In one embodiment, the compound disclosed herein is selected from the group consisting of the compounds exemplified herein, for example, in Examples 1-14, 16-252, or a pharmaceutically acceptable salt thereof.

The term "composition" is intended to encompass a product comprising the specified ingredients in the specified amounts, as well as any product which results, directly or indirectly, from combination of the specified ingredients in the specified amounts. The term "anti-cancer agent" means a drug (medicament or pharmaceutically active ingredient), or antibody for treating cancer. The term "compound" with reference to the antineoplastic agents, includes the agents that are antibodies The term "at least one" means one or more than one. The meaning of "at least one" with reference to the number of compounds of the invention is independent of the meaning with reference to the number of chemotherapeutic agents. The term "chemotherapeutic agent" means a drug (medicament or pharmaceutically active ingredient) for treating cancer (i.e., an antineoplastic agent). The term "compound" with reference to the antineoplastic agents, includes the agents that are antibodies. The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician. Thus, for example, in the methods of treating cancer described herein "effective amount" (or "therapeutically effective amount") means, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, or a therapeutically effective amount of the PRMT5 inhibitor (i.e., a compound of the invention) is that amount which results in the reduction in PRMT5 activity. The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., the Physicians' Desk Reference, $64^{th}$ Edition, 2010 (published by PDR Network, LLC at Montvale, NJ 07645-1725), presently accessible through www.pdr.net; the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula (1) and the chemotherapeutic agents will be regulated according to the judgment of the attending clinician (physician) considering such factors as age, condition and size of the patient as well as severity of the cancer being treated.

The compounds of the invention are also useful in preparing a medicament that is useful in treating cancer.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), $9^{th}$ edition (May 16, 2011), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, programmed cell death protein 1 (PD-1) inhibitors, programmed death-ligand 1 (PD-L1) inhibitors, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgment of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The anti-cancer agent can be administered according to therapeutic protocols well known in the art. It will be apparent to those skilled in the art that the administration of the anti-cancer agent can be varied depending on the cancer being treated and the known effects of the anti-cancer agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of anti-cancer agent will depend upon the diagnosis of the attending physicians and their judgment of the condition of the patient and the appropriate treatment protocol.

The determination of the order of administration, and the number of repetitions of administration of the anti-cancer agent during a treatment protocol, is well within the knowledge of the skilled physician after evaluation of the cancer being treated and the condition of the patient.

Thus, in accordance with experience and knowledge, the practicing physician can modify each protocol for the administration of an anti-cancer agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds, compositions and methods provided herein are useful for the treatment of cancer. Cancers that may be treated by the compounds, compositions and methods disclosed herein include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compound of formula (1) may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

PD-1 inhibitors include pembrolizumab (lambrolizumab), nivolumab and MPDL3280A. PDL-inhibitors include atezolizumab, avelumab, and durvalumab.

The invention further relates to a method of treating cancer in a human patient comprising administration of a compound of the invention (i.e., a compound of Formula I) and a PD-1 antagonist to the patient. The compound of the invention and the PD-1 antagonist may be administered concurrently or sequentially.

In particular embodiments, the PD-1 antagonist is an anti-PD-1 antibody, or antigen binding fragment thereof. In alternative embodiments, the PD-1 antagonist is an anti-PD-L1 antibody, or antigen binding fragment thereof. In some embodiments, the PD-1 antagonist is pembrolizumab (KEYTRUDA™, Merck & Co., Inc., Kenilworth, NJ, USA), nivolumab (OPDIVO™, Bristol-Myers Squibb Company, Princeton, NJ, USA), cemiplimab (LIBTAYO™, Regeneron Pharmaceuticals, Inc., Tarrytown, NY, USA), atezolizumab (TECENTRIQ™, Genentech, San Francisco, CA, USA), durvalumab (IMFINZI™, AstraZeneca Pharmaceuticals LP, Wilmington, DE), or avelumab (BAVENCIO™, Merck KGaA, Darmstadt, Germany).

In some embodiments, the PD-1 antagonist is pembrolizumab. In particular sub-embodiments, the method comprises administering 200 mg of pembrolizumab to the patient about every three weeks. In other sub-embodiments, the method comprises administering 400 mg of pembrolizumab to the patient about every six weeks.

In further sub-embodiments, the method comprises administering 2 mg/kg of pembrolizumab to the patient about every three weeks. In particular sub-embodiments, the patient is a pediatric patient.

In some embodiments, the PD-1 antagonist is nivolumab. In particular sub-embodiments, the method comprises administering 240 mg of nivolumab to the patient about every two weeks. In other sub-embodiments, the method comprises administering 480 mg of nivolumab to the patient about every four weeks.

In some embodiments, the PD-1 antagonist is cemiplimab. In particular sub-embodiments, the method comprises administering 350 mg of cemiplimab to the patient about every 3 weeks.

In some embodiments, the PD-1 antagonist is atezolizumab. In particular sub-embodiments, the method comprises administering 1200 mg of atezolizumab to the patient about every three weeks.

In some embodiments, the PD-1 antagonist is durvalumab. In particular sub-embodiments, the method comprises administering 10 mg/kg of durvalumab to the patient about every two weeks.

In some embodiments, the PD-1 antagonist is avelumab. In particular sub-embodiments, the method comprises administering 800 mg of avelumab to the patient about every two weeks.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refers to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, TDX258, the epothilones (see for example U.S. Pat. Nos. 6,284,781 and 6,288,237) and BMS188797. In an example the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an example inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680 (tozasertib).

"Antiproliferative agents" include antisense RNA and DNA oligonucleotides such as G3139, ODN698, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl) sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitor" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952), rosuvastatin (CRESTOR® U.S. Reissue Pat. No. RE37,314) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of the invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). For an example of the role of a prenyl-protein transferase inhibitor on angiogenesis see *European J. of Cancer*, Vol. 35, No. 9, pp. 1394-1401 (1999).

"Angiogenesis inhibitor" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83

(1995); *Clin, Orthop*. Vol. 313, p. 76 (1995); *J. Mol. Endocrinol*., Vol. 16, p. 107 (1996); *Jpn. J. Pharmacol*., Vol. 75, p. 105 (1997); *Cancer Res*., Vol. 57, p. 1625 (1997); *Cell*, Vol. 93, p. 705 (1998); *Intl. J. Mol. Med*., Vol. 2, p. 715 (1998); *J. Biol. Chem*., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refers to compounds that inhibit protein kinases that transduce cell cycle checkpoint signals, thereby sensitizing the cancer cell to DNA damaging agents. Such agents include inhibitors of ATR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refers to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signalling pathway" refers to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004/0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, U.S. Pat. Nos. 7,454,431, 7,589,068), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAIDs are directed to the use of NSAIDs which are potent COX-2 inhibiting agents. For purposes of the specification an NSAID is potent if it possesses an $IC_{50}$ for the inhibition of COX-2 of 1 M or less as measured by cell or microsomal assays.

The invention also encompasses combinations with NSAIDs which are selective COX-2 inhibitors. For purposes of the specification NSAIDs which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: rofecoxib, etoricoxib, parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RP14610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416), or a pharmaceutically acceptable salt thereof.

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the αvβ5 integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_5\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, ST1571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, ST1571A, N-4-chlorophenyl-4-(4-pyridylmethyl)-1-phthalazinamine, and EMD121974, or a pharmaceutically acceptable salt thereof.

Combinations with compounds other than anti-cancer compounds are also encompassed in the instant methods.

For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697), or a pharmaceutically acceptable salt thereof.

Another example of the instant invention is the use of the presently disclosed compounds in combination with gene therapy for the treatment of cancer. For an overview of genetic strategies to treating cancer see Hall et al., (*Am. J. Hum. Genet.* 61:785-789, 1997) and Kufe et al., (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar), or a pharmaceutically acceptable salt thereof.

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another example, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

A compound of the instant invention, or a pharmaceutically acceptable salt thereof, may also be administered with an agent useful in the treatment of anemia. Such an anemia treatment agent is, for example, a continuous erythropoiesis receptor activator (such as epoetin alfa).

A compound of the instant invention, or a pharmaceutically acceptable salt thereof, may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention, or a pharmaceutically acceptable salt thereof, may also be administered with an immunologic-enhancing drug, such as levamisole, isoprinosine and Zadaxin, or a pharmaceutically acceptable salt thereof.

A compound of the instant invention, or a pharmaceutically acceptable salt thereof, may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir, or a pharmaceutically acceptable salt thereof.

A compound of the instant invention, or a pharmaceutically acceptable salt thereof, may also be useful for treating or preventing cancer in combination with Pgp and/or BCRP inhibitors including: cyclosporinA, PSC833, GF120918, cremophorEL, fumitremorgin C, Ko132, Ko134, Iressa, Imatnib mesylate, EKI-785, Cl1033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol, or a pharmaceutically acceptable salt thereof.

A compound of the instant invention, or a pharmaceutically acceptable salt thereof, may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention, or a pharmaceutically acceptable salt thereof, may also be useful for treating or preventing breast cancer in combination with aromatase inhibitors. Examples of aromatase inhibitors include but are not limited to: anastrozole, letrozole and exemestane, or a pharmaceutically acceptable salt thereof.

A compound of the instant invention, or a pharmaceutically acceptable salt thereof, may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139), or a pharmaceutically acceptable salt thereof.

A compound of the instant invention, or a pharmaceutically acceptable salt thereof, may also be useful for treating or preventing cancer in combination with PARP inhibitors.

A compound of the instant invention, or a pharmaceutically acceptable salt thereof, may also be useful for treating cancer in combination with the following therapeutic agents: pembrolizumab (Keytruda®), abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); tale (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®), or a pharmaceutically acceptable salt thereof.

In an example, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an example, the estrogen receptor modulator is tamoxifen or raloxifene.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-5 agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention, or a pharmaceutically acceptable salt thereof, in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another example of the invention is a method of treating cancer that comprises administering a therapeutically effective amount of a compound of the instant invention, or a pharmaceutically acceptable salt thereof, in combination with paclitaxel or trastuzumab.

The invention further encompasses a method of treating or preventing cancer that comprises administering a therapeutically effective amount of a compound of the instant invention, or a pharmaceutically acceptable salt thereof, in combination with a COX-2 inhibitor, or a pharmaceutically acceptable salt thereof.

The therapeutic combination disclosed herein may be used in combination with one or more other active agents, including but not limited to, other anti-cancer agents that are used in the prevention, treatment, control, amelioration, or reduction of risk of a particular disease or condition (e.g., cell-proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, prior to, contemporaneously, or sequentially with a compound of the present disclosure.

The instant invention also includes a pharmaceutical composition useful for treating or preventing cancer that comprises a therapeutically effective amount of a compound of the instant invention, or a pharmaceutically acceptable salt thereof, and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

When any variable occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

The present invention includes compounds of structural formula I, Ia, Ib, Ic, or Id, as well as the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of the invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, 4-bromobenzenesulfonate, butyrate, camphorate, camphorsulfonate, camsylate, carbonate, chloride, clavulanate, citrate, cyclohexylamidosulfonate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glucuonate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, trifluoromethylsulfonate, p-toluenesulfonate, undeconate, valerate and the like.

Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts.

With basic reagents such as hydroxides, carbonates, hydrogencarbonates, alkoxides and ammonia, organic bases or alternatively basic amino acids the compounds of the formula I, Ia, Ib, Ic, or Id form stable alkali metal, alkaline earth metal or optionally substituted ammonium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethanolamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, orithine, piperazine, piperidine, polyamine resins, procaine, purines, theobromine, triethanolamine, triethylamine, trimethylamine, tripropylamine, trometamol, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The preparation of pharmacologically acceptable salts from compounds of the formula I, Ia, Ib, Ic, or Id capable of salt formation, including their stereoisomeric forms is carried out known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of formula I, Ia, Ib, Ic, or Id. Centers of asymmetry that are present in the compounds of formula I, Ia, Ib, Ic, or Id can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formulas. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of the invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of formula I, Ia, Ib, Ic, or Id, or it can be done on a final racemic product. Absolute stereochemistry may be determined by X-ray crystallography of crystalline products or crystalline intermediates which are derivatized, if necessary, with a reagent containing a stereogenic center of known configuration. Where compounds of the invention are capable of tautomerization, all individual tautomers as well as mixtures thereof are included in the scope of the invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Furthermore, compounds of the present invention may exist in amorphous form and/or one or more crystalline forms, and as such all amorphous and crystalline forms and mixtures thereof of the compounds of formula I, Ia, Ib, Ic, or Id are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of the invention, along with un-solvated and anhydrous forms.

The present invention includes compounds of structural formula I, Ia, Ib, Ic, or Id, or any other generic structural formula or specific compound described or claimed herein, and is intended to encompass the specific compound or compounds falling within the scope of the formula or embodiment.

The present invention includes compounds of structural formula I, Ia, Ib, Ic, or Id as well as salts thereof, particularly pharmaceutically acceptable salts, solvates of such compounds and solvated salt forms thereof, where such forms are possible unless specified otherwise.

Except where noted herein, "alkyl" refers to an aliphatic hydrocarbon group having one of its hydrogen atoms replaced with a bond. An alkyl group is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g.

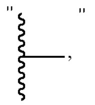

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

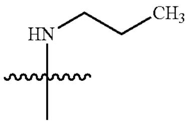 and 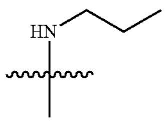

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

"Heterocycle" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or unsaturated. The heterocycle may be attached to the rest of the molecule via a ring carbon atom, a ring oxygen atom or a ring nitrogen atom. Non-limiting examples of heterocycles are described below.

Except where noted, the term "saturated heterocycle" refers to a stable 4- to 7-membered mono-cyclic or stable 7- to 12-membered bicyclic or stable 12- to 14-membered tricyclic heteroatom-containing ring system, and which consists of carbon atoms and from one to four heteroatoms independently selected from the group consisting of N, O and S, and wherein the nitrogen and sulfur heteroatoms may optionally be oxidized, and the nitrogen heteroatom may optionally be quaternized. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Representative examples include azetidine, oxetane, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperidine, oxane, thiane, piperazine, morpholine, thiomorpholine, dioxane, dithiane, trioxane, trithiane, azepane, oxepane, thiepane and homopiperazine.

Except where noted herein, the term "unsaturated heterocycle" refers to a monocyclic unsaturated heterocycle having a specified number of atom members (e.g., 4, 5, 6 or 7-membered), including a specified number of heteroatoms (e.g., 1, 2, 3 or 4 heteroatoms independently selected from N, O or S), or a bicyclic unsaturated ring system having a specified number of atom members (e.g., 7, 8, 9, 10, 11 or 12-membered) including a specified number of heteroatoms (e.g., 1, 2, 3, 4, 5, 6, 7, 8, 9 or 10 heteroatoms independently selected from N, S or O) or a tricyclic unsaturated ring system having a specified number of atom members (e.g., 12-, 13- or 14-membered) including a specified number of heteroatoms (e.g., 1, 2, 3, 4, 5, 6, 7, 8, 9 or 10 heteroatoms independently selected from N, S or O) e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen (triazole) atoms, five-membered aromatic rings containing one oxygen, one nitrogen or one sulfur atom, five-membered aromatic rings containing two heteroatoms independently selected from oxygen, nitrogen and sulfur (e.g., oxazole), 6-membered rings containing one nitrogen (pyridine), or one oxygen (pyran) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Additional examples are pyridine, pyrimidine, thiophene, imidazole, isothiazole, oxadiazole, and isoxazole.

Except where noted herein, the term "unsaturated bicyclic heterocycle" or "unsaturated tricyclic heterocycle" may refer to a heterocycle having fused rings in which at least one of the rings is not fully saturated, and is partially saturated, e.g.

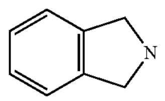

is a 9-membered unsaturated bicyclic heterocycle having one nitrogen atom.

Except where noted herein, "fluoroalkyl" may refer to a alkyl substituted with 1-3 halogens. The fluoroalkyl may be attached to the rest of the molecule at any carbon atom which results in a stable compound.

"Aryl" refers to an aromatic monocyclic or multicyclic ring moiety comprising 6 to 14 ring carbon atoms. In one embodiment, an aryl group contains from about 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Cycloalkyl" refers to a non-aromatic mono- or multicyclic ring system comprising about 3 to 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group as defined above, which is fused to an aryl or heteroaryl ring. Non-limiting examples of monocyclic cycloalkyls include cyclopropyl, cyclobutyl, cyclopentyl, cyclohexyl, cycloheptyl and cyclooctyl. Non-limiting examples of monocyclic cycloalkyl include cyclopropyl, cyclobutyl, cyclopentyl, cyclohexyl, cycloheptyl, and cyclooctyl. A cycloalkyl group is unsubstituted or substituted with one or more ring system substituents which may be the same or different, and are as defined within. The term $C_{1-6}$cycloalkyl" refers to a cycloalkyl group having 1 to 6 ring carbon atoms. The term $C_{3-6}$ cycloalkyl" refers to a cycloalkyl group having 3 to 6 ring carbon atoms.

Except where noted herein, the term "carbocycle" (and variations thereof such as "carbocyclic" or "carbocyclyl") as used herein, unless otherwise indicated, refers to a $C_3$ to $C_6$ monocyclic ring, e.g., $C_{3-6}$ monocyclic carbocycle, or a $C_9$ to $C_{12}$ bicyclic ring, e.g., $C_{9-12}$ bicyclic carbocycle. The carbocycle may be attached to the rest of the molecule at any carbon atom which results in a stable compound. Saturated carbocyclic rings include, for example, "cycloalkyl" rings, e.g., cyclopropyl, cyclobutyl, etc. Unsaturated carbocyclic rings include, for example

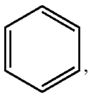,
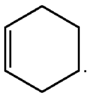.

Unsaturated bicyclic carbocyclic ring systems include fused ring systems where all ring system members are carbon atoms and where at least one of the fused rings is not saturated.

Except where noted herein, the term "unsaturated bicyclic carbocycle" or "unsaturated tricyclic carbocycle" refers to a carbocycle having fused rings in which at least one of the rings is not fully saturated, e.g.

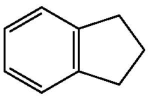

is a 9-membered unsaturated bicyclic carbocycle.

Carbocycle groups may be unsubstituted, or substituted on any one or more carbon atoms, with halogen, $C_1$-$C_{20}$ alkyl, $CF_3$, $NH_2$, NH($C_1$-$C_6$ alkyl), N($C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, HS(O)$_{0-2}$—, ($C_1$-$C_6$ alkyl)S(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$, ($C_1$-$C_6$ alkyl)C(O)NH—, HC(O)NH—, $H_2$N—C(NH)—, —O($C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)C(O)$_{1-2}$($C_1$-$C_6$ alkyl)-, ($C_1$-$C_6$ alkyl)C(O)$_{1-2}$—, HC(O)$_{1-2}$($C_1$-$C_6$ alkyl)-, ($C_1$-$C_6$ alkyl)OC(O)NH—, HOC(O)NH—, —P(O)(OH)$_2$, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound. In a preferred embodiment, carbocyle groups may be unsubstituted, or substituted on any one or more carbon atoms, with halogen, $C_{1-6}$alkyl, CN, OH, $OC_{1-6}$alkyl, $C_{1-6}$haloalkyl, =O, $C_{1-6}$cycloalkyl, C(O)$C_{1-6}$alkyl, $C_{3-6}$cycloalkyl, $C_{1-6}$fluoroalkyl, 5-membered heterocycle, OH, $OC_{1-6}$ alkoxy, $NC_{1-6}$alkyl.

Unless otherwise specified, carbocycle groups are unsubstituted.

Except where noted herein, structures containing substituent variables such as variable "R":

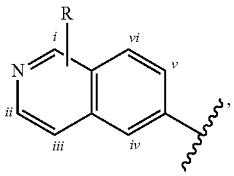

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, a bicyclic heterocycle can be a fused bicyclic heterocycle, e.g.,

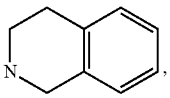, a bridged bicyclic heterocycle, e.g.,

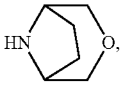

or a spiro bicyclic heterocycle, e.g.,

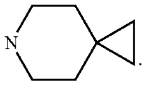.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions. The term "substituted" means that one or more hydrogens on the designated atom is replaced with a selected from the indicated group, provided that the designated atom's normal valency under the existing circumstances is not exceeded, and that the substitution results in a stable compound. Combinations of substituents and/or variables are permissible only if such combinations result in stable compounds. By "stable compound" is meant a compound that is sufficiently robust to survive isolation to a useful degree of purity from a reaction mixture, and formulation into an efficacious therapeutic agent.

If the compounds of formula I, Ia, Ib, Ic, or Id simultaneously contain acidic and basic groups in the molecule the invention also includes, in addition to the salt forms mentioned, inner salts or betaines (zwitterions). Salts can be obtained from the compounds of formula I, Ia, Ib, Ic, or Id by customary methods which are known to the person skilled in the art, for example by combination with an organic or inorganic acid or base in a solvent or dispersant, or by anion exchange or cation exchange from other salts. The present invention also includes all salts of the compounds of formula I, Ia, Ib, Ic, or Id which, owing to low physiological compatibility, are not directly suitable for use in pharmaceuticals but which can be used, for example, as intermediates for chemical reactions or for the preparation of physiologically acceptable salts.

The invention also includes derivatives of the compound of formula I, Ia, Ib, Ic, or Id, acting as prodrugs and solvates. Any pharmaceutically acceptable pro-drug modification of a compound of the invention which results in conversion in vivo to a compound within the scope of the invention is also within the scope of the invention. Prodrugs, following administration to the patient, are converted in the body by normal metabolic or chemical processes, such as through hydrolysis in the blood, to the compound of formula I, Ia, Ib, Ic, or Id. Such prodrugs include those that demonstrate enhanced bioavailability, tissue specificity, and/or cellular delivery, to improve drug absorption of the compound of I, Ia, Ib, Ic, or Id. The effect of such prodrugs may result from modification of physicochemical properties such as lipophilicity, molecular weight, charge, and other physicochemical properties that determine the permeation properties of the drug.

For example, esters can optionally be made by esterification of an available carboxylic acid group or by formation of an ester on an available hydroxy group in a compound. Similarly, labile amides can be made. Pharmaceutically acceptable esters or amides of the compounds of the invention may be prepared to act as pro-drugs which can be hydrolyzed back to an acid (or $—COO^-$ depending on the pH of the fluid or tissue where conversion takes place) or hydroxy form particularly in vivo and as such are encompassed within the scope of the invention. Examples of pharmaceutically acceptable pro-drug modifications include, but are not limited to, $—C_{1-6}$alkyl esters and $—C_{1-6}$alkyl substituted with phenyl esters.

When any variable occurs more than one time in any constituent or in formula I, its definition on each occurrence is independent of its definition at every other occurrence. Also, combinations of substituents and/or variables are permissible only if such combinations result in stable compounds.

Except where noted, the term "halogen" or "halo" means fluorine, chlorine, bromine or iodine.

"Haloalkyl" refers to an alkyl group as defined within, wherein one or more of the alkyl group's hydrogen atoms has been replaced with a halogen. In one embodiment, a haloalkyl group has from 1 to 6 carbon atoms. Non-limiting examples of haloalkyl groups include $CH_2F$, $CHF_2$, $CF_3$, $CH_2Cl$ and $CCl_3$. The term "$C_{1-6}$haloalkyl" refers to a haloalkyl group having from 1 to 6 carbons.

Where ring atoms are represented by variables such as "X", e.g,

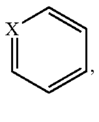

the variables are defined by indicating the atom located at the variable ring position without depicting the ring bonds associated with the atom. For example, when X in the above ring is nitrogen, the definition will show "N" and will not depict the bonds associated with it, e.g., will not show "═N—". Likewise, when X is a carbon atom that is substituted with bromide, the definition will show "C—Br" and will not depict the bonds associated with it, e.g., will not show

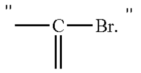

"Celite®" (Fluka) diatomite is diatomaceous earth, and can be referred to as "celite".

The invention also relates to medicaments containing at least one compound of the formula I, Ia, Ib, Ic, or Id and/or of a pharmaceutically acceptable salt of the compound of the formula I, Ia, Ib, Ic, or Id and/or an optionally stereoisomeric form of the compound of the formula I, Ia, Ib, Ic, or Id or a pharmaceutically acceptable salt of the stereoisomeric form of the compound of formula I, Ia, Ib, Ic, or Id, together with a pharmaceutically acceptable vehicle, carrier, additive and/or other active substances and auxiliaries.

The medicaments according to the invention can be administered by oral, inhalative, rectal or transdermal administration or by subcutaneous, intraarticular, intraperitoneal or intravenous injection. Oral administration is preferred. Coating of stents with compounds of the formula I, Ia, Ib, Ic, or Id and other surfaces which come into contact with blood in the body is possible.

The invention also relates to a process for the production of a medicament, which comprises bringing at least one compound of the formula I, Ia, Ib, Ic, or Id into a suitable administration form using a pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the compounds may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver about 0.01 mg per kg of body weight per day (mg/kg/day) to about 30 mg/kg/day, preferably 0.025-7.5 mg/kg/day, more preferably 0.1-2.5 mg/kg/day, and even more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The compounds of the invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of formula I, Ia, Ib, Ic, or Id hereinabove.

Methods for Making the Compounds of Present Invention

General Methods

The compounds of the present invention can be readily produced from known compounds or commercially available compounds by, for example, known processes described in published documents, and produced by production processes described below. The present invention is not limited to the production processes described below. The invention also includes processes for the preparation of compounds of the invention.

It should be noted that, when a compound of structural Formula I, Ia, Ib, Ic, or Id, has a reactive group such as hydroxy group, amino group, carboxyl group, or thiol group as its substituent, such group may be adequately protected with a protective group in each reaction step and the protective group may be removed at an subsequent stage. The process of such introduction and removal of the protective group may be adequately determined depending on the group to be protected and the type of the protective group, and such introduction and removal are conducted, for example, by the process described in the review section of Greene, T. W., et. al., "*Protective Groups in Organic Synthesis*", 2007, 4th Ed., Wiley, New York, or Kocienski, P., "*Protecting Groups*" 1994, Thieme.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

All solvents used were commercially available and were used without further purification. Reactions were typically run using anhydrous solvents under an inert atmosphere of nitrogen.

Starting materials used were either available from commercial sources or prepared according to literature procedures and had experimental data in accordance with those reported.

Abbreviations used are those conventional in the art of the following.

ACN acetonitrile
AcOH acetic acid
AcOK potassium acetate
$Ac_2O$ acetic anhydride
aq. aqueous
9-BBN 9-borabicyclo(3.3.1)nonane
BINAP (2,2'-bis(diphenylphosphino)-1,1'-binaphthyl)
$BH_3$-DMS borane-dimethylsulfide complex
$BH_3$-THF or $BH_3$·THF borane-tetrahydrofuran complex
BnBr benzyl bromide
BSA bovine serum albumin
° C. degree Celsius
$CDCl_3$ deuterated chloroform
$CD_3OD$ deuterated methanol
CO carbon monoxide
COD cis,cis-1,5-Cyclooctadiene
$Cs_2CO_3$ cesium carbonate
DAST diethylaminosulfur trifluoride
DCE 1,2-dichloroethane
DCM dichloromethane
DIAD di-tert-butylazodicarboxylate
DIEA N,N-diisopropylethylamine
DMA diemthylacetamide
DMAc N,N-dimethylacetamide
DMAP 4-(dimethylamino)pyridine
DME 1,2-dimethoxyethane
DMEA dimethylethanolamine
DMF N,N-dimethylformamide
DMSO dimethylsulfoxide
DPPA diphenylphosphoryl azide
DPPF 1,1'-Bis(diphenylphosphino)ferrocene
DTT dithiothreitol
EDC N-(3-dimethylaminopropyl)-N'-ethylcarbodiimide
equiv equivalents EtOAc ethyl acetate
EtOH ethanol
g gram
h hour
$H_2$ hydrogen
HATU N-[(Dimethylamino)-1H-1,2,3-triazolo-[4,5-b]pyridin-1-ylmethylene]-N-methylmethanaminium hexafluorophosphate N-oxide
HCl hydrochloric acid
HPLC high pressure liquid chromatography
$K_2CO_3$ potassium carbonate
KOH potassium hydroxide
i-PrOH isopropyl alcohol
Int. Intermediate
LAH lithium aluminium hydride
LCMS liquid chromatography and mass spectrometry
LiHMDS lithium bis(trimethylsilyl)amide
LiOH lithium hydroxide
$LiOH{\cdot}H_2O$ or LiOH—$H_2O$ Lithium hydroxide monohydrate
m-CPBA meta-chloroperoxybenzoic acid
M molar
MeOH methanol
MS mass spectrometry
MTBE methyl tert-butyl ether
mmol millimole
mg milligram
min minutes
mL milliliter
MPLC Medium pressure liquid chromatography
$NaBH_4$ sodium borohydride
NaH sodium hydride
$NaHCO_3$ sodium bicarbonate
NaHMDS sodium bis(trimethylsilyl)amide
NaOH sodium hydroxide
NBS N-Bromosuccinimide
nM nanomolar
NMP N-methyl-2-pyrrolidone
N normal
$NH_4HCO_3$ ammonium bicarbonate
NMR nuclear magnetic resonance
n-BuLi n-Butyllithium
Pd/C or Pd—C palladium on carbon
$PPh_3$ triphenylphosphine
$PdCl_2$(dppf) [1,1-bis(diphenylphosphine)ferrocene]dichloropalladium(II)
$Pd_2(dba)_3$ tris(dibenzylideneacetone)dipalladium(0)
$Pd(OAc)_2$ Palladium (II) acetate
Pd-PEPPSI-Ipent dichloro[1,3-bis(2,6-Di-3-pentylphenyl)imidazol-2-ylidene](3-chloropyridyl)palladium(II)
$Pd(PPh_3)_4$ tetrakis(triphenylphosphine)palladium(0)
$Pd(PPh_3)_2Cl_2$ bis(triphenylphosphine)palladium(II) dichloride
pet. ether petroleum ether
prep TLC preparative TLC
$POCl_3$ phosphorus(V) oxychloride
psi pound per square inch
PyAOP (7-Azabenzotriazol-1-yloxy)trispyrrolidinophosphonium hexafluorophosphate
rt room temperature
RuPhos-Pd-G3 (2-Dicyclohexylphosphino-2',6'-diisopropoxy-1,1'-biphenyl)[2-(2'-amino-1,1'-biphenyl)]palladium(II) methanesulfonate
Ruphos G2 Chloro(2-dicyclohexylphosphino-2',6'-diisopropoxy-1,1'-biphenyl)[2-(2'-amino-1,1'-biphenyl)]palladium(II)
sat. saturated
SM starting material
SFC Supercritical fluid chromatography
$SOCl_2$ thionyl chloride
T3P® 2,4,6-Tripropyl-1,3,5,2,4,6-trioxatriphosphorinane-2,4,6-trioxide
t-BuOH tert-butanol
t-BuOK sodium tert-butoxide
tBuXPhos 2-di-tert-butylphosphino-2',4',6'-triisopropylbiphenyl
TEA triethylamine
TFA trifluoroacetic acid
THF tetrahydrofuran
TLC thin layer chromatography
TsCl 4-Toluenesulfonyl chloride
$TMSCF_3$ Trifluoromethyltrimethylsilane
Wt. Weight
μL microliter
XantPhos 4,5-bis(diphenylphosphino)-9,9-dimethylxanthene
XPhos-Pd-G3 (2-Dicyclohexylphosphino-2',4',6'-triisopropyl-1,1'-biphenyl)[2-(2'-amino-1,1'-biphenyl)]palladium(II) methanesulfonate General Synthetic Schemes While the present invention has been described in conjunction with the specific examples set forth above, many alternatives, modifications and variations thereof will be apparent to those of ordinary skill in the art. In some cases the order of carrying out the steps of the reaction schemes may be varied to facilitate the reaction or to avoid unwanted reaction products. All such alternatives, modifications and variations are intended to fall within the spirit and scope of the present invention. Starting materials and intermediates are purchased from commercial sources, made from known procedures, or are otherwise illustrated.

Several methods for preparing the compounds of this invention are described in the following Schemes and Examples. Starting materials and intermediates are purchased from commercial sources, made from known procedures, or are otherwise illustrated. In some cases the order of carrying out the steps of the reaction schemes may be varied to facilitate the reaction or to avoid unwanted reaction products.

Unless otherwise indicated, all variables are as previously defined.

In schemes 1-4, R represents H, halogen, $C_{1-3}$ alkyl or $C_{1-3}$ alkoxy. In schemes 1-4, $Y^1$ represents H or OH.

Scheme 1

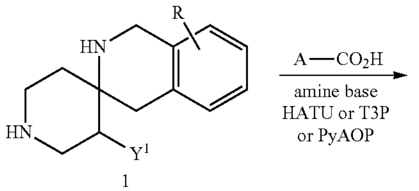

1

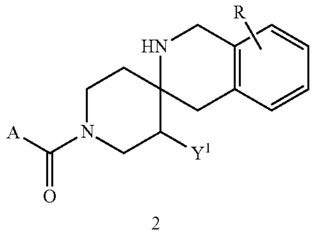

2

In Scheme 1, an optionally substituted spiroamine 1 can be coupled to an appropriately substituted carboxylic acid using standard amide coupling conditions to provide amide 2.

Scheme 2

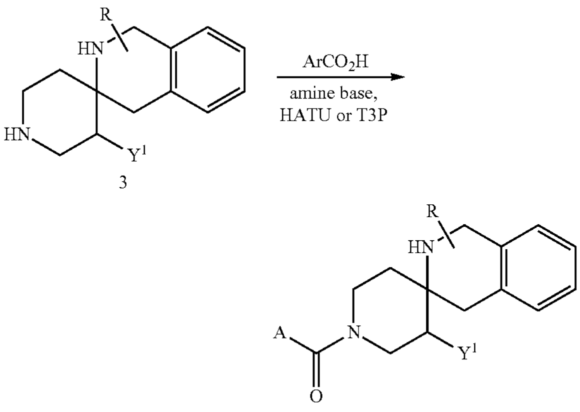

3

4

In Scheme 2, an optionally substituted spiroamine 3 can be coupled to an appropriately substituted carboxylic acid using standard amide coupling conditions to provide amide 4.

Scheme 3

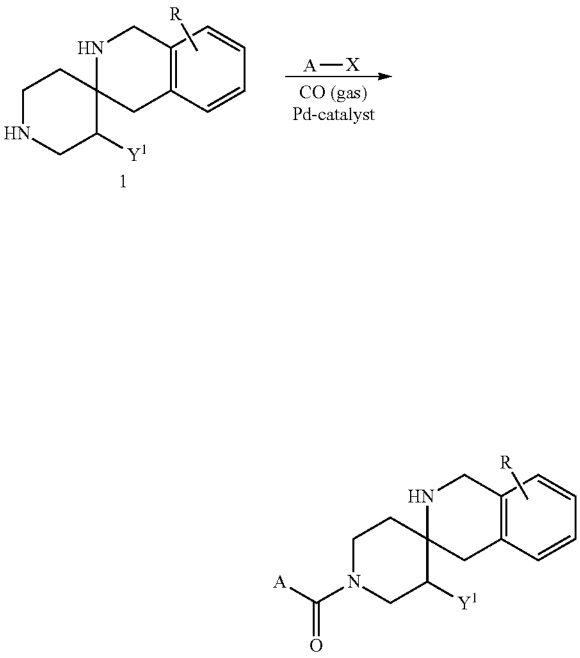

1

5

Ar = an appropriately substituted aryl or heteroaryl moiety
X = Cl, Br, I

In Scheme 3, an optionally substituted spiroamine 1 can be coupled to an appropriately substituted aryl or heteroaryl halide utilizing Pd-catalysis in the presence of carbon monoxide gas to afford amide 5.

Scheme 4

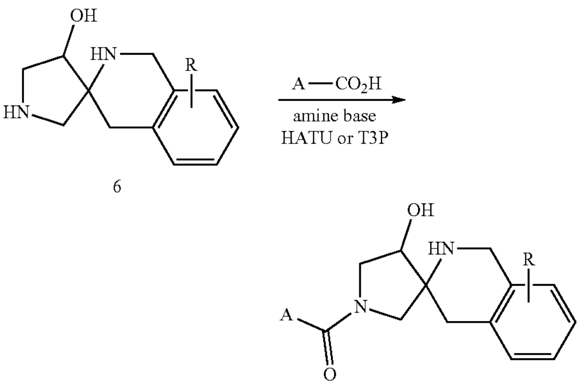

6

7

In Scheme 4, an optionally substituted spiroamine 6 can be coupled to an appropriately substituted carboxylic acid using standard amide coupling conditions to afford amide 7.

Scheme 5

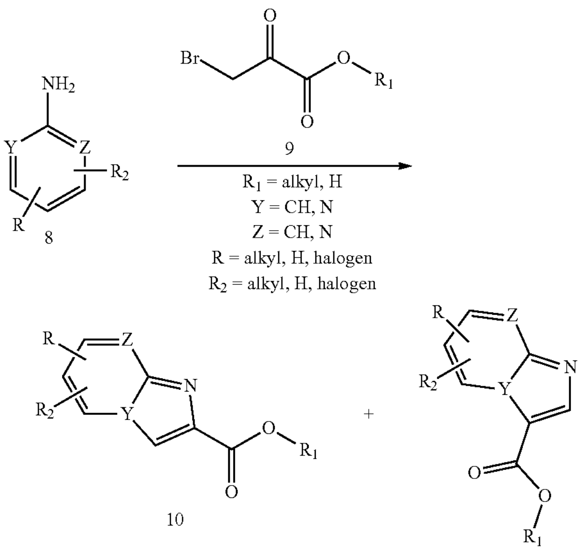

8

9

10

11

In scheme 5, an optionally substituted heteroaromatic amine 8 can be condensed with an alkyl 3-bromo-2-oxopropanoate (9) to form bicyclic products 10 and 11.

Synthesis of Intermediates

Intermediate 1: (3R,3'R)-1,4-dihydro-2H-spiro[isoquinoline-3,4'-piperidin]-3'-ol

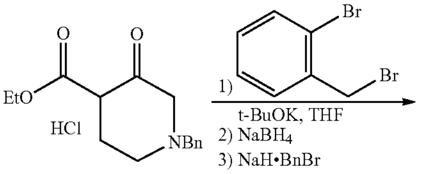

-continued

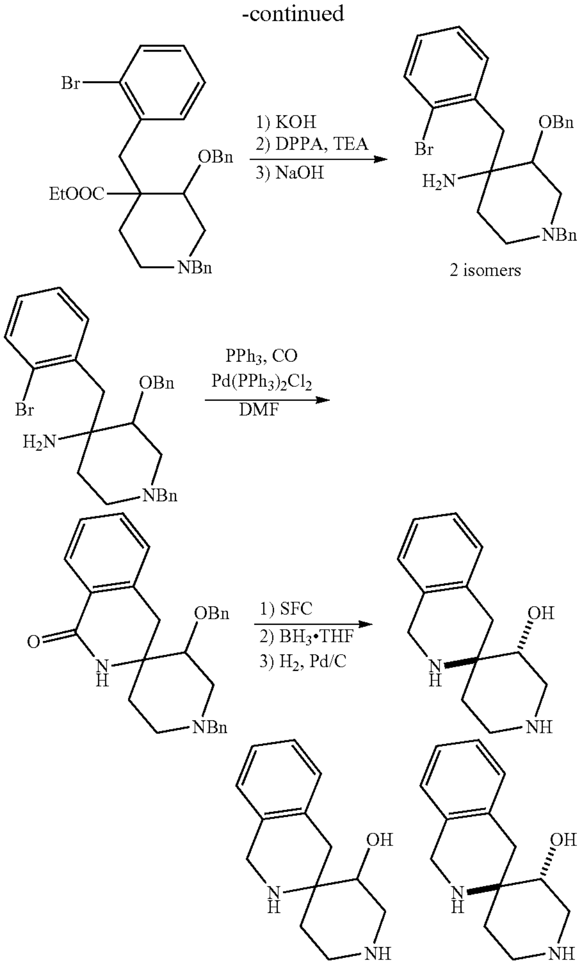

Step 1: Ethyl 1-benzyl-3-oxopiperidine-4-carboxylate (800 g, 2.69 mol) was added dropwise at 0° C. to a solution of t-BuOK (633 g, 5.64 mol) in THF (2 L) at 0° C. The mixture was stirred at 25° C. for 1 h. The mixture was cooled to 0° C. and a solution of 1-bromo-2-(bromomethyl)benzene (705 g, 2.82 mol) in THF (500 mL) was added dropwise over 0.5 h. The mixture was stirred at 25° C. for 5 h to afford a solution of ethyl 1-benzyl-4-(2-bromobenzyl)-3-oxopiperidine-4-carboxylate, which was used in the next step without further purification. MS: 430 and 432 (M+1).

Step 2: Ethyl 1-benzyl-4-(2-bromobenzyl)-3-oxopiperidine-4-carboxylate (1.00 kg, 2.32 mol) was added to EtOH (1 L) and the solution was purged and degassed with $N_2$ (3×). The resultant mixture was cooled to 0° C. and $NaBH_4$ (87.9 g, 2.32 mol) was added portionwise over 1 h. The mixture was then stirred at 25° C. for 2 h. The reaction mixture was concentrated under reduced pressure, diluted with $H_2O$ (200 mL), and extracted with ethyl acetate (200 mL×3). The combined organic layers were dried over anhydrous magnesium sulfate, filtered, and concentrated under reduced pressure to afford ethyl 1-benzyl-4-(2-bromobenzyl)-3-hydroxypiperidine-4-carboxylate. MS: 432 and 434 (M+1).

Step 3: A solution of ethyl 1-benzyl-4-(2-bromobenzyl)-3-hydroxypiperidine-4-carboxylate (622 g, 1.44 mol) in DMF (2.5 L) was purged and degassed with $N_2$ (3×) and then cooled to 0° C. NaH (69.1 g, 1.73 mol, 60% w/w) was added to the mixture portionwise at 0° C. over 1 h. The resultant mixture was stirred at 25° C. for 0.5 h. Benzyl bromide (197 g, 1.15 mol, 137 mL) was added dropwise to the mixture at 0° C. over 1 h and the resultant mixture was stirred at 25° C. for 5 h. The reaction was quenched with saturated aq. $NH_4Cl$ (1 L) at 0° C., and extracted with MTBE (300 mL×3). The combined organic layers were washed with sat. aqueous NaCl (200 mL×2), dried over anhydrous sodium sulfate, filtered, and concentrated under reduced pressure. The residue was purified by column chromatography on silica (50:1 to 1:1 petroleum ether:ethyl acetate) to provide ethyl 1-benzyl-3-(benzyloxy)-4-(2-bromobenzyl)piperidine-4-carboxylate. MS: 522 and 524 (M+1)

Step 4: Ethyl 1-benzyl-3-(benzyloxy)-4-(2-bromobenzyl)piperidine-4-carboxylate (500 g, 957 mmol) and KOH (805 g, 14.4 mol) were added to EtOH (4 L), and the resultant mixture was purged and degassed with $N_2$ (3×). The mixture was stirred at 100° C. for 12 h. The reaction mixture was concentrated under reduced pressure, and the residue was diluted with $H_2O$ (200 mL). The pH of the mixture was adjusted to pH 6 with 6 N aqueous HCl. The solid was filtered, washed with $H_2O$ (1 L), and concentrated to afford 1-benzyl-3-(benzyloxy)-4-(2-bromobenzyl)piperidine-4-carboxylic acid, which was used in the next step without further purification. MS: 494 and 496 (M+1)

Step 5: A solution of 1-benzyl-3-(benzyloxy)-4-(2-bromobenzyl)piperidine-4-carboxylic acid (200 g, 405 mmol), DPPA (134 g, 486 mmol, 105 mL) and TEA (123 g, 1.21 mol, 169 mL) in dioxane (1 L) was purged and degassed with $N_2$ (3×). The mixture was stirred at 25° C. for 3 h. MeOH (600 mL) was added to the mixture at 25° C. over 0.5 h, and the resultant mixture was stirred at 100° C. for 12 h. The reaction was quenched with saturated aq. $NaHCO_3$ (2 L) at 0° C., and then concentrated under reduced pressure. The residue was diluted with ethyl acetate (750 mL), washed with brine (150 mL), dried over anhydrous sodium sulfate, filtered, and concentrated under reduced pressure. The residue was purified by column chromatography on silica (3:1 petroleum ether:ethyl acetate) to provide methyl (1-benzyl-3-(benzyloxy)-4-(2-bromobenzyl)piperidin-4-yl)carbamate. MS: 523 and 525 (M+1).

Step 6: To a solution of methyl (1-benzyl-3-(benzyloxy)-4-(2-bromobenzyl)piperidin-4-yl)carbamate (130 g, 248 mmol) in DMSO (700 mL) that was purged and degassed with $N_2$ (3×) was added a solution of NaOH (89.4 g, 2.24 mol) in $H_2O$ (400 mL) at 25° C. The resultant mixture was heated to 100° C. and stirred for 1 h. The reaction was quenched with $H_2O$ (1 L) at 0° C. The mixture was extracted with ethyl acetate (300 mL×3), and the combined organic layers were concentrated under reduced pressure. The residue was purified by column chromatography on silica (petroleum ether:ethyl acetate) to provide 1-benzyl-3-(benzyloxy)-4-(2-bromobenzyl)piperidin-4-amine. MS: 465 and 467 (M+1).

Step 7: A mixture of 1-benzyl-3-(benzyloxy)-4-(2-bromobenzyl)piperidin-4-amine (270 g, 580 mmol), $PPh_3$ (10.6 g, 40.6 mmol) and $Pd(PPh_3)_2Cl_2$ (40.7 g, 58.0 mmol) in DMF (3 L) was stirred under CO (pressure: 50 psi) at 120° C. for 12 h. The reaction mixture was cooled to 0° C. and saturated aq. $NaHCO_3$ (6 L) was added. The mixture was extracted with ethyl acetate (2 L×3). The combined organic layers were washed with brine (1 L×2), dried over anhydrous sodium sulfate, filtered, and concentrated under reduced pressure to yield a solid. The solid was washed with MTBE (1 L×3) to afford 1'-benzyl-3'-(benzyloxy)-2H-spiro[isoquinoline-3,4'-piperidin]-1(4H)-one. MS: 413 (M+1). This solid, 1'-benzyl-3'-(benzyloxy)-2H-spiro[isoquinoline-3,4'-piperidin]-1(4H)-one, was further purified by SFC on a chiral column (Chiral Pak AD; Mobile phase: A for $CO_2$ and B for EtOH) to obtain two isomers: (3R,3'R)-1'-benzyl-3'-(benzyloxy)-2H-spiro[isoquinoline-3,4'-piperidin]-1(4H)-one. MS: 413 (M+1). (Second Eluting) (3S,3'S)-1'-benzyl-3'-(benzyloxy)-2H-spiro[isoquinoline-3,4'-piperidin]-1(4H)-one. MS: 413 (M+1).

Step 8: A mixture of (3R,3'R)-1'-benzyl-3'-(benzyloxy)-2H-spiro[isoquinoline-3,4'-piperidin]-1(4H)-one (32.0 g, 77.6 mmol) in THF (150 mL) that was purged and degassed with $N_2$ (3×) was stirred at 15° C. for 4 h. $BH_3$·THF (1 M in THF, 698 mL, 698 mmol) was added to the mixture dropwise at 0° C. over 0.5 h. The resultant mixture was heated to 80° C. and stirred for 48 h. The mixture was cooled to 0° C. and quenched with dropwise addition of MeOH (300 mL). The mixture was then heated to 80° C. and stirred for 20 h. The mixture was cooled to room temperature and concentrated under reduced pressure. The crude product was washed with MTBE (500 mL) to afford (3R,3'R)-1'-benzyl-3'-(benzyloxy)-1,4-dihydro-2H-spiro[isoquinoline-3,4'-piperidine]. MS: 399 (M+1).

Step 9: A solution of (3R,3'R)-1'-benzyl-3'-(benzyloxy)-1,4-dihydro-2H-spiro[isoquinoline-3,4'-piperidine](20.0 g, 50.2 mmol), HCl (2 M in MeOH, 100 mL, 200 mmol) in MeOH (200 mL) and Pd/C (10.0 g, 10 wt. %) at 25° C. was purged and degassed with $H_2$ (3×). The mixture was stirred under $H_2$ (pressure: 50 psi) at 50° C. for 12 h. The reaction mixture was filtered and concentrated under reduced pressure. The resulting residue was washed with EtOAc (30 mL×3) to afford (3R,3'R)-1,4-dihydro-2H-spiro[isoquinoline-3,4'-piperidin]-3'-ol. MS: 219 (M+1), $^1$HNMR: (500 MHz, $D_2O$) δ 7.44-7.33 (m, 3H), 7.33-7.26 (m, 1H), 4.54 (d, J=16.5 Hz, 1H), 4.49 (d, J=16.6 Hz, 1H), 4.33-4.24 (m, 1H), 3.61 (dd, J=12.9, 4.1 Hz, 1H), 3.52-3.39 (m, 2H), 3.37-3.19 (m, 3H), 2.32 (d, J=14.5 Hz, 1H), 2.11-2.01 (m, 1H).

TABLE 1

A similar procedure to the above was used, but without chiral chromatography, to generate achiral spiroamine, which was a mixture of four isomers.

| Intermediate # | Structure | Compound Name | Exact Mass [M + 1] |
|---|---|---|---|
| 2 | 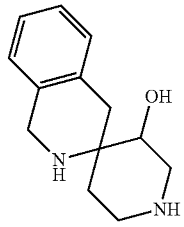 [SMILES: OC1CNCCC12Cc1ccccc1CN2] | 1,4-dihydro-2H-spiro[isoquinoline-3,4'-piperidin]-3'-ol | 219 |

Intermediate 3: 2-chloro-4-(1-cyclopropyl-1H-1,2,4-triazol-5-yl)benzoic acid

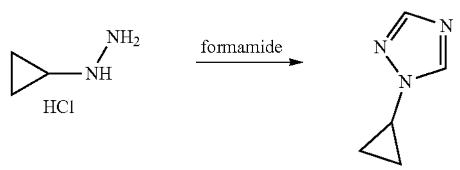 [SMILES: NNC1CC1 ; Cl ; c1ncn(C2CC2)n1]

-continued

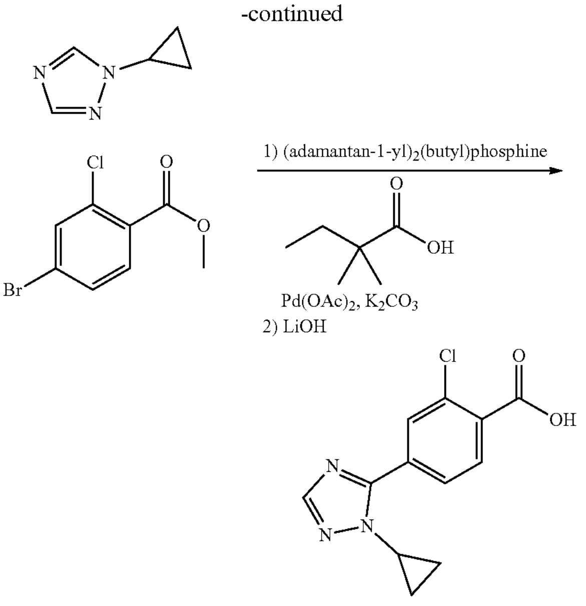

Intermediate 3

Step 1: A solution of cyclopropylhydrazine hydrochloride (4 g, 36.8 mmol) in formamide (14.6 mL, 368 mmol) was heated to 130° C. for 60 h. The mixture was added to brine (100 mL) and extracted with EtOAc (30 mL×3). The organic layer was washed with brine, dried over anhydrous magnesium sulfate, filtered, and concentrated under reduced pressure. The residue was purified by flash silica gel chromatography (ethyl acetate/pet. ether gradient) to give 1-cyclopropyl-1H-1, 2, 4-triazole. $^1$H NMR (400 MHz, $CDCl_3$) δ 8.09 (s, 1H), 7.84 (s, 1H), 3.54-3.58 (m, 1H), 1.06-1.22 (m, 4H).

Step 2: A mixture of 1-cyclopropyl-1H-1,2,4-triazole (100 mg, 0.916 mmol), methyl 4-bromo-2-chlorobenzoate (343 mg, 1.38 mmol), 2,2-dimethylbutanoic acid (31.9 mg, 0.275 mmol), di(adamantan-1-yl)(butyl)phosphine (131 mg, 0.367 mmol), $K_2CO_3$ (633 mg, 4.58 mmol) and palladium(II) acetate (41.1 mg, 0.183 mmol) in toluene (10 mL) was degassed and backfilled with $N_2$ (three times). The mixture was heated to 120° C. for 12 h. The mixture was then concentrated under reduced pressure. The residue was added to water (40 mL) and EtOAc (15 mL). The aqueous layer was re-extracted with EtOAc (20 mL×3). The combined organic layers were washed with brine (20 mL), dried over anhydrous sodium sulfate, filtered, and concentrated under reduced pressure. The residue was purified by preparative TLC (1:1 petroleum ether/EtOAc) to give methyl 2-chloro-4-(1-cyclopropyl-1H-1, 2, 4-triazol-5-yl)benzoate. MS: 278 (M+1).

Step 3: To a mixture of methyl 2-chloro-4-(1-cyclopropyl-1H-1,2,4-triazol-5-yl)benzoate (120 mg, 0.432 mmol) in MeOH (3 mL) and water (1 mL) was added lithium hydroxide hydrate (36.3 mg, 0.864 mmol) at 13° C. The solution was stirred at 13° C. for 2.5 h, then the mixture was concentrated to remove MeOH. To the residue was added $H_2O$ (20 mL) and the pH of the resulting mixture was adjusted pH~2 with aqueous HCl (1 M). The mixture was extracted with EtOAc (30 mL×3). The combined organic layers were washed with brine (20 mL), dried over sodium sulfate, filtered, and the filtrate was concentrated under reduced pressure to give 2-chloro-4-(1-cyclopropyl-1H-1,2,4-triazol-5-yl)benzoic acid, which was used without further purification. MS: 264 (M+1).

Intermediate 4: 2-((1-acetyl-3,3-difluoropiperidin-4-yl)amino)isonicotinic acid

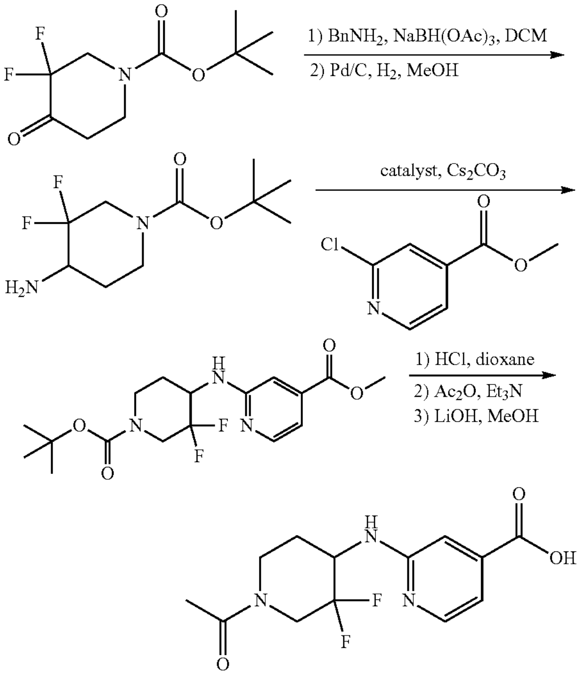

Step 1: To a solution of tert-butyl 3,3-difluoro-4-oxopiperidine-1-carboxylate (10 g, 42.5 mmol) in DCM (60 mL) was added phenylmethanamine (6.38 g, 59.5 mmol) and $NaBH(OAc)_3$ (27.0 g, 128 mmol) at 20° C. The reaction mixture was stirred at 20° C. for 10 h. The mixture was concentrated under reduced pressure. To the resulting residue was added water (40 mL), and the mixture was extracted with EtOAc (3×40 mL). The combined organic layers were dried over anhydrous sodium sulfate, filtered, and the filtrate concentrated under reduced pressure. The residue was purified by flash silica gel chromatography (EtOAc/petroleum ether gradient) to give tert-butyl 4-(benzylamino)-3,3-difluoropiperidine-1-carboxylate. MS: 327 (M+1). $^1H$ NMR (400 MHz, $CD_3Cl$) δ 7.41-7.19 (m, 5H), 4.19-3.97 (m, 1H), 3.93 (s, 2H), 3.80 (s, 1H), 3.40-3.23 (m, 1H), 3.12 (br t, J=10.1 Hz, 1H), 3.04-2.89 (m, 1H), 1.90 (br s, 1H), 1.59 (br s, 2H), 1.47 (s, 9H).

Step 2: To a solution of tert-butyl 4-(benzylamino)-3,3-difluoropiperidine-1-carboxylate (6.5 g, 19.9 mmol) in MeOH (20 mL) was added palladium/C (10%, 0.65 g, 0.61 mmol) under $H_2$ atmosphere. The mixture was degassed and backfilled with $H_2$ (three times). The resulting mixture was stirred under $H_2$ (pressure: 50 psi) at 25° C. for 10 h. The catalyst was filtered off, and the filtrate was concentrated under reduced pressure to give tert-butyl 4-amino-3,3-difluoropiperidine-1-carboxylate, which was used in the next step without further purification. $^1H$ NMR (400 MHz, MeOD-d4) δ 4.15 (br s, 1H), 3.96 (br d, J=14.1 Hz, 1H), 3.23 (br d, J=18.8 Hz, 1H), 2.92-3.14 (m, 2H), 1.81-1.94 (m, 1H), 1.49-1.56 (m, 1H), 1.46 (s, 9H).

Step 3: A mixture of tert-butyl 4-amino-3,3-difluoropiperidine-1-carboxylate (1.5 g, 6.35 mmol), methyl 2-chloroisonicotinate (1.31 g, 7.62 mmol), RuPhos G3 ((2-Dicyclohexylphosphino-2',6'-diisopropoxy-1,1'-biphenyl)[2-(2'-amino-1,1'-biphenyl)]palladium(II) methanesulfonate) (0.53 g, 0.635 mmol) and $Cs_2CO_3$ (4.14 g, 12.7 mmol) in 1,4-dioxane (15 mL) was stirred at 100° C. for 5 h. The mixture was then concentrated under reduced pressure. The residue was purified by flash silica gel chromatography (ethyl acetate/pet. ether gradient) to give methyl 2-((1-(tert-butoxycarbonyl)-3,3-difluoropiperidin-4-yl)amino)isonicotinate. MS: 372 (M+1).

Step 4: A mixture of methyl 2-((1-(tert-butoxycarbonyl)-3,3-difluoropiperidin-4-yl)amino)isonicotinate (2.3 g, 6.19 mmol) in 4 M HCl in 1,4-dioxane (50 mL) was stirred at 20° C. for 0.5 h. The mixture was concentrated under reduced pressure to give methyl 2-((3,3-difluoropiperidin-4-yl)amino)isonicotinate hydrochloride, which was used in the next step without further purification. MS: 272 (M+1).

Step 5: To a mixture of methyl 2-((3,3-difluoropiperidin-4-yl)amino)isonicotinate hydrochloride (1.9 g, 6.17 mmol) and $Et_3N$ (2.58 mL, 18.52 mmol) in DCM (20 mL) was added dropwise acetic anhydride (0.756 g, 7.41 mmol) at 20° C. The mixture was stirred at 20° C. for 1 h. The mixture was then concentrated under reduced pressure. The residue was purified by flash silica gel chromatography (ethyl acetate/pet. ether gradient) to give methyl 2-((1-acetyl-3,3-difluoropiperidin-4-yl)amino)isonicotinate. MS: 314 (M+1).

Step 6: A mixture of methyl 2-((1-acetyl-3,3-difluoropiperidin-4-yl)amino)isonicotinate (1.5 g, 4.79 mmol) and lithium hydroxide hydrate (0.502 g, 12.0 mmol) in MeOH (20 mL) and water (10 mL) was stirred at 20° C. for 2 h. The mixture was concentrated under reduced pressure to give lithium 2-((1-acetyl-3,3-difluoropiperidin-4-yl)amino)isonicotinate, which was used without further purification. MS: 300 (M+1).

Intermediate 5: 2-((1-acetylpiperidin-4-yl)amino)-5-chloroisonicotinic acid

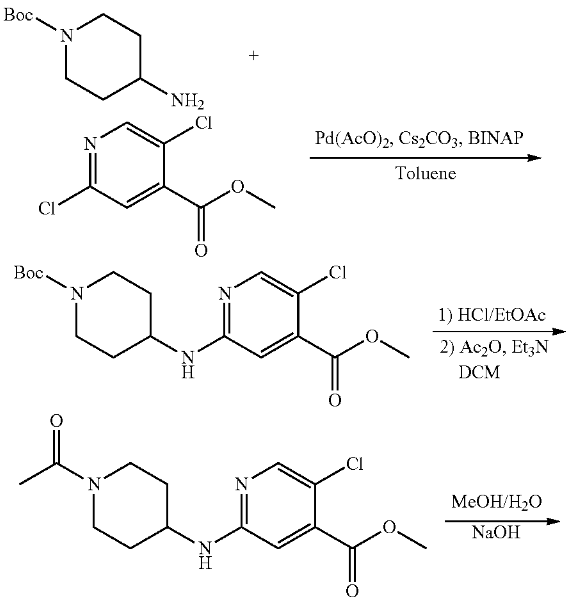

-continued

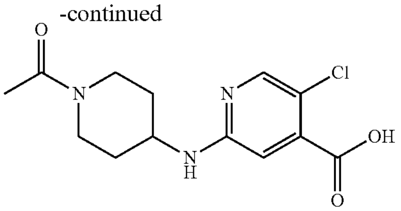

Step 1: To a solution of tert-butyl 4-aminopiperidine-1-carboxylate (4.6 g, 2.30 mmol) in toluene (20 mL) were added palladium(II) acetate (0.516 g, 2.30 mmol), $Cs_2CO_3$ (9.73 g, 29.9 mmol), 2,2'-bis(diphenylphosphino)-1,1'-binaphthalene (1.43 g, 2.30 mmol) and methyl 2,5-dichloroisonicotinate (4.50 g, 21.8 mmol) at 10° C. under $N_2$ (degassed and backfilled with $N_2$ three times). The reaction mixture was stirred at 90° C. for 10 h. Saturated aqueous NaCl solution (50 mL) was added to the mixture, and the resultant mixture was extracted with EtOAc (30 mL×3). The combined organic layers were dried over anhydrous $Na_2SO_4$, filtered, and the filtrate was evaporated under reduced pressure. The resulting residue was purified by flash silica gel chromatography (EtOAc/petroleum ether gradient) to give methyl 2-((1-(tert-butoxycarbonyl)piperidin-4-yl)amino)-5-chloroisonicotinate. MS: 370 (M+1). $^1$H NMR (400 MHz, $CD_3Cl$) δ 8.11 (s, 1H), 6.71 (s, 1H), 4.64 (br d, J=7.9 Hz, 1H), 4.04 (br s, 2H), 3.92 (s, 3H), 3.85-3.69 (m, 1H), 2.93 (br t, J=11.8 Hz, 2H), 2.07-1.94 (m, 2H), 1.46 (s, 9H), 1.40-1.26 (m, 2H).

Step 2: A mixture of methyl 2-((1-(tert-butoxycarbonyl)piperidin-4-yl)amino)-5-chloroisonicotinate (3.6 g, 9.73 mmol) in HCl in dioxane (1M, 30 mL) was stirred at 10° C. for 1 h. The mixture was concentrated under reduced pressure to afford methyl 5-chloro-2-(piperidin-4-ylamino)isonicotinate hydrochloride, which was used in the next step without further purification. $^1$H NMR (400 MHz, DMSO-$d_6$) δ 9.19 (br s, 2H), 8.09 (s, 1H), 7.11 (s, 1H), 4.10-3.94 (m, 1H), 3.86 (s, 3H), 3.28 (br d, J=12.7 Hz, 2H), 3.05-2.84 (m, 2H), 2.04 (br dd, J=3.4, 13.7 Hz, 2H), 1.61-1.85 (m, 2H).

Step 3: To a solution of methyl 5-chloro-2-(piperidin-4-ylamino)isonicotinate hydrochloride (2.9 g, 9.47 mmol) and TEA (3.96 mL, 28.4 mmol) in $CH_2Cl_2$ (16 mL) was added acetic anhydride (0.967 g, 9.47 mmol) at 0° C. The resulting mixture was stirred at 0° C. for 1.5 h. Saturated aqueous $NaHCO_3$ (50 mL) was added to the mixture, and the resultant mixture was extracted with DCM (30 mL×3). The combined organic layers were dried over anhydrous sodium sulfate, filtered, and the filtrate was evaporated under reduced pressure. The resulting residue was purified by flash silica gel chromatography (EtOAc/petroleum ether gradient) to give methyl 2-((1-acetylpiperidin-4-yl)amino)-5-chloroisonicotinate. MS: 312 (M+1). $^1$H NMR (400 MHz, $CD_3OD$) δ 8.02 (s, 1H), 6.81 (s, 1H), 4.46-4.33 (m, 1H), 4.05-3.85 (m, 5H), 3.29-3.22 (m, 1H), 2.98-2.81 (m, 1H), 2.18-1.92 (m, 5H), 1.55-1.28 (m, 2H).

Step 4: To a solution of methyl 2-((1-acetylpiperidin-4-yl)amino)-5-chloroisonicotinate (2.35 g, 7.54 mmol) in MeOH (30 mL) and water (2 mL) was added lithium hydroxide hydrate (0.443 g, 10.55 mmol). The mixture was stirred at 15° C. for 15 h. The mixture was then acidified with concentrated HCl to pH~2 and concentrated under reduced pressure to afford 2-((1-acetylpiperidin-4-yl)amino)-5-chloroisonicotinic acid. MS: 298 (M+1). $^1$H NMR (400 MHz, $CD_3OD$) δ 7.87 (s, 1H), 6.54 (s, 1H), 4.39 (br dd, J=1.5, 13.4 Hz, 1H), 3.99-3.81 (m, 2H), 3.28-3.21 (m, 1H), 2.97-2.82 (m, 1H), 2.14-1.92 (m, 5H), 1.50-1.27 (m, 2H).

TABLE 2

The following intermediate was prepared using a similar procedure as described in Intermediate 5.

| Intermediate # | Structure | Compound Name | Exact Mass [M + 1] |
|---|---|---|---|
| 6 | 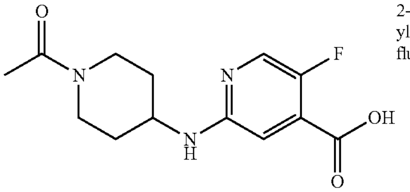 | 2-((l-acetylpiperidin-4-yl)amino)-5-fluoroisonicotinic acid | 282 |

Intermediate 7: 5-cyclopropyl-4-methyl-2-pyrimidinamine

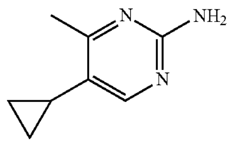

Step 1: A mixture of NBS (8.15 g, 45.8 mmol) and 4-methylpyrimidin-2-amine (5.0 g, 46 mmol) in $CHCl_3$ (100 mL) was stirred for 24 h at 15° C. The mixture was concentrated, treated with water (100 mL), and stirred for 30 min. The precipitate was filtered, washed with water, and dried to give 5-bromo-4-methylpyrimidin-2-amine. $^1$H NMR (400 MHz, DMSO-$d_6$) δ 8.19 (s, 1H), 6.76 (br s, 2H), 2.29 (s, 3H).

Step 2: To a solution of 5-bromo-4-methylpyrimidin-2-amine (2.0 g, 11 mmol) in THF (15 ml) and water (3 ml) were added $K_2CO_3$ (4.41 g, 31.9 mmol), cyclopropylboronic acid (4.57 g, 53.2 mmol) and Pd(dppf)$Cl_2$ (0.778 g, 1.06 mmol). The mixture was degassed and backfilled with $N_2$ (three times). The reaction was heated to 80° C. for 12 h. The mixture was concentrated and purified by flash silica gel chromatography (0-45% ethyl acetate/pet. ether) to give 5-cyclopropyl-4-methylpyrimidin-2-amine. MS: 150 (M+1).

Intermediate 8: 5-(2-methylcyclopropyl)pyrimidin-2-amine

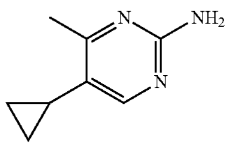

Step 1: To a mixture of 5-bromopyrimidin-2-amine (5.0 g, 29 mmol) in THF (100 mL) was added NaH (60%, 2.87 g, 71.8 mmol) at 0° C. The mixture was stirred at 0° C. for 0.5 h, treated with 1-(chloromethyl)-4-methoxybenzene (9.00 g, 57.5 mmol), and stirred at 15° C. for 12 h. The mixture was treated with a saturated aqueous $NH_4Cl$ solution (100 mL) and extracted with EtOAc (100 mL). The organic layer was concentrated and purified by silica gel chromatography (0-30% ethyl acetate in pet. ether) to give 5-bromo-N,N-bis (4-methoxybenzyl)pyrimidin-2-amine. MS: 414 and 416 (M+1). $^1$H NMR (400 MHz, $CDCl_3$) δ 8.32 (s, 2H), 7.15 (br d, J=8.3 Hz, 4H), 6.84 (br d, J=8.3 Hz, 4H), 4.72 (s, 4H), 3.79 (s, 6H).

Step 2: A mixture of $Cs_2CO_3$ (9.44 g, 29.0 mmol), $PdCl_2$(dppf) (0.706 g, 0.965 mmol), 4,4,5,5-tetramethyl-2-(2-methylcyclopropyl)-1,3,2-dioxaborolane (3.52 g, 19.3 mmol) and 5-bromo-N,N-bis(4-methoxybenzyl)pyrimidin-2-amine (4.0 g, 9.7 mmol) in dioxane (40 mL) and water (10 mL) was degassed and backfilled with $N_2$ (three times). The mixture was heated to 95° C. for 12 h. The mixture was cooled to room temperature, treated with water (100 mL), and extracted with EtOAc (100 mL). The organic layer was washed with brine, dried over $Na_2SO_4$, concentrated, and purified by column chromatography on silica gel (Pet. ether/ethyl acetate: 100/1 to 5/1, v/v) to give N,N-bis(4-methoxybenzyl)-5-(2-methylcyclopropyl)pyrimidin-2-amine. MS: 390 (M+1). $^1$H NMR (400 MHz, $CD_3OD$) δ 8.08 (s, 2H), 7.08 (d, J=8.3 Hz, 4H), 6.80 (d, J=8.3 Hz, 4H), 4.68 (s, 4H), 3.73 (s, 6H), 1.43 (td, J=4.6, 8.9 Hz, 1H), 1.17 (d, J=5.7 Hz, 3H), 1.02-0.93 (m, 1H), 0.85-0.78 (m, 1H), 0.70-0.63 (m, 1H).

Step 3: A mixture of N,N-bis(4-methoxybenzyl)-5-(2-methylcyclopropyl)pyrimidin-2-amine (3.0 g, 7.7 mmol) in DCM (10 mL), TFA (10 mL) and $CF_3SO_3H$ (0.1 mL) was stirred at 15° C. for 48 h. The mixture was concentrated, treated with water (50 mL), and basified with $NH_3H_2O$ to pH~10. The mixture was extracted with DCM (50 mL×3). The combined organic layers were washed with brine (50 mL), dried over anhydrous $Na_2SO_4$, concentrated, and purified by column chromatography on silica gel (Pet. ether/ethyl acetate=100/1 to 1/3, v/v) to give 5-(2-methylcyclopropyl)pyrimidin-2-amine. MS: 150 (M+1). $^1$H NMR (400 MHz, $CDCl_3$) δ 8.03 (s, 2H), 5.00 (br s, 2H), 1.39 (td, J=4.6, 8.9 Hz, 1H), 1.17 (d, J=6.1 Hz, 3H), 01.01-0.90 (m, 1H), 00.83-0.74 (m, 1H), 0.68 (td, J=5.1, 8.7 Hz, 1H).

Intermediate 9: 5-(2,2-difluorocyclopropyl)pyrimidin-2-amine

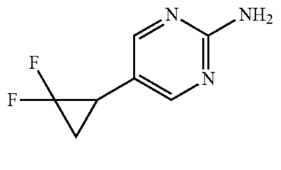 [SMILES: Nc1ncc(C2CC2(F)F)cn1]

Step 1: To a solution of 5-bromopyrimidin-2-amine (5 g, 28.7 mmol) in THF (30 mL) and water (4 mL) was added potassium vinyltrifluoroborate (3.85 g, 28.7 mmol), $Cs_2CO_3$ (28.1 g, 86 mmol) and $PdCl_2$(dppf) (4.21 g, 5.75 mmol). The reaction mixture was stirred at 85° C. for 2 h under $N_2$. LCMS showed the product was formed. The mixture was added water (40 mL) and extracted with EtOAc (30 ml*3). The combined organic layers were dried over anhydrous $Na_2SO_4$, filtered, and the filtrate was evaporated in vacuum to give the crude product which was purified by flash silica gel chromatography (ISCO®; 20 g SepaFlash® Silica Flash Column, eluent of ethyl acetate/pet. ether gradient @50 mL/min) to give 5-vinylpyrimidin-2-amine. MS: 122 (M+1).

Step 2: A mixture of tetrabutylammonium bromide (0.193 g, 0.598 mmol), 2-chloro-5-vinylpyrimidine (1.40 g, 9.96 mmol), and (bromodifluoromethyl)trimethylsilane (6.07 g, 29.9 mmol) in toluene (5 mL) was heated to 110° C. in a sealed tube for 2 h. After cooling to room temperature, the mixture was concentrated and purified by column chromatography on silica gel (Pet. ether/ethyl acetate=10/1 to 5/1, v/v) to give 2-chloro-5-(2,2-difluorocyclopropyl)pyrimidine.

$^1$H NMR (400 MHz, $CDCl_3$) δ 8.51 (s, 2H), 2.74-2.67 (m, 1H), 2.05-2.01 (m, 1H), 1.76-1.62 (m, 1H).

Step 3: A mixture of diphenylmethanimine (1.141 g, 6.30 mmol), XantPhos (0.304 g, 0.525 mmol), $Pd_2(dba)_3$ (0.480 g, 0.525 mmol), $Cs_2CO_3$ (5.13 g, 15.7 mmol), and 2-chloro-5-(2,2-difluorocyclopropyl)pyrimidine (1.0 g, 5.3 mmol) in dioxane (10 mL) was degassed and backfilled with $N_2$ (three times). The mixture was heated to 90° C. for 4 h. After cooling to room temperature, the mixture was filtered, and concentrated to give 5-(2,2-difluorocyclopropyl)-N-(diphenylmethylene)pyrimidin-2-amine. MS: 336 (M+1).

Step 4: A mixture of 5-(2,2-difluorocyclopropyl)-N-(diphenylmethylene)pyrimidin-2-amine (1.60 g, 4.77 mmol) in aqueous HCl solution (1 N) (10 mL) was stirred at 15° C. for 1 h. The mixture was concentrated and purified by reverse phase MPLC (C18, 10-50% $H_2O$ (0.5% TFA)/MeOH) to give 5-(2,2-difluorocyclopropyl)pyrimidin-2-amine. MS: 172 (M+1). $^1$H NMR (400 MHz, $CD_3OD$) δ 8.17 (s, 2H), 2.70 (dt, J=8.1, 12.2 Hz, 1H), 2.01-1.75 (m, 1H), 1.74-1.61 (m, 1H).

Intermediate 10: 5-cyclopropylpyrazin-2-amine

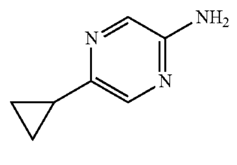

Step 1: To a mixture of 5-bromopyrazin-2-amine (10.0 g, 57.5 mmol) in DMF (120 mL) was added NaH (60%, 6.44 g, 161 mmol) at 0° C. The mixture was stirred at 0° C. for 0.5 h, treated with 1-(chloromethyl)-4-methoxybenzene (22.50 g, 144 mmol), and stirred at 20° C. for 30 min. The mixture was treated with a saturated aqueous $NH_4Cl$ solution (800 mL) and extracted with EtOAc (300 mL×3). The combined organic layers were concentrated and purified by silica gel chromatography (10% ethyl acetate in pet. ether) to give 5-bromo-N,N-bis(4-methoxybenzyl)pyrazin-2-amine. MS: 414 and 416 (M+1). $^1$H NMR (400 MHz, $CDCl_3$) δ 8.15 (d, J=1.3 Hz, 1H), 7.70 (d, J=1.3 Hz, 1H), 7.13 (d, J=8.3 Hz, 4H), 6.85 (d, J=8.8 Hz, 4H), 4.68 (s, 4H), 3.79 (s, 6H).

Step 2: A mixture of 5-bromo-N,N-bis(4-methoxybenzyl) pyrazin-2-amine (12.0 g, 29.0 mmol), cyclopropylboronic acid (4.98 g, 57.9 mmol), $Cs_2CO_3$ (28.3 g, 87 mmol), and $PdCl_2$(dppf) (2.12 g, 2.90 mmol) in 1,4-dioxane (120 mL) and water (30 mL) was heated to 100° C. under $N_2$ for 10 h. The mixture was treated with water and extracted with EtOAc (150 mL×3). The combined organics were washed with brine, dried over sodium sulfate, concentrated, and purified by silica gel chromatography (25% ethyl acetate in pet. ether) to give 5-cyclopropyl-N,N-bis(4-methoxybenzyl) pyrazin-2-amine. MS: 376 (M+1). $^1$H NMR (400 MHz, $CDCl_3$) δ 8.00 (d, J=1.3 Hz, 1H), 7.82 (d, J=1.3 Hz, 1H), 7.12-7.15 (m, 4H), 6.82-6.85 (m, 4H), 4.67 (s, 4H), 3.78 (s, 6H), 1.89-1.98 (m, 1H), 0.83-0.91 (m, 4H).

Step 3: A solution of 5-cyclopropyl-N,N-bis(4-methoxybenzyl)pyrazin-2-amine (6.0 g, 16 mmol) in DCM (60 mL) and TFA (15 mL) was stirred at 20° C. for 10 h. The mixture was treated with $H_2O$ (300 mL) and basified to pH 9 with sat. aqueous $NaHCO_3$. The mixture was extracted with EtOAc (150 mL×3). The combined organics were dried over $Na_2SO_4$, concentrated, and purified by silica gel chromatography (45% ethyl acetate in pet. ether) to give 5-cyclopropylpyrazin-2-amine. MS: 136 (M+1).

Intermediate 11:
5-(1-methoxyethyl)pyrimidin-2-amine

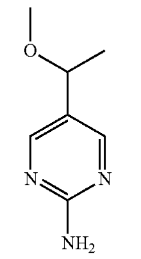

Step 1: A mixture of (2,4-dimethoxyphenyl)methanamine (75.0 g, 451 mmol) and 2,4-dimethoxybenzaldehyde (50.0 g, 301 mmol) in THF (600 mL) was stirred at 17° C. for 2 h. The mixture was treated with sodium triacetoxyborohydride (77.0 g, 361 mmol) at 17° C. and stirred at 17° C. for 12 h. The mixture was treated with $NaBH_4$ (11.38 g, 301 mmol) and stirred at 17° C. for 2 h. The mixture was treated with sat. aqueous $NaHCO_3$ (1500 mL) and extracted with EtOAc (300 mL×3). The combined organic layers were washed with brine (1000 mL), dried over anhydrous sodium sulfate, concentrated, and purified by silica gel chromatography (0-100% ethyl acetate in petroleum ether) to give bis(2,4-dimethoxybenzyl)amine. MS: 318 (M+1). $^1$H NMR (500 MHz, $CDCl_3$) δ 7.28 (s, 1H), 7.26 (s, 1H), 6.54 (s, 3H), 6.53 (d, J=2.4 Hz, 1H), 3.90 (d, J=3.7 Hz, 12H), 3.81 (s, 4H), 1.96 (br d, J=2.8 Hz, 1H). LCMS: 318 (M+1).

Step 2: A mixture of 5-bromo-2-chloropyrimidine (3.0 g, 16 mmol), bis(2,4-dimethoxybenzyl)amine (5.22 g, 16.4 mmol) and $Cs_2CO_3$ (15.16 g, 46.5 mmol) in thietane 1,1-dioxide (40 mL) was heated to 170° C. for 1 h. The mixture was treated with water (600 mL) and extracted with EtOAc (100 mL×3). The combined organic layers were washed with brine (600 mL), dried over anhydrous sodium sulfate, concentrated, and purified by silica gel chromatography (0-4% ethyl acetate in petroleum ether) to give 5-bromo-N,N-bis(2,4-dimethoxybenzyl)pyrimidin-2-amine. MS: 474 and 476 (M+1). $^1$H NMR (500 MHz, $CDCl_3$) δ 8.55 (s, 2H), 7.27 (d, J=8.4 Hz, 2H), 6.70 (d, J=2.3 Hz, 2H), 6.66 (dd, J=2.3, 8.2 Hz, 2H), 5.03 (s, 4H), 4.04 (s, 6H), 4.00 (s, 6H).

Step 3: To solution of 5-bromo-N,N-bis(2,4-dimethoxybenzyl)pyrimidin-2-amine (3.0 g, 6.3 mmol) in THF (60 mL) was added n-BuLi (2.5 M in cyclohexanes, 3.04 mL, 7.59 mmol) at −78° C. The mixture was stirred at −78° C. for 15 min. The mixture was treated with acetaldehyde (1.25 g, 28.5 mmol) at −78° C. The mixture was stirred at −78° C. for 10 min, treated with water (100 mL), and extracted with EtOAc (60 mL×3). The combined organic layers were washed with brine (100 mL), dried over anhydrous sodium sulfate, concentrated, and purified by silica gel chromatography (0-24% ethyl acetate in petroleum ether) to give 1-(2-(bis(2,4-dimethoxybenzyl)amino)pyrimidin-5-yl)ethanol. MS: 440 (M+1). $^1$H NMR (400 MHz, $CDCl_3$) δ 8.34 (s, 2H), 7.02 (s, 1H), 7.00 (s, 1H), 6.43 (d, J=2.2 Hz, 2H), 6.40 (d, J=2.6 Hz, 1H), 6.37 (d, J=2.2 Hz, 1H), 4.74-4.84 (m, 5H), 3.77 (s, 6H), 3.74 (s, 6H), 1.72 (d, J=3.5 Hz, 1H), 1.50 (d, J=6.6 Hz, 3H).

Step 4: To a solution of 1-(2-(bis(2,4-dimethoxybenzyl) amino)pyrimidin-5-yl)ethanol (2.0 g, 4.6 mmol) in ACN (40 mL) was added NaH (60%, 0.218 g, 5.46 mmol) followed by MeI (3.06 mL, 49.0 mmol) at 25° C. The mixture was stirred at 25° C. for 12 h and treated with water (50 mL). The mixture was concentrated and extracted with EtOAc (30 mL×3). The combined organic layers were washed with brine (50 mL), dried over anhydrous sodium sulfate, concentrated, and purified by silica gel chromatography (0-20% ethyl acetate in petroleum ether) to give N,N-bis(2,4-dimethoxybenzyl)-5-(1-methoxyethyl)pyrimidin-2-amine. MS: 454 (M+1). $^1$H NMR (500 MHz, $CDCl_3$) δ 8.28 (s, 2H), 7.04 (s, 1H), 7.02 (s, 1H), 6.43 (d, J=2.1 Hz, 2H), 6.40 (d, J=2.1 Hz, 1H), 6.39 (d, J=2.3 Hz, 1H), 4.81 (d, J=1.8 Hz, 4H), 4.13-4.19 (m, 1H), 3.78 (s, 6H), 3.74 (s, 6H), 3.19-3.25 (m, 3H), 1.44 (d, J=6.4 Hz, 3H).

Step 5: A mixture of N,N-bis(2,4-dimethoxybenzyl)-5-(1-methoxyethyl)pyrimidin-2-amine (1.65 g, 3.64 mmol) in DCM (40 mL) and TFA (18 mL) was stirred at 25° C. for 2 h. The mixture was poured slowly into sat. aqueous $NaHCO_3$ (500 mL). The mixture was extracted with EtOAc (100 mL×5). The combined organic layers were concentrated and purified by reversed MPLC (C18, 0-15% $H_2O$ (0.5‰ TFA)/MeOH) to give 5-(1-methoxyethyl)pyrimidin-2-amine. MS: 154 (M+1). $^1$H NMR (500 MHz, $CD_3OD$) δ 8.40 (s, 1H), 8.42-8.36 (m, 1H), 4.34 (q, J=6.4 Hz, 1H), 3.29 (s, 3H), 1.46 (d, J=6.4 Hz, 3H).

Intermediate 12: 4-butoxy-3-(2,2,2-trifluoroethyl) quinoline-7-carboxylic acid

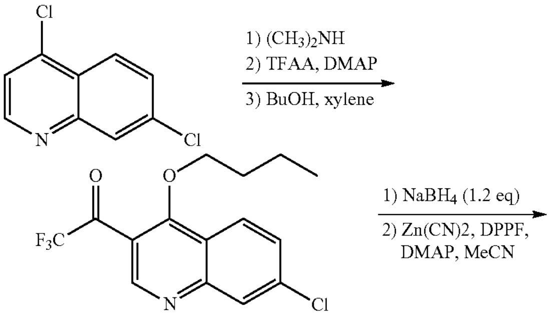

-continued

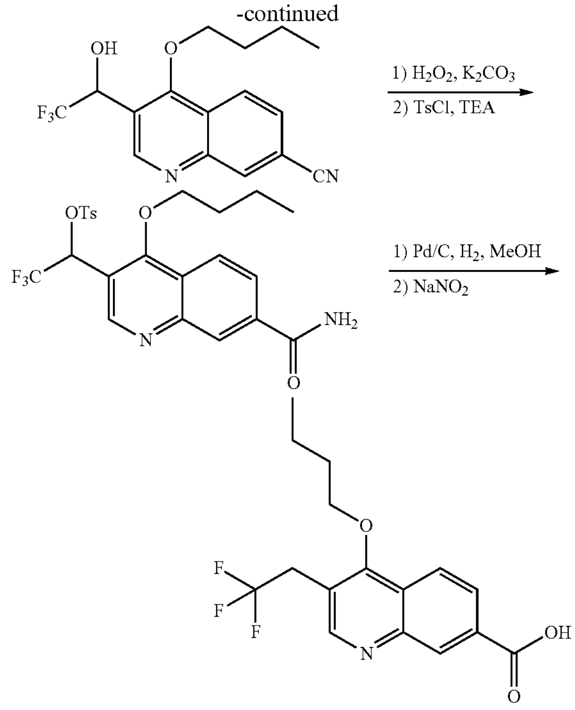

Step 1: A mixture of 4,7-dichloroquinoline (5 g, 25.2 mmol) and dimethylamine (24.1 g, 177 mmol) (33% Wt, in water) in acetonitrile (100 mL) was stirred at 50° C. for 48 h. Sat. aqueous $Na_2CO_3$ (200 mL) was added to the mixture, and the resultant mixture was concentrated under reduced pressure. The aqueous layer was extracted by EtOAc (100 mL×3). The combined organic layers were washed with brine (200 mL), dried over anhydrous sodium sulfate, filtered, and the filtrate was concentrated under reduced pressure. The residue was purified by flash silica gel chromatography (ethyl acetate/pet. ether gradient) to give 7-chloro-N,N-dimethylquinolin-4-amine. MS: 207 (M+1). $^1$H NMR (400 MHz, $CDCl_3$) δ 8.62 (d, J=5.3 Hz, 1H), 8.03-7.92 (m, 2H), 7.37 (dd, J=2.2, 9.0 Hz, 1H), 6.71 (d, J=5.3 Hz, 1H), 3.01 (s, 6H).

Step 2: To a solution of DMAP (8.51 g, 69.7 mmol) in xylene (80 mL) was added TFAA (9.84 mL, 69.7 mmol) at 15° C. The mixture was stirred at 15° C. for 30 min. To the mixture was added 7-chloro-N, N-dimethylquinolin-4-amine (4.8 g, 23.2 mmol) in xylene (40 mL) at 15° C. The resultant mixture was stirred at 130° C. for 12 h. After evaporation of solvent under reduced pressure, dichloromethane (100 mL) was added. The organic phase was washed with a saturated aqueous solution of sodium carbonate (200 mL), dried over anhydrous sodium sulfate, filtered, and the filtrate was concentrated under reduced pressure. The residue was purified by flash silica gel chromatography (ethyl acetate/pet. ether gradient) to give 1-(7-chloro-4-(dimethylamino)quinolin-3-yl)-2,2,2-trifluoroethanone. MS: 303 (M+1). $^1$H NMR (400 MHz, $CD_3Cl$) δ 8.95 (d, J=1.3 Hz, 1H), 8.12 (d, J=9.2 Hz, 1H), 8.04 (d, J=2.2 Hz, 1H), 7.47 (dd, J=2.2, 9.2 Hz, 1H), 3.13 (s, 6H).

Step 3: A mixture of 1-(7-chloro-4-(dimethylamino)quinolin-3-yl)-2,2,2-trifluoroethanone (3.0 g, 9.9 mmol) and butan-1-ol (7.35 g, 99 mmol) in xylene (60 mL) was stirred at 130° C. for 96 h. The mixture was concentrated under reduced pressure to give 1-(4-butoxy-7-chloroquinolin-3-yl)-2, 2, 2-trifluoroethane-1,1-diol, which was used in the next step without further purification. MS: 350 (M+1).

Step 4: To a solution of 1-(4-butoxy-7-chloroquinolin-3-yl)-2,2,2-trifluoroethane-1,1-diol (3.0 g, 8.6 mmol) in MeOH (100 mL) was added $NaBH_4$ (0.649 g, 17.2 mmol) at 25° C. The mixture was stirred at 25° C. for 0.5 h. The mixture was quenched with water (100 mL) and concentrated under reduced pressure. The mixture was extracted with EtOAc (50 mL×3). The combined organic layers were washed with brine (100 mL), dried over anhydrous sodium sulfate, filtered, and the filtrate was concentrated under reduced pressure. The residue was purified by flash silica gel chromatography (ethyl acetate/petroleum ether gradient) to give 1-(4-butoxy-7-chloroquinolin-3-yl)-2,2,2-trifluoroethanol. MS: 334 (M+1). $^1$H NMR (400 MHz, $CDCl_3$) δ 8.93 (s, 1H), 8.03 (d, J=2.2 Hz, 1H), 7.95 (d, J=8.8 Hz, 1H), 7.51 (dd, J=2.0, 9.0 Hz, 1H), 5.60 (q, J=7.0 Hz, 1H), 4.75 (br s, 1H), 4.21-4.03 (m, 2H), 1.98-1.85 (m, 2H), 1.59-1.53 (m, 2H), 1.01 (t, J=7.24 Hz, 3H).

Step 5: A mixture of 1-(4-butoxy-7-chloroquinolin-3-yl)-2,2,2-trifluoroethanol (280 mg, 0.84 mmol), nickel(II) chloride hexahydrate (19.9 mg, 0.084 mmol), $Zn(CN)_2$ (158 mg, 1.34 mmol), zinc (219 mg, 3.36 mmol), dppf (55.8 mg, 0.101 mmol) and DMAP (205 mg, 1.68 mmol) in ACN (10 mL) was degassed and backfilled with $N_2$ (three times). The mixture was stirred under $N_2$ atmosphere at 80° C. for 3 h. The reaction mixture was filtered, and the filtrate was concentrated under reduced pressure. The residue was purified by flash silica gel chromatography (ethyl acetate/pet. ether gradient) to give 4-butoxy-3-(2, 2, 2-trifluoro-1-hydroxyethyl)quinoline-7-carbonitrile. MS: 325 (M+1). $^1$H NMR (400 MHz, $CDCl_3$) δ 9.13 (s, 1H), 8.47 (d, J=1.3 Hz, 1H), 8.15 (d, J=8.3 Hz, 1H), 7.73 (dd, J=1.5, 8.6 Hz, 1H), 5.65 (br s, 1H), 4.22-4.10 (m, 2H), 4.01 (br s, 1H), 2.01-1.87 (m, 2H), 1.63-1.55 (m, 2H), 1.03 (t, J=7.2 Hz, 3H).

Step 6: To a solution of 4-butoxy-3-(2,2,2-trifluoro-1-hydroxyethyl)quinoline-7-carbonitrile (170 mg, 0.524 mmol) and $K_2CO_3$ (145 mg, 1.05 mmol) in DMSO (5 mL) was added $H_202$ (0.229 mL, 2.62 mmol) (35% Wt) at 25° C. The mixture was stirred at 25° C. for 15 min. The mixture was quenched with water (50 mL). To the aqueous layer was added sat. aqueous $Na_2SO_3$ (200 mL) slowly. The mixture was extracted with EtOAc (30 mL×3). The combined organic layers were washed with brine (50 mL), dried over anhydrous sodium sulfate, filtered, and the filtrate was concentrated under reduced pressure to give 4-butoxy-3-(2,2,2-trifluoro-1-hydroxyethyl)quinoline-7-carboxamide, which was used in the next step without further purification. MS: 343 (M+1). $^1$H NMR (400 MHz, DMSO-$d_6$) δ 9.01 (s, 1H), 8.59 (d, J=0.9 Hz, 1H), 8.32 (s, 1H), 8.19-8.14 (m, 1H), 8.11-8.06 (m, 1H), 7.64 (s, 1H), 7.24 (d, J=5.7 Hz, 1H), 5.64-5.48 (m, 1H), 4.16 (t, J=6.4 Hz, 2H), 1.93-1.78 (m, 2H), 1.53 (sxt, J=7.5 Hz, 2H), 0.97 (t, J=7.5 Hz, 3H).

Step 7: To a solution of 4-butoxy-3-(2,2,2-trifluoro-1-hydroxyethyl)quinoline-7-carboxamide (200 mg, 0.584 mmol) and TEA (0.244 mL, 1.75 mmol) in DCM (5 mL) and DMF (3 mL) was added TsCl (123 mg, 0.643 mmol) at 25° C. The mixture was stirred at 25° C. for 12 h. To the mixture was added pyridine (0.047 mL, 0.584 mmol), DMAP (71.4 mg, 0.584 mmol) and TsCl (123 mg, 0.643 mmol) at 25° C. The mixture was stirred at 25° C. for 1 h. The mixture was concentrated under reduced pressure. The mixture was quenched with water (30 mL). The mixture was extracted with EtOAc (20 mL×3). The combined organic layers were washed with brine (30 mL), dried over anhydrous sodium sulfate, filtered, and the filtrate was concentrated under reduced pressure. The residue was purified by Preparative TLC (ethyl acetate/petroleum ether) to give 1-(4-butoxy-7-carbamoylquinolin-3-yl)-2,2,2-trifluoroethyl 4-methylbenzenesulfonate. MS: 497 (M+1).

Step 8: To a solution of 1-(4-butoxy-7-carbamoylquinolin-3-yl)-2,2,2-trifluoroethyl 4-methylbenzenesulfonate (220 mg, 0.443 mmol) in MeOH (20 mL) was added Pd—C (10% Wt) (200 mg, 0.188 mmol) under $N_2$ atmosphere. The mixture was degassed and backfilled with $H_2$ (three times). The resulting mixture was stirred under $H_2$ (pressure: 15 psi) at 25° C. for 1 h. The catalyst was filtered off, and the filtrate was concentrated under reduced pressure to give 4-butoxy-3-(2,2,2-trifluoroethyl)quinoline-7-carboxamide. MS: 327 (M+1). $^1$H NMR (400 MHz, $CDCl_3$) δ 8.89 (s, 1H), 8.46 (s, 1H), 8.17-8.12 (m, 1H), 8.10-8.05 (m, 1H), 6.32 (s, 1H), 5.75 (s, 1H), 4.15 (t, J=6.8 Hz, 2H), 3.67 (q, J=10.5 Hz, 2H), 2.00-1.91 (m, 2H), 1.67-1.62 (m, 2H), 1.05 (t, J=7.2 Hz, 3H).

Step 9: To a solution of 4-butoxy-3-(2,2,2-trifluoroethyl)quinoline-7-carboxamide (120 mg, 0.368 mmol) in $H_2SO_4$ (70% Wt) (10 mL) was added sodium nitrite (76 mg, 1.10 mmol) at 25° C. The mixture was stirred at 40° C. for 30 min. The mixture was quenched with water (40 mL). The mixture was extracted with DCM (10 mL×15). The combined organic layers were dried over anhydrous sodium sulfate, filtered, and the filtrate was concentrated under reduced pressure to give 4-butoxy-3-(2,2,2-trifluoroethyl)quinoline-7-carboxylic acid. MS: 328 (M+1). $^1$H NMR (400 MHz, DMSO-$d_6$) δ 9.01 (s, 1H), 8.61 (s, 1H), 8.25 (d, J=8.3 Hz, 1H), 8.13 (dd, J=1.3, 8.8 Hz, 1H), 4.22 (t, J=6.6 Hz, 2H), 3.93 (q, J=11.3 Hz, 2H), 1.92-1.80 (m, 2H), 1.59-1.47 (m, 3H), 0.97 (t, J=7.45 Hz, 3H).

Intermediate 13: 6-(dimethylcarbamoyl)imidazo[1,2-a]pyridine-2-carboxylic acid

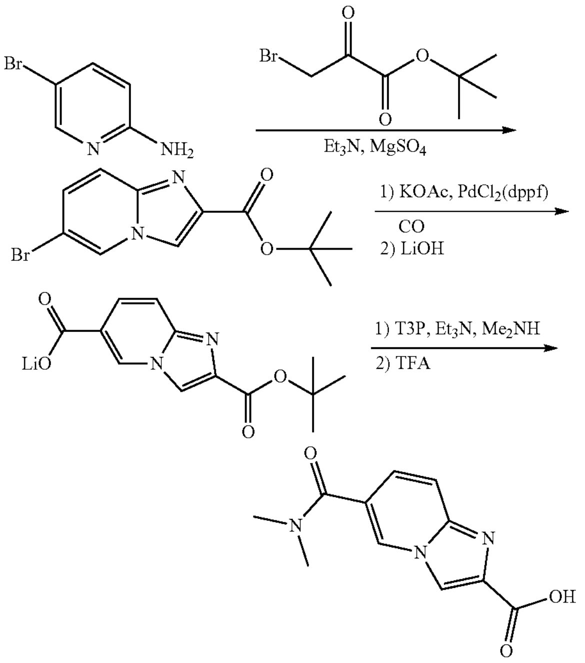

Step 1: To a mixture of 5-bromopyridin-2-amine (1.0 g, 5.8 mmol) in 1,4-dioxane (100 mL) was added $MgSO_4$ (2.09 g, 17.3 mmol) and tert-butyl 3-bromo-2-oxopropanoate (1.93 g, 8.67 mmol) at 25° C. The mixture was stirred at 80° C. for 12 h. After cooling to 25° C., TEA (1.21 mL, 8.67 mmol) was added and the mixture was stirred at 25° C. for 1 h. The precipitate was filtered off, and the filtrate was concentrated under reduced pressure. The residue was purified by flash silica gel chromatography (ethyl acetate/pet. ether gradient) to give tert-butyl 6-bromoimidazo[1,2-a]pyridine-2-carboxylate. MS: 297 and 299 (M+1). $^1$H NMR (400 MHz, DMSO-$d_6$) δ 8.93-8.81 (m, 1H), 8.37 (s, 1H), 7.60 (d, J=9.7 Hz, 1H), 7.44 (dd, J=1.8, 9.7 Hz, 1H), 1.53 (s, 9H).

Step 2: A mixture of tert-butyl 6-bromoimidazo[1,2-a]pyridine-2-carboxylate (1.2 g, 4.0 mmol), $PdCl_2$(dppf) (0.355 g, 0.485 mmol) and AcOK (1.19 g, 12.1 mmol) in EtOH (30 mL) was degassed and backfilled with CO (three times). The mixture was stirred under CO (pressure: 50 psi) at 80° C. for 12 h. The mixture was concentrated under reduced pressure. The residue was purified by flash silica gel chromatography (ethyl acetate/petroleum ether gradient) to give 2-tert-butyl 6-ethyl imidazo[1,2-a]pyridine-2,6-dicarboxylate. MS: 291 (M+1).

Step 3: To a solution of 2-tert-butyl 6-ethyl imidazo[1,2-a]pyridine-2,6-dicarboxylate (80 mg, 0.28 mmol) in EtOH (2 mL) and water (1 mL) was added lithium hydroxide hydrate (23.1 mg, 0.551 mmol). The mixture was stirred at 20° C. for 2 h. The mixture was concentrated to remove EtOH and lyophilized to give lithium 2-(tert-butoxycarbonyl)imidazo[1,2-a]pyridine-6-carboxylate. MS: 263 (M+1).

Step 4: To a mixture of lithium 2-(tert-butoxycarbonyl)imidazo[1,2-a]pyridine-6-carboxylate (60 mg, 0.22 mmol) in DMF (5 mL) was added DIEA (0.117 mL, 0.671 mmol) and T3P® (214 mg, 0.336 mmol) (50% in DMF). The mixture was stirred at 20° C. for 5 min and dimethylamine (12.1 mg, 0.268 mmol) was added at 20° C. The resulting mixture was stirred at 20° C. for 1 h. $H_2O$ (20 mL) and EtOAc (10 mL) were added to the mixture. The aqueous layer was re-extracted with EtOAc (10 mL×3). The combined organic layers were washed with brine (10 mL), dried over anhydrous $Na_2SO_4$, filtered, and concentrated under reduced pressure. The residue was purified by preparative TLC (pet.ether: EtOAc) to give tert-butyl 6-(dimethylcarbamoyl)imidazo[1,2-a]pyridine-2-carboxylate. MS: 290 (M+1).

Step 5: To a solution of tert-butyl 6-(dimethylcarbamoyl)imidazo[1,2-a]pyridine-2-carboxylate (30 mg, 0.10 mmol) in DCM (3 mL) was added TFA (1 mL, 13.0 mmol). The reaction mixture was stirred at 20° C. for 12 h. The mixture was concentrated under reduced pressure to give 6-(dimethylcarbamoyl)imidazo[1,2-a]pyridine-2-carboxylic acid. MS: 234 (M+1).

Intermediate 14: 6-bromo-8-(hydroxymethyl)imidazo[1,2-a]pyridine-2-carboxylic acid

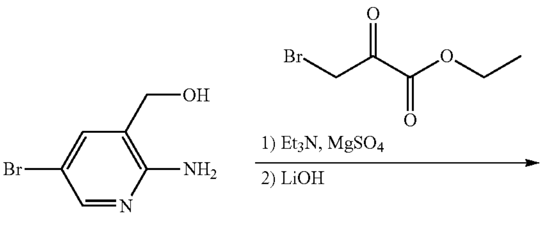

-continued

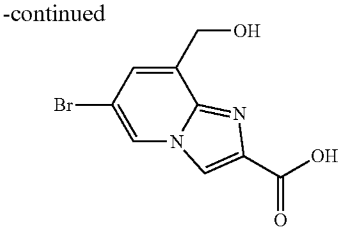

Step 1: To a mixture of (2-amino-5-bromopyridin-3-yl) methanol (1.0 g, 4.9 mmol) in 1,4-dioxane (80 mL) was added $MgSO_4$ (1.78 g, 14.8 mmol) and ethyl 3-bromo-2-oxopropanoate (2.06 g, 7.39 mmol) at 25° C. The mixture was stirred at 80° C. for 12 h. After cooling to 25° C., TEA (0.824 mL, 5.91 mmol) was added, and the mixture was stirred at 25° C. for 1 h. The precipitate was filtered off, and the filtrate was concentrated under reduced pressure. The residue was washed with EtOAc (50 mL) and filtered to give crude solid product, ethyl 6-bromo-8-(hydroxymethyl)imidazo[1,2-a]pyridine-2-carboxylate. MS: 299 and 301 (M+1). $^1H$ NMR (400 MHz, DMSO-$d_6$) δ 8.83-8.76 (m, 1H), 8.48 (s, 1H), 7.35 (d, J=1.8 Hz, 1H), 5.58 (t, J=5.7 Hz, 1H), 4.82 (d, J=5.7 Hz, 2H), 4.30 (q, J=7.2 Hz, 2H), 1.30 (t, J=7.2 Hz, 3H).

Step 2: To a mixture of ethyl 6-bromo-8-(hydroxymethyl) imidazo[1,2-a]pyridine-2-carboxylate (100 mg, 0.334 mmol) in ethanol (3 mL) was added lithium hydroxide hydrate (28.1 mg, 0.669 mmol) in water (1 mL) at 25° C. The mixture was stirred at 25° C. for 2 h. The mixture was concentrated under reduced pressure to give 6-bromo-8-(hydroxymethyl)imidazo[1,2-a]pyridine-2-carboxylic acid. MS: 271 and 273 (M+1).

Intermediate 15: 6-bromo-8-iodoimidazo[1,2-a]pyridine-2-carboxylic acid

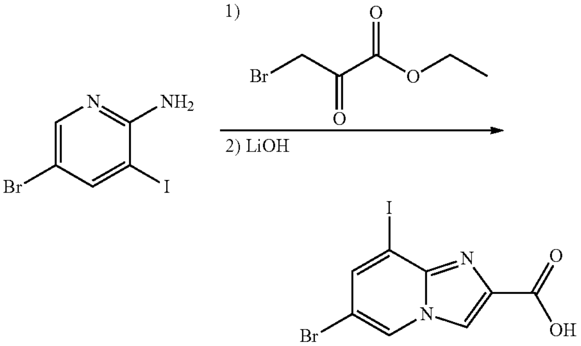

Step 1: To a solution of 5-bromo-3-iodopyridin-2-amine (500 mg, 1.67 mmol) in DME (5 mL) was added ethyl 3-bromo-2-oxopropanoate (398 mg, 2.04 mmol) dropwise. The reaction mixture was heated to 85° C. for 18 h. The mixture was filtered and concentrated under reduced pressure to afford the crude ethyl 6-bromo-8-iodoimidazo[1,2-a]pyridine-2-carboxylate. MS: 395 and 397 (M+1).

Step 2: A solution of ethyl 6-bromo-8-iodoimidazo[1,2-a]pyridine-2-carboxylate (250 mg, 0.633 mmol) and lithium hydroxide monohydrate (53.1 mg, 1.27 mmol) in MeOH (15 mL) and water (10 mL) was stirred at 20° C. for 1 h. Dilute HCl (1M) was added to the mixture dropwise until a pH<5.0 was achieved. The solvent was removed under reduced pressure to afford 6-bromo-8-iodoimidazo[1,2-a]pyridine-2-carboxylic acid. MS: 367 and 369 (M+1).

TABLE 3

The following intermediates were prepared using a similar procedure as Intermediate 15.

| Intermediate # | Structure | Compound Name | Exact Mass [M + 1] |
|---|---|---|---|
| 16 | 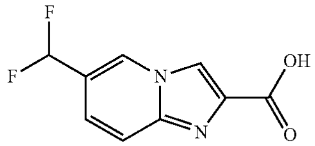 [SMILES: O=C(O)c1cn2cc(C(F)F)ccc2n1] | 6-(difluoromethyl)imidazo[l,2-a]pyridine-2-carboxylic acid | 213 |
| 17 | 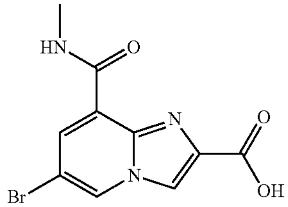 [SMILES: CNC(=O)c1cc(Br)cn2cc(C(=O)O)nc12] | 6-bromo-8-(methylcarbamoyl)imidazo[1,2-a]pyridine-2-carboxylic acid | 298 and 300 |
| 18 | 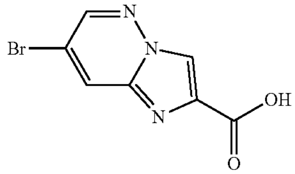 [SMILES: O=C(O)c1cn2ncc(Br)cc2n1] | 7-bromoimidazo [1,2-b]pyridazine-2-carboxylic acid | 242 and 244 |

Intermediate 19: 6-bromo-8-(2-oxopyrrolidin-1-yl) imidazo[1,2-a]pyridine-2-carboxylic acid

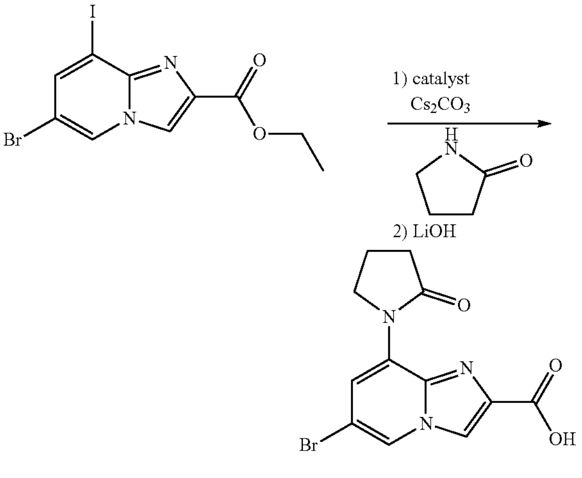

Step 1: A mixture of pyrrolidin-2-one (0.080 g, 0.94 mmol), RuPhos G1 (0.020 g, 0.025 mmol), ethyl 6-bromo-8-iodoimidazo[1,2-a]pyridine-2-carboxylate (100 mg, 0.253 mmol) and $Cs_2CO_3$ (0.25 g, 0.76 mmol) in THF (5 mL) was degassed and backfilled with $N_2$ (three times). The mixture was stirred at 80° C. for 12 h in a glove box. The mixture was diluted with DCM (5 mL) and MeOH (2 mL), filtered, and the filtrate was concentrated under reduced pressure. The residue was purified by prep-HPLC (ACN/water with 0.1% TFA modifier) to give a mixture of ethyl 6-bromo-8-(2-oxopyrrolidin-1-yl)imidazo[1,2-a]pyridine-2-carboxylate, MS: 352 and 354 (M+1); methyl 6-bromo-8-(2-oxopyrrolidin-1-yl)imidazo[1,2-a]pyridine-2-carboxylate, MS: 338 and 340 (M+1).

Step 2: A mixture of ethyl 6-bromo-8-(2-oxopyrrolidin-1-yl)imidazo[1,2-a]pyridine-2-carboxylate (14.8 mg, 0.042 mmol), methyl 6-bromo-8-(2-oxopyrrolidin-1-yl)imidazo[1,2-a]pyridine-2-carboxylate (4.8 mg, 0.014 mmol) and lithium hydroxide monohydrate (2.65 mg, 0.063 mmol) in THF (7 mL) and water (2 mL) was stirred at 25° C. for 10 min. The mixture was acidified with HCl/dioxane (4 M) to pH-3. The mixture was concentrated under reduced pressure to give the crude product 6-bromo-8-(2-oxopyrrolidin-1-yl) imidazo[1,2-a]pyridine-2-carboxylic acid, which was used without further purification. MS: 324 and 326 (M+1).

Intermediate 20: 8-(methoxymethyl)-6-(trifluoromethyl)imidazo[1,2-a]pyridine-2-carboxylic acid

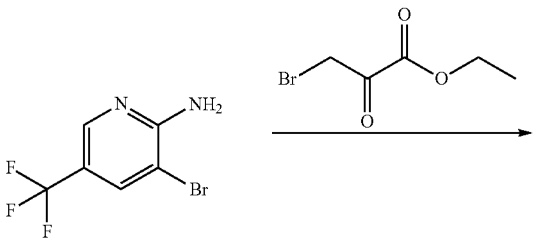

-continued

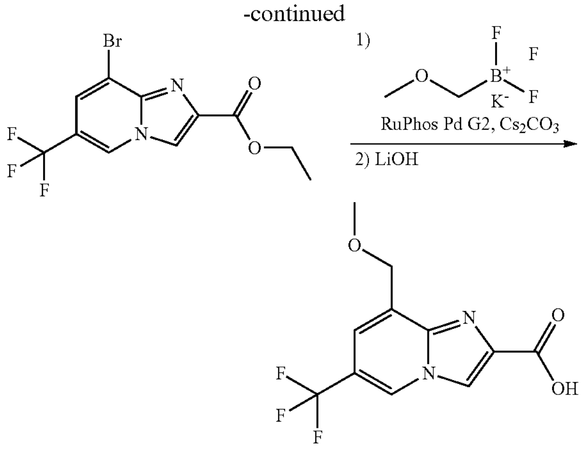

Step 1: To a solution of 3-bromo-5-(trifluoromethyl) pyridin-2-amine (5.0 g, 21 mmol) in DME (150 mL) was added ethyl 3-bromo-2-oxopropanoate (4.94 g, 25.3 mmol) dropwise. The reaction mixture was heated to 90° C. for 18 h. The mixture was concentrated under reduced pressure to give crude residue, which was purified by flash silica gel chromatography (ethyl acetate/petroleum ether gradient) to give ethyl 8-bromo-6-(trifluoromethyl)imidazo[1,2-a]pyridine-2-carboxylate. MS: 337 and 338 (M+1). $^1H$ NMR (400 MHz, $CD_3OD$) δ 9.21-9.07 (m, 1H), 8.64 (s, 1H), 7.98-7.87 (m, 1H), 4.42 (q, J=7.1 Hz, 2H), 1.49-1.32 (m, 3H).

Step 2: To a solution of ethyl 8-bromo-6-(trifluoromethyl) imidazo[1,2-a]pyridine-2-carboxylate (500 mg, 1.48 mmol) in tert-amyl alcohol (10 mL) was added chloro(2-dicyclohexylphosphino-2',6'-diisopropoxy-1,1'-biphenyl)[2-(2'-amino-1,1'-biphenyl)]palladium(II) (115 mg, 0.148 mmol), potassium methoxymethyltrifluoroborate (451 mg, 2.97 mmol) and $Cs_2CO_3$ (1.45 g, 4.45 mmol) in a glove box under an argon atmosphere at 25° C. The mixture was stirred at 100° C. for 18 h. The mixture was concentrated under reduced pressure. The residue was purified by preparative TLC (petroleum ether/EtOAc) to give ethyl 8-(methoxymethyl)-6-(trifluoromethyl)imidazo[1,2-a]pyridine-2-carboxylate. MS: 303 (M+1) Step 3: To a solution of ethyl 8-(methoxymethyl)-6-(trifluoromethyl)imidazo[1,2-a]pyridine-2-carboxylate (230 mg, 0.76 mmol) in EtOH (6 mL) and water (1 mL) was added $LiOH{\cdot}H_2O$ (38.3 mg, 0.91 mmol) at 25° C. The mixture was stirred at 25° C. for 2 h. The mixture was acidified with 1 M HCl (in water) to pH-3. The mixture was concentrated under reduced pressure to give the crude product 8-(methoxymethyl)-6-(trifluoromethyl)imidazo[1,2-a]pyridine-2-carboxylic acid. MS: 275 (M+1).

Intermediate 21: 3-cyclopropyl-4-hydroxyquinoline-7-carboxylic acid

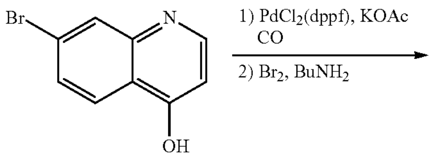

-continued

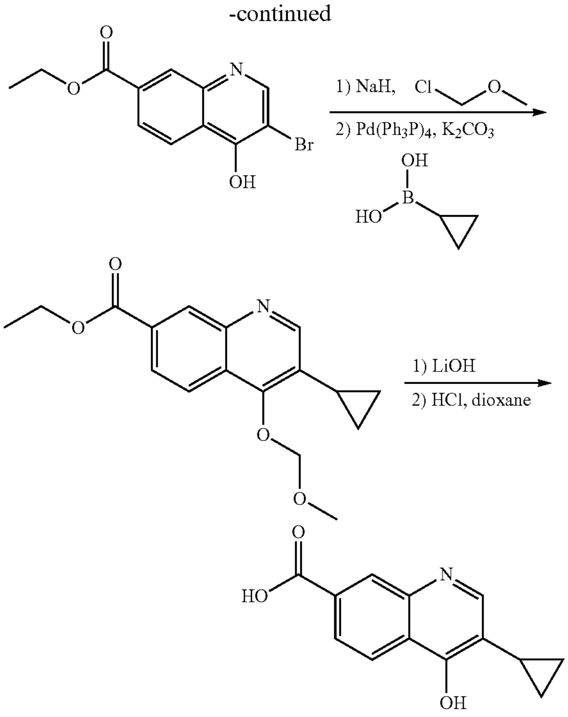

Step 1: To a solution of 7-bromoquinolin-4-ol (1.0 g, 4.5 mmol) and AcOK (1.31 g, 13.4 mmol) in EtOH (80 mL) was added $PdCl_2$(dppf) (0.327 g, 0.446 mmol) under a $N_2$ atmosphere. The mixture was degassed and backfilled with CO (three times). The resulting mixture was stirred under CO (pressure: 50 psi) at 80° C. for 3 h. The mixture was concentrated, and the residue was purified by flash silica gel chromatography (MeOH/DCM gradient) to give ethyl 4-hydroxyquinoline-7-carboxylate. MS: 218 (M+1). $^1$H NMR (400 MHz, $CD_3OD$) δ 8.32 (d, J=8.4 Hz, 1H), 8.29-8.24 (m, 1H), 8.05 (br d, J=7.1 Hz, 1H), 7.99-7.93 (m, 1H), 6.37 (d, J=7.3 Hz, 1H), 4.43 (q, J=7.1 Hz, 2H), 1.43 (t, J=7.1 Hz, 3H).

Step 2: A mixture of butan-1-amine (2.69 g, 36.8 mmol), $Br_2$ (0.285 mL, 5.52 mmol) and ethyl 4-hydroxyquinoline-7-carboxylate (800 mg, 3.68 mmol) in DMF (20 mL) was stirred at 15° C. for 10 min. $Na_2SO_3$ (0.1 M, 150 mL) was added to the mixture, and the resultant mixture was extracted with DCM (100×2). The combined organic layers were concentrated under reduced pressure to give ethyl 3-bromo-4-hydroxyquinoline-7-carboxylate. MS: 296 and 298 (M+1). $^1$H NMR (400 MHz, DMSO-$d_6$) δ 8.60 (s, 1H), 8.23 (d, J=8.5 Hz, 2H), 7.85 (dd, J=1.5, 8.4 Hz, 1H), 4.35 (q, J=7.1 Hz, 2H), 1.33 (t, J=7.1 Hz, 3H).

Step 3: To a solution of ethyl 3-bromo-4-hydroxyquinoline-7-carboxylate (0.40 g, 1.4 mmol) in DMF (8 mL) was added NaH (81 mg, 2.0 mmol) at 0° C. The mixture was stirred at 0° C. for 15 min. To the mixture was added chloro(methoxy)methane (0.585 mL, 7.70 mmol) at 0° C. The resultant mixture was stirred at 15° C. for 12 h. The mixture was quenched with sat. $NH_4Cl$ (100 mL) and diluted with EtOAc (50 mL). The aqueous layer was extracted with EtOAc (50 mL×4). The combined organic layers were dried over anhydrous sodium sulfate, filtered, and the filtrate was concentrated under reduced pressure. The residue was purified by flash silica gel chromatography (ethyl acetate/DCM gradient) to give ethyl 3-bromo-4-(methoxymethoxy)quinoline-7-carboxylate. MS: 340 and 342 (M+1). $^1$H NMR (400 MHz, $CD_3OD$) δ 8.73 (s, 1H), 8.51 (d, J=0.9 Hz, 1H), 8.43 (d, J=8.3 Hz, 1H), 8.06 (dd, J=1.3, 8.33 Hz, 1H), 5.68 (s, 2H), 4.45 (q, J=7.3 Hz, 2H), 3.40 (s, 3H), 1.43 (t, J=7.2 Hz, 3H)

Step 4: A solution of ethyl 3-bromo-4-(methoxymethoxy)quinoline-7-carboxylate (600 mg, 1.76 mmol), cyclopropylboronic acid (1.52 g, 17.6 mmol) and $K_2CO_3$ (731 mg, 5.29 mmol) in DME (10 mL) was purged with nitrogen followed by the addition of $Pd(Ph_3P)_4$ (408 mg, 0.353 mmol) under $N_2$. The resulting mixture was heated to 100° C. for 12 h. The mixture was cooled to room temperature and concentrated under reduced pressure. The residue was purified by column chromatography on silica gel (DCM/MeOH) to give ethyl 3-cyclopropyl-4-(methoxymethoxy)quinoline-7-carboxylate. MS: 302 (M+1). $^1$H NMR (400 MHz, $CD_3Cl$) δ 8.51 (d, J=8.3 Hz, 1H), 8.31 (d, J=0.9 Hz, 1H), 7.97 (dd, J=1.5, 8.6 Hz, 1H), 7.36 (s, 1H), 5.43 (s, 2H), 4.46-4.39 (m, 2H), 3.39-3.34 (m, 3H), 2.08-2.00 (m, 1H), 1.43 (t, J=7.2 Hz, 3H), 0.97-0.90 (m, 2H), 0.62-0.53 (m, 2H).

Step 5: A solution of ethyl 3-cyclopropyl-4-(methoxymethoxy)quinoline-7-carboxylate (600 mg, 1.99 mmol) in EtOH (5 mL) and water (1 mL) was added lithium hydroxide hydrate (167 mg, 3.98 mmol), and the mixture was stirred at 15° C. for 30 min. To the mixture was added HCl/MeOH (4 M) to acidify the mixture to pH 3. The solid was filtered to give 3-cyclopropyl-4-(methoxymethoxy)quinoline-7-carboxylic acid. MS: 274 (M+1). $^1$H NMR (400 MHz, $CD_3OD$) δ 8.49 (s, 1H), 8.42 (d, J=8.8 Hz, 1H), 8.01 (d, J=9.7 Hz, 1H), 7.94 (s, 1H), 5.64 (s, 2H), 3.35 (s, 3H), 1.99 (s, 1H), 0.96-0.90 (m, 2H), 0.68-0.62 (m, 2H).

Step 6: A mixture of 3-cyclopropyl-4-(methoxymethoxy)quinoline-7-carboxylic acid (100 mg, 0.366 mmol) in HCl/dioxane (4 M) (20 mL) and water (1 mL) was stirred at 80° C. for 12 h. The mixture was concentrated under reduced pressure to give 3-cyclopropyl-4-hydroxyquinoline-7-carboxylic acid. MS: 230 (M+1).

Intermediate 22: 6-bromo-8-methoxyimidazo[1,2-a]pyrazine-2-carboxylic acid

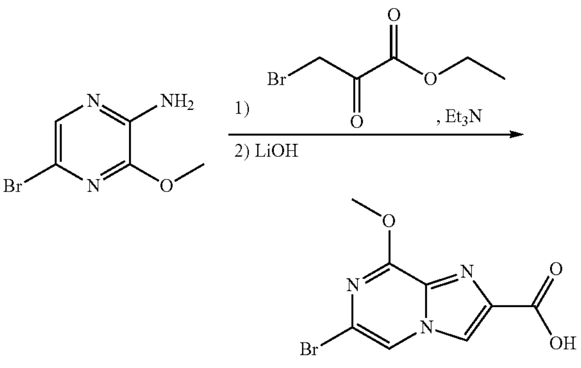

Step 1: A mixture of ethyl 3-bromo-2-oxopropanoate (5.73 g, 22.1 mmol) and 5-bromo-3-methoxypyrazin-2-amine (3.0 g, 15 mmol) in EtOH (30 mL) was stirred at 90° C. for 2 h. After cooling to rt, TEA (8.20 mL, 58.8 mmol) was added, and the mixture was stirred at 25° C. for 10 min. The mixture was concentrated under reduced pressure. The residue was recrystallized from petroleum/EtOAc to give crude ethyl 6-bromo-8-methoxyimidazo[1,2-a]pyrazine-2-carboxylate, which was used in the next step without further purification. MS: 300 and 302 (M+1).

Step 2: A mixture of ethyl 6-bromo-8-methoxyimidazo[1,2-a]pyrazine-2-carboxylate (160 mg, 0.533 mmol) and lithium hydroxide monohydrate (44.7 mg, 1.07 mmol) in EtOH (3 mL) and water (1 mL) was stirred at 25° C. for 2 h. The solvent was removed under reduced pressure, and the residue was dissolved in water (30 mL) and acidified with 1 M HCl to pH~3. The aqueous layer was extracted with EtOAc (30 mL×3), and the combined organic layers were washed with brine (80 mL), dried over anhydrous $Na_2SO_4$, filtered, and concentrated under reduced pressure to give 6-bromo-8-methoxyimidazo[1,2-a]pyrazine-2-carboxylic acid, which was used without further purification MS: 272 and 274 (M+1)

TABLE 4

The following intermediate was prepared using a similar procedure as Intermediate 22.

| Intermediate # | Structure | Compound Name | Exact Mass [M + 1] |
|---|---|---|---|
| 23 | 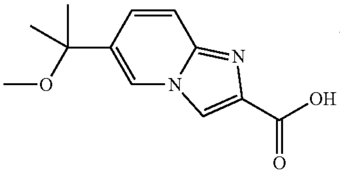 | 6-(2-methoxypropan-2-yl)imidazo[1,2-a]pyridine-2-carboxylic acid | 235 |

Intermediate 24: 6-bromo-8-isopropoxyimidazo[1,2-a]pyrazine-2-carboxylic acid

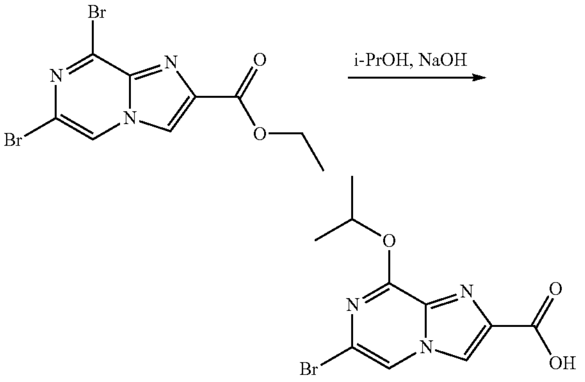

A mixture of ethyl 6,8-dibromoimidazo[1,2-a]pyrazine-2-carboxylate (50 mg, 0.14 mmol) and NaOH (22.9 mg, 0.573 mmol) in 2-propanol (1.5 mL) was stirred at 40° C. for 10 min. After cooling to room temperature, the mixture was added to $H_2O$ (0.129 mL, 7.16 mmol) at 25° C., and stirred at 25° C. for 5 min. The mixture was acidified with aq. HCl (1 M, in water) to pH-3. The resultant mixture was concentrated under reduced pressure to give the crude product 6-bromo-8-isopropoxyimidazo[1,2-a]pyrazine-2-carboxylic acid, which was used without further purification. MS: 300 and 302 (M+1). $^1H$ NMR (400 MHz, DMSO-$d_6$) δ 8.48 (s, 1H), 8.45 (s, 1H), 5.40 (q, J=6.1 Hz, 1H), 1.38 (d, J=6.1 Hz, 6H).

TABLE 5

The following intermediates were prepared using a similar procedure as Intermediate 24.

| Intermediate # | Structure | Compound Name | Exact Mass [M + 1] |
|---|---|---|---|
| 25 | 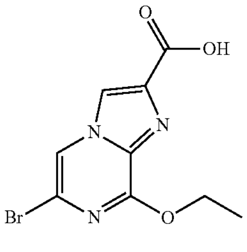 [SMILES: CCOc1nc(Br)cn2cc(C(=O)O)nc12] | 6-bromo-8-ethoxyimidazo[1,2-a]pyrazine-2-carboxylic acid | 286 and 288 |

TABLE 5-continued

The following intermediates were prepared using a similar procedure as Intermediate 24.

| Intermediate # | Structure | Compound Name | Exact Mass [M + 1] |
|---|---|---|---|
| 26 | 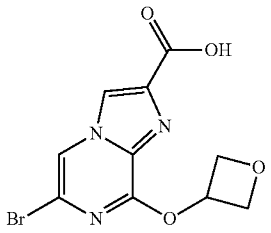 [SMILES: O=C(O)c1cn2cc(Br)nc(OC3COC3)c2n1] | 6-bromo-8-(oxetan-3-yloxy)imidazo[1,2-a]pyrazine-2-carboxylic acid | 314 and 316 |
| 27 and 28 | 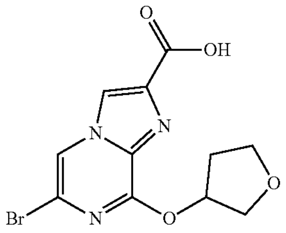 [SMILES: O=C(O)c1cn2cc(Br)nc(OC3CCOC3)c2n1] | 6-bromo-8-((tetrahydrofuran-3-yl)oxy)imidazo[1,2-a]pyrazine-2-carboxylic acid | 328 and 330 |
| 29 | 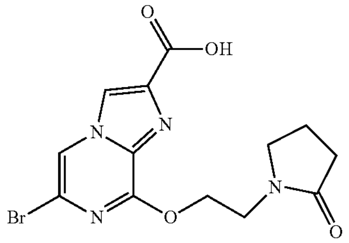 [SMILES: O=C(O)c1cn2cc(Br)nc(OCCN3CCCC3=O)c2n1] | 6-bromo-8-(2-(2-oxopyrrolidin-1-yl)ethoxy)imidazo[1,2-a]pyrazine-2-carboxylic acid | 369 and 371 |
| 30 and 31 | 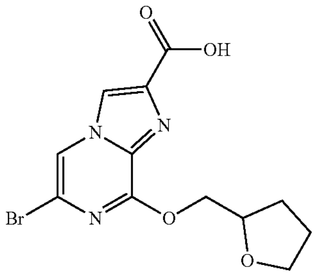 [SMILES: O=C(O)c1cn2cc(Br)nc(OCC3CCCO3)c2n1] | 6-bromo-8-((tetrahydrofuran-2-yl)methoxy)imidazo[1,2-a]pyrazine-2-carboxylic acid | 342 and 344 |
| 32 | 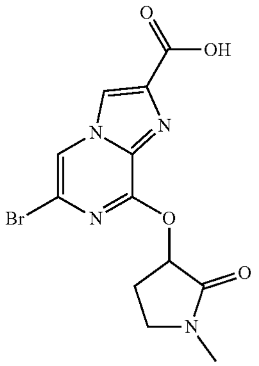 [SMILES: CN1CCC(Oc2nc(Br)cn3cc(C(=O)O)nc23)C1=O] | 6-bromo-8-((1-methyl-2-oxopyrrolidin-3-yl)oxy)imidazo[1,2-a]pyrazine-2-carboxylic acid | 355 and 357 |

TABLE 5-continued

The following intermediates were prepared using a similar procedure as Intermediate 24.

| Intermediate # | Structure | Compound Name | Exact Mass [M + 1] |
|---|---|---|---|
| 33 | 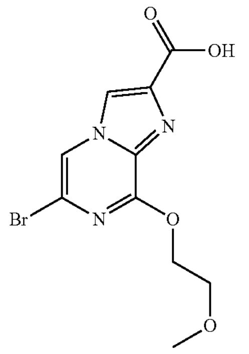 [SMILES: COCCOc1nc(Br)cn2cc(C(=O)O)nc12] | 6-bromo-8-(2-methoxyethoxy)imidazo[1,2-a]pyrazine-2-carboxylic acid | 316 and 318 |
| 34 | 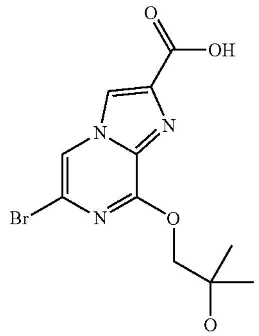 [SMILES: CC(C)(O)COc1nc(Br)cn2cc(C(=O)O)nc12] | 6-bromo-8-(2-hydroxy-2-methylpropoxy)imidazo[1,2-a]pyrazine-2-carboxylic acid | 330 and 332 |
| 35 | 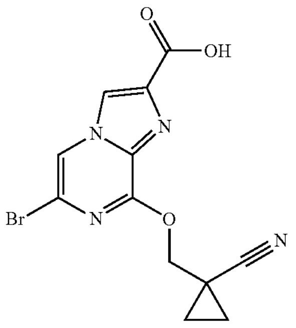 [SMILES: N#CC1(COc2nc(Br)cn3cc(C(=O)O)nc23)CC1] | 6-bromo-8-[(1-cyanocyclopropyl)methoxy]imidazo[1,2-a]pyrazine-2-carboxylic acid | 337 and 339 |

Intermediate 36: 2-ethyl-3-oxo-3,4-dihydro-2H-benzo[b][1,4]oxazine-6-carboxylic acid

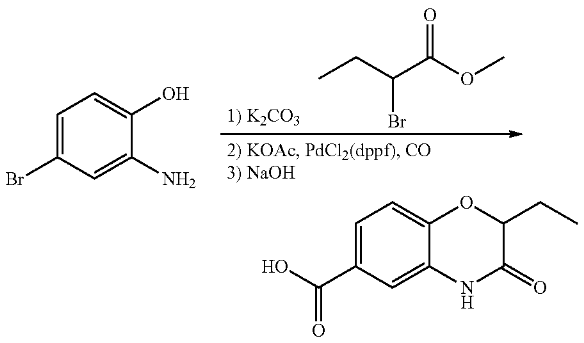

Step 1: To a stirred suspension of 2-amino-4-bromophenol (5.0 g, 27 mmol) and $K_2CO_3$ (3.85 g, 27.8 mmol) in acetone (80 mL) was added methyl 2-bromobutanoate (4.2 g, 23 mmol). The mixture was heated to 70° C. for 16 h. Then the reaction was stirred at 80° C. for another 16 h. The mixture was concentrated under reduced pressure, and the residue was dissolved in EtOAc (150 mL) and washed with water (100 mL×2). The organic layer was dried ($MgSO_4$), filtered, and concentrated under reduced pressure. The residue was purified by flash silica gel chromatography (MeOH/DCM gradient) to give 6-bromo-2-ethyl-2H-benzo[b][1,4]oxazin-3(4H)-one. MS: 256 and 258 (M+1). $^1$H NMR (400 MHz, $CD_3Cl$) δ 9.48 (br s, 1H), 7.08 (dd, J=2.4, 8.6 Hz, 1H), 6.99 (d, J=2.2 Hz, 1H), 6.85 (d, J=8.3 Hz, 1H), 4.51 (dd, J=4.4, 8.3 Hz, 1H), 2.03-1.84 (m, 2H), 1.09 (t, J=7.5 Hz, 3H).

Step 2: To a solution of 6-bromo-2-ethyl-2H-benzo[b][1,4]oxazin-3(4H)-one (500 mg, 1.95 mmol) in EtOH (40 mL) was added $PdCl_2$(dppf) (286 mg, 0.390 mmol) and potassium acetate (575 mg, 5.86 mmol) under argon. The mixture was degassed and backfilled with argon (three times). The resulting mixture was stirred under CO (pressure: 50 psi) at 80° C. for 16 h. The catalyst was filtered off, and the filtrate was concentrated under reduced pressure. The residue was purified by flash silica gel chromatography (ethyl acetate/pet. ether gradient) to give ethyl 2-ethyl-3-oxo-3,4-dihydro-2H-benzo[b][1,4]oxazine-6-carboxylate. MS: 250 (M+1).

Step 3: To a solution of ethyl 2-ethyl-3-oxo-3,4-dihydro-2H-benzo[b][1,4]oxazine-6-carboxylate (120 mg, 0.481 mmol) in EtOH (4 mL) and water (2 mL) was added sodium hydroxide (57.8 mg, 1.44 mmol). The mixture was stirred at 20° C. for 18 h. The mixture was acidified by addition of HCl in MeOH (4 M) to pH~3. The mixture was concentrated under reduced pressure to give 2-ethyl-3-oxo-3,4-dihydro-2H-benzo[b][1,4]oxazine-6-carboxylic acid. MS: 222 (M+1).

TABLE 6

The following intermediate was prepared using a similar procedure as Intermediate 36.

| Intermediate # | Structure | Compound Name | Exact Mass [M + 1] |
|---|---|---|---|
| 37 | 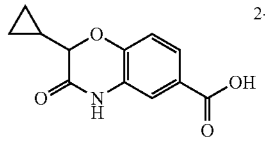 | 2-cyclopropyl-3-oxo-3,4-dihydro-2H-benzo[b][1,4]oxazine-6-carboxylic acid | 234 |

Intermediate 38, 39, 40: 8-(tetrahydrofuran-3-yl)-6-(trifluoromethyl)-5,6,7,8-tetrahydroimidazo[1,2-a]pyridine-2-carboxylic acid

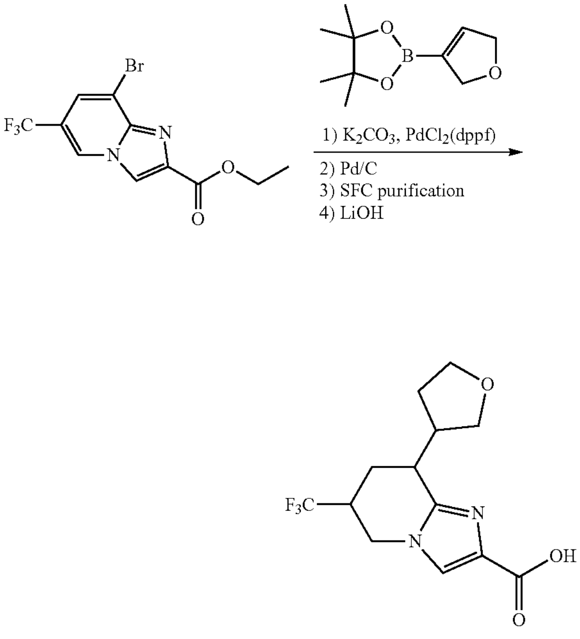

3 isomers

Step 1: A mixture of ethyl 8-bromo-6-(trifluoromethyl)imidazo[1,2-a]pyridine-2-carboxylate (851 mg, 2.52 mmol), 2-(2,5-dihydrofuran-3-yl)-4,4,5,5-tetramethyl-1,3,2-dioxaborolane (450 mg, 2.30 mmol), [1,1'-bis(diphenylphosphino)ferrocene]dichloropalladium(II) (336 mg, 0.459 mmol) and potassium carbonate (952 mg, 6.89 mmol) in 1,4-dioxane (5 mL) and water (1 mL) was stirred at 100° C. for 2 h under $N_2$. The mixture was concentrated under reduced pressure. The residue was purified by flash silica gel chromatography (ethyl acetate/pet. ether gradient) to afford ethyl 8-(2,5-dihydrofuran-3-yl)-6-(trifluoromethyl)imidazo[1,2-a]pyridine-2-carboxylate. MS: 327 (M+1). $^1$H NMR (400 MHz, $CD_3Cl$) δ 8.44 (s, 1H), 8.28 (s, 1H), 7.87 (s, 1H), 7.00 (s, 1H), 5.16-5.14 (m, 2H), 5.04-5.02 (m, 2H), 4.58 (q, J=5.4 Hz, 2H), 1.47 (t, J=7.2 Hz, 3H).

Step 2: A mixture of ethyl 8-(2,5-dihydrofuran-3-yl)-6-(trifluoromethyl)imidazo[1,2-a]pyridine-2-carboxylate (200 mg, 0.613 mmol) and Pd/C (130 mg, 0.123 mmol) (10% wt) in EtOH (5 mL) was stirred under $H_2$ (pressure: 15 psi) at 20° C. for 12 h. The mixture was filtered, and the filtrate was concentrated under reduced pressure to give ethyl 8-(tetrahydrofuran-3-yl)-6-(trifluoromethyl)-5,6,7,8-tetrahydroimidazo[1,2-a]pyridine-2-carboxylate, which was used in the next step without further purification. MS: 333 (M+1).

Step 3: The mixture of ethyl 8-(tetrahydrofuran-3-yl)-6-(trifluoromethyl)-5,6,7,8-tetrahydroimidazo[1,2-a]pyridine-2-carboxylate (125 mg, 0.376 mmol) was separated by SFC (IC Column, MeOH/$CO_2$) to afford three isomers.

ethyl 8-(tetrahydrofuran-3-yl)-6-(trifluoromethyl)-5,6,7,8-tetrahydroimidazo[1,2-a]pyridine-2-carboxylate. (Isomer 1, first eluting), (Isomer 2, second eluting) and (Isomer 3, third eluting). MS: 333. (M+1).

Step 4: Each of the three isomers was processed separately using a similar procedure as below. To a mixture of ethyl 8-(tetrahydrofuran-3-yl)-6-(trifluoromethyl)-5,6,7,8-tetrahydroimidazo[1,2-a]pyridine-2-carboxylate (25 mg, 0.075 mmol) in EtOH (2 mL) and water (1 mL) was added lithium hydroxide hydrate (9.47 mg, 0.226 mmol) at 20° C. The solution was stirred at 20° C. for 2 h. The mixture was concentrated to give 8-(tetrahydrofuran-3-yl)-6-(trifluoromethyl)-5,6,7,8-tetrahydroimidazo[1,2-a]pyridine-2-carboxylic acid, which was used in the next step without further purification. MS: 305 (M+1).

When the material from the third eluting peak in Step 3 was carried forward the material was hydrolyzed as indicated above, but after the subsequent coupling reaction was completed the residue from the reaction was separated into two isomers.

Intermediate 41 and 42: (R)-6-(1-methoxyethyl)imidazo[1,2-a]pyridine-2-carboxylic acid and (S)-6-(1-methoxyethyl)imidazo[1,2-a]pyridine-2-carboxylic acid

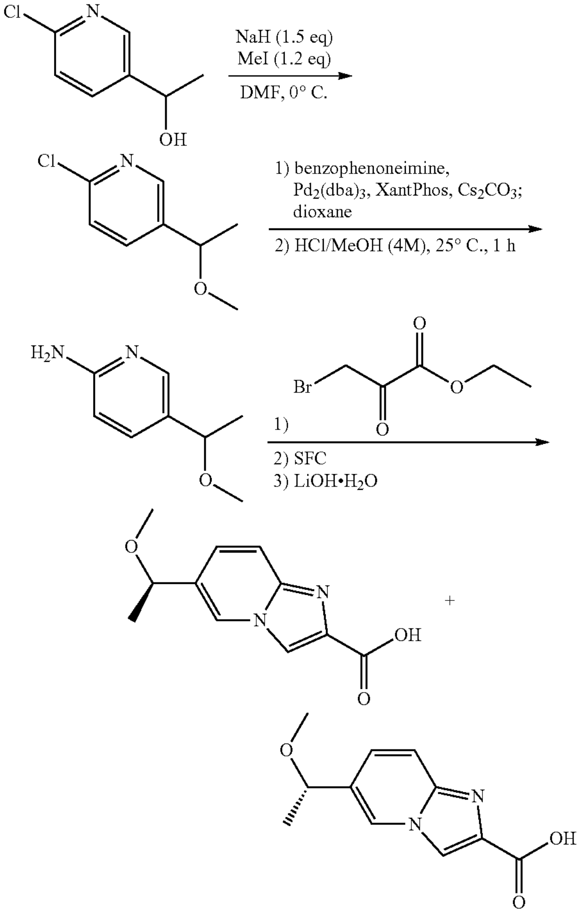

Step 1: To a mixture of 1-(6-chloropyridin-3-yl)ethanol (5.0 g, 32 mmol) in DMF (20 mL) was added sodium hydride (1.52 g, 38.1 mmol) (60%), and the mixture was stirred at 20° C. for 1 h. MeI (2.90 mL, 46.3 mmol) was added to the mixture, and the mixture was stirred at 20° C. for 1 h. Water (150 mL) and EtOAc (50 mL) were added to the mixture. The aqueous layer was re-extracted with EtOAc (50 mL×3). The combined organic layers were washed with brine (50 mL), dried over anhydrous $Na_2SO_4$, filtered, and the filtrate was evaporated under reduced pressure. The residue was purified by flash silica gel chromatography (ethyl acetate/pet. ether gradient) to give 2-chloro-5-(1-methoxyethyl)pyridine. MS: 172 (M+1). $^1H$ NMR (400 MHz, $CDCl_3$) δ 8.30 (d, J=2.2 Hz, 1H), 7.63 (dd, J=2.2, 8.3 Hz, 1H), 7.32 (d, J=8.3 Hz, 1H), 4.33 (q, J=6.6 Hz, 1H), 3.23 (s, 3H), 1.43 (d, J=6.6 Hz, 3H).

Step 2: To a solution of 2-chloro-5-(1-methoxyethyl)pyridine (6.0 g, 35 mmol), diphenylmethanimine (7.60 g, 42.0 mmol), and XantPhos (2.02 g, 3.50 mmol) in 1,4-dioxane (100 mL) was added $Cs_2CO_3$ (27.3 g, 84 mmol) and $Pd_2(dba)_3$ (1.60 g, 1.75 mmol) at 25° C. The resulting mixture was degassed and backfilled with $N_2$ (three times) and stirred at 90° C. for 12 h. The mixture was concentrated under reduced pressure, and $H_2O$ (300 mL) was added and the mixture was extracted with EtOAc (200 mL×3). The combined organic layers were dried over $Na_2SO_4$, filtered, and concentrated under reduced pressure. The residue was dissolved in MeOH (30 mL) and the pH was adjusted to pH 5 with aq. HCl solution (1 M). The mixture was stirred for 20 minutes and adjusted to pH 8 with $NH_3H_2O$ (25%) and then concentrated under reduced pressure. The residue was purified by flash silica gel chromatography (ethyl acetate/pet. ether gradient) to give 5-(1-methoxyethyl)pyridin-2-amine. MS: 153 (M+1).

Step 3: To a mixture of 5-(1-methoxyethyl)pyridin-2-amine (1.0 g, 6.6 mmol) in 1,4-dioxane (50 mL) was added ethyl 3-bromo-2-oxopropanoate (2.75 g, 9.86 mmol) at 25° C. The mixture was stirred at 80° C. for 12 h. After cooling to 25° C., TEA (1.37 mL, 9.86 mmol) was added, and the mixture was concentrated under reduced pressure. The residue was purified by Prep-HPLC (ACN/water with 0.1% TFA modifier) to give ethyl 6-(1-methoxyethyl)imidazo[1,2-a]pyridine-2-carboxylate. MS: 249 (M+1).

Step 4: The mixture of ethyl 6-(1-methoxyethyl)imidazo[1,2-a]pyridine-2-carboxylate (350 mg, 1.41 mmol) was separated by SFC (AD Column, MeOH/$CO_2$) to afford ethyl (R or S) 6-(1-methoxyethyl)imidazo[1,2-a]pyridine-2-carboxylate (Isomer 1, first eluting) and ethyl (S or R) 6-(1-methoxyethyl)imidazo[1,2-a]pyridine-2-carboxylate (Isomer 2, second eluting).

Step 5: To a solution of ethyl (R)-6-(1-methoxyethyl)imidazo[1,2-a]pyridine-2-carboxylate (80 mg, 0.32 mmol) in EtOH (2 mL) and water (1 mL) was added lithium hydroxide hydrate (43.1 mg, 1.03 mmol). The reaction was stirred at 15° C. for 2 h. The mixture was concentrated to give (R)-6-(1-methoxyethyl)imidazo[1,2-a]pyridine-2-carboxylic acid, which was used without further purification. MS: 221 (M+1).

The same reaction provided (S)-6-(1-methoxyethyl)imidazo[1,2-a]pyridine-2-carboxylic acid using ethyl (S)-6-(1-methoxyethyl)imidazo[1,2-a]pyridine-2-carboxylate. MS: 221 (M+1).

Intermediate 43: 6-bromo-7-methoxyimidazo[1,2-a]pyrimidine-2-carboxylic acid

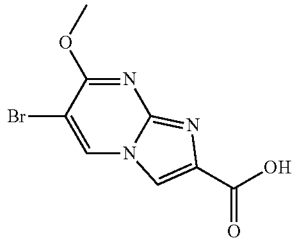

To a mixture of 5-bromo-4-methoxypyrimidin-2-amine (300 mg, 1.47 mmol) in EtOH (6 mL) was added 3-bromo-2-oxopropanoic acid (368 mg, 2.21 mmol) at 15° C. The mixture was heated to 85° C. for 12 h. The mixture was concentrated to give 6-bromo-7-methoxyimidazo[1,2-a]pyrimidine-2-carboxylic acid. MS: 272 and 274 (M+1).

TABLE 7

| The following intermediates were prepared using a similar procedure as Intermediate 43. | | | |
|---|---|---|---|
| Intermediate # | Structure | Compound Name | Exact Mass [M + 1] |
| 44 | 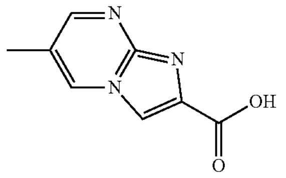 | 6-methylimidazo[1,2-a]pyrimidine-2-carboxylic acid | 178 |
| 45 | 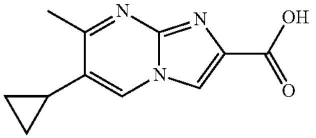 [SMILES: Cc1nc2nc(C(=O)O)cn2cc1C1CC1] | 6-cyclopropyl-7-methylimidazo[1,2-a]pyrimidine-2-carboxylic acid | 218 |
| 46 | 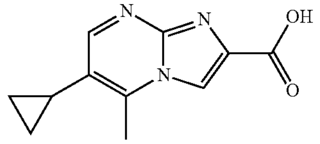 [SMILES: Cc1c(C2CC2)cnc2nc(C(=O)O)cn12] | 6-cyclopropyl-5-methylimidazo[1,2-a]pyrimidine-2-carboxylic acid | 218 |
| 47 | 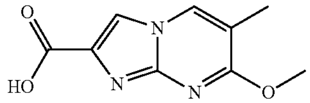 | 7-methoxy-6-methylimidazo[1,2-a]pyrimidine-2-carboxylic acid | 208 |
| 48 | 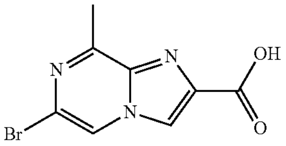 | 6-bromo-8-methylimidazo[1,2-a]pyrazine-2-carboxylic acid | 256 and 258 |
| 49 | 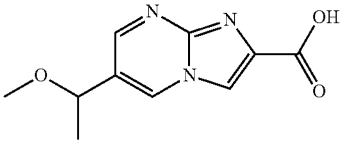 [SMILES: COC(C)c1cnc2nc(C(=O)O)cn2c1] | 6-(1-methoxyethyl)imidazo[1,2-a]pyrimidine-2-carboxylic acid | 222 |

Intermediate 50: 8-bromo-6-methylimidazo[1,2-a]pyrazine-2-carboxylic acid

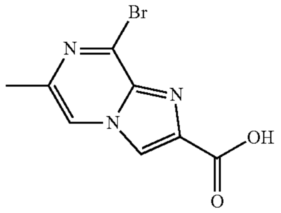

To a mixture of 3-bromo-5-methylpyrazin-2-amine (800 mg, 4.25 mmol) and $MgSO_4$ (2561 mg, 21.27 mmol) in 1,4-dioxane (15 mL) was added 3-bromo-2-oxopropanoic acid (1066 mg, 6.38 mmol) at 20° C. The mixture was heated to 80° C. for 12 h. The mixture was cooled to room temperature, filtered, and concentrated to give 8-bromo-6-methylimidazo[1,2-a]pyrazine-2-carboxylic acid. MS: 256 and 258 (M+1).

Intermediate 51: 6-bromoimidazo[1,2-a]pyrimidine-2-carboxylic acid

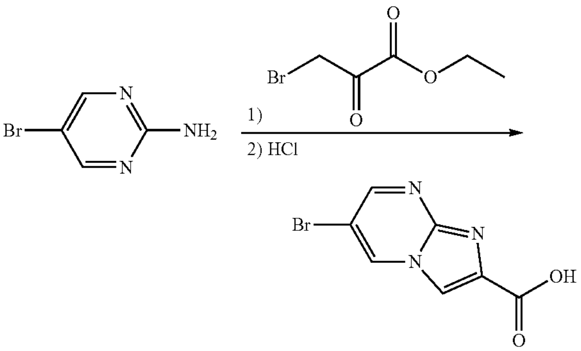

Step 1: To a solution of 5-bromopyrimidin-2-amine (3.0 g, 17 mmol) in EtOH (20 mL) was added ethyl 3-bromo-2-oxopropanoate (5.04 g, 25.9 mmol). The reaction was stirred at 80° C. for 3 h. After cooling to 25° C., TEA (2.40 mL, 17.2 mmol) was added. The mixture was stirred at 25° C. for 0.5 h. The mixture was concentrated and the residue was purified by flash silica gel chromatography (ethyl acetate/pet. ether gradient) to give ethyl 6-bromoimidazo[1,2-a]pyrimidine-2-carboxylate. MS: 270 and 272 (M+1). $^1$H NMR (500 MHz, $CDCl_3$) δ 8.70-8.62 (m, 2H), 8.12 (s, 1H), 4.46 (q, J=5.4 Hz, 2H), 1.43 (t, J=3.6 Hz, 3H) and ethyl 6-bromoimidazo[1,2-a]pyrimidine-3-carboxylate. MS: 270 and 272 (M+1). $^1$H NMR (500 MHz, $CDCl_3$) δ 9.72 (s, 1H), 8.40 (s, 1H), 8.01 (s, 1H), 4.44 (q, J=5.1 Hz, 2H), 1.44 (t, J=4.4 Hz, 3H).

Step 2: A solution of ethyl 6-bromoimidazo[1,2-a]pyrimidine-2-carboxylate (300 mg, 1.11 mmol) in HCl in $H_2O$ (4M; 8 mL) was stirred at 75° C. for 16 h. The mixture was concentrated to give 6-bromoimidazo[1,2-a]pyrimidine-2-carboxylic acid, which was used without further purification. MS: 242 and 244 (M+1).

TABLE 8

The following intermediate was prepared using a similar procedure as Intermediate 51.

| Intermediate # | Structure | Compound Name | Exact Mass [M + 1] |
|---|---|---|---|
| 52 | 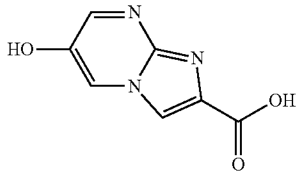 [SMILES: O=C(O)c1cn2cc(O)cnc2n1] | 6-hydroxyimidazo[1,2-a]pyrimidine-2-carboxylic acid | 180 |

Intermediate 53: 6-bromoimidazo[1,2-a]pyrimidine-3-carboxylic acid

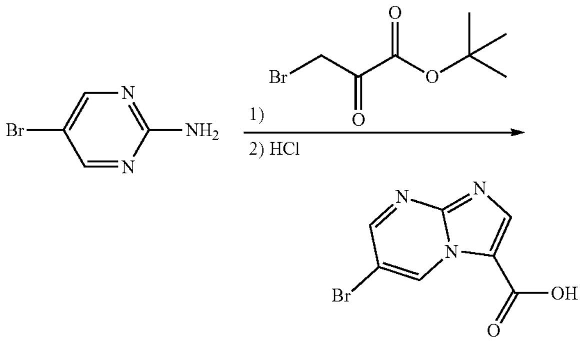

Step 1: To a solution of 5-bromopyrimidin-2-amine (1.0 g, 5.8 mmol) in 1,4-dioxane (20 mL) was added tert-butyl 3-bromo-2-oxopropanoate (1.92 g, 8.62 mmol). The reaction was stirred at 80° C. for 12 h. After cooling to 25° C., TEA (0.801 mL, 5.75 mmol) was added to the mixture, and the mixture was stirred at 25° C. for 0.5 h. The mixture was concentrated under reduced pressure, and the residue was purified by flash silica gel chromatography (ethyl acetate/pet. ether gradient) to give tert-butyl 6-bromoimidazo[1,2-a]pyrimidine-2-carboxylate and tert-butyl 6-bromoimidazo[1,2-a]pyrimidine-3-carboxylate. MS: 298 and 300 (M+1).

Step 2: A solution of tert-butyl 6-bromoimidazo[1,2-a]pyrimidine-3-carboxylate (200 mg, 0.671 mmol) in HCl (8 mL) was stirred at 75° C. for 1 h. The mixture was concentrated under reduced pressure to give 6-bromoimidazo[1,2-a]pyrimidine-3-carboxylic acid, which was used without further purification. MS: 242 and 244 (M+1).

Intermediate 54: Lithium 4-ethyl-5-oxo-2,3,4,5-tetrahydro-1H-benzo[e][1,4]diazepine-8-carboxylate

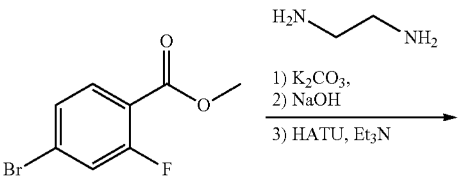

-continued

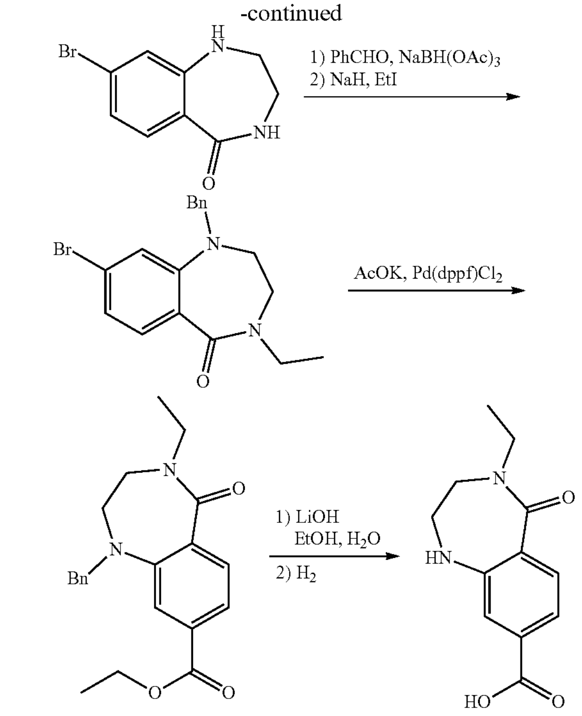

Step 1: A mixture of ethane-1,2-diamine (2.51 g, 41.7 mmol), methyl 4-bromo-2-fluorobenzoate (5.4 g, 23.2 mmol) and $K_2CO_3$ (3.20 g, 23.2 mmol) in DMF (20 mL) was stirred at 80° C. for 1 h. Water (150 mL) was added to the mixture, and then was extracted with EtOAc (150 mL×2).

The combined organic layers were washed with brine (100 mL), dried over anhydrous $Na_2SO_4$, filtered, and concentrated under reduced pressure. The residue was purified by flash silica gel chromatography (MeOH/EtOAc gradient) to give methyl 2-((2-aminoethyl)amino)-4-bromobenzoate. MS: 273 and 275 (M+1).

Step 2: To a solution of methyl 2-((2-aminoethyl)amino)-4-bromobenzoate (3.1 g, 11.4 mmol) in MeOH (200 mL) was added NaOH (9.85 g, 246 mmol) at 18° C. The mixture was stirred at 70° C. for 4 h. The mixture was acidified with conc. HCl to pH 7. The mixture was concentrated to give the crude product 2-((2-aminoethyl)amino)-4-bromobenzoic acid, which was used in the next step without further purification. MS: 259 and 261 (M+1).

Step 3: To a solution of 2-((2-aminoethyl)amino)-4-bromobenzoic acid (3 g, 11.6 mmol) and TEA (6.46 mL, 46.3 mmol) in DMF (100 mL) was added HATU (4.84 g, 12.7 mmol) at 18° C. The mixture was stirred at 18° C. for 0.5 h. Water (300 mL) was added to the mixture, and the mixture was extracted with EtOAc (300 mL×2). The combined organic layers were washed with brine (200 mL), dried over anhydrous $Na_2SO_4$, filtered, and concentrated under reduced pressure to give the crude product. The residue was purified by flash silica gel chromatography (EtOAc/pet. ether gradient) to afford 8-bromo-3,4-dihydro-1H-benzo[e][1,4]diazepin-5(2H)-one. MS: 241 and 243 (M+1).

Step 4: To a stirred solution of 8-bromo-3,4-dihydro-1H-benzo[e][1,4]diazepin-5(2H)-one (200 mg, 0.830 mmol) in DCE (5 mL) was added AcOH (2 drops), then benzaldehyde (0.336 mL, 3.32 mmol) and sodium triacetoxyborohydride (527 mg, 2.49 mmol) was added. The mixture was stirred at 20° C. for 14 h. The mixture was stirred at 40° C. for 2 h. Saturated aqueous $NaHCO_3$ (30 mL) was added to the mixture, and the mixture was extracted with DCM (30 mL×2). The combined organic layers were dried over $Na_2SO_4$, filtered, and concentrated under reduced pressure. The residue was purified by preparative TLC (EtOAc) to afford 1-benzyl-8-bromo-3,4-dihydro-1H-benzo[e][1,4]diazepin-5(2H)-one. MS: 331 and 333 (M+1).

Step 5: To a solution of 1-benzyl-8-bromo-3,4-dihydro-1H-benzo[e][1,4]diazepin-5(2H)-one (150 mg, 0.453 mmol) in DMF (1.5 mL) was added iodoethane (0.183 mL, 2.26 mmol), then NaH (23.6 mg, 0.589 mmol) (60% Wt) at −10° C. The mixture was stirred at −10° C. for 20 min. Iodoethane (0.183 mL, 2.264 mmol) was added to the mixture, and the mixture was stirred at 25° C. for 30 min. $NH_4Cl$ (20 mL) saturated solution was added to the mixture, and the mixture was extracted with EtOAc (15 mL×2). The combined organic layers were washed with brine (20 mL), dried over $Na_2SO_4$, and filtered. The filtrate was concentrated in vacuo. The residue was purified by preparative TLC (petroleum/EtOAc) to afford 1-benzyl-8-bromo-4-ethyl-3,4-dihydro-1H-benzo[e][1,4]diazepin-5(2H)-one. MS: 359 and 361 (M+1).

Step 6: To a solution of 1-benzyl-8-bromo-4-ethyl-3,4-dihydro-1H-benzo[e][1,4]diazepin-5(2H)-one (104 mg, 0.289 mmol) in EtOH (5 mL) was added $PdCl_2$(dppf) (21.2 mg, 0.029 mmol) and potassium acetate (85 mg, 0.868 mmol). The mixture was stirred under CO (pressure: 50 psi) at 80° C. for 16 h. The mixture was concentrated under reduced pressure. The residue was purified by preparative TLC (pet. ether: EtOAc) to give ethyl-1-benzyl-4-ethyl-5-oxo-2,3,4,5-tetrahydro-1H-benzo[e][1,4]diazepine-8-carboxylate. MS: 353 (M+1).

Step 7: To a solution of ethyl 1-benzyl-4-ethyl-5-oxo-2,3,4,5-tetrahydro-1H-benzo[e][1,4]diazepine-8-carboxylate (100 mg, 0.284 mmol) in EtOH (3 mL) was added Pd—C (302 mg, 0.284 mmol) (10% Wt) under $N_2$ atmosphere. The mixture was degassed and backfilled with $H_2$ (three times). The resulting mixture was stirred under $H_2$ (pressure: 15 psi) at 25° C. for 16 h. The catalyst was filtered off, and filtrate was concentrated under reduced pressure to give ethyl 4-ethyl-5-oxo-2,3,4,5-tetrahydro-1H-benzo[e][1,4]diazepine-8-carboxylate, which was used in the next step without further purification. MS: 263 (M+1).

Step 8: A mixture of ethyl 4-ethyl-5-oxo-2,3,4,5-tetrahydro-1H-benzo[e][1,4]diazepine-8-carboxylate (65 mg, 0.248 mmol) and $LiOH·H_2O$ (41.6 mg, 0.991 mmol) in EtOH (3 mL) and water (1 mL) was stirred at 25° C. for 0.5 h. The solvent was removed under reduced pressure to give lithium 4-ethyl-5-oxo-2,3,4,5-tetrahydro-1H-benzo[e][1,4]diazepine-8-carboxylate, which was used without further purification. MS: 235 (M+1).

TABLE 9

The following intermediate was prepared using a similar procedure as Intermediate 54.

| Intermediate # | Structure | Compound Name | Exact Mass [M + 1] |
|---|---|---|---|
| 55 | 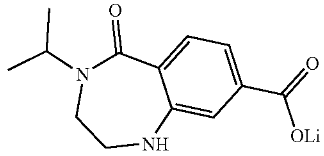 | lithium 4-isopropyl-5-oxo-2,3,4,5-tetrahydro-1H-benzo[e][1,4]diazepine-8-carboxylate | 255 |

Intermediate 56: 6-bromo-8-(methoxymethyl)imidazo[1,2-a]pyridine-2-carboxylic acid

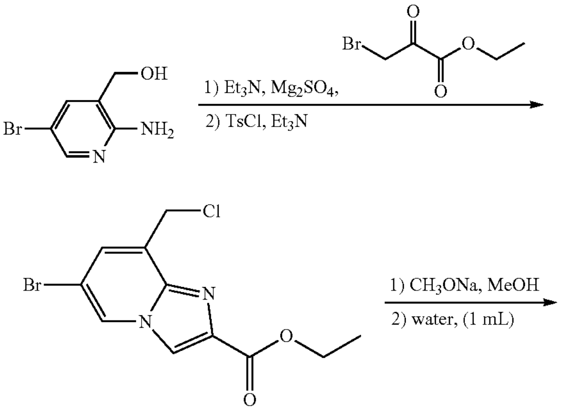

-continued

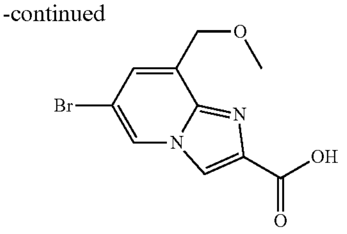

Step 1: To a mixture of (2-amino-5-bromopyridin-3-yl) methanol (1 g, 4.93 mmol) in 1,4-dioxane (80 mL) was added $MgSO_4$ (1.78 g, 14.8 mmol) and ethyl 3-bromo-2-oxopropanoate (2.06 g, 7.39 mmol) at 25° C. The mixture was stirred at 80° C. for 12 h. After cooling to 25° C., TEA (0.824 mL, 5.91 mmol) was added, and the mixture was stirred at 25° C. for 1 h. The precipitate was filtered off, and the filtrate was concentrated. The residue was washed with EtOAc (50 mL) and filtered to give ethyl 6-bromo-8-(hydroxymethyl)imidazo[1,2-a]pyridine-2-carboxylate, which was used in the next step without further purification. MS: 299 and 301 (M+1). $^1$H NMR (400 MHz, DMSO-$d_6$) δ 8.76-8.83 (m, 1H), 8.48 (s, 1H), 7.35 (d, J=1.8 Hz, 1H), 5.58 (t, J=5.7 Hz, 1H), 4.82 (d, J=5.7 Hz, 2H), 4.30 (q, J=7.2 Hz, 2H), 1.30 (t, J=7.2 Hz, 3H).

Step 2: To a mixture of ethyl 6-bromo-8-(hydroxymethyl) imidazo[1,2-a]pyridine-2-carboxylate (300 mg, 1.00 mmol) and TEA (0.419 mL, 3.01 mmol) in DCM (10 mL) was added 4-methylbenzene-1-sulfonyl chloride (287 mg, 1.50 mmol) at 0° C. The mixture was stirred at 25° C. for 12 h. The mixture was concentrated under reduced pressure, and the residue was purified by flash silica gel chromatography (ethyl acetate/pet. ether gradient) to give ethyl 6-bromo-8-(chloromethyl)imidazo[1,2-a]pyridine-2-carboxylate. MS: 317 and 319 (M+1). $^1$H NMR (400 MHz, DMSO-$d_6$) δ 8.93 (d, J=1.5 Hz, 1H), 8.54 (s, 1H), 7.69 (d, J=2.0 Hz, 1H), 5.04 (s, 2H), 4.35 (q, J=6.9 Hz, 2H), 1.34 (t, J=7.1 Hz, 3H).

Step 3: To a mixture of ethyl 6-bromo-8-(chloromethyl) imidazo[1,2-a]pyridine-2-carboxylate (50 mg, 0.157 mmol) in MeOH (2 mL) was added sodium methanolate (25.5 mg, 0.472 mmol) at 25° C. The mixture was stirred at 25° C. for 12 h. Water (0.5 mL) was added to the mixture, and the mixture was stirred at 25° C. for 1 h. The mixture was concentrated under reduced pressure, and the residue was dissolved in water (3 mL) and acidified with 1 M HCl to pH 6. The aqueous layer was extracted with EtOAc (5 mL×3), and the combined organic layers were washed with brine (5 mL), dried over anhydrous $Na_2SO_4$, filtered, and concentrated under reduced pressure to give 6-bromo-8-(methoxymethyl)imidazo[1,2-a]pyridine-2-carboxylic acid. MS: 285 and 287 (M+1).

Intermediate 57: 8-(hydroxymethyl)-6-(trifluoromethyl)imidazo[1,2-a]pyridine-2-carboxylic acid

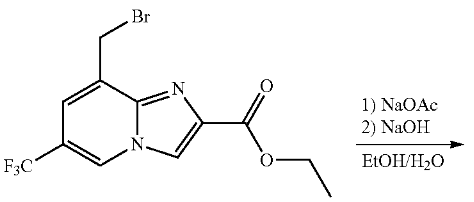

-continued

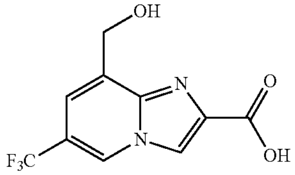

Step 1: A mixture of ethyl 8-(bromomethyl)-6-(trifluoromethyl)imidazo[1,2-a]pyridine-2-carboxylate (100 mg, 0.285 mmol) and sodium acetate (66 mg, 0.805 mmol) in DMF (2 mL) was heated to 45° C. for 0.5 h. The mixture was concentrated under reduced pressure. The residue was purified by preparative TLC (ethyl acetate/pet. ether) to give ethyl 8-(acetoxymethyl)-6-(trifluoromethyl)imidazo[1,2-a]pyridine-2-carboxylate. MS: 331 (M+1). $^1$H NMR (400 MHz, $CDCl_3$) δ 8.47 (s, 1H), 8.28 (s, 1H), 7.38 (s, 1H), 5.63 (s, 2H), 4.48 (q, J=7.1 Hz, 2H), 2.21 (s, 3H), 1.44 (t, J=7.2 Hz, 3H).

Step 2: To a solution of ethyl 8-(acetoxymethyl)-6-(trifluoromethyl)imidazo[1,2-a]pyridine-2-carboxylate (40 mg, 0.121 mmol) in EtOH (2 mL) was added NaOH (0.242 mL, 0.484 mmol; 2 M in water). The mixture was stirred at 20° C. for 1 h. The mixture was concentrated under reduced pressure to give 8-(hydroxymethyl)-6-(trifluoromethyl)imidazo[1,2-a]pyridine-2-carboxylic acid, which was used without further purification. MS: 261 (M+1).

Intermediate 58 and 59: (6R)-bromo-8-(2,2,2-trifluoro-1-hydroxyethyl)imidazo[1,2-a]pyridine-2-carboxylic acid and (6S)-bromo-8-(2,2,2-trifluoro-1-hydroxyethyl)imidazo[1,2-a]pyridine-2-carboxylic acid

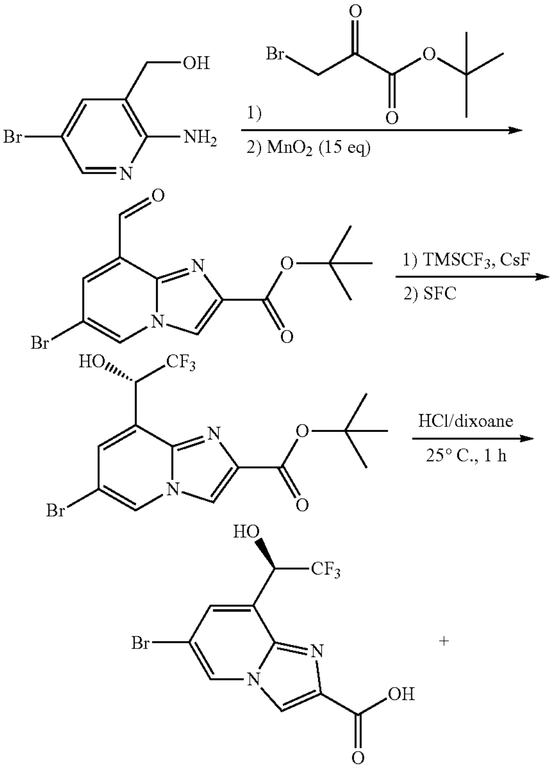

-continued

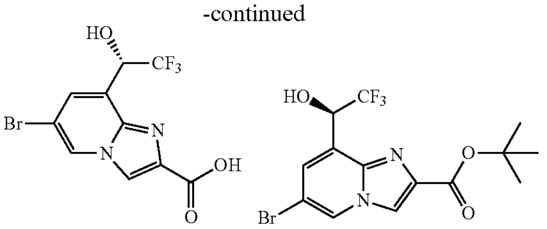

Step 1: To a mixture of (2-amino-5-bromopyridin-3-yl) methanol (1 g, 4.93 mmol) in 1,4-dioxane (80 mL) was added $MgSO_4$ (1.78 g, 14.8 mmol) and tert-butyl 3-bromo-2-oxopropanoate (1.65 g, 7.39 mmol) at 25° C. The mixture was stirred at 80° C. for 6 h. After cooling to 25° C., TEA (0.824 mL, 5.91 mmol) was added, and the mixture was stirred at 25° C. for 1 h. The precipitate was filtered off, and the filtrate was concentrated under reduced pressure. The residue was purified by flash silica gel chromatography (ethyl acetate/pet. ether gradient) to give tert-butyl 6-bromo-8-(hydroxymethyl)imidazo[1,2-a]pyridine-2-carboxylate. MS: 327 and 329 (M+1). $^1H$ NMR (400 MHz, DMSO-$d_6$) δ 8.77 (s, 1H), 8.38 (s, 1H), 7.33 (d, J=1.3 Hz, 1H), 5.56 (t, J=5.7 Hz, 1H), 4.81 (d, J=5.7 Hz, 2H), 1.53 (s, 9H).

Step 2: To a mixture of tert-butyl 6-bromo-8-(hydroxymethyl)imidazo[1,2-a]pyridine-2-carboxylate (850 mg, 2.60 mmol) in $CHCl_3$ (20 mL) was added manganese dioxide (3.39 g, 39.0 mmol) at 25° C. The mixture was stirred at 75° C. for 12 h. The solid was filtered off, and the filtrate was concentrated under reduced pressure to give tert-butyl 6-bromo-8-formylimidazo[1,2-a]pyridine-2-carboxylate, which was used in the next step without further purification. MS: 325 and 327 (M+1). $^1H$ NMR (400 MHz, $CDCl_3$) δ 10.84 (s, 1H), 8.51 (d, J=2.2 Hz, 1H), 8.16 (s, 1H), 7.94 (d, J=1.8 Hz, 1H), 1.65 (s, 9H).

Step 3: To a mixture of tert-butyl 6-bromo-8-formylimidazo[1,2-a]pyridine-2-carboxylate (200 mg, 0.615 mmol) in THF (10 mL) was added CsF (46.7 mg, 0.308 mmol) and trimethyl(trifluoromethyl)silane (262 mg, 1.845 mmol) at 0° C. The mixture was stirred at 25° C. for 2 h. Saturated $NH_4Cl$ (1 mL) was added to the mixture, and the resultant mixture was added to water (10 mL). The aqueous layer was re-extracted with EtOAc (10 mL×3). The combined organic layers were washed with brine (10 mL), dried over anhydrous $Na_2SO_4$, filtered, and concentrated under reduced pressure. The residue was purified by preparative TLC (ethyl acetate/pet. ether) to give tert-butyl 6-bromo-8-(2,2,2-trifluoro-1-hydroxyethyl)imidazo[1,2-a]pyridine-2-carboxylate. MS: 395 and 397 (M+1).

Step 4: The mixture of isomers of tert-butyl 6-bromo-8-(2,2,2-trifluoro-1-hydroxyethyl)imidazo[1,2-a]pyridine-2-carboxylate (120 mg, 0.304 mmol) was separated by SFC (AD Column, EtOH/$CO_2$) to afford tert-butyl (R or S)-6-bromo-8-(2,2,2-trifluoro-1-hydroxyethyl)imidazo[1,2-a]pyridine-2-carboxylate and tert-butyl (S or R)-6-bromo-8-(2,2,2-trifluoro-1-hydroxyethyl)imidazo[1,2-a]pyridine-2-carboxylate.

Step 5: A mixture of tert-butyl (S or R)-6-bromo-8-(2,2,2-trifluoro-1-hydroxyethyl)imidazo[1,2-a]pyridine-2-carboxylate (38 mg, 0.096 mmol) in HCl (4 M in dioxane, 2 mL) was stirred at 25° C. for 5 h. The mixture was concentrated under reduced pressure to give tert-Butyl (R or S)-6-bromo-8-(2,2,2-trifluoro-1-hydroxyethyl)imidazo[1,2-a]pyridine-2-carboxylate. MS: 339 and 341 (M+1).

The other isomer, tert-Butyl (R or S)-6-bromo-8-(2,2,2-trifluoro-1-hydroxyethyl)imidazo[1,2-a]pyridine-2-carboxylate was also subjected to the same condition. MS: 339 and 341 (M+1).

Intermediate 60: 2-oxo-1-(1,1,1-trifluoropropan-2-yl)-1,2-dihydropyridine-4-carboxylic acid

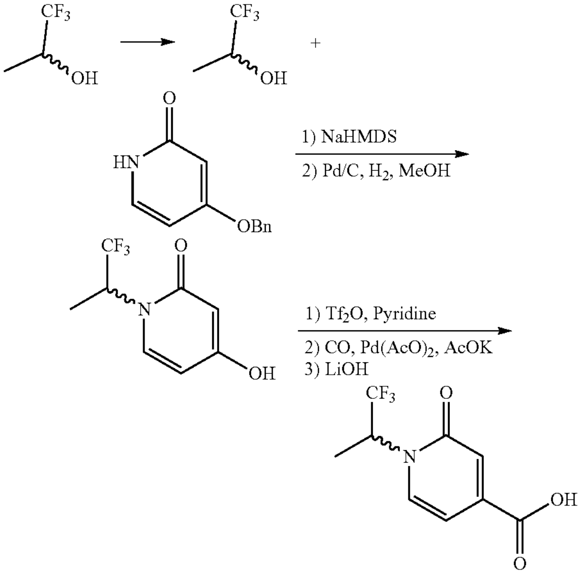

Step 1: To a mixture of 1,1,1-trifluoropropan-2-ol (8 g, 70.1 mmol) and TEA (29.3 mL, 210 mmol) in THF (80 mL) was added 4-methylbenzene-1-sulfonyl chloride (14.7 g, 77 mmol) at 20° C. The mixture was stirred at 20° C. for 16 h. The mixture was concentrated under reduced pressure, and the residue was dissolved in water (100 mL) and extracted with EtOAc (100 mL). The aqueous layer was extracted with EtOAc (50 mL×3). The combined organic layers were washed with brine (50 mL), dried over anhydrous $Na_2SO_4$, filtered, and concentrated under reduced pressure. The residue was purified by flash silica gel chromatography (petroleum ether/ethyl acetate gradient) to give 1,1,1-trifluoropropan-2-yl 4-methylbenzenesulfonate. $^1H$ NMR (400 MHz, $CDCl_3$) δ 7.80-7.82 (m, 2H), 7.27-7.38 (m, 2H), 4.80-4.87 (m, 1H), 2.47 (s, 3H), 1.47-1.48 (m, 3H).

Step 2: To a mixture of 4-(benzyloxy)pyridin-2(1H)-one (2 g, 9.94 mmol) in DMAc (15 mL) was added NaHMDS (10.9 mL, 10.9 mmol, 1M in THF). The mixture was stirred at 20° C. for 1 h. 1,1,1-trifluoropropan-2-yl 4-methylbenzenesulfonate (2.67 g, 9.94 mmol) was added to the mixture, and the mixture was stirred at 180° C. for 4 h. The mixture was added to water (100 mL) and extracted with DCM (30 mL×3). The combined organic layers were dried over anhydrous $Na_2SO_4$, filtered, and the filtrate was concentrated under reduced pressure to give the crude product which was purified by flash silica gel chromatography (petroleum ether/ethyl acetate gradient) to give 4-(benzyloxy)-1-(1,1,1-trifluoropropan-2-yl)pyridin-2(1H)-one. MS: 298 (M+1).

Step 3: To a mixture of 4-(benzyloxy)-1-(1,1,1-trifluoropropan-2-yl)pyridin-2(1H)-one (620 mg, 2.09 mmol) in MeOH (10 mL) was added Pd/C (222 mg, 0.209 mmol, 10% wt), under $N_2$ atmosphere. The mixture was degassed and backfilled with $H_2$ (three times). The resultant mixture was stirred under $H_2$ (pressure: 15 psi) at 25° C. for 16 h. The catalyst was filtered off, and the filtrate was concentrated under reduced pressure to give 4-hydroxy-1-(1,1,1-trifluoropropan-2-yl)pyridin-2(1H)-one, which was used in the next step without further purification. MS: 208 (M+1).

Step 4: To a mixture of 4-hydroxy-1-(1,1,1-trifluoropropan-2-yl)pyridin-2(1H)-one (430 mg, 2.07 mmol) in DCM (4 mL) was added pyridine (657 mg, 8.30 mmol) and trifluoromethanesulfonic anhydride (1.17 g, 4.15 mmol) at 0° C. The mixture was stirred at 0° C. for 1 h. Water (10 mL) was added to the mixture, and the mixture was extracted with DCM (5 mL). The aqueous layer was re-extracted with DCM (10 mL×3). The combined organic layers were washed with brine (10 mL), dried over anhydrous $Na_2SO_4$, filtered, and the filtrate was concentrated under reduced pressure. The residue was purified by flash silica gel chromatography (ethyl acetate/pet. ether gradient) to give 2-oxo-1-(1,1,1-trifluoropropan-2-yl)-1,2-dihydropyridin-4-yl trifluoromethanesulfonate. MS: 340 (M+1).

Step 5: To a solution of 2-oxo-1-(1,1,1-trifluoropropan-2-yl)-1,2-dihydropyridin-4-yl trifluoromethanesulfonate (520 mg, 1.53 mmol) and potassium acetate (451 mg, 4.60 mmol) in MeOH (5 mL) was added $PdCl_2$(dppf) (112 mg, 0.153 mmol) under $N_2$ atmosphere. The mixture was degassed and backfilled with CO (three times). The resulting mixture was stirred under CO (pressure: 50 psi) at 70° C. for 10 h. The catalyst was filtered off, and the filtrate was concentrated under reduced pressure. The residue was purified by flash silica gel chromatography (ethyl acetate/pet. ether gradient) to give methyl 2-oxo-1-(1,1,1-trifluoropropan-2-yl)-1,2-dihydropyridine-4-carboxylate. MS: 250 (M+1).

Step 6: To a mixture of methyl 2-oxo-1-(1,1,1-trifluoropropan-2-yl)-1,2-dihydropyridine-4-carboxylate (310 mg, 1.24 mmol) in THF (2 mL) and water (1 mL) was added lithium hydroxide hydrate (104 mg, 2.49 mmol). The mixture was stirred at 20° C. for 2 h. 1 M hydrochloric acid was added to the mixture to adjust pH of the mixture to pH 7. The mixture was then concentrated under reduced pressure to give the crude product 2-oxo-1-(1,1,1-trifluoropropan-2-yl)-1,2-dihydropyridine-4-carboxylic acid, which was used without further purification. MS: 236 (M+1). $^1$H NMR (400 MHz, DMSO-$d_6$) δ 7.89 (d, J=7.3 Hz, 1H), 6.92 (d, J=1.5 Hz, 1H), 6.63 (dd, J=2.0, 7.3 Hz, 1H), 5.82 (td, J=7.8, 15.3 Hz, 1H), 1.60 (d, J=7.3 Hz, 3H).

Intermediate 61 and 62: (R)-6-bromo-8-(1-methoxyethyl)imidazo[1,2-a]pyridine-2-carboxylic acid and (S)-6-bromo-8-(1-methoxyethyl)imidazo[1,2-a]pyridine-2-carboxylic acid

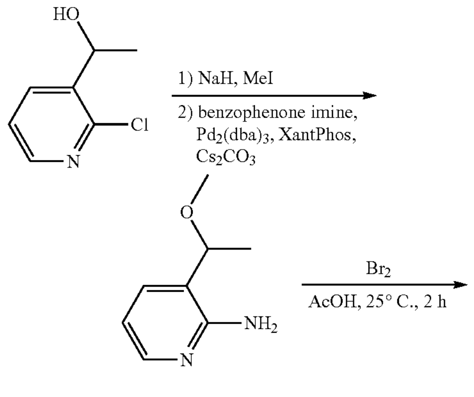

-continued

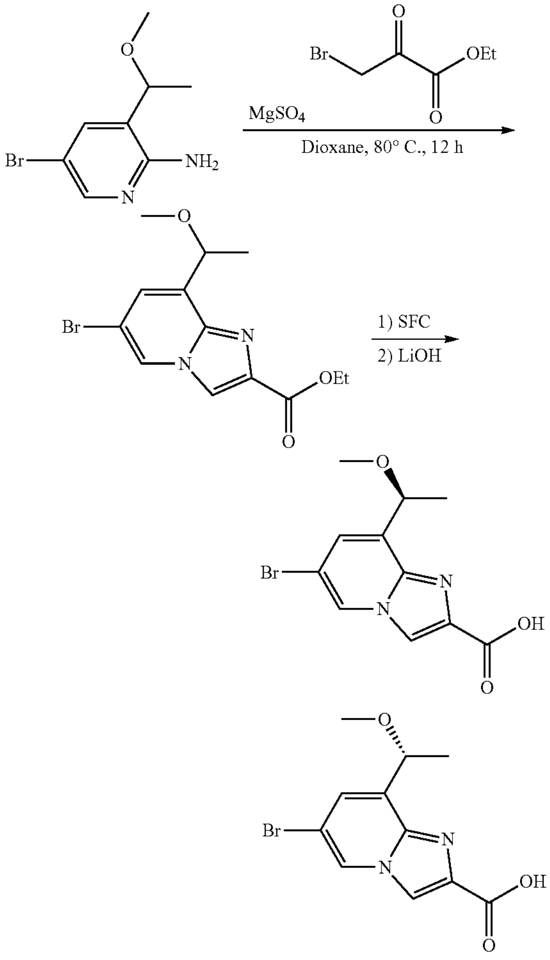

Step 1: To a mixture of 2-chloronicotinaldehyde (4.0 g, 28 mmol) in THF (100 mL) was added methylmagnesium bromide (3M in diethyl ether) (14.1 mL, 42.4 mmol) slowly dropwise at −78° C. The mixture was stirred at −78° C. for 0.5 h. Saturated $NH_4Cl$ (50 mL) and water (80 mL) were added to the mixture. The aqueous layer was extracted with ethyl acetate (70 mL×3). The combined organic layers were washed with brine (100 mL), dried over anhydrous $Na_2SO_4$, filtered, and concentrated under reduced pressure to give 1-(2-chloropyridin-3-yl)ethanol, which was used in the next step without further purification. MS: 158 and 160 (M+1). $^1$H NMR (400 MHz, $CDCl_3$) δ 8.23-8.28 (m, 1H), 7.96 (dd, J=1.3, 7.9 Hz, 1H), 7.24-7.30 (m, 1H), 5.18-5.26 (m, 1H), 2.60 (d, J=3.5 Hz, 1H), 1.49 (d, J=6.6 Hz, 3H).

Step 2: To a mixture of 1-(2-chloropyridin-3-yl)ethanol (4.4 g, 27.9 mmol) and MeI (2.22 mL, 35.4 mmol) in DMF (60 mL) was added NaH (1.34 g, 33.5 mmol) at 0° C. The mixture was stirred at 0° C. for 0.5 h. Water (500 mL) was added to the mixture. The aqueous layer was re-extracted with ethyl acetate (200 mL×3). The combined organic layers were washed with brine (300 mL), dried over anhydrous $Na_2SO_4$, filtered, and concentrated under reduced pressure. The residue was purified by flash silica gel chromatography (ethyl acetate/pet. ether gradient) to give 2-chloro-3-(1-methoxyethyl)pyridine. MS: 172 (M+1). $^1$H NMR (400 MHz, $CDCl_3$) δ 8.34 (dd, J=2.0, 4.9 Hz, 1H), 7.85 (dd, J=2.0, 7.8 Hz, 1H), 7.31 (dd, J=4.9, 7.8 Hz, 1H), 4.71 (q, J=6.4 Hz, 1H), 3.30 (s, 3H), 1.45 (d, J=6.4 Hz, 3H).

Step 3: To a solution of 2-chloro-3-(1-methoxyethyl) pyridine (4.3 g, 25 mmol), diphenylmethanimine (5.45 g, 30.1 mmol), XantPhos (1.45 g, 2.51 mmol) in 1,4-dioxane (60 mL) was added $Cs_2CO_3$ (19.6 g, 60.1 mmol) and $Pd_2(dba)_3$ (1.15 g, 1.25 mmol) at 25° C. The resultant mixture was degassed and backfilled with $N_2$ (three times) and stirred at 90° C. for 12 h. The mixture was concentrated under reduced pressure to remove dioxane and $H_2O$ (60 mL) was added. The mixture was extracted with Ethyl acetate (40 mL×3). The organic layers were dried over $Na_2SO_4$, filtered, and the filtrate was concentrated under reduced pressure. The residue was dissolved in MeOH (30 mL), and the mixture was adjusted to pH 5 with HCl solution (aq. 1 M) and stirred for 20 min. The mixture was basified with ammonium hydroxide (1 M) to pH 8, and the mixture was concentrated under reduced pressure. The residue was purified by flash silica gel chromatography (Ethyl acetate/pet. ether gradient) to give 3-(1-methoxyethyl)pyridin-2-amine. MS: 153 (M+1). $^1H$ NMR (400 MHz, $CDCl_3$) δ 8.02 (dd, J=1.7, 5.1 Hz, 1H), 7.26 (dd, J=2.0, 7.3 Hz, 1H), 6.63 (dd, J=4.9, 7.3 Hz, 1H), 5.10 (br s, 2H), 4.34 (q, J=6.9 Hz, 1H), 3.26-3.31 (m, 3H), 1.53 (d, J=6.9 Hz, 3H).

Step 4: To a mixture of 3-(1-methoxyethyl)pyridin-2-amine (500 mg, 3.29 mmol) in AcOH (5 mL) was added $Br_2$ (0.25 mL, 4.93 mmol) at 25° C. The mixture was stirred at 25° C. for 2 h. The mixture was concentrated under reduced pressure. The residue was dissolved in water (5 mL), and the mixture was adjusted to pH 8 with sat. $NaHCO_3$. The aqueous layer was extracted with Ethyl acetate (10 mL×5), and the combined organic layers were washed with brine (20 mL), dried over anhydrous $Na_2SO_4$, filtered, and concentrated under reduced pressure. The residue was purified by flash silica gel chromatography (Ethyl acetate/pet. ether gradient) to give 5-bromo-3-(1-methoxyethyl)pyridin-2-amine. MS: 231 and 233 (M+1). $^1H$ NMR (400 MHz, $CDCl_3$) δ 8.05 (d, J=2.5 Hz, 1H), 7.37 (d, J=2.5 Hz, 1H), 5.14 (br s, 2H), 4.23-4.33 (m, 1H), 3.29 (s, 3H), 1.51 (d, J=6.9 Hz, 3H).

Step 5: To a mixture of 5-bromo-3-(1-methoxyethyl) pyridin-2-amine (270 mg, 1.17 mmol) in 1,4-dioxane (15 mL) was added $MgSO_4$ (422 mg, 3.51 mmol) and ethyl 3-bromo-2-oxopropanoate (349 mg, 1.75 mmol) at 25° C. The mixture was stirred at 80° C. for 12 h. After cooling to 25° C., TEA (0.20 mL, 1.4 mmol) was added. The mixture was stirred at 25° C. for 1 h and the precipitate was filtered off. The filtrate was concentrated under reduced pressure. The residue was purified by flash silica gel chromatography (Ethyl acetate/pet. ether gradient) to give ethyl 6-bromo-8-(1-methoxyethyl)imidazo[1,2-a]pyridine-2-carboxylate. MS: 327 and 329 (M+1). $^1H$ NMR (400 MHz, $CDCl_3$) δ 8.20 (d, J=1.8 Hz, 1H), 8.13 (s, 1H), 7.37-7.42 (m, 1H), 5.20 (q, J=6.6 Hz, 1H), 4.42-4.50 (m, 2H), 3.38 (s, 3H), 1.54 (d, J=6.6 Hz, 3H), 1.42 (t, J=7.0 Hz, 3H).

Step 6: A mixture of isomers of ethyl 6-bromo-8-(1-methoxyethyl)imidazo[1,2-a]pyridine-2-carboxylate (210 mg, 0.64 mmol) was separated by SFC (AD Column, $NH_3 \cdot H_2O$/EtOH/$CO_2$) to afford ethyl (S or R)-6-bromo-8-(1-methoxyethyl)imidazo[1,2-a]pyridine-2-carboxylate (Peak 1) and ethyl (S or R)-6-bromo-8-(1-methoxyethyl) imidazo[1,2-a]pyridine-2-carboxylate (Peak 2).

Peak 1: MS: 327 and 329 (M+1). $^1H$ NMR (400 MHz, $CDCl_3$) δ 8.20 (d, J=1.8 Hz, 1H), 8.13 (s, 1H), 7.40 (s, 1H), 5.20 (q, J=6.6 Hz, 1H), 4.42-4.49 (m, 2H), 3.38 (s, 3H), 1.54 (d, J=6.6 Hz, 3H), 1.42 (t, J=7.2 Hz, 3H).

Peak 2: MS: 327 and 329 (M+1). $^1H$ NMR (400 MHz, $CDCl_3$) δ 8.20 (d, J=1.8 Hz, 1H), 8.13 (s, 1H), 7.37-7.43 (m, 1H), 5.14-5.25 (m, 1H), 4.40-4.49 (m, 2H), 3.38 (s, 3H), 1.55 (d, J=6.1 Hz, 3H), 1.42 (t, J=7.2 Hz, 3H).

Step 7: To a mixture of ethyl (R or S)-6-bromo-8-(1-methoxyethyl)imidazo[1,2-a]pyridine-2-carboxylate (70 mg, 0.21 mmol) in EtOH (2 mL) and water (0.5 mL) was added $LiOH \cdot H_2O$ (178 mg, 0.43 mmol) at 25° C. The mixture was stirred at 25° C. for 2 h. The mixture was concentrated under reduced pressure to give crude product (R or S)-6-bromo-8-(1-methoxyethyl)imidazo[1,2-a]pyridine-2-carboxylic acid, which was used in the next step without further purification. MS: 299 and 301 (M+1). The same was carried out with ethyl (S or R)-6-bromo-8-(1-methoxyethyl)imidazo[1,2-a]pyridine-2-carboxylate isomer.

Intermediate 63 and 64: (R or S)-6-bromo-8-[1-hydroxyethyl]imidazo[1,2-a]pyridine-2-carboxylic acid and (S or R)-6-bromo-8-[1-hydroxyethyl]imidazo[1,2-a]pyridine-2-carboxylic

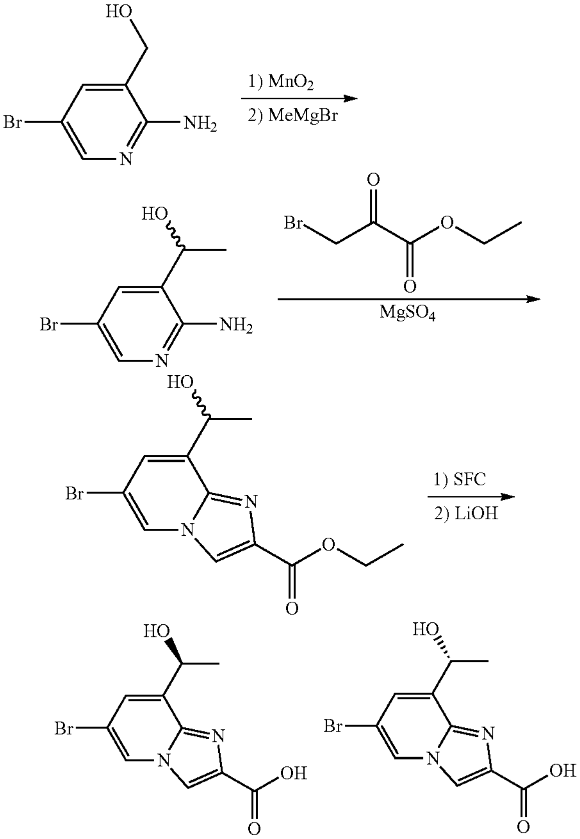

Step 1: To a mixture of (2-amino-5-bromopyridin-3-yl) methanol (0.80 g, 3.9 mmol) in DCM (20 mL) was added manganese dioxide (5.14 g, 59.1 mmol) at 25° C. The mixture was stirred at 25° C. for 12 h. The solid was filtered off, and the filtrate was concentrated under reduced pressure to give 2-amino-5-bromonicotinaldehyde, which was used in the next step without further purification. MS: 201 and 203 (M+1). $^1H$ NMR (400 MHz, DMSO-$d_6$) δ 9.81 (s, 1H), 8.30 (d, J=2.2 Hz, 1H), 8.23 (d, J=2.2 Hz, 1H), 7.68 (br s, 2H).

Step 2: To a mixture of 2-amino-5-bromonicotinaldehyde (670 mg, 3.33 mmol) in THF (20 mL) was added methylmagnesium bromide (3M in diethyl ether, 2.22 mL, 6.67 mmol) slowly dropwise at 0° C. The mixture was stirred at 20° C. for 1 h. Saturated $NH_4Cl$ (10 mL) and water (30 mL) were added to the mixture. The aqueous layer was extracted with ethyl acetate (30 mL×3). The combined organic layers were washed with brine (50 mL), dried over anhydrous $Na_2SO_4$, filtered, and concentrated under reduced pressure. The residue was purified by flash silica gel chromatography (ethyl acetate/pet. ether gradient) to give 1-(2-amino-5-bromopyridin-3-yl)ethanol. MS: 217 and 219 (M+1). $^1H$ NMR (400 MHz, DMSO-$d_6$) δ 7.86 (d, J=2.4 Hz, 1H), 7.50 (d, J=2.4 Hz, 1H), 5.95 (s, 2H), 4.61-4.70 (m, 1H), 1.25 (d, J=6.2 Hz, 3H).

Step 3: To a mixture of 1-(2-amino-5-bromopyridin-3-yl) ethanol (280 mg, 1.29 mmol) in 1,4-dioxane (15 mL) was added $MgSO_4$ (466 mg, 3.87 mmol) and ethyl 3-bromo-2-oxopropanoate (385 mg, 1.94 mmol) at 25° C. The mixture was stirred at 80° C. for 12 h. After cooling to 25° C., TEA (0.22 mL, 1.6 mmol) was added. The mixture was stirred at 25° C. for 1 h. The precipitate was filtered off, and the filtrate was concentrated under reduced pressure. The residue was purified by flash silica gel chromatography (ethyl acetate/pet. ether gradient) to give ethyl 6-bromo-8-(1-hydroxyethyl)imidazo[1,2-a]pyridine-2-carboxylate. MS: 313 and 315 (M+1). $^1H$ NMR (400 MHz, DMSO-$d_6$) δ 8.81 (d, J=2.0 Hz, 1H), 8.45-8.56 (m, 1H), 7.40 (dd, J=1.0, 2.0 Hz, 1H), 5.24 (quin, J=5.9 Hz, 1H), 4.29-4.39 (m, 2H), 1.49 (d, J=6.5 Hz, 3H), 1.33 (t, J=7.1 Hz, 3H).

Step 4: A mixture of ethyl 6-bromo-8-(1-hydroxyethyl) imidazo[1,2-a]pyridine-2-carboxylate (190 mg, 0.61 mmol) was separated by SFC (AD Column, MeOH/$CO_2$+modifier $NH_3 \cdot H_2O$) to afford ethyl (S or R)-6-bromo-8-(1-hydroxyethyl)imidazo[1,2-a]pyridine-2-carboxylate and ethyl (R or S)-6-bromo-8-(1-hydroxyethyl)imidazo[1,2-a]pyridine-2-carboxylate.

Step 5: To either isomer of ethyl (S or R)-6-bromo-8-(1-hydroxyethyl)imidazo[1,2-a]pyridine-2-carboxylate (60 mg, 0.19 mmol) in EtOH (1 mL) was added $LiOH \cdot H_2O$ (24.1 mg, 0.5 mmol) in water (0.3 mL) at 25° C. The mixture was stirred at 25° C. for 2 h. The mixture was concentrated under reduced pressure to give (S or R)-6-bromo-8-(1-hydroxyethyl)imidazo[1,2-a]pyridine-2-carboxylic acid, which was used without further purification. MS: 285 and 287 (M+1). The same procedure was carried out with ethyl (S or R)-6-bromo-8-(1-hydroxyethyl)imidazo[1,2-a]pyridine-2-carboxylate isomer.

Intermediate 65 and 66: (6R,8S)-8-(2-cyanoethyl)-6-(trifluoromethyl)-5,6,7,8-tetrahydroimidazo[1,2-a]pyridine-2-carboxylic acid and (6S,8R)-8-(2-cyanoethyl)-6-(trifluoromethyl)-5,6,7,8-tetrahydroimidazo[1,2-a]pyridine-2-carboxylic acid

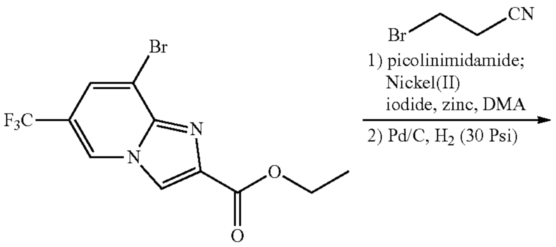

-continued

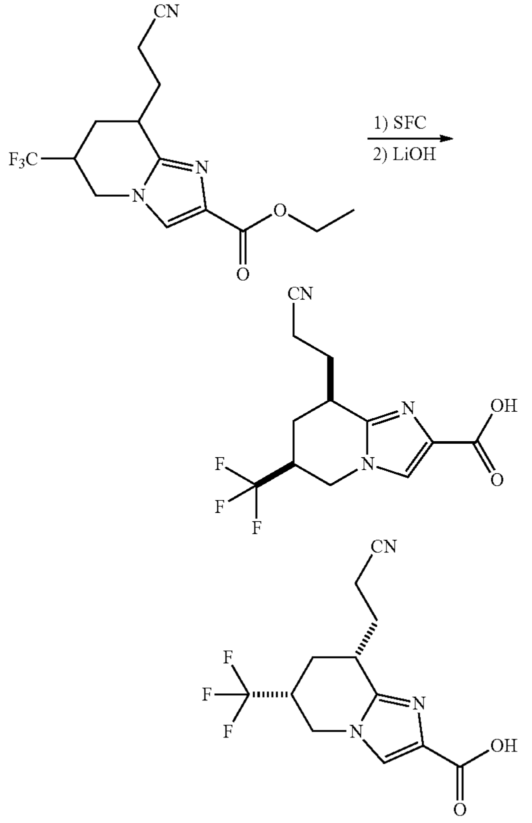

Step 1: To a solution of 3-bromo-5-(trifluoromethyl) pyridin-2-amine (15.0 g, 62.2 mmol) in DME (250 mL) was added ethyl 3-bromo-2-oxopropanoate (14.8 g, 76 mmol) dropwise at room temperature. The reaction mixture was heated to 90° C. for 18 h. The 1,2-dimethoxyethane was removed under reduced pressure to give crude product, which was purified by flash silica gel chromatography (ethyl acetate/pet. ether gradient) to give ethyl 8-bromo-6-(trifluoromethyl)imidazo[1,2-a]pyridine-2-carboxylate. $^1H$ NMR (400 MHz, MeOD-$d_4$) δ 9.11 (d, J=1.1 Hz, 1H), 8.62 (d, J=2.4 Hz, 1H), 7.89 (br d, J=2.7 Hz, 1H), 4.42 (dq, J=1.8, 7.1 Hz, 2H), 1.41 (dt, J=1.0, 7.1 Hz, 3H).

Step 2: A mixture of picolinimidamide compound with pyridine (1:1, 14.3 mg, 0.071 mmol), $NiI_2$ (27.8 mg, 0.089 mmol) and Zn (233 mg, 3.56 mmol) in DMA (15 mL) was stirred at 25° C. for 20 min under $N_2$. Ethyl 8-bromo-6-(trifluoromethyl)imidazo[1,2-a]pyridine-2-carboxylate (600 mg, 1.78 mmol) and 3-bromopropanenitrile (358 mg, 2.67 mmol) were added and the resultant mixture was stirred at 110° C. for 14 h. Water (150 mL) and EtOAc (100 mL) were added to the mixture. The aqueous layer was re-extracted with EtOAc (80 mL×3). The combined organic layers were washed with brine (100 mL), dried over anhydrous $Na_2SO_4$, filtered, and concentrated under reduced pressure. The residue was purified by flash silica gel chromatography (ethyl acetate/pet. ether gradient) to give ethyl 8-(2-cyanoethyl)-6-(trifluoromethyl)imidazo[1,2-a]pyridine-2-carboxylate. MS: 312 (M+1). $^1H$ NMR (400 MHz, $CDCl_3$) δ 8.48 (s, 1H), 8.27 (s, 1H), 7.31 (s, 1H), 4.47 (q, J=7.2 Hz, 2H), 3.40 (t, J=7.0 Hz, 2H), 3.04 (t, J=7.1 Hz, 2H), 1.43 (t, J=7.1 Hz, 3H).

Step 3: To a solution of ethyl 8-(2-cyanoethyl)-6-(trifluoromethyl)imidazo[1,2-a]pyridine-2-carboxylate (320 mg, 1.03 mmol) in MeOH (15 mL) was added Pd/C (109 mg, 0.103 mmol, 10% on C) under $N_2$ atmosphere. The mixture was degassed and backfilled with $H_2$ (three times). The resultant mixture was stirred under $H_2$ (pressure: 30 psi) at 25° C. for 3 h. The catalyst was filtered off, and the filtrate was concentrated under reduced pressure. The residue was purified by preparative TLC (ethyl acetate/pet. ether) to give racemic ethyl 8-(2-cyanoethyl)-6-(trifluoromethyl)-5,6,7,8-tetrahydroimidazo[1,2-a]pyridine-2-carboxylate. MS: 316 (M+1).

Step 4: Racemic ethyl 8-(2-cyanoethyl)-6-(trifluoromethyl)-5,6,7,8-tetrahydroimidazo[1,2-a]pyridine-2-carboxylate (100 mg) was separated by chiral SFC (IC column, ethanol/$CO_2$) to give ethyl (6R,8S)-8-(2-cyanoethyl)-6-(trifluoromethyl)-5,6,7,8-tetrahydroimidazo[1,2-a]pyridine-2-carboxylate and ethyl (6S,8R)-8-(2-cyanoethyl)-6-(trifluoromethyl)-5,6,7,8-tetrahydroimidazo[1,2-a]pyridine-2-carboxylate.

Step 5: To ethyl (6R,8S)-8-(2-cyanoethyl)-6-(trifluoromethyl)-5,6,7,8-tetrahydroimidazo[1,2-a]pyridine-2-carboxylate compound (40 mg, 0.13 mmol) in EtOH (2 mL) and water (0.5 mL) was added $LiOH \cdot H_2O$ (10.7 mg, 0.25 mmol) at 25° C. The mixture was stirred at 25° C. for 2 h. The mixture was concentrated under reduced pressure to give (6R,8S)-8-(2-cyanoethyl)-6-(trifluoromethyl)-5,6,7,8-tetrahydroimidazo[1,2-a]pyridine-2-carboxylic acid and the other isomer under the same conditions provided (6S,8R)-8-(2-cyanoethyl)-6-(trifluoromethyl)-5,6,7,8-tetrahydroimidazo [1,2-a]pyridine-2-carboxylic acid, which was used in the next step without further purification. MS: 288 (M+1).

Intermediate 67 and 68: (6R,8S)-8-methyl-6-(trifluoromethyl)-5,6,7,8-tetrahydroimidazo[1,2-a]pyridine-2-carboxylic acid and (6S,8R)-8-methyl-6-(trifluoromethyl)-5,6,7,8-tetrahydroimidazo[1,2-a]pyridine-2-carboxylic acid

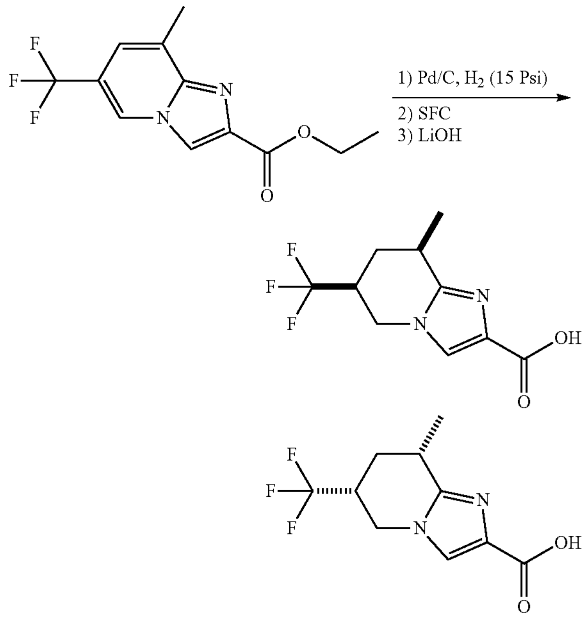

Step 1: To a solution of ethyl 8-methyl-6-(trifluoromethyl)imidazo[1,2-a]pyridine-2-carboxylate (323 mg, 1.19 mmol) in Ethanol (10 mL) was added Pd—C (10%, 283 mg, 0.27 mmol) under $N_2$ atmosphere. The mixture was degassed and backfilled with $H_2$ (three times). The resultant mixture was stirred under $H_2$ (pressure: 30 psi) at 30° C. for 4 h. The catalyst was filtered off, and the filtrate was concentrated under reduced pressure to give ethyl 8-methyl-6-(trifluoromethyl)-5,6,7,8-tetrahydroimidazo[1,2-a]pyridine-2-carboxylate, which was used in the next step without further purification.

Step 2: The mixture of ethyl 8-methyl-6-(trifluoromethyl)-5,6,7,8-tetrahydroimidazo[1,2-a]pyridine-2-carboxylate (500 mg, 1.81 mmol) was separated by chiral SFC (IC column, $NH_3 \cdot H_2O/MeOH/CO_2$) to give ethyl (6S,8R) or (6R,8S)-8-methyl-6-(trifluoromethyl)-5,6,7,8-tetrahydroimidazo[1,2-a]pyridine-2-carboxylate (Peak 1) and ethyl (6R,8S) or (6S,8R) 8-methyl-6-(trifluoromethyl)-5,6,7,8-tetrahydroimidazo[1,2-a]pyridine-2-carboxylate. Peak 1: MS: 277 (M+1). Peak 2: MS: 277 (M+1).

Step 3: A solution of ethyl (6S,8R) or (6R,8S)-8-methyl-6-(trifluoromethyl)-5,6,7,8-tetrahydroimidazo[1,2-a]pyridine-2-carboxylate (164 mg, 0.59 mmol) and $LiOH \cdot H_2O$ (37.4 mmol, 0.89 mmol) in ethanol (2.0 mL) and water (1.0 mL) was stirred at 25° C. for 2 h. The solvent was removed under reduced pressure, and the residue was dissolved in water (10.0 mL). The mixture was adjusted to pH~6 with 2.0 N HCl. The aqueous layer was concentrated to give (6S,8R) or (6R,8S)-8-methyl-6-(trifluoromethyl)-5,6,7,8-tetrahydroimidazo [1,2-a]pyridine-2-carboxylic acid, which was used without further purification. MS: 249 (M+1).

The isomer of the second peak was synthesized by the similar procedure:

MS: 249 (M+1).

Intermediate 69: 6-chloro-8-(methoxymethyl)imidazo[1,2-a]pyridine-2-carboxylic acid

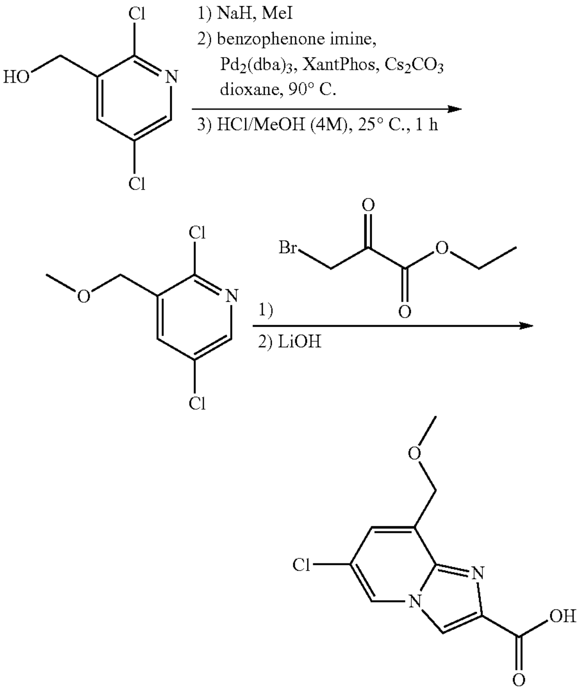

Step 1: To a mixture of 2,5-dichloronicotinic acid (2 g, 10.4 mmol) in THF (20 mL) was added $BH_3 \cdot THF$ (1 M in THF, 41.7 mL, 41.7 mmol) dropwise at 0° C. under $N_2$. The mixture was stirred at 25° C. for 5 h. MeOH (50 mL) was added to the mixture, and the mixture was stirred at 80° C. for 2 h. The mixture was concentrated under reduced pressure. The residue was purified by flash silica gel chromatography (ethyl acetate/pet. ether gradient) to give (2,5-dichloropyridin-3-yl)methanol. MS: 178 and 180 (M+1). $^1$H NMR (400 MHz, $CDCl_3$) δ 8.27 (d, J=2.6 Hz, 1H), 7.88-7.96 (m, 1H), 4.73-4.80 (m, 1H), 4.77 (d, J=4.8 Hz, 1H), 2.32 (br s, 1H).

Step 2: To a mixture of (2,5-dichloropyridin-3-yl)methanol (1.0 g, 5.6 mmol) in DMF (15 mL) was added NaH (0.270 g, 6.74 mmol) at 0° C., and the mixture was stirred at 0° C. for 0.5 h. Iodomethane (2.66 g, 18.7 mmol) was added to the mixture at 0° C., and the mixture was stirred at 25° C. at 1 h. Water (200 mL) and EtOAc (100 mL) were then added to the mixture. The aqueous layer was re-extracted with EtOAc (100 mL×3). The combined organic layers were washed with brine (200 mL), dried over anhydrous $Na_2SO_4$, filtered, and concentrated under reduced pressure. The residue was purified by flash silica gel chromatography (ethyl acetate/pet. ether gradient) to give 2,5-dichloro-3-(methoxymethyl)pyridine. MS: 192 (M+1). $^1$H NMR (400 MHz, $CD_3OD$) δ 8.30 (d, J=2.6 Hz, 1H), 7.88-7.97 (m, 1H), 4.51 (s, 2H), 3.50 (s, 3H).

Step 3: To a solution of 2,5-dichloro-3-(methoxymethyl)pyridine (300 mg, 1.56 mmol), benzophenone imine (340 mg, 1.88 mmol), XantPhos (90 mg, 0.16 mmol) in 1,4-dioxane (10 mL) was added $Cs_2CO_3$ (1.22 g, 3.75 mmol) and $Pd_2(dba)_3$ (71.5 mg, 0.08 mmol) at 25° C. The resultant mixture was degassed and backfilled with $N_2$ (three times) and stirred at 90° C. for 12 h. The mixture was concentrated under reduced pressure to remove 1,4-dioxane and $H_2O$ (30 mL) was added. The mixture was extracted with Ethyl acetate (20 mL×3). The organic layers were dried over $Na_2SO_4$, filtered, and the filtrate was concentrated under reduced pressure. The residue was dissolved in MeOH (20 mL), the pH was adjusted to pH 5 with HCl solution (aq. 1 M), and then the mixture was stirred for 20 min. The mixture was adjusted to pH 8 with ammonium hydroxide. The mixture was concentrated under reduced pressure. The residue was purified by preparative TLC (Ethyl acetate/pet. ether) to give 5-chloro-3-(methoxymethyl)pyridin-2-amine. MS: 173 (M+1). $^1$H NMR (400 MHz, $CDCl_3$) δ 7.98 (d, J=2.4 Hz, 1H), 7.30 (d, J=2.4 Hz, 1H), 4.96 (br s, 2H), 4.37 (s, 2H), 3.34 (s, 3H).

Step 4: To a mixture of 5-chloro-3-(methoxymethyl)pyridin-2-amine (100 mg, 0.579 mmol) in 1,4-dioxane (10 mL) was added $MgSO_4$ (209 mg, 1.74 mmol) and ethyl 3-bromo-2-oxopropanoate (173 mg, 0.87 mmol) at 25° C. The mixture was stirred at 80° C. for 12 h. After cooling to 25° C., TEA (0.10 mL, 0.70 mmol) was added, and the mixture was stirred at 25° C. for 1 h. The precipitate was filtered off, and the filtrate was concentrated under reduced pressure. The residue was purified by flash silica gel chromatography (ethyl acetate/pet. ether gradient) to give ethyl 6-chloro-8-(methoxymethyl)imidazo[1,2-a]pyridine-2-carboxylate. MS: 269 (M+1). $^1$H NMR (400 MHz, $CDCl_3$) δ 8.14 (s, 1H), 8.09-8.13 (m, 1H), 7.35 (d, J=1.3 Hz, 1H), 4.94 (s, 2H), 4.46 (q, J=7.0 Hz, 2H), 3.55 (s, 3H), 1.42 (t, J=7.2 Hz, 3H).

Step 5: To a mixture of ethyl 6-chloro-8-(methoxymethyl)imidazo[1,2-a]pyridine-2-carboxylate (80 mg, 0.30 mmol) in EtOH (4 mL) and water (1 mL) was added $LiOH \cdot H_2O$ (25 mg, 0.60 mmol) at 25° C. The mixture was stirred at 25° C. for 3 h. The mixture was concentrated under reduced pressure to give 6-chloro-8-(methoxymethyl)imidazo[1,2-a]pyridine-2-carboxylic acid, which was used without further purification. MS: 241 (M+1).

Intermediate 70: 8-(methoxymethyl)-6-methylimidazo[1,2-a]pyridine-2-carboxylic acid

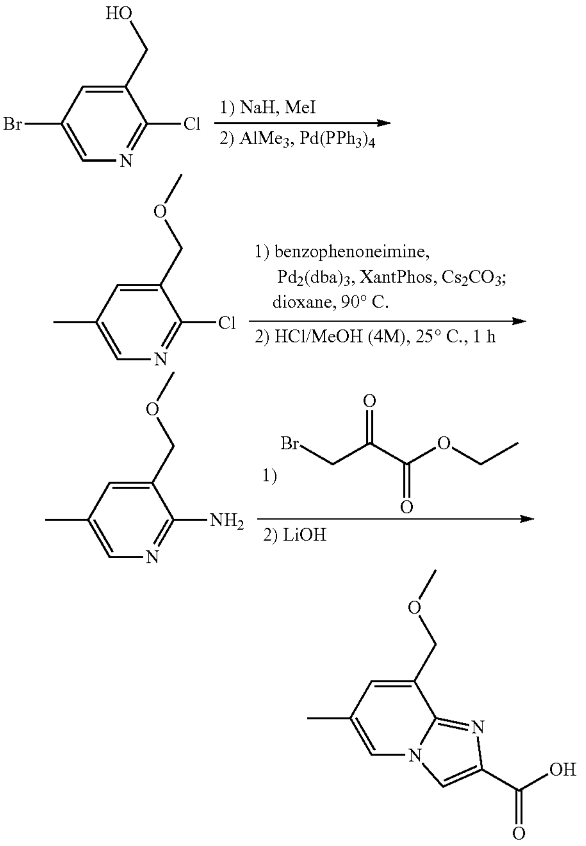

Step 1: To a mixture of methyl 5-bromo-2-chloronicotinate (5.0 g, 20 mmol) and calcium chloride (8.86 g, 80 mmol) in EtOH (60 mL) and THF (60 mL) was added $NaBH_4$ (6.04 g, 160 mmol) at 0° C. The mixture was stirred at 25° C. for 12 h. Water (500 mL) was added to the mixture, and the aqueous layer was re-extracted with EtOAc (200 mL×3). The combined organic layers were washed with brine (200 mL), dried over anhydrous $Na_2SO_4$, filtered, and concentrated to give (5-bromo-2-chloropyridin-3-yl)methanol, which was used in the next step without further purification. MS: 222 and 224 (M+1). $^1$H NMR (400 MHz, $CDCl_3$) δ 8.36 (d, J=2.6 Hz, 1H), 8.00-8.09 (m, 1H), 4.77 (br s, 2H), 2.30 (br s, 1H).

Step 2: To a mixture of (5-bromo-2-chloropyridin-3-yl)methanol (4.1 g, 18 mmol) in DMF (50 mL) was added NaH (0.885 g, 22.1 mmol) at 0° C. The mixture was stirred at 0° C. for 0.5 h. Iodomethane (7.35 g, 51.8 mmol) was added to the mixture at 0° C., and the mixture was stirred at 25° C. at 1 h. Water (500 mL) and EtOAc (200 mL) were then added to the mixture. The aqueous layer was re-extracted with EtOAc (200 mL×3). The combined organic layers were washed with brine (200 mL), dried over anhydrous $Na_2SO_4$, filtered, and concentrated under reduced pressure. The residue was purified by flash silica gel chromatography (ethyl acetate/pet. ether gradient) to give 5-bromo-2-chloro-3-

(methoxymethyl)pyridine. MS: 236 and 238 (M+1). $^1$H NMR (400 MHz, $CDCl_3$) δ 8.36 (s, 1H), 7.97 (d, J=1.3 Hz, 1H), 4.49 (s, 2H), 3.51 (s, 3H).

Step 3: To a mixture of 5-bromo-2-chloro-3-(methoxymethyl)pyridine (3.6 g, 15 mmol) in THF (50 mL) was added trimethylaluminum (2 M in toluene, 8.37 mL, 16.7 mmol) and $Pd(PPh_3)_4$ (1.76 g, 1.52 mmol) at 25° C. under $N_2$. The mixture was stirred at 80° C. for 2 h. Anhydrous $Na_2SO_4$ (20 g) and water (1 mL) were then added to the mixture. The solid was filtered off, and the filtrate was concentrated under reduced pressure. The residue was purified by flash silica gel chromatography (ethyl acetate/pet. ether gradient) to give 2-chloro-3-(methoxymethyl)-5-methylpyridine. MS: 172 (M+1). $^1$H NMR (400 MHz, $CDCl_3$) δ 8.12 (s, 1H), 7.63 (d, J=0.9 Hz, 1H), 4.50 (s, 2H), 3.49 (s, 3H), 2.33 (s, 3H).

Step 4: To a solution of 2-chloro-3-(methoxymethyl)-5-methylpyridine (1.3 g, 7.6 mmol), diphenylmethanimine (1.65 g, 9.09 mmol), XantPhos (0.438 g, 0.757 mmol) in 1,4-dioxane (30 mL) was added $Cs_2CO_3$ (5.92 g, 18.2 mmol) and $Pd_2(dba)_3$ (0.347 g, 0.379 mmol) at 25° C. The resultant mixture was degassed and backfilled with $N_2$ (three times) and stirred at 90° C. for 12 h. The mixture was concentrated under reduced pressure to remove dioxane. Water (60 mL) was added and the mixture was extracted with EtOAc (40 mL×3). The organic layers were dried over $Na_2SO_4$, filtered, and the filtrate was concentrated under reduced pressure. The residue was dissolved in MeOH (30 mL), the pH of the solution was adjusted to pH 5 with HCl solution (aq. 1 M), and then the mixture was stirred for 20 min. The mixture was basified with ammonium hydroxide to pH 8. The mixture was concentrated under reduced pressure. The residue was purified by flash silica gel chromatography (ethyl acetate/pet. ether gradient) to give 3-(methoxymethyl)-5-methylpyridin-2-amine. MS: 153 (M+1). $^1$H NMR (400 MHz, $CDCl_3$) δ 7.86 (s, 1H), 7.15 (d, J=1.8 Hz, 1H), 4.79 (br s, 2H), 4.38 (s, 2H), 3.34 (s, 3H), 2.18 (s, 3H).

Step 5: To a mixture of 3-(methoxymethyl)-5-methylpyridin-2-amine (600 mg, 3.94 mmol) in 1,4-dioxane (30 mL) was added $MgSO_4$ (1.42 g, 11.8 mmol) and ethyl 3-bromo-2-oxopropanoate (1.18 g, 5.91 mmol) at 25° C. The mixture was stirred at 80° C. for 12 h. After cooling to 25° C., TEA (0.659 mL, 4.73 mmol) was added, and the mixture was stirred at 25° C. for 1 h. The precipitate was filtered off, and the filtrate was concentrated under reduced pressure. The resulting residue was purified by flash silica gel chromatography (ethyl acetate/pet. ether gradient) to give ethyl 8-(methoxymethyl)-6-methylimidazo[1,2-a]pyridine-2-carboxylate. MS: 249 (M+1). $^1$H NMR (400 MHz, $CDCl_3$) δ 8.09 (s, 1H), 7.82 (s, 1H), 7.21 (d, J=1.3 Hz, 1H), 4.93 (s, 2H), 4.44 (q, J=7.3 Hz, 2H), 3.55 (s, 3H), 2.33 (s, 3H), 1.42 (t, J=7.2 Hz, 3H).

Step 6: To a mixture of ethyl 8-(methoxymethyl)-6-methylimidazo[1,2-a]pyridine-2-carboxylate (500 mg, 2.014 mmol) in EtOH (8 mL) and water (2 mL) was added $LiOH{\cdot}H_2O$ (169 mg, 4.03 mmol) at 25° C. The mixture was stirred at 25° C. for 2 h. The mixture was concentrated under reduced pressure to give 8-(methoxymethyl)-6-methylimidazo[1,2-a]pyridine-2-carboxylic acid, which was used without further purification. MS: 221 (M+1).

Intermediate 71: 8-bromo-4-(2,2,2-trifluoroethyl)-1,2,3,4-tetrahydro-5H-benzo[e][1,4]diazepin-5-one

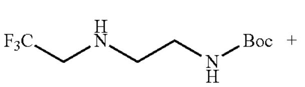

-continued

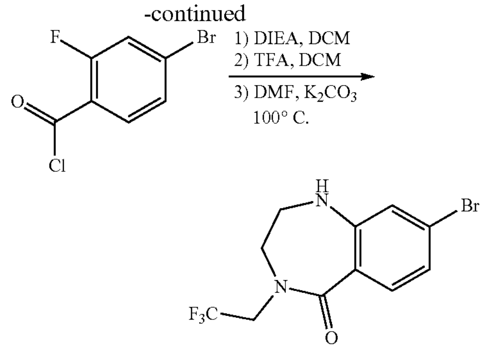

Step 1-3: To a mixture of 4-bromo-2-fluorobenzoyl chloride (530 mg, 2.23 mmol) in DCM (4 mL) was added a solution of tert-butyl (2-((2,2,2-trifluoroethyl)amino)ethyl) carbamate (530 mg, 2.19 mmol) and DIEA (0.420 mL, 2.41 mmol) in DCM (4 mL). The mixture was stirred for 10 min at room temperature. Tert-butyl (2-((2,2,2-trifluoroethyl) amino)ethyl)carbamate (530 mg, 2.19 mmol) was added to the mixture, and the resultant mixture was stirred overnight at room temperature. The mixture was concentrated under reduced pressure. The residue was dissolved in 1:1 TFA/DCM (5 mL) and stirred for 30 min at room temperature. The mixture was concentrated under reduced pressure. To this crude material was added DMF (4.0 mL) and potassium carbonate (907 mg, 6.56 mmol) and the resultant mixture was heated to 100° C. for 2 h. The reaction was diluted with water (20 mL) and stirred for 1 h at room temperature. A precipitate formed which was filtered, dried in vacuo to provide 8-bromo-4-(2,2,2-trifluoroethyl)-1,2,3,4-dihydro-1H-benzo[e][1,4]diazepin-5-one, which was used without further purification. MS 323 and 325 (M+1).

Intermediate 72: 1,4-dihydro-2H-spiro[isoquinoline-3,4'-piperidine]

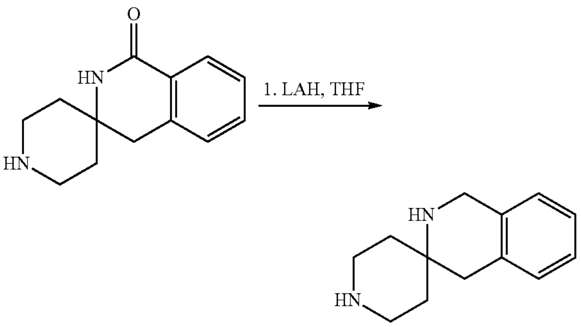

A mixture of 2,4-dihydro-1H-spiro[isoquinoline-3,4'-piperidin]-1-one (3.90 g, 18.0 mmol) in THF (75 mL) was degassed 3× under nitrogen, cooled to 0° C. A solution of $LiAlH_4$ (1 M in THF, 100 mL, 100 mmol) was added dropwise over ~20 min. The solution was heated to 60° C. overnight. The reaction was cooled to 0° C. and quenched by slow addition of sodium sulfate decahydrate (29 g, 90 mmol). After ~5 min, the reaction was poured into EtOAc (250 mL) and vigorously stirred for 1 h. The reaction was filtered through Celite® and washed with 10:1 EtOAc/MeOH (100 mL). The filtrate was concentrated in vacuo. The residue was purified via achiral SFC purification (Column IG, MeOH w/0.25% DMEA % modifier in $CO_2$) to provide 1,4-dihydro-2H-spiro[isoquinoline-3,4'-piperidine]. MS 203 (M+1)

TABLE 10

The following intermediate was prepared using a similar procedure as Intermediate 72 with $LiAlD_4$.

| Inter-mediate # | Structure | Compound Name | Exact Mass [M + 1] |
|---|---|---|---|
| 73 | 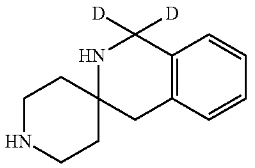 [SMILES: [2H]C1([2H])NC2(CCNCC2)Cc2ccccc21] | 1,4-dihydro-2H-spiro[isoquinoline-3,4'-piperidine]-1,1-$d_2$ | 205 |

Intermediate 74: 6-bromo-8-(2-hydroxypropan-2-vl) imidazo[1,2-a]pyridine-2-carboxylic acid

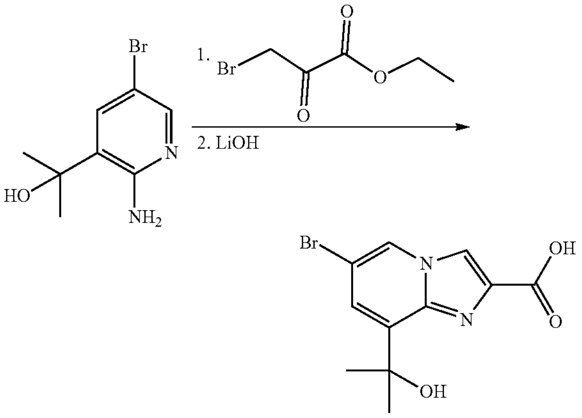

Step 1: To a mixture of 2-(2-amino-5-bromopyridin-3-yl) propan-2-ol (997 mg, 4.31 mmol) in DME (10 mL) was added ethyl bromo pyruvate (0.624 mL, 4.96 mmol) and the resultant mixture was stirred for 2 h at room temperature. A precipitate formed and then was filtered off, and the filtrate was subsequently dried under reduced pressure for 10 min. The solid material was dissolved in EtOH (20 mL) and heated to reflux for 2 h. The solvents were removed under reduced pressure. The resulting solid, ethyl 6-bromo-8-(2-hydroxypropan-2-yl)imidazo[1,2-a]pyridine-2-carboxylate, which was used in the next step without further purification. MS: 327 and 329 (M+1, M+3).

Step 2: To a mixture of ethyl 6-bromo-8-(2-hydroxypropan-2-yl)imidazo[1,2-a]pyridine-2-carboxylate (407 mg, 1.24 mmol) in THF (5.18 mL), water (0.52 mL) and ethanol (0.52 mL) was added lithium hydroxide (59.6 mg, 2.49 mmol). The mixture was heated to 40° C. for 2 h. A suspension formed which was filtered off to provide 6-bromo-8-(2-hydroxypropan-2-yl)imidazo[1,2-a]pyridine-2-carboxylic acid. MS 299, 301 (M+1).

Intermediate 75: 4-(3-oxa-8-azabicyclo[3.2.1]octane-8-carbonyl)-2-ethoxybenzoic acid

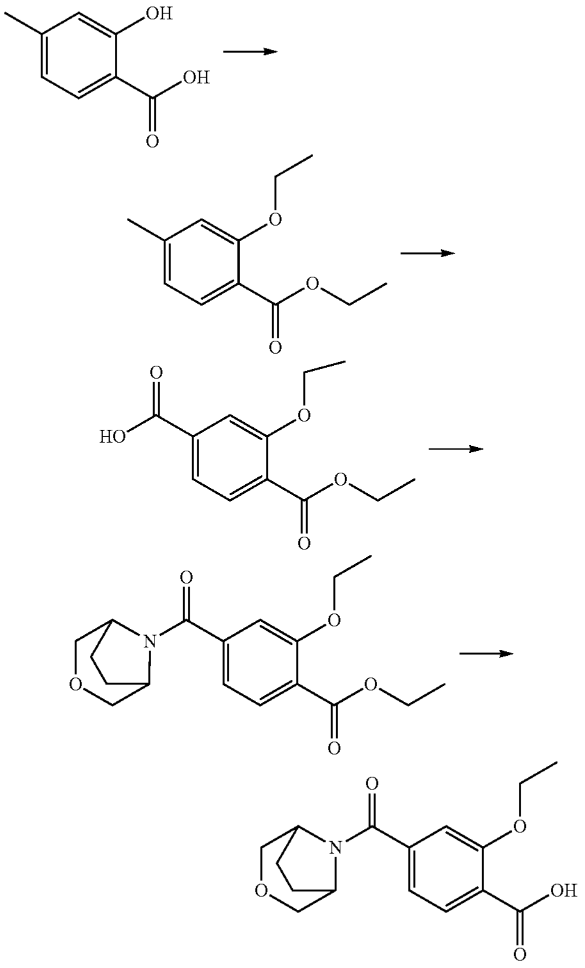

Step 1: To a mixture of 2-hydroxy-4-methylbenzoic acid (50 g, 329 mmol) and $K_2CO_3$ (136 g, 986 mmol) in DMSO (700 mL) at 40° C. was added ethyl iodide (77 g, 493 mmol) dropwise over a period of 30 min. The reaction was stirred for 2 h and additional ethyl iodide (77 g, 493 mmol) was added over 30 min at 40° C. The resulting mixture was stirred for 8 h at 40° C. The mixture was added into water (7 L) and the aqueous layer was extracted with EtOAc (3 L×3). The combined organic layers were washed with brine (1 L), dried over anhydrous $Na_2SO_4$, filtered, and concentrated under reduced pressure to give ethyl 2-ethoxy-4-methylbenzoate (69 g), which was used in the next step without further purification. MS: 209 (M+1). $^1H$ NMR (400 MHz, $CDCl_3$-d) δ 7.68 (d, J=7.43 Hz, 1H), 6.65-6.82 (m, 2H), 4.31 (q, J=7.04 Hz, 2H), 4.00-4.13 (m, 2H), 2.34 (s, 3H), 1.43 (t, J=7.04 Hz, 3H), 1.35 (t, J=7.04 Hz, 3H).

Step 2: To a solution of ethyl 2-ethoxy-4-methylbenzoate (46 g, 221 mmol) in pyridine (115 mL) and water (345 mL) was added $KMnO_4$ (34.9 g, 221 mmol). The resulting mixture was heated at 50° C. for 48 h, then cooled to room temperature and stirred at room temperature for 24 h. The mixture was filtered, and the filter cake washed with hot water. The combined aqueous filtrates were washed with EtOAc (1 L×3) and acidified with 2M aqueous HCl solution to pH 3. The mixture was extracted with EtOAc (2 L×3). The combined organic layers were washed with brine, dried over ($Na_2SO_4$), and concentrated under reduced pressure to give 3-ethoxy-4-(ethoxycarbonyl)benzoic acid, which was used in the next step without further purification. MS: 239 (M+1). $^1$H NMR (400 MHz, $CDCl_3$-d) δ 7.80 (d, J=7.94 Hz, 1H), 7.64-7.74 (m, 2H), 4.39 (q, J=7.20 Hz, 2H), 4.14-4.25 (m, 2H), 1.48 (t, J=6.95 Hz, 3H), 1.40 (t, J=7.06 Hz, 3H).

Step 3: To a mixture of 3-oxa-8-azabicyclo[3.2.1]octane hydrochloride (10 g, 66.8 mmol), 3-ethoxy-4-(ethoxycarbonyl)benzoic acid (15.9 g, 66.8 mmol) and HATU (30.5 g, 80 mmol) in DCM (120 mL) was added DIEA (35 mL, 201 mmol). The mixture was stirred for 20 min and then concentrated in vacuo. The residue was purified by flash silica gel chromatography (ethyl acetate/pet. ether gradient) to give ethyl 4-(3-oxa-8-azabicyclo[3.2.1]octane-8-carbonyl)-2-ethoxybenzoate. MS: 356 (M+Na). $^1$H NMR (400 MHz, $CDCl_3$-d) δ 7.75 (d, J=7.6 Hz, 1H), 7.06 (s, 1H), 6.99 (d, J=8.0 Hz, 1H), 4.68 (s, 1H), 4.32 (q, J=7.2 Hz, 2H), 4.11 (q, J=7.2 Hz, 2H), 3.82-4.00 (m, 2H), 3.69-3.62 (m, 2H), 3.56 (m, 1H), 2.02-1.89 (m, 4H), 1.44 (t, J=6.8 Hz, 3H), 1.35 (t, J=6.8 Hz, 3H).

Step 4: To a solution of ethyl 4-(3-oxa-8-azabicyclo[3.2.1]octane-8-carbonyl)-2-ethoxybenzoate (24 g, 72.0 mmol) in THF (150 mL), MeOH (50 mL) and water (15 mL) was added $LiOH{\cdot}H_2O$ (15.1 g, 360 mmol). The resultant mixture was stirred at room temperature for 12 h. The mixture was concentrated under reduced pressure. Water (500 mL) was added to the residue and the mixture was acidified with 4 M aqueous HCl solution to pH 2. The mixture was extracted with $CH_2Cl_2$ (200 mL×3). The combined organic layers were washed with brine (200 mL), dried over $Na_2SO_4$, filtered, and the filtrate was concentrated under reduced pressure to give 4-(3-oxa-8-azabicyclo[3.2.1]octane-8-carbonyl)-2-ethoxybenzoic acid, which was used without further purification. MS: 306 (M+1). $^1$H NMR (400 MHz, $CDCl_3$-d) δ 10.86 (s, 1H), 8.19 (d, J=8.4 Hz, 1H), 7.21 (s, 1H), 7.14 (d, J=7.6 Hz, 1H), 4.71 (s, 1H), 4.35 (q, J=7.2 Hz, 2H), 3.91-3.84 (m, 2H), 3.72-3.60 (m, 3H), 2.06-1.94 (m, 4H), 1.56 (t, J=7.2 Hz, 3H).

Intermediate 76: 7-bromo-4-methyl-1,4-dihydro-2H-3,1-benzoxazin-2-one

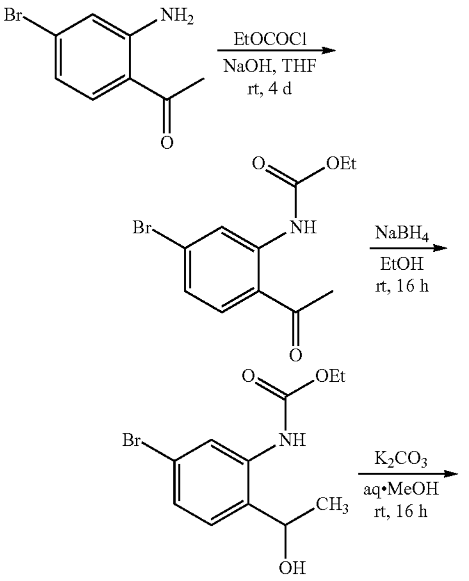

-continued

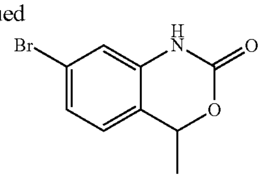

Step 1: A solution of 1-(2-amino-4-bromophenyl)ethanone (90.0 g, 0.51 mol) and ethyl chloroformate (74 mL, 0.77 mol) in THF (500 mL) was charged with 20% aqueous NaOH (450 mL) dropwise over 40 min at −10° C. The reaction mixture was stirred at room temperature for 4 days. The reaction mixture was treated with water (1.5 L) and extracted with EtOAc (3×1.5 L). The combined organic layers were washed with brine (1.0 L), dried over anhydrous $Na_2SO_4$, and concentrated under reduced pressure. The residue was purified by silica-gel chromatography to afford ethyl (2-acetyl-5-bromophenyl)carbamate. $^1$H NMR (400 MHz, $CDCl_3$) δ 8.76 (d, J=2.0 Hz, 1H), 7.72 (d, J=8.4 Hz, 1H), 7.19 (dd, J=8.4 Hz, 2.0 Hz, 1H), 4.26-4.21 (m, 2H), 2.63 (s, 3H) 1.35 (t, J=7.0 Hz, 3H).

Step 2: A solution of ethyl (2-acetyl-5-bromophenyl) carbamate (109 g, 0.38 mol) in THF (1.0 L) was charged with $NaBH_4$ (13.7 g, 0.38 mol) portion wise over 30 min at −10° C. The reaction mixture was stirred at room temperature for 16 h. The reaction mixture was treated with saturated aqueous $NaHCO_3$ (250 mL) and extracted with EtOAc (3×1.0 L). The combined organic layers were washed with water (1.0 L) and brine (1.0 L), dried over anhydrous $Na_2SO_4$, and concentrated under reduced pressure to afford ethyl [5-bromo-2-(1-hydroxyethyl)phenyl]carbamate. $^1$H NMR (400 MHz, $CDCl_3$) δ 8.42 (s, 1H), 8.26 (s, 1H), 7.14 (dd, J=8.4 Hz, 2.0 Hz, 1H), 6.99 (d, J=8.0 Hz, 1H), 4.98-4.92 (m, 1H), 4.25-4.20 (m, 2H), 2.25 (d, J=4.4 Hz 1H), 1.60 (t, J=7.2 Hz, 3H), 1.34 (t, J=7.2 Hz, 3H).

Step 3: A solution of ethyl [5-bromo-2-(1-hydroxyethyl) phenyl]carbamate (90.0 g, 0.31 mol) in MeOH (900 mL) was charged with a solution of $K_2CO_3$ (86.0 g, 0.624 mol) in water (200 mL) at 0° C. The reaction mixture was stirred at room temperature for 16 h. The reaction mixture was concentrated under reduced pressure, and the residue was diluted with EtOAc (2.0 L). The organic phase was washed with water (1.0 L) and brine (1.0 L), dried over anhydrous $Na_2SO_4$, and concentrated under reduced pressure to afford 7-bromo-4-methyl-1,4-dihydro-2H-3,1-benzoxazin-2-one. $^1$H NMR (400 MHz, $CD_3OD$) δ 7.09 (dd, J=8.0, 2.0 Hz, 1H), 7.00-6.94 (m, 2H), 5.39-5.34 (m, 1H), 1.51 (d, J=6.8 Hz, 3H).

Intermediate 77: potassium [1,2,4]triazolo[1,5-a] pyrazine-6-carboxylate

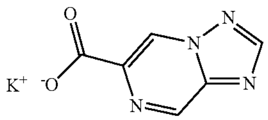

A solution of 6-bromo[1,2,4]triazolo[1,5-a]pyrazine (175 g), Pd(dppf)$Cl_2$ (50 g) and $Et_3N$ (300 mL) in EtOH (1 L) was heated to 115° C. under CO overnight. The mixture was cooled to room temperature and filtered. The filtrate was concentrated and recrystallized by EtOAc. The solid was dissolved in THF (500 mL) and MeOH (500 mL) at 0° C., and then treated with KOH (1 eq). The mixture was stirred at 0° C. for 1 h and at room temperature for 2 h. The mixture was filtered to give potassium [1,2,4]triazolo[1,5-a]pyrazine-6-carboxylate. MS: 165 (M+1).

Intermediate 78: 5-(1H-tetrazol-1-yl)-2-pyridinecarboxylic acid

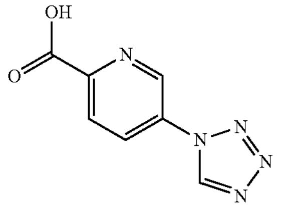 [SMILES: O=C(O)c1ccc(-n2cnnn2)cn1]

A 3-L, 3-necked round-bottom flask was charged with a solution of 5-aminopicolinic acid (50.0 g, 362 mmol) in acetic acid (1250 mL) and trimethoxymethane (115 g, 1.08 mol). The resulting solution was stirred at room temperature for 2 h and treated with sodium azide (70.5 g, 1.08 mol) in portions. The reaction mixture was heated to 80° C. for 3 h and cooled to room temperature overnight. The reaction solution was cooled to 10° C. and diluted with 1000 mL of ice water. The solid was collected by filtration and washed with 2×200 mL of water and dried in an oven to give 5-(1H-tetrazol-1-yl)-2-pyridinecarboxylic acid. MS: 190 (M−1). $^1$H NMR (400 MHz, DMSO-$d_6$) δ 10.26 (s, 1H), 9.25 (s, 1H), 8.50 (d, J=8 Hz, 1H), 8.28 (d, J=8 Hz, 1H).

Intermediate 79: 8-(1-methoxyethyl)-6-methylimidazo[1,2-a]pyridine-2-carboxylic acid

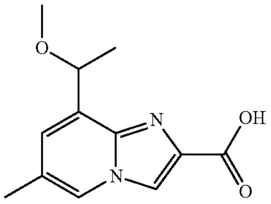 [SMILES: COC(C)c1cc(C)cn2cc(C(=O)O)nc12]

Step 1: A mixture of tetrakis(triphenylphosphine)palladium(0) (0.353 g, 0.306 mmol), $K_2CO_3$ (1.267 g, 9.17 mmol), ethyl 6-bromo-8-(1-methoxyethyl)imidazo[1,2-a]pyridine-2-carboxylate (1.00 g, 3.06 mmol) and 2,4,6-trimethyl-1,3,5,2,4,6-trioxatri-borinane (1.918 g, 15.28 mmol) in dioxane (10 mL) was heated to 110° C. for 4 h. The mixture was cooled to room temperature and concentrated. The residue was purified by silica gel chromatography (50% ethyl acetate in pet. ether) to give ethyl 8-(1-methoxyethyl)-6-methylimidazo[1,2-a]pyridine-2-carboxylate. MS: 263 (M+1). $^1$H NMR (400 MHz, $CDCl_3$) δ 8.09 (s, 1H), 7.81 (s, 1H), 7.17 (s, 1H), 5.21 (q, J=6.1 Hz, 1H), 4.40-4.49 (m, 2H), 3.37 (s, 3H), 2.34 (d, J=0.9 Hz, 3H), 1.54 (d, J=6.6 Hz, 3H), 1.41 (t, J=7.0 Hz, 3H).

Step 2: To a solution of ethyl 8-(1-methoxyethyl)-6-methylimidazo[1,2-a]pyridine-2-carboxylate (340 mg, 1.30 mmol) in MeOH (3 mL) and water (0.6 mL) was added LiOH (62.1 mg, 2.59 mmol) at 25° C. The mixture was stirred at 25° C. for 3 h. The mixture was concentrated and purified by Prep-HPLC (TFA condition) to give 8-(1-methoxyethyl)-6-methylimidazo[1,2-a]pyridine-2-carboxylic acid. MS: 235 (M+1). $^1$H NMR (400 MHz, $CD_3OD$) δ 8.60 (s, 1H), 8.49 (s, 1H), 7.80 (s, 1H), 4.93-4.98 (m, 1H), 3.35 (s, 3H), 2.47 (s, 3H), 1.53 (d, J=6.1 Hz, 3H).

Intermediate 80: 6-cyclopropyl-8-(1-methoxyethyl)imidazo[1,2-a]pyridine-2-carboxylic acid

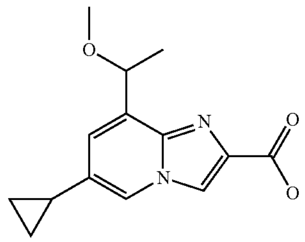 [SMILES: COC(C)c1cc(C2CC2)cn2cc(C(=O)O)nc12]

Step 1: A mixture of ethyl 6-bromo-8-(1-methoxyethyl)imidazo[1,2-a]pyridine-2-carboxylate (50 mg, 0.15 mmol), cyclopropylboronic acid (26.3 mg, 0.306 mmol), $Cs_2CO_3$ (149 mg, 0.458 mmol) and $PdCl_2$(dppf) (11.18 mg, 0.015 mmol) in 1,4-dioxane (2 mL) and water (0.5 mL) was heated to 100° C. under $N_2$ for 10 h. The mixture was purified by prep-HPLC (with TFA modifier) to give ethyl 6-cyclopropyl-8-(1-methoxyethyl)imidazo[1,2-a]pyridine-2-carboxylate. MS: 289 (M+1).

Step 2: A mixture of ethyl 6-cyclopropyl-8-(1-methoxyethyl)imidazo[1,2-a]pyridine-2-carboxylate (30 mg, 0.10 mmol) and lithium hydroxide hydrate (8.73 mg, 0.208 mmol) in MeOH (2 ml) and water (0.5 ml) was stirred at 20° C. for 10 h. The mixture was concentrated to give 6-cyclopropyl-8-(1-methoxyethyl)imidazo[1,2-a]pyridine-2-carboxylic acid. MS: 261 (M+1).

Intermediate 81: 6-isopropyl-8-(1-methoxyethyl)imidazo[1,2-a]pyridine-2-carboxylic acid

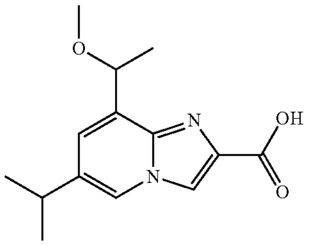 [SMILES: COC(C)c1cc(C(C)C)cn2cc(C(=O)O)nc12]

Step 1: A mixture of [1,1'-bis(diphenylphosphino)ferrocene]dichloropalladium(II) (0.224 g, 0.306 mmol), $Cs_2CO_3$ (2.99 g, 9.17 mmol), ethyl 6-bromo-8-(1-methoxyethyl)imidazo[1,2-a]pyridine-2-carboxylate (1.00 g, 3.06 mmol) and isopropylboronic acid (404 mg, 4.59 mmol) in toluene (8 mL) was stirred at 110° C. for 10 h. The mixture was cooled to room temperature and concentrated. The residue was purified by silica gel chromatography (50% ethyl acetate/pet. ether) to give ethyl 6-isopropyl-8-(1-methoxyethyl)imidazo[1,2-a]pyridine-2-carboxylate. MS: 291 (M+1). $^1$H NMR (500 MHz, $CDCl_3$) δ 8.16 (s, 1H), 7.87 (s, 1H), 7.26 (s, 1H), 4.46-4.56 (m, 3H), 3.43 (s, 3H), 2.65 (s, 1H), 1.47 (t, J=7.10 Hz, 3H), 1.26-1.34 (m, 3H), 1.07 (br d, J=7.17 Hz, 6H).

Step 2: To a solution of ethyl 6-isopropyl-8-(1-methoxyethyl)imidazo[1,2-a]pyridine-2-carboxylate (290 mg, 0.999 mmol) in MeOH (3 mL) and water (0.6 mL) was added LiOH (47.8 mg, 2.00 mmol) at 25° C. The mixture was stirred at 25° C. for 3 h. The mixture was concentrated and purified by Prep-HPLC (TFA condition) to give ethyl 6-isopropyl-8-(1-methoxyethyl)imidazo[1,2-a]pyridine-2-carboxylate. MS: 263 (M+1). $^1$H NMR (500 MHz, $CD_3OD$) δ 8.56-8.61 (m, 1H), 8.49 (br s, 1H), 7.78 (br s, 1H), 5.00 (q, J=6.41 Hz, 1H), 3.37-3.39 (m, 3H), 2.77 (t, J=7.55 Hz, 2H), 1.77 (sxt, J=7.45 Hz, 2H), 1.53-1.58 (m, 3H), 1.04 (t, J=7.32 Hz, 3H).

Intermediate 82: 6-(1-cyanoethyl)imidazo[1,2-a]pyridine-2-carboxylic acid

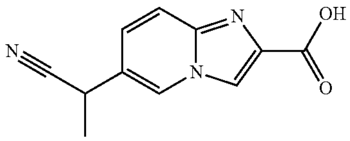 [SMILES: CC(C#N)c1ccc2nc(C(=O)O)cn2c1]

Step 1: A mixture of sodium tert-butoxide (9.99 g, 104 mmol), $PdCl_2$(dppf)-$CH_2Cl_2$ adduct (2.122 g, 2.60 mmol), 5-bromo-2-chloropyridine (10.0 g, 52.0 mmol) and tert-butyl 2-cyanoacetate (8.07 g, 57.2 mmol) in THF (200 mL) was degassed and backfilled with $N_2$ (three times). The mixture was heated to 75° C. for 12 h. MeI (9.61 mL, 154 mmol) was added to the mixture and the mixture was stirred at 15° C. for 3 h. The mixture was treated with water (100 mL) and extracted with EtOAc (100 mL). The organic layer was washed with brine, dried over $Na_2SO_4$, concentrated, and purified by silica gel chromatography (0-6% ethyl acetate/pet. ether) to give tert-butyl 2-(6-chloropyridin-3-yl)-2-cyanopropanoate. MS: 267 (M+1).

Step 2: A mixture of tert-butyl 2-(6-chloropyridin-3-yl)-2-cyanopropanoate (3.8 g, 14 mmol), XantPhos (0.824 g, 1.43 mmol), $Pd_2(dba)_3$ (1.305 g, 1.425 mmol), $Cs_2CO_3$ (13.93 g, 42.7 mmol) and tert-butyl carbamate (8.34 g, 71.2 mmol) in dioxane (30 mL) was degassed and backfilled with $N_2$ (three times). The mixture was heated to 90° C. for 12 h. After cooling to room temperature, the precipitate was filtered off and the filtrate was concentrated. The mixture was diluted with water (100 mL) and extracted with EtOAc (50 mL×3). The combined organic layers were washed with brine (100 mL), dried over anhydrous sodium sulfate, filtered, and the filtrate was concentrated under reduced pressure. The residue was purified by silica gel chromatography (20% ethyl acetate/petroleum ether) to give tert-butyl 2-(6-((tert-butoxycarbonyl)amino)pyridin-3-yl)-2-cyanopropanoate. MS: 348 (M+1).

Step 3: A mixture of tert-butyl 2-(6-((tert-butoxycarbonyl)amino)pyridin-3-yl)-2-cyanopro-panoate (1.60 g, 4.61 mmol) in DCM (20 mL) and TFA (10 mL) was stirred at 40° C. for 2 h. The mixture was extracted with EtOAc (20 mL×3), and the combined organic layers were washed with brine (20 mL), dried over anhydrous $Na_2SO_4$, concentrated, and purified by silica gel chromatography (10% ethyl acetate/pet. ether) to give 2-(6-aminopyridin-3-yl)propanenitrile. MS: 148 (M+1). $^1$H NMR (500 MHz, $CDCl_3$) δ 7.77 (s, 1H), 7.73 (br d, J=9.16 Hz, 1H), 6.86 (d, J=9.16 Hz, 1H), 3.86 (q, J=7.17 Hz, 1H), 1.63 (d, J=7.32 Hz, 2H), 1.61-1.65 (m, 1H).

Step 4: A mixture of ethyl 3-bromo-2-oxopropanoate (255 mg, 1.02 mmol) and 2-(6-aminopyridin-3-yl)propanenitrile (100 mg, 0.679 mmol) in dioxane (4 mL) was stirred at 80° C. for 2 h. The mixture was concentrated under reduced pressure, and purified by prep-HPLC (TFA) to give ethyl 6-(1-cyanoethyl)imidazo[1,2-a]pyridine-2-carboxylate. MS: 244.0 (M+1). $^1$H NMR (400 MHz, $CDCl_3$) δ 8.28 (s, 1H), 8.21 (s, 1H), 7.91 (d, J=9.65 Hz, 1H), 7.30 (dd, J=1.97, 9.43 Hz, 1H), 4.46 (q, J=7.02 Hz, 2H), 3.98 (q, J=7.31 Hz, 1H), 1.73 (d, J=7.45 Hz, 3H), 1.44 (t, 3H).

Step 5: To a solution of ethyl 6-(1-cyanoethyl)imidazo[1,2-a]pyridine-2-carboxylate (100 mg, 0.411 mmol) in MeOH (3 mL) and water (0.6 mL) was added LiOH (19.69 mg, 0.822 mmol) at 25° C. The mixture was stirred at 25° C. for 1 h. The mixture was concentrated and purified by Prep-HPLC (TFA condition) to give 6-(1-cyanoethyl)imidazo[1,2-a]pyridine-2-carboxylic acid. MS: 216 (M+1). $^1$H NMR (500 MHz, $CD_3OD$) δ 8.87 (br s, 1H), 8.67 (br s, 1H), 7.88-8.01 (m, 2H), 4.43 (q, J=7.17 Hz, 1H), 1.75 (d, J=7.17 Hz, 3H).

Intermediate 83: 6-(1-cyanocyclopropyl)imidazo[1,2-a]pyridine-2-carboxylic acid

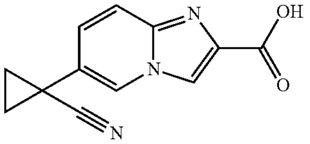 [SMILES: N#CC1(c2ccc3nc(C(=O)O)cn3c2)CC1]

Step 1: To a mixture of 5-bromopyridin-2-amine (5.00 g, 28.9 mmol) in DMF (20 mL) was added NaH (60%, 2.89 g, 72.2 mmol). The mixture was stirred for 0.5 h, treated with 1-(chloromethyl)-4-methoxybenzene (9.96 g, 63.6 mmol) and stirred at 15° C. for 30 min. The mixture was treated with water (100 mL) and extracted with EtOAc (100 mL). The organic layer was concentrated and purified by silica gel chromatography (7% ethyl acetate/pet. ether) to give 5-bromo-N,N-bis(4-methoxybenzyl)pyridin-2-amine. MS: 413 and 415 (M+1). $^1$H NMR (400 MHz, $CDCl_3$) δ 7.19 (s, 1H), 7.16 (d, J=8.33 Hz, 4H), 6.85 (d, J=8.77 Hz, 4H), 6.71 (d, J=7.45 Hz, 1H), 6.32 (d, J=8.33 Hz, 1H), 4.66 (s, 4H), 3.79 (s, 6H).

Step 2: A mixture of cyclopropanecarbonitrile (1.217 g, 18.15 mmol), 5-bromo-N,N-bis (4-methoxybenzyl)pyridin-2-amine (5.00 g, 12.10 mmol), 4,6-bis(diphenylphosphino)-10H-phenoxazine (1.001 g, 1.815 mmol), and $Pd(OAc)_2$ (0.407 g, 1.815 mmol) was evacuated and refilled with $N_2$ three times. THF (30 mL) and methoxycyclopentane (30 mL) were then added to the mixture. The mixture was stirred for 5 min before LiHMDS (30.2 mL, 30.2 mmol, 1M) was added dropwise at room temperature. The reaction mixture was heated to 60° C. for 3 h, cooled to room temperature, and concentrated. The residue was purified by silica gel chromatography (10% ethyl acetate/pet. ether) to give 1-(6-(bis(4-methoxybenzyl)amino)pyridin-3-yl)cyclopropanecarbonitrile. MS: 400 (M+1).

Step 3: A mixture of 1-(6-(bis(4-methoxybenzyl)amino)pyridin-3-yl)cyclopropanecarbonitrile (2.00 g, 5.01 mmol) in DCM (10 mL) and TFA (10 mL) was stirred at 40° C. for 10 h. The mixture was poured into $H_2O$ (60 mL), and the pH was adjusted to pH 9 with sat. aq. $NaHCO_3$. The mixture was extracted with DCM (40 mL×3), and the combined organic layers were concentrated. The residue was purified by silica gel chromatography (45% ethyl acetate/pet. ether) to give 1-(6-amino-pyridin-3-yl)cyclopropanecarbonitrile. MS: 160 (M+1).

Step 4: A mixture of ethyl 3-bromo-2-oxopropanoate (735 mg, 3.77 mmol) and 1-(6-aminopyridin-3-yl)cyclopropanecarbonitrile (300 mg, 1.89 mmol) in MeOH (3 mL) was stirred at 80° C. for 2 h. The mixture was cooled to room temperature, concentrated, and purified by Prep-HPLC (TFA condition) to give ethyl 6-(1-cyanocyclopropyl)imidazo [1,2-a]pyridine-2-carboxylate. MS: 256 (M+1).

Step 5: To a solution of ethyl 6-(1-cyanocyclopropyl) imidazo [1,2-a]pyridine-2-carboxylate (600 mg, 2.35 mmol) in MeOH (5 mL) and water (1 mL) was added LiOH (113 mg, 4.70 mmol) at 25° C. The mixture was stirred at 25° C. for 1 h. The mixture was concentrated and purified by Prep-HPLC (TFA condition) to give 6-(1-cyanocyclopropyl) imidazo[1,2-a]pyridine-2-carboxylic acid. MS: 228 (M+1). $^1$H NMR (500 MHz, $CD_3OD$) δ 8.72 (s, 1H), 7.72-7.76 (m, 1H), 7.65 (dd, J=7.02, 9.16 Hz, 1H), 7.33 (d, J=7.17 Hz, 1H), 1.92-1.95 (m, 2H), 1.60-1.63 (m, 2H).

Intermediate 84: 6-(2,2-dimethylcyclopropyl)imidazo[1,2-a]pyrimidine-2-carboxylic acid

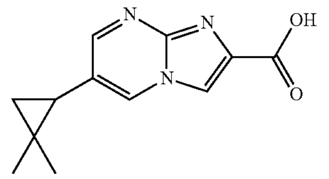 [SMILES: CC1(C)CC1c1cnc2nc(C(=O)O)cn2c1]

Step 1: To a mixture of 5-bromopyrimidin-2-amine (10.0 g, 57.5 mmol) in DMF (20 mL) was added NaH (60%, 5.75 g, 144 mmol). The mixture was stirred for 0.5 h, treated with 1-(chloromethyl)-4-methoxybenzene (19.80 g, 126 mmol), and left stirred at 15° C. for 30 min. The mixture was treated with water (100 mL), extracted with EtOAc (100 mL), and the organic layer was concentrated. The residue was purified by silica gel chromatography (7% ethyl acetate/pet. ether) to give 5-bromo-N,N-bis(4-methoxybenzyl)pyrimidin-2-amine. MS: 414 and 416 (M+1).

Step 2: A suspension of pyridine-2,6-bis(carboximidamide) hydrochloride (0.092 g, 0.46 mmol), nickel(II) iodide (0.072 g, 0.23 mmol) and zinc (0.303 g, 4.63 mmol) in anhydrous DMA (10 mL) was stirred at 25° C. for 10 mins. A solution of 1,3-dioxoisoindolin-2-yl2,2-dimethylcyclopropanecarboxylate (0.300 g, 1.16 mmol) and 5-bromo-N,N-bis(4-methoxybenzyl)pyrimidin-2-amine (10 g, 24 mmol) in DMA (5 mL) was then added to the mixture. The mixture was stirred at 80° C. under $N_2$ for 16 h. The mixture was treated with water (100 mL), extracted with EtOAc (100 mL), and the organic layer was washed with brine, dried over $Na_2SO_4$, concentrated, and purified by silica gel chromatography (20% ethyl acetate/pet. ether) to give 5-(2,2-dimethylcyclopropyl)-N,N-bis(4-methoxybenzyl)pyrimidin-2-amine. MS: 404 (M+1).

Step 3: A mixture of 5-(2,2-dimethylcyclopropyl)-N,N-bis(4-methoxybenzyl)pyrimidin-2-amine (210 mg, 0.520 mmol) in DCM (5 mL) and TFA (5 mL) was stirred at 40° C. for 10 h. The mixture was poured into $H_2O$ (60 mL), and the pH was adjusted to pH 9 with sat. aq. $NaHCO_3$. The mixture was extracted with DCM (40 mL×3). The combined organic layers were concentrated and purified by TLC to give 5-(2,2-dimethylcyclopropyl)pyrimidin-2-amine. MS:

164 (M+1). $^1$H NMR (500 MHz, $CDCl_3$) δ 8.10-8.12 (m, 2H), 1.60-1.63 (m, 1H), 1.21 (s, 3H), 0.82 (s, 3H), 0.78-0.81 (m, 1H), 0.67 (t, J=5.3 Hz, 1H)

Step 4: A mixture of 5-(2,2-dimethylcyclopropyl)pyrimidin-2-amine (70 mg, 0.43 mmol) and 3-bromo-2-oxopropanoic acid (107 mg, 0.643 mmol) in dioxane (2 mL) was stirred at 80° C. for 2 h. The mixture was cooled to room temperature and purified by prep-HPLC (TFA modifier) to give 6-(2,2-dimethylcyclopropyl)imidazo[1,2-a]pyrimidine-2-carboxylic acid. MS: 232 (M+1). $^1$H NMR (400 MHz, $CD_3OD$) δ 8.75 (s, 2H), 8.33 (br s, 1H), 1.31 (s, 3H), 1.17 (br s, 1H), 1.04 (d, J=5.26 Hz, 1H), 0.98 (d, J=5.26 Hz, 1H), 0.90 (s, 3H).

Intermediate 85: 6-(1-methoxyethyl)pyrazolo[1,5-a] pyrimidine-2-carboxylic acid

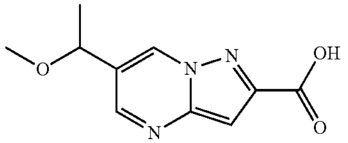 [SMILES: COC(C)c1cnc2cc(C(=O)O)nn2c1]

Step 1: A mixture of 5-nitro-1H-pyrazole-3-carboxylic acid (5.00 g, 31.8 mmol), butan-1-ol (20 g, 270 mmol) and $H_2SO_4$ (1.70 ml, 31.8 mmol) was stirred at 80° C. for 12 h. The mixture was cooled to room temperature and purified by reversed MPLC (C18, 10%-20% $H_2O$/MeOH) to give butyl 5-nitro-1H-pyrazole-3-carboxylate. $^1$H NMR (500 MHz, $CDCl_3$) δ 7.39 (s, 1H), 4.40 (t, J=6.64 Hz, 2H), 1.73-1.80 (m, 2H), 1.46 (sxt, J=7.48 Hz, 2H), 0.98 (t, J=7.40 Hz, 3H)

Step 2: A mixture of butyl 5-nitro-1H-pyrazole-3-carboxylate (6.00 g, 28.1 mmol) and Pd—C (3.00 g, 2.81 mmol) in MeOH (50 mL) was stirred under $H_2$ (pressure: 15 psi) at 25° C. for 2 h. The mixture was filtered and concentrated to give butyl 5-amino-1H-pyrazole-3-carboxylate. MS: 184 (M+1).

Step 3: To a solution of butyl 5-amino-1H-pyrazole-3-carboxylate (5.00 g, 27.3 mmol) and HCl (2.465 mL, 30.0 mmol) in EtOH (50 mL) was added 2-bromomalonaldehyde (4.12 g, 27.3 mmol) at 25° C. The mixture was stirred at 25° C. for 12 h. The mixture was concentrated and purified by silica gel chromatography (5% ethyl acetate/pet. ether) to give butyl 6-bromopyrazolo[1,5-a]pyrimidine-2-carboxylate. MS: 298 and 300 (M+1). $^1$H NMR (400 MHz, $CDCl_3$) δ 8.85 (d, J=1.3 Hz, 1H), 8.53 (d, J=2.2 Hz, 1H), 7.23 (s, 1H), 4.41 (t, J=6.8 Hz, 2H), 1.74-1.83 (m, 2H), 1.46 (m, 2H), 0.96 (t, J=7.5 Hz, 3H)

Step 4: A mixture of zinc (525 mg, 8.03 mmol), nickel(II) iodide (125 mg, 0.40 mmol) and pyridine-2,6-bis(carboximidamide) hydrochloride (160 mg, 0.80 mmol) in DMA (8 mL) was stirred at 25° C. for 15 min under $N_2$. The mixture was treated with 1,3-dioxoisoindolin-2-yl 2-methoxypropanoate (500 mg, 2.01 mmol) and butyl 6-bromopyrazolo [1,5-a]pyrimidine-2-carboxylate (658 mg, 2.21 mmol) and heated to 80° C. for 10 h. The mixture was cooled to room temperature, treated with water (50 mL), and extracted with EtOAc (30 mL×3). The combined organic layers were concentrated and purified by silica gel chromatography (15% ethyl acetate/pet. ether) to give butyl 6-(1-methoxyethyl)pyrazolo[1,5-a]pyrimidine-2-carboxylate. MS: 278 (M+1).

Step 5: A mixture of butyl 6-(1-methoxyethyl)pyrazolo [1,5-a]pyrimidine-2-carboxylate (230 mg, 0.829 mmol) and LiOH·$H_2O$ (87 mg, 2.073 mmol) in MeOH (2 mL) and water (0.5 mL) was stirred at 25° C. for 2 h. The mixture was concentrated to give 6-(1-methoxyethyl)pyrazolo[1,5-a]pyrimidine-2-carboxylic acid. MS: 222 (M+1).

Intermediate 86: 6-(1-cyano-2,2-dimethylcyclopropyl)imidazo[1,2-a]pyrimidine-2-carboxylic acid

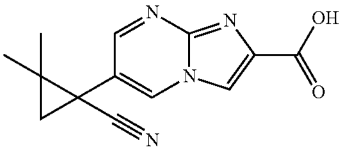 [SMILES: CC1(C)CC1(C#N)c1cnc2nc(C(=O)O)cn2c1]

Step 1: A mixture of 4,6-bis(diphenylphosphino)-10H-phenoxazine (1.598 g, 2.90 mmol), 2,2-dimethylcyclopropanecarbonitrile (2.76 g, 29.0 mmol), 5-bromo-N,N-bis(4-methoxybenzyl)pyrimidin-2-amine (8.00 g, 19.3 mmol) and $Pd(OAc)_2$ (0.650 g, 2.90 mmol) was evacuated and refilled with $N_2$ three times. THF (30 mL) and methoxycyclopentane (30 mL) were then added to the mixture. The mixture was stirred for 5 min before LiHMDS (48.3 mL, 48.3 mmol, 1M) was added dropwise at room temperature. The reaction mixture was heated to 60° C. for 2 h. The mixture was concentrated and purified by silica gel chromatography (15% ethyl acetate/pet. ether) to give 1-(2-(bis(4-methoxybenzyl)amino)pyrimidin-5-yl)-2,2-dimethylcyclopropanecarbonitrile. MS: 429 (M+1).

Step 2: A mixture of 1-(2-(bis(4-methoxybenzyl)amino)pyrimidin-5-yl)-2,2-dimethylcyclopropanecarbonitrile (1.40 g, 3.27 mmol) in DCM (15 mL) and TFA (15 mL) was stirred at 40° C. for 10 h. The mixture was poured into $H_2O$ (60 mL), and the pH was adjusted to pH 9 with sat. aq. $NaHCO_3$. The mixture was extracted with DCM (40 mL×3). The combined organic layers were concentrated and purified by silica gel chromatography (45% ethyl acetate/pet. ether) to give 1-(2-aminopyrimidin-5-yl)-2,2-dimethylcyclopropanecarbonitrile. MS: 189 (M+1). $^1H$ NMR (400 MHz, $CDCl_3$) δ 8.24 (s, 2H), 5.32 (br s, 2H), 1.53 (s, 3H), 1.47 (d, J=5.7 Hz, 1H), 1.37 (d, J=5.3 Hz, 1H), 0.92 (s, 3H).

Step 3: To a solution of 1-(2-aminopyrimidin-5-yl)-2,2-dimethylcyclopropanecarbonitrile (450 mg, 2.39 mmol) in 1,4-dioxane (10 mL) was added 3-bromo-2-oxopropanoic acid (599 mg, 3.59 mmol). The reaction mixture was heated to 60° C. for 2 h. The mixture was cooled to room temperature and concentrated give 6-(1-cyano-2,2-dimethylcyclopropyl)imidazo[1,2-a]pyrimidine-2-carboxylic acid. MS: 257 (M+1).

Intermediate 87: 6-(1-cyanospiro[2.2]pent-1-yl)imidazo[1,2-a]pyrimidine-2-carboxylic acid

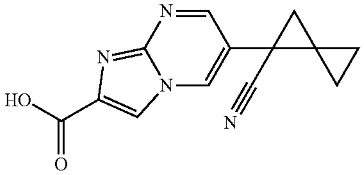 [SMILES: N#CC1(c2cnc3nc(C(=O)O)cn3c2)CC12CC2]

Step 1: A mixture of 4,6-bis(diphenylphosphino)-10H-phenoxazine (0.959 g, 1.74 mmol), spiro[2.2]pentane-1-carbonitrile (1.618 g, 17.38 mmol), 5-bromo-N,N-bis(4-methoxybenzyl)pyrimidin-2-amine (4.8 g, 12 mmol) and $Pd(OAc)_2$ (0.390 g, 1.74 mmol) was evacuated and refilled with $N_2$ three times. THF (30 mL) and methoxycyclopentane (30 mL) were then added to the mixture. The mixture was stirred for 5 min before LiHMDS (29.0 mL, 29.0 mmol) (1 M solution in THF) was added dropwise at room temperature. The reaction mixture was heated to 60° C. for 3 h, cooled to room temperature, and concentrated. The residue was purified by silica gel chromatography (15% ethyl acetate/pet. ether) to give 1-(2-(bis(4-methoxybenzyl)amino)pyrimidin-5-yl)spiro[2.2]pentane-1-carbonitrile. MS: 427 (M+1).

$^1H$ NMR (400 MHz, $CDCl_3$) δ 8.29 (s, 2H), 7.16 (d, J=8.77 Hz, 4H), 6.84 (d, J=8.33 Hz, 4H), 4.70-4.83 (m, 4H), 3.79 (s, 6H), 2.17 (d, J=4.82 Hz, 1H), 1.70 (d, J=4.82 Hz, 1H), 1.33 (td, J=4.71, 9.87 Hz, 1H), 1.07-1.23 (m, 3H)

Step 2: A mixture of 1-(2-(bis(4-methoxybenzyl)amino)pyrimidin-5-yl)spiro[2.2]pentane-1-carbonitrile (2.25 g, 5.28 mmol) in DCM (15 mL) and TFA (15 mL) was stirred at 40° C. for 10 h. The mixture was cooled to room temperature, poured into $H_2O$ (60 mL), and the pH was adjusted to pH 9 with sat. aq. $NaHCO_3$. The mixture was extracted with DCM (40 mL×3). The combined organic layers were concentrated and purified by silica gel chromatography (45% ethyl acetate/pet. ether) to give 1-(2-aminopyrimidin-5-yl)spiro[2.2]pentane-1-carbonitrile. MS: 187 (M+1). $^1H$ NMR (400 MHz, $CDCl_3$) δ 8.22 (s, 2H), 5.21 (br s, 2H), 2.20 (d, J=4.8 Hz, 1H), 1.71 (d, J=4.8 Hz, 1H), 1.29-1.37 (m, 1H), 1.18 (ddt, J=5.5, 9.0, 14.5 Hz, 2H), 1.01-1.09 (m, 1H).

Step 3: To a solution of 1-(2-aminopyrimidin-5-yl)spiro[2.2]pentane-1-carbonitrile (950 mg, 5.10 mmol) in 1,4-dioxane (10 mL) was added 3-bromo-2-oxopropanoic acid (1278 mg, 7.65 mmol). The reaction was heated to 80° C. for 2 h. The mixture was cooled to room temperature, concentrated and purified by pre-HPLC to give (Z)-3-bromo-2-((5-(1-cyanospiro[2.2]pentan-1-yl)pyrimidin-2-yl)imino)propanoic acid. MS: 335 and 337 (M+1).

Step 4: To a solution of (Z)-3-bromo-2-((5-(1-cyanospiro[2.2]pentan-1-yl)pyrimidin-2-yl)imino)propanoic acid (350 mg, 1.044 mmol) in DMF (5 mL) was added NaH (60%, 125 mg, 3.13 mmol) at 25° C. The reaction mixture was stirred at 25° C. for 20 min. The mixture was purified by pre-HPLC (ACN/water with 0.1% TFA modifier) to give 6-(1-cyanospiro[2.2]pentan-1-yl)imidazo[1,2-a]pyrimidine-2-carboxylic acid. MS: 255 (M+1).

Intermediate 88: 6-bromo-7-hydroxyimidazo[1,2-a]pyridine-2-carboxylic acid

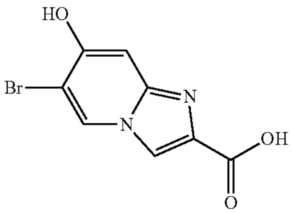 [SMILES: O=C(O)c1cn2cc(Br)c(O)cc2n1]

Step 1: To a solution of 4-methoxypyridin-2-amine (2.0 g, 16 mmol) in acetonitrile (40 mL) was added NBS (2.87 g, 16.1 mmol) at 0° C. The mixture was stirred at 10° C. for 1.5 h. The mixture was concentrated, diluted with DCM (40 mL), washed with aq. $NaHCO_3$ (20 mL), dried over anhydrous $Na_2SO_4$, and concentrated to give 5-bromo-4-methoxypyridin-2-amine, which was used in the next step without further purification. MS: 203 and 205 (M+1). $^1$HNMR (500 MHz, $CDCl_3$) δ 7.98-8.07 (m, 1H), 5.94-6.05 (m, 1H), 4.49 (br s, 2H), 3.87 (s, 3H).

Step 2: To a solution of 5-bromo-4-methoxypyridin-2-amine (2.6 g, 12.8 mmol) in EtOH (30 mL) was added ethyl 3-bromo-2-oxopropanoate (3.75 g, 19.2 mmol) and heated to 80° C. for 16 h. The mixture was cooled to room temperature, treated with TEA (3.57 mL, 25.6 mmol) and stirred for 20 min. The mixture was concentrated and purified by silica gel chromatography (0-30% ethyl acetate in DCM) to give ethyl 6-bromo-7-methoxyimidazo[1,2-a] pyridine-2-carboxylate. MS: 299 and 301 (M+1). $^1$H NMR (500 MHz, $CDCl_3$) δ 8.26 (s, 1H), 7.99 (s, 1H), 6.96 (s, 1H), 4.42 (q, J=7.2 Hz, 2H), 3.89-3.96 (m, 3H), 1.41 (t, J=7.1 Hz, 3H).

Step 3: A mixture of ethyl 6-bromo-7-methoxyimidazo[1,2-a]pyridine-2-carboxylate (100 mg, 0.334 mmol) and pyridine hydrochloride (386 mg, 3.34 mmol) was heated to 160° C. for 1.5 h. The mixture was concentrated to give 6-bromo-7-hydroxyimidazo[1,2-a]pyridine-2-carboxylic acid. MS: 257 and 259 (M+1).

Intermediate 89: 6-bromo-3-methylpyrazolo[1,5-a] pyrimidine-2-carboxylic acid

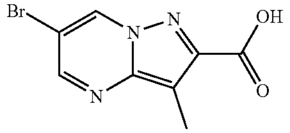

Step 1: To a solution of LiHMDS (103 mL, 103 mmol) (1.0 M in THF) and THF (150 mL) under $N_2$ at −78° C. was added propiononitrile (6.98 g, 127 mmol) dropwise over 2 minutes, and the mixture was stirred for 1 hour. The mixture was treated with diethyl oxalate (15.0 g, 103 mmol) dropwise over 5 minutes, stirred at −78° C. for 45 minutes, and stirred at 0° C. for 1 hour. The mixture was diluted with $H_2O$ (300 mL) and extracted with $Et_2O$ (200 mL). The aqueous phase was adjusted to pH 5 with 6 M HCl and then extracted with $Et_2O$ (200 mL×3). The organic extracts were washed with brine (100 mL), dried over $MgSO_4$, and concentrated to afford ethyl 3-cyano-2-oxobutanoate, which was used in the next step without further purification. $^1$H NMR (400 MHz, $CDCl_3$) δ 4.04-4.47 (m, 2H), 1.97-2.04 (m, 3H), 1.19-1.45 (m, 3H).

Step 2: To a suspension of hydrazine hydrochloride (1.325 g, 19.34 mmol) in EtOH (30 mL) was added ethyl 3-cyano-2-oxobutanoate (3.0 g, 19 mmol). The reaction mixture was heated to 100° C. for 16 hours, then cooled to ambient temperature. The reaction mixture was diluted with sat. $NaHCO_3$ (100 mL), extracted with DCM (60 mL×3), and the combined organic phases were dried over $MgSO_4$ and concentrated. The residue was purified by silica gel chromatography (27% MeOH/$H_2O$) to afford ethyl 5-amino-4-methyl-1H-pyrazole-3-carboxylate. MS: 170 (M+1). $^1$H NMR (400 MHz, DMSO-$d_6$) δ 9.42 (br s, 3H), 4.28 (q, J=7.0 Hz, 2H), 2.13 (s, 3H), 1.28 (t, J=7.2 Hz, 3H).

Step 3: To a solution of ethyl 5-amino-4-methyl-1H-pyrazole-3-carboxylate (259 mg, 1.53 mmol) and HCl (0.138 mL, 1.68 mmol) in EtOH (30 mL) was added 2-bromomalonaldehyde (231 mg, 1.53 mmol) at 15° C. The mixture was stirred at 15° C. for 12 h. The mixture was concentrated under reduced pressure. The residue was purified by pre-HPLC (TFA modifier) to give ethyl 6-bromo-3-methylpyrazolo[1,5-a]pyrimidine-2-carboxylate. MS: 284 and 286M+1). $^1$H NMR (400 MHz, DMSO-$d_6$) δ 9.59 (d, J=2.2 Hz, 1H), 8.63 (d, J=2.2 Hz, 1H), 4.34 (q, J=7.3 Hz, 2H), 2.44 (s, 3H), 1.32 (t, J=7.0 Hz, 3H).

Step 4: A mixture of ethyl 6-bromo-3-methylpyrazolo[1,5-a]pyrimidine-2-carboxylate (50 mg, 0.18 mmol) in HCl (12 M, 2 mL) was heated to 80° C. for 3 h. The mixture was concentrated to give 6-bromo-3-methylpyrazolo[1,5-a]pyrimidine-2-carboxylic acid. MS: 256 and 258 (M+1).

Intermediate 90: 6-(difluoromethyl)-8-(1-methoxyethyl)imidazo[1,2-a]pyridine-2-carboxylic acid

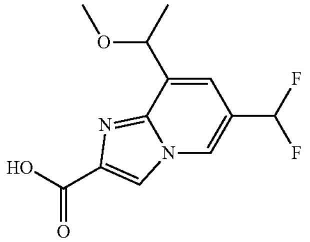 [SMILES: COC(C)c1cc(C(F)F)cn2cc(C(=O)O)nc12]

Step 1: To a mixture of 3-(1-methoxyethyl)pyridin-2-amine (3.5 g, 23 mmol) in AcOH (50 mL) was added $Br_2$ (1.777 mL, 34.5 mmol) at 18° C. The mixture was stirred at 18° C. for 2 h. The mixture was diluted with water (500 mL) and the pH was adjusted to pH 8 with sat.$NaHCO_3$. The mixture was extracted with EtOAc (200 mL×3), and the combined organic layers were washed with brine (200 mL), dried over anhydrous $Na_2SO_4$, filtered, and concentrated. The residue was purified by silica gel chromatography (24% ethyl acetate/pet. ether) to give 5-bromo-3-(1-methoxyethyl) pyridin-2-amine. MS: 230 and 232 (M+1). $^1$H NMR (400 MHz, $CDCl_3$) δ 8.02 (d, J=2.6 Hz, 1H), 7.33 (d, J=2.2 Hz, 1H), 5.16 (br s, 2H), 4.25 (q, J=6.6 Hz, 1H), 3.26 (s, 3H), 1.48 (d, J=7.0 Hz, 3H).

Step 2: To a mixture of 5-bromo-3-(1-methoxyethyl) pyridin-2-amine (3.0 g, 13 mmol) in DMF (30 mL) was added NaH (60%, 1.30 g, 32.5 mmol) at 0° C. The mixture was stirred at 0° C. for 0.5 h, treated with 1-(chloromethyl)-4-methoxybenzene (5.69 g, 36.3 mmol), and stirred at 15° C. for 30 min. The mixture was treated with water (100 mL) and extracted with EtOAc (100 mL×3). The combined organic layers were concentrated and purified by silica gel chromatography (10% ethyl acetate/pet. ether) to give 5-bromo-N,N-bis(4-methoxybenzyl)-3-(1-methoxyethyl) pyridin-2-amine. MS: 471 and 473 (M+1).

Step 3: To a solution of 5-bromo-N,N-bis(4-methoxybenzyl)-3-(1-methoxyethyl)pyridin-2-amine (1.8 g, 3.8 mmol) in EtOH (20 mL) were added $PdCl_2$(dppf) (0.279 g, 0.382 mmol) and potassium acetate (1.124 g, 11.46 mmol). The mixture was heated to 80° C. under CO (pressure: 50 psi) for 12 h. The reaction mixture was cooled to room temperature and extracted with EtOAc (20 mL×3). The combined organic layers were washed with brine (20 mL), dried over anhydrous $Na_2SO_4$, filtered, and concentrated. The residue was purified by silica gel chromatography (42% ethyl acetate/pet. ether) to give ethyl 6-(bis(4-methoxybenzyl) amino)-5-(1-methoxyethyl)nicotinate. MS: 465 (M+1).

Step 4: To a mixture of LAH (0.139 g, 3.66 mmol) in THF (10 mL) was added ethyl 6-(bis(4-methoxybenzyl)amino)-5-(1-methoxyethyl)nicotinate (1.7 g, 3.7 mmol) at 0° C. The mixture was stirred at 25° C. for 2 h. The mixture was extracted with EtOAc (20 mL×3), and the combined organic layers were washed with brine (20 mL), dried over anhydrous $Na_2SO_4$, filtered, and concentrated. The residue was purified by silica gel chromatography (70% ethyl acetate/pet. ether) to give (6-(bis(4-methoxybenzyl)amino)-5-(1-methoxyethyl) pyridin-3-yl) methanol. MS: 423 (M+1). $^1H$ NMR (400 MHz, $CDCl_3$) δ 8.31 (d, J=2.2 Hz, 1H), 7.72 (d, J=2.6 Hz, 1H), 7.15 (d, J=8.3 Hz, 4H), 6.80 (d, J=8.8 Hz, 4H), 4.88 (q, J=6.1 Hz, 1H), 4.68 (s, 2H), 4.05-4.18 (m, 4H), 3.77 (s, 6H), 2.97 (s, 3H), 1.33 (d, J=6.6 Hz, 3H).

Step 5: To a solution of (6-(bis(4-methoxybenzyl)amino)-5-(1-methoxyethyl)pyridin-3-yl) methanol (1.5 g, 3.6 mmol) in chloroform (20 mL) was added manganese dioxide (2.160 g, 24.85 mmol). The mixture was heated to 60° C. for 4 h under $N_2$. The reaction was extracted with EtOAc (20 mL×3), and the combined organic layers were washed with brine (20 mL), dried over anhydrous $Na_2SO_4$, filtered, and concentrated. The residue was purified by silica gel chromatography (20% ethyl acetate/pet. ether) to give 6-(bis(4-methoxybenzyl)amino)-5-(1-methoxyethyl)nicotinaldehyde. MS: 421 (M+1). $^1H$ NMR (500 MHz, $CDCl_3$) δ 10.10 (s, 1H), 8.79 (d, J=2.1 Hz, 1H), 8.36 (d, J=2.3 Hz, 1H), 7.27 (d, J=8.5 Hz, 4H), 7.00 (d, J=8.5 Hz, 4H), 4.78-4.89 (m, 1H), 4.51-4.72 (m, 4H), 3.87-4.02 (m, 6H), 3.18-3.28 (m, 3H), 1.64 (d, J=6.3 Hz, 3H).

Step 6: To a solution of 6-(bis(4-methoxybenzyl)amino)-5-(1-methoxyethyl)nicotinaldehyde (1.4 g, 3.3 mmol) in chloroform (20 mL) was added DAST (0.572 mL, 4.33 mmol). The mixture was heated to 70° C. for 2 h under $N_2$. The mixture was treated with water (40 mL) and extracted with DCM (20 mL×3). The combined organic layers were washed with brine (15 mL), dried over anhydrous $Na_2SO_4$, filtered, and concentrated to give crude 5-(difluoromethyl)-N,N-bis(4-methoxybenzyl)-3-(1-methoxyeth-yl)pyridin-2-amine, which was used in the next step without further purification. MS: 443 (M+1).

Step 7: To a solution of 5-(difluoromethyl)-N,N-bis(4-methoxybenzyl)-3-(1-methoxyethyl) pyridin-2-amine (1.1 g, 2.5 mmol) in acetonitrile (10 mL) and TFA (5 mL) was added trifluoromethanesulfonic acid (10 mg, 0.067 mmol). The mixture was concentrated, treated with water (20 mL), and basified to pH 10 with $NH_3$—$H_2O$. The aqueous layer was extracted with DCM (20 mL×3), and the combined organic layers were washed with brine (20 mL), dried over anhydrous $Na_2SO_4$, filtered, and concentrated to 5-(difluoromethyl)-3-(1-methoxyethyl)pyridin-2-amine, which was used in the next step without further purification. MS: 203 (M+1).

Step 8: A mixture of 5-(difluoromethyl)-3-(1-methoxyethyl)pyridin-2-amine (500 mg, 2.47 mmol) and 3-bromo-2-oxopropanoic acid (495 mg, 2.97 mmol) in dioxane (10 mL) was heated to 80° C. for 2 h. The mixture was cooled to room temperature and purified by Prep-HPLC (TFA condition) to give 6-(difluoromethyl)-8-(1-methoxy-ethyl) imidazo[1,2-a]pyridine-2-carboxylic acid. MS: 271 (M+1).

Intermediate 91: 6-(1-methyl-1H-pyrazol-5-yl)imidazo[1,2-a]pyrimidine-2-carboxylic acid

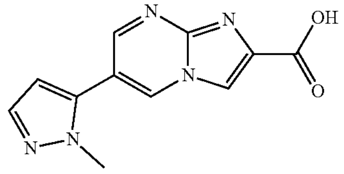 [SMILES: Cn1nccc1-c1cnc2nc(C(=O)O)cn2c1]

Step 1: A mixture of (2,4-dimethoxyphenyl)methanamine (75 g, 450 mmol) and 2,4-dimethoxybenzaldehyde (50 g, 300 mmol) in THF (600 mL) was stirred at 17° C. for 2 h. The mixture was treated with sodium triacetoxyborohydride (77 g, 360 mmol) at 17° C. The mixture was stirred at 17° C. for 12 h. The mixture was treated with $NaBH_4$ (11.38 g, 301 mmol) and stirred at 17° C. for 2 h. The mixture was treated with sat. $NaHCO_3$ (1500 mL) and extracted with EtOAc (300 mL×3). The combined organic layers were washed with brine (1000 mL), dried over anhydrous sodium sulfate, concentrated under reduced pressure, and purified by silica gel chromatography (10% ethyl acetate/petroleum ether) to give bis(2,4-dimethoxybenzyl)amine. MS: 318 (M+1). $^1H$ NMR (500 MHz, $CDCl_3$) δ 7.28 (s, 1H), 7.26 (s, 1H), 6.54 (s, 3H), 6.53 (d, J=2.4 Hz, 1H), 3.90 (d, J1=3.7 Hz, 12H), 3.81 (s, 4H), 1.96 (br d, J=2.8 Hz, 1H)

Step 2: A mixture of 5-bromo-2-chloropyrimidine (3.0 g, 16 mmol), bis(2,4-dimeth-oxybenzyl)amine (5.22 g, 16.4 mmol) and $Cs_2CO_3$ (15.16 g, 46.5 mmol) was heated to 170° C. for 1 h. The mixture was treated with water (600 mL) and extracted with EtOAc (100 mL×3). The combined organic layers were washed with brine (600 mL), dried over anhydrous sodium sulfate, concentrated under reduced pressure, and purified by silica gel chromatography (20% ethyl acetate/petroleum ether) to give 5-bromo-N,N-bis(2,4-dimethoxybenzyl)pyrimidin-2-amine. MS: 474 and 476 (M+1). $^1H$ NMR (500 MHz, $CDCl_3$) δ 8.55 (s, 2H), 7.27 (d, J=8.4 Hz, 2H), 6.70 (d, J=2.3 Hz, 2H), 6.66 (dd, J=2.3, 8.2 Hz, 2H), 5.03 (s, 4H), 4.04 (s, 6H), 4.00 (s, 6H).

Step 3: A mixture of potassium acetate (1.862 g, 18.97 mmol), $PdCl_2$(dppf) (0.463 g, 0.632 mmol), 5-bromo-N,N-bis(2,4-dimethoxybenzyl)pyrimidin-2-amine (3.0 g, 6.3 mmol), and 4,4,4',4',5,5,5',5'-octamethyl-2,2'-bi(1,3,2-dioxaborolane) (4.82 g, 19.0 mmol) in dioxane (30 mL) was degassed and backfilled with $N_2$ (three times). The mixture was heated to 70° C. for 12 h. After cooling to rt, the precipitate was filtered off, and the filtrate was concentrated under reduced pressure. The residue was purified by silica gel chromatography (5% ethyl acetate/petroleum ether) to give N,N-bis(2,4-dimethoxybenzyl)-5-(4,4,5,5-tetramethyl-1,3,2-dioxaborolan-2-yl)pyrimidin-2-amine. MS: 522 (M+1).

Step 4: A mixture of $K_2CO_3$ (1.11 g, 8.06 mmol), $PdCl_2$ (dppf) (0.196 g, 0.269 mmol), N,N-bis(2,4-dimethoxybenzyl)-5-(4,4,5,5-tetramethyl-1,3,2-dioxaborolan-2-yl)pyrimidin-2-amine (1.4 g, 2.7 mmol), and 5-bromo-1-methyl-1H-pyrazole (0.476 g, 2.95 mmol) in THF (10 mL) and water (2 mL) was degassed and backfilled with $N_2$ (three times). The mixture was heated to 70° C. for 2 h. After cooling to rt, the reaction was extracted with EtOAc (20 mL×3), and the combined organic layers were washed with brine (20 mL), dried over anhydrous $Na_2SO_4$, and concentrated under reduced pressure. The residue was purified by silica gel chromatography (12% ethyl acetate/petroleum ether) to give N,N-bis(2,4-dimethoxybenzyl)-5-(1-methyl-1H-pyrazol-5-yl)pyrimidin-2-amine. MS: 476 (M+1). $^1$H NMR (400 MHz, $CDCl_3$) δ 8.36 (s, 2H), 7.05 (d, J=8.3 Hz, 2H), 6.37-6.46 (m, 4H), 4.85 (s, 4H), 3.77 (d, J=12.3 Hz, 12H), 2.67 (s, 3H), 2.41 (s, 3H).

Step 5: A mixture of N,N-bis(2,4-dimethoxybenzyl)-5-(1-methyl-1H-pyrazol-5-yl)pyrimidin-2-amine (700 mg, 1.47 mmol) in DCM (10 mL) and TFA (10 mL) was heated to 40° C. for 3 h. The reaction mixture was extracted with EtOAc (20 mL×3), and the combined organic layers were washed with brine (20 mL), dried over anhydrous $Na_2SO_4$, and concentrated under reduced pressure. The residue was purified by silica gel chromatography (78% ethyl acetate/petroleum ether) to give 5-(1-methyl-11H-pyrazol-5-yl)pyrimidin-2-amine. MS: 176 (M+1). $^1$H NMR (500 MHz, $CDCl_3$) δ 8.36 (s, 2H), 7.53 (d, J=1.8 Hz, 1H), 6.30 (d, J=1.8 Hz, 1H), 5.21 (br s, 2H), 3.78-3.95 (m, 3H).

Step 6: A mixture of 3-bromo-2-oxopropanoic acid (114 mg, 0.685 mmol) and 5-(1-methyl-1H-pyrazol-5-yl)pyrimidin-2-amine (100 mg, 0.571 mmol) in dioxane (10 mL) was heated to 80° C. for 2 h. The mixture was cooled to room temperature and purified by reverse phase HPLC (MeCN/$H_2O$ with 0.1% TFA modifier) to give 6-(1-methyl-1H-pyrazol-5-yl)imidazo[1,2-a]pyrimidine-2-carboxylic acid. MS: 244 (M+1).

TABLE 11

The following intermediate was prepared using a similar procedure as Intermediate 91.

| Intermediate # | Structure | Compound Name | Exact Mass [M + 1] |
|---|---|---|---|
| 92 | 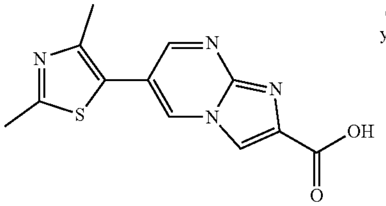 | 6-(2,4-dimethyl-1,3-thiazol-5-yl)imidazo[1,2-a]pyrimidine-2-carboxylic acid | 275 |

Intermediate 93: 6-bromo-7-methylimidazo[1,2-a]pyrimidine-2-carboxylic acid

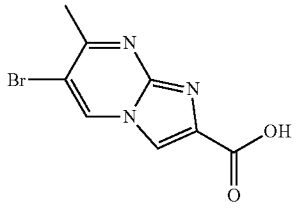

Step 1: To a mixture of 5-bromo-4-methylpyrimidin-2-amine (5.0 g, 27 mmol) in EtOH (50 mL) was added ethyl 3-bromo-2-oxopropanoate (10.37 g, 39.9 mmol) at 20° C. The mixture was heated to 80° C. for 12 h. The mixture was concentrated under reduced pressure, and purified by reverse phase HPLC (ACN/water with 0.1% TFA modifier) to give ethyl 6-bromo-7-methylimidazo[1,2-a]pyrimidine-2-carboxylate (peak 1) and ethyl 6-bromo-5-methylimidazo[1,2-a]pyrimidine-2-carboxylate (peak 2). MS: 284 and 286 (M+1). For ethyl 6-bromo-7-methylimidazo[1,2-a]pyrimidine-2-carboxylate: $^1$H NMR (400 MHz, $CDCl_3$) δ 8.72 (s, 1H), 8.09 (s, 1H), 4.41 (q, J=7.2 Hz, 2H), 2.79 (s, 3H), 1.39 (t, J=7.0 Hz, 3H). For ethyl 6-bromo-5-methylimidazo[1,2-a]pyrimidine-2-carboxylate: $^1$H NMR (400 MHz, $CDCl_3$) δ 8.71 (s, 1H), 8.13 (s, 1H), 4.44 (q, J=7.2 Hz, 2H), 2.85 (s, 3H), 1.41 (t, J=7.2 Hz, 3H).

Step 2: A mixture of ethyl 6-bromo-7-methylimidazo[1,2-a]pyrimidine-2-carboxylate (1.0 g, 3.5 mmol) in HCl (12 M, 8 mL) was heated to 75° C. for 2 h. The mixture was concentrated under reduced pressure to give 6-bromo-7-methylimidazo[1,2-a]pyrimidine-2-carboxylic acid. MS: 256 and 258 (M+1).

TABLE 12

The following intermediates were prepared using a similar procedure as Intermediate 93.

| Intermediate # | Structure | Compound Name | Exact Mass [M + 1] |
|---|---|---|---|
| 94 | 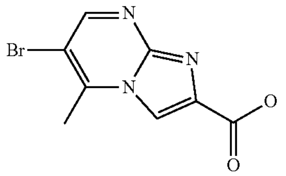 | 6-bromo-5-methylimidazo[1,2-a]pyrimidine-2-carboxylic acid | 256 and 258 |
| 95 | 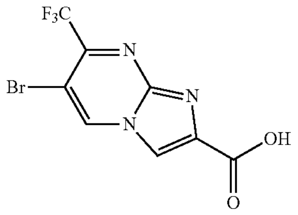 [SMILES: O=C(O)c1cn2cc(Br)c(C(F)(F)F)nc2n1] | 6-bromo-7-(trifluoromethyl)imidazo[1,2-a]pyrimidine-2-carboxylic acid | 310 and 312 |
| 96 | 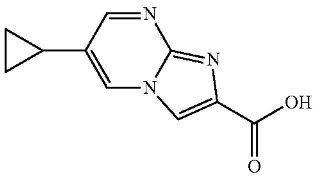 [SMILES: O=C(O)c1cn2cc(C3CC3)cnc2n1] | 6-cyclopropylimidazo[1,2-a]pyrimidine-2-carboxylic acid | 204 |
| 97 | 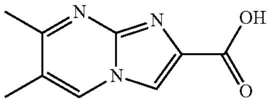 | 6,7-dimethylimidazo[1,2-a]pyrimidine-2-carboxylic acid | 192 |
| 98 | 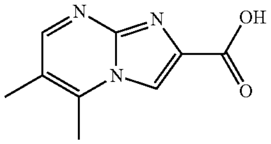 | 5,6-dimethylimidazo[1,2-a]pyrimidine-2-carboxylic acid | 192 |
| 99 | 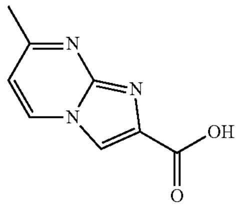 | 7-methylimidazo[1,2-a]pyrimidine-2-carboxylic acid | 178 |
| 100 | 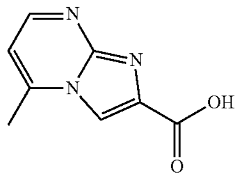 | 5-methylimidazo[1,2-a]pyrimidine-2-carboxylic acid | 178 |
| 101 | 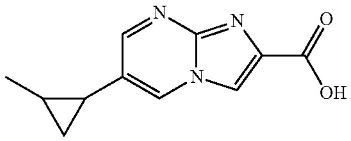 [SMILES: CC1CC1c1cnc2nc(C(=O)O)cn2c1] | 6-(2-methylcyclopropyl)imidazo[1,2-a]pyrimidine-2-carboxylic acid | 218 |

TABLE 12-continued

| The following intermediates were prepared using a similar procedure as Intermediate 93. | | | |
|---|---|---|---|
| Intermediate # | Structure | Compound Name | Exact Mass [M + 1] |
| 102 | 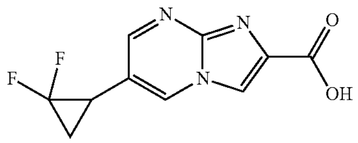 [SMILES: O=C(O)c1cn2cc(C3CC3(F)F)cnc2n1] | 6-(2,2-difluorocyclopropyl)imidazo[1,2-a]pyrimidine-2-carboxylic acid | 240 |

Intermediate 103: 6-cyclopropylimidazo[1,2-a]pyrazine-2-carboxylic acid

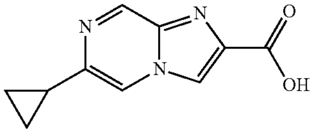 [SMILES: O=C(O)c1cn2cc(C3CC3)ncc2n1]

Step 1: To a mixture of 5-cyclopropylpyrazin-2-amine (0.50 g, 3.7 mmol) in EtOH (10 mL) was added ethyl 3-bromo-2-oxopropanoate (1.443 g, 5.55 mmol) at 20° C. The mixture was heated to 80° C. for 2 h, then concentrated under reduced pressure, and purified by silica gel chromatography (25% ethyl acetate in petroleum ether) to give ethyl 6-cyclopropylimidazo[1,2-a]pyrazine-2-carboxylate. MS: 232 (M+1)

Step 2: To a mixture of ethyl 6-cyclopropylimidazo[1,2-a]pyrazine-2-carboxylate (40 mg, 0.17 mmol) in MeOH (1 mL) and water (0.3 mL) was added $LiOH \cdot H_2O$ (14.52 mg, 0.346 mmol) at 20° C. The mixture was stirred at 20° C. for 12 h. The mixture was concentrated under reduced pressure to give 6-cyclopropylimidazo[1,2-a]pyrazine-2-carboxylic acid. MS: 204 (M+1).

Intermediate 104: 8-(1-methoxyethyl)-6-(trifluoromethyl)imidazo[1,2-a]pyridine-2-carboxylic acid

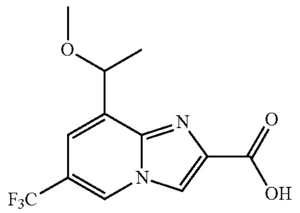

Step 1: A mixture of ethyl 6-bromo-8-(1-methoxyethyl)imidazo[1,2-a]pyridine-2-carboxylate (100 mg, 0.306 mmol), CuI (116 mg, 0.611 mmol) and (1,10-phenanthroline)(trifluoromethyl)copper(I) (287 mg, 0.917 mmol) in DMF (3 mL) was stirred at 80° C. for 12 h in a glove-box. The mixture was purified by reverse phase HPLC (MeCN/$H_2O$ with 0.1% TFA modifier) to give ethyl 8-(1-methoxyethyl)-6-(trifluoromethyl)imidazo[1,2-a]pyridine-2-carboxylate. MS: 317 (M+1).

Step 2: To a solution of ethyl 8-(1-methoxyethyl)-6-(trifluoromethyl)imidazo[1,2-a]pyridine-2-carboxylate (60 mg, 0.190 mmol) in EtOH (2 mL) and water (0.5 mL) was added $LiOH \cdot H_2O$ (11.94 mg, 0.285 mmol) at 25° C. The mixture was stirred at 25° C. for 1 h. The mixture was adjusted to pH-3 with HCl/dioxane (4 M). The mixture was then concentrated under reduced pressure to give 8-(1-methoxyethyl)-6-(trifluoromethyl)imidazo[1,2-a]pyridine-2-carboxylic acid. MS: 289 (M+1).

Intermediate 105: 6-cyclopropylpyrazolo[1,5-a]pyrimidine-2-carboxylic acid

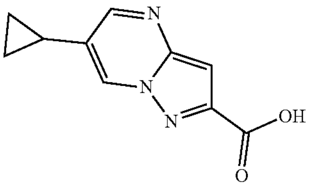 [SMILES: O=C(O)c1cc2ncc(C3CC3)cn2n1]

Step 1: A mixture of butyl 6-bromopyrazolo[1,5-a]pyrimidine-2-carboxylate (200 mg, 0.671 mmol), cyclopropylboronic acid (115 mg, 1.34 mmol), $PdCl_2$(dppf) (49.1 mg, 0.067 mmol) and $Cs_2CO_3$ (656 mg, 2.01 mmol) in 1,4-dioxane (10 mL) and water (1 mL) was heated to 100° C. under $N_2$ for 10 h. The mixture was concentrated under reduced pressure and purified by silica gel chromatography (25% ethyl acetate in petroleum ether) to give butyl 6-cyclopropylpyrazolo[1,5-a]pyrimidine-2-carboxylate. MS: 260 (M+1).

Step 2: A mixture of butyl 6-cyclopropylpyrazolo[1,5-a]pyrimidine-2-carboxylate (80 mg, 0.31 mmol) in HCl (12 M) (1.5 mL) was heated to 40° C. for 3 h. The mixture was concentrated under reduced pressure to 6-cyclopropylpyrazolo[1,5-a]pyrimidine-2-carboxylic acid. MS: 204 (M+1).

Intermediate 106: 6-(1-cyanoethyl)imidazo[1,2-a]pyrimidine-2-carboxylic acid

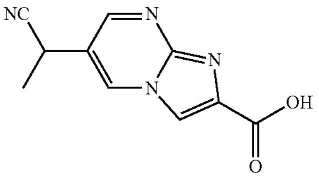 [SMILES: CC(C#N)c1cnc2nc(C(=O)O)cn2c1]

Step 1: A mixture of sodium tert-butoxide (8.84 g, 92 mmol), $PdCl_2$(dppf)-$CH_2Cl_2$ adduct (1.877 g, 2.299 mmol), 5-bromopyrimidin-2-amine (8.0 g, 46 mmol) and tert-butyl 2-cyanoacetate (7.14 g, 50.6 mmol) in 1,4-dioxane (100 mL)

was degassed and backfilled with $N_2$ (three times). The mixture was heated to 80° C. for 12 h. The mixture was treated with MeI (9.79 mL, 157 mmol) and stirred at 20° C. for 1 h. The mixture was concentrated under reduced pressure, diluted with brine (200 mL), and stirred at 20° C. for 20 min. The mixture was filtered, and the filtrate was concentrated under reduced pressure. The residue was diluted with petroleum ether/EtOAc (130 mL) (10:3) and stirred at 20° C. for 20 min. The mixture was filtered, and the filtrate was concentrated under reduced pressure to give tert-butyl 2-(2-aminopyrimidin-5-yl)-2-cyanopropanoate. MS: 249 (M+1).

Step 2: A mixture of tert-butyl 2-(2-aminopyrimidin-5-yl)-2-cyanopropanoate (1.2 g, 4.8 mmol) in DCM (10 mL) and TFA (10 mL) was heated to 40° C. for 12 h. The mixture was concentrated under reduced pressure and purified by reverse phase HPLC (ACN/water with 0.1% TFA modifier) to give 2-(2-aminopyrimidin-5-yl)propanenitrile. MS: 149 (M+1). $^1H$ NMR (500 MHz, $CD_3OD$) δ 8.44-8.52 (m, 2H), 4.16 (q, J=7.3 Hz, 1H), 1.64 (d, J=7.2 Hz, 3H).

Step 3: A mixture of 2-(2-aminopyrimidin-5-yl)propanenitrile (100 mg, 0.675 mmol) and 3-bromo-2-oxopropanoic acid (146 mg, 0.877 mmol) in EtOH (3 mL) was heated to 80° C. for 3 h. The mixture was concentrated under reduced pressure to give 6-(1-cyanoethyl)imidazo[1,2-a]pyrimidine-2-carboxylic acid. MS: 217 (M+1).

Intermediate 107: 8-methyl-6-(trifluoromethyl)imidazo[1,2-a]pyrazine-2-carboxylic acid

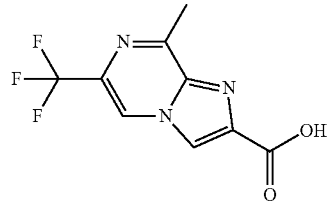 [SMILES: Cc1nc(C(F)(F)F)cn2cc(C(=O)O)nc12]

Step 1: To a solution of 3-methylpyrazin-2-amine (500 mg, 4.58 mmol) and TFA (0.106 mL, 1.38 mmol) in MeCN (15 mL) was added NIS (1546 mg, 6.87 mmol) at 17° C. The mixture was stirred at 17° C. for 12 h. The mixture was treated with sat. $NaHCO_3$ (50 mL) and extracted with EtOAc (20 mL×3). The combined organic layers were washed with brine (30 mL), dried over anhydrous sodium sulfate, concentrated under reduced pressure, and purified by silica gel chromatography (0-60% ethyl acetate in petroleum ether) to give 5-iodo-3-methylpyrazin-2-amine. MS: 236 (M+1). $^1H$ NMR (400 MHz, $CDCl_3$) δ 8.10 (s, 1H), 4.50 (br s, 2H), 2.38 (s, 3H).

Step 2: A mixture of ethyl 3-bromo-2-oxopropanoate (1915 mg, 7.66 mmol) and 5-iodo-3-methylpyrazin-2-amine (900 mg, 3.83 mmol) in 1,4-dioxane (80 mL) was heated to 80° C. for 2 h. The mixture was concentrated under reduced pressure and purified by silica gel chromatography (0-80% DCM in petroleum ether) to give ethyl 6-iodo-8-methylimidazo[1,2-a]pyrazine-2-carboxylate. MS: 332 (M+1). $^1H$ NMR (500 MHz, $CDCl_3$) δ 8.30 (s, 1H), 8.13 (s, 1H), 4.48 (q, J=7.1 Hz, 2H), 2.92 (s, 3H), 1.43 (t, J=7.1 Hz, 3H).

Step 3: A mixture of ethyl 6-iodo-8-methylimidazo[1,2-a]pyrazine-2-carboxylate (200 mg, 0.604 mmol), methyl 2,2-difluoro-2-(fluorosulfonyl)acetate (580 mg, 3.02 mmol), copper(I) iodide (230 mg, 1.21 mmol) and hexamethylphosphoramide (216 mg, 1.21 mmol) in DMF (10 mL) was heated to 80° C. for 2 h. The mixture was treated with water (100 mL) and extracted with EtOAc (30 mL×3). The combined organic layers were washed with brine (100 mL), dried over anhydrous sodium sulfate, concentrated under reduced pressure, and purified by Prep-TLC (1:2 ethyl acetate/petroleum ether) to give ethyl 8-methyl-6-(trifluoromethyl)imidazo[1,2-a]pyrazine-2-carboxylate. MS: 274 (M+1). $^1H$ NMR (500 MHz, $CDCl_3$) δ 8.42 (s, 1H), 8.31 (s, 1H), 4.50 (q, J=7.1 Hz, 2H), 3.01 (s, 3H), 1.45 (t, J=7.2 Hz, 3H).

Step 4: A mixture of ethyl 8-methyl-6-(trifluoromethyl)imidazo[1,2-a]pyrazine-2-carboxylate (50 mg, 0.18 mmol) and $LiOH \cdot H_2O$ (11.52 mg, 0.275 mmol) in EtOH (2 mL) and water (0.6 mL) was stirred at 20° C. for 2 h. The mixture was acidified with aq. HCl (1 M) to pH ~3. The mixture was concentrated under reduced pressure to give 8-methyl-6-(trifluoromethyl)imidazo[1,2-a]pyrazine-2-carboxylic acid. MS: 246 (M+1).

Intermediate 108: 6-(trifluoromethyl)pyrazolo[1,5-a]pyrimidine-2-carboxylic acid

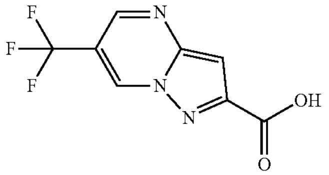 [SMILES: O=C(O)c1cc2ncc(C(F)(F)F)cn2n1]

Step 1: A mixture of 5-nitro-1H-pyrazole-3-carboxylic acid (3.4 g, 22 mmol), butan-1-ol (30 g, 410 mmol) and $H_2SO_4$ (1.15 mL, 21.6 mmol) was heated to 80° C. for 12 h. The mixture was cooled to room temperature and purified by reverse phase HPLC (C18, 10%-20% $H_2O$ (0.5% TFA modifier)/MeOH) to give butyl 5-nitro-1H-pyrazole-3-carboxylate. $^1H$ NMR (400 MHz, DMSO-$d_6$) δ 7.45 (s, 1H), 4.28 (t, J=6.4 Hz, 2H), 1.61-1.70 (m, 2H), 1.39 (m, 2H), 0.89 (t, J=7.5 Hz, 3H).

Step 2: A mixture of butyl 5-nitro-1H-pyrazole-3-carboxylate (4.5 g, 21 mmol) and Pd—C (2.246 g, 2.11 mmol) in MeOH (30 mL) was stirred under $H_2$ (pressure: 15 psi) at 15° C. for 2 h. The mixture was filtered, and the filtrate was concentrated under reduced pressure to give butyl 5-amino-1H-pyrazole-3-carboxylate. MS: 184 (M+1)

Step 3: To a solution of butyl 5-amino-1H-pyrazole-3-carboxylate (3.7 g, 20 mmol) and HCl (1.82 mL, 22.2 mmol) in EtOH (40 mL) was added 2-bromomalonaldehyde (3.05 g, 20.2 mmol) at 15° C. The mixture was stirred at 15° C. for 12 h. The mixture was concentrated under reduced pressure, and purified by silica gel chromatography (25% ethyl acetate in petroleum ether) to give butyl 6-bromopyrazolo[1,5-a]pyrimidine-2-carboxylate. MS: 298 and 300 (M+1). $^1H$ NMR (400 MHz, $CDCl_3$) δ 8.86 (dd, J=0.9, 2.2 Hz, 1H), 8.54 (d, J=2.2 Hz, 1H), 7.24 (s, 1H), 7.23-7.25 (m, 1H), 4.42 (t, J=6.8 Hz, 2H), 1.75-1.84 (m, 2H), 1.47 (qd, J=7.5, 14.9 Hz, 2H), 0.97 (t, J=7.2 Hz, 3H).

Step 4: A mixture of butyl 6-bromopyrazolo[1,5-a]pyrimidine-2-carboxylate (300 mg, 1.01 mmol), methyl 2,2-difluoro-2-(fluorosulfonyl)acetate (967 mg, 5.03 mmol), copper(I) iodide (383 mg, 2.01 mmol) and hexamethylphosphoramide (361 mg, 2.01 mmol) in DMF (6 mL) was heated to 80° C. for 3 h. The reaction was purified by reverse phase HPLC (MeCN/$H_2O$ with 0.1% TFA modifier) to give butyl 6-(trifluoromethyl)pyrazolo[1,5-a]pyrimidine-2-carboxylate. MS: 288 (M+1). $^1$H NMR (400 MHz, $CDCl_3$) δ 9.04 (s, 1H), 8.73 (d, J=1.8 Hz, 1H), 7.34 (s, 1H), 4.45 (t, J=6.8 Hz, 2H), 1.78-1.86 (m, 2H), 1.45-1.53 (m, 2H), 0.99 (t, J=7.5 Hz, 3H).

Step 5: A solution of butyl 6-(trifluoromethyl)pyrazolo[1,5-a]pyrimidine-2-carboxylate (30 mg, 0.10 mmol) in HCl (12 M) (1 mL) and THF (1 mL) was heated to 80° C. for 1 h. The reaction was concentrated under reduced pressure to give 6-(trifluoromethyl)pyrazolo[1,5-a]pyrimidine-2-carboxylic acid. MS: 232 (M+1).

Intermediate 109: 6-bromo-7-cyclopropylimidazo[1,2-a]pyrimidine-2-carboxylic acid

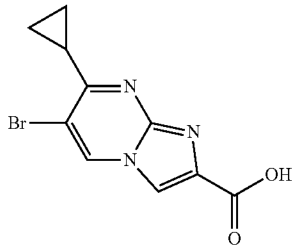 [SMILES: O=C(O)c1cn2cc(Br)c(C3CC3)nc2n1]

Step 1: To a solution of 2,4-dichloropyrimidine (10.0 g, 67.1 mmol) and iron(III) acetylacetonate (4.74 g, 13.4 mmol) in THF (60 mL) and NMP (10 mL) was added cyclopropylmagnesium bromide (268 mL, 134 mmol) (0.5 M solution in THF) dropwise via syringe at 0° C. The resulting mixture was warmed to 25° C. and stirred for 1 h. The reaction mixture was treated with water (500 mL) and extracted with EtOAc (200 mL×3). The combined organic layers were washed with brine (150 mL×2), dried over anhydrous $Na_2SO_4$, concentrated under reduced pressure, and purified by silica gel chromatography (5% ethyl acetate in petroleum ether) to give 2-chloro-4-cyclopropylpyrimidine. MS: 155 (M+1). $^1$H NMR (400 MHz, $CDCl_3$) δ 8.33 (d, J=4.8 Hz, 1H), 7.06 (d, J=4.8 Hz, 1H), 1.92-2.00 (m, 1H), 1.16-1.21 (m, 2H), 1.09-1.15 (m, 2H).

Step 2: A mixture of 2-chloro-4-cyclopropylpyrimidine (3.0 g, 19 mmol) and ammonium hydroxide (30 mL, 220 mmol) in a sealed tube was heated to 100° C. for 5 h. The mixture was cooled to room temperature, concentrated under reduced pressure, and purified by silica gel chromatography (40% ethyl acetate in petroleum ether) to give 4-cyclopropylpyrimidin-2-amine. MS: 136 (M+1). $^1$H NMR (400 MHz, $CDCl_3$) δ 8.05 (d, J=5.3 Hz, 1H), 6.44 (d, J=4.8 Hz, 1H), 4.99 (br s, 2H), 1.77-1.84 (m, 1H), 1.00-1.04 (m, 2H), 0.98 (td, J=2.9, 7.9 Hz, 2H).

Step 3: To a solution of 4-cyclopropylpyrimidin-2-amine (1.5 g, 11 mmol) in DCM (15 mL) was added NBS (2.173 g, 12.21 mmol). The mixture was stirred at 25° C. for 1 h, then concentrated under reduced pressure, and purified by silica gel chromatography (12% ethyl acetate in petroleum ether) to give 5-bromo-4-cyclopropylpyrimidin-2-amine. MS: 214 and 216 (M+1). $^1$H NMR (400 MHz, $CDCl_3$) δ 8.16 (s, 1H), 4.91 (br s, 2H), 2.29-2.38 (m, 1H), 1.08-1.13 (m, 2H), 1.03 (td, J=3.1, 7.89 Hz, 2H).

Step 4: To a solution of 5-bromo-4-cyclopropylpyrimidin-2-amine (1.0 g, 4.7 mmol) in 1,4-dioxane (15 mL) was added 3-bromo-2-oxopropanoic acid (0.936 g, 5.61 mmol). The reaction was heated to 80° C. for 15 min. The mixture was cooled to room temperature, concentrated under pressure, and purified by reverse phase HPLC (ACN/water with 0.1% TFA modifier) to give 6-bromo-7-cyclopropylimidazo[1,2-a]pyrimidine-2-carboxylic acid. LCMS: 282 and 284 (M+1). $^1$H NMR (500 MHz, $CD_3OD$) δ 9.18 (s, 1H), 8.23 (s, 1H), 2.70 (br t, J=6.1 Hz, 1H), 1.27-1.30 (m, 4H).

Intermediate 110: 6-cyclopropyl-8-methyl-5,6,7,8-tetrahydroimidazo[1,2-a]pyrimidine-2-carboxylic acid

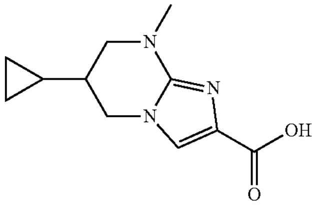 [SMILES: CN1CC(C2CC2)Cn2cc(C(=O)O)nc21]

Step 1: To a solution of ethyl 6-cyclopropylimidazo[1,2-a]pyrimidine-2-carboxylate (1.5 g, 6.5 mmol) in EtOH (4 mL) was added platinum(IV) oxide (0.295 g, 1.297 mmol) under $N_2$ atmosphere. The mixture was degassed and back-filled with $H_2$ (three times). The resulting mixture was stirred under $H_2$ (pressure: 15 psi) at 15° C. for 12 h. The mixture was filtered and concentrated under reduced pressure to give ethyl 6-cyclopropyl-5,6,7,8-tetrahydroimidazo[1,2-a]pyrimidine-2-carboxylate. MS: 236 (M+1).

Step 2: To a solution of ethyl 6-cyclopropyl-5,6,7,8-tetrahydroimidazo[1,2-a]pyrimidine-2-carboxylate (400 mg, 1.70 mmol) in DMF (5 mL) was added NaH (0.075 g, 1.870 mmol) at 0° C. The mixture was stirred at 0° C. for 0.5 h, then treated with MeI (2.40 g, 16.9 mmol). The reaction was stirred at 15° C. for 1.5 h. The mixture was treated with acetone (0.5 mL) and then purified by reverse phase HPLC ($MeCN/H_2O$ with 0.1% TFA modifier) to give ethyl 6-cyclopropyl-8-methyl-5,6,7,8-tetrahydroimidazo[1,2-a]pyrimidine-2-carboxylate. MS: 250 (M+1).

Step 3: To a solution of ethyl 6-cyclopropyl-8-methyl-5,6,7,8-tetrahydroimidazo[1,2-a]pyrimidine-2-carboxylate (120 mg, 0.481 mmol) in ethanol (3 mL) and water (1 mL) was added lithium hydroxide hydrate (101 mg, 2.41 mmol). The mixture was stirred at 20° C. for 2 h. The mixture was concentrated under reduced pressure to give 6-cyclopropyl-8-methyl-5,6,7,8-tetrahydroimidazo[1,2-a]pyrimidine-2-carboxylic acid. MS: 222 (M+1).

TABLE 13

| The following intermediate was prepared using a similar procedure as Intermediate 110. | | | |
|---|---|---|---|
| Intermediate # | Structure | Compound Name | Exact Mass [M + 1] |
| 111 | 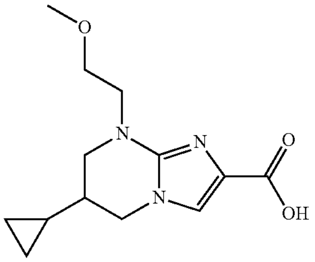 [SMILES: COCCN1CC(C2CC2)Cn2cc(C(=O)O)nc21] | 6-cyclopropyl-8-(2-methoxyethyl)-5,6,7,8-tetrahydroimidazo[1,2-a]pyrimidine-2-carboxylic acid | 266 |

Intermediate 112: 6-((1-acetylpiperidin-4-yl)amino) pyrimidine-4-carboxylic acid

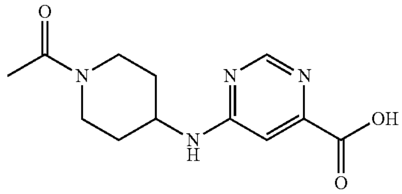 [SMILES: CC(=O)N1CCC(Nc2cc(C(=O)O)ncn2)CC1]

Step 1: To a solution of tert-butyl piperidin-4-ylcarbamate (10.0 g, 49.9 mmol) and TEA (10.44 mL, 74.9 mmol) in $CH_2Cl_2$ (50 mL) was added acetic anhydride (5.10 g, 49.9 mmol) at 0° C. The resulting mixture was stirred at 0° C. for 1.5 h. The reaction was quenched with water (30 mL), and separated. The organic layer was washed with saturated $NaHCO_3$ (50 mL), dried over anhydrous $Na_2SO_4$, filtered, and concentrated under reduced pressure to give tert-butyl (1-acetylpiperidin-4-yl)carbamate, which was used in the next step without further purification. $^1$H NMR (400 MHz, $CDCl_3$) δ 4.36-4.51 (m, 2H), 3.56-3.78 (m, 2H), 3.09 (m, 1H), 2.69 (t, J=11.54 Hz, 1H), 2.05 (s, 3H), 1.84-1.93 (m, 1H), 1.40 (s, 9H), 1.18-1.31 (m, 2H).

Step 2: To a solution of tert-butyl (1-acetylpiperidin-4-yl)carbamate (13.3 g, 54.8 mmol) in $CH_2Cl_2$ (25 mL) was added TFA (24 mL, 312 mmol). The resulting mixture was stirred at 20° C. for 30 min. The reaction was concentrated under reduced pressure to give 1-(4-aminopiperidin-1-yl) ethanone trifluoroacetate, which was used in the next step without further purification. $^1$H NMR (400 MHz, $CD_3OD$) δ 4.56 (d, J=13.89 Hz, 1H), 3.95-4.06 (m, 1H), 3.31-3.42 (m, 1H), 3.14-3.25 (m, 1H), 2.66-2.77 (m, 1H), 2.12 (s, 3H), 1.97-2.10 (m, 2H), 1.37-1.65 (m, 2H).

Step 3: To a solution of 1-(4-aminopiperidin-1-yl)ethanone hydrochloride (24.0 g, 134 mmol) in 2-propanol (80 mL) were added DIEA (23.5 mL, 134 mmol) and 4,6-dichloropyrimidine (20 g, 134 mmol). The resulting mixture was stirred at 100° C. for 4 h under $N_2$. The mixture was concentrated under reduced pressure, and the residue was dissolved in water (60 mL) and extracted with EtOAc (80 mL×3). The combined organic layers were washed with brine (60 mL), dried over anhydrous $Na_2SO_4$, filtered, and concentrated under reduced pressure. The residue was purified by column chromatography (0-5% DCM/MeOH) to give 1-(4-((6-chloropyrimidin-4-yl)amino)piperidin-1-yl) ethanone. $^1$H NMR (400 MHz, $CDCl_3$) δ 8.35 (s, 1H), 6.42 (s, 1H), 5.41 (d, J=7.03 Hz, 1H), 4.54 (d, J=13.30 Hz, 1H), 3.83 (dd, J=2.13, 13.93 Hz, 1H), 3.60-3.74 (m, 2H), 3.23 (m, 1H), 3.10 (dq, J=4.39, 7.40 Hz, 2H), 2.78-2.88 (m, 1H), 2.11 (s, 3H).

Step 4: To a solution of 1-(4-((6-chloropyrimidin-4-yl) amino)piperidin-1-yl)ethanone (10 g, 39.3 mmol) and potassium acetate (11.6 g, 118 mmol) in EtOH (90 mL) was added $PdCl_2$(dppf) (2.87 g, 3.93 mmol). The mixture was degassed and backfilled with CO (three times). The resulting mixture was stirred under CO (pressure: 50 psi) at 70° C. for 16 h. The mixture was concentrated under reduced pressure. The residue was purified by flash silica gel chromatography (ethyl acetate/MeOH) to give ethyl 6-((1-acetylpiperidin-4-yl)amino)pyrimidine-4-carboxylate. MS: 293 (M+1). $^1$H NMR (400 MHz, $CD_3OD$) δ 8.48 (d, J=0.78 Hz, 1H), 7.13 (s, 1H), 4.32-4.47 (m, 2H), 4.20 (s, 1H), 3.85-3.97 (m, 1H), 3.23-3.33 (m, 2H), 2.82-2.96 (m, 1H), 2.11 (s, 3H), 1.96-2.09 (m, 2H), 1.42-1.54 (m, 2H), 1.36-1.40 (m, 3H).

Step 5: To a solution of ethyl 6-((1-acetylpiperidin-4-yl) amino)pyrimidine-4-carboxylate (7.5 g, 25.7 mmol) in MeOH (60 mL) and water (5 mL) was added lithium hydroxide hydrate (1.40 g, 33.4 mmol). The mixture was stirred at 20° C. for 1.5 h. The mixture was acidified by HCl (12 N, 2 mL) and concentrated under reduced pressure to give 6-((1-acetylpiperidin-4-yl)amino)pyrimidine-4-carboxylic acid, which was used without further purification. MS: 265 (M+1). $^1$H NMR (400 MHz, $CD_3OD$) δ 8.36-8.44 (m, 1H), 6.96 (s, 1H), 4.43 (d, J=14.09 Hz, 11H), 3.22-3.29 (m, 1H), 3.92 (d, J=14.09 Hz, 1H), 2.89 (t, J=11.15 Hz, 1H), 2.12 (s, 3H), 2.07 (s, 1H), 2.00 (d, J=10.96 Hz, 1H), 1.37-1.52 (m, 2H).

Intermediate 113: 4-(3-oxa-8-azabicyclo[3.2.1]octane-8-carbonyl)benzoic acid

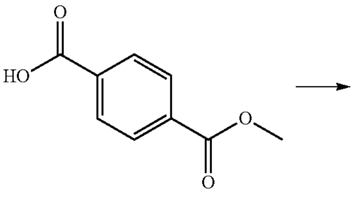

-continued

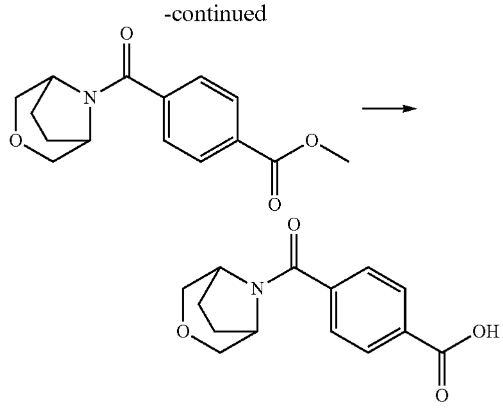

Step 1: To a solution of 4-(methoxycarbonyl)benzoic acid (10 g, 55.5 mmol) and HATU (25.3 g, 66.6 mmol) in DCM (150 ml) was added DIEA (29.1 ml, 167 mmol). The mixture was stirred at 25° C. for 5 min. 3-oxa-8-azabicyclo[3.2.1]octane hydrochloride (8.72 g, 58.3 mmol) was then added to the mixture at 25° C. The mixture was stirred at 25° C. for 10 min and concentrated under reduced pressure. The residue was purified by flash silica gel chromatography (ethyl acetate/petroleum ether) to give methyl 4-(3-oxa-8-azabicyclo[3.2.1]octane-8-carbonyl)benzoate. MS: 276 (M+1). $^1$H NMR (400 MHz, $CDCl_3$) δ 8.06 (d, J=8.41 Hz, 2H), 7.52 (d, J=8.41 Hz, 2H), 4.71 (br s, 1H), 3.91 (s, 3H), 3.85 (br d, J=10.17 Hz, 2H), 3.51-3.76 (m, 3H), 2.02-2.09 (m, 2H), 1.81-2.00 (m, 2H)

Step 2: To a solution of methyl 4-(3-oxa-8-azabicyclo[3.2.1]octane-8-carbonyl)benzoate (10 g, 36.3 mmol) in MeOH (60 mL) was added sodium hydroxide (2.1 g, 54.5 mmol) in water (30 mL). The mixture was stirred at 30° C. for 1.5 h. The resultant mixture was quenched with water (30 mL) and extracted with ethyl acetate (30 mL×3). The combined organic layers were concentrated under reduced pressure to give 4-(3-oxa-8-azabicyclo[3.2.1]octane-8-carbonyl)benzoic acid, which was used without further purification. MS: 262 (M+1). $^1$H NMR (400 MHz, $CDCl_3$) δ 8.15 (d, J=8.22 Hz, 2H), 7.58 (d, J=8.61 Hz, 2H), 4.76 (br s, 1H), 3.89 (br d, J=10.17 Hz, 2H), 3.65-3.76 (m, 2H), 3.57-3.65 (m, 1H), 1.87-2.10 (m, 4H)

Intermediate 114: 4-(3-oxa-8-azabicyclo[3.2.1]octane-8-carbonyl)-2-cyclopropoxybenzoic acid

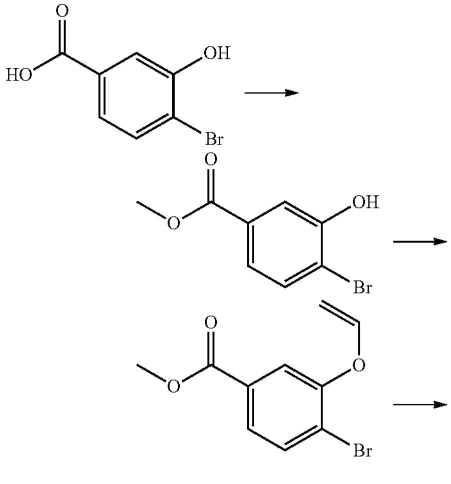

-continued

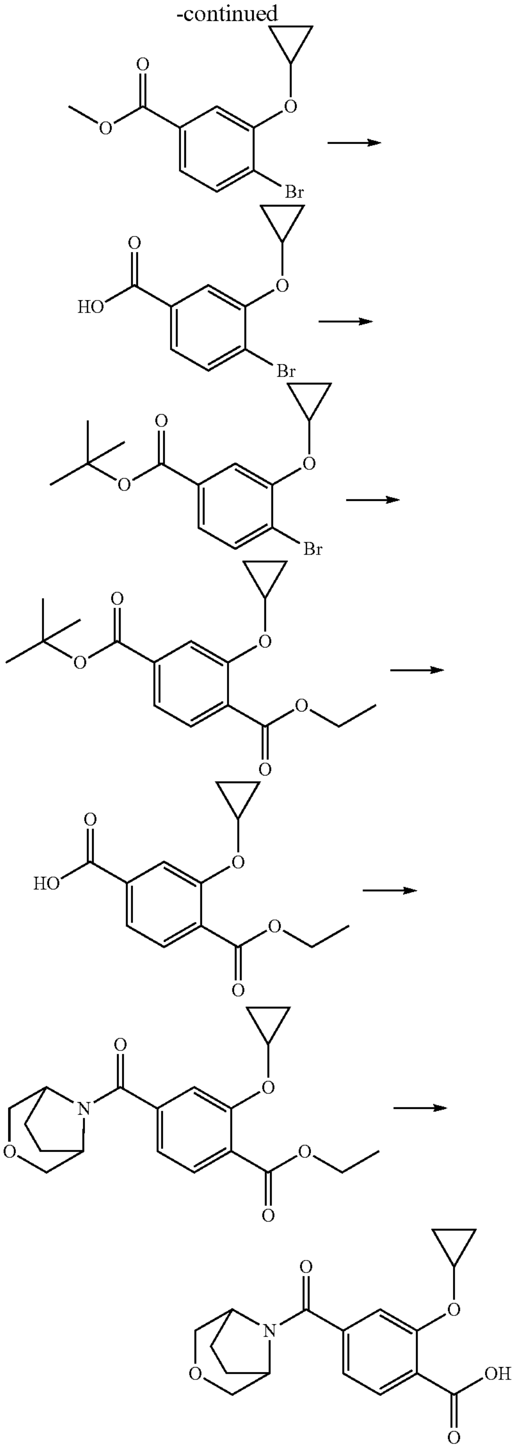

Step 1: To a solution of 4-bromo-3-hydroxybenzoic acid (10 g, 46.1 mmol) in MeOH (200 mL) was added $SOCl_2$ (6.73 mL, 92 mmol) slowly at 15° C. The mixture was stirred at 80° C. for 4 h. The mixture was concentrated under reduced pressure. The residue was purified by flash silica gel chromatography (ethyl acetate/petroleum ether) to give methyl 4-bromo-3-hydroxybenzoate. $^1$H NMR (400 MHz, $CDCl_3$) δ 7.66 (d, J=1.76 Hz, 1H), 7.43-7.56 (m, 2H), 5.75 (s, 1H), 3.89 (s, 3H).

Step 2: A mixture of methyl 4-bromo-3-hydroxybenzoate (14 g, 60.6 mmol), vinyl acetate (11.2 mL, 121 mmol), $Na_2CO_3$ (5.14 g, 48.5 mmol) and chloro(1,5-cyclooctadiene) iridium(I) dimer (2.04 g, 3.03 mmol) in $PhCH_3$ (130 mL) was degassed and backfilled with $N_2$ (three times). The mixture was heated to 100° C. for 12 h. The mixture was concentrated under reduced pressure. The residue was purified by flash silica gel chromatography (ethyl acetate/petroleum ether) to give methyl 4-bromo-3-(vinyloxy)benzoate. $^1H$ NMR (400 MHz, $CDCl_3$) δ 7.55-7.70 (m, 3H), 6.61 (dd, J=5.97, 13.60 Hz, 1H), 4.76-4.90 (m, 1H), 4.52-4.65 (m, 1H), 3.90 (s, 3H).

Step 3: To a solution of methyl 4-bromo-3-(vinyloxy) benzoate (11 g, 42.8 mmol) in DCM (100 mL) was added chloroiodomethane (12.6 mL, 171 mmol) at 20° C. Diethylzine (171 mL, 171 mmol) was added to the mixture slowly at 0° C. under $N_2$. The reaction was warmed to 20° C. and stirred for 48 h under $N_2$. The mixture was added slowly into aq. $NH_4Cl$ (100 mL), and extracted with DCM (100 mL×3). The organic layers were dried over $Na_2SO_4$, filtered, and the filtrate was concentrated under reduced pressure. The residue was purified by flash silica gel chromatography (ethyl acetate/petroleum ether) to give methyl 4-bromo-3-cyclopropoxybenzoate. $^1H$ NMR (400 MHz, $CDCl_3$) δ 7.88 (d, J=1.98 Hz, 1H), 7.56-7.61 (m, 1H), 7.48-7.54 (m, 1H), 3.91-3.94 (m, 3H), 3.85-3.90 (m, 1H), 0.81-0.97 (m, 4H).

Step 4: To a solution of methyl 4-bromo-3-cyclopropoxybenzoate (5.2 g, 19.2 mmol) in MeOH (40 mL) and water (20 mL) was added LiOH·$H_2O$ (1.378 g, 57.5 mmol). The mixture was stirred at 20° C. for 1 h. The mixture was concentrated under reduced pressure. To the residue was added $H_2O$ (20 mL), and the mixture was acidified with citric acid solution to a pH of 5. The mixture was extracted with EtOAc (40 mL×3). The combined organic layers were washed with brine (40 mL), dried over $Na_2SO_4$, filtered, and the filtrate was concentrated under reduced pressure to give 4-bromo-3-cyclopropoxybenzoic acid, which was used in the next step without further purification. $^1H$ NMR (400 MHz, $CDCl_3$) δ 7.94 (br d, J=1.56 Hz, 1H), 7.50-7.69 (m, 2H), 3.78-3.93 (m, 1H), 0.87 (br s, 4H).

Step 5: To a mixture of 4-bromo-3-cyclopropoxybenzoic acid (4.5 g, 17.50 mmol) in $PhCH_3$ (70 mL) was added dropwise 1,1-di-tert-butoxy-N,N-dimethylmethanamine (14.3 g, 70.0 mmol) at 80° C. The mixture was stirred at 80° C. for 4 h. The mixture was concentrated under reduced pressure. The residue was purified by flash silica gel chromatography (ethyl acetate/petroleum ether) to give tert-butyl 4-bromo-3-cyclopropoxybenzoate. $^1H$ NMR (400 MHz, $CDCl_3$) δ 7.86 (d, J=1.76 Hz, 1H), 7.52-7.56 (m, 1H), 7.45 (dd, J=1.98, 8.16 Hz, 1H), 3.86 (td, J=4.49, 8.88 Hz, 1H), 1.59 (s, 9H), 0.84-0.88 (m, 4H).

Step 6: To a solution of tert-butyl 4-bromo-3-cyclopropoxybenzoate (3.8 g, 12.1 mmol) and potassium acetate (2.38 g, 24.3 mmol) in ethanol (50 mL) was added $PdCl_2$ (dppf) (1.77 g, 2.43 mmol) under $N_2$ atmosphere. The mixture was degassed and backfilled with CO (three times).

The resultant mixture was stirred under CO (pressure: 50 psi) at 75° C. for 12 h. The mixture was concentrated under reduced pressure. The residue was purified by flash silica gel chromatography (ethyl acetate/petroleum ether) to give 4-tert-butyl 1-ethyl 2-cyclopropoxyterephthalate. $^1H$ NMR (400 MHz, $CDCl_3$) δ 7.94 (d, J=1.37 Hz, 1H), 7.73 (d, J=8.02 Hz, 1H), 7.55 (dd, J=1.56, 8.02 Hz, 1H), 4.32 (q, J=7.11 Hz, 2H), 3.80-3.89 (m, 1H), 1.59 (s, 9H), 1.35 (t, J=7.14 Hz, 3H), 0.80-0.86 (m, 4H)

Step 7: A solution of 4-tert-butyl 1-ethyl 2-cyclopropoxyterephthalate (3.2 g, 10.5 mmol) in HCl/EtOAc (1M, 20 mL) was stirred at 25° C. for 4 h. The mixture was concentrated under reduced pressure to give 3-cyclopropoxy-4-(ethoxycarbonyl)benzoic acid which was used in the next step without further purification. $^1H$ NMR (400 MHz, $CDCl_3$) δ 8.04 (d, J=1.17 Hz, 1H), 7.76-7.82 (m, 1H), 7.68-7.75 (m, 1H), 4.35 (q, J=7.04 Hz, 2H), 3.88 (td, J=2.49, 5.58 Hz, 1H), 1.36 (t, J=7.14 Hz, 3H), 0.80-0.90 (m, 4H).

Step 8: To a mixture of 3-cyclopropoxy-4-(ethoxycarbonyl)benzoic acid (100 mg, 0.400 mmol), HATU (198 mg, 0.519 mmol) and DIEA (0.209 mL, 1.20 mmol) in DCM (4 mL) was added 3-oxa-8-azabicyclo[3.2.1]octane hydrochloride (71.7 mg, 0.480 mmol) in DCM (1 mL) at 20° C. The resultant mixture was stirred at 20° C. for 15 min. The mixture was concentrated under reduced pressure. The residue was purified by preparative TLC (ethyl acetate/petroleum ether) to give ethyl 4-(3-oxa-8-azabicyclo[3.2.1]octane-8-carbonyl)-2-cyclopropoxybenzoate. MS: 346 (M+1). $^1H$ NMR (400 MHz, $CDCl_3$) δ 7.78 (d, J=7.89 Hz, 1H), 7.48 (d, J=1.32 Hz, 1H), 7.06 (dd, J=1.32, 7.89 Hz, 1H), 4.73 (br s, 1H), 4.34 (q, J=7.31 Hz, 2H), 3.79-4.00 (m, 3H), 3.50-3.76 (m, 3H), 1.84-2.14 (m, 4H), 1.37 (t, J=7.02 Hz, 3H), 0.82-0.88 (m, 4H).

Step 9: To a solution of ethyl 4-(3-oxa-8-azabicyclo [3.2.1]octane-8-carbonyl)-2-cyclopropoxybenzoate (90 mg, 0.261 mmol) in MeOH (3 mL) and water (1 mL) was added LiOH·$H_2O$ (12.5 mg, 0.521 mmol). The mixture was stirred at 20° C. for 1 h. The mixture was concentrated under reduced pressure, and $H_2O$ (10 mL) was added to the residue. The mixture was acidified with citric acid solution (1 M) to pH 5. The mixture was extracted with EtOAc (10 mL×3). The combined organic layers were washed with brine (10 mL), dried over $Na_2SO_4$, filtered, and the filtrate was concentrated under reduced pressure to give 4-(3-oxa-8-azabicyclo[3.2.1]octane-8-carbonyl)-2-cyclopropoxybenzoic acid, which was used without further purification. MS: 318 (M+1).

Intermediate 115: 8-(1-hydroxyethyl)-6-(trifluoromethyl)imidazo[1,2-a]pyridine-2-carboxylic acid

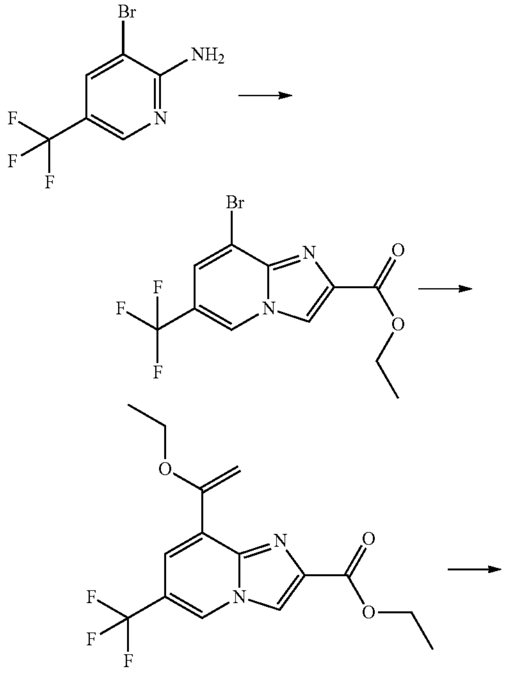

-continued

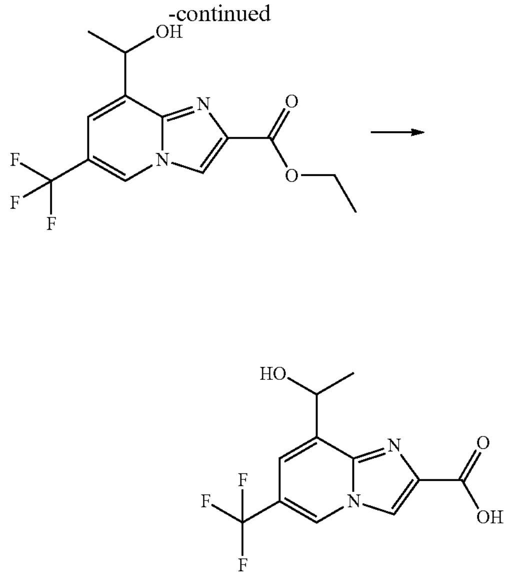

Step 1: To a solution of 3-bromo-5-(trifluoromethyl) pyridin-2-amine (10 g, 41.5 mmol) in DME (50 mL) was added ethyl 3-bromo-2-oxopropanoate (14.1 g, 50.6 mmol) dropwise. The reaction mixture was heated to 80° C. for 18 h. The reaction was concentrated under reduced pressure to give crude material, which was purified by flash silica gel chromatography (ethyl acetate/petroleum ether) to give ethyl 8-bromo-6-(trifluoromethyl)imidazo[1,2-a]pyridine-2-carboxylate. MS: 337 and 339 (M+1).

Step 2: A mixture of tetrakis(triphenylphosphine)palladium(0) (51.4 mg, 0.044 mmol), ethyl 8-bromo-6-(trifluoromethyl)imidazo[1,2-a]pyridine-2-carboxylate (100 mg, 0.297 mmol) and tributyl(1-ethoxyvinyl)stannane (0.200 g, 0.554 mmol) in 1,4-dioxane (5 mL) was stirred at 100° C. for 12 h under $N_2$, (degassed and backfilled with $N_2$ three times). The mixture was concentrated under reduced pressure, and the residue was purified by preparative TLC (ethyl acetate/petroleum ether) to give ethyl 8-(1-ethoxyvinyl)-6-(trifluoromethyl)imidazo[1,2-a]pyridine-2-carboxylate. MS: 329 (M+1). $^1H$ NMR (400 MHz, $CDCl_3$) δ 8.43 (s, 1H), 8.25 (s, 1H), 7.82 (d, J=1.32 Hz, 1H), 6.53 (d, J=2.63 Hz, 1H), 4.87 (d, J=2.19 Hz, 1H), 4.46 (q, J=7.02 Hz, 2H), 4.01 (q, J=7.02 Hz, 2H), 0.92 (t, J=7.24 Hz, 611)

Step 3: To a solution of ethyl 8-acetyl-6-(trifluoromethyl) imidazo[1,2-a]pyridine-2-carboxylate (70 mg, 0.233 mmol) in MeOH (10 mL) was added $NaBH_4$ (2.65 mg, 0.070 mmol) at 25° C. The mixture was stirred at 25° C. for 5 min. The reaction was quenched with acetone (1 mL). The mixture was concentrated under reduced pressure, and the residue was purified by preparative TLC (ethyl acetate/petroleum ether) to give ethyl 8-(1-hydroxyethyl)-6-(trifluoromethyl) imidazo[1,2-a]pyridine-2-carboxylate. MS: 303 (M+1).

Step 4: A solution of ethyl 8-(1-hydroxyethyl)-6-(trifluoromethyl)imidazo[1,2-a]pyridine-2-carboxylate (45 mg, 0.149 mmol) and lithium hydroxide monohydrate (12.5 mg, 0.298 mmol) in THF (4 mL) and water (2 mL) was stirred at 25° C. for 1 h. Dilute HCl (1 M) was added dropwise to the mixture until the pH was <5.0. The solvent was removed under reduced pressure to afford 8-(1-hydroxyethyl)-6-(trifluoromethyl)imidazo[1,2-a]pyridine-2-carboxylic acid. MS: 275 (M+1).

Intermediate 116: 8-(2-cyanoethyl)-6-(trifluoromethyl)imidazo[1,2-a]pyridine-2-carboxylic acid

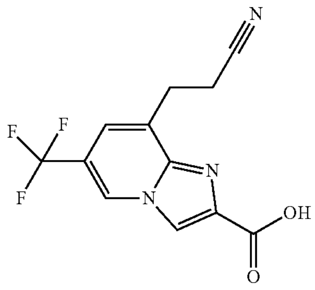 [SMILES: N#CCCc1cc(C(F)(F)F)cn2cc(C(=O)O)nc12]

To a mixture of ethyl 8-(2-cyanoethyl)-6-(trifluoromethyl)imidazo[1,2-a]pyridine-2-carboxylate (50 mg, 0.161 mmol) in EtOH (1 mL) was added lithium hydroxide monohydrate (10.1 mg, 0.241 mmol) in water (0.3 mL) at 25° C. The mixture was stirred at 25° C. for 2 h. The mixture was concentrated under reduced pressure to give 8-(2-cyanoethyl)-6-(trifluoromethyl)imidazo[1,2-a]pyridine-2-carboxylic acid, which was used without further purification.

Intermediate 117: 8-methyl-6-(trifluoromethyl)imidazo[1,2-a]pyridine-2-carboxylic acid

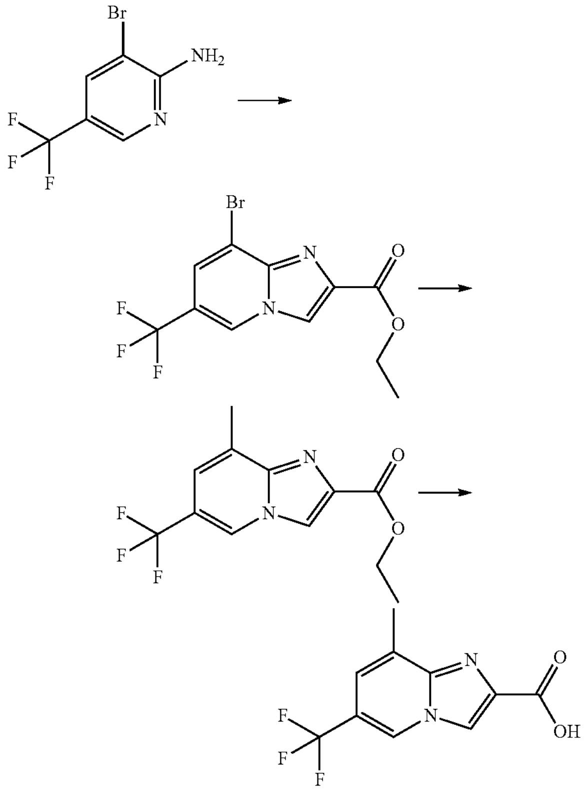

Step 1: To a solution of 3-bromo-5-(trifluoromethyl) pyridin-2-amine (10 g, 41.5 mmol) in DME (200 ml) was added ethyl 3-bromo-2-oxopropanoate (13.2 g, 50.6 mmol) dropwise. The reaction mixture was heated to 90° C. for 18 h. The reaction was concentrated under reduced pressure to give crude residue, which was purified by flash silica gel chromatography (ethyl acetate/petroleum ether) to give ethyl 8-bromo-6-(trifluoromethyl)imidazo[1,2-a]pyridine-2-carboxylate. $^1$H NMR (400 MHz, $CDCl_3$) δ 8.52-8.66 (m, 1H), 8.39 (s, 1H), 7.71 (d, J=1.34 Hz, 1H), 4.42-4.57 (m, 2H), 1.46 (t, J=7.15 Hz, 3H).

Step 2: A mixture of ethyl 8-bromo-6-(trifluoromethyl) imidazo[1,2-a]pyridine-2-carboxylate (500 mg, 1.48 mmol), 2,4,6-trimethyl-1,3,5,2,4,6-trioxatriborinane (186 mg, 1.48 mmol), $K_3PO_4$ (315 mg, 1.48 mmol) and $PdCl_2$(dppf) (1.09 g, 1.48 mmol) in 1,4-dioxane (8 mL) was stirred at 90° C. for 4 h. The mixture was concentrated under reduced pressure. The residue was purified by flash silica gel chromatography (ethyl acetate/petroleum ether) to give ethyl 8-methyl-6-(trifluoromethyl)imidazo[1,2-a]pyridine-2-carboxylate. MS: 273 (M+1). $^1$H NMR (400 MHz, $CDCl_3$) δ 8.38 (s, 1H), 8.25 (s, 1H), 7.18 (s, 1H), 4.48 (q, J=7.02 Hz, 2H), 2.71 (s, 3H), 1.44 (t, J=7.24 Hz, 3H).

Step 3: A mixture of ethyl 8-methyl-6-(trifluoromethyl) imidazo[1,2-a]pyridine-2-carboxylate (50 mg, 0.184 mmol) and $LiOH \cdot H_2O$ (11.6 mg, 0.276 mmol) in ethanol (2.0 ml) and water (1.0 ml) was stirred at 25° C. for 2 h. The solvent was removed under reduced pressure, and the residue was dissolved in water (10.0 mL) and acidified with 2.0 N HCl to pH 6. The aqueous layer was concentrated under reduced pressure to give 8-methyl-6-(trifluoromethyl)imidazo[1,2-a] pyridine-2-carboxylic acid, which was used without further purification.

Intermediate 118: 7-methyl-5,6,7,8-tetrahydroimidazo[1,2-a]pyrazine-2-carboxylic acid

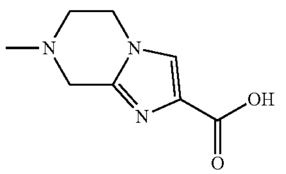

Step 1: To a solution of pyrazin-2-amine (5.0 g, 53 mmol) in DME (60 mL) was added ethyl 3-bromo-2-oxopropanoate (12.3 g, 63.1 mmol). The resulting mixture was heated to 60° C. for 12 h. The mixture was cooled to room temperature, concentrated under reduced pressure, and purified by column chromatography on silica gel (Petroleum ether/ethyl acetate=1:1 to 1:3) to give ethyl imidazo[1,2-a]pyrazine-2-carboxylate. $^1$H NMR (400 MHz, $CDCl_3$) δ 9.48 (br s, 1H), 8.43 (s, 1H), 8.36 (br s, 1H), 8.17 (br d, J=4.4 Hz, 1H), 4.49 (q, J=7.2 Hz, 2H), 1.45 (t, J=7.2 Hz, 3H).

Step 2: A mixture of ethyl imidazo[1,2-a]pyrazine-2-carboxylate (400 mg, 2.09 mmol) and Pd/C (2227 mg, 2.092 mmol) in EtOH (10 mL) and HCl/EtOAc (4 N) (0.1 mL) was stirred at 15° C. under $H_2$ (pressure: 50 psi) for 12 h. The mixture was filtered, washed with EtOH, and concentrated under reduced pressure to give ethyl 5,6,7,8-tetrahydroimidazo[1,2-a]pyrazine-2-carboxylate. MS: 196 (M+1).

Step 3: To a solution of ethyl 5,6,7,8-tetrahydroimidazo [1,2-a]pyrazine-2-carboxylate (400 mg, 2.05 mmol) and formaldehyde (1663 mg, 20.49 mmol) in ethanol (10 mL) and TEA (0.1 mL) was added $NaCNBH_4$ (258 mg, 4.10 mmol). The reaction was stirred at 15° C. for 12 h. The mixture was diluted with $CH_2Cl_2$ (50 mL) and washed with 50% $K_2CO_3$ aq. solution (20 mL). The organic layer was separated, dried, and concentrated under reduced pressure to give ethyl 7-methyl-5,6,7,8-tetrahydroimidazo[1,2-a]pyrazine-2-carboxylate. MS: 210 (M+1).

Step 4: A solution of ethyl 7-methyl-5,6,7,8-tetrahydroimidazo[1,2-a]pyrazine-2-carboxylate (400 mg, 1.91 mmol) and LiOH (92 mg, 3.8 mmol) in MeOH (10 mL) and water (5 mL) was stirred at 15° C. for 12 h. The mixture was treated with HCl (1N, 1 mL) and concentrated under reduced pressure to give 7-methyl-5,6,7,8-tetrahydroimidazo[1,2-a] pyrazine-2-carboxylic acid. MS: 182 (M+1).

Intermediate 119: 8-hydroxy-6-methylimidazo[1,2-a]pyrazine-2-carboxylic acid

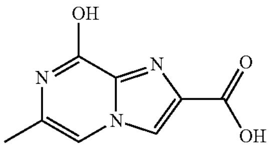

Step 1: To a solution of 3-chloro-5-methylpyrazin-2-amine (0.70 g, 4.9 mmol) in 1,4-dioxane (10 ml) was added ethyl 3-bromo-2-oxopropanoate (1.426 g, 7.31 mmol) at 15° C. The mixture was heated to 80° C. for 2 h. After cooling to 15° C., TEA (0.815 ml, 5.85 mmol) was added. The mixture was stirred at 15° C. for 0.5 h, the precipitate was filtered off, and then the filtrate was concentrated. The residue was purified by pre-HPLC to give ethyl 8-chloro-6-methylimidazo[1,2-a]pyrazine-2-carboxylate (MS: 240 (M+1)) and ethyl 8-hydroxy-6-methylimidazo[1,2-a]pyrazine-2-carboxylate (MS: 222 (M+1)).

Step 2: A mixture of ethyl 8-hydroxy-6-methylimidazo[1,2-a]pyrazine-2-carboxylate (50 mg, 0.23 mmol) in HCl (12 M, 2 ml) was heated to 80° C. for 3 h. The mixture was concentrated to give 8-hydroxy-6-methylimidazo[1,2-a] pyrazine-2-carboxylic acid. MS: 194 (M−1)

Intermediates 120 and 121: (R)-8-bromo-6-(1-methoxyethyl)imidazo[1,2-a]pyridine-2-carboxylic acid and (S)-8-bromo-6-(1-methoxyethyl)imidazo[1,2-a]pyridine-2-carboxylic acid

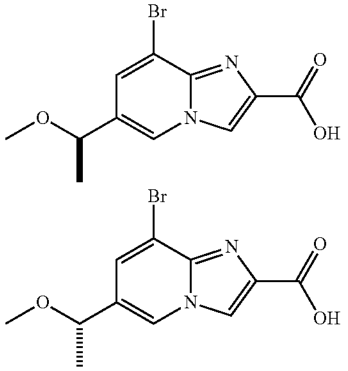

Step 1: To a solution of 1-(5-bromo-6-chloropyridin-3-yl)ethanol (1.2 g, 5.1 mmol) in DMF (20 ml) was added NaH (0.304 g. 7.61 mmol) at 15° C. The mixture was stirred at 15° C. for 10 min. Iodomethane (0.781 ml. 12.5 mmol) at 15° C. was added to the mixture, and the mixture was stirred at 15° C. for 30 min. The mixture was treated with water (200 mL) and extracted with EtOAc (50 mL×4). The combined organic layers were washed with brine (200 mL), dried over anhydrous sodium sulfate, filtered, and the filtrate was concentrated under reduced pressure. The residue was purified by flash silica gel chromatography (0-18% ethyl acetate/petroleum ether gradient) to give 3-bromo-2-chloro-5-(1-methoxyethyl)pyridine. MS: 250 and 252 (M H).

Step 2: A mixture of 3-bromo-2-chloro-5-(1-methoxyethyl)pyridine (260 mg, 1.04 mmol), (2,4-dimethoxyphenyl) methanamine (347 mg, 2.08 mmol), and $Cs_2CO_3$ (845 mg, 2.59 mmol) in sulfolane (2 ml) was heated to 190° C. for 2 h. $H_2O$ (20 mL) was added and the mixture was extracted with EtOAc (20 mL×3). The combined organic layers were concentrated and purified by Prep-TLC (1:3 ethyl acetate/petroleum ether, $R_f$=0.6) to give 3-bromo-N-(2,4-dimethoxybenzyl)-5-(1-methoxyethyl)pyridin-2-amine. MS: 381 and 383 (M+1). $^1$H NMR (500 MHz, $CDCl_3$) δ 8.00 (d, J=1.8 Hz, 1H), 7.63 (d, J=1.8 Hz, 1H), 7.27 (d, J=8.2 Hz, 1H), 6.51 (d, J=2.1 Hz, 1H), 6.46 (dd, J=2.3, 8.2 Hz, 1H), 5.46-5.60 (m, 1H), 4.62 (d, J=5.8 Hz, 2H), 4.16-4.22 (m, 1H), 3.88 (s, 3H), 3.82 (s, 3H), 3.21 (s, 3H), 1.42 (d, J=6.6 Hz, 3H)

Step 3: A mixture of 3-bromo-N-(2,4-dimethoxybenzyl)-5-(1-methoxyethyl)pyridin-2-amine (190 mg, 0.498 mmol) in DCM (1.5 ml) and TFA (1.5 mL) was stirred at 15° C. for 30 min. The mixture was basicified with $NH_3 \cdot H_2O$ to pH~10. The mixture was concentrated under reduced pressure to give 3-bromo-5-(1-methoxyethyl)pyridin-2-amine. MS: 231 and 233 (M+1).

Step 4: A mixture of 3-bromo-5-(1-methoxyethyl)pyridin-2-amine (2.0 g, 8.7 mmol) and ethyl 3-bromo-2-oxopropanoate (1.69 g, 8.65 mmol) in 1,4-dioxane (50 ml) was heated to 80° C. for 2 h. The mixture was concentrated under reduced pressure. The mixture was purified by prep-HPLC (TFA) to give ethyl 8-bromo-6-(1-methoxyethyl)imidazo[1,2-a]pyridine-2-carboxylate. MS: 327 and 329 (M+1). $^1$H NMR (400 MHz, $CDCl_3$) δ 8.23 (s, 1H), 8.08 (s, 1H), 7.56 (d, J=0.9 Hz, 1H), 4.44 (q, J=7.3 Hz, 2H), 4.31 (q, J=6.1 Hz, 1H), 3.31 (s, 3H), 1.48 (d, J=6.6 Hz, 3H), 1.41 (t, J=7.2 Hz, 3H).

Step 5: Ethyl 8-bromo-6-(1-methoxyethyl)imidazo[1,2-a] pyridine-2-carboxylate (80 mg, 0.25 mmol) was separated by SFC (DAICEL CHIRALPAK IC column, 0.1% $NH_3H_2O/EtOH/CO_2$) to give the ethyl (S or R)-8-bromo-6-(1-methoxyethyl)imidazo[1,2-a]pyridine-2-carboxylate and ethyl (R or S) 8-bromo-6-(I-methoxyethyl)imidazo[1,2-a] pyridine-2-carboxylate.

Step 6: A mixture of ethyl (S or R) 8-bromo-6-(1-methoxyethyl)imidazo[1,2-a]pyridine-2-carboxylate (30 mg, 0.092 mmol) and $LiOH \cdot H_2O$ (7.70 mg, 0.183 mmol) in EtOH (2 ml) and water (0.5 ml) was stirred at 25° C. for 1 h. The mixture was concentrated under reduced pressure to give (S or R) 8-bromo-6-(1-methoxyethyl)imidazo[1,2-a] pyridine-2-carboxylic acid. MS: 299 and 301 (M+1).

Intermediate 122: 6-bromo-8-(1-cyanocyclopropyl) imidazo[1,2-a]pyridine-2-carboxylic acid

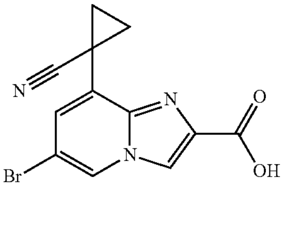 [SMILES: N#CC1(c2cc(Br)cn3cc(C(=O)O)nc23)CC1]

Step 1: A solution of BINAP (1.94 g, 3.12 mmol) and $Pd_2(dba)_3$ (1.19 g, 1.30 mmol) in THF (100 ml) was stirred for 20 mins under $N_2$. A solution of 3-bromo-2-chloropyridine (5.0 g, 26 mmol) and cyclopropanecarbonitrile (2.61 g, 39.0 mmol)) in THF (20 ml)) was added into the mixture. LiHMDS (1 M, 39.0 ml, 39.0 mmol) was then added into the resulting mixture. The reaction mixture was heated to 80° C. for 12 hours under $N_2$. The reaction mixture was poured into water (50 mL) and extracted with ethyl acetate (50 mL×3). The organic layers were washed with water (30 mL), dried over $Na_2SO_4$, filtered and concentrated, and the crude product was purified by Prep-TLC (silica gel, ethyl acetate/pet. ether=5/1, v/v) to give 1-(2-chloropyridin-3-yl)cyclopropanecarbonitrile. MS: 178 (M+1).

Step 2: A mixture of benzophenone imine (4.51 ml, 26.9 mmol), XantPhos (0.777 g, 1.34 mmol), $Pd_2(dba)_3$ (1.23 g, 1.34 mmol), $Cs_2CO_3$ (13.1 g, 40.3 mmol) and 1-(2-chloropyridin-3-yl)cyclopropanecarbonitrile (2.4 g, 13.4 mmol) in dioxane (10 ml) was degassed and backfilled with $N_2$ (3×). The mixture was heated to 90° C. for 4 h. After cooling to rt, the precipitate was filtered off, and the filtrate was concentrated to give 1-(2-((diphenylmethylene)amino)pyridin-3-yl)cyclopropanecarbonitrile. MS: 324 (M+1).

Step 3: A mixture of 1-(2-((diphenylmethylene)amino) pyridin-3-yl)cyclopropanecarbonitrile (4.0 g, 12 mmol) in HCl (1 N. 10 ml) was stirred at 15° C. for 1 h. Solvent was removed under reduced pressure, and purified by Prep-TLC (silica gel, ethyl acetate/MeOH=10/1, v/v) to give 1-(2-aminopyridin-3-yl)cyclopropanecarbonitrile. $^1$H NMR (400 MHz, $CDCl_3$) δ 7.78 (d, J=6.6 Hz, 1H), 6.88 (s, 1H), 6.38 (br d, J=7.1 Hz, 1H), 3.82 (s, 3H), 2.02-2.05 (m, 2H), 1.62-1.70 (m, 2H).

Step 4: To a solution of 1-(2-aminopyridin-3-yl)cyclopropanecarbonitrile (250 mg, 1.57 mmol) in THF (3 ml) was added NBS (84 mg, 0.47 mmol) and the mixture was stirred at 15° C. for 0.5 h. The mixture was purified by Prep-TLC (silica gel, ethyl acetate/pet. ether=2/1, v/v) to give 1-(2-amino-5-bromopyridin-3-yl)cyclopropanecarbonitrile. MS: 238 and 240 (M+1). $^1$H NMR (400 MHz, $CDCl_3$) δ 8.12 (s, 1H), 6.59 (s, 1H), 1.79-1.86 (m, 3H), 1.37 (s, 2H).

Step 5: A mixture of 1-(2-amino-5-bromopyridin-3-yl) cyclopropanecarbonitrile (80 mg, 0.34 mmol) and 3-bromo-2-oxopropanoic acid (112 mg, 0.672 mmol) in dioxane (2 ml) was heated to 80° C. for 2 h. The mixture was concentrated under reduced pressure to give 6-bromo-8-(1-cyanocyclopropyl)imidazo[1,2-a]pyridine-2-carboxylic acid. MS: 306 and 308 (M+1).

Intermediate 123: 6-cyclopropyl-7-hydroxyimidazo [1,2-a]pyrimidine-2-carboxylic acid

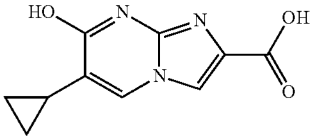 [SMILES: O=C(O)c1cn2cc(C3CC3)c(O)nc2n1]

Step 1: To a solution of 5-bromo-4-methoxypyrimidin-2-amine (2.0 g, 9.8 mmol) in THF (30 ml) and water (3 ml) were added $K_2CO_3$ (4.06 g, 29.4 mmol), cyclopropylboronic acid (4.21 g, 49.0 mmol), and [1,1'-bis(diphenylphosphino) ferrocene]dichloropalladium(II) (0.717 g, 0.980 mmol). The mixture was degassed and backfilled with $N_2$ (three times). The reaction was heated to 80° C. for 12 h. The mixture was concentrated and purified by flash silica gel chromatography (0-45% ethyl acetate/pet. ether) to 5-cyclopropyl-4-methoxypyrimidin-2-amine. MS: 166 (M+1).

Step 2: A solution of 5-cyclopropyl-4-methoxypyrimidin-2-amine (800 mg, 4.84 mmol) and ethyl 3-bromo-2-oxopropanoate (1133 mg, 5.81 mmol) in dioxane (10 ml) was heated to 85° C. for 4 h. The solvent was removed under reduced pressure to give ethyl 6-cyclopropyl-7-hydroxyimidazo[1,2-a]pyrimidine-2-carboxylate. MS: 248 (M+1).

Step 3: A solution of ethyl 6-cyclopropyl-7-hydroxyimidazo[1,2-a]pyrimidine-2-carboxylate (500 mg, 2.02 mmol) in HCl (12 N, 10 ml) was heated to 75° C. for 12 h. The solvent was removed under reduced pressure to give 6-cyclopropyl-7-hydroxyimidazo[1,2-a]pyrimidine-2-carboxylic acid. MS: 220 (M+1).

Examples

The following experimental procedures detail the preparation of specific examples of the instant disclosure. The examples are for illustrative purposes only and are not intended to limit the scope of the instant disclosure in any way.

Example 1: (6-bromoimidazo[1,2-a]pyridin-2-yl)((3R,3'R)-3'-hydroxy-1,4-dihydro-2H-spiro[isoquinoline-3,4'-piperidin]-1'-yl)methanone

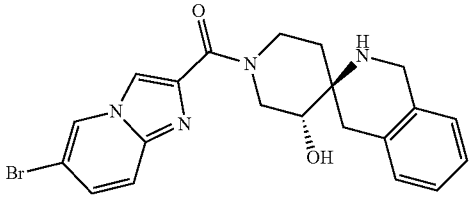 [SMILES: O=C(c1cn2cc(Br)ccc2n1)N1CC[C@]2(Cc3ccccc3CN2)[C@H](O)C1]

To a mixture of 6-bromoimidazo[1,2-a]pyridine-2-carboxylic acid (30 mg, 0.124 mmol) in DMF (2 mL) was added DIEA (0.065 mL, 0.373 mmol) and 2,4,6-tripropyl-1,3,5,2,4,6-trioxatriphosphinane 2,4,6-trioxide (82 mg, 0.128 mmol, 50% in DMF). The mixture was stirred at 13° C. for 5 min and (3R,3'R)-1,4-dihydro-2H-spiro[isoquinoline-3,4'-piperidin]-3'-ol (32.6 mg, 0.149 mmol) was added at 13° C. The resulting mixture was stirred at 13° C. for 1 h. The mixture was concentrated under reduced pressure. The residue was purified by preparative HPLC (C18 column, ACN/water with 10 mM $NH_4HCO_3$ modifier) to give (6-bromoimidazo[1,2-a]pyridin-2-yl)((3R,3'R)-3'-hydroxy-2,4-dihydro-1H-spiro[isoquinoline-3,4'-piperidin]-1'-yl)methanone. MS: 441 and 443 (M+1). $^1$H NMR (400 MHz, $CD_3OD$) δ 8.76 (s, 1H), 8.17-8.15 (m, 1H), 7.55-7.46 (m, 2H), 7.13-7.01 (m, 4H), 4.89-4.34 (m, 1H), 4.31-4.05 (m, 3H), 3.99-3.88 (m, 1H), 3.87-3.86 (m, 1H), 3.63-3.62 (m, 1H), 3.31-3.30 (m, 1H), 3.08-2.78 (m, 1H), 1.97-1.92 (m, 1H), 1.53-1.57 (m, 1H).

Example 2: 2-((3R,3'R)-3'-hydroxy-2,4-dihydro-1H-spiro[isoquinoline-3,4'-piperidin]-1'-ylcarbonyl)-N,N-dimethylimidazo[1,2-a]pyridine-6-carboxamide

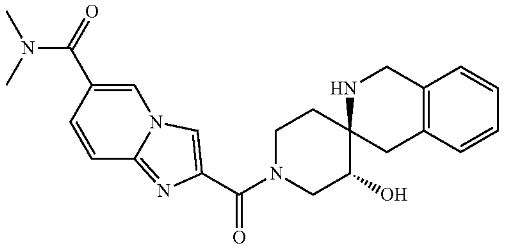 [SMILES: CN(C)C(=O)c1ccc2nc(C(=O)N3CC[C@]4(Cc5ccccc5CN4)[C@H](O)C3)cn2c1]

To a solution of 6-(dimethylcarbamoyl)imidazo[1,2-a]pyridine-2-carboxylic acid (25 mg, 0.107 mmol) in DMF (2 mL) was added DIEA (0.056 mL, 0.322 mmol), 1-propanephosphonic anhydride (142 mg, 0.214 mmol, 48% in DMF), and (3R,3'R)-1,4-dihydro-2H-spiro[isoquinoline-3,4'-piperidin]-3'-ol (25.7 mg, 0.118 mmol). The mixture was stirred at 20° C. for 1 h. The mixture was purified by preparative HPLC (C18 column, water/MeCN, 10 mM $NH_4HCO_3$) to give 2-((3R,3'R)-3'-hydroxy-2,4-dihydro-1H-spiro[isoquinoline-3,4'-piperidin]-1'-ylcarbonyl)-N,N-dimethylimidazo[1,2-a]pyridine-6-carboxamide. MS: 434 (M+1). H NMR (400 MHz, $CD_3Cl$) δ 8.27 (s, 1H), 8.03-8.0 (m, 1H), 7.46-7.49 (m, 1H), 7.25-7.23 (m, 1H), 7.08-6.95 (m, 4H), 4.40-4.37 (m, 2H), 3.98-3.93 (m, 2H), 3.84-3.80 (m, 1H), 3.53 (s, 1H), 3.20-3.14 (m, 1H), 3.028 (s, 6H), 2.89-2.84 (m, 1H), 2.71-2.67 (m, 1H), 1.97-1.89 (m, 1H), 1.52-1.49 (m, 1H).

Example 3: (6-chloroimidazo[1,2-a]pyrimidin-2-yl)((3R,3'R)-3'-hydroxy-1,4-dihydro-2H-spiro[isoquinoline-3,4'-piperidin]-1'-yl)methanone

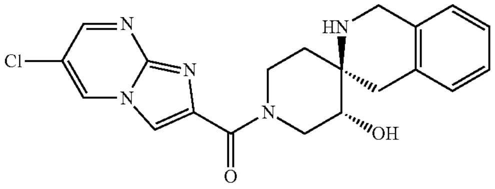 [SMILES: O=C(c1cn2cc(Cl)cnc2n1)N1CC[C@]2(Cc3ccccc3CN2)[C@H](O)C1]

6-chloroimidazo[1,2-a]pyrimidine-2-carboxylic acid HCl (168 mg, 0.718 mmol), (3R,3'R)-1,4-dihydro-2H-spiro[isoquinoline-3,4'-piperidin]-3'-ol 2HCl (230 mg, 0.790 mmol) were charged with DMF (2.4 mL), DIEA (501 μl, 2.87 mmol) followed by 1-propanephosphonic anhydride (641 μl, 1.08 mmol) and stirred overnight at room temperature. The reaction was concentrated in vacuo, loaded onto a silica column and purified 0-20% MeOH/DCM w/1% $NH_3$ followed by re-purification 5-20% MeOH/DCM w/ 1% NH3 to provide (6-chloroimidazo[1,2-a]pyrimidin-2-yl)(3'-hydroxy-2,4-dihydro-1H-spiro[isoquinoline-3,4'-piperidin]-1'-yl)methanone. MS: 398 (M+1). 1H NMR (600 MHz, $CDCl_3$) δ 8.53 (s, 2H), 8.04 (s, 1H) 7.21-7.08 (m, 3H), 7.05-7.01 (m, 1H), 4.56 (d, J=13.9 Hz, 1H), 4.37 (d, J=12.5 Hz, 1H), 4.07-3.95 (m, 3H), 3.63 (s, 1H), 3.37-3.27 (m, 1H), 2.93 (d, J=16.5 Hz, 1H), 2.76 (d, J=16.5 Hz, 1H), 2.03-1.93 (m, 1H), 1.59 (d, J=14.3 Hz, 1H).

TABLE 14

The following examples were made following a protocol similar to examples above.

| Ex | Structure | Compound Name | Exact Mass [M + 1] |
|---|---|---|---|
| 4 | 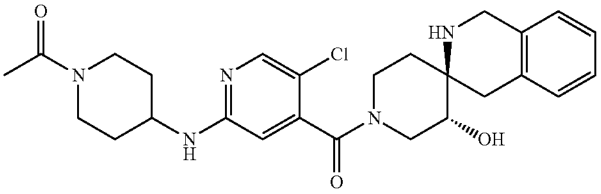 [SMILES: CC(=O)N1CCC(Nc2cc(C(=O)N3CC[C@]4(Cc5ccccc5CN4)[C@H](O)C3)c(Cl)cn2)CC1] | 11-(4-((5-chloro-4-((3R,3'R)-3'-hydroxy-1,4-dihydro-2H-spiro[isoquinoline-3,4'-piperidine]-1'-carbonyl)pyridin-2-yl)amino)piperidin-1-yl)ethan-1-one | 498 |
| 5 | 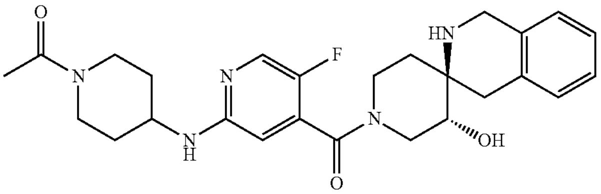 [SMILES: CC(=O)N1CCC(Nc2cc(C(=O)N3CC[C@]4(Cc5ccccc5CN4)[C@H](O)C3)c(F)cn2)CC1] | 1-(4-((5-fluoro-4-((3R,3'R)-3'-hydroxy-1,4-dihydro-2H-spiro[isoquinoline-3,4'-piperidine]-1'-carbonyl)pyridin-2-yl)amino)piperidin-1-yl)ethan-1-one | 482 |
| 6 | 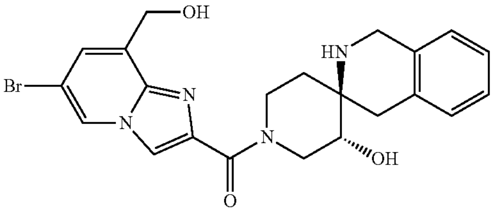 [SMILES: O=C(c1cn2cc(Br)cc(CO)c2n1)N1CC[C@]2(Cc3ccccc3CN2)[C@H](O)C1] | (6-bromo-8-(hydroxymethyl)imidazo[1,2-a]pyridin-2-yl)((3R,3'R)-3'-hydroxy-1,4-dihydro-2H-spiro[isoquinoline-3,4'-piperidin]-1'-yl)methanone | 471 and 473 |
| 7 | 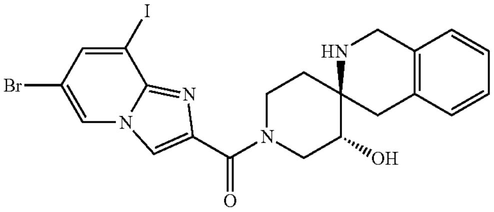 [SMILES: O=C(c1cn2cc(Br)cc(I)c2n1)N1CC[C@]2(Cc3ccccc3CN2)[C@H](O)C1] | (6-bromo-8-iodoimidazo[1,2-a]pyridin-2-yl)(3R,3'R)-3'-hydroxy-1,4-dihydro-1'H,2H-spiro[isoquinoline-3,4'-piperidin]-1'-yl)methanone | 567 and 569 |
| 8 | 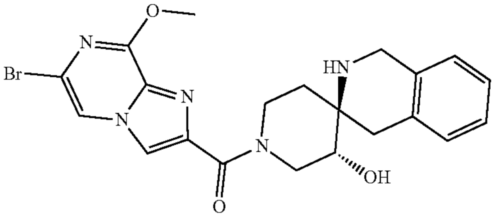 [SMILES: COc1nc(Br)cn2cc(C(=O)N3CC[C@]4(Cc5ccccc5CN4)[C@H](O)C3)nc12] | (6-bromo-8-methoxyimidazo[1,2-a]pyrazin-2-yl)(3R,3'R)-3'-hydroxy-1,4-dihydro-1'H,2H-spiro[isoquinoline-3,4'-piperidin]-1'-yl)methanone | 472 and 474 |
| 9 | 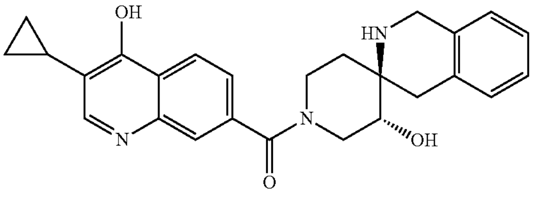 [SMILES: O=C(c1ccc2c(O)c(C3CC3)cnc2c1)N1CC[C@]2(Cc3ccccc3CN2)[C@H](O)C1] | (3-cyclopropyl-4-hydroxyquinolin-7-yl)((3R,3'R)-3'-hydroxy-1,4-dihydro-1'H,2H-spiro[isoquinoline-3,4'-piperidin]-1'-yl)methanone | 430 |
| 10 | 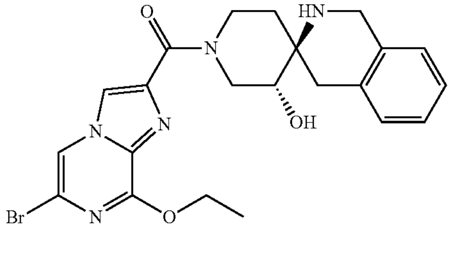 [SMILES: CCOc1nc(Br)cn2cc(C(=O)N3CC[C@]4(Cc5ccccc5CN4)[C@H](O)C3)nc12] | (6-bromo-8-ethoxyimidazo[1,2-a]pyrazin-2-yl)(3R,3'R)-3'-hydroxy-1,4-dihydro-1'H,2H-spiro[isoquinoline-3,4'-piperidin]-1'-yl)methanone | 486 and 488 |

TABLE 14-continued

The following examples were made following a protocol similar to examples above.

| Ex | Structure | Compound Name | Exact Mass [M + 1] |
|---|---|---|---|
| 11 | 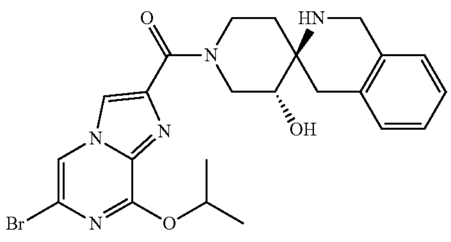 [SMILES: CC(C)Oc1nc(Br)cn2cc(C(=O)N3CC[C@]4(Cc5ccccc5CN4)[C@H](O)C3)nc12] | {6-bromo-8-[(propan-2-yl)oxy]imidazo[1,2-a]pyrazin-2-yl}((3R,3'R)-3'-hydroxy-1,4-dihydro-1'H,2H-spiro[isoquinoline-3,4'-piperidin]-1'-yl)methanone | 500 and 502 |
| 12 | 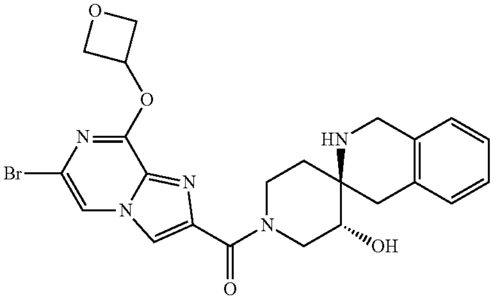 [SMILES: O=C(c1cn2cc(Br)nc(OC3COC3)c2n1)N1CC[C@]2(Cc3ccccc3CN2)[C@H](O)C1] | (6-bromo-8-(oxetan-3-yloxy)imidazo[1,2-a]pyrazin-2-yl)((3R,3'R)-3'-hydroxy-1,4-dihydro-2H-spiro[isoquinoline-3,4'-piperidin]-1'-yl)methanone | 514 and 516 |
| 13 | 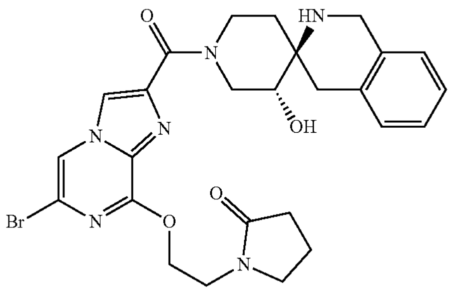 [SMILES: O=C1CCCN1CCOc1nc(Br)cn2cc(C(=O)N3CC[C@]4(Cc5ccccc5CN4)[C@H](O)C3)nc12] | 1-(2-((6-bromo-2-((3R,3'R)-3'-hydroxy-1,4-dihydro-2H-spiro[isoquinoline-3,4'-piperidine]-1'-carbonyl)imidazo[1,2-a]pyrazin-8-yl)oxy)ethyl)pyrrolidin-2-one | 569 and 571 |
| 14 | 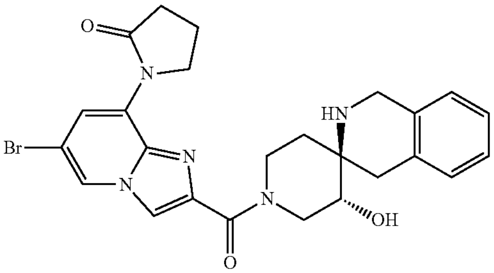 [SMILES: O=C(c1cn2cc(Br)cc(N3CCCC3=O)c2n1)N1CC[C@]2(Cc3ccccc3CN2)[C@H](O)C1] | 1-(6-bromo-2-((3R3'R)-3'-hydroxy-1,4-dihydro-2H-spiro[isoquinoline-3,4'-piperidine]-1'-carbonyl)imidazo[1,2-a]pyridin-8-yl)pyrrolidin-2-one | 524 and 526 |
| 16 | 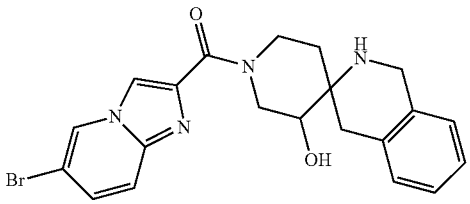 [SMILES: O=C(c1cn2cc(Br)ccc2n1)N1CCC2(Cc3ccccc3CN2)C(O)C1] | A diastereomer of (6-bromoimidazo[1,2-a]pyridin-2-yl)(3'-hydroxy-1,4-dihydro-1'H,2H-spiro[isoquinoline-3,4'-piperidin]-1'-yl)methanone | 441 and 443 |

TABLE 14-continued

The following examples were made following a protocol similar to examples above.

| Ex | Structure | Compound Name | Exact Mass [M + 1] |
|---|---|---|---|
| 17 | 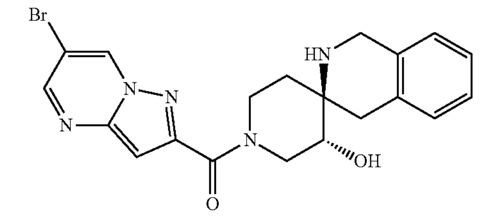 [SMILES: O=C(c1cc2ncc(Br)cn2n1)N1CC[C@]2(Cc3ccccc3CN2)[C@H](O)C1] | (6-bromopyrazolo[1,5-a]pyrimidin-2-yl)((3R,3'R)-3'-hydroxy-1,4-dihydro-1'H,2H-spiro[isoquinoline-3,4'-piperidin]-1'-yl)methanone | 442 and 444 |
| 18 | 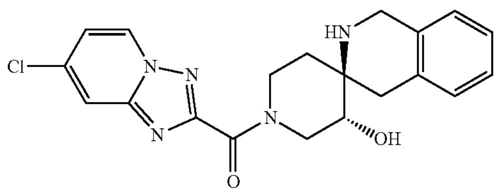 [SMILES: O=C(c1nc2cc(Cl)ccn2n1)N1CC[C@]2(Cc3ccccc3CN2)[C@H](O)C1] | (7-chloro[1,2,4]triazolo[1,5-a]pyridin-2-yl)(3R,3'R)-3'-hydroxy-1,4-dihydro-1'H,2H-spiro[isoquinoline-3,4'-piperidin]-1'-yl)methanone | 398 |
| 19 | 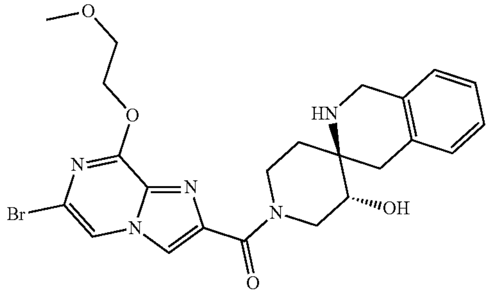 [SMILES: COCCOc1nc(Br)cn2cc(C(=O)N3CC[C@]4(Cc5ccccc5CN4)[C@H](O)C3)nc12] | (6-bromo-8-(2-methoxyethoxy)imidazo[1,2-a]pyrazin-2-yl)((3R,3'R)-3'-hydroxy-1,4-dihydro-2H-spiro[isoquinoline-3,4'-piperidin]-1'-yl)methanone | 516 and 518 |
| 20 | 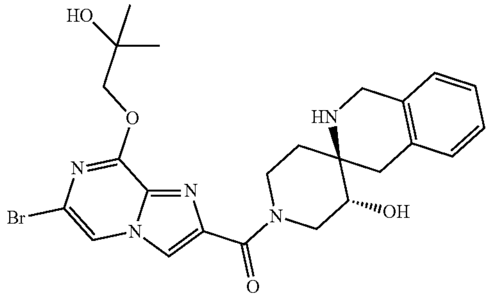 [SMILES: CC(C)(O)COc1nc(Br)cn2cc(C(=O)N3CC[C@]4(Cc5ccccc5CN4)[C@H](O)C3)nc12] | (6-bromo-8-(2-hydroxy-2-methylpropoxy)imidazo[1,2-a]pyrazin-2-yl)((3R,3'R)-3'-hydroxy-1,4-dihydro-2H-spiro[isoquinoline-3,4'-piperidin]-1'-yl)methanone | 530 and 532 |
| 21 | 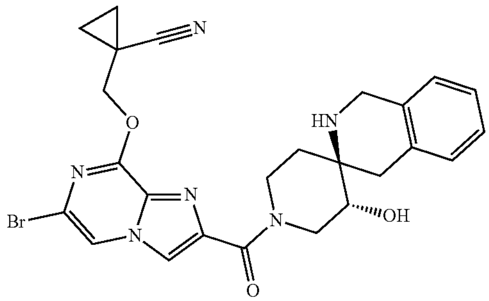 [SMILES: N#CC1(COc2nc(Br)cn3cc(C(=O)N4CC[C@]5(Cc6ccccc6CN5)[C@H](O)C4)nc23)CC1] | 1-(((6-bromo-2-((3R,3'R)-3'-hydroxy-1,4-dihydro-2H-spiro[isoquinoline-3,4'-piperidine]-1'-carbonyl)imidazo[1,2-a]pyrazin-8-yl)oxy)methyl)cyclopropane-1-carbonitrile | 537 and 539 |
| 22 | 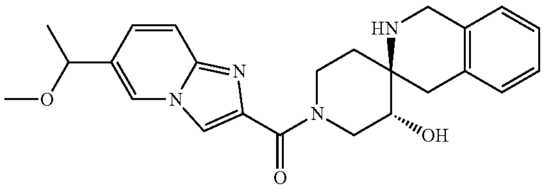 [SMILES: COC(C)c1ccc2nc(C(=O)N3CC[C@]4(Cc5ccccc5CN4)[C@H](O)C3)cn2c1] | ((3R,3'R)-3'-hydroxy-1,4-dihydro-2H-spiro[isoquinoline-3,4'-piperidin]-1'-yl)(6-((S or R)-1-methoxyethyl)imidazo[1,2-a]pyridin-2-yl)methanone | 421 |

TABLE 14-continued

The following examples were made following a protocol similar to examples above.

| Ex | Structure | Compound Name | Exact Mass [M + 1] |
|---|---|---|---|
| 23 | 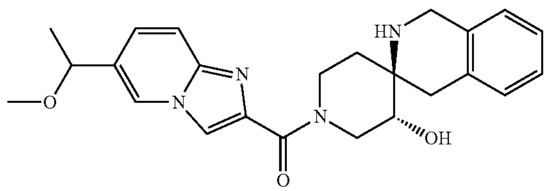 [SMILES: COC(C)c1ccc2nc(C(=O)N3CC[C@]4(Cc5ccccc5CN4)[C@H](O)C3)cn2c1] | ((3R,3'R)-3'-hydroxy-1,4-dihydro-2H-spiro[isoquinoline-3,4'-piperidin]-1-yl)(6-((R or S)-1-methoxyethyl)imidazo[1,2-a]pyridin-2-yl)methanone | 421 |
| 24 | 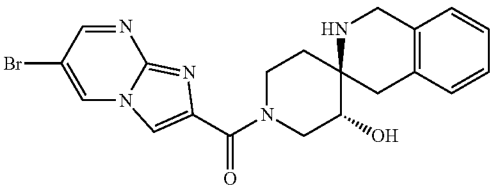 | (6-bromoimidazo[1,2-a]pyrimidin-2-yl)((3R,3'RR)-3'-hydroxy-1,4-dihydro-1'H,2H-spiro[isoquinoline-3,4'-piperidin]-1'-yl)methanone | 442 and 444 |
| 25 | 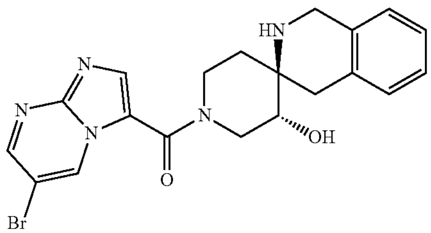 | (6-bromoimidazo[1,2-a]pyrimidin-3-yl)((3R,3'R)-3'-hydroxy-1,4-dihydro-1'H,2H-spiro[isoquinoline-3,4'-piperidin]-1'-yl)methanone | 442 and 444 |
| 26 | 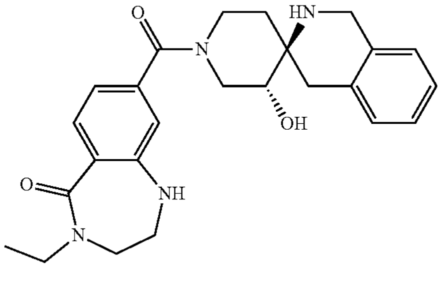 [SMILES: CCN1CCNc2cc(C(=O)N3CC[C@]4(Cc5ccccc5CN4)[C@H](O)C3)ccc2C1=O] | 4-ethyl-8-((3R,3'R)-3'-hydroxy-1,4-dihydro-1'H,2H-spiro[isoquinoline-3,4'-piperidine]-1'-carbonyl)-1,2,3,4-tetrahydro-5H-1,4-benzodiazepin-5-one | 435 |
| 27 | 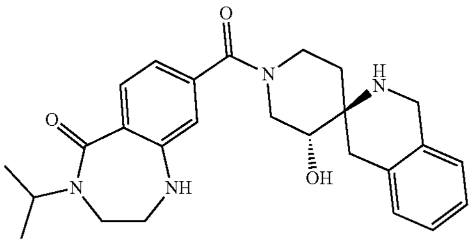 [SMILES: CC(C)N1CCNc2cc(C(=O)N3CC[C@]4(Cc5ccccc5CN4)[C@H](O)C3)ccc2C1=O] | 8-((3R,3'R)-3'-hydroxy-1,4-dihydro-1'H,2H-spiro[isoquinoline-3,4'-piperidine]-1'-carbonyl)-4-(propan-2-yl)-1,2,3,4-tetrahydro-5H-1,4-benzodiazepin-5-one | 449 |
| 28 | 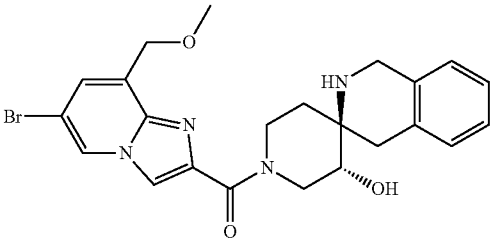 [SMILES: COCc1cc(Br)cn2cc(C(=O)N3CC[C@]4(Cc5ccccc5CN4)[C@H](O)C3)nc12] | (6-bromo-8-(methoxymethyl)imidazo[1,2-a]pyridin-2-yl)((3R,3'R)-3'-hydroxy-1,4-dihydro-2H-spiro[isoquinoline-3,4'-piperidin]-1'-yl)methanone | 485 and 487 |

TABLE 14-continued

| Ex | Structure | Compound Name | Exact Mass [M + 1] |
|---|---|---|---|
| | The following examples were made following a protocol similar to examples above. | | |
| 29 | 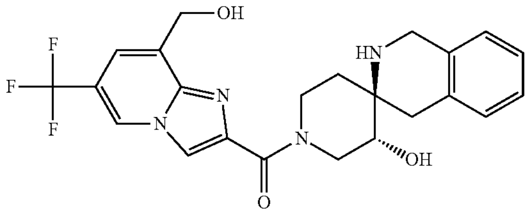 [SMILES: O=C(c1cn2cc(C(F)(F)F)cc(CO)c2n1)N1CC[C@]2(Cc3ccccc3CN2)[C@H](O)C1] | ((3R,3'R)-3'-hydroxy-1,4-dihydro-1'H,2H-spiro[isoquinoline-3,4'-piperidin]-1'-yl)[8-(hydroxymethyl)-6-(trifluoromethyl)imidazo[1,2-a]pyridin-2-yl]methanone | 461 |
| 30 | 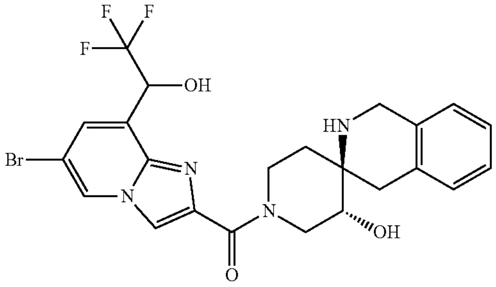 [SMILES: O=C(c1cn2cc(Br)cc(C(O)C(F)(F)F)c2n1)N1CC[C@]2(Cc3ccccc3CN2)[C@H](O)C1] | (6-bromo-8-((R or S)-2,2,2-trifluoro-1-hydroxyethyl)imidazo[1,2-a]pyridin-2-yl)((3R,3'R)-3'-hydroxy-1,4-dihydro-2H-spiro[isoquinoline-3,4'-piperidin]-1'-yl)methanone | 539 and 541 |
| 31 | 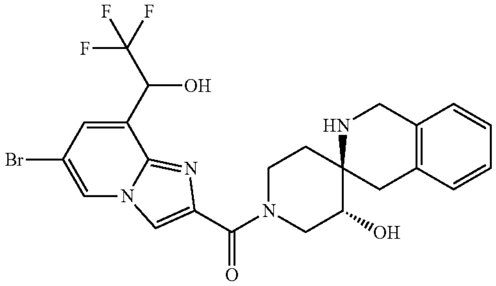 [SMILES: O=C(c1cn2cc(Br)cc(C(O)C(F)(F)F)c2n1)N1CC[C@]2(Cc3ccccc3CN2)[C@H](O)C1] | (6-bromo-8-((S or R)-2,2,2-trifluoro-1-hydroxyethyl)imidazo[1,2-a]pyridin-2-yl)((3R,3'R)-3'-hydroxy-1,4-dihydro-2H-spiro[isoquinoline-3,4'-piperidin]-1'-yl)methanone | 539 and 541 |
| 32 | 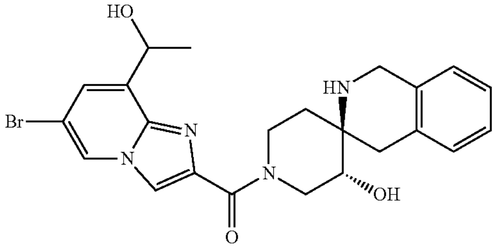 | (6-bromo-8-((R or S)-1-hydroxyethyl)imidazo[1,2-a]pyridin-2-yl)((3R,3'R)-3'-hydroxy-1,4-dihydro-2H-spiro[isoquinoline-3,4'-piperidin]-1'-yl)methanone | 485 and 487 |
| 33 | 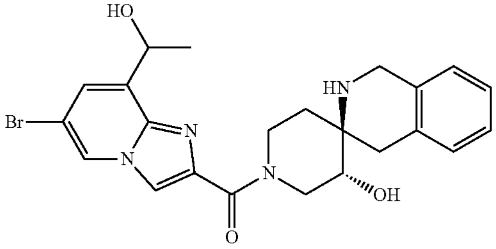 [SMILES: CC(O)c1cc(Br)cn2cc(C(=O)N3CC[C@]4(Cc5ccccc5CN4)[C@H](O)C3)nc12] | (6-bromo-8-((S or R)-1-hydroxyethyl)imidazo[1,2-a]pyridin-2-yl)((3R,3'R)-3'-hydroxy-1,4-dihydro-2H-spiro[isoquinoline-3,4'-piperidin]-1'-yl)methanone | 485 and 487 |

TABLE 14-continued

The following examples were made following a protocol similar to examples above.

| Ex | Structure | Compound Name | Exact Mass [M + 1] |
|---|---|---|---|
| 34 | 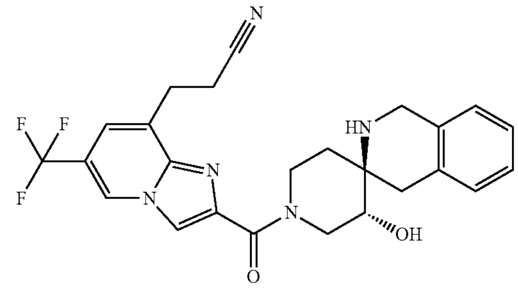 [SMILES: N#CCCc1cc(C(F)(F)F)cn2cc(C(=O)N3CC[C@]4(Cc5ccccc5CN4)[C@H](O)C3)nc12] | 3-(2-((3R,3'R)-3'-hydroxy-1,4-dihydro-2H-spiro[isoquinoline-3,4'-piperidine]-1'-carbonyl)-6-(trifluoromethyl)imidazo[1,2-a]pyridin-8-yl)propanenitrile | 484 |
| 35 | 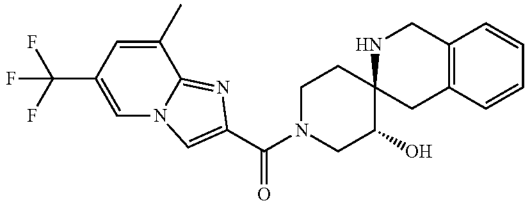 [SMILES: Cc1cc(C(F)(F)F)cn2cc(C(=O)N3CC[C@]4(Cc5ccccc5CN4)[C@H](O)C3)nc12] | ((3R,3'R)-3'-hydroxy-1,4-dihydro-2H-spiro[isoquinoline-3,4'-piperidin]-1'-yl)(8-methyl-6-(trifluoromethyl)imidazo[1,2-a]pyridin-2-yl)methanone | 445 |
| 36 | 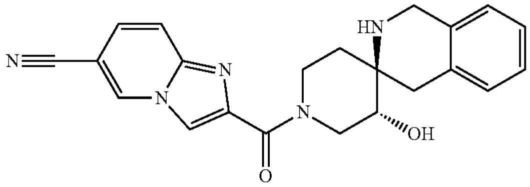 [SMILES: N#Cc1ccc2nc(C(=O)N3CC[C@]4(Cc5ccccc5CN4)[C@H](O)C3)cn2c1] | 2-((3R,3'R)-3'-hydroxy-1,4-dihydro-2H-spiro[isoquinoline-3,4'-piperidine]-1'-carbonyl)imidazo[1,2-a]pyridine-6-carbonitrile | 388 |
| 37 | 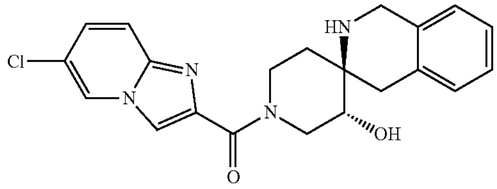 [SMILES: O=C(c1cn2cc(Cl)ccc2n1)N1CC[C@]2(Cc3ccccc3CN2)[C@H](O)C1] | (6-chloroimidazo[1,2-a]pyridin-2-yl)((3R,3'R)-3'-hydroxy-1,4-dihydro-2H-spiro[isoquinoline-3,4'-piperidin]-1'-yl)methanone | 397 |
| 38 | 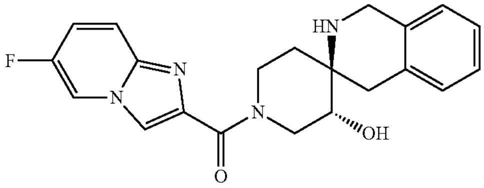 [SMILES: O=C(c1cn2cc(F)ccc2n1)N1CC[C@]2(Cc3ccccc3CN2)[C@H](O)C1] | (6-fluoroimidazo[1,2-a]pyridin-2-yl)((3R,3'R)-3'-hydroxy-1,4-dihydro-2H-spiro[isoquinoline-3,4'-piperidin]-1'-yl)methanone | 381 |
| 39 | 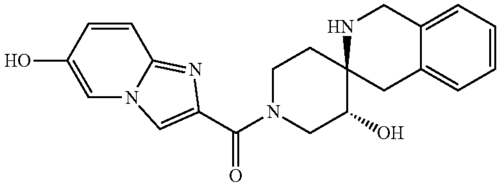 [SMILES: O=C(c1cn2cc(O)ccc2n1)N1CC[C@]2(Cc3ccccc3CN2)[C@H](O)C1] | ((3R,3'R)-3'-hydroxy-1,4-dihydro-2H-spiro[isoquinoline-3,4'-piperidin]-1'-yl)(6-hydroxyimidazo[1,2-a]pyridin-2-yl)methanone | 379 |
| 40 | 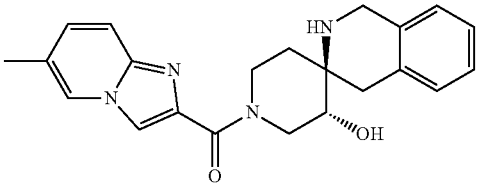 [SMILES: Cc1ccc2nc(C(=O)N3CC[C@]4(Cc5ccccc5CN4)[C@H](O)C3)cn2c1] | ((3R,3'R)-3'-hydroxy-1,4-dihydro-2H-spiro[isoquinoline-3,4'-piperidin]-1'-yl)(6-methylimidazo[2,2-a]pyridin-2-yl)methanone | 377 |

TABLE 14-continued

The following examples were made following a protocol similar to examples above.

| Ex | Structure | Compound Name | Exact Mass [M + 1] |
|---|---|---|---|
| 41 | 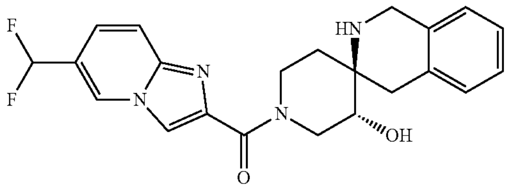 [SMILES: O=C(c1cn2cc(C(F)F)ccc2n1)N1CC[C@]2(Cc3ccccc3CN2)[C@H](O)C1] | (6-(difluoromethyl)imidazo[1,2-a]pyridin-2-yl)((3R,3'R)-3'-hydroxy-1,4-dihydro-2H-spiro[isoquinoline-3,4'-piperidin]-1'-yl)methanone | 413 |
| 42 | 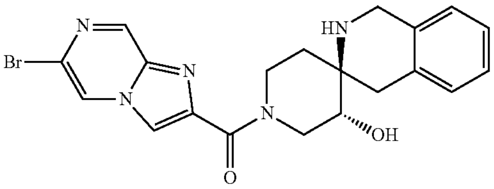 | (6-bromoimidazo[1,2-a]pyrazin-2-yl)((3R,3'R)-3'-hydroxy-1,4-dihydro-2H-spiro[isoquinoline-3,4'-piperidin]-1'-yl)methanone | 442 and 444 |
| 43 | 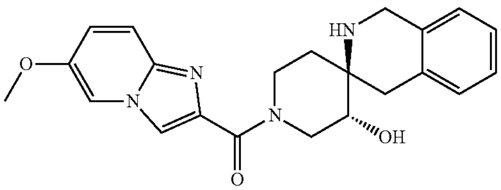 [SMILES: COc1ccc2nc(C(=O)N3CC[C@]4(Cc5ccccc5CN4)[C@H](O)C3)cn2c1] | ((3R,3'R)-3'-hydroxy-1,4-dihydro-2H-spiro[isoquinoline-3,4'-piperidin]-1'-yl)(6-methoxyimidazo[1,2-a]pyridin-2-yl)methanone | 393 |
| 44 | 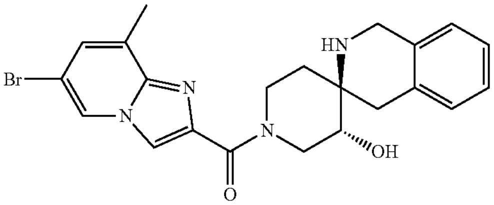 | (6-bromo-8-methylimidazo[1,2-a]pyridin-2-yl)((3R,3'R)-3'-hydroxy-1,4-dihydro-2H-spiro[isoquinoline-3,4'-piperidin]-1'-yl)methanone | 455 and 457 |
| 45 | 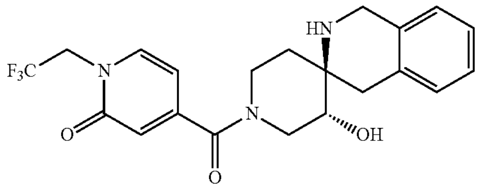 [SMILES: O=C(c1ccn(CC(F)(F)F)c(=O)c1)N1CC[C@]2(Cc3ccccc3CN2)[C@H](O)C1] | 4-((3R,3'R)-3'-hydroxy-1,4-dihydro-2H-spiro[isoquinoline-3,4'-piperidine]-1'-carbonyl)-1-(2,2,2-trifluoroethyl)pyridin-2(1H)-one | 422 |
| 46 | 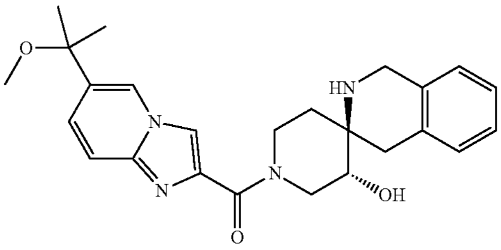 [SMILES: COC(C)(C)c1ccc2nc(C(=O)N3CC[C@]4(Cc5ccccc5CN4)[C@H](O)C3)cn2c1] | (3'-hydroxy-2,4-dihydro-1H-spiro[isoquinoline-3,4'-piperidin]-1'-yl)(6-(2-methoxypropan-2-yl)imidazo[1,2-a]pyridin-2-yl)methanone | 435 |
| 47 | 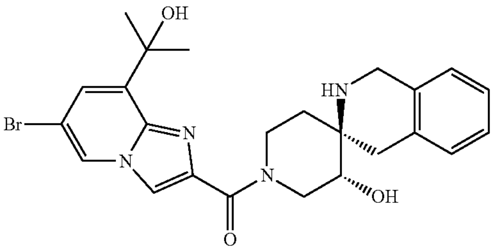 [SMILES: CC(C)(O)c1cc(Br)cn2cc(C(=O)N3CC[C@]4(Cc5ccccc5CN4)[C@H](O)C3)nc12] | (6-bromo-8-(2-hydroxypropan-2-yl)imidazo[1,2-a]pyridin-2-yl)((3R,3'R)-3'-hydroxy-1,4-dihydro-2H-spiro[isoquinoline-3,4'-piperidin]-1'-yl)methanone | 499 and 501 |

TABLE 14-continued

| Ex | Structure | Compound Name | Exact Mass [M + 1] |
|---|---|---|---|
| The following examples were made following a protocol similar to examples above. | | | |
| 48 | 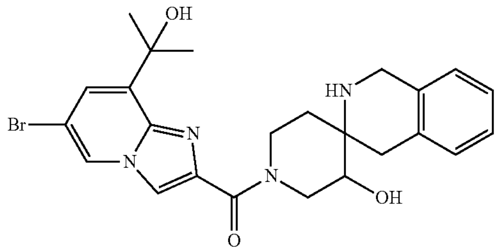 [SMILES: CC(C)(O)c1cc(Br)cn2cc(C(=O)N3CCC4(Cc5ccccc5CN4)C(O)C3)nc12] | A diastereomer of [6-bromo-8-(2-hydroxy-2-propanyl)imidazo[1,2-a]pyridin-2-yl](3'-hydroxy-1,4-dihydro-1'H,2H-spiro[isoquinoline-3,4'-piperidin]-1'-yl)methanone | 499 and 501 |
| 49 | 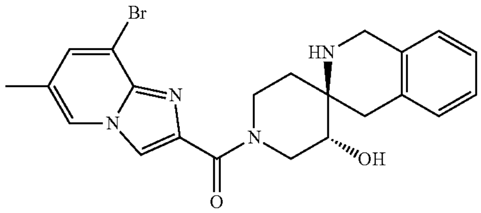 [SMILES: Cc1cc(Br)c2nc(C(=O)N3CC[C@]4(Cc5ccccc5CN4)[C@H](O)C3)cn2c1] | (8-bromo-6-methylimidazo[1,2-a]pyridin-2-yl)((3R,3'R)-3'-hydroxy-1,4-dihydro-2H-spiro[isoquinoline-3,4'-piperidin]-1'-yl)methanone | 455 and 457 |
| 50 | 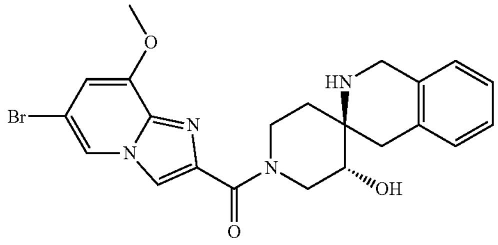 [SMILES: COc1cc(Br)cn2cc(C(=O)N3CC[C@]4(Cc5ccccc5CN4)[C@H](O)C3)nc12] | (6-bromo-8-methoxyimidazo[1,2-a]pyridin-2-yl)((3R,3'R)-3'-hydroxy-1,4-dihydro-2H-spiro[isoquinoline-3,4'-piperidin]-1'-yl)methanone | 471 and 473 |
| 51 | 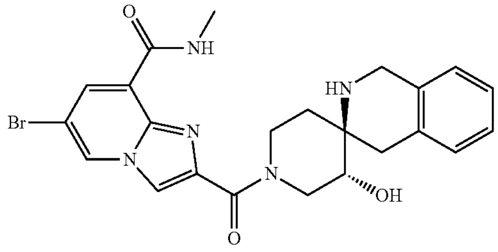 [SMILES: CNC(=O)c1cc(Br)cn2cc(C(=O)N3CC[C@]4(Cc5ccccc5CN4)[C@H](O)C3)nc12] | 6-bromo-2-((3R,3'R)-3'-hydroxy-1,4-dihydro-2H-spiro[isoquinoline-3,4'-piperidine]-1'-carbonyl)-N-methylimidazo[1,2-a]pyridine-8-carboxamide | 498 and 500 |
| 52 | 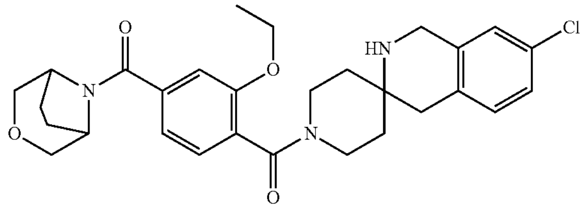 [SMILES: CCOc1cc(C(=O)N2C3CCC2COC3)ccc1C(=O)N1CCC2(CC1)Cc1ccc(Cl)cc1CN2] | [4-(7-chloro-1,4-dihydro-1H,2H-spiro[isoquinoline-3,4'-piperidine]-1'-carbonyl)-3-ethoxyphenyl](3-oxa-8-azabicyclo[3.2.1]octan-8-yl)methanone | 524 |
| 53 | 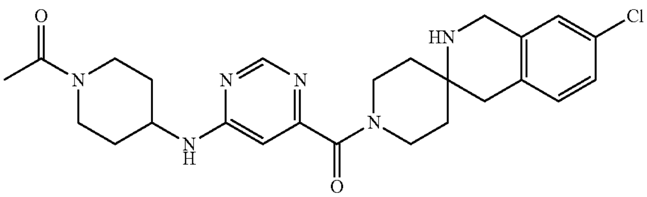 [SMILES: CC(=O)N1CCC(Nc2cc(C(=O)N3CCC4(CC3)Cc3ccc(Cl)cc3CN4)ncn2)CC1] | 1-(4-{[6-(7-chloro-1,4-dihydro-1'H,2H-spiro[isoquinoline-3,4'-piperidine]-1'-carbonyl)pyrimidin-4-yl]amino}piperidin-1-yl)ethan-1-one | 483 |

TABLE 14-continued

| Ex | Structure | Compound Name | Exact Mass [M + 1] |
|---|---|---|---|
| The following examples were made following a protocol similar to examples above. | | | |
| 54 | 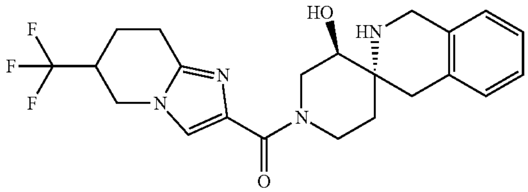 [SMILES: O=C(c1cn2c(n1)CCC(C(F)(F)F)C2)N1CC[C@]2(Cc3ccccc3CN2)[C@H](O)C1] | [(3R,3'R)-3'-hydroxy-1,4-dihydro-1'H,2H-spiro[isoquinoline-3,4'-piperidin]-1'-yl][6-(trifluoromethyl)-5,6,7,8-tetrahydroimidazo[1,2-a]pyridin-2-yl]methanone | 435 |
| 55 | 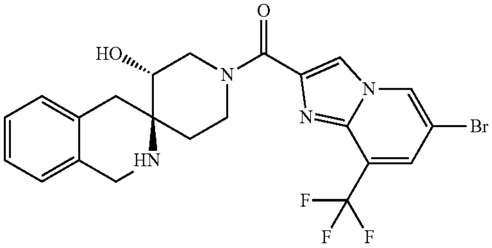 [SMILES: O=C(c1cn2cc(Br)cc(C(F)(F)F)c2n1)N1CC[C@]2(Cc3ccccc3CN2)[C@H](O)C1] | [6-bromo-8-(trifluoromethyl)imidazo[1,2-a]pyridin-2-yl][(3R,3'R)-3'-hydroxy-1,4-dihydro-1'H,2H-spiro[isoquinoline-3,4'-piperidin]-1'-yl]methanone | 509 and 511 |
| 56 | 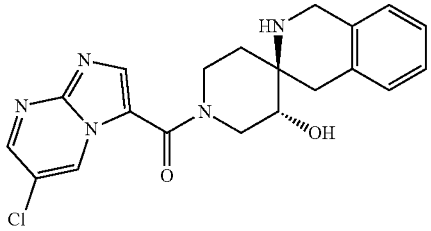 [SMILES: O=C(c1cnc2ncc(Cl)cn12)N1CC[C@]2(Cc3ccccc3CN2)[C@H](O)C1] | (6-chloroimidazo[1,2-a]pyrimidin-3-yl)[(3R,3'R)-3'-hydroxy-1,4-dihydro-1'H,2H-spiro[isoquinoline-3,4'-piperidin]-1'-yl]methanone | 398 |
| 57 | 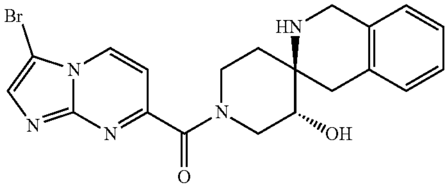 [SMILES: O=C(c1ccn2c(Br)cnc2n1)N1CC[C@]2(Cc3ccccc3CN2)[C@H](O)C1] | (3-bromoimidazo[1,2-a]pyrimidin-7-yl)[(3R,3'R)-3'-hydroxy-1,4-dihydro-1'H,2H-spiro[isoquinoline-3,4'-piperidin]-1'-yl]methanone | 442 and 444 |
| 58 | 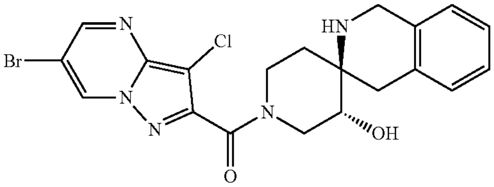 [SMILES: O=C(c1nn2cc(Br)cnc2c1Cl)N1CC[C@]2(Cc3ccccc3CN2)[C@H](O)C1] | (6-bromo-3-chloropyrazolo[1,5-a]pyrimidin-2-yl)[(3R,3'R)-3'-hydroxy-1,4-dihydro-1'H,2H-spiro[isoquinoline-3,4'-piperidin]-1'-yl]methanone | 476 and 478 |
| 59 | 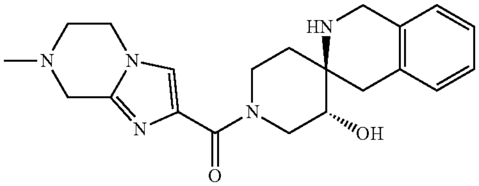 [SMILES: CN1CCn2cc(C(=O)N3CC[C@]4(Cc5ccccc5CN4)[C@H](O)C3)nc2C1] | [(3R,3'R)-3'-hydroxy-1,4-dihydro-1'H,2H-spiro[isoquinoline-3,4'-piperidin]-1'-yl](7-methyl-5,6,7,8-tetrahydroimidazo[1,2-a]pyrazin-2-yl)methanone | 382 |
| 60 | 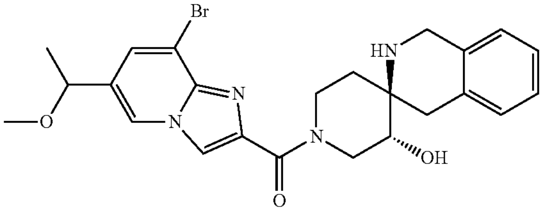 [SMILES: COC(C)c1cc(Br)c2nc(C(=O)N3CC[C@]4(Cc5ccccc5CN4)[C@H](O)C3)cn2c1] | A diastereomer of [8-bromo-6-(1-methoxyethyl)imidazo[1,2-a]pyridin-2-yl][(3R,3'R)-3'-hydroxy-1,4-dihydro-1'H,2H-spiro[isoquinoline-3,4'-piperidin]-1'-yl]methanone | 499 and 501 |

TABLE 14-continued

| The following examples were made following a protocol similar to examples above. | | | |
|---|---|---|---|
| Ex | Structure | Compound Name | Exact Mass [M + 1] |
| 61 | 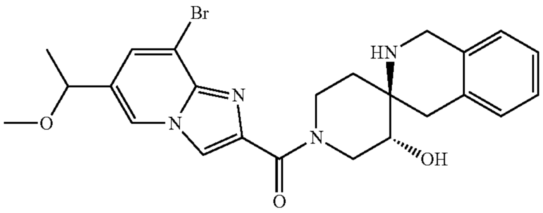 [SMILES: COC(C)c1cc(Br)c2nc(C(=O)N3CC[C@]4(Cc5ccccc5CN4)[C@H](O)C3)cn2c1] | A diastereomer of [8-bromo-6-(1-methoxyethyl)imidazo[1,2-a]pyridin-2-yl][(3R,3'R)-3'-hydroxy-1,4-dihydro-1'H,2H-spiro[isoquinoline-3,4'-piperidin]-1'-yl]methanone | 499 and 501 |
| 62 | 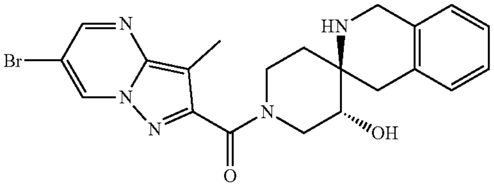 [SMILES: Cc1c(C(=O)N2CC[C@]3(Cc4ccccc4CN3)[C@H](O)C2)nn2cc(Br)cnc12] | (6-bromo-3-methylpyrazolo[1,5-a]pyrimidin-2-yl)[(3R,3'R)-3'-hydroxy-1,4-dihydro-1'H,2H-spiro[isoquinoline-3,4'-piperidin]-1'-yl]methanone | 456 and 458 |
| 63 | 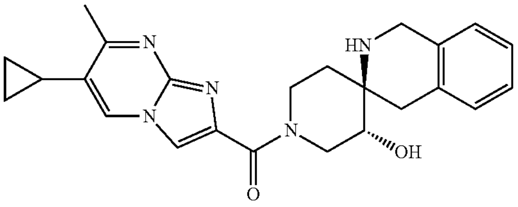 [SMILES: Cc1nc2nc(C(=O)N3CC[C@]4(Cc5ccccc5CN4)[C@H](O)C3)cn2cc1C1CC1] | (6-cyclopropyl-7-methylimidazo[1,2-a]pyrimidin-2-yl)[(3R,3'R)-3'-hydroxy-1,4-dihydro-1'H,2H-spiro[isoquinoline-3,4'-piperidin]-1'-yl]methanone | 418 |
| 64 | 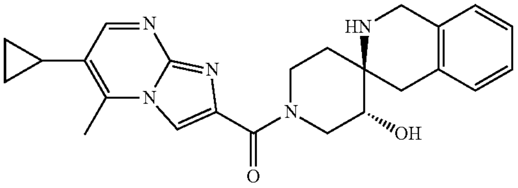 [SMILES: Cc1c(C2CC2)cnc2nc(C(=O)N3CC[C@]4(Cc5ccccc5CN4)[C@H](O)C3)cn12] | (6-cyclopropyl-5-methylimidazo[1,2-a]pyrimidin-2-yl)[(3R,3'R)-3'-hydroxy-1,4-dihydro-1'H,2H-spiro[isoquinoline-3,4'-piperidin]-1'-yl]methanone | 418 |
| 65 | 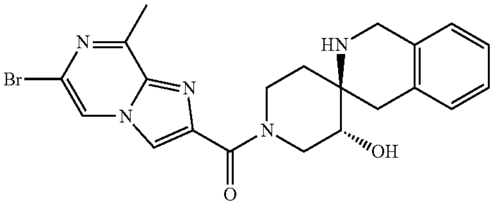 [SMILES: Cc1nc(Br)cn2cc(C(=O)N3CC[C@]4(Cc5ccccc5CN4)[C@H](O)C3)nc12] | (6-bromo-8-methylimidazo[1,2-a]pyrazin-2-yl)[(3R,3'R)-3'-hydroxy-1,4-dihydro-1'H,2H-spiro[isoquinoline-3,4'-piperidin]-1'-yl]methanone | 456 and 458 |
| 66 | 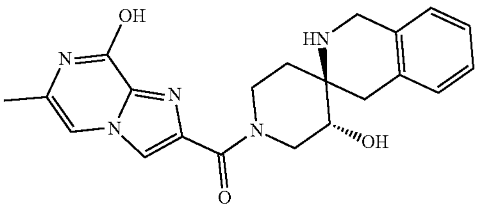 [SMILES: Cc1cn2cc(C(=O)N3CC[C@]4(Cc5ccccc5CN4)[C@H](O)C3)nc2c(O)n1] | 2-{[(3R,3'R)-3'-hydroxy-1,4-dihydro-1'H,2H-spiro[isoquinoline-3,4'-piperidin]-1'-yl]carbonyl}-6-methylimidazo[1,2-a]pyrazin-8(7H)-one | 394 |

TABLE 14-continued

The following examples were made following a protocol similar to examples above.

| Ex | Structure | Compound Name | Exact Mass [M + 1] |
|---|---|---|---|
| 67 | 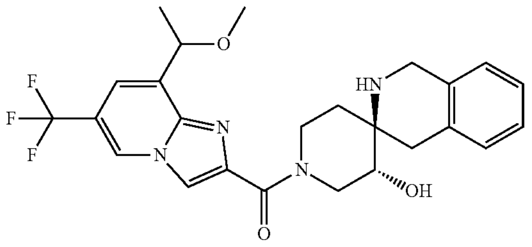 [SMILES: COC(C)c1cc(C(F)(F)F)cn2cc(C(=O)N3CC[C@]4(Cc5ccccc5CN4)[C@H](O)C3)nc12] | [(3R,3'R)-3'-hydroxy-1,4-dihydro-1'H,2H-spiro[isoquinoline-3,4'-piperidin]-1'-yl][8-(1-methoxyethyl)-6-(trifluoromethyl)imidazo[1,2-a]pyridin-2-yl]methanone | 489 |
| 68 | 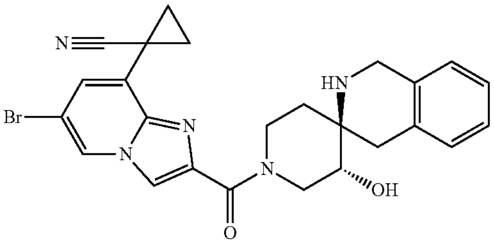 [SMILES: N#CC1(c2cc(Br)cn3cc(C(=O)N4CC[C@]5(Cc6ccccc6CN5)[C@H](O)C4)nc23)CC1] | 1-(6-bromo-2-{[(3R,3'R)-3'-hydroxy-1,4-dihydro-1'H,2H-spiro[isoquinoline-3,4'-piperidin]-1'-yl]carbonyl}imidazo[1,2-a]pyridin-8-yl)cyclopropanecarbonitrile | 506 and 508 |
| 69 | 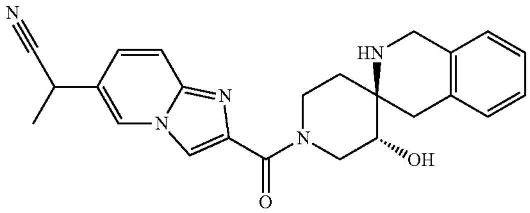 [SMILES: CC(C#N)c1ccc2nc(C(=O)N3CC[C@]4(Cc5ccccc5CN4)[C@H](O)C3)cn2c1] | 2-(2-{[(3R,3'R)-3'-hydroxy-1,4-dihydro-1'H,2H-spiro[isoquinoline-3,4'-piperidin]-1'-yl]carbonyl}imidazo[1,2-a]pyridin-6-yl)propanenitrile | 416 |
| 70 | 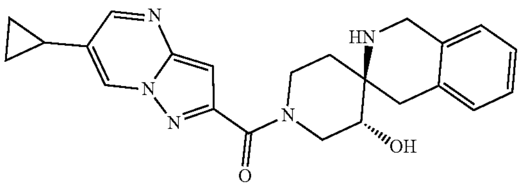 [SMILES: O=C(c1cc2ncc(C3CC3)cn2n1)N1CC[C@]2(Cc3ccccc3CN2)[C@H](O)C1] | (6-cyclopropylpyrazolo[1,5-a]pyrimidin-2-yl)[(3R,3'R)-3'-hydroxy-1,4-dihydro-1'H,2H-spiro[isoquinoline-3,4'-piperidin]-1'-yl]methanone | 404 |
| 71 | 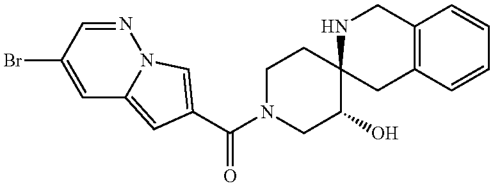 [SMILES: O=C(c1cc2cc(Br)cnn2c1)N1CC[C@]2(Cc3ccccc3CN2)[C@H](O)C1] | (7-bromoimidazo[1,2-b]pyridazin-2-yl)[(3R,3'R)-3'-hydroxy-1,4-dihydro-1'H,2H-spiro[isoquinoline-3,4'-piperidin]-1'-yl]methanone | 442 and 444 |
| 72 | 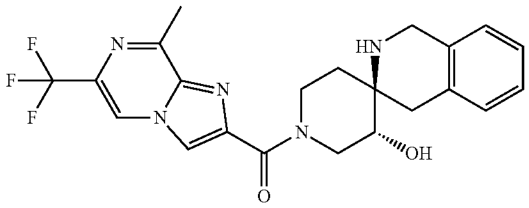 [SMILES: Cc1nc(C(F)(F)F)cn2cc(C(=O)N3CC[C@]4(Cc5ccccc5CN4)[C@H](O)C3)nc12] | [(3R,3'R)-3'-hydroxy-1,4-dihydro-1'H,2H-spiro[isoquinoline-3,4'-piperidin]-1'-yl][8-methyl-6-(trifluoromethyl)imidazo[1,2-a]pyrazin-2-yl]methanone | 446 |

TABLE 14-continued

| The following examples were made following a protocol similar to examples above. | | | |
|---|---|---|---|
| Ex | Structure | Compound Name | Exact Mass [M + 1] |
| 73 | 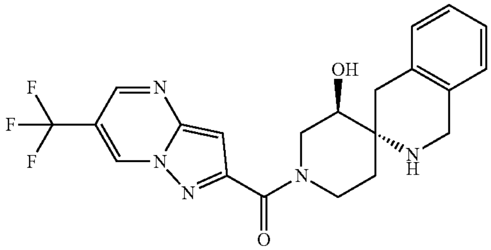 [SMILES: O=C(c1cc2ncc(C(F)(F)F)cn2n1)N1CC[C@]2(Cc3ccccc3CN2)[C@H](O)C1] | [(3R,3'R)-3'-hydroxy-1,4-dihydro-1'H,2H-spiro[isoquinoline-3,4'-piperidin]-1'-yl][6-(trifluoromethyl)pyrazolo[1,5-a]pyrimidin-2-yl]methanone | 432 |
| 74 | 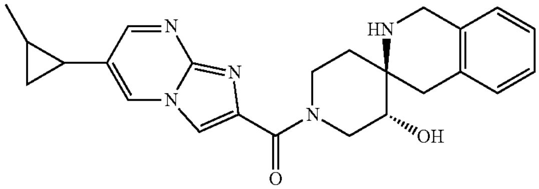 [SMILES: CC1CC1c1cnc2nc(C(=O)N3CC[C@]4(Cc5ccccc5CN4)[C@H](O)C3)cn2c1] | A diastereomer of [(3R,3'R)-3'-hydroxy-1,4-dihydro-1'H,2H-spiro[isoquinoline-3,4'-piperidin]-1'-yl][6-(2-methylcyclopropyl)imidazo[1,2-a]pyrimidin-2-yl]methanone | 418 |
| 75 | 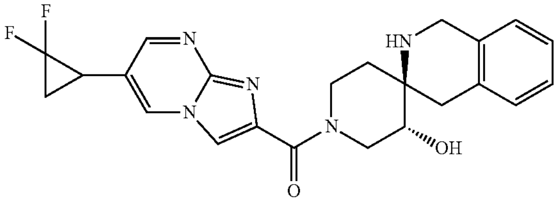 [SMILES: O=C(c1cn2cc(C3CC3(F)F)cnc2n1)N1CC[C@]2(Cc3ccccc3CN2)[C@H](O)C1] | A diastereomer of [6-(2,2-difluorocyclopropyl)imidazo[1,2-a]pyrimidin-2-yl][(3R,3'R)-3'-hydroxy-1,4-dihydro-1'H,2H-spiro[isoquinoline-3,4'-piperidin]-1'-yl]methanone | 440 |
| 76 | 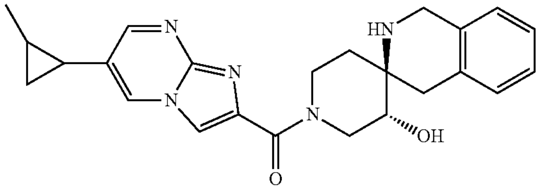 [SMILES: CC1CC1c1cnc2nc(C(=O)N3CC[C@]4(Cc5ccccc5CN4)[C@H](O)C3)cn2c1] | A diastereomer of [(3R,3'R)-3'-hydroxy-1,4-dihydro-1'H,2H-spiro[isoquinoline-3,4'-piperidin]-1'-yl][6-(2-methylcyclopropyl)imidazo[1,2-a]pyrimidin-2-yl]methanone | 418 |
| 77 | 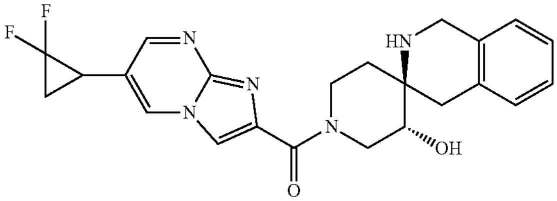 [SMILES: O=C(c1cn2cc(C3CC3(F)F)cnc2n1)N1CC[C@]2(Cc3ccccc3CN2)[C@H](O)C1] | A diastereomer of [6-(2,2-difluorocyclopropyl)imidazo[1,2-a]pyrimidin-2-yl][(3R,3'R)-3'-hydroxy-1,4-dihydro-1'H,2H-spiro[isoquinoline-3,4'-piperidin]-1'-yl]methanone | 440 |
| 78 | 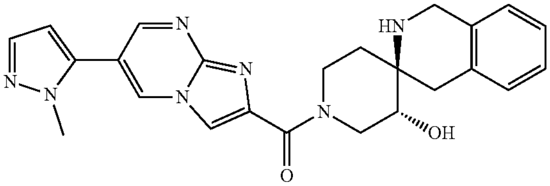 [SMILES: Cn1nccc1-c1cnc2nc(C(=O)N3CC[C@]4(Cc5ccccc5CN4)[C@H](O)C3)cn2c1] | [(3R,3'R)-3'-hydroxy-1,4-dihydro-1'H,2H-spiro[isoquinoline-3,4'-piperidin]-1'-yl][6-(1-methyl-1H-pyrazol-5-yl)imidazo[1,2-a]pyrimidin-2-yl]methanone | 444 |
| 79 | 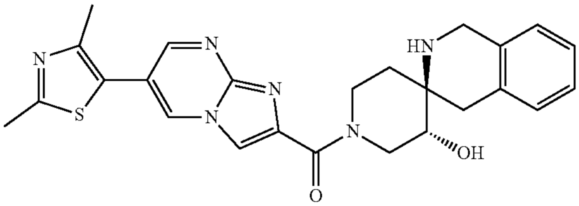 [SMILES: Cc1nc(C)c(-c2cnc3nc(C(=O)N4CC[C@]5(Cc6ccccc6CN5)[C@H](O)C4)cn3c2)s1] | [6-(2,4-dimethyl-1,3-thiazol-5-yl)imidazo[1,2-a]pyrimidin-2-yl][(3R,3'R)-3'-hydroxy-1,4-dihydro-1'H,2H-spiro[isoquinoline-3,4'-piperidin]-1'-yl]methanone | 475 |

TABLE 14-continued

The following examples were made following a protocol similar to examples above.

| Ex | Structure | Compound Name | Exact Mass [M + 1] |
|---|---|---|---|
| 80 | 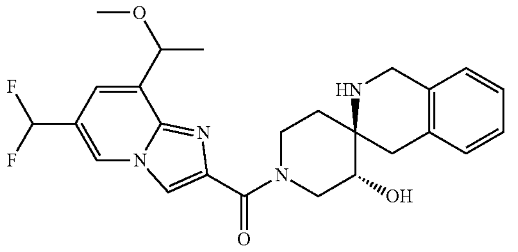 [SMILES: COC(C)c1cc(C(F)F)cn2cc(C(=O)N3CC[C@]4(Cc5ccccc5CN4)[C@H](O)C3)nc12] | A diastereomer of [6-(difluoromethyl)-8-(1-methoxyethyl)imidazo[1,2-a]pyridin-2-yl][(3R,3'R)-3'-hydroxy-1,4-dihydro-1'H,2H-spiro[isoquinoline-3,4'-piperidin]-1'-yl]methanone | 471 |
| 81 | 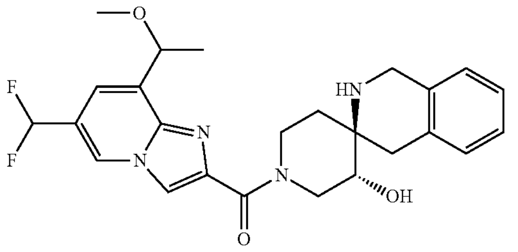 [SMILES: COC(C)c1cc(C(F)F)cn2cc(C(=O)N3CC[C@]4(Cc5ccccc5CN4)[C@H](O)C3)nc12] | A diastereomer of [6-(difluoromethyl)-8-(1-methoxyethyl)imidazo[1,2-a]pyridin-2-yl][(3R,3'R)-3'-hydroxy-1,4-dihydro-1'H,2H-spiro[isoquinoline-3,4'-piperidin]-1'-yl]methanone | 471 |
| 82 | 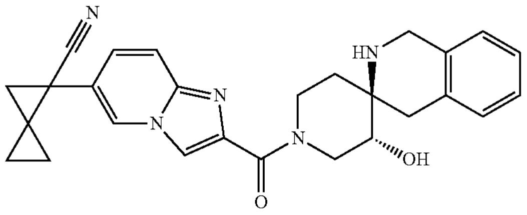 [SMILES: N#CC1(c2ccc3nc(C(=O)N4CC[C@]5(Cc6ccccc6CN5)[C@H](O)C4)cn3c2)CC12CC2] | A diastereomer of 1-{2-[(3R,3'R)-3'-hydroxy-1,4-dihydro-1'H,2H-spiro[isoquinoline-3,4'-piperidine]-1'-carbonyl]imidazo[1,2-a]pyrimidin-6-yl}spiro[2.2]pentane-1-carbonitrile | 455 |
| 83 | 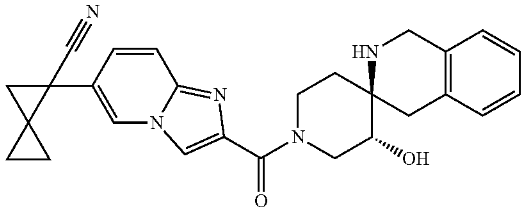 [SMILES: N#CC1(c2ccc3nc(C(=O)N4CC[C@]5(Cc6ccccc6CN5)[C@H](O)C4)cn3c2)CC12CC2] | A diastereomer of 1-{2-[(3R,3'R)-3'-hydroxy-1,4-dihydro-1'H,2H-spiro[isoquinoline-3,4'-piperidine]-1'-carbonyl]imidazo[1,2-a]pyrimidin-6-yl}spiro[2.2]pentane-1-carbonitrile | 455 |
| 84 | 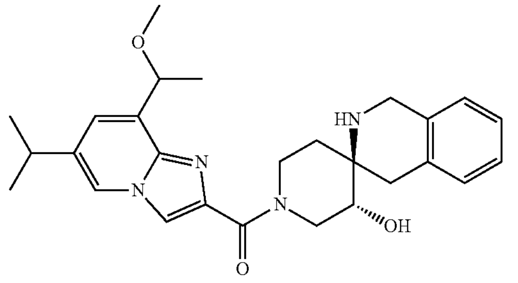 [SMILES: COC(C)c1cc(C(C)C)cn2cc(C(=O)N3CC[C@]4(Cc5ccccc5CN4)[C@H](O)C3)nc12] | A diastereomer of [(3R,3'R)-3'-hydroxy-1,4-dihydro-1'H,2H-spiro[isoquinoline-3,4'-piperidin]-1'-yl][6-isopropyl-8-(1-methoxyethyl)imidazo[1,2-a]pyridin-2-yl]methanone | 463 |

TABLE 14-continued

| The following examples were made following a protocol similar to examples above. | | | |
|---|---|---|---|
| Ex | Structure | Compound Name | Exact Mass [M + 1] |
| 85 | 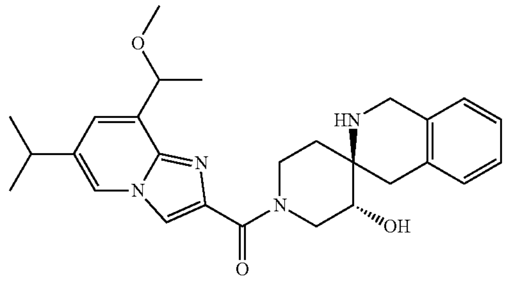 [SMILES: COC(C)c1cc(C(C)C)cn2cc(C(=O)N3CC[C@]4(Cc5ccccc5CN4)[C@H](O)C3)nc12] | A diastereomer of [(3R,3'R)-3'-hydroxy-1,4-dihydro-1'H,2H-spiro[isoquinoline-3,4'-piperidin]-1'-yl][6-isopropyl-8-(1-methoxyethyl)imidazo[1,2-a]pyridin-2-yl]methanone | 435 |

TABLE 15

| The following examples were using similar coupling conditions as above, but used achiral spiroamine in the coupling reaction. The resultant products were then separated using SFC. | | | |
|---|---|---|---|
| | Structure | Compound Name | Exact Mass [M + 1] |
| 86 | 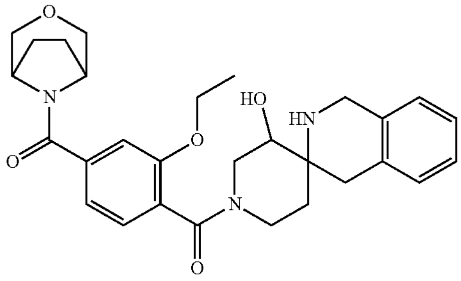 [SMILES: CCOc1cc(C(=O)N2C3CCC2COC3)ccc1C(=O)N1CCC2(Cc3ccccc3CN2)C(O)C1] | A diastereomer of {3-ethoxy-4-[(3'-hydroxy-1,4-dihydro-1'H,2H-spiro[isoquinoline-3,4'-piperidin]-1'-yl)carbonyl]phenyl}(3-oxa-8-azabicyclo[3.2.1]oct-8-yl)methanone | 506 |
| 87 | 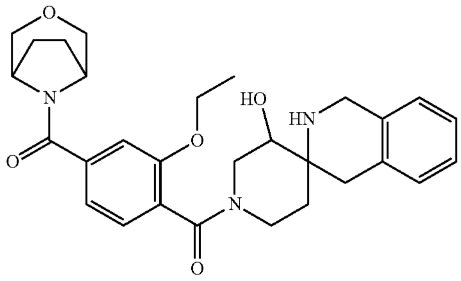 [SMILES: CCOc1cc(C(=O)N2C3CCC2COC3)ccc1C(=O)N1CCC2(Cc3ccccc3CN2)C(O)C1] | A diastereomer of {3-ethoxy-4-[(3'-hydroxy-1,4-dihydro-1'H,2H-spiro[isoquinoline-3,4'-piperidin]-1'-yl)carbonyl]phenyl}(3-oxa-8-azabicyclo[3.2.1]oct-8-yl)methanone | 506 |
| 88 | 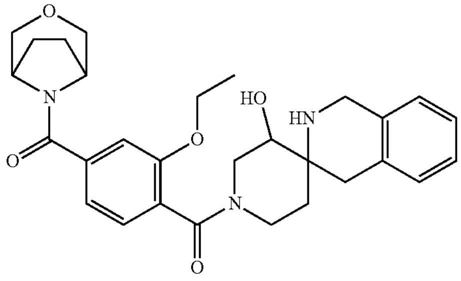 [SMILES: CCOc1cc(C(=O)N2C3CCC2COC3)ccc1C(=O)N1CCC2(Cc3ccccc3CN2)C(O)C1] | A diastereomer of {3-ethoxy-4-[(3'-hydroxy-1,4-dihydro-1'H,2H-spiro[isoquinoline-3,4'-piperidin]-1'-yl)carbonyl]phenyl}(3-oxa-8-azabicyclo[3.2.1]oct-8-yl)methanone | 506 |

TABLE 15-continued

The following examples were using similar coupling conditions as above, but used achiral spiroamine in the coupling reaction. The resultant products were then separated using SFC.

| | Structure | Compound Name | Exact Mass [M + 1] |
|---|---|---|---|
| 89 | 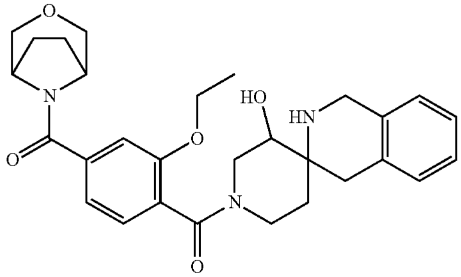 [SMILES: CCOc1cc(C(=O)N2C3CCC2COC3)ccc1C(=O)N1CCC2(Cc3ccccc3CN2)C(O)C1] | A diastereomer of {3-ethoxy-4-[(3'-hydroxy-1,4-dihydro-1'H,2H-spiro[isoquinoline-3,4'-piperidin]-1'-yl)carbonyl]phenyl}(3-oxa-8-azabicyclo[3.2.1]oct-8-yl)methanone | 506 |
| 90 | 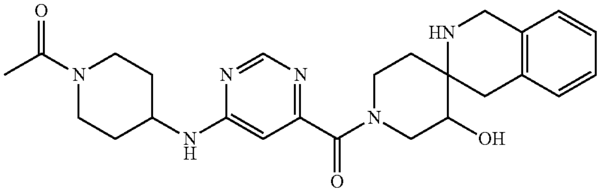 [SMILES: CC(=O)N1CCC(Nc2cc(C(=O)N3CCC4(Cc5ccccc5CN4)C(O)C3)ncn2)CC1] | A diastereomer of 1-[4-({6-[(3'-hydroxy-1,4-dihydro-1'H,2H-spiro[isoquinoline-3,4'-piperidin]-1'-yl)carbonyl]-4-pyrimidinyl}amino)-1-piperidinyl]ethanone | 465 |
| 91 | 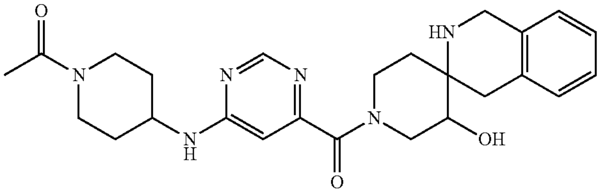 [SMILES: CC(=O)N1CCC(Nc2cc(C(=O)N3CCC4(Cc5ccccc5CN4)C(O)C3)ncn2)CC1] | A diastereomer of 1-[4-({6-[(3'-hydroxy-1,4-dihydro-1'H,2H-spiro[isoquinoline-3,4'-piperidin]-1'-yl)carbonyl]-4-pyrimidinyl}amino)-1-piperidinyl]ethanone | 465 |
| 92 | 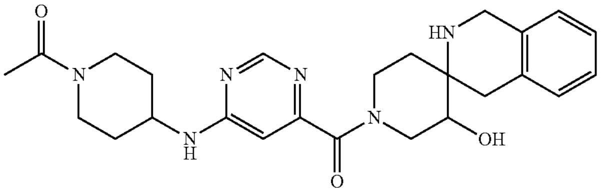 [SMILES: CC(=O)N1CCC(Nc2cc(C(=O)N3CCC4(Cc5ccccc5CN4)C(O)C3)ncn2)CC1] | A diastereomer of 1-[4-({6-[(3'-hydroxy-1,4-dihydro-1'H,2H-spiro[isoquinoline-3,4'-piperidin]-1'-yl)carbonyl]-4-pyrimidinyl}amino)-1-piperidinyl]ethanone | 465 |
| 93 | 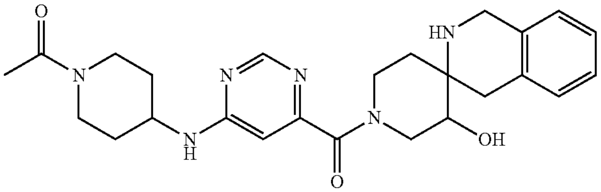 [SMILES: CC(=O)N1CCC(Nc2cc(C(=O)N3CCC4(Cc5ccccc5CN4)C(O)C3)ncn2)CC1] | A diastereomer of 1-[4-({6-[(3'-hydroxy-1,4-dihydro-1'H,2H-spiro[isoquinoline-3,4'-piperidin]-1'-yl)carbonyl]-4-pyrimidinyl}amino)-1-piperidinyl]ethanone | 465 |

Example 94: (R or S)-3-((6-bromo-2-((3R,3'R)-3'-hydroxy-1,4-dihydro-2H-spiro[isoquinoline-3,4'-piperidine]-1'-carbonyl)imidazo[1,2-a]pyrazin-8-yl)oxy)-1-methylpyrrolidin-2-one Example 95: (R or S)-3-((6-bromo-2-((3R,3'R)-3'-hydroxy-1,4-dihydro-2H-spiro[isoquinoline-3,4'-piperidine]-1'-carbonyl)imidazo[1,2-a]pyrazin-8-yl)oxy)-1-methylpyrrolidin-2-one

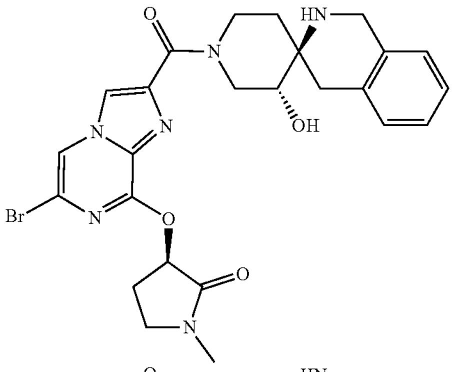

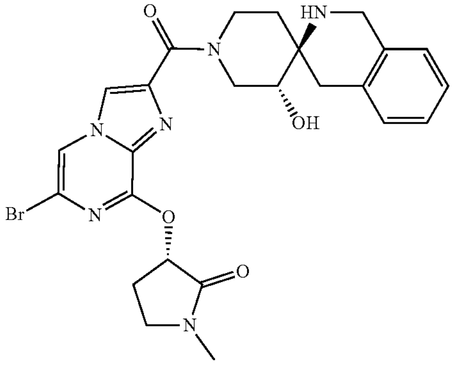

Step 1: To a solution of 6-bromo-8-((1-methyl-2-oxopyrrolidin-3-yl)oxy)imidazo[1,2-a]pyrazine-2-carboxylic acid (80 mg, 0.225 mmol), (3R,3'R)-1,4-dihydro-2H-spiro[isoquinoline-3,4'-piperidin]-3'-ol (54.1 mg, 0.248 mmol) and DIEA (0.118 mL, 0.676 mmol) in DMF (1 mL) was added T3P® (448 mg, 0.676 mmol, 48% wt, in DMF) at 25° C. The mixture was stirred at 25° C. for 10 min. The reaction mixture was purified by preparative HPLC (ACN/water, 10 mM $NH_4HCO_3$ modifier) to give 3-((6-bromo-2-((3R,3'R)-3'-hydroxy-2,4-dihydro-1H-spiro[isoquinoline-3,4'-piperidin]-1'-ylcarbonyl)imidazo[1,2-a]pyrazin-8-yl)oxy)-1-methylpyrrolidin-2-one. MS: 555 and 557 (M+1).

Step 2: The mixture of 3-((6-bromo-2-((3R,3'R)-3'-hydroxy-2,4-dihydro-1H-spiro[isoquinoline-3,4'-piperidin]-1'-ylcarbonyl)imidazo[1,2-a]pyrazin-8-yl)oxy)-1-methylpyrrolidin-2-one (65 mg, 0.117 mmol) was separated by SFC (AS Column, MeOH/$CO_2$) to give (R or S)-3-((6-bromo-2-((3R,3'R)-3'-hydroxy-2,4-dihydro-1H-spiro[isoquinoline-3,4'-piperidin]-1'-ylcarbonyl)imidazo[1,2-a]pyrazin-8-yl)oxy)-1-methylpyrrolidin-2-one (peak 1, Example 60), MS: 555 and 557 (M+1). $^1$H NMR (400 MHz, $CD_3OD$) δ 8.38-8.47 (m, 1H), 8.28 (s, 1H), 7.14 (br d, J=4.77 Hz, 3H), 7.03-7.10 (m, 1H), 5.85-6.01 (m, 1H), 4.06-4.25 (m, 2H), 3.84-4.05 (m, 3H), 3.48-3.78 (m, 4H), 2.91-3.10 (m, 4H), 2.67-2.87 (m, 2H), 2.17-2.32 (m, 1H), 1.84-1.97 (m, 1H), 1.45-1.63 (m, 1H);

(S or R)-3-((6-bromo-2-((3R,3'R)-3'-hydroxy-2,4-dihydro-JH-spiro[isoquinoline-3,4'-piperidin]-1'-ylcarbonyl)imidazo[1,2-a]pyrazin-8-yl)oxy)-1-methylpyrrolidin-2-one (peak 2, Example 61). MS: 555 and 557 (M+1). $^1$H NMR (400 MHz, $CD_3OD$) δ 8.39-8.45 (m, 1H), 8.24-8.30 (m, 1H), 7.14 (d, J=2.9 Hz, 3H), 7.07 (br d, J=3.3 Hz, 1H), 5.94 (dd, J=8.2 Hz, 1H), 4.06-4.34 (m, 2H), 3.82-4.05 (m, 3H), 3.48-3.81 (m, 4H), 2.96 (br d, J=5.1 Hz, 4H), 2.66-2.86 (m, 2H), 2.16-2.33 (m, 1H), 1.81-1.98 (m, 1H), 1.47-1.64 (m, 1H).

Example 96: 1—((S or R)-3,3-difluoro-4-((4-((3R,3'R)-3'-hydroxy-1,4-dihydro-2H-spiro[isoquinoline-3,4'-piperidine]-1'-carbonyl)pyridin-2-yl)amino)piperidin-1-yl)ethan-1-one Example 97: 1—((S or R)-3,3-difluoro-4-((4-((3R,3'R)-3'-hydroxy-1,4-dihydro-2H-spiro[isoquinoline-3,4'-piperidine]-1'-carbonyl)pyridin-2-yl)amino)piperidin-1-yl)ethan-1-one

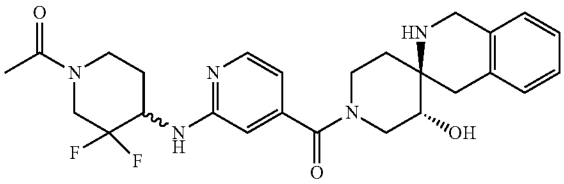 [SMILES: CC(=O)N1CCC(Nc2cc(C(=O)N3CC[C@]4(Cc5ccccc5CN4)[C@H](O)C3)ccn2)C(F)(F)C1]

Step 1: To a mixture of 2-((1-acetyl-3,3-difluoropiperidin-4-yl)amino)isonicotinic acid (60 mg, 0.20 mmol) and DIEA (0.105 mL, 0.601 mmol) in DMF (2 mL) was added 2,4,6-tripropyl-1,3,5,2,4,6-trioxatriphosphinane 2,4,6-trioxide (128 mg, 0.200 mmol) at 20° C. The mixture was stirred at 20° C. for 30 min, then (3R,3'R)-1,4-dihydro-2H-spiro[isoquinoline-3,4'-piperidin]-3'-ol (43.8 mg, 0.20 mmol) was added. The mixture was stirred at 20° C. for 1 h. The mixture was concentrated under reduced pressure. The residue was purified by preparative HPLC (ACN/water with 0.05% ammonia hydroxide modifier) to give 1-(3,3-difluoro-4-((4-((3R,3'R)-3'-hydroxy-2,4-dihydro-1H-spiro[isoquinoline-3,4'-piperidin]-1'-ylcarbonyl)pyridin-2-yl)amino)piperidin-1-yl)ethanone. MS: 500 (M+1).

Step 2: A mixture of 1-(3,3-difluoro-4-((4-(3'-hydroxy-2,4-dihydro-1H-spiro[isoquinoline-3,4'-piperidin]-1'-ylcarbonyl)pyridin-2-yl)amino)piperidin-1-yl)ethanone (45 mg, 0.090 mmol) was separated by SFC (AD Column, isopropanol/$CO_2$) to afford 1-((R or S)-3,3-difluoro-4-((4-((3R,3'R)-3'-hydroxy-1,4-dihydro-2H-spiro[isoquinoline-3,4'-piperidine]-1'-carbonyl)pyridin-2-yl)amino)piperidin-1-yl)ethan-1-one. MS: 500 (M+1). $^1$H NMR (400 MHz, $CD_3OD$) δ 8.04 (br d, J=5.4 Hz, 1H), 7.11 (s, 3H), 6.99-7.08 (m, 1H), 6.56-6.66 (m, 2H), 4.45-4.79 (m, 2H), 4.19 (br s, 1H), 3.93-4.03 (m, 3H), 3.53-3.90 (m, 3H), 3.33-3.51 (m, 3H), 2.87-3.23 (m, 2H), 2.64-2.80 (m, 1H), 2.11-2.22 (m, 3H), 1.94-2.09 (m, 1H), 1.74-1.92 (m, 1H), 1.37-1.57 (m, 1H);

1-((S or R)-3,3-difluoro-4-((4-((3R,3'R)-3'-hydroxy-1,4-dihydro-2H-spiro[isoquinoline-3,4'-piperidine]-1'-carbonyl)pyridin-2-yl)amino)piperidin-1-yl)ethan-1-one. MS: 500 (M+1). $^1$H NMR (400 MHz, $CD_3OD$) δ 8.04 (d, J=5.4 Hz, 1H), 7.08-7.16 (m, 3H), 6.99-7.07 (m, 1H), 6.55-6.69 (m, 2H), 4.41-4.78 (m, 2H), 4.19 (br s, 1H), 3.87-4.07 (m, 3H), 3.52-3.85 (m, 3H), 3.34-3.52 (m, 3H), 2.87-3.24 (m, 2H), 2.74 (t, J=15.4 Hz, 1H), 2.11-2.20 (m, 3H), 1.95-2.11 (m, 1H), 1.70-1.94 (m, 1H), 1.35-1.69 (m, 1H).

TABLE 16

The following examples were made following a protocol similar to examples above.

| Ex | Structure | Compound Name | Exact Mass [M + 1] |
|---|---|---|---|
| 98 | 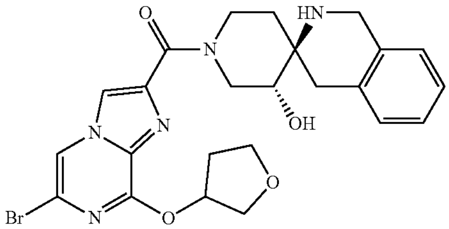 [SMILES: O=C(c1cn2cc(Br)nc(OC3CCOC3)c2n1)N1CC[C@]2(Cc3ccccc3CN2)[C@H](O)C1] | (6-bromo-8-(((S or R)(tetrahydrofuran-3-yl)oxy)imidazo[1,2-a]pyrazin-2-yl)((3R,3'R)-3'-hydroxy-1,4-dihydro-2H-spiro[isoquinoline-3,4'-piperidin]-1'-yl)methanone | 528 and 530 |
| 99 | 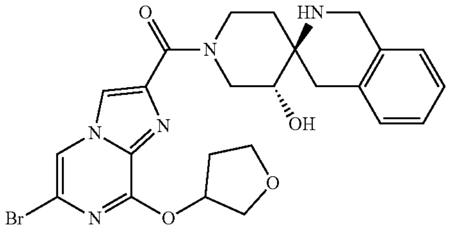 [SMILES: O=C(c1cn2cc(Br)nc(OC3CCOC3)c2n1)N1CC[C@]2(Cc3ccccc3CN2)[C@H](O)C1] | (6-bromo-8-(((S or R)(tetrahydrofuran-3-yl)oxy)imidazo[1,2-a]pyrazin-2-yl)((3R,3'R)-3'-hydroxy-1,4-dihydro-2H-spiro[isoquinoline-3,4'-piperidin]-1'-yl)methanone | 528 and 530 |
| 100 | 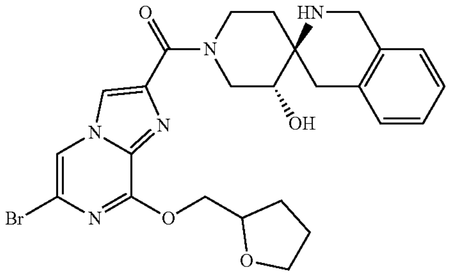 [SMILES: O=C(c1cn2cc(Br)nc(OCC3CCCO3)c2n1)N1CC[C@]2(Cc3ccccc3CN2)[C@H](O)C1] | (6-bromo-8-(((S or R)-tetrahydrofuran-2-yl)methoxy)imidazo[1,2-a]pyrazin-2-yl)((3R,3'R)-3'-hydroxy-1,4-dihydro-2H-spiro[isoquinoline-3,4'-piperidin]-1'-yl)methanone | 542 and 544 |
| 101 | 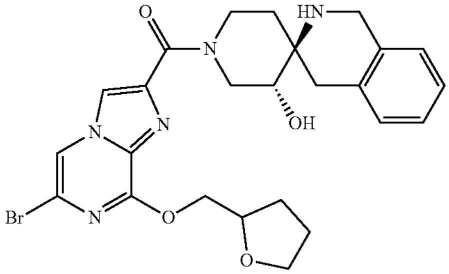 [SMILES: O=C(c1cn2cc(Br)nc(OCC3CCCO3)c2n1)N1CC[C@]2(Cc3ccccc3CN2)[C@H](O)C1] | (6-bromo-8-(((S or R)-tetrahydrofuran-2-yl)methoxy)imidazo[1,2-a]pyrazin-2-yl)((3R,3'R)-3'-hydroxy-1,4-dihydro-2H-spiro[isoquinoline-3,4'-piperidin]-1'-yl)methanone | 542 and 544 |
| 102 | 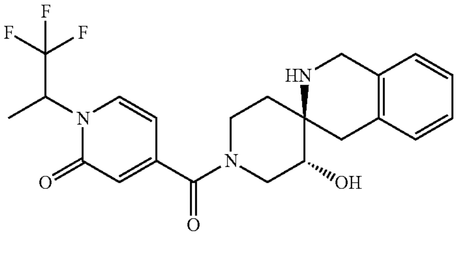 [SMILES: CC(n1ccc(C(=O)N2CC[C@]3(Cc4ccccc4CN3)[C@H](O)C2)cc1=O)C(F)(F)F] | 4-((3R,3'R)-3'-hydroxy-2,4-dihydro-1H-spiro[isoquinoline-3,4'-piperidin]-1'-ylcarbonyl)-1-((S or R)-1,1,1-trifluoropropan-2-yl)pyridin-2(1H)-one | NMR data, but not MS |
| 103 | 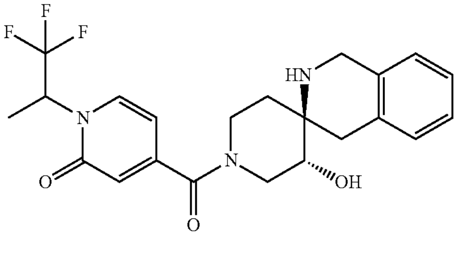 [SMILES: CC(n1ccc(C(=O)N2CC[C@]3(Cc4ccccc4CN3)[C@H](O)C2)cc1=O)C(F)(F)F] | 4-((3R,3'R)-3'-hydroxy-2,4-dihydro-1H-spiro[isoquinoline-3,4'-piperidin]-1'-ylcarbonyl)-1-((R or S)1,1,1-trifluoropropan-2-yl)pyridin-2(1H)-one | NMR data, but not MS |

TABLE 16-continued

| The following examples were made following a protocol similar to examples above. | | | |
|---|---|---|---|
| Ex | Structure | Compound Name | Exact Mass [M + 1] |
| 104 | 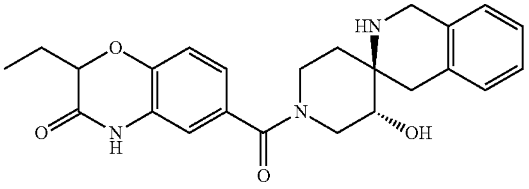 [SMILES: CCC1Oc2ccc(C(=O)N3CC[C@]4(Cc5ccccc5CN4)[C@H](O)C3)cc2NC1=O] | (2R or 2S)-2-ethyl-6-((3R,3'R)-3'-hydroxy-1,4-dihydro-2H-spiro[isoquinoline-3,4'-piperidine]-1'-carbonyl)-2H-benzo[b][1,4]oxazin-3(4H)-one | 422 |
| 105 | 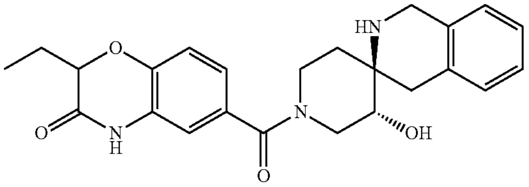 [SMILES: CCC1Oc2ccc(C(=O)N3CC[C@]4(Cc5ccccc5CN4)[C@H](O)C3)cc2NC1=O] | (2S or 2R)-2-ethyl-6-((3R,3'R)-3'-hydroxy-1,4-dihydro-2H-spiro[isoquinoline-3,4'-piperidine]-1'-carbonyl)-2H-benzo[b][1,4]oxazin-3(4H)-one | 422 |
| 106 | 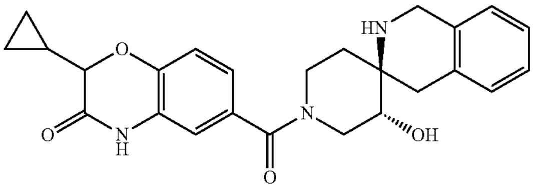 [SMILES: O=C1Nc2cc(C(=O)N3CC[C@]4(Cc5ccccc5CN4)[C@H](O)C3)ccc2OC1C1CC1] | (2R or 2S)-2-cyclopropyl-6-((3R,3'R)-3'-hydroxy-1,4-dihydro-2H-spiro[isoquinoline-3,4'-piperidine]-1'-carbonyl)-2H-benzo[b][1,4]oxazin-3(4H)-one | 434 |
| 107 | 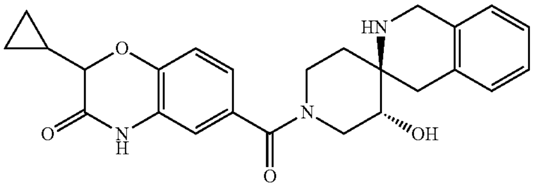 [SMILES: O=C1Nc2cc(C(=O)N3CC[C@]4(Cc5ccccc5CN4)[C@H](O)C3)ccc2OC1C1CC1] | (2S or 2R)-2-cyclopropyl-6-((3R,3'R)-3'-hydroxy-1,4-dihydro-2H-spiro[isoquinoline-3,4'-piperidine]-1'-carbonyl)-2H-benzo[b][1,4]oxazin-3(4H)-one | 434 |
| 108 | 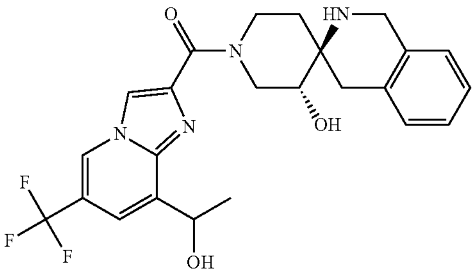 [SMILES: CC(O)c1cc(C(F)(F)F)cn2cc(C(=O)N3CC[C@]4(Cc5ccccc5CN4)[C@H](O)C3)nc12] | ((3R,3'R)-3'-hydroxy-1,4-dihydro-2H-spiro[isoquinoline-3,4'-piperidin]-1'-yl)(8-(1-hydroxyethyl)-6-(trifluoromethyl)imidazo[1,2-a]pyridin-2-yl)methanone | 475 |
| 109 | 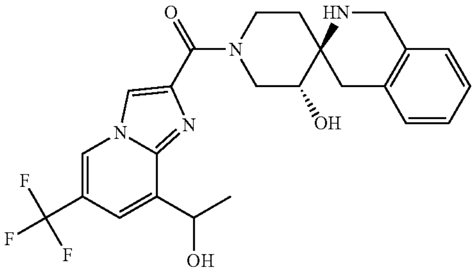 [SMILES: CC(O)c1cc(C(F)(F)F)cn2cc(C(=O)N3CC[C@]4(Cc5ccccc5CN4)[C@H](O)C3)nc12] | ((3R,3'R)-3'-hydroxy-1,4-dihydro-2H-spiro[isoquinoline-3,4'-piperidin]-1'-yl)(8-(1-hydroxyethyl)-6-(trifluoromethyl)imidazo[1,2-a]pyridin-2-yl)methanone | 475 |

Example 110: (2-chloro-4-(1-cyclopropyl-1H-1,2,4-triazol-5-yl)phenyl)((3R,3'R)-3'-hydroxy-1,4-dihydro-2H-spiro[isoquinoline-3,4'-piperidin]-1'-yl) methanone

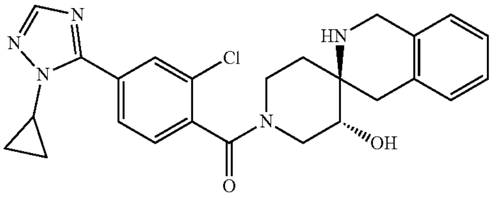 [SMILES: O=C(c1ccc(-c2ncnn2C2CC2)cc1Cl)N1CC[C@]2(Cc3ccccc3CN2)[C@H](O)C1]

Step 1: To a mixture of 2-chloro-4-(1-cyclopropyl-1H-1,2,4-triazol-5-yl)benzoic acid (50 mg, 0.19 mmol) and DIEA (0.099 mL, 0.57 mmol) in DCM (4 mL) was added HATU (87 mg, 0.23 mmol) at 20° C. The mixture was stirred at 20° C. for 30 min, then (3R,3'R)-1,4-dihydro-2H-spiro[isoquinoline-3,4'-piperidin]-3'-ol (49.7 mg, 0.228 mmol) was added. The mixture was stirred at 20° C. for 10 h. The mixture was concentrated under reduced pressure, and the residue was purified by preparative HPLC (ACN/water with 0.05% ammonia hydroxide modifier) to give (2-chloro-4-(1-cyclopropyl-1H-1,2,4-triazol-5-yl)phenyl)((3R,3'R)-3'-hydroxy-1,4-dihydro-2H-spiro[isoquinoline-3,4'-piperidin]-1'-yl)methanone. MS: 464 (M+1). $^{1}$H NMR (400 MHz, $CD_3OD$) δ 8.00-8.04 (m, 1H), 7.92-7.99 (m, 2H), 7.56-7.68 (m, 1H), 7.08-7.17 (m, 3H), 6.99-7.07 (m, 1H), 4.05-4.26 (m, 1H), 3.91-4.05 (m, 3H), 3.86 (qt, J=3.5, 7.0 Hz, 1H), 3.57-3.76 (m, 1H), 3.40-3.56 (m, 1H), 3.17-3.29 (m, 1H), 2.65-3.10 (m, 2H), 1.71-2.00 (m, 1H), 1.34-1.67 (m, 1H), 1.02-1.23 (m, 4H).

Example 111: [(3R,3'R)-3'-hydroxy-1,4-dihydro-1'H,2H-spiro[isoquinoline-3,4'-piperidin]-1'-yl](7-methylimidazo[1,2-a]pyrimidin-2-yl)methanone

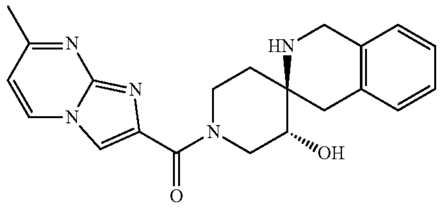 [SMILES: Cc1ccn2cc(C(=O)N3CC[C@]4(Cc5ccccc5CN4)[C@H](O)C3)nc2n1]

Step 1: To a solution of 7-methylimidazo[1,2-a]pyrimidine-2-carboxylic acid (45 mg, 0.25 mmol) in DMF (3 mL) were added HATU (116 mg, 0.305 mmol), DIEA (0.133 ml, 0.762 mmol), and (3R,3'R)-1,4-dihydro-2H-spiro[isoquinoline-3,4'-piperidin]-3'-ol (49.9 mg, 0.229 mmol). The mixture was stirred at 15° C. for 0.5 h. The mixture was concentrated and purified by preparative HPLC (water/MeCN, 10 mM $NH_4HCO_3$) to give [(3R,3'R)-3'-hydroxy-1,4-dihydro-1$^{1}$H,2H-spiro[isoquinoline-3,4'-piperidin]-1'-yl](7-methylimidazo[1,2-a]pyrimidin-2-yl)methanone. MS: 378 (M+1). $^{1}$H NMR (400 MHz, $CD_3OD$) δ 8.73 (br d, J=7.0 Hz, 1H), 8.06 (br s, 1H), 7.11 (d, J=2.6 Hz, 3H), 6.98-7.07 (m, 2H), 4.03-4.25 (m, 2H), 3.99 (br s, 3H), 3.54-3.78 (m, 2H), 2.90-3.08 (m, 1H), 2.68-2.86 (m, 1H), 2.61 (br s, 3H), 1.80-1.99 (m, 1H), 1.55 (br d, J=15.4 Hz, 1H).

TABLE 17

The following examples were made following a protocol similar to examples above.

| Ex | Structure | Compound Name | Exact Mass [M + 1] |
|---|---|---|---|
| 112 | 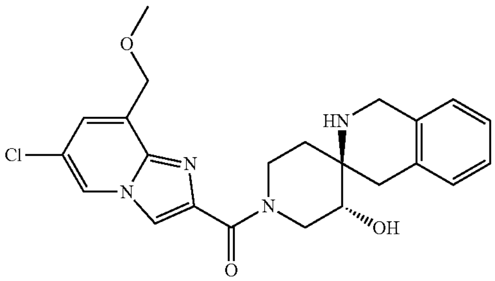 [SMILES: COCc1cc(Cl)cn2cc(C(=O)N3CC[C@]4(Cc5ccccc5CN4)[C@H](O)C3)nc12] | (6-chloro-8-(methoxymethyl)imidazo[1,2-a]pyridin-2-yl)((3R,3'R)-3'-hydroxy-1,4-dihydro-2H-spiro[isoquinoline-3,4'-piperidin]-1'-yl)methanone | 441 |
| 113 | 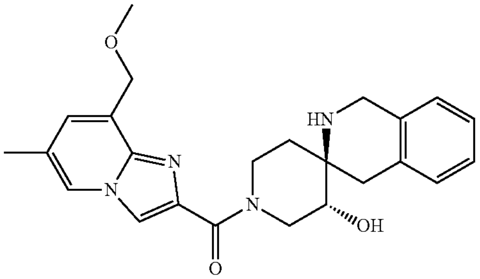 [SMILES: COCc1cc(C)cn2cc(C(=O)N3CC[C@]4(Cc5ccccc5CN4)[C@H](O)C3)nc12] | ((3R,3'R)-3'-hydroxy-1,4-dihydro-2H-spiro[isoquinoline-3,4'-piperidin]-1'-yl)(8-(methoxymethyl)-6-methylimidazo[1,2-a]pyridin-2-yl)methanone | 421 |

TABLE 17-continued

The following examples were made following a protocol similar to examples above.

| Ex | Structure | Compound Name | Exact Mass [M + 1] |
|---|---|---|---|
| 114 | 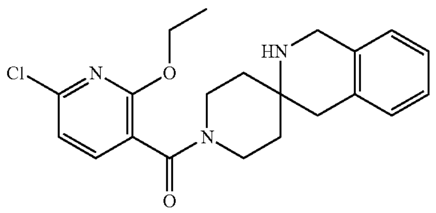 [SMILES: CCOc1nc(Cl)ccc1C(=O)N1CCC2(CC1)Cc1ccccc1CN2] | (6-chloro-2-ethoxypyridin-3-yl)(1,4-dihydro-1'H,2H-spiro[isoquinoline-3,4'-piperidin]-1'-yl)methanone | 386 |
| 115 | 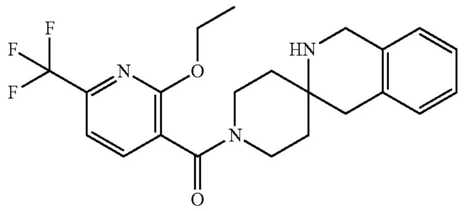 [SMILES: CCOc1nc(C(F)(F)F)ccc1C(=O)N1CCC2(CC1)Cc1ccccc1CN2] | (1,4-dihydro-1'H,2H-spiro[isoquinoline-3,4'-piperidin]-1'-yl)[2-ethoxy-6-(trifluoromethyl)pyridin-3-yl]methanone | 420 |
| 116 | 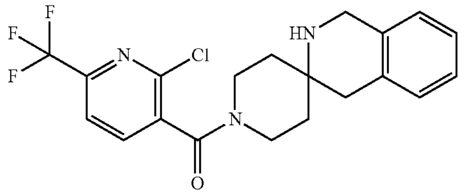 [SMILES: O=C(c1ccc(C(F)(F)F)nc1Cl)N1CCC2(CC1)Cc1ccccc1CN2] | [2-chloro-6-(trifluoromethyl)pyridin-3-yl](1,4-dihydro-1'H,2H-spiro[isoquinoline-3,4'-piperidin]-1'-yl)methanone | 410 |
| 117 | 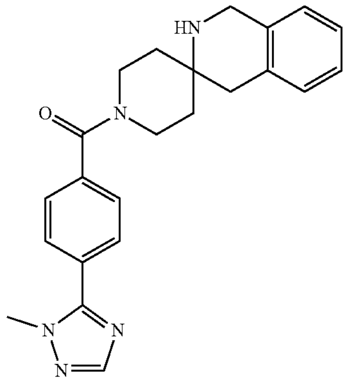 [SMILES: Cn1ncnc1-c1ccc(C(=O)N2CCC3(CC2)Cc2ccccc2CN3)cc1] | (1,4-dihydro-1'H,2H-spiro[isoquinoline-3,4'-piperidin]-1'-yl)[4-(1-methyl-1H-1,2,4-triazol-5-yl)phenyl]methanone | 388 |
| 118 | 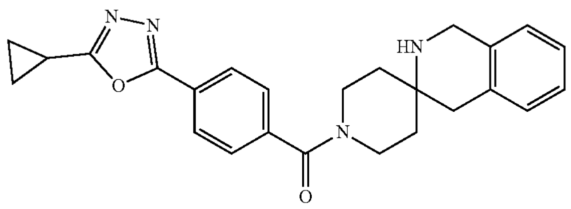 [SMILES: O=C(c1ccc(-c2nnc(C3CC3)o2)cc1)N1CCC2(CC1)Cc1ccccc1CN2] | [4-(5-cyclopropyl-1,3,4-oxadiazol-2-yl)phenyl](1,4-dihydro-1'H,2H-spiro[isoquinoline-3,4'-piperidin]-1'-yl)methanone | 415 |
| 119 | 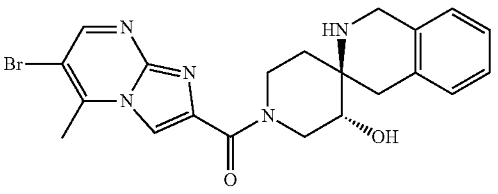 [SMILES: Cc1c(Br)cnc2nc(C(=O)N3CC[C@]4(Cc5ccccc5CN4)[C@H](O)C3)cn12] | (6-bromo-5-methylimidazo[1,2-a]pyrimidin-2-yl)[(3R,3'R)-3'-hydroxy-1,4-dihydro-1'H,2H-spiro[isoquinoline-3,4'-piperidin]-1'-yl]methanone | 456 and 458 |

TABLE 17-continued

The following examples were made following a protocol similar to examples above.

| Ex | Structure | Compound Name | Exact Mass [M + 1] |
|---|---|---|---|
| 120 | 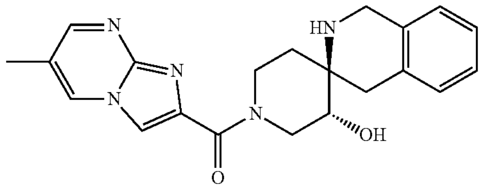 [SMILES: Cc1cnc2nc(C(=O)N3CC[C@]4(Cc5ccccc5CN4)[C@H](O)C3)cn2c1] | [(3R,3'R)-3'-hydroxy-1,4-dihydro-1'H,2H-spiro[isoquinoline-3,4'-piperidin]-1'-yl](6-methylimidazo[1,2-a]pyrimidin-2-yl)methanone | 378 |
| 121 | 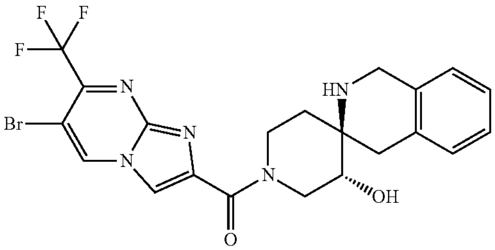 [SMILES: O=C(c1cn2cc(Br)c(C(F)(F)F)nc2n1)N1CC[C@]2(Cc3ccccc3CN2)[C@H](O)C1] | [6-bromo-7-(trifluoromethyl)imidazo[1,2-a]pyrimidin-2-yl][(3R,3'R)-3'-hydroxy-1,4-dihydro-1'H,2H-spiro[isoquinoline-3,4'-piperidin]-1'-yl]methanone | 510 and 512 |
| 122 | 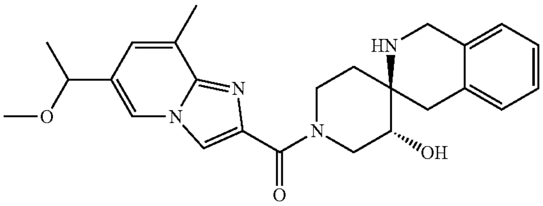 [SMILES: COC(C)c1cc(C)c2nc(C(=O)N3CC[C@]4(Cc5ccccc5CN4)[C@H](O)C3)cn2c1] | A diastereomer of [(3R,3'R)-3'-hydroxy-1,4-dihydro-1'H,2H-spiro[isoquinoline-3,4'-piperidin]-1'-yl][6-(1-methoxyethyl)-8-methylimidazo[1,2-a]pyridin-2-yl]methanone | 435 |
| 123 | 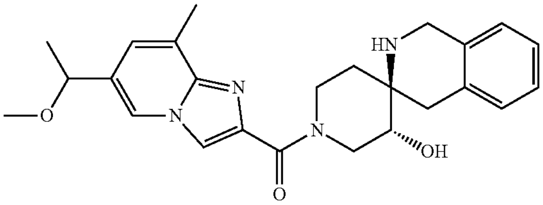 [SMILES: COC(C)c1cc(C)c2nc(C(=O)N3CC[C@]4(Cc5ccccc5CN4)[C@H](O)C3)cn2c1] | A diastereomer of [(3R,3'R)-3'-hydroxy-1,4-dihydro-1'H,2H-spiro[isoquinoline-3,4'-piperidin]-1'-yl][6-(1-methoxyethyl)-8-methylimidazo[1,2-a]pyridin-2-yl]methanone | 435 |
| 124 | 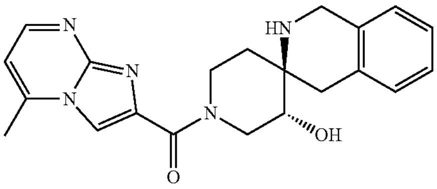 [SMILES: Cc1ccnc2nc(C(=O)N3CC[C@]4(Cc5ccccc5CN4)[C@H](O)C3)cn12] | [(3R,3'R)-3'-hydroxy-1,4-dihydro-1'H,2H-spiro[isoquinoline-3,4'-piperidin]-1'-yl](5-methylimidazo[1,2-a]pyrimidin-2-yl)methanone | 378 |
| 125 | 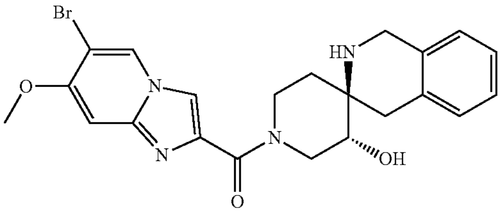 [SMILES: COc1cc2nc(C(=O)N3CC[C@]4(Cc5ccccc5CN4)[C@H](O)C3)cn2cc1Br] | (6-bromo-7-methoxyimidazo[1,2-a]pyridin-2-yl)[(3R,3'R)-3'-hydroxy-1,4-dihydro-1'H,2H-spiro[isoquinoline-3,4'-piperidin-1'-yl]methanone | 471 and 473 |
| 126 | 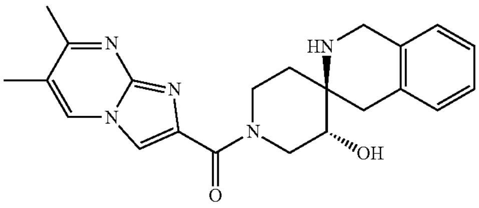 [SMILES: Cc1cn2cc(C(=O)N3CC[C@]4(Cc5ccccc5CN4)[C@H](O)C3)nc2nc1C] | (6,7-dimethylimidazo[1,2-a]pyrimidin-2-yl)[(3R,3'R)-3'-hydroxy-1,4-dihydro-1'H,2H-spiro[isoquinoline-3,4'-piperidin]-1'-yl]methanone | 392 |

TABLE 17-continued

| Ex | Structure | Compound Name | Exact Mass [M + 1] |
|---|---|---|---|
| The following examples were made following a protocol similar to examples above. | | | |
| 127 | 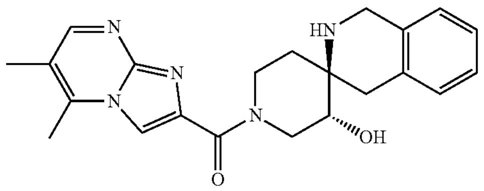 [SMILES: Cc1cnc2nc(C(=O)N3CC[C@]4(Cc5ccccc5CN4)[C@H](O)C3)cn2c1C] | (5,6-dimethylimidazo[1,2-a]pyrimidin-2-yl)[(3R,3'R)-3'-hydroxy-1,4-dihydro-1'H,2H-spiro[isoquinoline-3,4'-piperidin]-1'-yl]methanone | 392 |
| 128 | 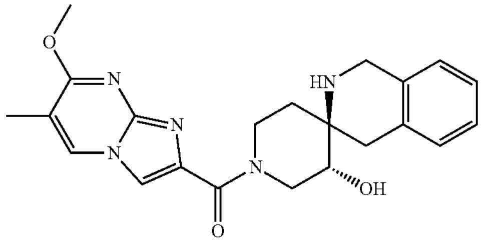 [SMILES: COc1nc2nc(C(=O)N3CC[C@]4(Cc5ccccc5CN4)[C@H](O)C3)cn2cc1C] | [(3R,3'R)-3'-hydroxy-1,4-dihydro-1'H,2H-spiro[isoquinoline-3,4'-piperidin]-1'-yl](7-methoxy-6-methylimidazo[1,2-a]pyrimidin-2-yl)methanone | 408 |
| 129 | 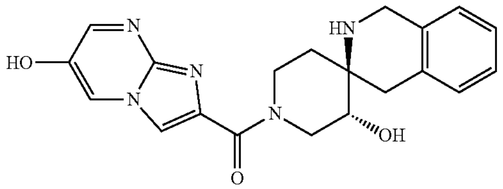 [SMILES: O=C(c1cn2cc(O)cnc2n1)N1CC[C@]2(Cc3ccccc3CN2)[C@H](O)C1] | [(3R,3'R)-3'-hydroxy-1,4-dihydro-1'H,2H-spiro[isoquinoline-3,4'-piperidin]-1'-yl](6-hydroxyimidazo[1,2-a]pyrimidin-2-yl)methanone | 380 |
| 130 | 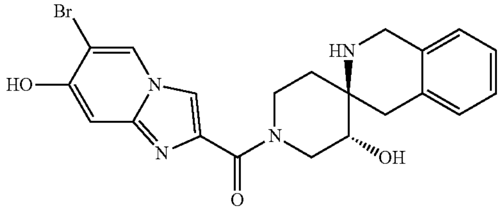 [SMILES: O=C(c1cn2cc(Br)c(O)cc2n1)N1CC[C@]2(Cc3ccccc3CN2)[C@H](O)C1] | (6-bromo-7-hydroxy imidazo[1,2-a]pyridin-2-yl)[(3R,3'R)-3'-hydroxy-1,4-dihydro-1'H,2H-spiro[isoquinoline-3,4'-piperidin]-1'-yl]methanone | 457 |
| 131 | 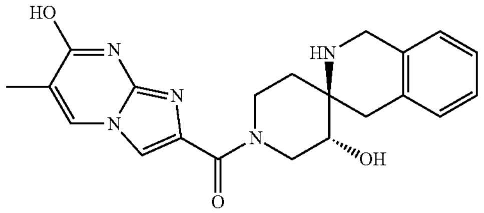 [SMILES: Cc1cn2cc(C(=O)N3CC[C@]4(Cc5ccccc5CN4)[C@H](O)C3)nc2nc1O] | 2-{[(3R,3'R)-3'-hydroxy-1,4-dihydro-1'H,2H-spiro[isoquinoline-3,4'-piperidin]-1'-yl]carbonyl}-6-methylimidazo[1,2-a]pyrimidin-7(1H)-one | 394 |
| 132 | 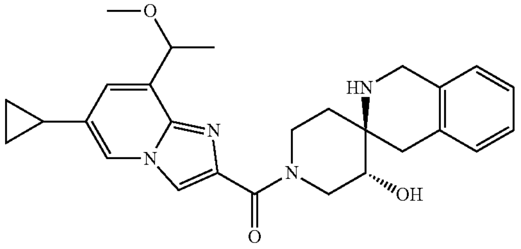 [SMILES: COC(C)c1cc(C2CC2)cn2cc(C(=O)N3CC[C@]4(Cc5ccccc5CN4)[C@H](O)C3)nc12] | [6-cyclopropyl-8-(1-methoxyethyl)imidazo[1,2-a]pyridin-2-yl][(3R,3'R)-3'-hydroxy-1,4-dihydro-1'H,2H-spiro[isoquinoline-3,4'-piperidin]-1'-yl]methanone | 461 |

TABLE 17-continued

The following examples were made following a protocol similar to examples above.

| Ex | Structure | Compound Name | Exact Mass [M + 1] |
|---|---|---|---|
| 133 | 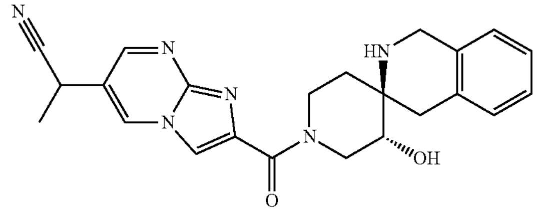 [SMILES: CC(C#N)c1cnc2nc(C(=O)N3CC[C@]4(Cc5ccccc5CN4)[C@H](O)C3)cn2c1] | 2-(2-{[(3R,3'R)-3'-hydroxy-1,4-dihydro-1'H,2H-spiro[isoquinoline-3,4'-piperidin]-1'-yl]carbonyl}imidazo[1,2-a]pyrimidin-6-yl)propanenitrile | 417 |
| 134 | 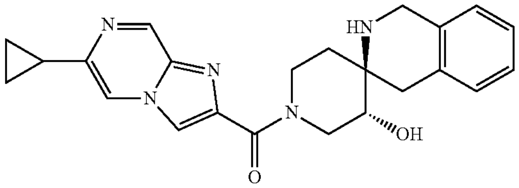 [SMILES: O=C(c1cn2cc(C3CC3)ncc2n1)N1CC[C@]2(Cc3ccccc3CN2)[C@H](O)C1] | (6-cyclopropylimidazo[1,2-a]pyrazin-2-yl)[(3R,3'R)-3'-hydroxy-1,4-dihydro-1'H,2H-spiro[isoquinoline-3,4'-piperidin]-1'-yl]methanone | 404 |
| 135 | 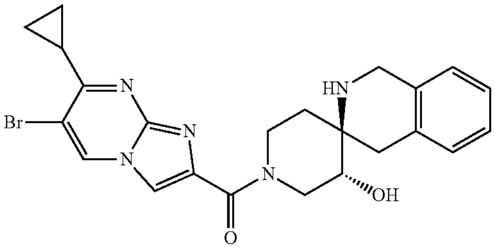 [SMILES: O=C(c1cn2cc(Br)c(C3CC3)nc2n1)N1CC[C@]2(Cc3ccccc3CN2)[C@H](O)C1] | (6-bromo-7-cyclopropylimidazo[1,2-a]pyrimidin-2-yl)[(3R,3'R)-3'-hydroxy-1,4-dihydro-1'H,2H-spiro[isoquinoline-3,4'-piperidin]-1'-yl]methanone | 482 and 484 |
| 136 | 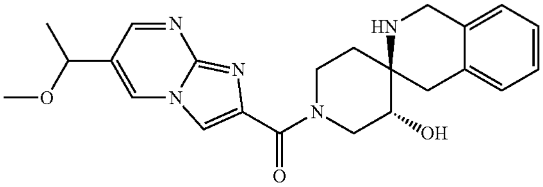 [SMILES: COC(C)c1cnc2nc(C(=O)N3CC[C@]4(Cc5ccccc5CN4)[C@H](O)C3)cn2c1] | A diastereomer of [(3R,3'R)-3'-hydroxy-1,4-dihydro-1'H,2H-spiro[isoquinoline-3,4'-piperidin]-1'-yl][6-(1-methoxyethyl)imidazo[1,2-a]pyrimidin-2-yl]methanone | 422 |
| 137 | 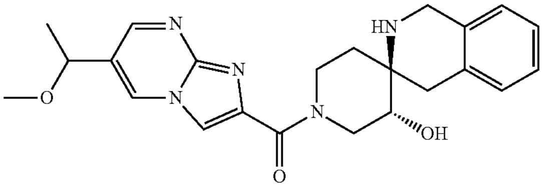 [SMILES: COC(C)c1cnc2nc(C(=O)N3CC[C@]4(Cc5ccccc5CN4)[C@H](O)C3)cn2c1] | A diastereomer of [(3R,3'R)-3'-hydroxy-1,4-dihydro-1'H,2H-spiro[isoquinoline-3,4'-piperidin]-1'-yl][6-(1-methoxyethyl)imidazo[1,2-a]pyrimidin-2-yl]methanone | 422 |
| 138 | 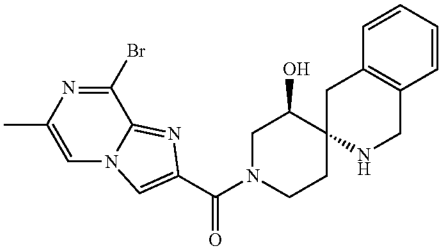 [SMILES: Cc1cn2cc(C(=O)N3CC[C@]4(Cc5ccccc5CN4)[C@H](O)C3)nc2c(Br)n1] | (8-bromo-6-methylimidazo[1,2-a]pyrazin-2-yl)[(3R,3'R)-3'-hydroxy-1,4-dihydro-1'H,2H-spiro[isoquinoline-3,4'-piperidin]-1'-yl]methanone | 456 and 458 |

TABLE 17-continued

| The following examples were made following a protocol similar to examples above. | | | |
|---|---|---|---|
| Ex | Structure | Compound Name | Exact Mass [M + 1] |
| 139 | 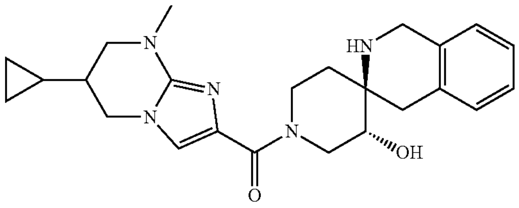 [SMILES: CN1CC(C2CC2)Cn2cc(C(=O)N3CC[C@]4(Cc5ccccc5CN4)[C@H](O)C3)nc21] | A diastereomer of (6-cyclopropyl-8-methyl-5,6,7,8-tetrahydroimidazo[1,2-a]pyrimidin-2-yl)[(3R,3'R)-3'-hydroxy-1,4-dihydro-1'H,2H-spiro[isoquinoline-3,4'-piperidin]-1'-yl]methanone | 422 |
| 140 | 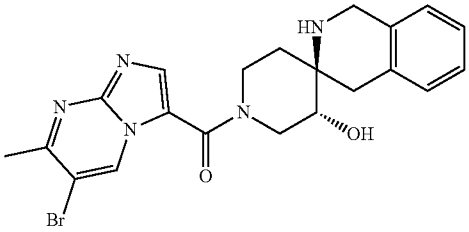 [SMILES: Cc1nc2ncc(C(=O)N3CC[C@]4(Cc5ccccc5CN4)[C@H](O)C3)n2cc1Br] | (6-bromo-7-methylimidazo[1,2-a]pyrimidin-3-yl)[(3R,3'R)-3'-hydroxy-1,4-dihydro-1'H,2H-spiro[isoquinoline-3,4'-piperidin]-1'-yl]methanone | 456 and 458 |
| 141 | 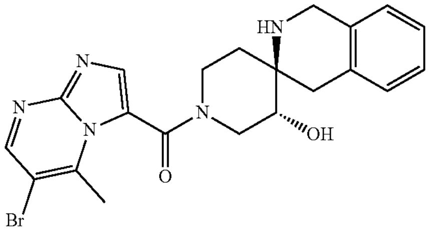 [SMILES: Cc1c(Br)cnc2ncc(C(=O)N3CC[C@]4(Cc5ccccc5CN4)[C@H](O)C3)n12] | (6-bromo-5-methylimidazo[1,2-a]pyrimidin-3-yl)[(3R,3'R)-3'-hydroxy-1,4-dihydro-1'H,2H-spiro[isoquinoline-3,4'-piperidin]-1'-yl]methanone | 456 and 458 |
| 142 | 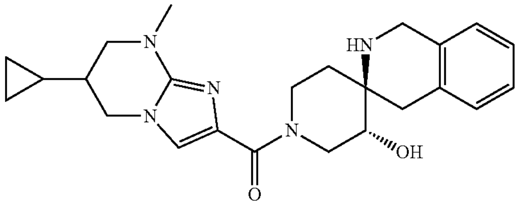 [SMILES: CN1CC(C2CC2)Cn2cc(C(=O)N3CC[C@]4(Cc5ccccc5CN4)[C@H](O)C3)nc21] | A diastereomer of (6-cyclopropyl-8-methyl-5,6,7,8-tetrahydroimidazo[1,2-a]pyrimidin-2-yl)[(3R,3'R)-3'-hydroxy-1,4-dihydro-1'H,2H-spiro[isoquinoline-3,4'-piperidin]-1'-yl]methanone | 422 |
| 143 | 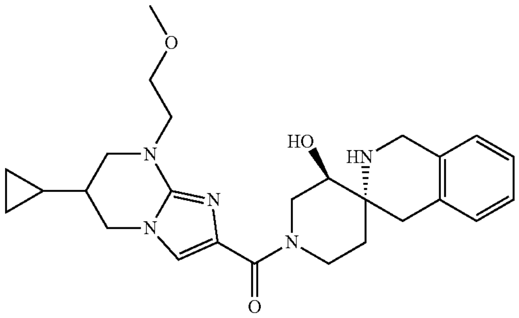 [SMILES: COCCN1CC(C2CC2)Cn2cc(C(=O)N3CC[C@]4(Cc5ccccc5CN4)[C@H](O)C3)nc21] | A diastereomer of [6-cyclopropyl-8-(2-methoxyethyl)-5,6,7,8-tetrahydroimidazo[1,2-a]pyrimidin-2-yl][(3R,3'R)-3'-hydroxy-1,4-dihydro-1'H,2H-spiro[isoquinoline-3,4'-piperidin]-1'-yl]methanone | 466 |

TABLE 17-continued

| The following examples were made following a protocol similar to examples above. | | | |
|---|---|---|---|
| Ex | Structure | Compound Name | Exact Mass [M + 1] |
| 144 | 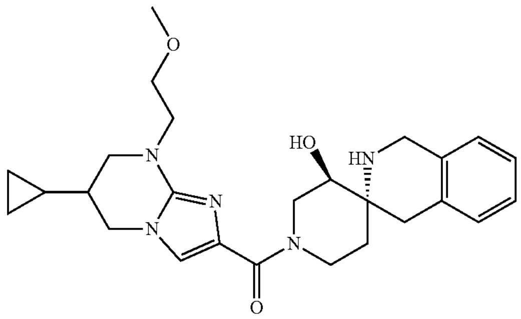 [SMILES: COCCN1CC(C2CC2)Cn2cc(C(=O)N3CC[C@]4(Cc5ccccc5CN4)[C@H](O)C3)nc21] | A diastereomer of [6-cyclopropyl-8-(2-methoxyethyl)-5,6,7,8-tetrahydroimidazo[1,2-a]pyrimidin-2-yl][(3R,3'R)-3'-hydroxy-1,4-dihydro-1'H,2H-spiro[isoquinoline-3,4'-piperidin]-1'-yl]methanone | 466 |
| 145 | 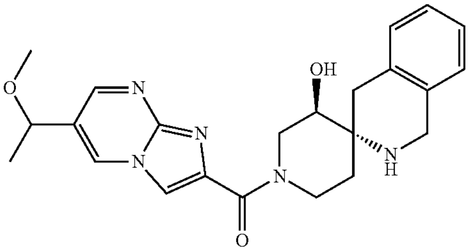 [SMILES: COC(C)c1cnc2nc(C(=O)N3CC[C@]4(Cc5ccccc5CN4)[C@H](O)C3)cn2c1] | A diastereomer of [(3R,3'R)-3'-hydroxy-1,4-dihydro-1'H,2H-spiro[isoquinoline-3,4'-piperidin]-1'-yl][6-(1-methoxyethyl)pyrazolo[1,5-a]pyrimidin-2-yl]methanone | 422 |
| 146 | 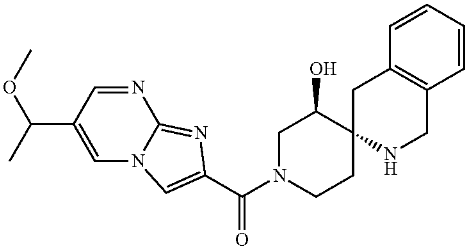 [SMILES: COC(C)c1cnc2nc(C(=O)N3CC[C@]4(Cc5ccccc5CN4)[C@H](O)C3)cn2c1] | A diastereomer of [(3R,3'R)-3'-hydroxy-1,4-dihydro-1'H,2H-spiro[isoquinoline-3,4'-piperidin]-1'-yl][6-(1-methoxyethyl)pyrazolo[1,5-a]pyrimidin-2-yl]methanone | 422 |
| 147 | 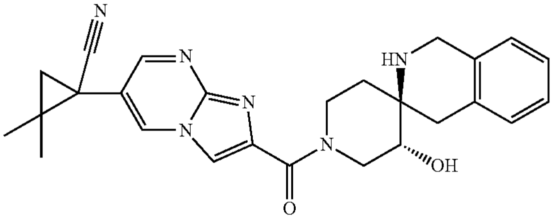 [SMILES: CC1(C)CC1(C#N)c1cnc2nc(C(=O)N3CC[C@]4(Cc5ccccc5CN4)[C@H](O)C3)cn2c1] | A diastereomer of 1-{2-[(3R,3'R)-3'-hydroxy-1,4-dihydro-1'H,2H-spiro[isoquinoline-3,4'-piperidine]-1'-carbonyl]imidazo[1,2-a]pyrimidin-6-yl}-2,2-dimethylcyclopropane-1-carbonitrile | 457 |
| 148 | 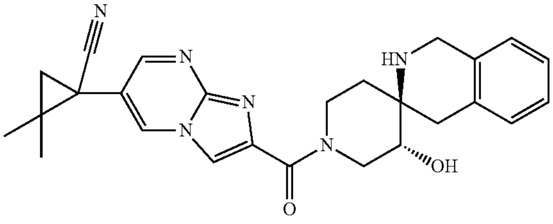 [SMILES: CC1(C)CC1(C#N)c1cnc2nc(C(=O)N3CC[C@]4(Cc5ccccc5CN4)[C@H](O)C3)cn2c1] | A diastereomer of 1-{2-[(3R,3'R)-3'-hydroxy-1,4-dihydro-1'H,2H-spiro[isoquinoline-3,4'-piperidine]-1'-carbonyl]imidazo[1,2-a]pyrimidin-6-yl}-2,2-dimethylcyclopropane-1-carbonitrile | 457 |

TABLE 18

The following examples were using similar coupling conditions as above, but used achiral spiroamine in the coupling reaction. The resultant products were then separated using SFC.

| Ex | Structure | Compound Name | Exact Mass [M + 1] |
|---|---|---|---|
| 149 | 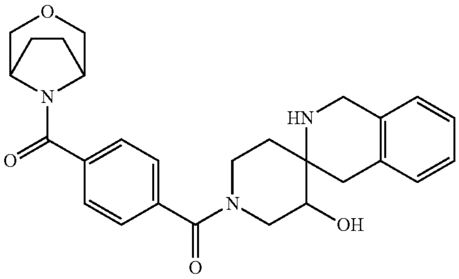 [SMILES: O=C(c1ccc(C(=O)N2C3CCC2COC3)cc1)N1CCC2(Cc3ccccc3CN2)C(O)C1] | A diastereomer of (3'-hydroxy-1,4-dihydro-1'H,2H-spiro[isoquinoline-3,4'-piperidin]-1' -yl)[4-(3-oxa-8-azabicyclo[3.2.1]oct-8-ylcarbonyl)phenyl]methanone | 462 |
| 150 | 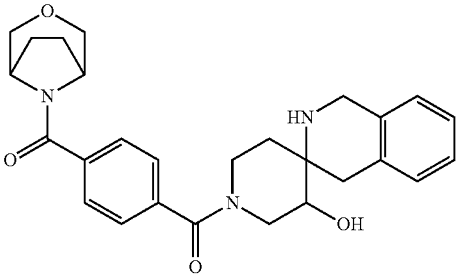 [SMILES: O=C(c1ccc(C(=O)N2C3CCC2COC3)cc1)N1CCC2(Cc3ccccc3CN2)C(O)C1] | A diastereomer of (3'-hydroxy-1,4-dihydro-1'H,2H-spiro[isoquinoline-3,4'-piperidin]-1'-yl)[4-(3-oxa-8-azabicyclo[3.2.1]oct-8-ylcarbonyl)phenyl]methanone | 462 |
| 151 | 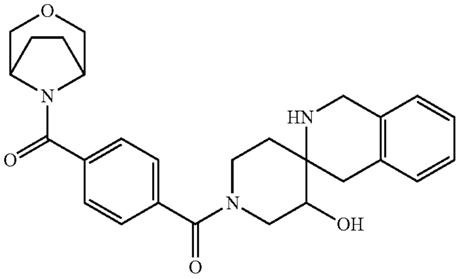 [SMILES: O=C(c1ccc(C(=O)N2C3CCC2COC3)cc1)N1CCC2(Cc3ccccc3CN2)C(O)C1] | A diastereomer of (3'-hydroxy-1,4-dihydro-1'H,2H-spiro[isoquinoline-3,4'-piperidin]-1'-yl)[4-(3-oxa-8-azabicyclo[3.2.1]oct-8-ylcarbonyl)phenyl]methanone | 462 |
| 152 | 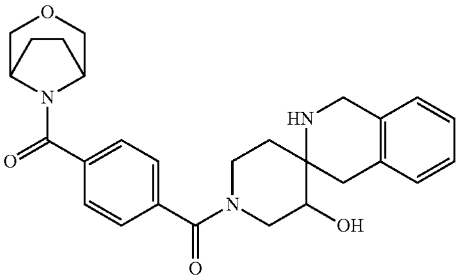 [SMILES: O=C(c1ccc(C(=O)N2C3CCC2COC3)cc1)N1CCC2(Cc3ccccc3CN2)C(O)C1] | A diastereomer of (3'-hydroxy-1,4-dihydro-1'H,2H-spiro[isoquinoline-3,4'-piperidin]-1'-yl)[4-(3-oxa-8-azabicyclo[3.2.1]oct-8-ylcarbonyl)phenyl]methanone | 462 |

Example 153: ((3R,3'R)-3'-hydroxy-1,4-dihydro-2H-spiro[isoquinoline-3,4'-piperidin]-1'-yl)(4-hydroxy-3-(2,2,2-trifluoroethyl)quinolin-7-yl)methanone

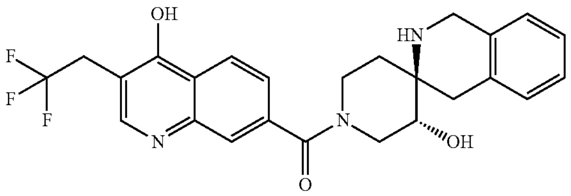 [SMILES: O=C(c1ccc2c(O)c(CC(F)(F)F)cnc2c1)N1CC[C@]2(Cc3ccccc3CN2)[C@H](O)C1]

Step 1: To a solution of 4-butoxy-3-(2,2,2-trifluoroethyl) quinoline-7-carboxylic acid (30 mg, 0.092 mmol), (3R,3'R)-1,4-dihydro-2H-spiro[isoquinoline-3,4'-piperidin]-3'-ol (22.0 mg, 0.101 mmol) and DIEA (0.048 mL, 0.28 mmol) in DMF (1 mL) was added 2,4,6-tripropyl-1,3,5,2,4,6-trioxatriphosphinane 2,4,6-trioxide (117 mg, 0.183 mmol, 48% wt, in DMF) at 25° C. The mixture was stirred at 25° C. for 10 min. Water (10 mL) was added to the mixture, and the mixture was extracted with EtOAc (5 mL×3). The combined organic layers were washed with brine (10 mL), dried over anhydrous sodium sulfate, filtered, and the filtrate was concentrated under reduced pressure to give the crude product (4-butoxy-3-(2,2,2-trifluoroethyl)quinolin-7-yl) ((3R,3'R)-3'-hydroxy-2,4-dihydro-JH-spiro[isoquinoline-3,4'-piperidin]-1'-yl)methanone, which was used in the next step without further purification. MS: 528 (M+1).

Step 2: To a solution of (4-butoxy-3-(2,2,2-trifluoroethyl) quinolin-7-yl)((3R,3'R)-3'-hydroxy-2,4-dihydro-1H-spiro [isoquinoline-3,4'-piperidin]-1'-yl)methanone (28 mg, 0.053 mmol) in DCM (5 mL) was added $BBr_3$ (0.100 mL, 1.06 mmol) at 25° C. The mixture was stirred at 25° C. for 12 h. MeOH (20 mL) was added to the mixture, and the mixture was concentrated under reduced pressure. The residue was purified by preparative HPLC (ACN/water with 10 mM $NH_4HCO_3$ modifier) to give ((3R,3'R)-3'-hydroxy-1,4-dihydro-2H-spiro[isoquinoline-3,4'-piperidin]-1'-yl)(4-hydroxy-3-(2,2,2-trifluoroethyl)quinolin-7-yl)methanone. MS: 472 (M+1). $^1$H NMR (400 MHz, $CD_3OD$) δ 8.35 (d, J=8.3 Hz, 1H), 8.13 (s, 1H), 7.66 (br d, J=11.0 Hz, 1H), 7.48 (br dd, J=8.3, 13.0 Hz, 1H), 7.13 (s, 3H), 7.06 (br d, J=3.7 Hz, 1H), 3.96-4.12 (m, 3H), 3.39-3.79 (m, 6H), 2.89-3.08 (m, 1H), 2.70-2.84 (m, 1H), 1.77-2.01 (m, 1H), 1.42-1.67 (m, 1H).

Example 154: ((3R,3'R)-3'-hydroxy-2,4-dihydro-1H-spiro[isoquinoline-3,4'-piperidin]-1'-yl)(8-(tetrahydrofuran-3-yl)-6-(trifluoromethyl)imidazo[1,2-a]pyridin-2-yl)methanone

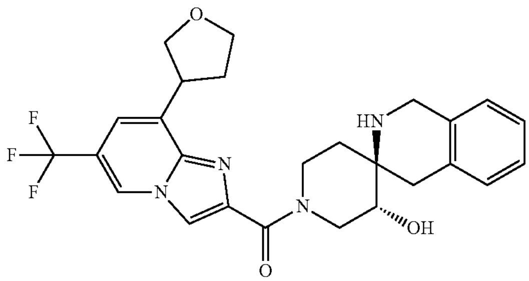 [SMILES: O=C(c1cn2cc(C(F)(F)F)cc(C3CCOC3)c2n1)N1CC[C@]2(Cc3ccccc3CN2)[C@H](O)C1]

Step 1: A mixture of ethyl 8-bromo-6-(trifluoromethyl) imidazo[1,2-a]pyridine-2-carboxylate (851 mg, 2.52 mmol), 2-(2,5-dihydrofuran-3-yl)-4,4,5,5-tetramethyl-1,3,2-dioxaborolane (450 mg, 2.30 mmol), $(dppf)_2PdCl_2$ (336 mg, 0.459 mmol) and potassium carbonate (952 mg, 6.89 mmol) in 1,4-dioxane (5 mL) and water (1 mL) was stirred at 100° C. for 2 h under $N_2$. The mixture was concentrated under reduced pressure. The residue was purified by flash silica gel chromatography (ethyl acetate/pet. ether gradient) to afford ethyl 8-(2,5-dihydrofuran-3-yl)-6-(trifluoromethyl)imidazo [1,2-a]pyridine-2-carboxylate. MS: 327 (M+1).

Step 2: To a mixture of ethyl 8-(2,5-dihydrofuran-3-yl)-6-(trifluoromethyl)imidazo[1,2-a]pyridine-2-carboxylate (80 mg, 0.25 mmol) in EtOH (4 mL) and water (1 mL) was added lithium hydroxide hydrate (30.9 mg, 0.736 mmol) at 20° C. The mixture was stirred at 20° C. for 2 h. The mixture was concentrated to remove EtOH, and $H_2O$ (10 mL) was added. The pH of the solution was adjusted to pH 2 with aq. HCl (1M). The mixture was extracted with EtOAc (5 mL×3). The combined organic layers were washed with brine (5 mL), dried over $Na_2SO_4$, filtered, and concentrated under reduced pressure to give 8-(2,5-dihydrofuran-3-yl)-6-(trifluoromethyl)imidazo[1,2-a]pyridine-2-carboxylic acid, which was used in the next step without further purification. MS: 299 (M+1).

Step 3: To a solution of 8-(2,5-dihydrofuran-3-yl)-6-(trifluoromethyl)imidazo[1,2-a]pyridine-2-carboxylic acid (55 mg, 0.18 mmol) in DCM (4 mL) was added DIEA (0.097 mL, 0.55 mmol), HATU (84 mg, 0.22 mmol) and (3R,3'R)-1,4-dihydro-2H-spiro[isoquinoline-3,4'-piperidin]-3'-ol (44.3 mg, 0.20 mmol). The mixture was stirred at 25° C. for 0.5 h. The mixture was concentrated under reduced pressure. The residue was purified by preparative TLC (ethyl acetate/pet. ether) to give (8-(2,5-dihydrofuran-3-yl)-6-(trifluoromethyl)imidazo[1,2-a]pyridin-2-yl)((3R,3'R)-3'-hydroxy-1,4-dihydro-2H-spiro[isoquinoline-3,4'-piperidin]-1'-yl) methanone. MS: 499 (M+1).

Step 4: A mixture of (8-(2,5-dihydrofuran-3-yl)-6-(trifluoromethyl)imidazo[1,2-a]pyridin-2-yl)((3R,3'R)-3'-hydroxy-1,4-dihydro-2H-spiro[isoquinoline-3,4'-piperidin]-1'-yl)methanone (85 mg, 0.17 mmol) and tris (triphenylphosphine)rhodium(I) chloride (31.6 mg, 0.034 mmol) in THF (2 mL) and tBuOH (2 mL) was stirred under $H_2$ (pressure: 50 psi) at 40° C. for 12 h. The mixture was filtered and concentrated under reduced pressure. The residue was purified by preparative HPLC (water/MeCN, 10 mM $NH_4HCO_3$) to give ((3R,3'R)-3'-hydroxy-2,4-dihydro-1H-spiro[isoquinoline-3,4'-piperidin]-1'-yl)(8-(tetrahydrofuran-3-yl)-6-(trifluoromethyl)imidazo[1,2-a]pyridin-2-yl) methanone. MS: 501 (M+1). $^1$H NMR (500 MHz, $CD_3OD$) δ 8.94 (s, 1H), 8.30 (s, 1H), 7.35-7.38 (m, 1H), 7.06-7.13 (m, 4H), 4.21-4.42 (m, 2H), 3.96-4.07 (m, 8H), 3.64-3.73 (m, 2H), 2.96-3.06 (m, 1H), 2.77-2.84 (m, 1H), 2.45-2.47 (m, 1H), 2.28-2.30 (m, 1H), 1.89-1.92 (m, 1H), 1.56-1.59 (m, 1H).

Example 155-156: [(3R,3'R)-3'-hydroxy-1,4-dihydro-1'H,2H-spiro[isoquinoline-3,4'-piperidin]-1'-yl][(6R,8S)-8-(methoxymethyl)-6-(trifluoromethyl)-5,6,7,8-tetrahydroimidazo[1,2-a]pyridin-2-yl]methanone and [(3R,3'R)-3'-hydroxy-1,4-dihydro-1'H,2H-spiro[isoquinoline-3,4'-piperidin]-1'-yl][(6S,8R)-8-(methoxymethyl)-6-(trifluoromethyl)-5,6,7,8-tetrahydroimidazo[1,2-a]pyridin-2-yl]methanone

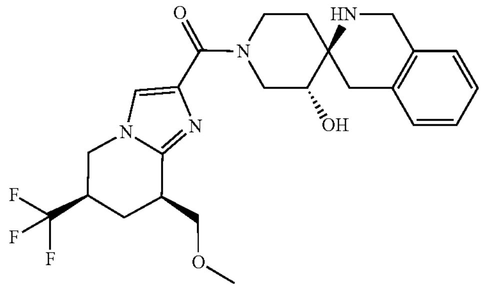

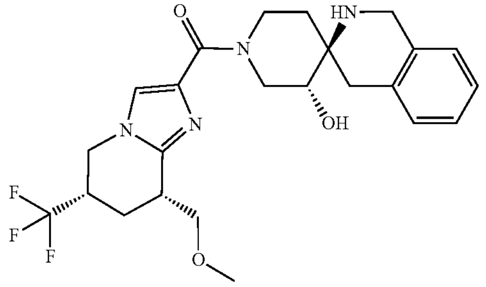

Step 1: To a solution of [(3R,3'R)-3'-hydroxy-1,4-dihydro-1'H,2H-spiro[isoquinoline-3,4'-piperidin]-1'-yl][8-(methoxymethyl)-6-(trifluoromethyl)imidazo[1,2-a]pyridin-2-yl]methanone (215 mg, 0.45 mmol) in MeOH (80 mL) was added Pd/C (10% wt, 537 mg, 0.45 mmol) under $N_2$ atmosphere at 25° C. The mixture was degassed and backfilled with $H_2$ (three times). The resultant mixture was stirred under $H_2$ (pressure: 15 psi) at 25° C. for 12 h. The mixture was filtered, and filtrate was concentrated under reduced pressure. The residue was purified by preparative TLC (DCM/MeOH) to give [(3R,3'R)-3'-hydroxy-1,4-dihydro-1'H,2H-spiro[isoquinoline-3,4'-piperidin]-1'-yl][8-(methoxymethyl)-6-(trifluoromethyl)-5,6,7,8-tetrahydroimidazo[1,2-a]pyridin-2-yl]methanone. MS: 479 (M+1)

Step 2: The mixture of [(3R,3'R)-3'-hydroxy-1,4-dihydro-1'H,2H-spiro[isoquinoline-3,4'-piperidin]-1'-yl][8-(methoxymethyl)-6-(trifluoromethyl)-5,6,7,8-tetrahydroimidazo[1,2-a]pyridin-2-yl]methanone (40 mg, 84 umol) was separated by SFC (AD Column, iso-propanol/$CO_2$) to two isomers.

Peak 1: $^1$H NMR (400 MHz, $CD_3OD$) δ 7.38 (br s, 1H), 7.02 (d, J=2.9 Hz, 3H), 6.95 (br d, J=3.5 Hz, 1H), 4.30 (br dd, J=5.0, 12.0 Hz, 1H), 4.05 (br s, 1H), 3.83-4.00 (m, 5H), 3.80 (br dd, J=3.31, 9.3 Hz, 1H), 3.58-3.68 (m, 1H), 3.47 (br s, 1H), 3.26 (br s, 3H), 2.93-3.17 (m, 2H), 2.84 (br d, J=16.1 Hz, 1H), 2.50-2.75 (m, 1H), 2.25-2.36 (m, 1H), 1.66-1.84 (m, 2H), 1.29-1.55 (m, 1H), 1.19 (br d, J=3.5 Hz, 1H); Peak 2: $^1$H NMR (400 MHz, $CD_3OD$) δ 7.37 (s, 1H), 6.99-7.06 (m, 3H), 6.90-6.98 (m, 1H), 4.30 (br dd, J=4.6, 12.4 Hz, 1H), 4.04 (br d, J=10.1 Hz, 1H), 3.83-3.99 (m, 5H), 3.79 (dd, J=3.4, 9.4 Hz, 1H), 3.67 (br s, 1H), 3.48 (br s, 1H), 3.26 (s, 3H), 3.09 (br dd, J=5.0, 10.0 Hz, 1H), 3.00 (br s, 1H), 2.85 (br d, J=15.0 Hz, 1H), 2.57-2.71 (m, 1H), 2.30 (br dd, J=5.7, 12.8 Hz, 1H), 1.66-1.84 (m, 2H), 1.41 (br s, 1H), 1.15-1.22 (m, 1H).

Example 157-159: Diastereomers of [(3R,3'R)-3'-hydroxy-1,4-dihydro-1'H,2H-spiro[isoquinoline-3,4'-piperidin]-1'-yl][8-(methoxymethyl)-6-methyl-5,6,7,8-tetrahydroimidazo[1,2-a]pyridin-2-yl]methanone

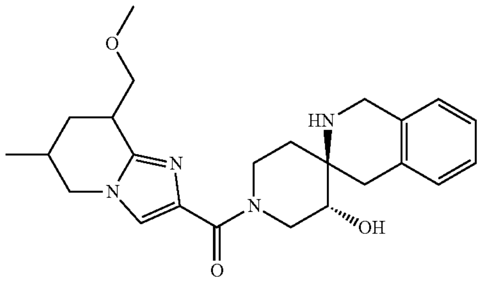 [SMILES: COCC1CC(C)Cn2cc(C(=O)N3CC[C@]4(Cc5ccccc5CN4)[C@H](O)C3)nc21]

Step 1: To a solution of ((3R,3'R)-3'-hydroxy-1,4-dihydro-2H-spiro[isoquinoline-3,4'-piperidin]-1'-yl)(8-(methoxymethyl)-6-methylimidazo[1,2-a]pyridin-2-yl)methanone (50 mg, 0.12 mmol) in MeOH (5 mL) was added Pd—C (12.6 mg, 0.012 mmol) under $N_2$ atmosphere. The mixture was degassed and backfilled with $H_2$ (three times). The resulting mixture was stirred under $H_2$ (pressure: 15 psi) at 25° C. for 5 h. The catalyst was filtered off, and the filtrate was concentrated under reduced pressure. The residue was purified by preparative HPLC (ACN/water, 10 mM $NH_4HCO_3$ modifier) to give [(3R,3'R)-3'-hydroxy-1,4-dihydro-1'H,2H-spiro[isoquinoline-3,4'-piperidin]-1'-yl][8-(methoxymethyl)-6-methyl-5,6,7,8-tetrahydroimidazo[1,2-a]pyridin-2-yl]methanone. MS: 425 (M+1).

Step 2: A mixture of [(3R,3'R)-3'-hydroxy-1,4-dihydro-1'H,2H-spiro[isoquinoline-3,4'-piperidin]-1'-yl][8-(methoxymethyl)-6-methyl-5,6,7,8-tetrahydroimidazo[1,2-a]pyridin-2-yl]methanone (80 mg, 0.19 mmol) was separated by chiral SFC (AD column, ethanol/$CO_2$) to give separated isomers.

(Isomer 1, first eluting): $^1$H NMR (400 MHz, $CD_3OD$) δ 7.25-7.32 (m, 1H), 7.01 (d, J=2.7 Hz, 3H), 6.95 (br d, J=3.3 Hz, 1H), 3.98-4.16 (m, 2H), 3.80-3.97 (m, 3H), 3.74 (dd, J=3.3, 9.26 Hz, 1H), 3.58 (dd, J=6.8, 9.0 Hz, 1H), 3.31-3.52 (m, 3H), 3.24 (br d, J=1.5 Hz, 3H), 2.77-3.05 (m, 2H), 2.53-2.69 (m, 1H), 1.93-2.08 (m, 2H), 1.67-1.82 (m, 1H), 1.28-1.49 (m, 2H), 1.02 (d, J=6.4 Hz, 3H).

(Isomer 2, second eluting): $^1$H NMR (400 MHz, $CD_3OD$) δ 7.38 (s, 1H), 7.09-7.14 (m, 3H), 7.05 (br d, J=2.2 Hz, 1H), 3.93-4.22 (m, 5H), 3.84 (dd, J=3.5, 9.2 Hz, 1H), 3.73 (br s, 1H), 3.41-3.62 (m, 3H), 3.33 (s, 3H), 2.89-3.15 (m, 2H), 2.64-2.85 (m, 1H), 2.04-2.19 (m, 2H), 1.76-1.91 (m, 1H), 1.42-1.58 (m, 2H), 1.12 (d, J=6.6 Hz, 3H).

(Isomer 3, third eluting): $^1$H NMR (400 MHz, CD3OD) δ 7.38 (br s, 1H), 7.12 (d, J=2.9 Hz, 3H), 7.05 (br d, J=2.4 Hz, 1H), 4.03-4.26 (m, 3H), 3.82-4.01 (m, 3H), 3.41-3.72 (m, 5H), 3.32 (br s, 3H), 3.20 (br s, 1H), 2.89-3.13 (m, 1H), 2.64-2.85 (m, 1H), 2.35 (br s, 1H), 2.09 (br d, J=13.9 Hz, 1H), 1.79-1.92 (m, 1H), 1.64-1.78 (m, 1H), 1.39-1.58 (m, 1H), 1.12 (d, J=6.6 Hz, 1H), 1.08 (d, J=6.6 Hz, 2H).

Example 160: ((3R,3'R)-3'-hydroxy-1,4-dihydro-2H-spiro[isoquinoline-3,4'-piperidin]-1'-yl)((6S,8S or 6R,8R)-8-((S or R)-tetrahydrofuran-3-yl)-6-(trifluoromethyl)-5,6,7,8-tetrahydroimidazo[1,2-a]pyridin-2-yl)methanone

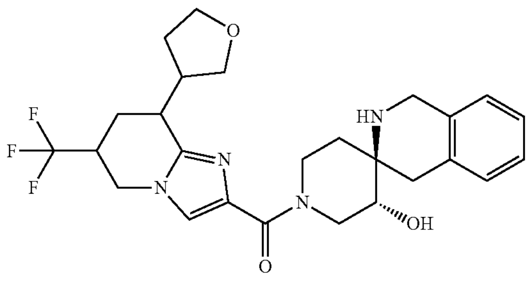 [SMILES: O=C(c1cn2c(n1)C(C1CCOC1)CC(C(F)(F)F)C2)N1CC[C@]2(Cc3ccccc3CN2)[C@H](O)C1]

To a solution of 8-(tetrahydrofuran-3-yl)-6-(trifluoromethyl)-5,6,7,8-tetrahydroimidazo[1,2-a]pyridine-2-carboxylic acid (25 mg, 0.082 mmol) in DMF (2 mL) was added DIEA (0.043 mL, 0.246 mmol), 1-propanephosphonic anhydride (109 mg, 0.164 mmol) (48% in DMF) and (3R,3'R)-2,4-dihydro-1H-spiro[isoquinoline-3,4'-piperidin]-3'-ol (19.7 mg, 0.090 mmol). The mixture was stirred at 20° C. for 1 h. The mixture was concentrated under reduced pressure. The crude product was purified by preparative HPLC (water/MeOH+10 mM $NH_4HCO_3$) to give ((3R,3'R)-3'-hydroxy-1,4-dihydro-2H-spiro[isoquinoline-3,4'-piperidin]-1'-yl)((6R or 6S,8S or 8S)-8-((S or R)-tetrahydrofuran-3-yl)-6-(trifluoromethyl)-5,6,7,8-tetrahydroimidazo[1,2-a]pyridin-2-yl) methanone. MS: 505 (M+1). $^1$H NMR (400 MHz, $CD_3OD$) δ 7.50 (s, 1H), 7.05-7.12 (m, 4H), 4.38-4.40 (m, 1H), 3.99-4.03 (m, 5H), 3.79-3.92 (m, 4H), 3.59-3.61 (m, 3H), 3.07-3.30 (m, 5H), 2.31-2.32 (m, 2H), 1.87-1.91 (m, 2H), 1.72-1.75 (m, 1H), 1.28-1.51 (m, 1H).

The following examples were made following a protocol similar to example 92, except for examples 94 and 95, which were generated from Intermediate 29. When Intermediate 29 was used in the coupling reaction, the residue from the reaction was separated into two isomers, yielding examples 94 and 95.

TABLE 19

The following examples were made following a protocol similar to examples above.

| Ex | Structure | Compound Name | Exact Mass [M + 1] |
|---|---|---|---|
| 161 | 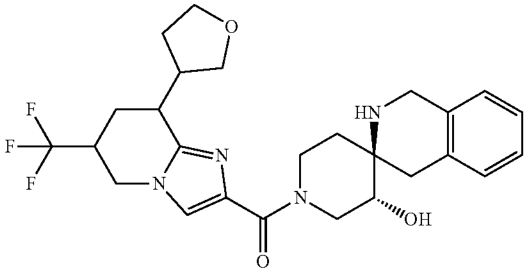 [SMILES: O=C(c1cn2c(n1)C(C1CCOC1)CC(C(F)(F)F)C2)N1CC[C@]2(Cc3ccccc3CN2)[C@H](O)C1] | ((3R,3'R)-3'-hydroxy-1,4-dihydro-2H-spiro[isoquinoline-3,4'-piperidin]-1'-yl)((6S,8S or 6R,8R)-8-((S or R)-tetrahydrofuran-3-yl)-6-(trifluoromethyl)-5,6,7,8-tetrahydroimidazo[1,2-a]pyridin-2-yl)methanone | 505 |
| 162 | 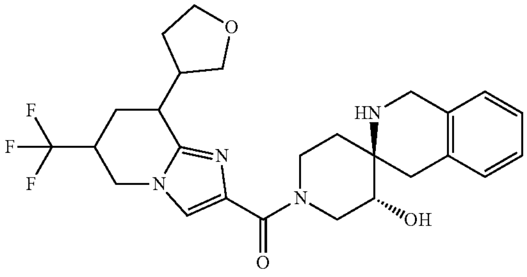 [SMILES: O=C(c1cn2c(n1)C(C1CCOC1)CC(C(F)(F)F)C2)N1CC[C@]2(Cc3ccccc3CN2)[C@H](O)C1] | ((3R,3'R)-3'-hydroxy-1,4-dihydro-2H-spiro[isoquinoline-3,4'-piperidin]-1'-yl)((6S,8S or 6R,8R)-8-((S or R)-tetrahydrofuran-3-yl)-6-(trifluoromethyl)-5,6,7,8-tetrahydroimidazo[1,2-a]pyridin-2-yl)methanone | 505 |
| 163 | 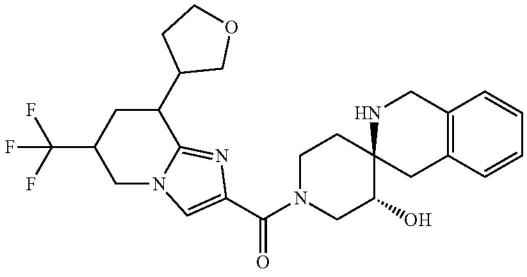 [SMILES: O=C(c1cn2c(n1)C(C1CCOC1)CC(C(F)(F)F)C2)N1CC[C@]2(Cc3ccccc3CN2)[C@H](O)C1] | ((3R,3'R)-3'-hydroxy-1,4-dihydro-2H-spiro[isoquinoline-3,4'-piperidin]-1'-yl)((6S,8S or 6R,8R)-8-((S or R)-tetrahydrofuran-3-yl)-6-(trifluoromethyl)-5,6,7,8-tetrahydroimidazo[1,2-a]pyridin-2-yl)methanone | 505 |

TABLE 19-continued

| The following examples were made following a protocol similar to examples above. | | | |
|---|---|---|---|
| Ex | Structure | Compound Name | Exact Mass [M + 1] |
| 164 | 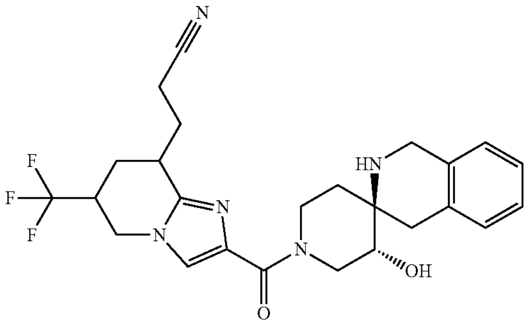 [SMILES: N#CCCC1CC(C(F)(F)F)Cn2cc(C(=O)N3CC[C@]4(Cc5ccccc5CN4)[C@H](O)C3)nc21] | 3-((6R,8S or 6S,8R)-2-((3R,3'R)-3'-hydroxy-1,4-dihydro-2H-spiro[isoquinoline-3,4'-piperidine]-1'-carbonyl)-6-(trifluoromethyl)-5,6,7,8-tetrahydroimidazo[1,2-a]pyridin-8-yl)propanenitrile | 488 |
| 165 | 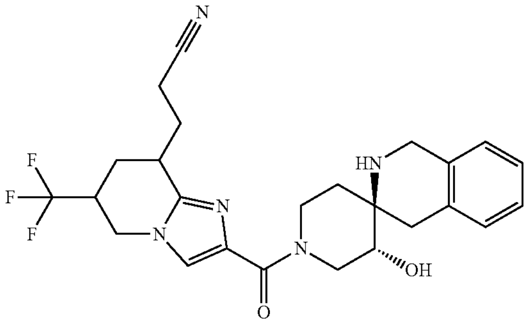 [SMILES: N#CCCC1CC(C(F)(F)F)Cn2cc(C(=O)N3CC[C@]4(Cc5ccccc5CN4)[C@H](O)C3)nc21] | 3-((6R,8S or 6S,8R)-2-((3R,3'R)-3'-hydroxy-1,4-dihydro-2H-spiro[isoquinoline-3,4'-piperidine]-1'-carbonyl)-6-(trifluoromethyl)-5,6,7,8-tetrahydroimidazo[1,2-a]pyridin-8-yl)propanenitrile | 488 |
| 166 | 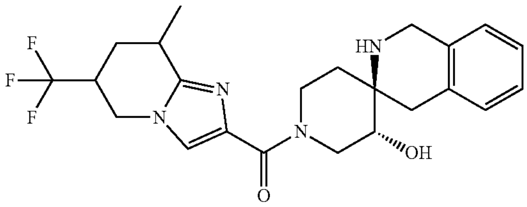 [SMILES: CC1CC(C(F)(F)F)Cn2cc(C(=O)N3CC[C@]4(Cc5ccccc5CN4)[C@H](O)C3)nc21] | ((3R,3'R)-3'-hydroxy-1,4-dihydro-2H-spiro[isoquinoline-3,4'-piperidin]-1'-yl)((6R,8R or 6S,8S)-8-methyl-6-(trifluoromethyl)-5,6,7,8-tetrahydroimidazo[1,2-a]pyridin-2-yl)methanone | 449 |
| 167 | 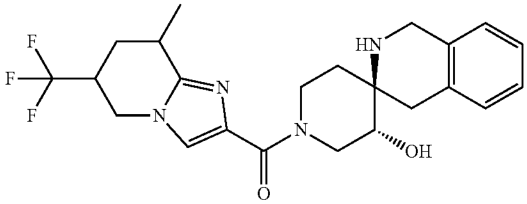 [SMILES: CC1CC(C(F)(F)F)Cn2cc(C(=O)N3CC[C@]4(Cc5ccccc5CN4)[C@H](O)C3)nc21] | ((3R,3'R)-3'-hydroxy-1,4-dihydro-2H-spiro[isoquinoline-3,4'-piperidin]-1'-yl)((6R,8R or 6S,8S)-8-methyl-6-(trifluoromethyl)-5,6,7,8-tetrahydroimidazo[1,2-a]pyridin-2-yl)methanone | 449 |

Example 168: [(3R,3'R)-3'-hydroxy-1,4-dihydro-1'H,2H-spiro[isoquinoline-3,4'-piperidin]-1'-yl][6-(trifluoromethyl)imidazo[1,2-a]pyrimidin-3-yl] methanone Example 169: [(3R,3'R)-3'-hydroxy-1,4-dihydro-1'H,2H-spiro[isoquinoline-3,4'-piperidin]-1'-yl][6-(trifluoromethyl)imidazo[1,2-a]pyrimidin-2-yl] methanone

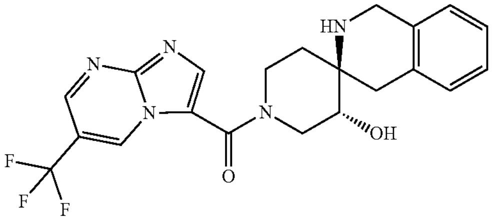

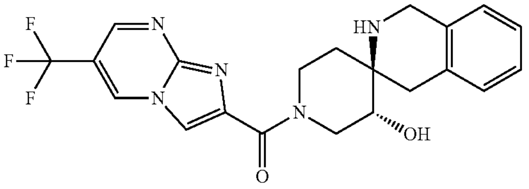

Step 1: A mixture of 5-(trifluoromethyl)pyrimidin-2-amine (220 mg, 1.35 mmol) and 3-bromo-2-oxopropanoic acid (236 mg, 1.42 mmol) in 1,4-dioxane (20 mL) was stirred at 100° C. for 12 h. The mixture was concentrated under reduced pressure to give 6-(trifluoromethyl)imidazo[1,2-a]pyrimidine-2-carboxylic acid and 6-(trifluoromethyl)imidazo[1,2-a]pyrimidine-3-carboxylic acid (1:1), which was used in the next step without further purification. MS: 232 (M+1).

Step 2: To a mixture of 6-(trifluoromethyl)imidazo[1,2-a]pyrimidine-2-carboxylic acid and 6-(trifluoromethyl)imidazo[1,2-a]pyrimidine-3-carboxylic acid (220 mg, 0.476 mmol) in DMF (3 mL) was added DIEA (0.240 mL, 1.37 mmol) at 25° C., and the mixture was stirred at 25° C. for 5 min. T3P® (48% in DMF, 607 mg, 0.916 mmol) and (3R,3'R)-1,4-dihydro-2H-spiro[isoquinoline-3,4'-piperidin]-3'-ol (100 mg, 0.458 mmol) were added to the mixture, and the mixture was stirred at 25° C. for 0.5 h. The mixture was concentrated under reduced pressure. The residue was purified by preparative HPLC (ACN/water with 10 mM $NH_4HCO_3$ modifier) to give two compounds.

[(3R,3'R)-3'-hydroxy-1,4-dihydro-1'H,2H-spiro[isoquinoline-3,4'-piperidin]-1'-yl][6-(trifluoromethyl)imidazo[1,2-a]pyrimidin-2-yl]methanone: MS: 432 (M+1). $^1$H NMR (400 MHz, $CD_3OD$) δ 9.63 (br s, 1H), 8.95 (d, J=2.4 Hz, 1H), 8.31 (br s, 1H), 7.09-7.17 (m, 3H), 7.03-7.09 (m, 1H), 3.88-4.29 (m, 5H), 3.62 (br s, 2H), 2.96 (br d, J=16.1 Hz, 1H), 2.68-2.81 (m, 1H), 1.83-1.97 (m, 1H), 1.60 (td, J=4.1, 13.7 Hz, 1H).

[(3R,3'R)-3'-hydroxy-1,4-dihydro-1'H,2H-spiro[isoquinoline-3,4'-piperidin]-1'-yl][6-(trifluoromethyl)imidazo[1,2-a]pyrimidin-3-yl]methanone. MS: 432 (M+1. $^1$H NMR (400 MHz, $CD_3OD$-$d_4$) δ 9.51 (br d, J=6.1 Hz, 1H), 8.87 (br d, J=8.3 Hz, 1H), 8.25-8.31 (m, 1H), 7.02-7.20 (m, 4H), 4.18-4.38 (m, 1H), 3.93-4.15 (m, 1H), 3.93-4.15 (m, 1H), 3.93-4.15 (m, 1H), 3.56-3.92 (m, 3H), 2.96-3.18 (m, 1H), 2.74-2.94 (m, 1H), 1.92 (br d, J=12.3 Hz, 1H), 1.53-1.68 (m, 1H).

Example 170: 8-{[(3R,3'R)-3'-hydroxy-1,4-dihydro-1'H,2H-spiro[isoquinoline-3,4'-piperidin]-1'-yl]carbonyl}-4-(2,2,2-trifluoroethyl)-1,2,3,4-tetrahydro-5H-1,4-benzodiazepin-5-one

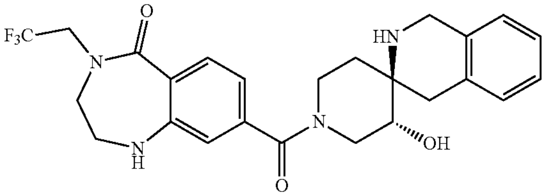 [SMILES: O=C(c1ccc2c(c1)NCCN(CC(F)(F)F)C2=O)N1CC[C@]2(Cc3ccccc3CN2)[C@H](O)C1]

To a mixture of 8-bromo-4-(2,2,2-trifluoroethyl)-3,4-dihydro-1H-benzo[e][1,4]diazepin-5(2H)-one (0.070 g, 0.22 mmol), TEA (0.060 mL, 0.43 mmol), and (3R,3'R)-1,4-dihydro-2H-spiro[isoquinoline-3,4'-piperidin]-3'-ol HCl (0.055 g, 0.217 mmol) in ACN (2.2 mL) was added [1,1'-bis(diphenylphosphino)ferrocene]dichloropalladium(II) (0.016 g, 0.022 mmol) at room temperature under an argon atmosphere. The reaction was degassed and back-filled with carbon monoxide. The reaction was stirred under CO (pressure: 80 psi) at 80° C. for 18 h. The mixture was concentrated under reduced pressure. The residue was purified by mass triggered reverse phase HPLC (0-100% ACN/water with 0.1% TFA modifier) to afford 8-{[(3R,3'R)-3'-hydroxy-1,4-dihydro-1'H,2H-spiro[isoquinoline-3,4'-piperidin]-1'-yl]carbonyl}-4-(2,2,2-trifluoroethyl)-1,2,3,4-tetrahydro-5H-1,4-benzodiazepin-5-one TFA salt. MS: 489 (M+1). $^1$H NMR (500 MHz, DMSO-$d_6$): δ 9.29 (brs, 1H), 9.19 (brs, 1H), 7.77-7.62 (m, 1H), 7.32-7.22 (m, 3H), 6.79-6.68 (m, 1H), 6.61-6.48 (m, 1H), 6.35-6.22 (m, 1H), 6.19-6.04 (m, 1H), 4.50-4.32 (m, 3H), 4.32-4.19 (m, 2H), 3.83-3.72 (m, 1H), 3.72-3.57 (m, 3H), 3.55-3.44 (m, 2H), 3.39-3.12 (m, 3H), 3.12-2.89 (m, 1H), 1.93-1.71 (m, 1H), 1.69-1.51 (m, 1H).

TABLE 20

| Ex | Structure | Compound Name | Exact Mass [M + 1] |
|---|---|---|---|
| The following example were prepared as above example 104 via carbonylation. | | | |
| 171 | 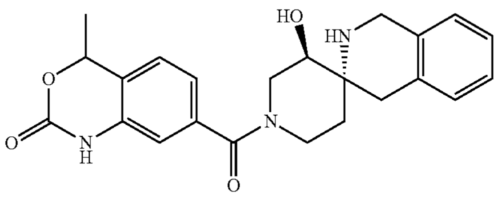 [SMILES: CC1OC(=O)Nc2cc(C(=O)N3CC[C@]4(Cc5ccccc5CN4)[C@H](O)C3)ccc21] | 7-{[(3R,3'R)-3'-hydroxy-1,4-dihydro-1'H,2H-spiro[isoquinoline-3,4'-piperidin]-1'-yl]carbonyl}-4-methyl-1,4-dihydro-2H-3,1-benzoxazin-2-one | 408 |

Example 172: (4-(3-oxa-8-azabicyclo[3.2.1]octane-8-carbonyl)-2-ethoxyphenyl)(1,4-dihydro-2H-spiro[isoquinoline-3,4'-piperidin]-1'-yl)methanone

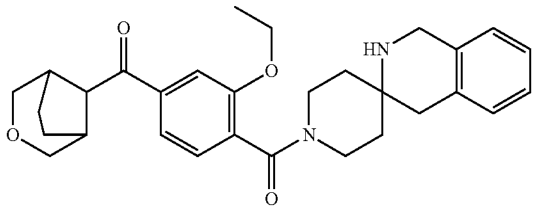 [SMILES: CCOc1cc(C(=O)C2C3CCC2COC3)ccc1C(=O)N1CCC2(CC1)Cc1ccccc1CN2]

To a mixture of 2,4-dihydro-1H-spiro[isoquinoline-3,4'-piperidine](33.1 mg, 0.164 mmol), 4-(3-oxa-8-azabicyclo[3.2.1]octane-8-carbonyl)-2-ethoxybenzoic acid (25 mg, 0.082 mmol), HATU (40.5 mg, 0.106 mmol) in DMF (1.0 mL) was added TEA (45.6 L, 0.328 mmol). The mixture was stirred at room temperature for 1 h. The reaction was concentrated under reduced pressure, and the residue was purified by mass directed RP-HPLC to provide (4-(3-oxa-8-azabicyclo[3.2.1]octane-8-carbonyl)-2-ethoxyphenyl)(2,4-dihydro-1H-spiro[isoquinoline-3,4'-piperidin]-1'-yl)methanone. MS: 490 (M+1). $^1$H NMR (500 MHz, DMSO-d6): δ 9.34 (br s, 1H), 9.25 (s, 1H), 7.33-7.19 (m, 3H), 7.14-7.05 (m, 2H), 4.51 (br s, 2H), 4.45-4.29 (m, 3H), 4.27-4.09 (m, 3H), 3.89 (br s, 1H), 3.64 (br s, 3H), 3.52 (hr s, 1H), 3.41-3.25 (m, 2H), 3.24-3.14 (m, 2H), 3.14-3.03 (m, 2H), 1.88-1.86 (m, 2H), 1.82-1.63 (m, 4H), 1.33 (dt, J=17.8, 6.7 Hz, 3H).

TABLE 21

| Ex | Structure | Compound Name | Exact Mass [M + 1] |
|---|---|---|---|
| The following examples were prepared as above example 75. | | | |
| 173 | 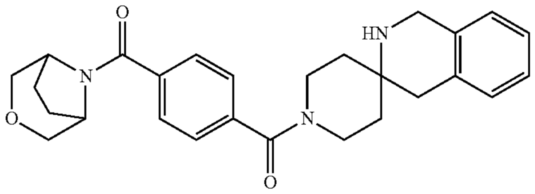 [SMILES: O=C(c1ccc(C(=O)N2C3CCC2COC3)cc1)N1CCC2(CC1)Cc1ccccc1CN2] | (4-(3-oxa-8-azabicyclo[3.2.1]octane-8-carbonyl)phenyl)(1,4-dihydro-2H-spiro[isoquinoline-3,4'-piperidin]-1'-yl)methanone | 446 |
| 174 | 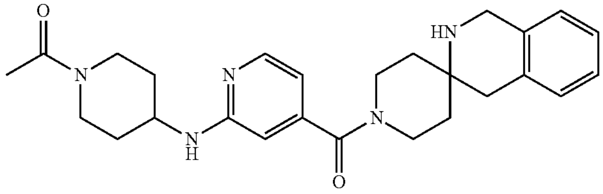 [SMILES: CC(=O)N1CCC(Nc2cc(C(=O)N3CCC4(CC3)Cc3ccccc3CN4)ccn2)CC1] | 1-(4-((4-(1,4-dihydro-2H-spiro[isoquinoline-3,4'-piperidine]-1'-carbonyl)pyridin-2-yl)amino)piperidin-1-yl)ethan-1-one | 448 |
| 175 | 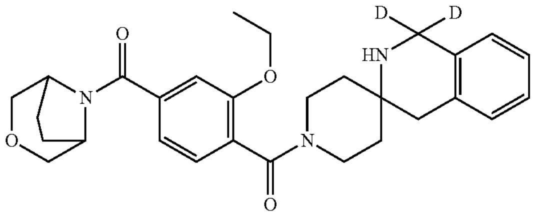 [SMILES: [2H]C1([2H])NC2(CCN(C(=O)c3ccc(C(=O)N4C5CCC4COC5)cc3OCC)CC2)Cc2ccccc21] | (4-(3-oxa-8-azabicyclo[3.2.1]octane-8-carbonyl)-2-ethoxyphenyl)(1,4-dihydro-2H-spiro[isoquinoline-3,4'-piperidin]-1'-yl-1,1-d2)methanone | 492 |

TABLE 21-continued

| The following examples were prepared as above example 75. | | | |
|---|---|---|---|
| Ex | Structure | Compound Name | Exact Mass [M + 1] |
| 176 | 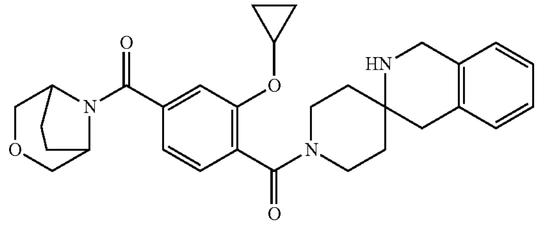 [SMILES: O=C(c1ccc(C(=O)N2C3CCC2COC3)cc1OC1CC1)N1CCC2(CC1)Cc1ccccc1CN2] | (4-(3-oxa-8-azabicyclo[3.2.1]octane-8-carbonyl)-2-cyclopropoxyphenyl)(1,4-dihydro-2H-spiro[isoquinoline-3,4'-piperidin]-1'-yl)methanone | 502 |

Example 177: (5,5-dioxido-6,7-dihydro-4H-pyrazolo[5,1-c][1,4]thiazin-2-yl)((3R,3'R)-3'-hydroxy-1,4-dihydro-2H-spiro[isoqiuinoline-3,4'-piperidin]-1'-yl)methanone

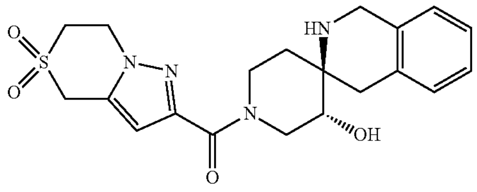 [SMILES: O=C(c1cc2n(n1)CCS(=O)(=O)C2)N1CC[C@]2(Cc3ccccc3CN2)[C@H](O)C1]

To 6,7-dihydro-4H-pyrazolo[5,1-c][1,4]thiazine-2-carboxylic acid 5,5-dioxide (43 mg, 0.2 mmol) was added a solution of ((3H-[1,2,3]triazolo[4,5-b]pyridin-3-yl)oxy)tri(pyrrolidin-1-yl)phosphonium hexafluorophosphate(V) (104 mg, 0.2 mmol) in DMF (0.5 mL), followed by TEA (84 μL, 0.6 mmol) and a suspension of (3R,3'R)-1,4-dihydro-2H-spiro[isoquinoline-3,4'-piperidin]-3'-ol hydrochloride (51 mg, 0.2 mmol) in DMF (0.5 mL). The reaction mixture was stirred for 18 h at room temperature. The mixture was diluted with DMSO/MeOH (1 mL), filtered, and purified by mass triggered reverse phase HPLC (0-100% ACN/water with 0.1% $NH_4OH$ modifier) to afford (5,5-dioxido-6,7-dihydro-4H-pyrazolo[5,1-c][1,4]thiazin-2-yl)((3R,3'R)-3'-hydroxy-1,4-dihydro-2H-spiro[isoquinoline-3,4'-piperidin]-1'-yl)methanone. MS: 417 (M+1). $^1$H NMR (600 MHz, DMSO-$d_6$): δ 7.08-6.95 (m, 4H), 6.39 (d, J=11.1 Hz, 1H), 4.95 (dd, J=47.9, 4.1 Hz, 1H), 4.70 (d, J=6.0 Hz, 2H), 4.59-4.52 (m, 2H), 3.93-3.75 (m, 6H), 3.65-3.57 (m, 1H), 3.38 (s, 1H), 3.26 (s, 1H), 2.72 (dd, J=36.2, 16.4 Hz, 1H), 2.52 (dd, J=21.9, 17.0 Hz, 1H), 2.24 (s, 1H), 1.69-1.58 (m, 1H), 1.32-1.23 (m, 1H).

TABLE 22

| The compounds in the following table were prepared using the methodology herein and the general procedure described in Example 95. | | | |
|---|---|---|---|
| Ex | Structure | Compound Name | Exact Mass [M + 1] |
| 178 | 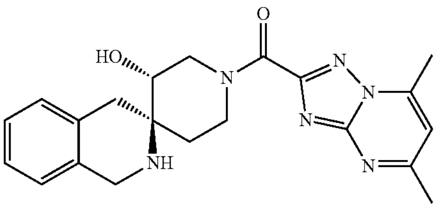 [SMILES: Cc1cc(C)n2nc(C(=O)N3CC[C@]4(Cc5ccccc5CN4)[C@H](O)C3)nc2n1] | (5,7-dimethyl-[1,2,4]triazolo[1,5-a]pyrimidin-2-yl)((3R,3'R)-3'-hydroxy-1,4-dihydro-2H-spiro[isoquinoline-3,4'-piperidin]-1'-yl)methanone | 393 |
| 179 | 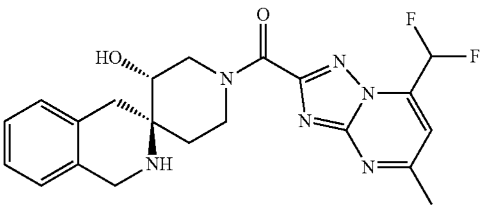 [SMILES: Cc1cc(C(F)F)n2nc(C(=O)N3CC[C@]4(Cc5ccccc5CN4)[C@H](O)C3)nc2n1] | (7-(difluoromethyl)-5-methyl-[1,2,4]triazolo[1,5-a]pyrimidin-2-yl)((3R,3'R)-3'-hydroxy-1,4-dihydro-2H-spiro[isoquinoline-3,4'-piperidin]-1'-yl)methanone | 429 |

TABLE 22-continued

The compounds in the following table were prepared using the methodology herein and the general procedure described in Example 95.

| Ex | Structure | Compound Name | Exact Mass [M + 1] |
|---|---|---|---|
| 180 | 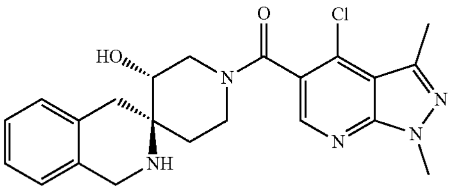 [SMILES: Cc1nn(C)c2ncc(C(=O)N3CC[C@]4(Cc5ccccc5CN4)[C@H](O)C3)c(Cl)c12] | (4-chloro-1,3-dimethyl-1H-pyrazolo[3,4-b]pyridin-5-yl)((3R,3'R)-3'-hydroxy-1,4-dihydro-2H-spiro[isoquinoline-3,4'-piperidin]-1'-yl)methanone | 426 |
| 181 | 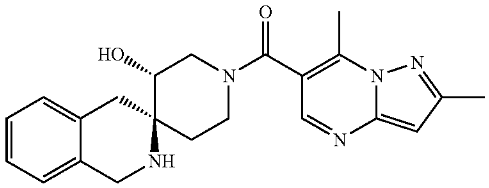 [SMILES: Cc1cc2ncc(C(=O)N3CC[C@]4(Cc5ccccc5CN4)[C@H](O)C3)c(C)n2n1] | (2,7-dimethylpyrazolo[1,5-a]pyrimidin-6-yl)((3R,3'R)-3'-hydroxy-1,4-dihydro-2H-spiro[isoquinoline-3,4'-piperidin]-1'-yl)methanone | 392 |
| 182 | 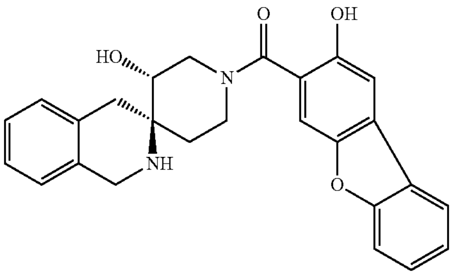 [SMILES: O=C(c1cc2oc3ccccc3c2cc1O)N1CC[C@]2(Cc3ccccc3CN2)[C@H](O)C1] | ((3R,3'R)-3'-hydroxy-1,4-dihydro-2H-spiro[isoquinoline-3,4'-piperidin]-1'-yl)(2-hydroxydibenzo[b,d]furan-3-yl)methanone | 429 |
| 183 | 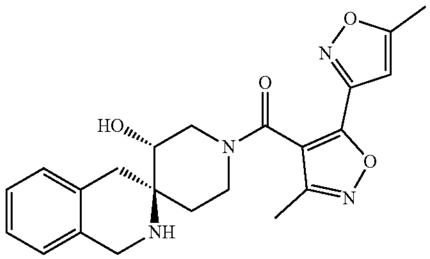 [SMILES: Cc1cc(-c2onc(C)c2C(=O)N2CC[C@]3(Cc4ccccc4CN3)[C@H](O)C2)no1] | (3',5-dimethyl-[3,5'-biisoxazol]-4'-yl)((3R,3'R)-3'-hydroxy-1,4-dihydro-2H-spiro[isoquinoline-3,4'-piperidin]-1'-yl)methanone | 409 |
| 184 | 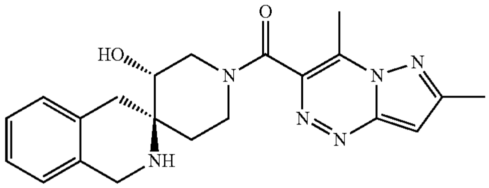 [SMILES: Cc1cc2nnc(C(=O)N3CC[C@]4(Cc5ccccc5CN4)[C@H](O)C3)c(C)n2n1] | (4,7-dimethylpyrazolo[5,1-c][1,2,4]triazin-3-yl)((3R,3'R)-3'-hydroxy-1,4-dihydro-2H-spiro[isoquinoline-3,4'-piperidin]-1'-yl)methanone | 393 |
| 185 | 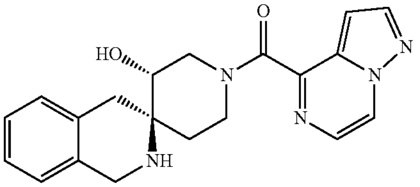 [SMILES: O=C(c1nccn2nccc12)N1CC[C@]2(Cc3ccccc3CN2)[C@H](O)C1] | ((3R,3'R)-3'-hydroxy-1,4-dihydro-2H-spiro[isoquinoline-3,4'-piperidin]-1'-yl)(pyrazolo[1,5-a]pyrazin-4-yl)methanone | 364 |

TABLE 22-continued

| The compounds in the following table were prepared using the methodology herein and the general procedure described in Example 95. | | | |
|---|---|---|---|
| Ex | Structure | Compound Name | Exact Mass [M + 1] |
| 186 | 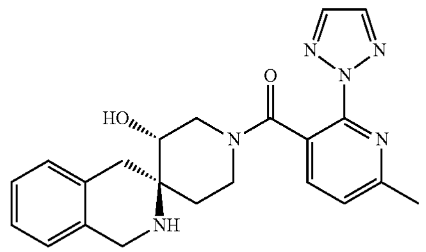 [SMILES: Cc1ccc(C(=O)N2CC[C@]3(Cc4ccccc4CN3)[C@H](O)C2)c(-n2nccn2)n1] | ((3R,3'R)-3'-hydroxy-1,4-dihydro-2H-spiro[isoquinoline-3,4'-piperidin]-1'-yl)(6-methyl-2-(2H-1,2,3-triazol-2-yl)pyridin-3-yl)methanone | 405 |
| 187 | 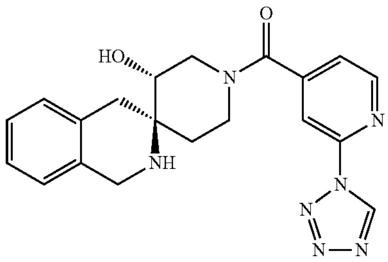 [SMILES: O=C(c1ccnc(-n2cnnn2)c1)N1CC[C@]2(Cc3ccccc3CN2)[C@H](O)C1] | (2-(1H-tetrazol-1-yl)pyridin-4-yl)((3R,3'R)-3'-hydroxy-1,4-dihydro-2H-spiro[isoquinoline-3,4'-piperidin]-1'-yl)methanone | 392 |
| 188 | 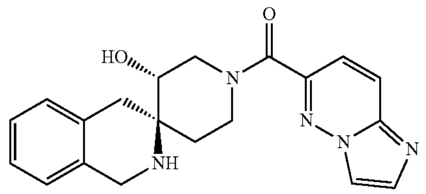 [SMILES: O=C(c1ccc2nccn2n1)N1CC[C@]2(Cc3ccccc3CN2)[C@H](O)C1] | ((3R,3'R)-3'-hydroxy-1,4-dihydro-2H-spiro[isoquinoline-3,4'-piperidin]-1'-yl)(imidazo[1,2-b]pyridazin-6-yl)methanone | 364 |
| 189 | 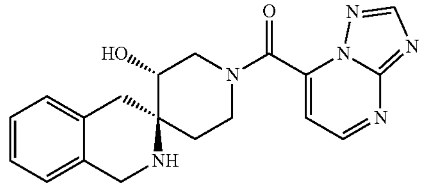 [SMILES: O=C(c1ccnc2ncnn12)N1CC[C@]2(Cc3ccccc3CN2)[C@H](O)C1] | [1,2,4]triazolo[1,5-a]pyrimidin-7-yl((3R,3'R)-3'-hydroxy-1,4-dihydro-2H-spiro[isoquinoline-3,4'-piperidin]-1'-yl)methanone | 365 |
| 190 | 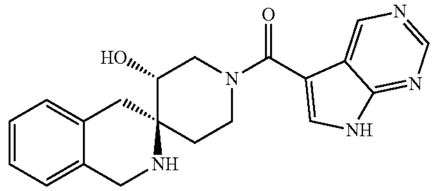 [SMILES: O=C(c1c[nH]c2ncncc12)N1CC[C@]2(Cc3ccccc3CN2)[C@H](O)C1] | [(3R,3'R)-3'-hydroxy-1,4-dihydro-1'H,2H-spiro[isoquinoline-3,4'-piperidin]-1'-yl](1H-pyrrolo[2,3-d]pyrimidin-5-yl)methanone | 364 |
| 191 | 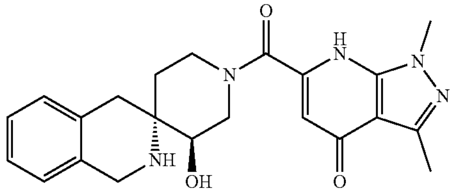 [SMILES: Cc1nn(C)c2[nH]c(C(=O)N3CC[C@]4(Cc5ccccc5CN4)[C@H](O)C3)cc(=O)c12] | 6-{[(3R,3'R)-3'-hydroxy-1,4-dihydro-1'H,2H-spiro[isoquinoline-3,4'-piperidin]-1'-yl]carbonyl}-1,3-dimethyl-1,7-dihydro-4H-pyrazolo[3,4-b]pyridin-4-one | 408 |

TABLE 22-continued

The compounds in the following table were prepared using the methodology herein and the general procedure described in Example 95.

| Ex | Structure | Compound Name | Exact Mass [M + 1] |
|---|---|---|---|
| 192 | 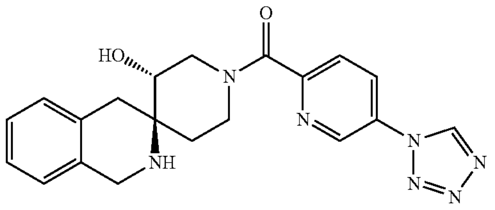 [SMILES: O=C(c1ccc(-n2cnnn2)cn1)N1CC[C@]2(Cc3ccccc3CN2)[C@H](O)C1] | [(3R,3'R)-3'-hydroxy-1,4-dihydro-1'H,2H-spiro[isoquinoline-3,4'-piperidin]-1'-yl][5-(1H-tetrazol-1-yl)-2-pyridinyl]methanone | 392 |
| 193 | 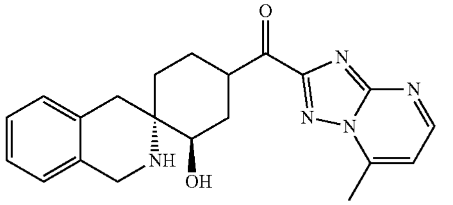 [SMILES: Cc1ccnc2nc(C(=O)C3CC[C@]4(Cc5ccccc5CN4)[C@H](O)C3)nn12] | [(3R,3'R)-3'-hydroxy-1,4-dihydro-1'H,2H-spiro[isoquinoline-3,4'-piperidin]-1'-yl](7-methyl[1,2,d]triazolo[1,5-a]pyrimidin-2-yl)methanone | 379 |
| 194 | 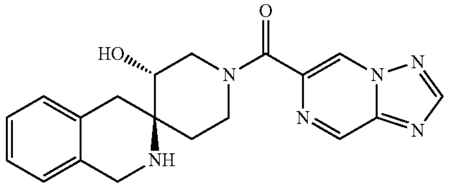 [SMILES: O=C(c1cn2ncnc2cn1)N1CC[C@]2(Cc3ccccc3CN2)[C@H](O)C1] | [(3R,3'R)-3'-hydroxy-1,4-dihydro-1'H,2H-spiro[isoquinoline-3,4'-piperidin]-1'-yl]([1,2,d]triazolo[1,5-a]pyrazin-6-yl)methanone | 365 |
| 195 | 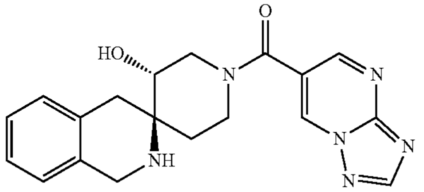 [SMILES: O=C(c1cnc2ncnn2c1)N1CC[C@]2(Cc3ccccc3CN2)[C@H](O)C1] | [(3R,3'R)-3'-hydroxy-1,4-dihydro-1'H,2H-spiro[isoquinoline-3,4'-piperidin]-1'-yl]([1,2,d]triazolo[1,5-a]pyrimidin-6-yl)methanone | 365 |
| 196 | 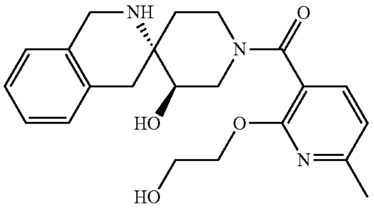 [SMILES: Cc1ccc(C(=O)N2CC[C@]3(Cc4ccccc4CN3)[C@H](O)C2)c(OCCO)n1] | [(3R,3'R)-3'-hydroxy-1,4-dihydro-1'H,2H-spiro[isoquinoline-3,4'-piperidin]-1'-yl][2-(2-hydroxyethoxy)-6-methyl-3-pyridinyl]methanone | 398 |
| 197 | 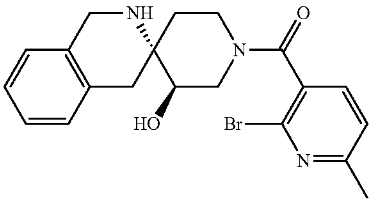 [SMILES: Cc1ccc(C(=O)N2CC[C@]3(Cc4ccccc4CN3)[C@H](O)C2)c(Br)n1] | (2-bromo-6-methyl-3-pyridinyl)[(3R,3'R)-3'-hydroxy-1,4-dihydro-1'H,2H-spiro[isoquinoline-3,4'-piperidin]-1'-yl]methanone | 416 and 418 |
| 198 | 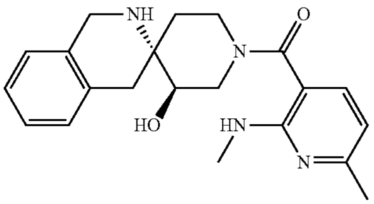 [SMILES: CNc1nc(C)ccc1C(=O)N1CC[C@]2(Cc3ccccc3CN2)[C@H](O)C1] | [(3R,3'R)-3'-hydroxy-1,4-dihydro-1'H,2H-spiro[isoquinoline-3,4'-piperidin]-1'-yl][6-methyl-2-(methylamino)-3-pyridinyl]methanone | 367 |

TABLE 22-continued

The compounds in the following table were prepared using the methodology herein and the general procedure described in Example 95.

| Ex | Structure | Compound Name | Exact Mass [M + 1] |
|---|---|---|---|
| 199 | 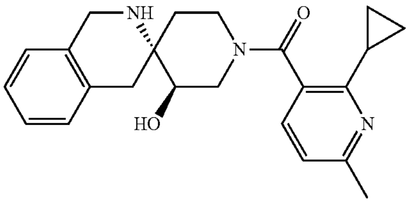 [SMILES: Cc1ccc(C(=O)N2CC[C@]3(Cc4ccccc4CN3)[C@H](O)C2)c(C2CC2)n1] | (2-cyclopropyl-6-methyl-3-pyridinyl)[(3R,3'R)-3'-hydroxy-1,4-dihydro-1'H,2H-spiro[isoquinoline-3,4'-piperidin]-1'-yl]methanone | 378 |
| 200 | 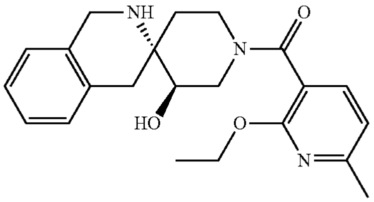 [SMILES: CCOc1nc(C)ccc1C(=O)N1CC[C@]2(Cc3ccccc3CN2)[C@H](O)C1] | (2-ethoxy-6-methyl-3-pyridinyl)[(3R,3'R)-3'-hydroxy-1,4-dihydro-1'H,2H-spiro[isoquinoline-3,4'-piperidin]-1'-yl]methanone | 382 |
| 201 | 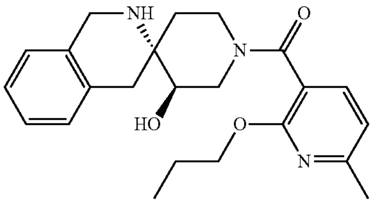 [SMILES: CCCOc1nc(C)ccc1C(=O)N1CC[C@]2(Cc3ccccc3CN2)[C@H](O)C1] | [(3R,3'R)-3'-hydroxy-1,4-dihydro-1'H,2H-spiro[isoquinoline-3,4'-piperidin]-1'-yl](6-methyl-2-propoxy-3-pyridinyl)methanone | 396 |
| 202 | 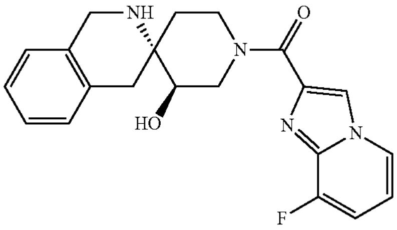 [SMILES: O=C(c1cn2cccc(F)c2n1)N1CC[C@]2(Cc3ccccc3CN2)[C@H](O)C1] | (8-fluoroimidazo[1,2-a]pyridin-2-yl)[(3R,3'R)-3'-hydroxy-1,4-dihydro-1'H,2H-spiro[isoquinoline-3,4'-piperidin]-1'-yl]methanone | 381 |
| 203 | 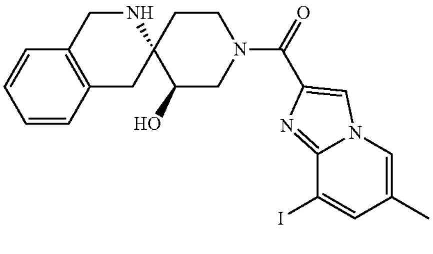 [SMILES: Cc1cc(I)c2nc(C(=O)N3CC[C@]4(Cc5ccccc5CN4)[C@H](O)C3)cn2c1] | [(3R,3'R)-3'-hydroxy-1,4-dihydro-1'H,2H-spiro[isoquinoline-3,4'-piperidin]-1'-yl](8-iodo-6-methylimidazo[1,2-a]pyridin-2-yl)methanone | 503 |
| 204 | 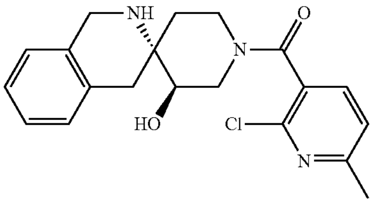 [SMILES: Cc1ccc(C(=O)N2CC[C@]3(Cc4ccccc4CN3)[C@H](O)C2)c(Cl)n1] | (2-chloro-6-methyl-3-pyridinyl)[(3R,3'R)-3'-hydroxy-1,4-dihydro-1'H,2H-spiro[isoquinoline-3,4'-piperidin]-1'-yl]methanone | 372 |

TABLE 22-continued

The compounds in the following table were prepared using the methodology herein and the general procedure described in Example 95.

| Ex | Structure | Compound Name | Exact Mass [M + 1] |
|---|---|---|---|
| 205 | 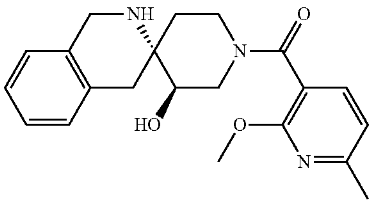 [SMILES: COc1nc(C)ccc1C(=O)N1CC[C@]2(Cc3ccccc3CN2)[C@H](O)C1] | [(3R,3'R)-3'-hydroxy-1,4-dihydro-1'H,2H-spiro[isoquinoline-3,4'-piperidin]-1'-yl](2-methoxy-6-methyl-3-pyridinyl)methanone | 368 |
| 206 | 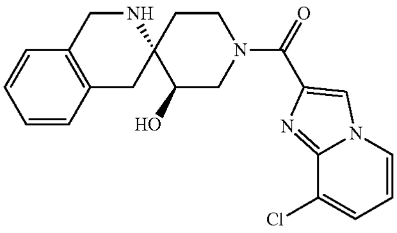 [SMILES: O=C(c1cn2cccc(Cl)c2n1)N1CC[C@]2(Cc3ccccc3CN2)[C@H](O)C1] | (8-chloroimidazo[1,2-a]pyridin-2-yl)[(3R,3'R)-3'-hydroxy-1,4-dihydro-1'H,2H-spiro[isoquinoline-3,4'-piperidin]-1'-yl]methanone | 397 |
| 207 | 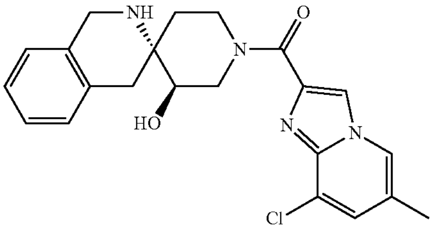 [SMILES: Cc1cc(Cl)c2nc(C(=O)N3CC[C@]4(Cc5ccccc5CN4)[C@H](O)C3)cn2c1] | (8-chloro-6-methylimidazo[1,2-a]pyridin-2-yl)[(3R,3'R)-3'-hydroxy-1,4-dihydro-1'H,2H-spiro[isoquinoline-3,4'-piperidin]-1'-yl]methanone | 411 |
| 208 | 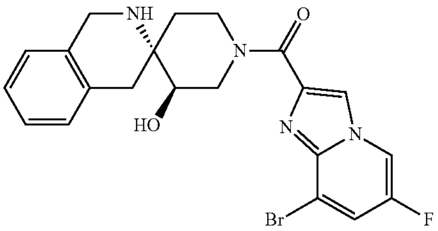 [SMILES: O=C(c1cn2cc(F)cc(Br)c2n1)N1CC[C@]2(Cc3ccccc3CN2)[C@H](O)C1] | (8-bromo-6-fluoroimidazo[1,2-a]pyridin-2-yl)[(3R,3'R)-3'-hydroxy-1,4-dihydro-1'H,2H-spiro[isoquinoline-3,4'-piperidin]-1'-yl]methanone | 459 and 461 |
| 209 | 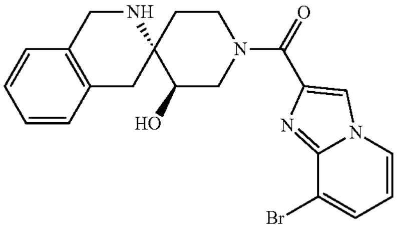 | (8-bromoimidazo[1,2-a]pyridin-2-yl)[(3R,3'R)-3'-hydroxy-1,4-dihydro-1'H,2H-spiro[isoquinoline-3,4'-piperidin]-1'-yl]methanone | 441 and 443 |
| 210 | 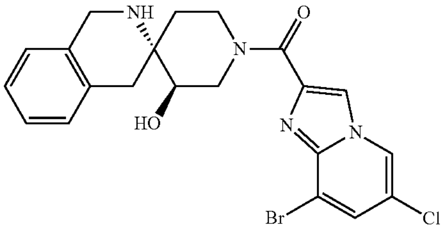 [SMILES: O=C(c1cn2cc(Cl)cc(Br)c2n1)N1CC[C@]2(Cc3ccccc3CN2)[C@H](O)C1] | (8-bromo-6-chloroimidazo[1,2-a]pyridin-2-yl)[(3R,3'R)-3'-hydroxy-1,4-dihydro-1'H,2H-spiro[isoquinoline-3,4'-piperidin]-1'-yl]methanone | 475 and 477 |

TABLE 22-continued

| The compounds in the following table were prepared using the methodology herein and the general procedure described in Example 95. | | | |
|---|---|---|---|
| Ex | Structure | Compound Name | Exact Mass [M + 1] |
| 211 | 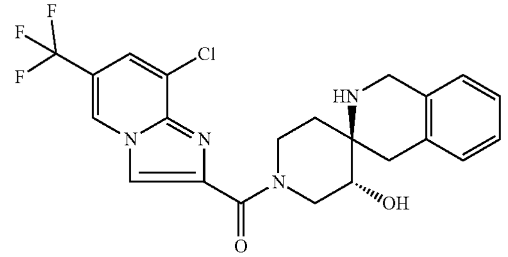 [SMILES: O=C(c1cn2cc(C(F)(F)F)cc(Cl)c2n1)N1CC[C@]2(Cc3ccccc3CN2)[C@H](O)C1] | [8-chloro-6-(trifluoromethyl)imidazo[1,2-a]pyridin-2-yl][(3R,3'R)-3'-hydroxy-1,4-dihydro-1'H,2H-spiro[isoquinoline-3,4'-piperidin]-1'-yl]methanone | 465 |
| 212 | 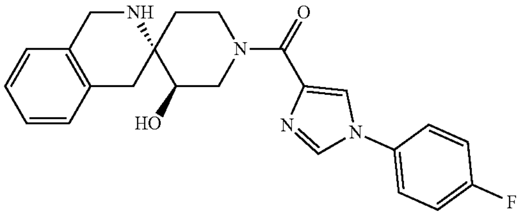 [SMILES: O=C(c1cn(-c2ccc(F)cc2)cn1)N1CC[C@]2(Cc3ccccc3CN2)[C@H](O)C1] | [1-(4-fluorophenyl)-1H-imidazol-4-yl][(3R,3'R)-3'-hydroxy-1,4-dihydro-1'H,2H-spiro[isoquinoline-3,4'-piperidin]-1'-yl]methanone | 407 |
| 213 | 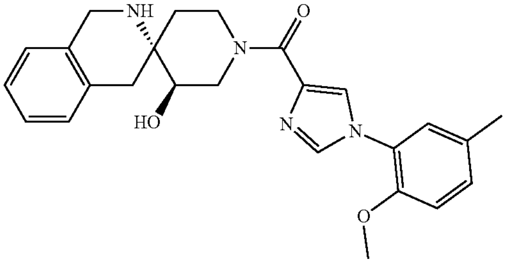 [SMILES: COc1ccc(C)cc1-n1cnc(C(=O)N2CC[C@]3(Cc4ccccc4CN3)[C@H](O)C2)c1] | [(3R,3'R)-3'-hydroxy-1,4-dihydro-1'H,2H-spiro[isoquinoline-3,4'-piperidin]-1'-yl][1-(2-methoxy-5-methylphenyl)-1H-imidazol-4-yl]methanone | 433 |
| 214 | 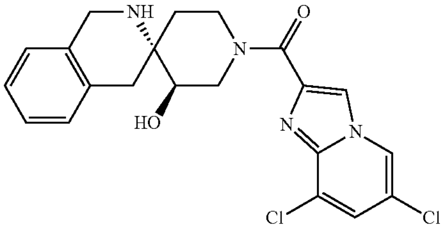 [SMILES: O=C(c1cn2cc(Cl)cc(Cl)c2n1)N1CC[C@]2(Cc3ccccc3CN2)[C@H](O)C1] | (6,8-dichloroimidazo[1,2-a]pyridin-2-yl)[(3R,3'R)-3'-hydroxy-1,4-dihydro-1'H,2H-spiro[isoquinoline-3,4'-piperidin]-1'-yl]methanone | 431 |
| 215 | 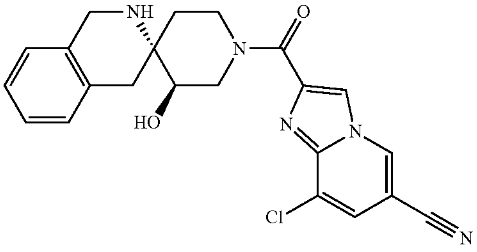 [SMILES: N#Cc1cc(Cl)c2nc(C(=O)N3CC[C@]4(Cc5ccccc5CN4)[C@H](O)C3)cn2c1] | 8-chloro-2-{[(3R,3'R)-3'-hydroxy-1,4-dihydro-1'H,2H-spiro[isoquinoline-3,4'-piperidin]-1'-yl]carbonyl}imidazo[1,2-a]pyridine-6-carbonitrile | 422 |

TABLE 22-continued

The compounds in the following table were prepared using the methodology herein and the general procedure described in Example 95.

| Ex | Structure | Compound Name | Exact Mass [M + 1] |
|---|---|---|---|
| 216 | 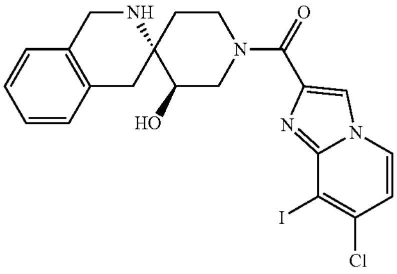 [SMILES: O=C(c1cn2ccc(Cl)c(I)c2n1)N1CC[C@]2(Cc3ccccc3CN2)[C@H](O)C1] | (7-chloro-8-iodoimidazo[1,2-a]pyridin-2-yl)[(3R,3'R)-3'-hydroxy-1,4-dihydro-1'H,2H-spiro[isoquinoline-3,4'-piperidin]-1'-yl]methanone | 523 |
| 217 | 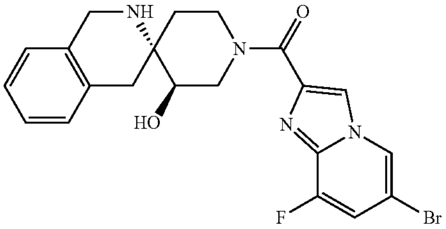 [SMILES: O=C(c1cn2cc(Br)cc(F)c2n1)N1CC[C@]2(Cc3ccccc3CN2)[C@H](O)C1] | (6-bromo-8-fluoroimidazo[1,2-a]pyridin-2-yl)[(3R,3'R)-3'-hydroxy-1,4-dihydro-1'H,2H-spiro[isoquinoline-3,4'-piperidin]-1'-yl]methanone | 459 and 461 |
| 218 | 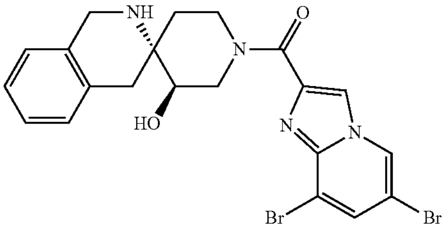 [SMILES: O=C(c1cn2cc(Br)cc(Br)c2n1)N1CC[C@]2(Cc3ccccc3CN2)[C@H](O)C1] | (6,8-dibromoimidazo[1,2-a]pyridin-2-yl)[(3R,3'R)-3'-hydroxy-1,4-dihydro-1'H,2H-spiro[isoquinoline-3,4'-piperidin]-1'-yl]methanone | 521 |
| 219 | 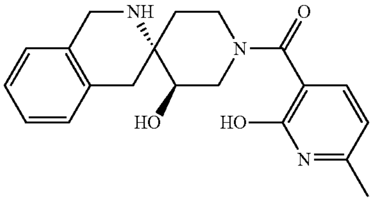 [SMILES: Cc1ccc(C(=O)N2CC[C@]3(Cc4ccccc4CN3)[C@H](O)C2)c(O)n1] | 3-{[(3R,3'R)-3'-hydroxy-1,4-dihydro-1'H,2H-spiro[isoquinoline-3,4'-piperidin]-1'-yl]carbonyl}-6-methyl-2(1H)-pyridinone | 354 |
| 220 | 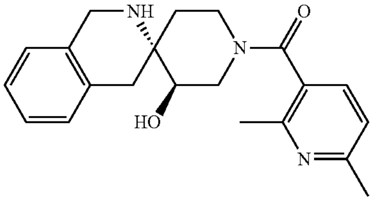 [SMILES: Cc1ccc(C(=O)N2CC[C@]3(Cc4ccccc4CN3)[C@H](O)C2)c(C)n1] | (2,6-dimethyl-3-pyridinyl)[(3R,3'R)-3'-hydroxy-1,4-dihydro-1'H,2H-spiro[isoquinoline-3,4'-piperidin]-1'-yl]methanone | 352 |
| 221 | 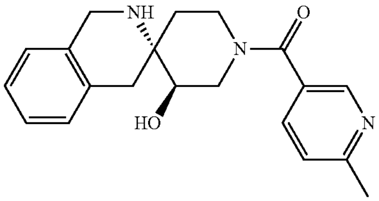 [SMILES: Cc1ccc(C(=O)N2CC[C@]3(Cc4ccccc4CN3)[C@H](O)C2)cn1] | [(3R,3'R)-3'-hydroxy-1,4-dihydro-1'H,2H-spiro[isoquinoline-3,4'-piperidin]-1'-yl](6-methyl-3-pyridinyl)methanone | 338 |

TABLE 22-continued

| The compounds in the following table were prepared using the methodology herein and the general procedure described in Example 95. | | | |
|---|---|---|---|
| Ex | Structure | Compound Name | Exact Mass [M + 1] |
| 222 | 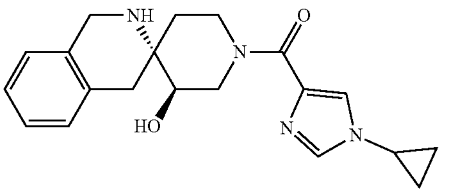 [SMILES: O=C(c1cn(C2CC2)cn1)N1CC[C@]2(Cc3ccccc3CN2)[C@H](O)C1] | (1-cyclopropyl-1H-imidazol-4-yl)[(3R,3'R)-3'-hydroxy-1,4-dihydro-1'H,2H-spiro[isoquinoline-3,4'-piperidin]-1'-yl]methanone | 353 |
| 223 | 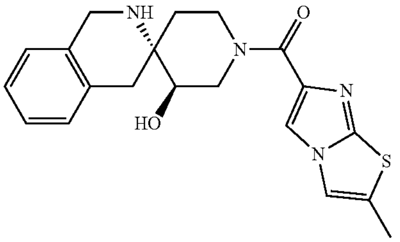 [SMILES: Cc1cn2cc(C(=O)N3CC[C@]4(Cc5ccccc5CN4)[C@H](O)C3)nc2s1] | [(3R,3'R)-3'-hydroxy-1,4-dihydro-1'H,2H-spiro[isoquinoline-3,4'-piperidin]-1'-yl](2-methylimidazo[2,1-b][1,3]thiazol-6-yl)methanone | 383 |
| 224 | 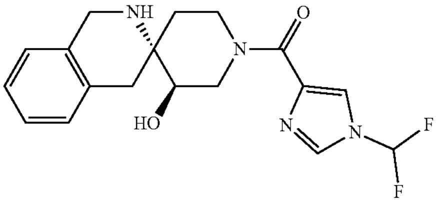 [SMILES: O=C(c1cn(C(F)F)cn1)N1CC[C@]2(Cc3ccccc3CN2)[C@H](O)C1] | [1-(difluoromethyl)-1H-imidazol-4-yl][(3R,3'R)-3'-hydroxy-1,4-dihydro-1'H,2H-spiro[isoquinoline-3,4'-piperidin]-1'-yl]methanone | 363 |

Examples 225 and 226: [6-bromo-8-(1-methoxyethyl)imidazo[1,2-a]pyridin-2-yl][(3R,3'R)-6-chloro-3'-hydroxy-1,4-dihydro-1'H,2H-spiro[isoquinoline-3,4'-piperidin]-1'-yl]methanone and [6-bromo-8-(1-methoxyethyl)imidazo[1,2-a]pyridin-2-yl][(3R,3'R)-7-chloro-3'-hydroxy-1,4-dihydro-1'H,2H-spiro[isoquinoline-3,4'-piperidin]-1'-yl]methanone

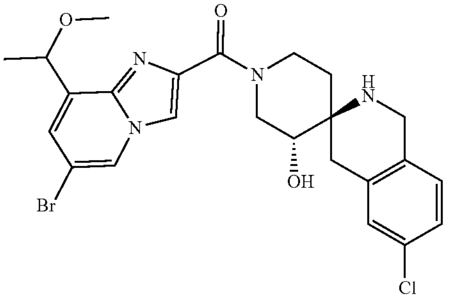

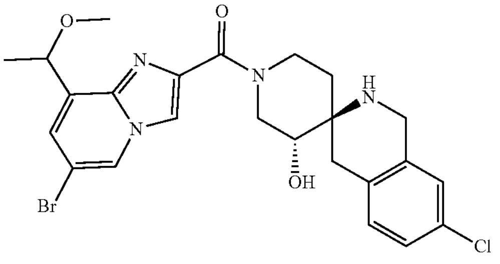

Step 1: Di-tert-butyl dicarbonate (2.66 mL, 11.5 mmol) was added to a solution of (3R,3'R)-2,4-dihydro-1H-spiro[isoquinoline-3,4'-piperidin]-3'-ol (500. mg, 2.29 mmol), DMAP (280 mg, 2.3 mmol) and triethylamine (0.96 mL, 6.9 mmol) in DCM (5 mL). The reaction was stirred at room temperature overnight. Additional di-tert-butyl dicarbonate (2.66 mL, 11.5 mmol) was added and the reaction was stirred overnight. Again, additional di-tert-butyl dicarbonate (2.66 mL, 11.5 mmol) and DMAP (280 mg, 2.29 mmol) were added, and the reaction was stirred overnight. The reaction was treated with brine (5 mL) and extracted with DCM (2×10 mL). The combined organics were dried over sodium sulfate, concentrated, and purified by column chromatography on silica gel eluting with EtOAc/isohexane (0% to 100%) to afford (3R,3'R)-di-tert-butyl 3'-((tert-butoxycarbonyl)oxy)-1H-spiro[isoquinoline-3,4'-piperidine]-1',2(4H)-dicarboxylate. MS: 541 (M+Na).

Step 2: In a glovebox, a 500 mL Schlenck flask microwave vial was charged with 4,4'-di-tert-butyl-2,2'-bipyridine (217 mg, 0.808 mmol), bis(pinacolato)diboron (3.08 g, 12.1 mmol) and (1,5-cyclooctadiene)(methoxy)iridium(I) dimer (268 mg, 0.404 mmol). The flask was sealed and removed from the glovebox. Cyclohexane (40 mL) was added and the vessel was sealed and heated to 80° C. for 1 h. Then a solution of (3R,3'R)-di-tert-butyl 3'-((tert-butoxycarbonyl)oxy)-1H-spiro[isoquinoline-3,4'-piperidine]-1',2(4H)-dicarboxylate (4.19 g, 8.08 mmol) in cyclohexane (40 mL) was added. The reaction was heated to 80° C. overnight. The crude material was cooled to room temperature and concentrated. Copper(II) chloride (6.52 g, 48.5 mmol) was dissolved in water (40 mL) and a solution of the crude from above in MeOH (40.0 mL) was added, and the reaction was then heated to 90° C. overnight. The reaction mixture was cooled, filtered through Celite®, concentrated, and purified by column chromatography on silica gel eluting with MeOH/DCM (0% to 100%). The desired fractions were concentrated and the material was dissolved in MeOH/Water (1:1, 200 mL). Dowex 50WX2 (100 g) was added and the mixture stirred at room temperature for 2 h. The mixture was then filtered, and the resin washed with MeOH/Water (1:1) to provide (3R,3'R)-6/7-chloro-2,4-dihydro-1H-spiro[isoquinoline-3,4'-piperidin]-3'-ol as a mixture of regioisomers. MS: 253 (M+1).

Step 3: 1-propanephosphonic anhydride (378 mg, 0.593 mmol) was added to a solution of 6-bromo-8-(1-methoxyethyl)imidazo[1,2-a]pyridine-2-carboxylic acid (118 mg, 0.396 mmol), (3R,3'R)-7/6-chloro-2,4-dihydro-1H-spiro[isoquinoline-3,4'-piperidin]-3'-ol (100 mg, 0.40 mmol), and Hunig's Base (346 μl, 1.98 mmol) in N,N-dimethylformamide (2000 μL) and the reaction was stirred at room temperature for 1 h. The mixture was purified by preparative HPLC reverse phase (C-18), eluting with MeCN/Water+0.1% TFA. The material was then further purified by SFC (OJ-H column, MeOH/$CO_2$/0.1% $NH_4OH$) to afford [6-bromo-8-(1-methoxyethyl)imidazo[1,2-a]pyridin-2-yl][(3R,3'R)-6-chloro-3'-hydroxy-1,4-dihydro-1'H,2H-spiro[isoquinoline-3,4'-piperidin]-1'-yl]methanone (isomer 1, first eluting) and [6-bromo-8-(1-methoxyethyl)imidazo[1,2-a]pyridin-2-yl][(3R,3'R)-7-chloro-3'-hydroxy-1,4-dihydro-1'H,2H-spiro[isoquinoline-3,4'-piperidin]-1'-yl]methanone (isomer 2, second eluting). Isomer 1: MS: 535 (M+1). $^1H$ NMR (600 MHz, DMSO-$d_6$) δ 8.85 (d, J=12.1 Hz, 1H), 8.24 (s, 1H), 7.32-7.23 (m, 1H), 7.19-7.12 (m, 2H), 7.09-7.02 (m, 1H), 5.18 (d, J=3.4 Hz, 1H), 4.92-4.82 (m, 1H), 4.28-3.67 (m, 5H), 3.36-3.31 (m, 4H), 2.83-2.52 (m, 4H), 1.52-1.42 (m, 3H). Isomer 2: MS: 535 (M+1). $^1H$ NMR (600 MHz, $CDCl_3$) δ 8.85 (d, J=12.0 Hz, 1H), 8.24 (s, 1H), 7.32-7.24 (m, 1H), 7.18-7.08 (m, 3H), 5.17 (d, J=3.5 Hz, 1H), 4.91-4.84 (m, 1H), 4.27-3.67 (m, 5H), 3.37-3.30 (m, 4H), 2.80-2.51 (m, 4H), 1.53-1.43 (m, 3H).

Example 227 and 228: (6-cyclopropylimidazo[1,2-a]pyrimidin-2-yl)[(3R,3'R)-3'-hydroxy-6-methyl-1,4-dihydro-1'H,2H-spiro[isoquinoline-3,4'-piperidin]-1'-yl]methanone and (6-cyclopropylimidazo[1,2-a]pyrimidin-2-yl)[(3R,3'R)-3'-hydroxy-7-methyl-1,4-dihydro-1'H,2H-spiro[isoquinoline-3,4'-piperidin-1'-yl]methanone

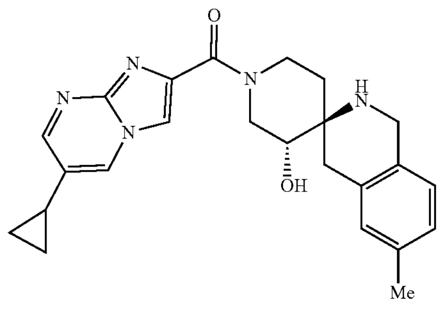

-continued

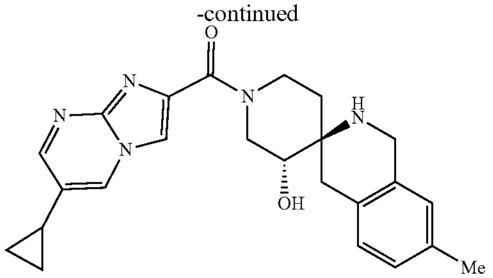

Step 1: A 20 mL microwave vial was charged with methyl 6-chloroimidazo[1,2-a]pyrimidine-2-carboxylate (580 mg, 2.74 mmol) and Pd-PEPPSI-IPent (218 mg, 0.274 mmol). The vial was evacuated and backfilled with argon (3×), then cyclopropylzine bromide (11.0 mL, 5.50 mmol) was added and the reaction was stirred at room temperature for 2 h. The reaction was treated with a few drops of acetic acid and concentrated. The residue was purified by column chromatography on silica gel, eluting with EtOAc/isohexane (0% to 100%) to give methyl 6-cyclopropylimidazo[1,2-a]pyrimidine-2-carboxylate. MS: 218 (M+1).

Step 2: Lithium hydroxide (61.4 mg, 2.56 mmol) was charged in a 20 mL microwave vial and a solution of methyl 6-cyclopropylimidazo[1,2-a]pyrimidine-2-carboxylate (371 mg, 1.71 mmol) in MeOH (1 mL) was added followed by water (1 mL). The reaction was heated to 80° C. overnight. The reaction was neutralized with 1M HCl and the precipitate was filtered off. The filtrate was concentrated to provide 6-cyclopropylimidazo[1,2-a]pyrimidine-2-carboxylic acid. MS: MS: 204 (M+1).

Step 3: 1-propanephosphonic anhydride (438 mg, 0.688 mmol) was added to a solution of 6-cyclopropylimidazo[1,2-a]pyrimidine-2-carboxylic acid (93 mg, 0.46 mmol), (3R,3'R)-7/6-chloro-2,4-dihydro-1H-spiro[isoquinoline-3,4'-piperidin]-3'-ol (116 mg, 0.459 mmol), and Hunig's base (401 μL, 2.30 mmol) in N,N-dimethylformamide (2000 μL) and the reaction was stirred at room temperature for 1 h. The mixture was purified by preparative HPLC reverse phase (C-18), eluting with MeCN/Water+0.1% TFA to provide ((3R,3'R)-6/7-chloro-3'-hydroxy-2,4-dihydro-1H-spiro[isoquinoline-3,4'-piperidin]-1'-yl)(6-cyclopropylimidazo[1,2-a]pyrimidin-2-yl)methanone as mixture of regioisomers.

Step 4: Pd-PEPPSI-IPent (14 mg, 0.017 mmol) was charged in a 2 mL microwave vial. The vial was evacuated and backfilled with argon (3×). A solution of ((3R,3'R)-6/7-chloro-3'-hydroxy-2,4-dihydro-1H-spiro[isoquinoline-3,4'-piperidin]-1'-yl)(6-cyclopropylimidazo[1,2-a]pyrimidin-2-yl)methanone (15 mg, 0.034 mmol) in THF (1713 L) was added followed by dimethylzinc (68.5 μL, 2M in toluene, 0.137 mmol). The reaction was stirred at room temperature overnight. The reaction was treated with a few drops of AcOH and then concentrated. The crude mixture was purified by preparative HPLC reverse phase (C-18), eluting with Acetonitrile/Water+0.05% $NH_3$ to provide (6-cyclopropylimidazo[1,2-a]pyrimidin-2-yl)((3R,3'R)-3'-hydroxy-6-methyl-2,4-dihydro-1H-spiro[isoquinoline-3,4'-piperidin]-1'-yl)methanone.

The material was then separated by SFC (Luna diol column, MeOH/$CO_2$/0.1% $NH_4OH$) to afford (6-cyclopropylimidazo[1,2-a]pyrimidin-2-yl)[(3R,3'R)-3'-hydroxy-6-methyl-1,4-dihydro-1'H,2H-spiro[isoquinoline-3,4'-piperidin]-1'-yl]methanone (Isomer 1, first eluting) and (6-cyclopropylimidazo[1,2-a]pyrimidin-2-yl)[(3R,3'R)-3'- hydroxy-7-methyl-1,4-dihydro-1'H,2H-spiro[isoquinoline-3,4'-piperidin]-1'-yl]methanone (Isomer 2, second eluting).

Isomer 1: MS: 418 (M+1). 1H NMR (600 MHz, $CD_3OD$) δ 8.96 (s, 1H), 8.61 (d, J=2.3 Hz, 1H), 8.15-8.08 (m, 1H), 7.13-6.94 (m, 3H), 4.58 (s, 1H), 4.29 (s, 1H), 4.23-3.99 (m, 3H), 3.84-3.70 (m, 3H), 3.64 (s, 1H), 3.22-3.12 (m, 1H), 3.03-2.92 (m, 1H), 2.31 (s, 3H), 2.15-2.07 (m, 1H), 2.03-1.95 (m, 1H), 1.72-0.74 (m, 3H). Isomer 2: MS: 418 (M+1). $^1$H NMR (600 MHz, $CD_3OD$) δ 8.63 (s, 1H), 8.54 (d, J=9.7 Hz, 1H), 8.05 (d, J=9.2 Hz, 1H), 7.04-6.85 (m, 3H), 4.28-4.06 (m, 2H), 4.03-3.82 (m, 3H), 3.76-3.53 (m, 2H), 3.04-2.89 (m, 1H), 2.83-2.66 (m, 1H), 2.27 (s, 3H), 2.11-1.99 (m, 1H), 1.90 (s, 1H), 1.61-1.46 (m, 2H), 1.37-0.76 (m, 3H).

Example 229: [(3R,3'R)-3'-hydroxy-1,4-dihydro-1'H,2H-spiro[isoquinoline-3,4'-piperidin]-1'-yl]{8-[(1R)-1-methoxyethyl]-6-[(2-methoxyethyl)(methyl)amino]imidazo[1,2-a]pyridin-2-yl}methanone

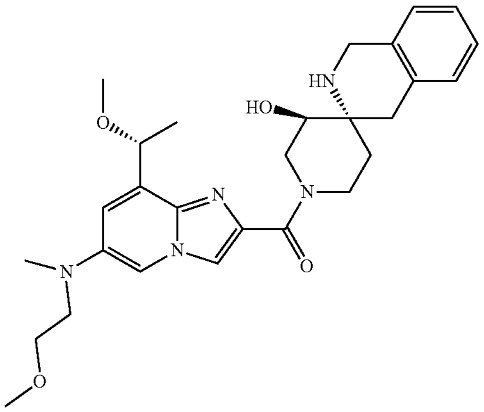 [SMILES: COCCN(C)c1cc([C@@H](C)OC)c2nc(C(=O)N3CC[C@]4(Cc5ccccc5CN4)[C@H](O)C3)cn2c1]

In a nitrogen filled glovebox were mixed (6-bromo-8-((R)-1-methoxyethyl)imidazo[1,2-a]pyridin-2-yl)((3R,3'R)-3'-hydroxy-1,4-dihydro-2H-spiro[isoquinoline-3,4'-piperidin]-1'-yl)methanone (25.0 mg, 0.050 mmol), $(tBuXPhosPd)_2COD$ (29.3 mg, 0.025 mmol), and 2-MeTHF (375 uL). The resulting mixture was stirred at room temperature for 40 min. 2-Methoxy-N-methylethan-1-amine (8.2 uL, 0.075 mmol) and 1-Ethyl-2,2,4,4,4-pentakis(dimethylamino)-2$\lambda^5$,4$\lambda^5$-catenadi(phosphazene) (67 uL, 0.20 mmol) were added, and the resulting mixture was stirred at room temperature for 1 h. To the reaction vessel were added acetic acid (8.6 uL, 0.15 mmol), SiliaMetS®DMT (200 mg), and $CH_2Cl_2$ (0.5 mL). The suspension was stirred at room temperature for 1 h, filtered through a pad of Celite®, washing with $CH_2Cl_2$ and MeOH. The combined organic fractions were concentrated and purified by preparative HPLC (ACN/water with 0.1% TFA modifier) to give [(3R,3'R)-3'-hydroxy-1,4-dihydro-1'H,2H-spiro[isoquinoline-3,4'-piperidin]-1'-yl]{8-[(1R)-1-methoxyethyl]-6-[(2-methoxyethyl)(methyl)amino]imidazo[1,2-a]pyridin-2-yl}methanone trifluoroacetate. MS 508 (M+1). $^1$H NMR (600 MHz, DMSO-$d_6$) δ 9.28 (s, 1H), 9.20 (s, 1H), 8.24 (s, 1H), 7.79 (d, J=18.3 Hz, 1H), 7.37-7.21 (m, 4H), 5.13 (s, 1H), 4.93 (s, 1H), 4.82 (s, 1H), 4.55 (s, 1H), 4.42-4.22 (m, 3H), 3.55-3.44 (m, 6H), 3.32-3.21 (m, 7H), 2.98-2.86 (m, 3H), 2.62 (d, J=10.3 Hz, 1H), 2.55-2.52 (m, 1H), 1.94-1.81 (m, 1H), 1.69 (s, 1H), 1.50 (s, 1H), 1.43 (s, 1H).

TABLE 23

The compounds in the following table were prepared using the methodology herein and the general procedure described in Example 229.

| Ex | Structure | Compound Name | Exact Mass [M + 1] |
|---|---|---|---|
| 230 | 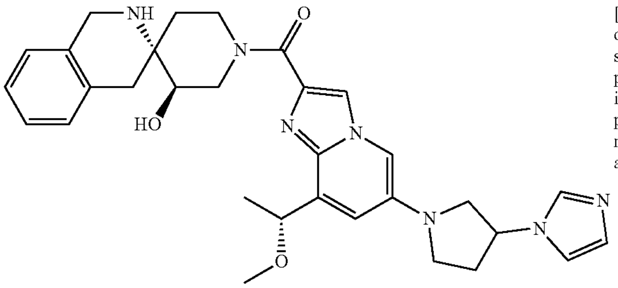 | [(3R,3'R)-3'-hydroxy-1,4-dihydro-1'H,2H-spiro[isoquinoline-3,4'-piperidin]-1'-yl]{6-[3-(1H-imidazol-1-yl)-1-pyrrolidinyl]-8-[(1R)-1-methoxyethyl]imidazo[1,2-a]pyridin-2-yl}methanone | 556 |
| 231 | 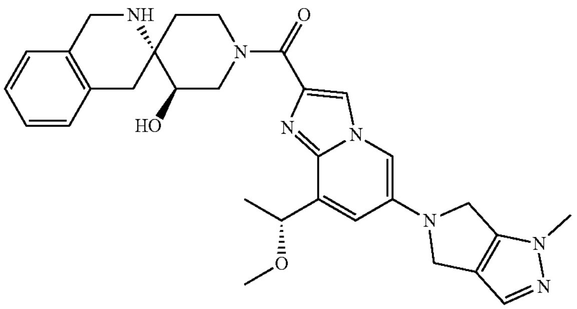 [SMILES: CO[C@H](C)c1cc(N2Cc3cnn(C)c3C2)cn2cc(C(=O)N3CC[C@]4(Cc5ccccc5CN4)[C@H](O)C3)nc12] | [(3R,3'R)-3'-hydroxy-1,4-dihydro-1'H,2H-spiro[isoquinoline-3,4'-piperidin]-1'-yl]{8-[(1R)-1-methoxyethyl]-6-(1-methyl-4,6-dihydropyrrolo[3,4-c]pyrazol-5(1H)-yl)imidazo[1,2-a]pyridin-2-yl}methanone | 542 |

TABLE 23-continued

| The compounds in the following table were prepared using the methodology herein and the general procedure described in Example 229. | | | |
|---|---|---|---|
| Ex | Structure | Compound Name | Exact Mass [M + 1] |
| 232 | 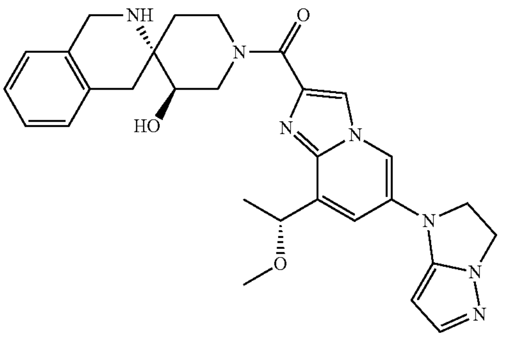 [SMILES: CO[C@H](C)c1cc(N2CCn3nccc32)cn2cc(C(=O)N3CC[C@]4(Cc5ccccc5CN4)[C@H](O)C3)nc12] | {6-(2,3-dihydro-1H-imidazo[1,2-b]pyrazol-1-yl)-8-[(1R)-1-methoxyethyl]imidazo[1,2-a]pyridin-2-yl}[(3R,3'R)-3'-hydroxy-1,4-dihydro-1'H,2H-spiro[isoquinoline-3,4'-piperidin]-1'-yl]methanone | 528 |
| 233 | 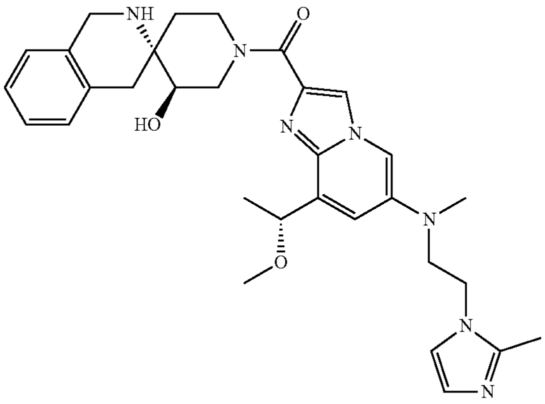 [SMILES: CO[C@H](C)c1cc(N(C)CCn2ccnc2C)cn2cc(C(=O)N3CC[C@]4(Cc5ccccc5CN4)[C@H](O)C3)nc12] | [(3R,3'R)-3'-hydroxy-1,4-dihydro-1'H,2H-spiro[isoquinoline-3,4'-piperidin]-1'-yl](8-[(1R)-1-methoxyethyl]-6-{methyl[2-(2-methyl-1H-imidazol-1-yl)ethyl]amino}imidazo[1,2-a]pyridin-2-yl)methanone | 558 |
| 234 | 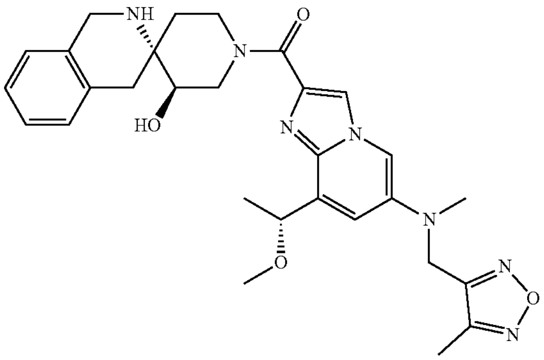 [SMILES: CO[C@H](C)c1cc(N(C)Cc2nonc2C)cn2cc(C(=O)N3CC[C@]4(Cc5ccccc5CN4)[C@H](O)C3)nc12] | [(3R,3'R)-3'-hydroxy-1,4-dihydro-1'H,2H-spiro[isoquinoline-3,4'-piperidin]-1'-yl](8-[(1R)-1-methoxyethyl]-6-{methyl[(4-methyl-1,2,5-oxadiazol-3-yl)methyl]amino}imidazo[1,2-a]pyridin-2-yl)methanone | 546 |
| 235 | 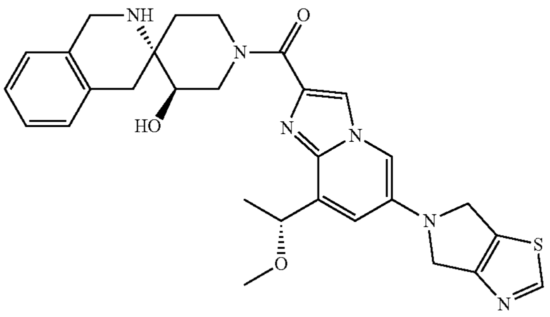 [SMILES: CO[C@H](C)c1cc(N2Cc3ncsc3C2)cn2cc(C(=O)N3CC[C@]4(Cc5ccccc5CN4)[C@H](O)C3)nc12] | {6-(4,6-dihydro-5H-pyrrolo[3,4-d][1,3]thiazol-5-yl)-8-[(1R)-1-methoxyethyl]imidazo[1,2-a]pyridin-2-yl}[(3R,3'R)-3'-hydroxy-1,4-dihydro-1'H,2H-spiro[isoquinoline-3,4'-piperidin]-1'-yl]methanone | 545 |

TABLE 23-continued

| The compounds in the following table were prepared using the methodology herein and the general procedure described in Example 229. | | | |
|---|---|---|---|
| Ex | Structure | Compound Name | Exact Mass [M + 1] |
| 236 | 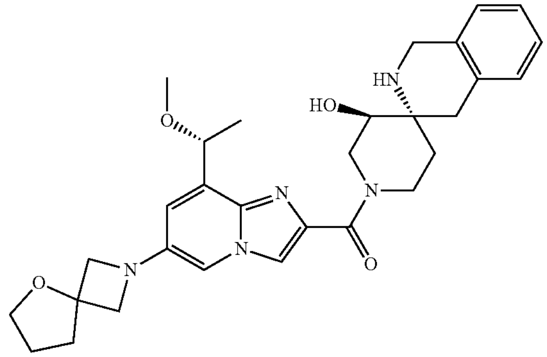 [SMILES: CO[C@H](C)c1cc(N2CC3(CCCO3)C2)cn2cc(C(=O)N3CC[C@]4(Cc5ccccc5CN4)[C@H](O)C3)nc12] | [(3R,3'R)-3'-hydroxy-1,4-dihydro-1'H,2H-spiro[isoquinoline-3,4'-piperidin]-1'-yl]{8-[(1R)-1-methoxyethyl]-6-(5-oxa-2-azaspiro[3.4]oct-2-yl)imidazo[1,2-a]pyridin-2-yl}methanone | 532 |
| 237 | 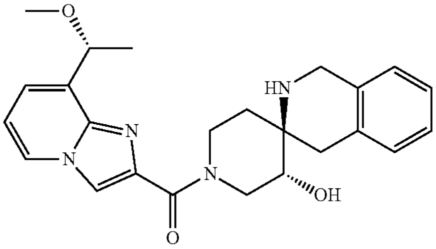 [SMILES: CO[C@H](C)c1cccn2cc(C(=O)N3CC[C@]4(Cc5ccccc5CN4)[C@H](O)C3)nc12] | [(3R,3'R)-3'-hydroxy-1,4-dihydro-1'H,2H-spiro[isoquinoline-3,4'-piperidin]-1'-yl]{8-[(1R)-1-methoxyethyl]imidazo[1,2-a]pyridin-2-yl}methanone | 421 |

Example 238: [(3R,3'R)-3'-hydroxy-1,4-dihydro-1'H,2H-spiro[isoquinoline-3,4'-piperidin]-1'-yl]{8-[(1R)-1-methoxyethyl]-6-(3-methoxy-2-pyridinyl)imidazo[1,2-a]pyridin-2-yl}methanone

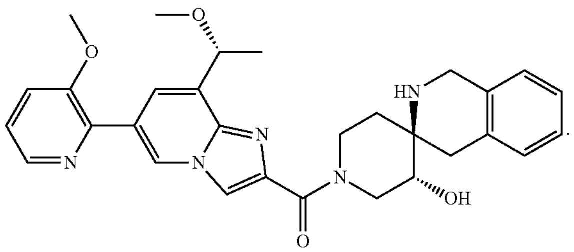 [SMILES: COc1cccnc1-c1cc([C@@H](C)OC)c2nc(C(=O)N3CC[C@]4(Cc5ccccc5CN4)[C@H](O)C3)cn2c1]

To a mixture of (6-bromo-8-((R)-1-methoxyethyl)imidazo[1,2-a]pyridin-2-yl)((3R,3'R)-3'-hydroxy-1,4-dihydro-2H-spiro[isoquinoline-3,4'-piperidin]-1'-yl)methanone (74.9 mg, 0.15 mmol), XPhos-Pd-G3 (12.7 mg, 0.015 mmol), 3-methoxy-2-(4,4,5,5-tetramethyl-1,3,2-dioxaborolan-2-yl)pyridine (52.9 mg, 0.225 mmol) were added THF (0.7 mL) and 2 M $K_3PO_4$ in water (0.26 mL, 0.53 mmol). The resulting biphasic mixture was heated to 60° C. overnight and cooled to rt. The reaction was treated with DCM and water. The organic layer was separated by passage through a phase separator, and the aqueous phase was extracted with DCM. The combined organic layers were concentrated and purified by preparative HPLC (ACN/water with 0.1% TFA modifier) to give [(3R,3'R)-3'-hydroxy-1,4-dihydro-1'H,2H-spiro[isoquinoline-3,4'-piperidin]-1'-yl]{8-[(1R)-1-methoxyethyl]-6-(3-methoxy-2-pyridinyl)imidazo[1,2-a]pyridin-2-yl}methanone trifluoroacetate. MS 528 (M+1). $^1H$ NMR (600 MHz, DMSO-$d_6$) δ 9.39 (d, J=9.6 Hz, 1H), 9.23 (s, 1H), 8.90-8.77 (m, 2H), 8.46 (s, 1H), 7.75-7.67 (m, 1H), 7.46 (d, J=23.7 Hz, 1H), 7.35-7.23 (m, 3H), 5.10 (d, J=12.0 Hz, 1H), 5.07-5.01 (m, 1H), 4.97 (d, J=11.7 Hz, 1H), 4.94-4.88 (m, 1H), 4.61-4.53 (m, 1H), 4.41-4.32 (m, 1H), 4.32-4.25 (m, 1H), 4.15-4.06 (m, 3H), 3.86-3.80 (m, 1H), 3.49-3.38 (m, 1H), 3.34-3.24 (m, 3H), 3.19-3.10 (m, 1H), 3.01-2.94 (m, 1H), 1.95-1.83 (m, 1H), 1.78-1.66 (m, 1H), 1.56 (d, J=6.2 Hz, 1H), 1.48 (d, J=6.2 Hz, 2H).

TABLE 24

The compounds in the following table were prepared using the methodology herein and the general procedure described in Example 238.

| Ex | Structure | Compound Name | Exact Mass [M + 1] |
|---|---|---|---|
| 239 | 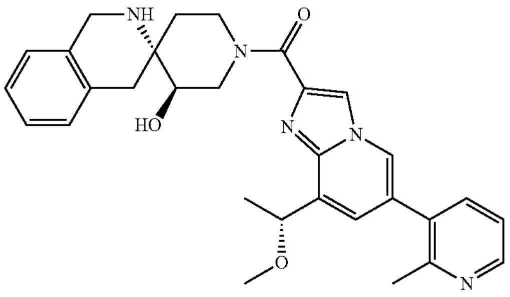 [SMILES: CO[C@H](C)c1cc(-c2cccnc2C)cn2cc(C(=O)N3CC[C@]4(Cc5ccccc5CN4)[C@H](O)C3)nc12] | [(3R,3'R)-3'-hydroxy-1,4-dihydro-1'H,2H-spiro[isoquinoline-3,4'-piperidin]-1'-yl]{8-[(1R)-1-methoxyethyl]-6-(2-methyl-3-pyridinyl)imidazo[1 2-a]pyridin-2-yl}methanone | 512 |
| 240 | 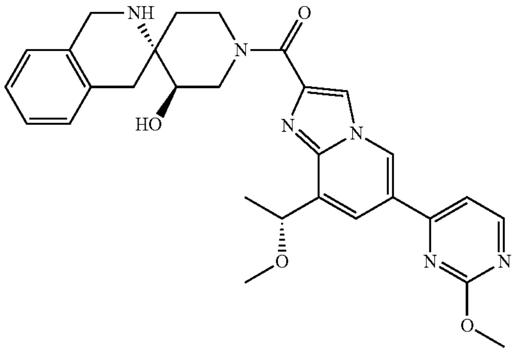 [SMILES: COc1nccc(-c2cc([C@@H](C)OC)c3nc(C(=O)N4CC[C@]5(Cc6ccccc6CN5)[C@H](O)C4)cn3c2)n1] | [(3R,3'R)-3'-hydroxy-1,4-dihydro-1'H,2H-spiro[isoquinoline-3,4'-piperidin]-1'-yl]{8-[(1R)-1-methoxyethyl]-6-(2-methoxy-4-pyrimidinyl)imidazo[1,2-a]pyridin-2-yl}methanone | 529 |
| 241 | 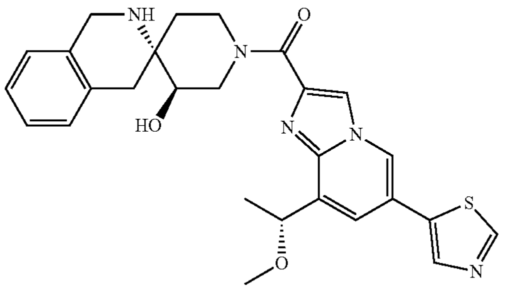 [SMILES: CO[C@H](C)c1cc(-c2cncs2)cn2cc(C(=O)N3CC[C@]4(Cc5ccccc5CN4)[C@H](O)C3)nc12] | [(3R,3'R)-3'-hydroxy-1,4-dihydro-1'H,2H-spiro[isoquinoline-3,4'-piperidin]-1'-yl]{8-[(1R)-1-methoxyethyl]-6-(1,3-thiazol-5-yl)imidazo[1,2-a]pyridin-2-yl}methanone | 504 |
| 242 | 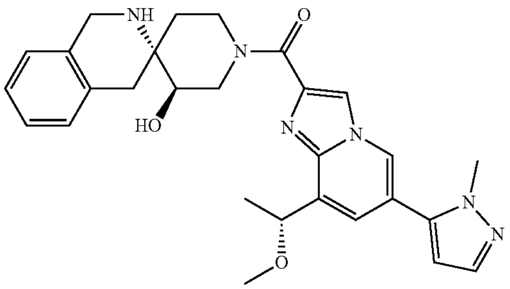 [SMILES: CO[C@H](C)c1cc(-c2ccnn2C)cn2cc(C(=O)N3CC[C@]4(Cc5ccccc5CN4)[C@H](O)C3)nc12] | [(3R,3'R)-3'-hydroxy-1,4-dihydro-1'H,2H-spiro[isoquinoline-3,4'-piperidin]-1'-yl]{8-[(1R)-1-methoxyethyl]-6-(1-methyl-1H-pyrazol-5-yl)imidazo[1,2-a]pyridin-2-yl}methanone | 501 |

TABLE 24-continued

The compounds in the following table were prepared using the methodology herein and the general procedure described in Example 238.

| Ex | Structure | Compound Name | Exact Mass [M + 1] |
|---|---|---|---|
| 243 | 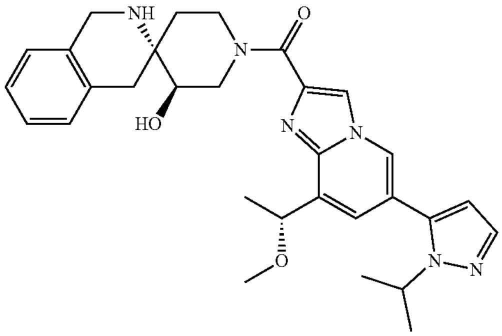 [SMILES: CO[C@H](C)c1cc(-c2ccnn2C(C)C)cn2cc(C(=O)N3CC[C@]4(Cc5ccccc5CN4)[C@H](O)C3)nc12] | [(3R,3'R)-3'-hydroxy-1,4-dihydro-1'H,2H-spiro[isoquinoline-3,4'-piperidin]-1'-yl]{6-(1-isopropyl-1H-pyrazol-5-yl)-8-[(1R)-1-methoxyethyl]imidazo[1,2-a]pyridin-2-yl}methanone | 529 |
| 244 | 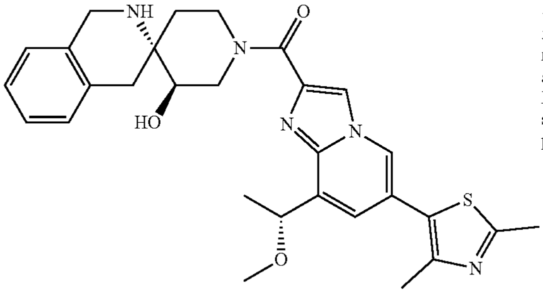 | {6-(2,4-dimethyl-1,3-thiazol-5-yl)-8-[(1R)-1-methoxyethyl]imidazo[1,2-a]pyridin-2-yl}[(3R,3'R)-3'-hydroxy-1,4-dihydro-1'H,2H-spiro[isoquinoline-3,4'-piperidin]-1'-yl]methanone | 532 |
| 245 | 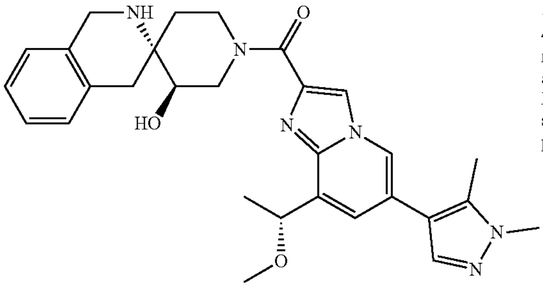 [SMILES: CO[C@H](C)c1cc(-c2cnn(C)c2C)cn2cc(C(=O)N3CC[C@]4(Cc5ccccc5CN4)[C@H](O)C3)nc12] | {6-(1,5-dimethyl-1H-pyrazol-4-yl)-8-[(1R)-1-methoxyethyl]imidazo[1,2-a]pyridin-2-yl}[(3R,3'R)-3'-hydroxy-1,4-dihydro-1'H,2H-spiro[isoquinoline-3,4'-piperidin]-1'-yl]methanone | 515 |
| 246 | 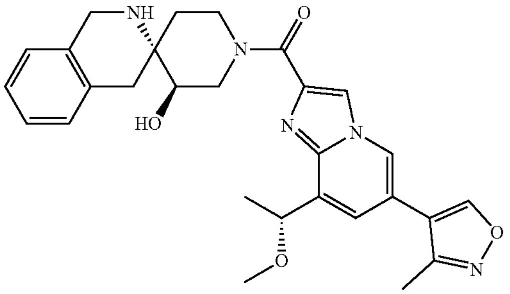 [SMILES: CO[C@H](C)c1cc(-c2conc2C)cn2cc(C(=O)N3CC[C@]4(Cc5ccccc5CN4)[C@H](O)C3)nc12] | [(3R,3'R)-3'-hydroxy-1,4-dihydro-1'H,2H-spiro[isoquinoline-3,4'-piperidin]-1'-yl]{8-[(1R)-1-methoxyethyl]-6-(3-methyl-4-isoxazolyl)imidazo[1,2-a]pyridin-2-yl}methanone | 502 |

Example 247: [(3R,3'R)-3'-hydroxy-1,4-dihydro-1'H,2H-spiro[isoquinoline-3,4'-piperidin]-1'-yl]{8-[(1R)-1-methoxyethyl]-6-(1-pyrrolidinylmethyl) imidazo[1,2-a]pyridin-2-yl}methanone

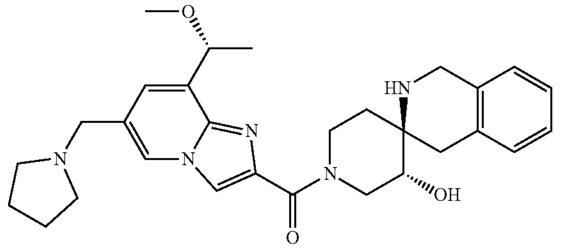 [SMILES: CO[C@H](C)c1cc(CN2CCCC2)cn2cc(C(=O)N3CC[C@]4(Cc5ccccc5CN4)[C@H](O)C3)nc12]

To a mixture of (6-bromo-8-((R)-1-methoxyethyl)imidazo[1,2-a]pyridin-2-yl)((3R,3'R)-3'-hydroxy-1,4-dihydro-2H-spiro[isoquinoline-3,4'-piperidin]-1'-yl)methanone (74.9 mg, 0.15 mmol), RuPhos-Pd-G3 (12.6 ng, 0.015 mmol), (pyrrolidinium-1-ylmethyl)trifluoroborate (27.5 mg, 0.18 mmol) were added toluene (1.5 mL) and 1.5 M $Cs_2CO_3$ in water (0.36 mL, 0.54 mmol) under a nitrogen atmosphere. The resulting biphasic mixture was heated to 100° C. overnight and cooled to rt. The reaction was DCM and the organic layer was separated by passage through a phase separator. The aqueous layer was extracted with DCM. The combined organic layers were concentrated and purified by preparative HPLC (ACN/water with 0.1% NH4OH modifier) to give [(3R,3'R)-3'-hydroxy-1,4-dihydro-1'H,2H-spiro [isoquinoline-3,4'-piperidin]-1'-yl]{8-[(1R)-1-methoxyethyl]-6-(1-pyrrolidinylmethyl)imidazo[1,2-a]pyridin-2-yl}methanone. MS 504 (M+1). $^1$H NMR (600 MHz, DMSO-$d_6$) δ 8.44-8.37 (m, 1H), 8.25 (s, 1H), 7.28-7.18 (m, 1H), 7.14-7.06 (m, 3H), 7.03 (s, 1H), 5.45-5.40 (m, 1H), 5.09-5.05 (m, 1H), 4.86 (q, J=6.1 Hz, 1H), 4.30-4.17 (m, 1H), 4.05 (d, J=12.3 Hz, 1H), 4.00-3.92 (m, 1H), 3.91-3.83 (m, 2H), 3.83-3.73 (m, 1H), 3.63-3.54 (m, 2H), 3.47-3.37 (m, 1H), 3.32-3.23 (m, 3H), 2.85-2.74 (m, 1H), 2.67-2.54 (m, 1H), 2.47 (s, 3H), 2.40-2.27 (m, 1H), 1.72 (s, 4H), 1.50-1.43 (m, 3H), 1.42-1.30 (m, 1H).

Example 248 and 249: (6-bromo-7-methoxyimidazo [1,2-a]pyrimidin-2-yl)[(3R,3'R)-3'-hydroxy-1,4-dihydro-1'H,2H-spiro[isoquinoline-3,4'-piperidin]-1'-yl]methanone and 6-bromo-2-{[(3R,3'R)-3'-hydroxy-1,4-dihydro-1'H,2H-spiro[isoquinoline-3,4'-piperidin]-1'-yl]carbonyl}-8-methylimidazo[1,2-a] pyrimidin-7(8H)-one

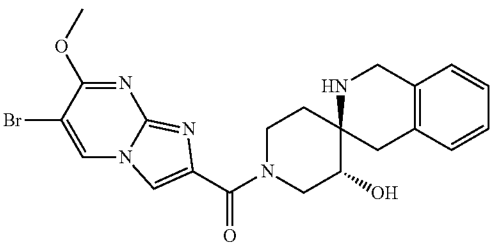

-continued

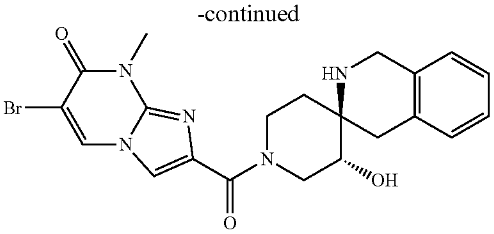

Step 1: To a mixture of 5-bromo-4-methoxypyrimidin-2-amine (150 mg, 0.735 mmol) in EtOH (3 ml) was added 3-bromo-2-oxopropanoic acid (184 mg, 1.10 mmol) at 15° C. The mixture was heated to 85° C. for 12 h. The mixture was concentrated, dissolved in EtOAc (5 mL), and stirred for 20 min. The mixture was filtered, and washed with EtOAc. The solid was dried to give 6-bromo-7-hydroxyimidazo[1,2-a]pyrimidine-2-carboxylic acid. MS: 258 and 260 (M+1). $^1$H NMR (400 MHz, DMSO-$d_6$) δ 8.85 (s, 1H), 7.84 (s, 1H)

Step 2: To a mixture of 6-bromo-7-hydroxyimidazo[1,2-a]pyrimidine-2-carboxylic acid (100 mg, 0.39 mmol) in DMF (2 mL) were added HATU (177 mg, 0.465 mmol), DIEA (0.203 mL, 1.16 mmol), and 2,4-dihydro-1H-spiro [isoquinoline-3,4'-piperidin]-3'-ol (85 mg, 0.39 mmol) at 15° C. The mixture was stirred at 15° C. for 0.5 h and purified by prep-HPLC (TFA) to give (6-bromo-7-hydroxy-imidazo[1,2-a]pyrimidin-2-yl)(3'-hydroxy-2,4-dihydro-1H-spiro[isoquinoline-3,4'-piperidin]-1'-yl)methanone. MS: 458 and 460 (M+1).

Step 3: To a mixture of (6-bromo-7-hydroxyimidazo[1,2-a]pyrimidin-2-yl)(3'-hydroxy-2,4-dihydro-1H-spiro[isoquinoline-3,4'-piperidin]-1'-yl)methanone (60 mg, 0.13 mmol) and TEA (0.036 mL, 0.26 mmol) in acetonitrile (2 mL) and MeOH (0.2 mL) was added trimethylsilyl diazomethane (0.131 mL, 0.262 mmol) at 15° C. The mixture was stirred at 15° C. for 0.5 h and purified by prep-HPLC (Neu.) to give the first eluted peak 6-bromo-2-(3'-hydroxy-2,4-dihydro-1H-spiro[isoquinoline-3,4'-piperidin]-1'-ylcarbonyl)-8-methylimidazo[1,2-a]pyrimidin-7(8H)-one and the second eluted peak (6-bromo-7-methoxyimidazo[1,2-a]pyrimidin-2-yl)(3'-hydroxy-2,4-dihydro-1H-spiro[isoquinoline-3,4'-piperidin]-1'-yl)methanone.

MS: 472 and 474 (M+1). NMR_Peak 1: $^1$H NMR (400 MHz, $CD_3OD$) δ 8.80 (br s, 1H), 7.74 (s, 1H), 7.11 (d, J=2.6 Hz, 3H), 7.05 (br d, J=3.1 Hz, 1H), 4.04-4.30 (m, 2H), 3.89-4.02 (m, 3H), 3.56-3.72 (m, 5H), 2.96 (br d, J=17.1 Hz, 1H), 2.69-2.84 (m, 1H), 1.83-1.92 (m, 1H), 1.53 (br d, J=12.3 Hz, 1H). NMR_Peak 2: $^1$H NMR (400 MHz, $CD_3OD$) δ 9.03 (br s, 1H), 7.91 (br s, 1H), 7.12 (br d, J=2.7 Hz, 3H), 7.05 (br s, 1H), 4.10 (s, 5H), 3.99 (br s, 3H), 3.52-3.71 (m, 2H), 2.92-3.08 (m, 1H), 2.71-2.84 (m, 1H), 1.91 (br d, J=16.6 Hz, 1H), 1.53 (br s, 1H).

Example 250: [(3R,3'R)-3'-hydroxy-1,4-dihydro-1'H,2H-spiro[isoquinoline-3,4'-piperidin]-1'-yl][8-(methoxymethyl)-6-methylimidazo[1,2-a]pyrazin-2-yl]methanone

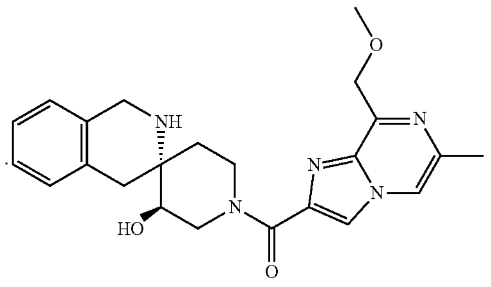 [SMILES: COCc1nc(C)cn2cc(C(=O)N3CC[C@]4(Cc5ccccc5CN4)[C@H](O)C3)nc12]

A mixture of (8-bromo-6-methylimidazo[1,2-a]pyrazin-2-yl)(3'-hydroxy-2,4-dihydro-1H-spiro[isoquinoline-3,4'-piperidin]-1'-yl)methanone (500 mg, 1.10 mmol), tributyl (methoxymethyl)stannane (1836 mg, 5.48 mmol), $Pd(PPh_3)_2Cl_2$ (154 mg, 0.219 mmol) and copper(I) iodide (41.7 mg, 0.219 mmol) in THF (15 ml) was heated to 80° C. under $N_2$ for 10 h. The mixture was concentrated in vacuum. The residue was purified by prep-HPLC to give [(3R,3'R)-3'-hydroxy-1,4-dihydro-1'H,2H-spiro[isoquinoline-3,4'-piperidin]-1'-yl][8-(methoxymethyl)-6-methylimidazo[1,2-a]pyrazin-2-yl]methanone. MS: 422 (M+1). $^1H$ NMR (400 MHz, $CDCl_3$) δ 8.23-8.28 (m, 2H), 7.11 (br, 3H), 7.05 (br, 1H), 4.10-4.16 (m, 2H), 3.99-4.07 (m, 5H), 3.57-3.64 (m, 2H), 3.49-3.51 (m, 3H), 2.92-3.00 (m, 1H), 2.70-2.77 (m, 1H), 2.50 (s, 3H) 1.89-1.91 (m, 1H), 1.51-1.58 (m, 1H).

Example 251: (6-cyclopropyl-7-methoxyimidazo[1,2-a]pyrimidin-2-yl)[(3R,3'R)-3'-hydroxy-1,4-dihydro-1'H,2H-spiro[isoquinoline-3,4'-piperidin]-1'-yl]methanone

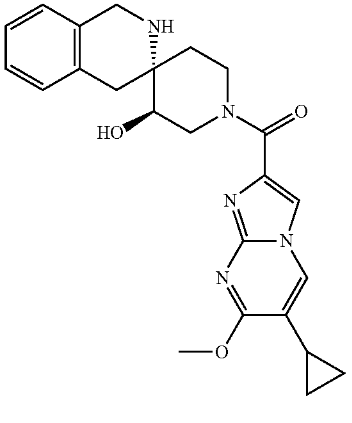 [SMILES: COc1nc2nc(C(=O)N3CC[C@]4(Cc5ccccc5CN4)[C@H](O)C3)cn2cc1C1CC1]

Step 1: To a solution of DIEA (0.96 ml, 5.5 mmol), 6-cyclopropyl-7-hydroxyimidazo[1,2-a]pyrimidine-2-carboxylic acid (400 mg, 1.83 mmol) and (3R,3'R)-1,4-dihydro-2H-spiro[isoquinoline-3,4'-piperidin]-3'-ol (478 mg, 2.19 mmol) in DMF (3 ml) was added 1-propanephosphonic anhydride (1742 mg, 2.74 mmol). The mixture was stirred at 15° C. for 2 h. The mixture was concentrated and purified by reversed MPLC (Biotage; 40 g Agela, C18, 20~35 μm, eluent of 10%~50% $H_2O$ (0.5‰ TFA)/MeOH gradient@35 mL/min) to give 6-cyclopropyl-2-{[(3R,3'R)-3'-hydroxy-1,4-dihydro-1'H,2H-spiro[isoquinoline-3,4'-piperidin]-1'-yl] carbonyl}imidazo[1,2-a]pyrimidin-7(1H)-one. MS:420 (M+1).

Step 2: A mixture of TMS-diazomethane (0.238 ml, 0.477 mmol) and 6-cyclopropyl-2-{[(3R,3'R)-3'-hydroxy-1,4-dihydro-1'H,2H-spiro[isoquinoline-3,4'-piperidin]-1'-yl] carbonyl}imidazo[1,2-a]pyrimidin-7(1H)-one (200 mg, 0.477 mmol) in MeOH (10 ml) was stirred at 15° C. for 12 h. The mixture was concentrated and purified by Prep-TLC (silica gel, ethyl acetate/MeOH=10/1, v/v) to give (6-cyclopropyl-7-methoxyimidazo[1,2-a]pyrimidin-2-yl)[(3R,3'R)-3'-hydroxy-1,4-dihydro-1'H,2H-spiro[isoquinoline-3,4'-piperidin]-1'-yl]methanone. MS: 434 (M+1). $^1H$ NMR (400 MHz, $CD_3OD$) δ 8.00 (s, 1H), 7.70 (s, 1H), 7.18 (br s, 3H), 7.11 (br d, J=5.3 Hz, 1H), 4.46-4.76 (m, 1H), 4.07-4.22 (m, 2H), 3.89 (br d, J=9.2 Hz, 1H), 3.65-3.76 (m, 2H), 3.54-3.64 (m, 3H), 2.85-3.26 (m, 2H), 1.81-1.97 (m, 2H), 1.28 (s, 1H), 0.77-0.99 (m, 4H), 0.58-0.72 (m, 2H).

Example 252: (8-chloro-6-methylimidazo[1,2-a]pyrazin-2-yl)[(3R,3'R)-3'-hydroxy-1,4-dihydro-1'H,2H-spiro[isoquinoline-3,4'-piperidin]-1'-yl]methanone

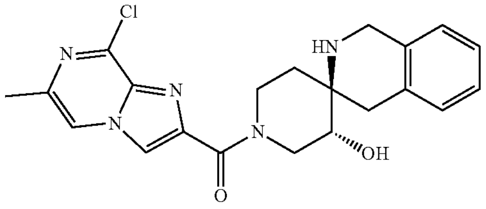 [SMILES: Cc1cn2cc(C(=O)N3CC[C@]4(Cc5ccccc5CN4)[C@H](O)C3)nc2c(Cl)n1]

Step 1: A mixture of 8-hydroxy-6-methylimidazo[1,2-a]pyrazine-2-carboxylic acid (87 mg, 0.45 mmol) in $POCl_3$ (3185 μl, 34.2 mmol) was heated to 100° C. for 10 h. The mixture was then concentrated to give 8-chloro-6-methylimidazo[1,2-a]pyrazine-2-carbonyl chloride (104 mg, 0.452 mmol).

Step 2: To a mixture of (3R,3'R)-1,4-dihydro-2H-spiro[isoquinoline-3,4'-piperidin]-3'-ol (48 mg, 0.2 mmol) and DIEA (0.115 ml, 0.66 mmol) in DCM (2 ml) was added 8-chloro-6-methylimidazo[1,2-a]pyrazine-2-carbonyl chloride (101 mg, 0.44 mmol). The mixture was stirred at 15° C. for 1 h and purified by pre-HPLC using Xtimate C18 150*25 mm*5 um column and water (10 mM $NH_4HCO_3$)-ACN as eluent to give (8-chloro-6-methylimidazo[1,2-a]pyrazin-2-yl)[(3R,3'R)-3'-hydroxy-1,4-dihydro-1'H,2H-spiro[isoquinoline-3,4'-piperidin]-1'-yl]methanone. MS: 412 (M+1). $^1H$ NMR (400 MHz, $CD_3OD$) δ 8.29-8.34 (m, 2H), 7.11 (br s, 3H), 7.05 (br s, 1H), 4.05-4.16 (m, 2H), 4.00 (br s, 2H), 3.75-3.96 (m, 1H), 3.49-3.71 (m, 2H), 2.90-3.07 (m, 1H), 2.68-2.84 (m, 1H), 2.42-2.49 (m, 3H), 1.83-1.96 (m, 1H), 1.57 (br d, J=14.5 Hz, 1H).

PRMT5-MEP50 Enzyme Methylation Assay (Version A)

PRMT5-MEP50 biochemical assay is a direct measurement of the methylation activity of the enzyme complex on a short peptide substrate derived from the N-terminus of H4 histone. Methylation experiment was performed with recombinant PRMT5-MEP50 protein complex. The assessment of inhibitory effect of small molecules was measured by the effectiveness of the compounds to inhibit this reaction ($EC_{50}$).

In this assay, the potency ($EC_{50}$) of each compound was determined from a twenty-point (1:2 serial dilution; top compound concentration of 100000 nM) titration curve using the following outlined procedure. To each well of a white ProxiPlus 384 well-plate, 100 nL of compound (1% DMSO in final assay volume of 10 μL) was dispensed, followed by the addition of 8 μL of 1× assay buffer (50 mM Bicine pH 8.0, 1 mM DTT, 0.004% Tween20, 0.01% BSA) containing 1.25 nM of Full-length (FL)-PRMT5-MEP50 enzyme complex (recombinant proteins from baculovirus-transfected Sf21 cells: FL-PRMT5; MW=73837 kDa and FL-MEP50; MW=38614) and 1 μL of 150 μM S-(5'-Adenosyl)-L-Methionine Chloride (SAM). A plate were sealed and placed in a 37° C. humidified chamber for a 60 minutes pre-incubation with compound. Subsequently, each reaction was initiated by the addition of 1 μL 1× assay buffer containing 750 nM biotinylated H4R3(Me1) peptide. The final reaction in each well of 10 μL consists of 1.0 nM PRMT5-MEP50, 75 nM biotinylated-peptide, and 15 μM SAM. Methylation reactions were allowed to proceed for 150 minutes in a sealed plate at 37° C. Reactions were immediately quenched by the addition of 1 μL of 5% formic acid. A plate was then frozen and shipped to SAMDI™ Tech Inc. to determine the percent conversion from H4R3(Me1) to H4R3(Me2). Dose-response curves were generated by plotting percent effect (% product conversion; Y-axis) vs. Log 10 compound concentrations (X-axis). $EC_{50}$ values were determined by non-linear regression according to models for either sigmoidal (4 parameters) or biphasic (7 parameters) dose-response curves.

PRMT5-MEP50 Enzyme Methylation Assay (Version B)

PRMT5/MEP50 biochemical assay is a direct measurement of the methylation activity of the enzyme complex on a short peptide substrate derived from the N-terminus of H4 histone. Methylation experiment was performed with recombinant protein. The assessment of inhibitory effect ($IC_{50}$) of small molecules was measured by the effectiveness of the compounds to inhibit this reaction.

In this assay, the potency ($IC_{50}$) of each compound was determined from a twenty-point (1:2 serial dilution; top compound concentration of 100000 nM) titration curve using the following outlined procedure. To each well of a white ProxiPlus 384 well-plate, 100 nL of compound (1% DMSO in final assay volume of 10 μL) was dispensed, followed by the addition of 8 μL of 1× assay buffer (50 mM Bicine pH 8.0, 1 mM DTT, 0.004% Tween20, 0.01% BSA) containing 0.5 nM of Full-length (FL)-PRMT5-MEP50 enzyme complex (recombinant proteins from baculovirus-transfected Sf21 cells: FL-PRMT5; MW=73837 kDa and FL-MEP50; MW=38614). Plates were sealed and placed in a 37° C. humidified chamber for 30 minutes pre-incubation with compounds. Subsequently, each reaction was initiated by the addition of 2 μL 1× assay buffer containing 75 nM biotinylated H4R3 (Me1) peptide, and 15 μM S-(5'-Adenosyl)-L-Methionine Chloride (SAM). The final reaction in each well of 10 μL consists of 0.5 nM PRMT5-MEP50, 75 nM biotinylated-peptide, and 15 μM SAM. Methylation reactions were allowed to proceed for 150 minutes in a sealed plate at 37° C. Reactions were immediately quenched by the addition of 1 μL of 10% formic acid. Plates were then frozen and shipped to SAMDI™ Tech Inc. to determine the percent conversion from K4R3(Me1) to K4R3(Me2). $EC_{50}$ values were determined by non-linear regression according to models for either sigmoidal (4 parameters) or biphasic (7 parameters) dose-response curves.

PRMT5 Cell Target Engagement (TE) Assay

The PRMT5 TE assay is a biomarker assay for identifying compounds that inhibit symmetric dimethylation of arginine (SDMA) of PRMT5 substrates. The following substrates have been reported for PRMT5: histone H2A and H4 R3, Histone H3 R2, Histone H3 R8, spliceosome Sm proteins, ribosomal protein RPS10, p53, FEN1, nucleoplasmin, nucleolin, EGFR and EBNA. The assay focuses on detecting symmetrically dimethylated nuclear proteins using high content imaging technology. Detection of the expression of symmetrically dimethylated nuclear proteins is through a mixture of primary rabbit monoclonal antibodies to SDMA (CST 13222), which in turn recognized by an Alexafluor 488 dye-conjugated anti-rabbit IgG secondary antibody. The IN Cell Analyzer 2200 or Opera-Phenix measures nuclear Alexafluor 488 fluorescent dye intensity that is directly related to the level of expression of symmetrically dimethylated nuclear proteins at the single cell level. Nuclear AF488 dye intensities are compared to the mean value for DMSO treated cells (MIN) to report percent of inhibition for each compound-treated well.

In this assay, the cell potency ($EC_{50}$) of each compound was determined from a ten point (1:3 serial dilution; top compound concentration of 10000 nM) titration curve using the following outlined procedure. Each well of a BD falcon collagen coated black/clear bottom 384-well plate was seeded with 4000 MCF-7 cells in 30 μl media and allowed to attach for 5 h. Media is ATCC-formulated Eagle's Minimum Essential Medium, Catalog No. 30-2003. To make the complete growth medium, the following components were added to the base medium: 0.01 mg/mL human recombinant insulin; fetal bovine serum to a final concentration of 10%. Additional 30 μl of media containing 2× compounds were added to each well. Cells were treated for 3 days in 37° C. $CO_2$ incubator. On day 3, cells were fixed with Cytofix, permeabilized with 0.4% Triton-X-100/Cytofix, and washed with D-PBS without Ca/Mg. Cells were blocked with Licor Odessey blocking reagent for 1 h at room temperature, followed by incubation with anti-SDMA (1:1000) antibody at 4° C. overnight. 1° antibody was removed, followed by three washings with DPBS without Ca/Mg and 0.05% Tween20. Hoechst (5 μg/mL), Cell Mask deep stain (1:2000) and Alexa488-conjugated goat anti-rabbit IgG (2 μg/mL) was added for 1 h at room temperature. A final washing step (three washes) was performed before sealing plate for imaging on In Cell Analyzer 2200 or Opera-Phenix. Images from analyzer were uploaded to Columbus (at WP or BOS) for image analysis. $IC_{50}$ values were determined by 4 parameters robust fit of percent fluorescence units vs. ($Log_{10}$) compound concentrations.

TABLE 25

When only one $EC_{50}$ is shown, the data was fit to a 4 parameter single site sigmodal model. When two EC50s are shown, the data was fit to a 7 parameter biphasic model.

| Ex. No. | Enzyme Methylation Assay Version A ($EC_{50}$ or $EC_{50}$ 1, nM; $EC_{50}$ 2, nM) | Enzyme Methylation Assay Version B ($EC_{50}$ or $EC_{50}$ 1, nM; $EC_{50}$ 2, nM) | TE Assay ($EC_{50}$, nM) |
|---|---|---|---|
| 1 | 0.5012, 75.28 | N/A | 2.92 |
| 2 | 0.6288, 1380 | N/A | 75.79 |
| 3 | 1.448, 918.3 | N/A | 14.52 |
| 4 | N/A | 2.63, 1531 | 55.92 |
| 5 | N/A | 5.182, 1109 | 38.65 |
| 6 | 0.7101, 220 | N/A | 3.239 |

TABLE 25-continued

When only one $EC_{50}$ is shown, the data was fit to a 4 parameter single site sigmodal model. When two EC50s are shown, the data was fit to a 7 parameter biphasic model.

| Ex. No. | Enzyme Methylation Assay Version A ($EC_{50}$ or $EC_{50}$ 1, nM; $EC_{50}$ 2, nM) | Enzyme Methylation Assay Version B ($EC_{50}$ or $EC_{50}$ 1, nM; $EC_{50}$ 2, nM) | TE Assay ($EC_{50}$, nM) |
|---|---|---|---|
| 7 | 0.6389, 52.48 | N/A | 0.5449 |
| 8 | 1.534, 402.7 | N/A | 3.63 |
| 9 | 13.49, 4677 | N/A | 693.9 |
| 10 | 0.8145, 179.9 | N/A | 4.206 |
| 11 | 0.4948, 88.61 | N/A | 4.196 |
| 12 | 0.2312, 158.5 | N/A | 9.482 |
| 13 | 0.406, 319.9 | N/A | 8.162 |
| 14 | 100, 57540 | N/A | 547.3 |
| 16 | 2.016, 1585 | N/A | 50.93 |
| 17 | 1.508, 794.3 | N/A | 14.14 |
| 18 | 63.1, 57540 | N/A | 1013 |
| 19 | 0.3051, 105.5 | N/A | 10.17 |
| 20 | 0.4381, 150.7 | N/A | 16.49 |
| 21 | 0.1907 | N/A | 2.128 |
| 22 | 0.6739, 439 | N/A | 16.83 |
| 23 | 1.8, 851.1 | N/A | 46.35 |
| 24 | 0.4607, 145.9 | N/A | 4.088 |
| 25 | 7.12, 2042 | N/A | 30.24 |
| 26 | 1.444, 683.9 | N/A | 12.32 |
| 27 | 3.652, 3350 | N/A | 36.77 |
| 28 | 0.8162 | N/A | 2.75 |
| 29 | 0.4281, 653.1 | N/A | 18.41 |
| 30 | 0.5837, 99.43 | N/A | 3.617 |
| 31 | 0.2148, 72.44 | N/A | 4.488 |
| 32 | 0.8437, 281.8 | N/A | 5.148 |
| 33 | 0.5654, 215.4 | N/A | 3.713 |
| 34 | 0.9091, 229.1 | N/A | 4.003 |
| 35 | 0.7656, 248.3 | N/A | 5.66 |
| 36 | 6.259, 2818 | N/A | 13.17 |
| 37 | 0.7568, 251.2 | N/A | 1.606 |
| 38 | 3.841, 2455 | N/A | 16.16 |
| 39 | 95.5, 29170 | N/A | 571.2 |
| 40 | 0.814, 467.7 | N/A | 8.696 |
| 41 | 0.5129, 208.9 | N/A | 2.436 |
| 42 | 5.346, 3236 | N/A | 24.85 |
| 43 | 3.225, 1445 | N/A | 19.09 |
| 44 | 0.6871, 42.07 | N/A | 1.322 |
| 45 | 69.98, 16030 | N/A | 223.5 |
| 46 | 0.4977, 138 | N/A | 27.07 |
| 47 | 0.4212, 402.7 | N/A | 9.81 |
| 48 | 4.915, 2985 | N/A | 245.9 |
| 49 | 1.152, 346.7 | N/A | 3.875 |
| 50 | 0.3798, 62.37 | N/A | 1.479 |
| 51 | 7.015, 1496 | N/A | 13.73 |
| 52 | N/A | 6.711, 2251 | 87.71 |
| 53 | N/A | 6.212, 5549 | 488.2 |
| 54 | 8.008, 2661 | N/A | 169.4 |
| 55 | 0.8168, 169.8 | N/A | 1.167 |
| 56 | 12.37, 10000 | N/A | 82.1 |
| 57 | 63.1, 54950 | N/A | 2192 |
| 58 | 0.7145, 312.6 | N/A | 10.05 |
| 59 | 20.17 | N/A | 6104 |
| 60 | 0.4564, 271.2 | N/A | 7.487 |
| 61 | 0.669, 421.7 | N/A | 16.92 |
| 62 | 0.3945, 555.9 | N/A | 30.96 |
| 63 | 0.5834, 416.9 | N/A | 45.84 |
| 64 | 19.05, 9772 | N/A | 756.4 |
| 65 | 1.192, 1365 | N/A | 99.07 |
| 66 | 13.71, 9333 | N/A | 4410 |
| 67 | 0.3536, 312.6 | N/A | 7.977 |
| 68 | 1.172, 1059 | N/A | 99.63 |
| 69 | 0.4046, 43.65 | N/A | 12.67 |
| 70 | 0.2697, 239.9 | N/A | 263.3 |
| 71 | 134.9, 8318 | N/A | 1497 |
| 72 | 3.846, 335 | N/A | 78.48 |
| 73 | 4.433, 344.1 | N/A | 339.2 |
| 74 | 13.88 | N/A | 8.37 |
| 75 | 1.661, 112.2 | N/A | 27.49 |
| 76 | 0.9829, 73.28 | N/A | 4.018 |
| 77 | 1.456, 108.4 | N/A | 23.81 |
| 78 | 0.5082, 76.74 | N/A | 45.34 |
| 79 | 1.083 | N/A | 5.299 |
| 80 | 1.245 | N/A | 8.382 |
| 81 | 3.807 | N/A | 25.01 |
| 82 | 0.746 | N/A | 7.753 |
| 83 | 3.277, 3162 | N/A | 90.84 |
| 84 | 0.464, 291.7 | N/A | 10.9 |
| 85 | 5.598, 3055 | N/A | 115.1 |
| 86 | N/A | 82.22, 28840 | 1466 |
| 87 | N/A | 3.545, 670.9 | 9.162 |
| 88 | N/A | 964.3 | 4294 |
| 89 | N/A | 4.808, 1980 | 6.878 |
| 90 | N/A | 206.4 | 10000 |
| 91 | N/A | 1.647, 512.9 | 304.9 |
| 92 | N/A | 944.5 | 10000 |
| 93 | N/A | 3.112, 1072 | 27.28 |
| 94 | 0.8256, 316.2 | N/A | 19.72 |
| 95 | 1.015, 467.7 | N/A | 28.7 |
| 96 | N/A | 19.72, 34280 | 766.7 |
| 97 | N/A | 4.539, 7413 | 215.5 |
| 98 | 0.1907, 103.9 | N/A | 6.856 |
| 99 | 0.4266, 146.8 | N/A | 7.798 |
| 100 | 0.2661, 60.6 | N/A | 4.134 |
| 101 | 0.2944, 56.23 | N/A | 7.017 |
| 102 | 52.08, 34670 | N/A | 800.3 |
| 103 | 171.1, 80040 | N/A | 2863 |
| 104 | 1.437, 1406 | N/A | 83.13 |
| 105 | 0.5194, 146.2 | N/A | 4.39 |
| 106 | 0.43, 1012 | N/A | 36.79 |
| 107 | 0.2723 | N/A | 6.675 |
| 108 | 4.248, 206.5 | N/A | 12.92 |
| 109 | 0.2764, 125.9 | N/A | 8.275 |
| 110 | N/A | 3.308, 8710 | 52.98 |
| 111 | 41.21, 35890 | N/A | 2712 |
| 112 | 0.7034, 271.2 | N/A | 6.746 |
| 113 | 0.6823, 338.8 | N/A | 17.2 |
| 114 | N/A | 15.08, 14950 | 7551 |
| 115 | N/A | 86.27, 55020 | 10000 |
| 116 | N/A | 807.2, 100000 | 10000 |
| 117 | N/A | 689.5, 100000 | 10000 |
| 118 | N/A | 509.6, 100000 | 10000 |
| 119 | 11.76, 6457 | N/A | 274.5 |
| 120 | 0.4995, 350.8 | N/A | 28.81 |
| 121 | 4.881, 3311 | N/A | 65.46 |
| 122 | 0.3041, 144.5 | N/A | 5.559 |
| 123 | 0.3783, 182 | N/A | 11.81 |
| 124 | 8.492, 2417 | N/A | 3318 |
| 125 | 0.5155, 298.5 | N/A | 13.75 |
| 126 | 7.153, 5012 | N/A | 399.2 |
| 127 | 61.66, 34280 | N/A | 3948 |
| 128 | 5.327, 2692 | N/A | 194.7 |
| 129 | 836.2 | N/A | 10000 |
| 130 | 21.38, 19720 | N/A | 9597 |
| 131 | 70.79, 74130 | N/A | 10000 |
| 132 | 0.2442, 123 | N/A | 6.611 |
| 133 | 3.785, 16.22 | N/A | 77.37 |
| 134 | 142.9 | N/A | 184.5 |
| 135 | 10.62 | N/A | 6.858 |
| 136 | 32.93 | N/A | 146.4 |
| 137 | 1.919, 251.2 | N/A | 123.6 |
| 138 | 201.7 | N/A | 321.6 |
| 139 | 8.194, 767.4 | N/A | 212.3 |
| 140 | 1388 | N/A | 2087 |
| 141 | 101.2, 3715 | N/A | 4381 |
| 142 | 29.51, 1862 | N/A | 620.2 |
| 143 | 184.1 | N/A | 318.4 |
| 144 | 65.92 | N/A | 173.3 |
| 145 | 74.99, 35480 | N/A | 10000 |
| 146 | 109.6, 44670 | N/A | 10000 |
| 147 | 0.4089 | N/A | 2.28 |

TABLE 25-continued

When only one $EC_{50}$ is shown, the data was fit to a 4 parameter single site sigmodal model. When two EC50s are shown, the data was fit to a 7 parameter biphasic model.

| Ex. No. | Enzyme Methylation Assay Version A ($EC_{50}$ or $EC_{50}$ 1, nM; $EC_{50}$ 2, nM) | Enzyme Methylation Assay Version B ($EC_{50}$ or $EC_{50}$ 1, nM; $EC_{50}$ 2, nM) | TE Assay ($EC_{50}$, nM) |
|---|---|---|---|
| 148 | 1.114, 1905 | N/A | 120.7 |
| 149 | N/A | 298.5, 100000 | 9842 |
| 150 | N/A | 5.61, 1841 | 245.6 |
| 151 | N/A | 882.1 | 4183 |
| 152 | N/A | 1.202, 335 | 27.73 |
| 153 | 4.305, 2951 | N/A | 413.6 |
| 154 | 0.8021, 266.1 | N/A | 4.418 |
| 155 | 5.26, 3981 | N/A | 121.6 |
| 156 | 42.66, 15850 | N/A | 642 |
| 157 | 8.943, 6457 | N/A | 275.1 |
| 158 | 71.61, 29850 | N/A | 1701 |
| 159 | 61.66, 22390 | N/A | 527 |
| 160 | 9.521, 9477 | N/A | 289.2 |
| 161 | 5.902, 9120 | N/A | 374.4 |
| 162 | 260, 93330 | N/A | 7517 |
| 163 | 96.61, 36730 | N/A | 1591 |
| 164 | 4.825, 4624 | N/A | 204.6 |
| 165 | 82.22, 26610 | N/A | 841 |
| 166 | 3.635, 1641 | N/A | 33.68 |
| 167 | 9.55, 3631 | N/A | 193.7 |
| 168 | 2.559, 384.6 | N/A | 50.23 |
| 169 | 1.508, 426.6 | N/A | 89 |
| 170 | 2.559, 1778 | N/A | 19 |
| 171 | 0.9293, 732.8 | N/A | 6.47 |
| 172 | N/A | 5.42, 1936 | 88.86 |
| 173 | N/A | 32.31, 14440 | 5306 |
| 174 | N/A | 13.34, 8845 | 797.1 |
| 175 | N/A | 6.322, 2491 | 156.4 |
| 176 | N/A | 11.02, 2859 | 253.3 |
| 177 | 1909 | N/A | 10000 |
| 178 | 128.8, 85110 | N/A | 3211 |
| 179 | 512.9, 69180 | N/A | 8759 |
| 180 | 51.29, 52480 | N/A | 1325 |
| 181 | 20.89, 3981 | N/A | 924.4 |
| 182 | 4.571, 1349 | N/A | 154.9 |
| 183 | 4.875, 7943 | N/A | 297 |
| 184 | 16.22, 21880 | N/A | 994.8 |
| 185 | 23.99, 26920 | N/A | 1538 |
| 186 | 0.241, 501.2 | N/A | 71.19 |
| 187 | 75.86, 26920 | N/A | 4280 |
| 188 | 144.5, 74130 | N/A | 3319 |
| 189 | 30.2, 66070 | N/A | 3499 |
| 190 | 343.4 | N/A | 10000 |
| 191 | 2882 | N/A | 10000 |
| 192 | 112.2, 34670 | N/A | 10000 |
| 193 | 26990 | N/A | 9606 |
| 194 | 478.6, 100000 | N/A | 10000 |
| 195 | 15670 | N/A | 10000 |
| 196 | 15.29, 6310 | N/A | 408.6 |
| 197 | 14.24, 16030 | N/A | 1309 |
| 198 | 19.34, 16030 | N/A | 1071 |
| 199 | 4.078, 7244 | N/A | 503.1 |
| 200 | 6.73, 3020 | N/A | 214.2 |
| 201 | 1.356, 1023 | N/A | 168 |
| 202 | 26.3, 16220 | N/A | 795.1 |
| 203 | 0.846, 291.7 | N/A | 25.69 |
| 204 | 21.88, 14620 | N/A | 1594 |
| 205 | 2.799, 2754 | N/A | 324.2 |
| 206 | 4.335, 7244 | N/A | 363.2 |
| 207 | 0.3815, 288.4 | N/A | 27.6 |
| 208 | 0.7629, 691.8 | N/A | 100.4 |
| 209 | 3.741, 3890 | N/A | 256.1 |
| 210 | 0.2075, 54.95 | N/A | 12.43 |
| 211 | 0.1907, 71.61 | N/A | 7.99 |
| 212 | 901.6, 21380 | N/A | 3117 |
| 213 | 4.33, 342.8 | N/A | 209 |
| 214 | 1.121, 47.86 | N/A | 9.003 |
| 215 | 56.68 | N/A | 122.3 |
| 216 | 26.3, 2541 | N/A | 711 |
| 217 | 0.7303, 40.27 | N/A | 11.28 |

TABLE 25-continued

When only one $EC_{50}$ is shown, the data was fit to a 4 parameter single site sigmodal model. When two EC50s are shown, the data was fit to a 7 parameter biphasic model.

| Ex. No. | Enzyme Methylation Assay Version A ($EC_{50}$ or $EC_{50}$ 1, nM; $EC_{50}$ 2, nM) | Enzyme Methylation Assay Version B ($EC_{50}$ or $EC_{50}$ 1, nM; $EC_{50}$ 2, nM) | TE Assay ($EC_{50}$, nM) |
|---|---|---|---|
| 218 | 1.972 | N/A | 4.067 |
| 219 | 204.2, 17380 | N/A | 4162 |
| 220 | 83.18, 2600 | N/A | 2102 |
| 221 | 43.65, 3508 | N/A | 2545 |
| 222 | 431.5, 25410 | N/A | 10000 |
| 223 | 22.13, 631 | N/A | 445.2 |
| 224 | 3508, 66830 | N/A | 10000 |
| 225 | 2.1, 398.1 | N/A | 22.65 |
| 226 | 1.397 | N/A | 5.044 |
| 227 | 8.468 | N/A | 26.72 |
| 228 | 144.1 | N/A | 254.3 |
| 229 | 0.6017, 234.4 | N/A | 22.62 |
| 230 | 5.381 | N/A | 124.5 |
| 231 | 11.31 | N/A | 66.42 |
| 232 | 4.995 | N/A | 67.35 |
| 233 | 3.695 | N/A | 76.25 |
| 234 | 6.82 | N/A | 23.84 |
| 235 | 20.63 | N/A | 62.67 |
| 236 | 7.093 | N/A | 20.59 |
| 237 | 9.131, 1841 | N/A | 257.7 |
| 238 | 1.275 | N/A | 4.251 |
| 239 | 0.613 | N/A | 3.328 |
| 240 | 0.3758, 112.2 | N/A | 20.96 |
| 241 | 0.9322, 211.3 | N/A | 4.868 |
| 242 | 0.7004 | N/A | 1.81 |
| 243 | 1.17 | N/A | 3.591 |
| 244 | 0.6754 | N/A | 1.677 |
| 245 | 1.24 | N/A | 2.655 |
| 246 | 0.977 | N/A | 6.308 |
| 247 | 0.6607, 645.7 | N/A | 75.3 |
| 248 | 0.5565, 153.1 | N/A | 9.354 |
| 249 | 20.77, 8511 | N/A | 310.7 |
| 250 | 610.5 | N/A | 1728 |
| 251 | 546.7 | N/A | 1850 |
| 252 | 11.75, 7079 | N/A | 679.7 |

What is claimed is:

1. A compound of formula I, (I)

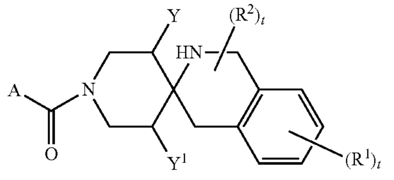

or a pharmaceutically acceptable salt thereof, wherein

Y is H or OH;

$Y^1$ is H or OH;

$R^1$ is H, halogen, or $C_{1-6}$alkyl optionally substituted with halogen;

$R^2$ is H or D;

each t is independently 0, 1, or 2;

A is (a) phenyl, optionally substituted with one or two moieties independently selected from $OC_{1-6}$alkyl, halogen, $C(O)R^5$, O-cyclopropyl, or an unsaturated heterocycle having 1-3 nitrogen atoms and 0-1 oxygen atoms wherein the unsaturated heterocycle is optionally substituted with $C_{1-6}$alkyl, wherein $R^5$ is a saturated heterocycle having 1 nitrogen atom and 1 oxygen atom;

(b) an unsaturated 6-membered heterocycle with 1-2 N atoms, wherein the heterocycle is substituted with $NHR^3$, wherein the heterocycle is additionally optionally substituted with 1 or 2 halogens, wherein $R^3$ is saturated heterocycle with 1 nitrogen atom, wherein the $R^3$ nitrogen is substituted with C(O)$C_{1-6}$alkyl and wherein the $R^3$ heterocycle is optionally substituted with 1 or 2 halogens;

(c) an unsaturated 6-membered heterocycle with 1 N atom optionally substituted with one, two or three moieties independently selected from halogen, =O, $C_{1-6}$alkyl, $C_{3-6}$cycloalkyl, $C_{1-6}$fluoroalkyl, 5-membered unsaturated heterocycle having 3 or 4 N atoms, OH, $OC_{1-6}$alkyl, $OC_{1-6}$alkoxy, $NC_{1-6}$alkyl, or $NHR^4$, wherein $R^4$ is saturated heterocycle having 1N atom optionally substituted with one or two C(O)$C_{1-6}$alkyl and wherein the C(O)$C_{1-6}$alkyl is optionally substituted with one or two fluoro atoms;

(d)

i. an unsaturated 5-membered heterocycle with 1 or 2 Nitrogen atoms and 0-1 Oxygen atom optionally substituted with a 5-membered unsaturated heterocycle with 1 nitrogen atom and 1 oxygen atom wherein each heterocycle is independently optionally substituted with $C_{1-6}$alkyl, ii. an unsaturated 5-membered heterocycle with 2 N atoms optionally substituted with $CHF_2$, cyclopropyl, or a phenyl optionally mono-substituted, independently disubstituted, or independently trisubstituted with halogen, $C_{1-6}$alkyl, $OC_{1-6}$alkyl, or $C_{1-6}$fluoroalkyl, (e) an unsaturated 8-11-membered bicyclic heterocycle with 1-4 nitrogen atoms, 0-1 oxygen atoms, and 0-1 sulfur atoms, unsubstituted, mono-substituted, independently disubstituted, or independently trisubstituted with i) $CR^6R^7R^8$, wherein $R^6$ is H, $C_{1-6}$alkyl, or halogen, $R^7$ is H, $C_{1-6}$alkyl, halogen or OH, and $R^8$ is H, CN, $C_{1-6}$alkyl optionally substituted with CN, halogen, OH, $OC_{1-6}$alkyl, or $C_{1-6}$haloalkyl;

ii) $C(O)NR^9R^{10}$, wherein $R^9$ is H, $C_{1-6}$alkyl, halogen, or $C_{1-6}$haloalkyl, and $R^{10}$ is H, $C_{1-6}$alkyl, $C_{1-6}$alkyl $(C_{1-6}alkyl)_{1-2}$, halogen, or $C_{1-6}$haloalkyl, iii) CN;

iv) $C_3$ to $C_6$ saturated or unsaturated carbocycle optionally mono-substituted, independently disubstituted, or independently trisubstituted with $C_{1-6}$alkyl, 1-3 halogens, or CN;

v) halogen;

vi) $C_{0-6}alkylO(CH_2)_{0-2}R^{11}$, wherein:

$R^{11}$ is H, $C_{1-6}$alkyl, ($C_{1-6}$alkyl)($OC_{1-6}$alkyl), $OC_{1-6}$alkyl, $C_{1-6}$alkyl$(C_{1-6}alkyl)_{1-2}$, $C_{1-6}$alkyl $(C_{1-6}alkyl)_{1-2}$OH, $C_{3-6}$heterocycle or $C_{3-6}$cycloalkyl wherein the $C_{3-6}$heterocycle or $C_{3-6}$cycloalkyl are optionally mono-substituted, independently disubstituted, or independently trisubstituted with $C_{1-6}$alkyl, halogen, CN, or =O;

vii) =O;

viii) $C_{3-6}$heterocycle or $C_{3-6}$cycloalkyl wherein the $C_{3-6}$heterocycle or $C_{3-6}$cycloalkyl are optionally mono-substituted, independently disubstituted, or independently trisubstituted with $C_{1-6}$alkyl, $C_{1-6}$cycloalkyl, halogen, CN, or =O;

ix) N($C_{1-6}$alkyl)($C_{1-6}$alkyl)($OC_{1-6}$alkyl) or N($C_{1-6}$alkyl)($C_{1-6}$alkyl), wherein the alkyl moiety is optionally substituted with 5-membered unsaturated ring with 2 nitrogen atoms, 0-1 oxygen atom, wherein the ring is optionally substituted with $C_{1-6}$alkyl, halogen, or $C_{1-6}$haloalkyl;

xi) $C_{3-6}$heterocycle optionally mono-substituted, independently disubstituted, or independently trisubstituted with 5-membered unsaturated ring with 2 nitrogen, xii) an unsaturated 8-11 membered bicyclic heterocycle with 1-4 nitrogen atoms, 0-1 oxygen atoms, and 0-1 sulfur atoms, unsubstituted, mono-substituted, independently disubstituted, or independently trisubstituted with $C_{1-6}$alkyl, or halogen, xiii) unsaturated 5- or 6-membered heterocycle with 1-2 nitrogen atoms, 0-1 oxygen atoms, and 0-1 sulfur atoms optionally mono-substituted or independently disubstituted with $C_{1-6}$alkyl or $OC_{1-6}$ alkyl, wherein the alkyl is optionally substituted with 1-3 halogens xiv) $C_{1-6}$alkyl optionally substituted with CN or halogen; or (f) unsaturated 13-membered tricyclic heterocycle with 1 oxygen, wherein the tricyclic heterocycle is optionally substituted with OH, provided that the compound of formula I is not:

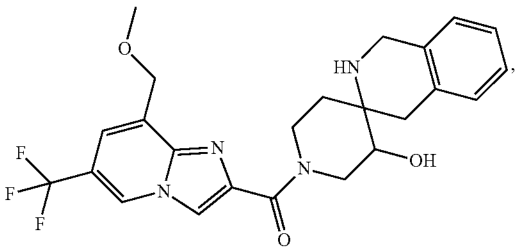
,

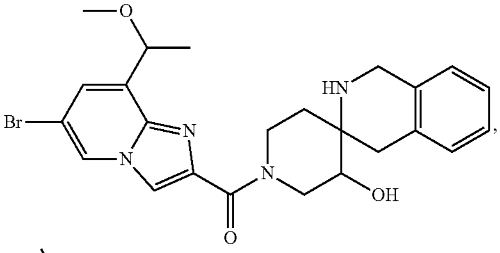
,

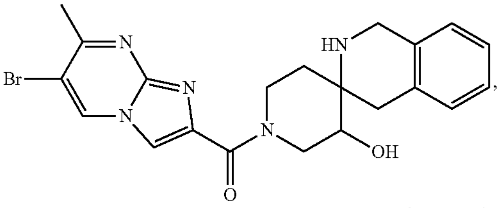
, or

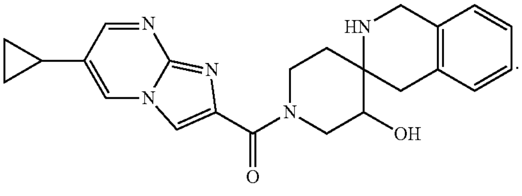
.

2. The compound of claim 1, or a pharmaceutically acceptable salt thereof, wherein Y is H or OH;

$Y^1$ is H or OH;

(a) phenyl, optionally substituted with one or two moieties independently selected from $OC_{1-6}$alkyl, halogen, $C(O)R^5$, O-cyclopropyl, or an unsaturated heterocycle having 1-3 nitrogen atoms and 0-1 oxygen atoms wherein the unsaturated heterocycle is optionally substituted with $C_{1-6}$alkyl, wherein $R^5$ is a saturated heterocycle having 1 nitrogen atom and 1 oxygen atom;

(b) an unsaturated 6-membered heterocycle with 1-2 N atoms, wherein the heterocycle is substituted with $NHR^3$, wherein the heterocycle is additionally optionally substituted with 1 or 2 halogens, wherein $R^3$ is saturated heterocycle with 1 nitrogen atom, wherein the $R^3$ nitrogen is substituted with $C(O)C_{1-6}$alkyl and wherein the $R^3$ heterocycle is optionally substituted with 1 or 2 halogens;

(c) an unsaturated 6-membered heterocycle with 1 N atom optionally substituted with one, two or three moieties independently selected from halogen, =O, $C_{1-6}$alkyl, $C_{3-6}$cycloalkyl, $C_{1-6}$fluoroalkyl, 5-membered unsaturated heterocycle having 3 or 4 N atoms, OH, $OC_{1-6}$alkyl, $OC_{1-6}$alkoxy, $NC_{1-6}$alkyl, or $NHR^4$, wherein $R^4$ is saturated heterocycle having 1N atom optionally substituted with one or two $C(O)C_{1-6}$alkyl and wherein the $C(O)C_{1-6}$alkyl is optionally substituted with one or two fluoro atoms;

(d)

i. an unsaturated 5-membered heterocycle with 1 or 2 Nitrogen atoms and 0-1 Oxygen atom optionally substituted with a 5-membered unsaturated heterocycle with 1 nitrogen atom and 1 oxygen atom wherein each heterocycle is independently optionally substituted with $C_{1-6}$alkyl, ii. an unsaturated 5-membered heterocycle with 2 N atoms optionally substituted with $CHF_2$, cyclopropyl, or an phenyl optionally mono-substituted, independently disubstituted, or independently trisubstituted with halogen, $C_{1-6}$alkyl, $OC_{1-6}$alkyl, or $C_{1-6}$fluoroalkyl, (e) an unsaturated 8-11-membered bicyclic heterocycle with 1-4 nitrogen atoms, 0-1 oxygen atoms, and 0-1 sulfur atoms, unsubstituted, mono-substituted, independently disubstituted, or independently trisubstituted with i) $CR^6R^7R^8$, wherein $R^6$ is H, $CH_3$, or F, $R^7$ is H, $CH_3$, F or OH, and $R^8$ is H, CN, $CH_3$, F, OH, $OCH_3$, $CF_3$, or $CH_2CN$;

ii) $C(O)NR^9R^{10}$, wherein $R^9$ is H, $CH_3$, F, or $CF_3$, and $R^{10}$ is H, $CH_3$, $CH_3(CH_3)_2$, F, or $CF_3$, iii) CN;

iv) $C_3$ to $C_6$ saturated or unsaturated carbocycle optionally mono-substituted, independently disubstituted, or independently trisubstituted with $C_{1-6}$alkyl, 1-3 halogens, or CN;

v) halogen;

vi) $C_{0-6}$alkyl$O(CH_2)_{0-2}R^{11}$, wherein:

$R^{11}$ is H, $CH_3$, $CH_2OCH_3$, $OCH_3$, $CH(CH_3)_2$, $C(CH_3)_2OH$,

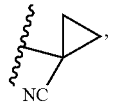 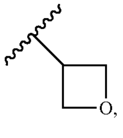 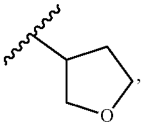

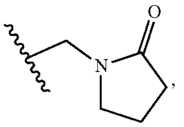 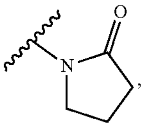 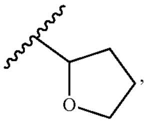 or

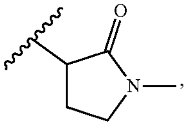

vii) =O;

viii)

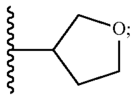

ix)

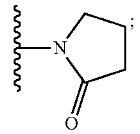

x) $N(C_{1-6}alkyl)(C_{1-6}alkyl)(OC_{1-6}alkyl)$ or $N(C_{1-6}alkyl)(C_{1-6}alkyl)$, wherein the alkyl moiety is optionally substituted with 5-membered unsaturated ring with 2 nitrogen atoms, 0-1 oxygen atom, wherein the ring is optionally substituted with $C_{1-6}$alkyl, halogen, or $C_{1-6}$haloalkyl;

xi)

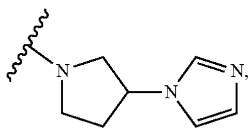 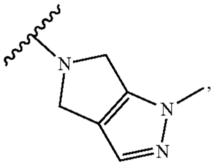

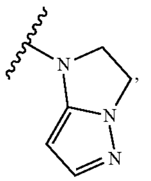 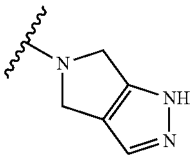

xii)

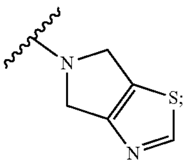 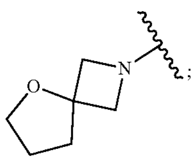 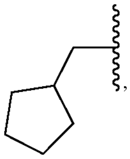

-continued

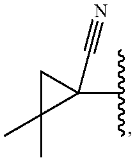, or 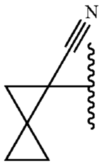

xiii) unsaturated 5- or 6-membered heterocycle with 1-2 nitrogen atoms, 0-1 oxygen atoms, and 0-1 sulfur atoms optionally mono-substituted or independently disubstituted with $C_{1-6}$alkyl or $OC_{1-6}$ alkyl, wherein the alkyl is optionally substituted with 1-3 halogens xiv) $C_{1-6}$alkyl optionally substituted with CN or halogen; or (f) unsaturated 13-membered tricyclic heterocycle with 1 oxygen, wherein the tricyclic heterocycle is optionally substituted with OH.

3. The compound claim 1, or a pharmaceutically acceptable salt thereof, wherein Y is H or OH;

$Y^1$ is H or OH;

A is (a) phenyl, optionally substituted with one or two moieties independently selected from $OCH_2CH_3$, Cl, O-cyclopropyl, $C(O)R^5$, or an unsaturated 5-membered heterocycle having 1-3 nitrogen atoms and 0-1 oxygen atoms wherein the unsaturated heterocycle is optionally substituted with cyclopropyl or $C_{1-6}$alkyl, wherein $R^5$ is

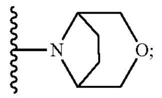 [SMILES: *N1C2CCC1COC2];

(b) an unsaturated 6-membered heterocycle with 1 or 2 N atoms substituted with $NHR^3$, wherein the heterocycle is additionally optionally substituted with 1 or 2 halogens, wherein $R^3$ is a saturated heterocycle with 1 nitrogen atom wherein the $R^3$ nitrogen is substituted with $C(O)CH_3$, and wherein the $R^3$ heterocycle is additionally optionally independently substituted with 1 or 2 halogens;

(c) unsaturated 6-membered heterocycle with 1 N atom optionally substituted with one, two or three moieties independently selected from Cl, Br, F, =O, $CH_3$, $CF_3$, $CH_2CF_3$, $CH(CH_3)CF_3$, $OCH_2CH_2OH$, $NHCH_3$, cyclopropyl, $OCH_2CH_3$, $OCH_2CH_2CH_3$, $OCH_3$, OH, or 5-membered unsaturated heterocycle having 3 or 4 nitrogen atoms;

(d)

i. unsaturated 5-membered heterocycle with 1 nitrogen atom and 1 oxygen atom substituted with 5-membered unsaturated heterocycle with 1 nitrogen atom and 1 oxygen atom wherein each heterocycle is optionally independently substituted with $CH_3$, ii. unsaturated 5-membered heterocycle with 2 nitrogen atoms optionally substituted with $CHF_2$, cyclopropyl or an phenyl wherein the phenyl is optionally mono-substituted, independently disubstituted, or independently trisubstituted with F, $CH_3$, $OCH_3$, cyclopropyl, or $CHF_2$;

(e) unsaturated 8-11-membered bicyclic heterocycle with 1-4 nitrogen atoms, 0-1 oxygen atoms, and 0-1 sulfur atoms, unsubstituted, mono-substituted, independently disubstituted, or independently trisubstituted with Br, F, Cl, I, $CH_3$, CN, $CH(CH_3)_2$, $CH_2OH$, $C(CH_3)_2OH$, $C(O)NHCH_3$, $C(O)N(CH_3)_2$, $CF_3$, $CHF_2$, $C(CH_3)_2OCH_3$, $CH(CH_3)OCH_3$, $CH_2OCH_3$, $CH_2CH_2OCH_3$, $CH(OH)CF_3$, $CH(OH)CH_3$, $(CH_2)_2CN$, $CH_2CF_3$, $CH(CH_3)_2$, $CH_2CH_3$, cyclopropyl, cyclopropyl-$CH_3$, =O, OH, $OCH_3$, $OCH_2CH_3$, $OCH(CH_3)_2$, $O(CH_2)_2OCH_3$, $OCH_2C(CH_3)_2OH$, $N(CH_3)(CH_2)_2OCH_3$, $CH(CH_3)CN$,

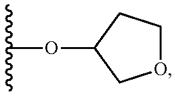 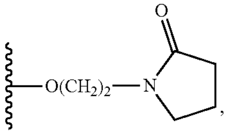

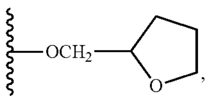 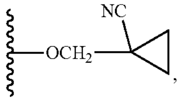 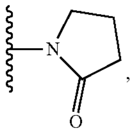

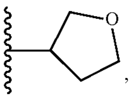 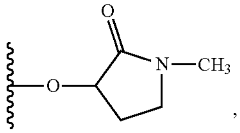 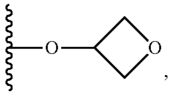

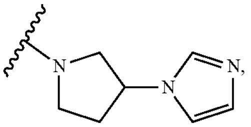 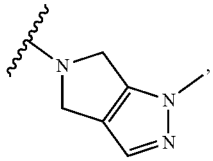

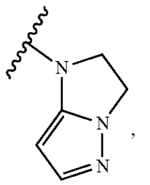 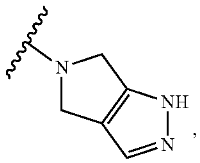 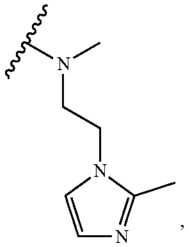

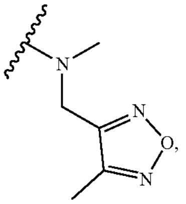 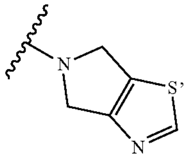 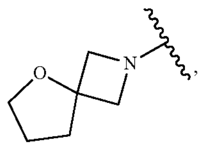

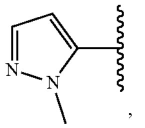 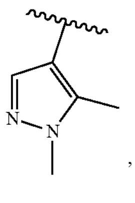 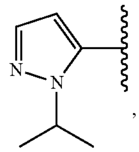

-continued

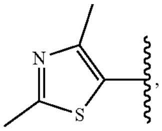, 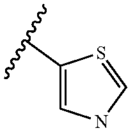, 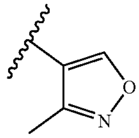,

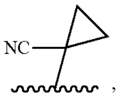, 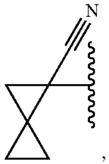, 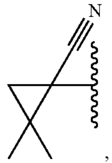, 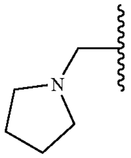,

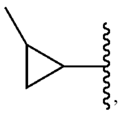, 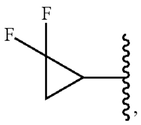, 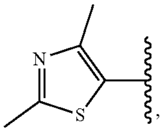,

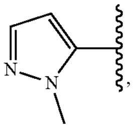, 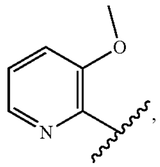, 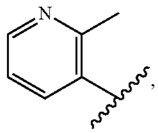, or

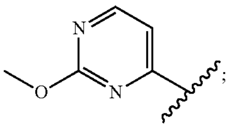;

or (f) unsaturated 13-membered tricyclic heterocycle with 1 O, wherein the tricyclic heterocycle is optionally substituted with OH.

4. The compound of claim 3, or a pharmaceutically acceptable salt thereof, wherein Y is H or OH;

$Y^1$ is H or OH;

A is (a) phenyl, optionally substituted with one or two moieties independently selected from $OCH_2CH_3$, Cl, O-cyclopropyl, $C(O)R^5$, or an unsaturated 5-membered heterocycle having 3 nitrogen atoms substituted with cyclopropyl or $CH_3$, or an unsaturated 5-membered heterocycle having 2 nitrogen atoms and 1 oxygen atom optionally substituted with cyclopropyl, wherein $R^5$ is

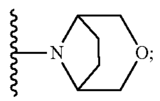;

(b)

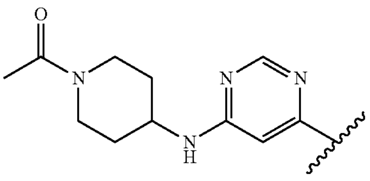 or

-continued

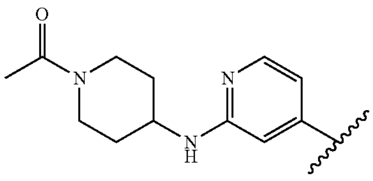

optionally substituted with 1 or 2 moieties independently selected from F or Cl;

(c)

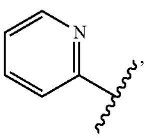, 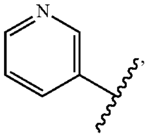, or 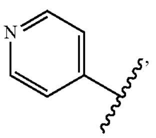, optionally substituted with 1, 2, or 3 moieties independently selected from Cl, F, Br, =O, $CH_3$, $CF_3$, $CH_2CF_3$, $CH(CH_3)CF_3$, $OCH_2CH_2OH$, $NHCH_3$, cyclopropyl, $OCH_2CH_3$, $OCH_2CH_2CH_3$, $OCH_3$, OH,

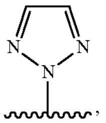, or 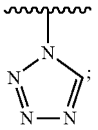;

(d)

i

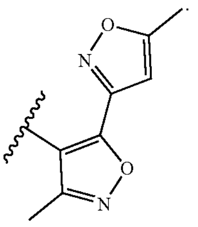

ii

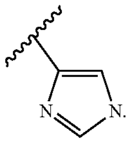.

optionally substituted with $CHF_2$, cyclopropyl or an phenyl, wherein the phenyl is optionally mono-substituted, independently disubstituted, or independently trisubstituted with F, $CH_3$, $OCH_3$, cyclopropyl, or $CHF_2$, (e) an unsaturated 8-11-membered bicyclic heterocycle with 1-4 nitrogen atoms, 0-1 oxygen atoms, and 0-1 sulfur atoms, selected from

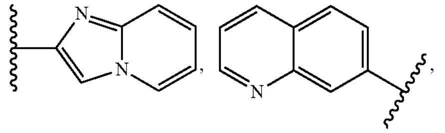

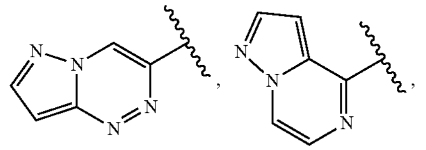

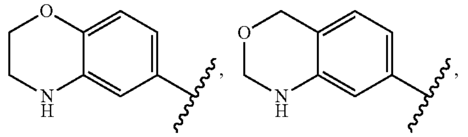

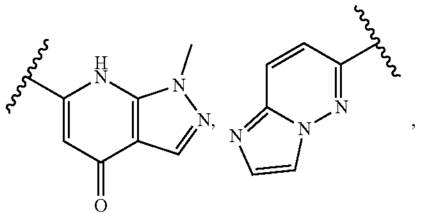

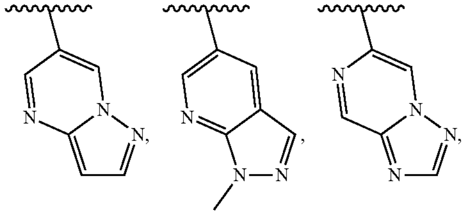

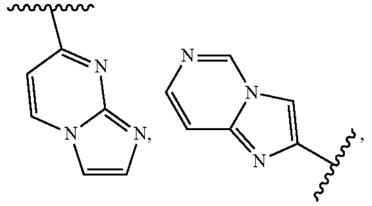

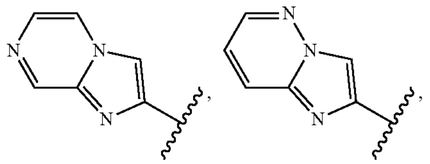

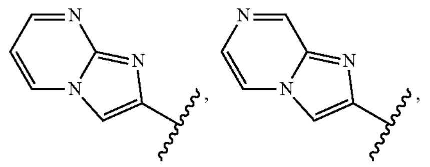

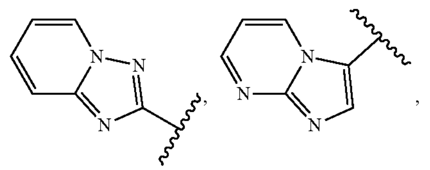

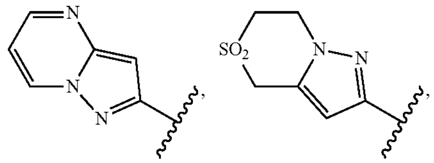

-continued

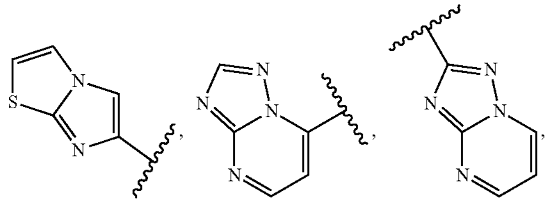

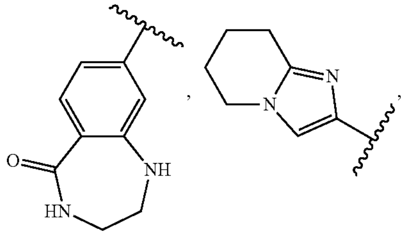

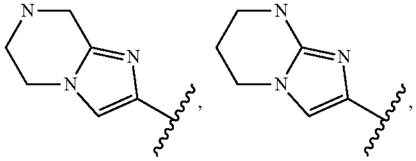

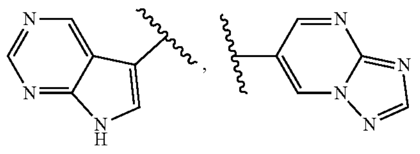

wherein the bicyclic heterocycle is unsubstituted, mono-substituted, independently disubstituted, or independently trisubstituted with Br, F, Cl, I, $CH_3$, CN, $CH(CH_3)_2$, $CH_2OH$, $C(CH_3)_2OH$, $C(O)NHCH_3$, $C(O)N(CH_3)_2$, $CF_3$, $CHF_2$, $C(CH_3)_2OCH_3$, $CH(CH_3)OCH_3$, $CH_2OCH_3$, $CH_2CH_2OCH_3$, $CH(OH)CF_3$, $CH(OH)CH_3$, $(CH_2)_2CN$, $CH_2CF_3$, $CH(CH_3)_2$, $CH_2CH_3$, cyclopropyl, cyclopropyl-$CH_3$, =O, OH, $OCH_3$, $OCH_2CH_3$, $OCH(CH_3)_2$, $O(CH_2)_2OCH_3$, $OCH_2C(CH_3)_2OH$, $N(CH_3)(CH_2)_2OCH_3$, $CH(CH_3)CN$,

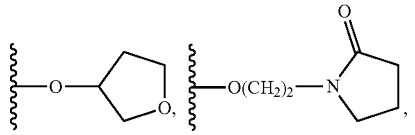

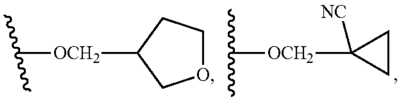

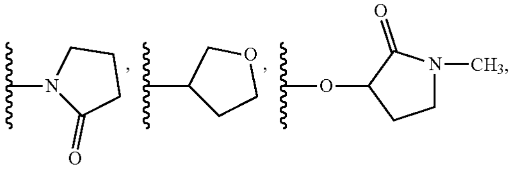

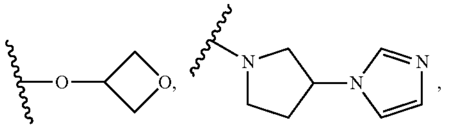

-continued
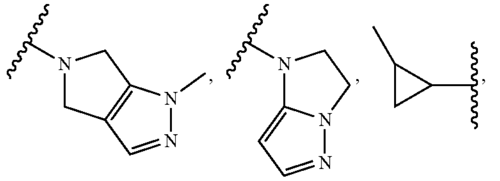
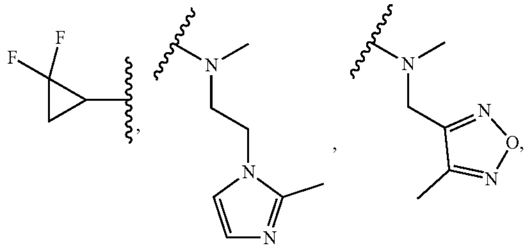
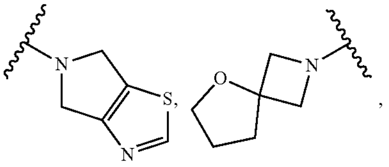
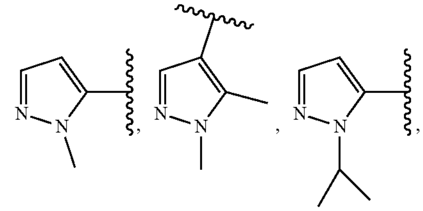
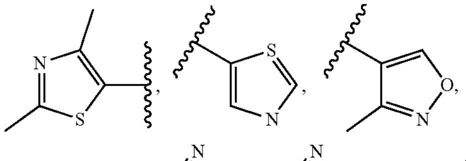
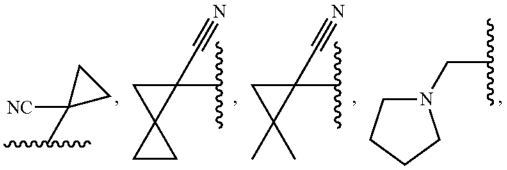
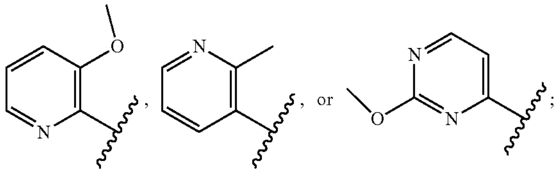
or
(f)
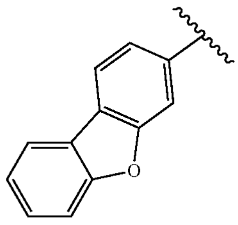 [SMILES: *c1ccc2c(c1)oc1ccccc12]
substituted with OH.
5. The compound of claim 4, or a pharmaceutically acceptable salt thereof, wherein A is selected from
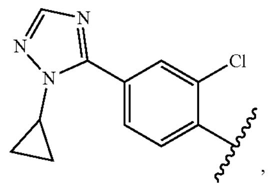
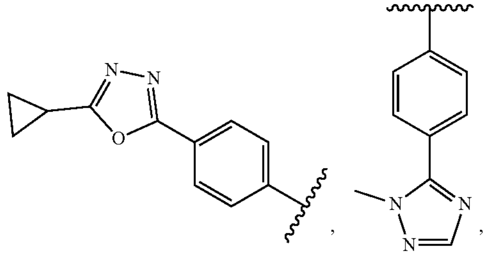
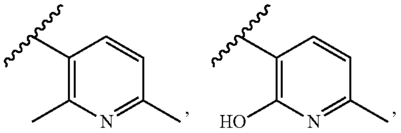
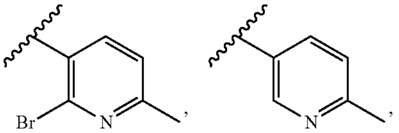
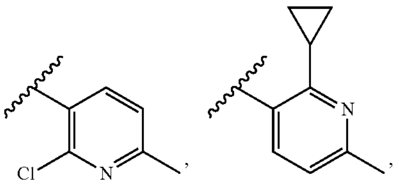
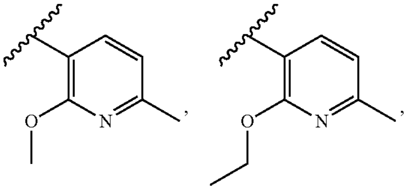
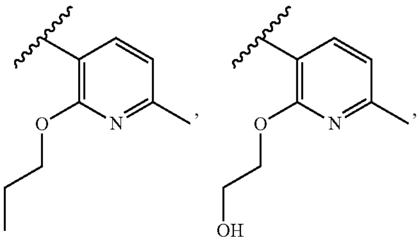
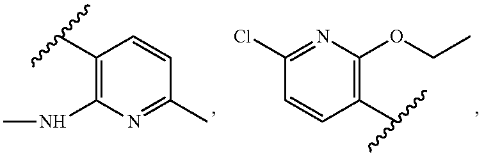
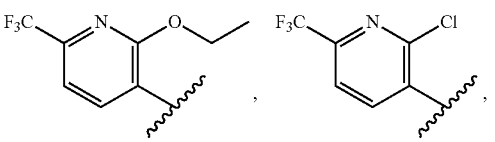

-continued
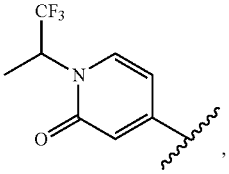
,
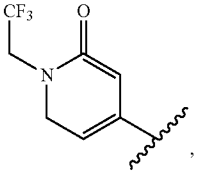
,
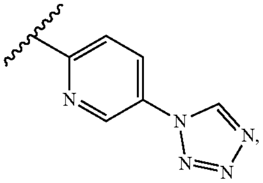
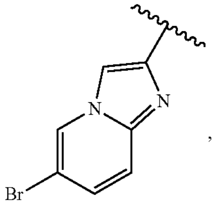
,
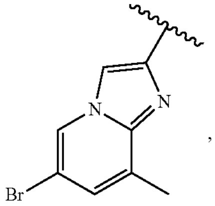
,
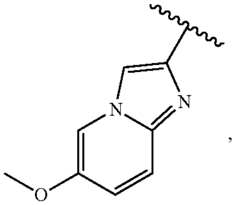
,
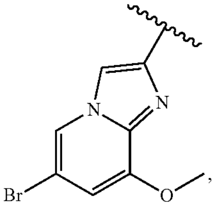
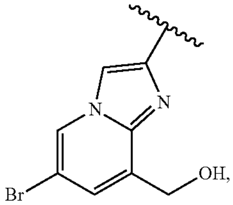
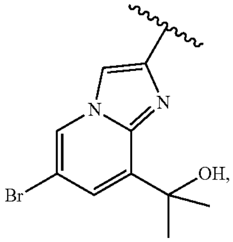
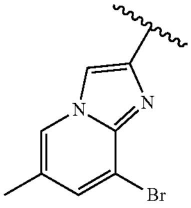
,
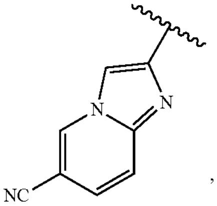
,
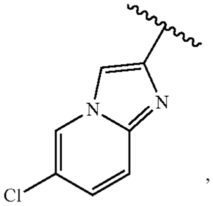
,
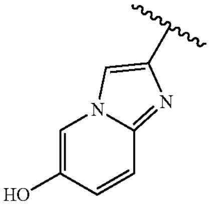
,
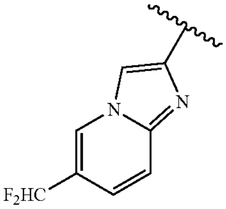
,
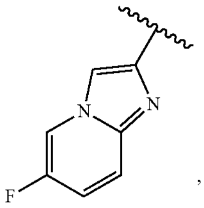
,
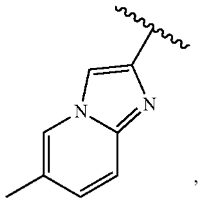
,
-continued
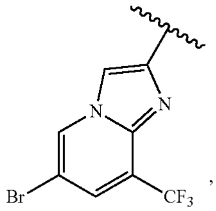
,
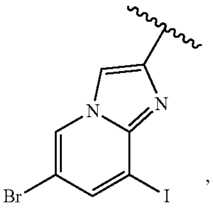
,
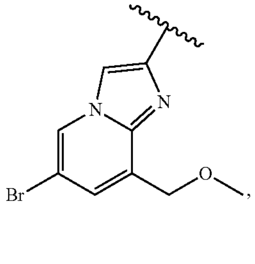
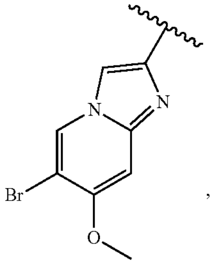
,
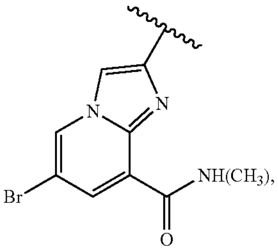
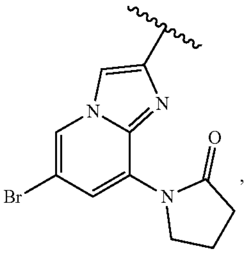
,
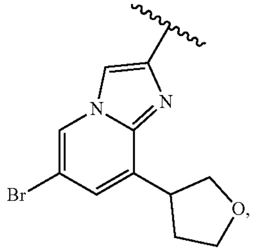
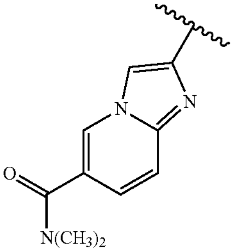
,
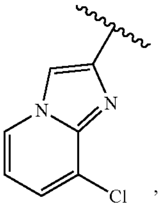
,
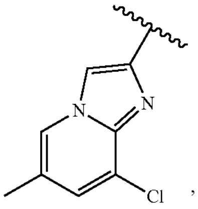
,
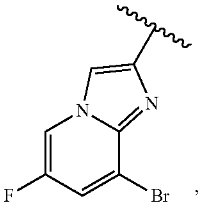
,
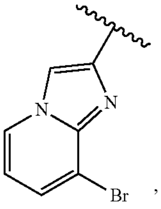
,
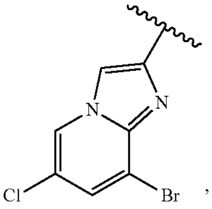
,
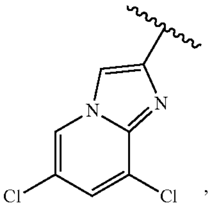
,
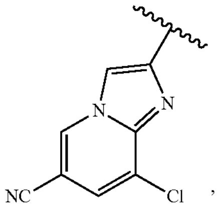
, -continued
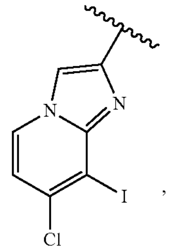,
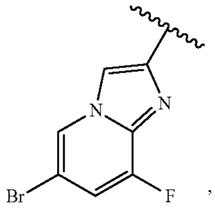,
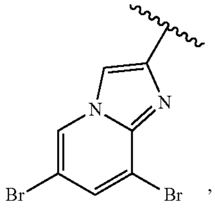,
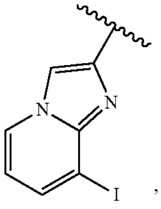,
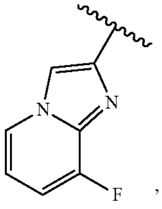,
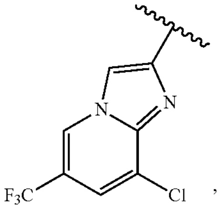,
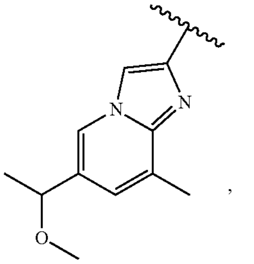,
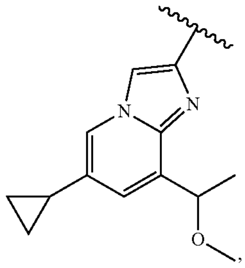,
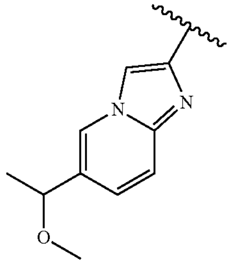,
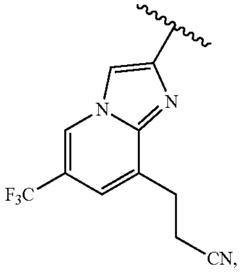,
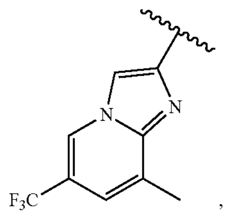,
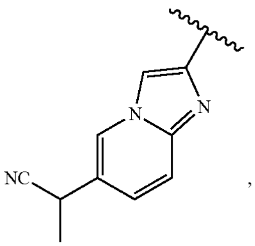,
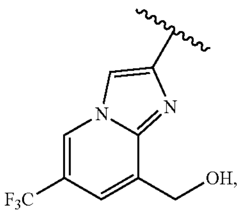,
-continued
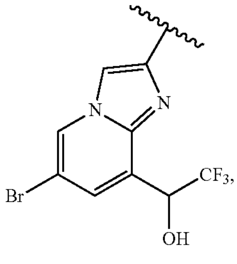,
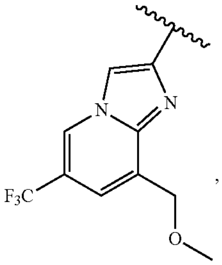,
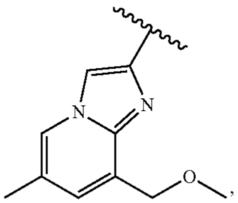,
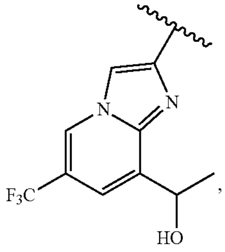,
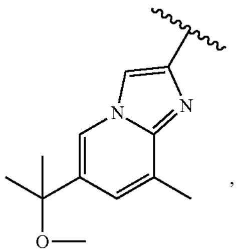,
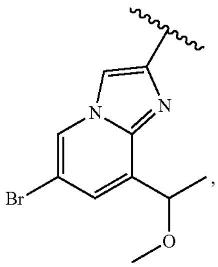,
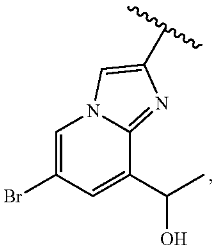,
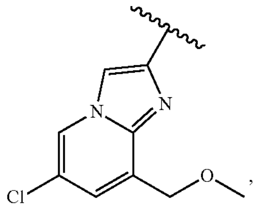,
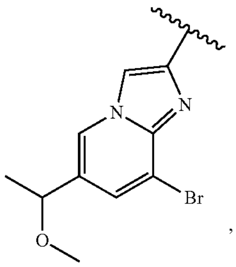,
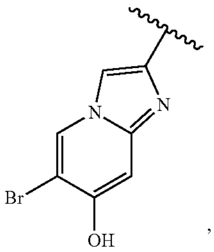,
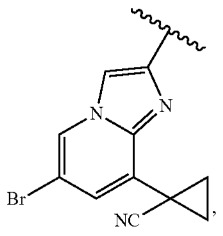,
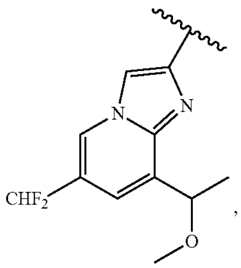, -continued
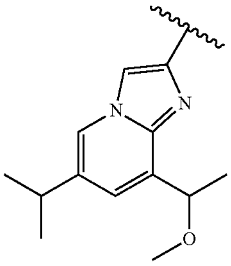,
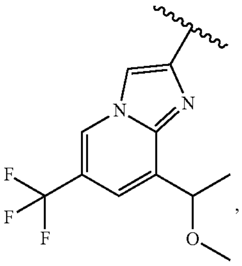,
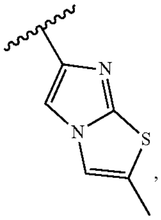,
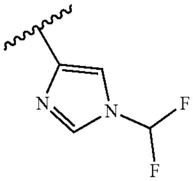,
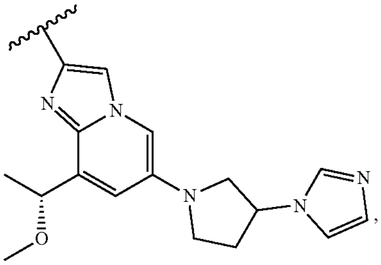,
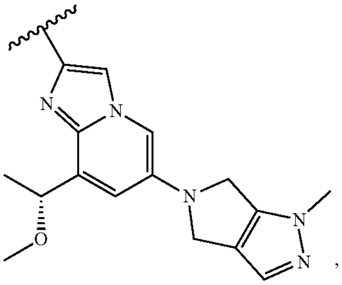,
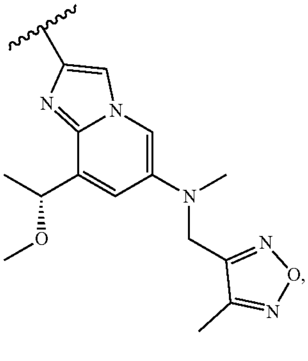
-continued
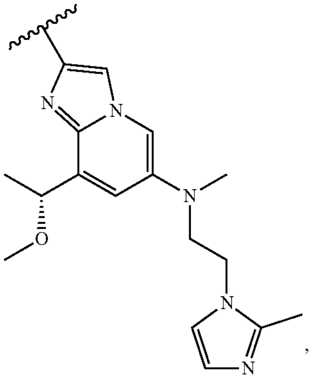,
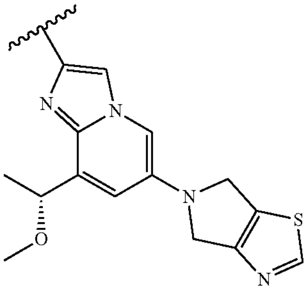,
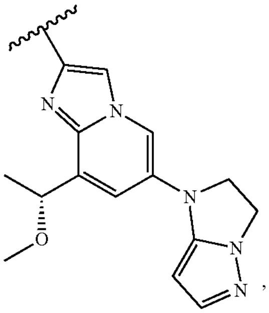,
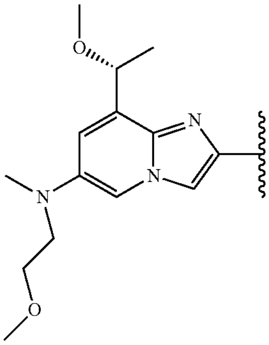,
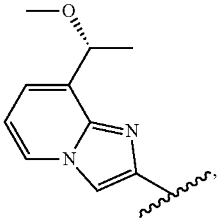,
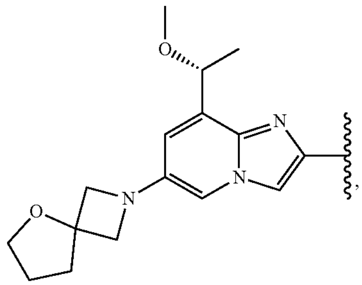, -continued
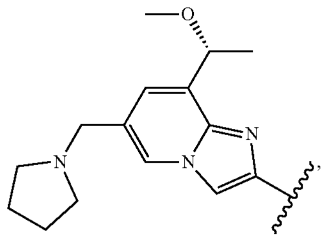
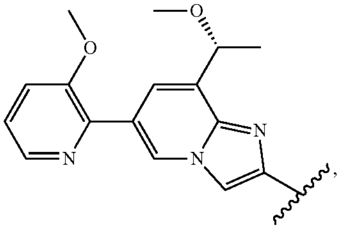
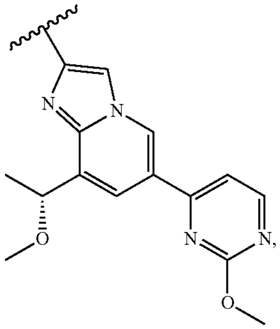
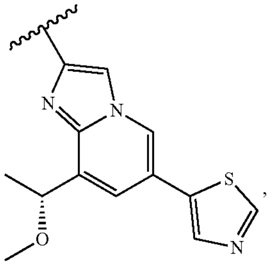
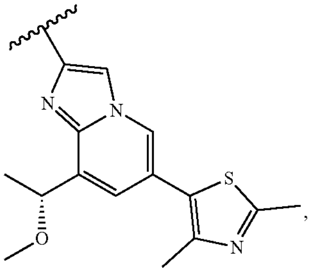
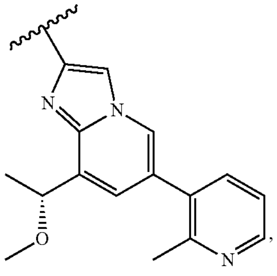
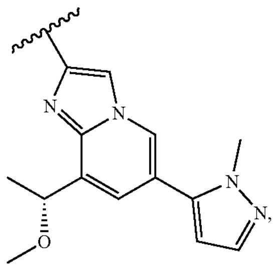
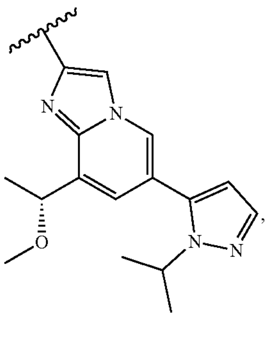
-continued
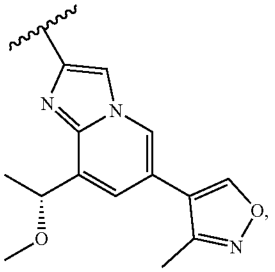
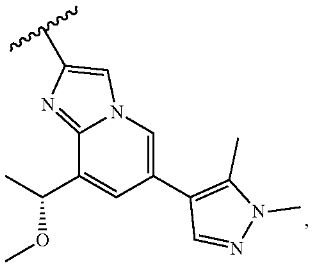
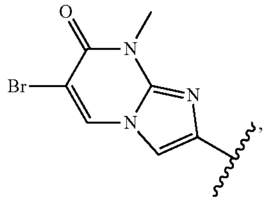
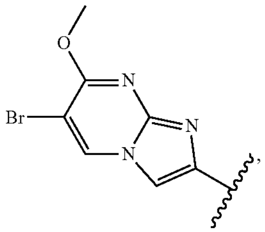
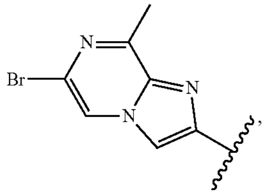
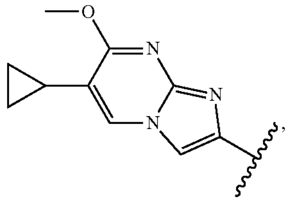
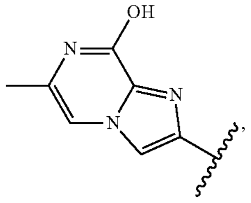
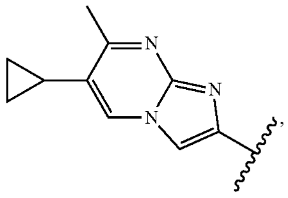
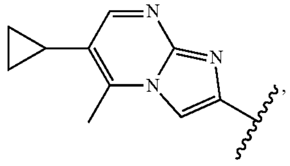
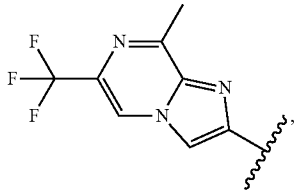
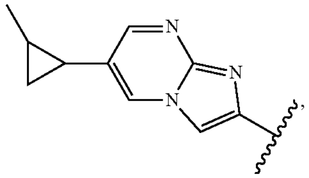
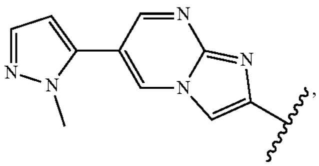

-continued
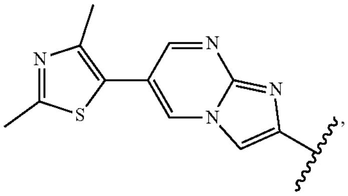,
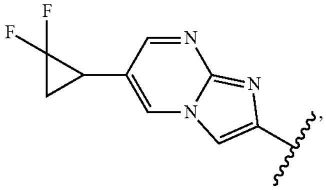,
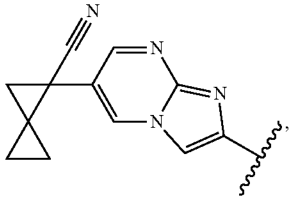, 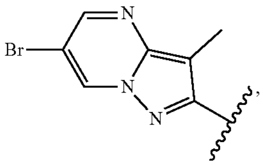,
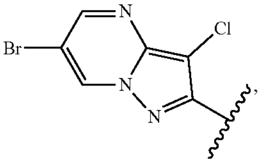, 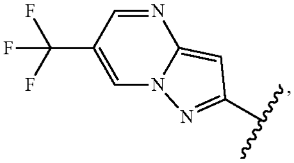,
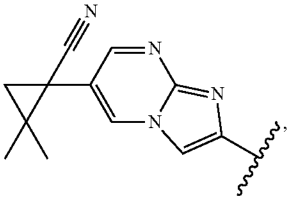, 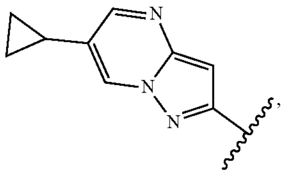,
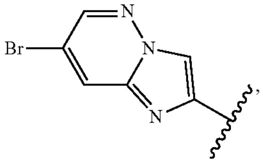, 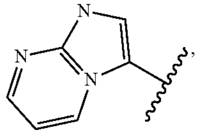,
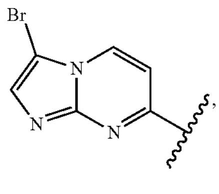, 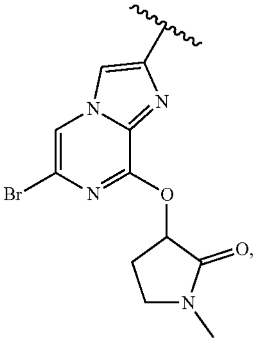
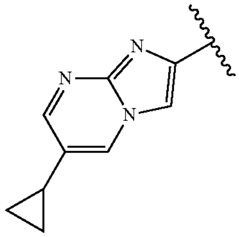, 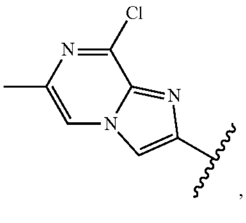,
-continued
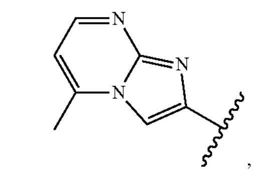, 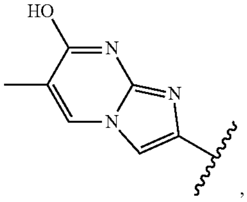,
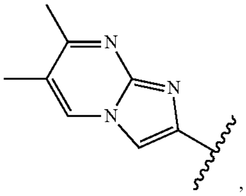, 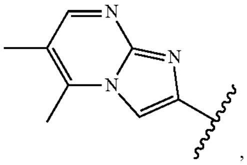,
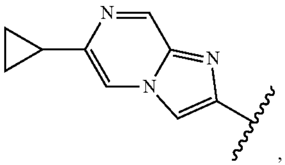, 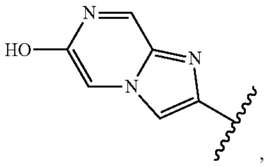,
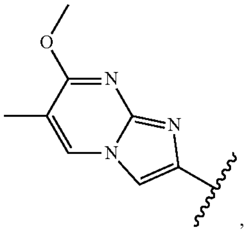, 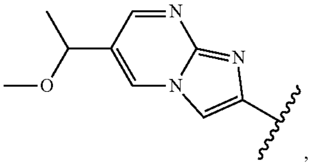,
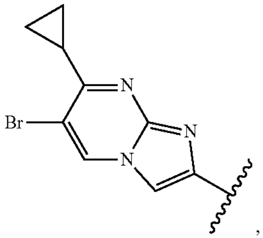, 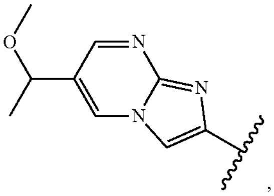,
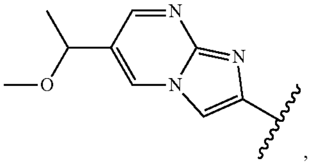,
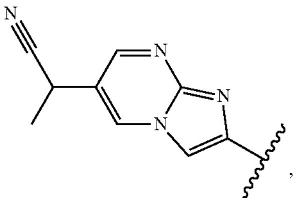, 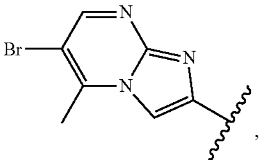,
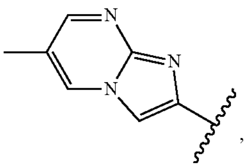, 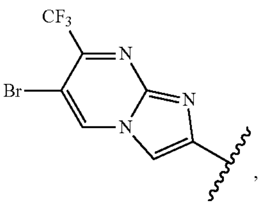, -continued
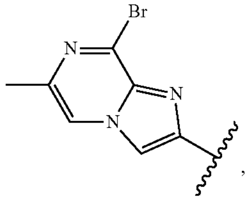, 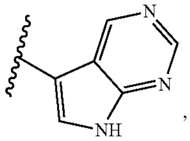,
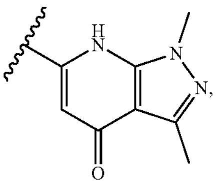 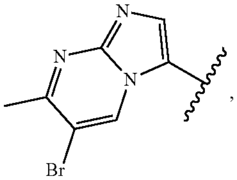,
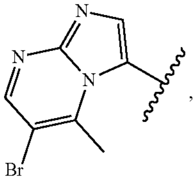, 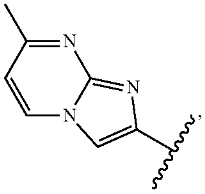
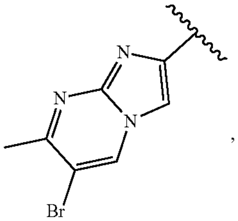, 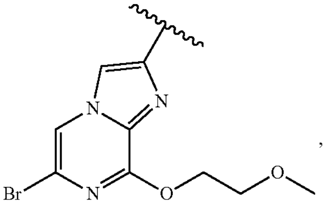,
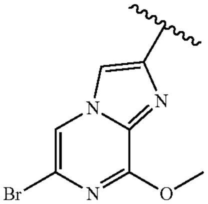, 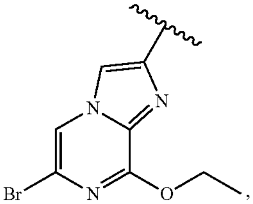
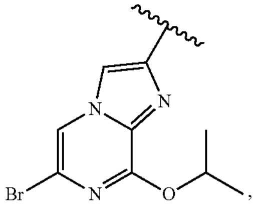, 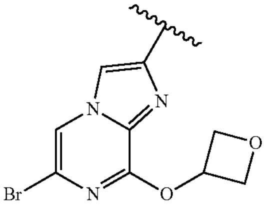,
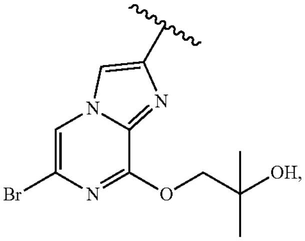 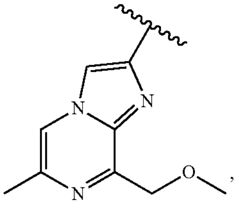,
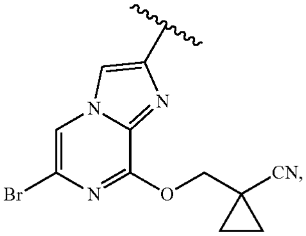 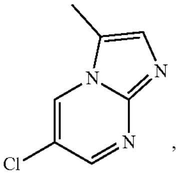,
-continued
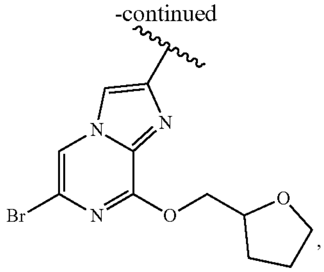
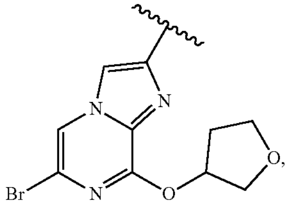 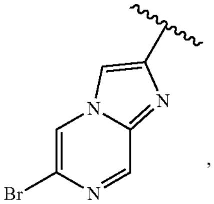,
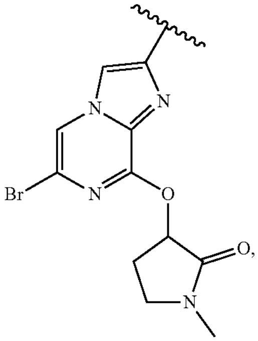
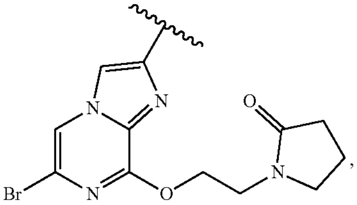 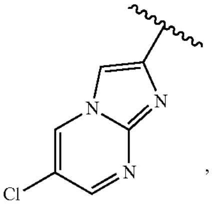,
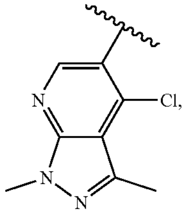 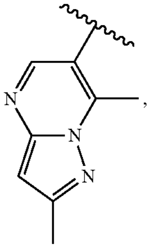 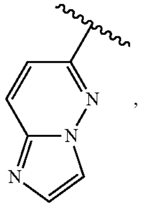,
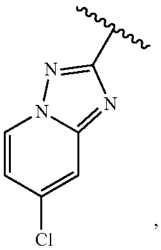, 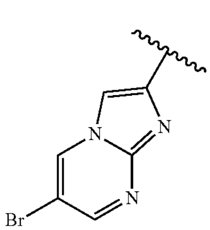, 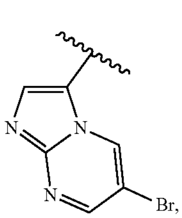
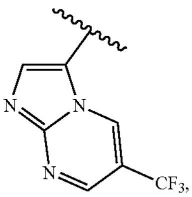 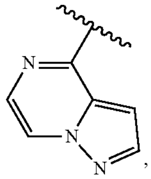, 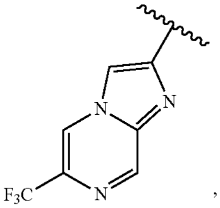, -continued
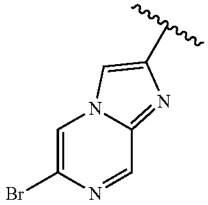,
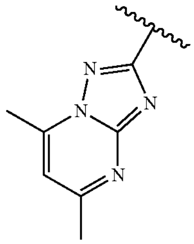,
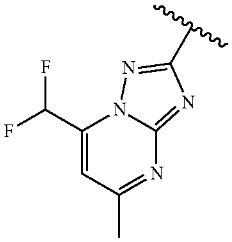,
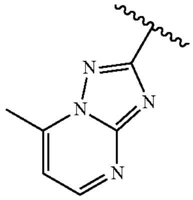,
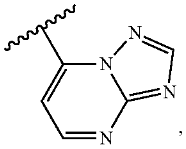,
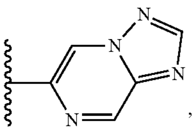,
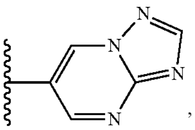,
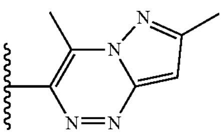,
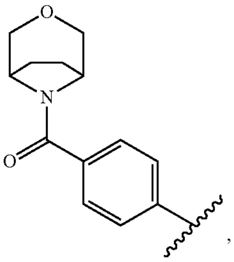,
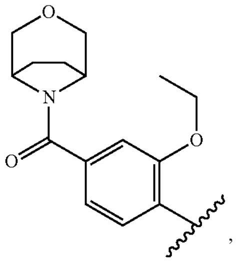,
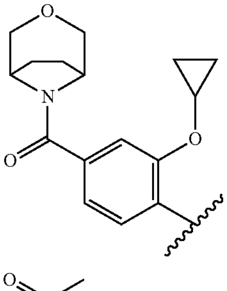,
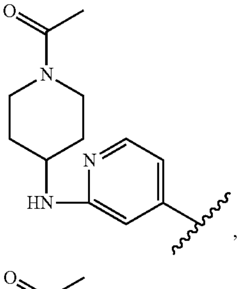,
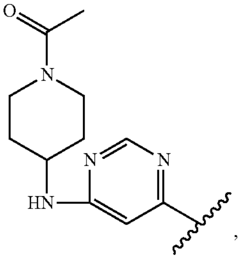,
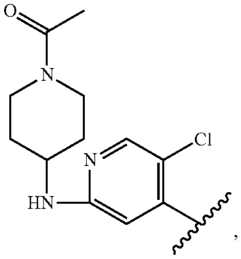,
-continued
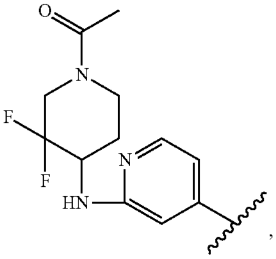,
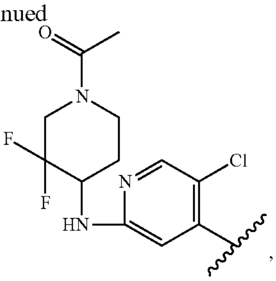,
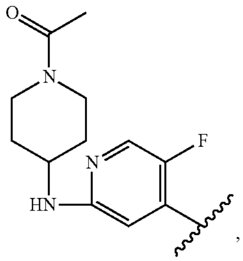,
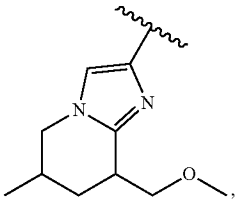
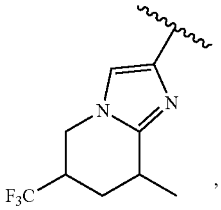,
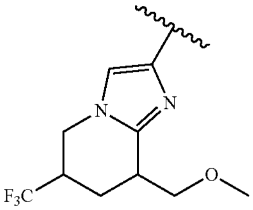
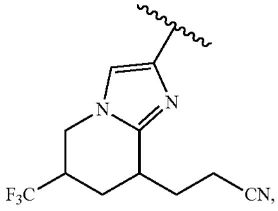
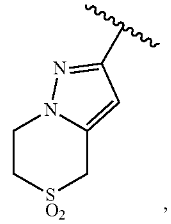,
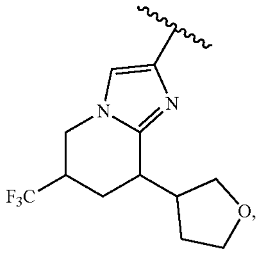
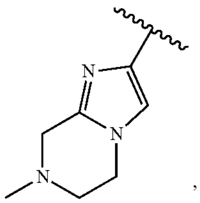,
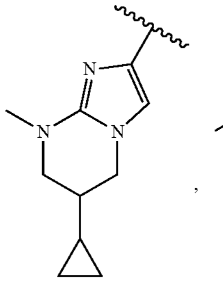,
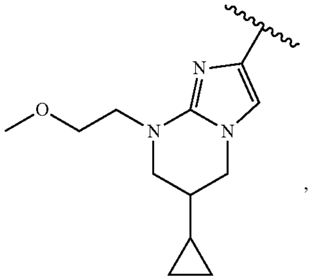,
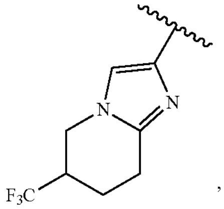,
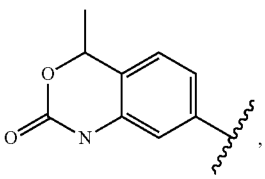, -continued

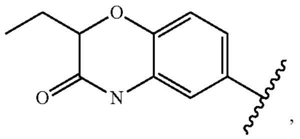

,

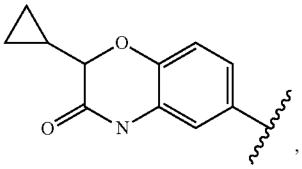

,

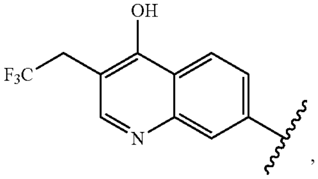

,

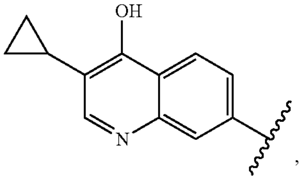

,

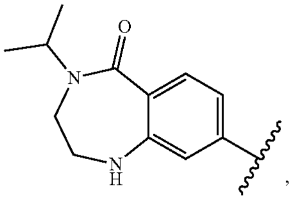

,

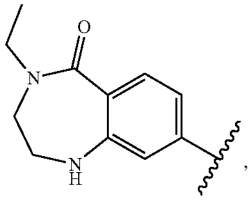

,

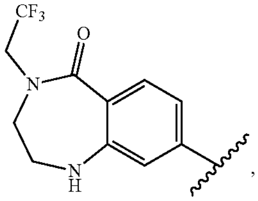

,

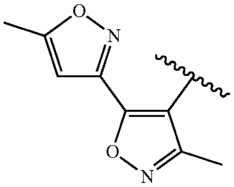

,

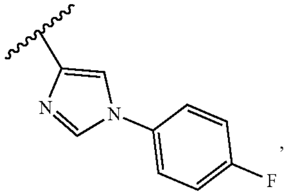

,

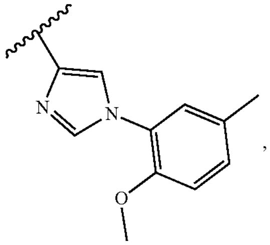

,

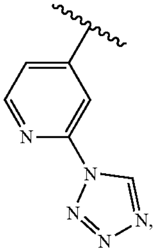

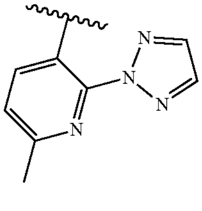

,

-continued

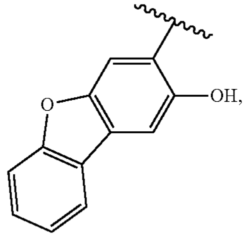

6. The compound of claim 5, or a pharmaceutically acceptable salt thereof, wherein Y is OH and $Y^1$ is H.

7. The compound of claim 5 or a pharmaceutically acceptable salt thereof, wherein Y is H and $Y^1$ is OH.

8. The compound of claim 5, or a pharmaceutically acceptable salt thereof, wherein Y is H and $Y^1$ is H.

9. The compound of claim 1, of formula Ia (Ia)

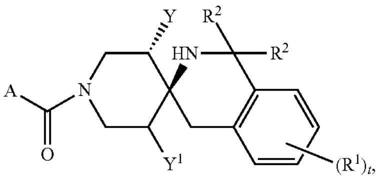

or a pharmaceutically acceptable salt thereof.

10. The compound of claim 1, of formula Ib (Ib)

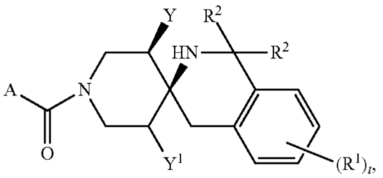

or a pharmaceutically acceptable salt thereof.

11. The compound of claim 1, of formula Ic, (Ic)

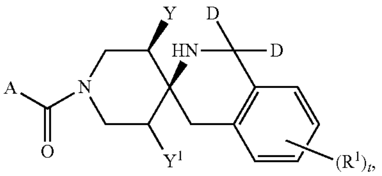

or a pharmaceutically acceptable salt thereof.

12. The compound of claim 1, which is one of the following:
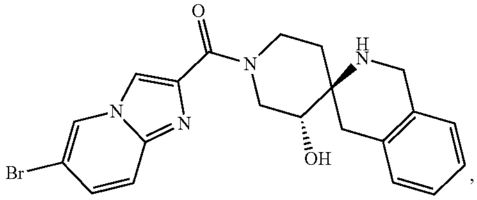
,
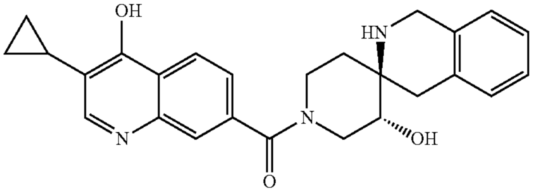
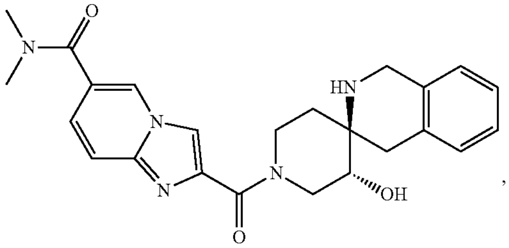
,
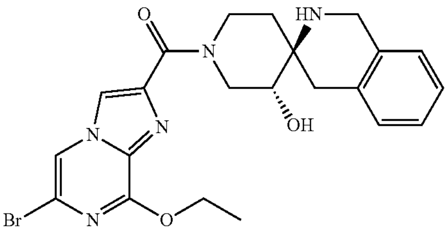
,
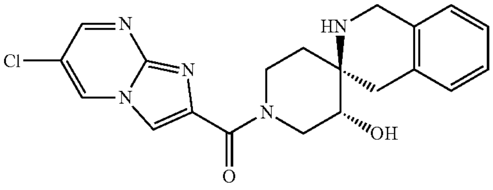
,
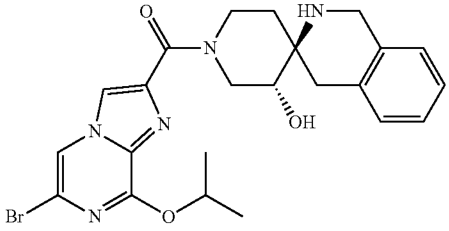
,
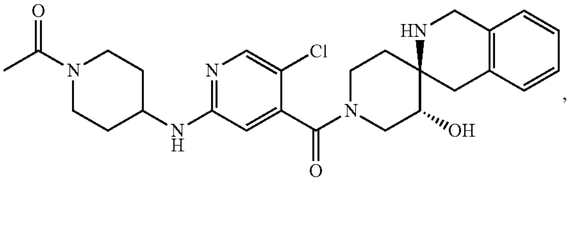
,
-continued
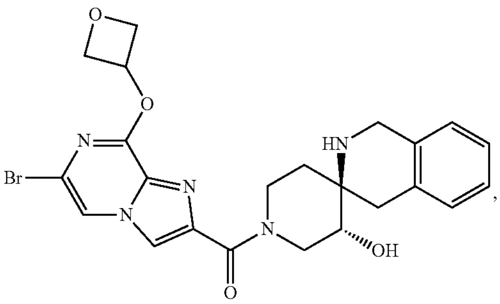
,
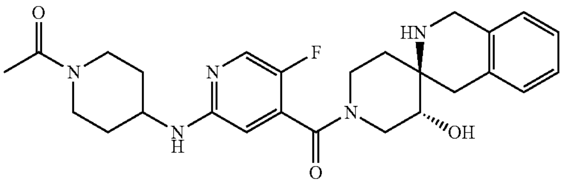
,
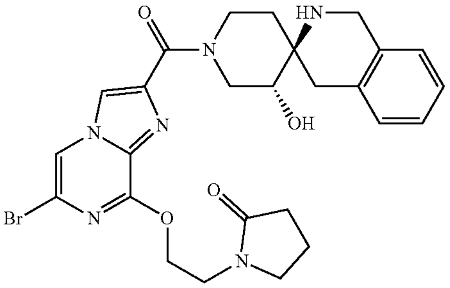
,
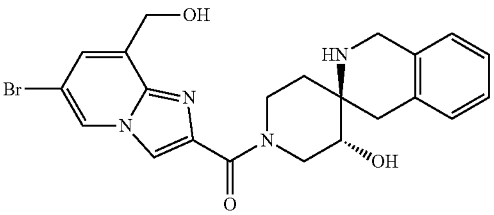
,
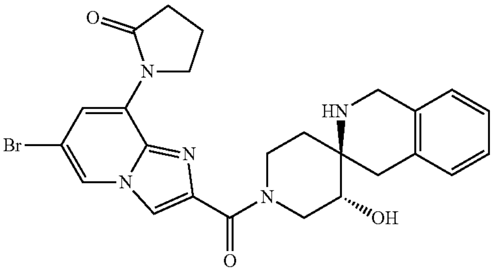
,
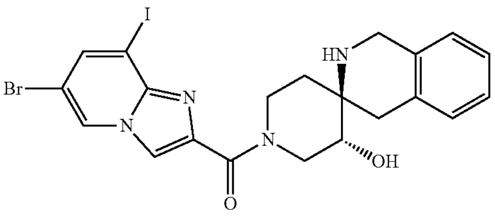
,
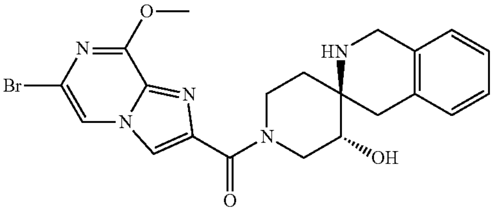
, -continued
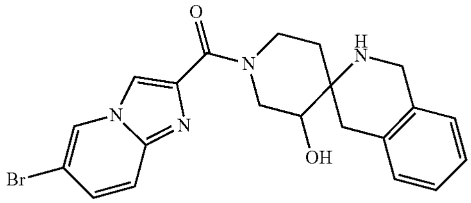
,
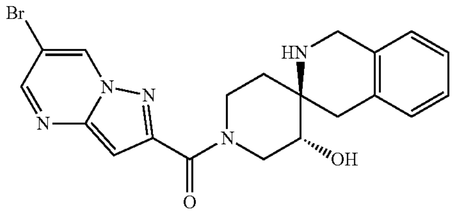
,
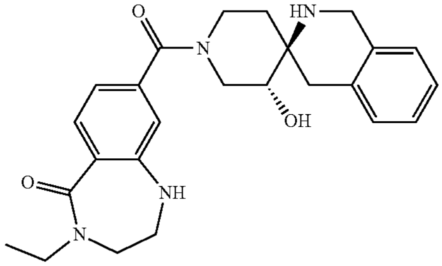
,
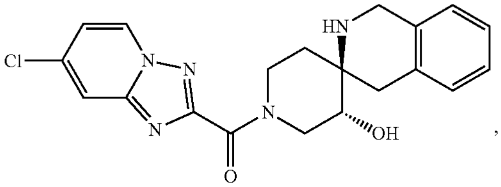
,
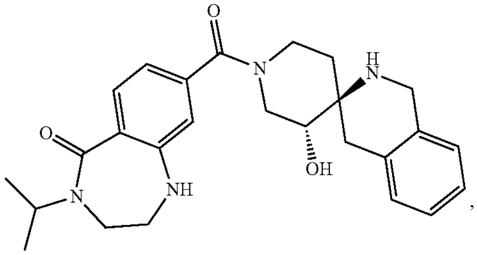
,
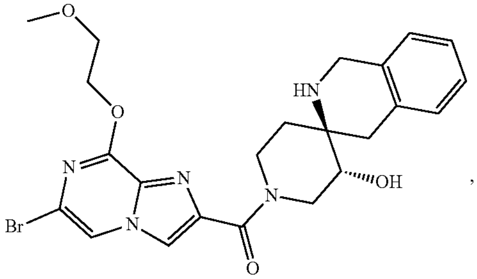
,
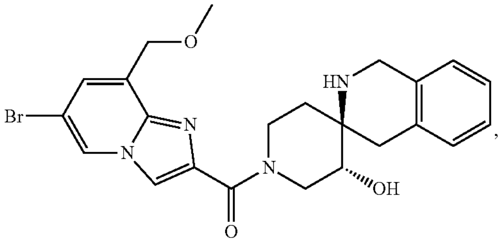
,
-continued
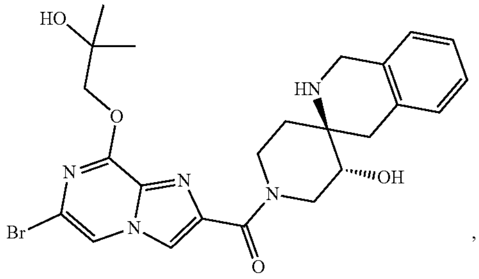
,
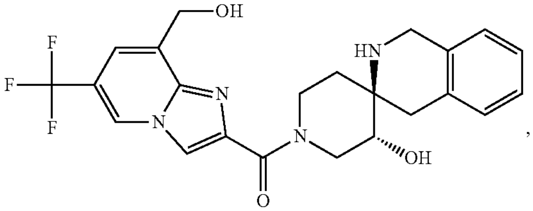
,
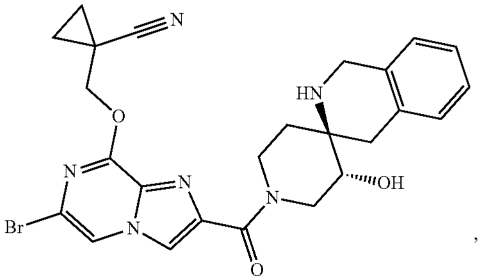
,
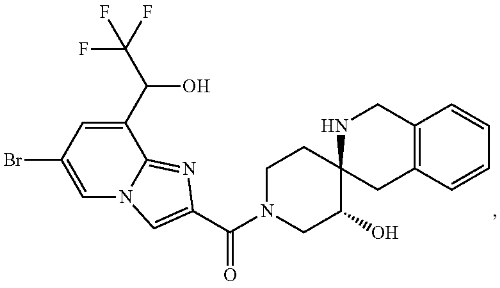
,
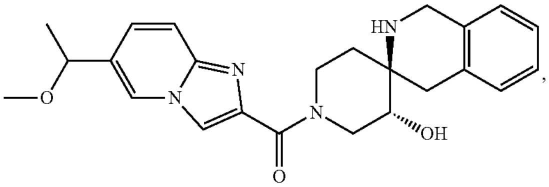
,
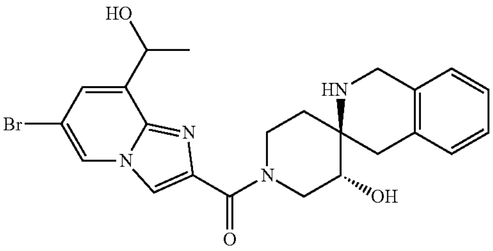
,
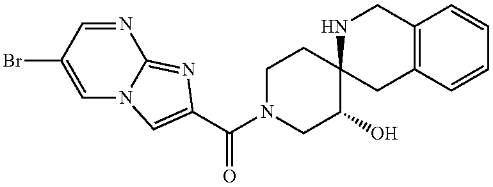
, -continued
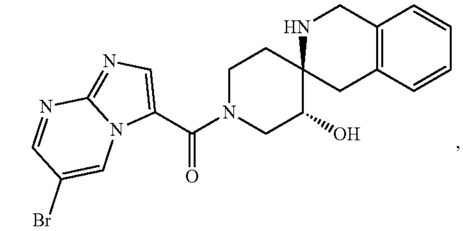,
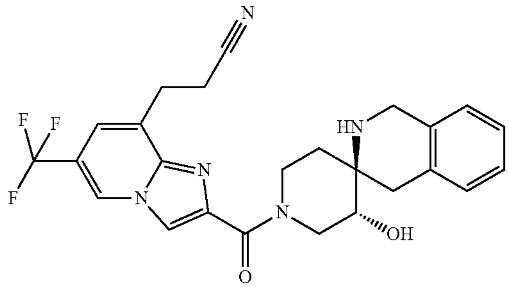,
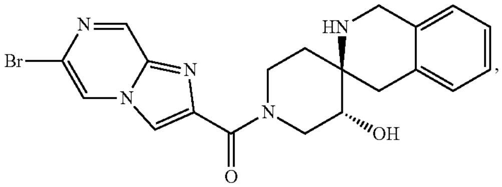,
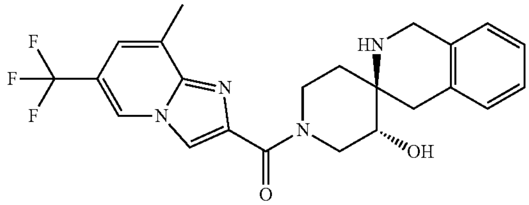,
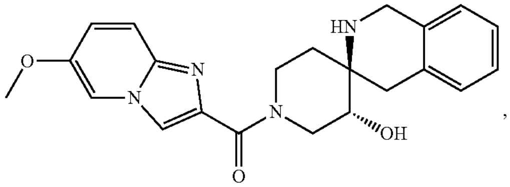,
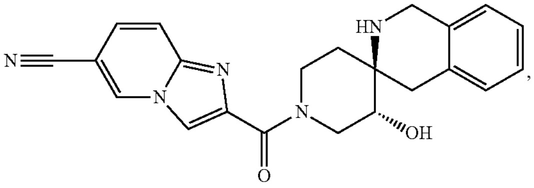,
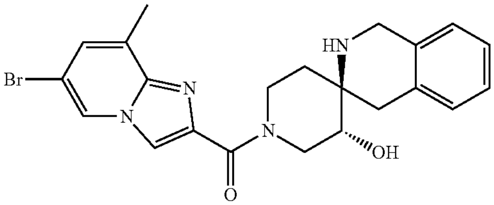,
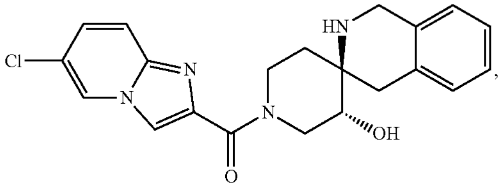,
-continued
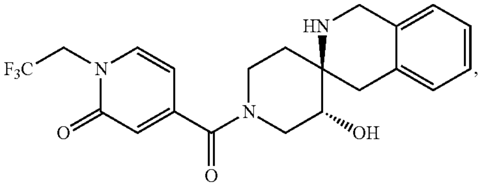,
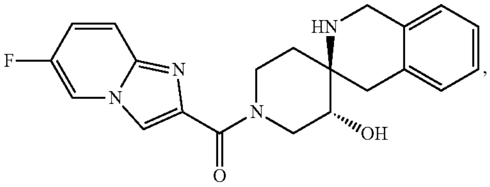,
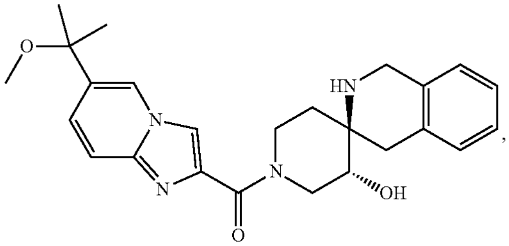,
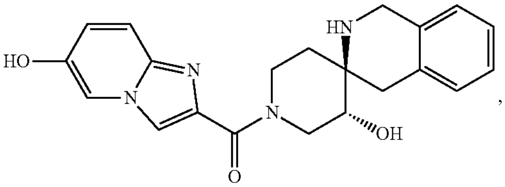,
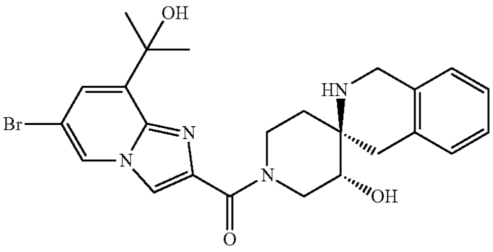,
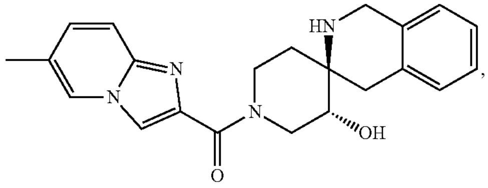,
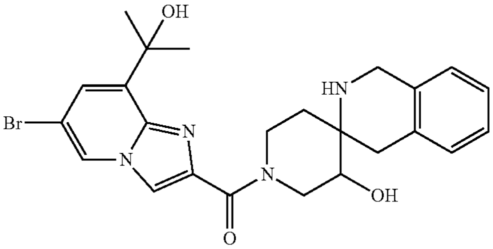,
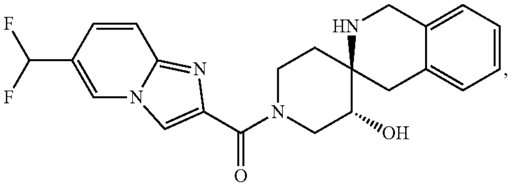, -continued
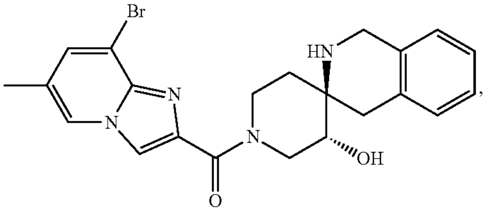,
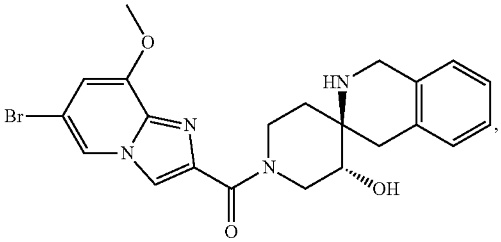,
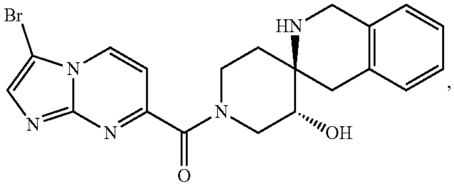,
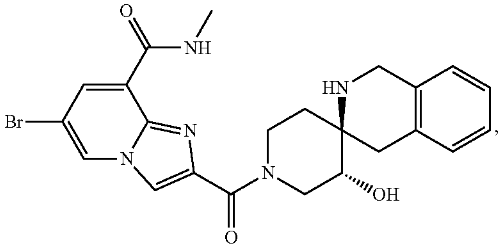,
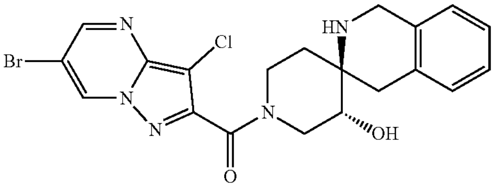,
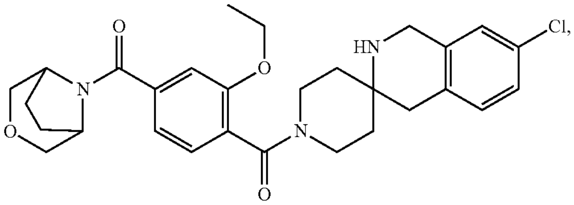
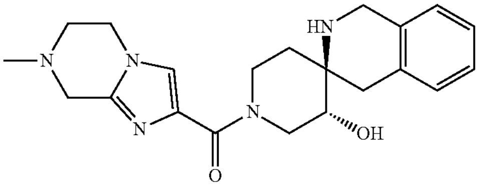,
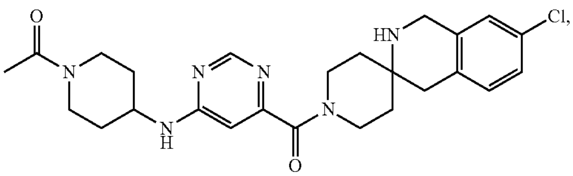
-continued
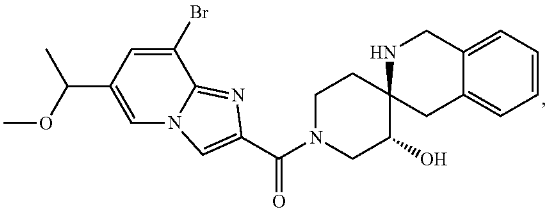,
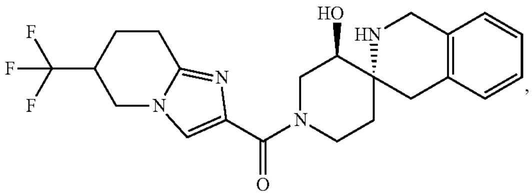,
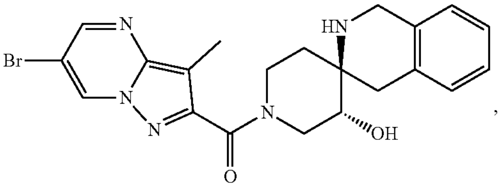,
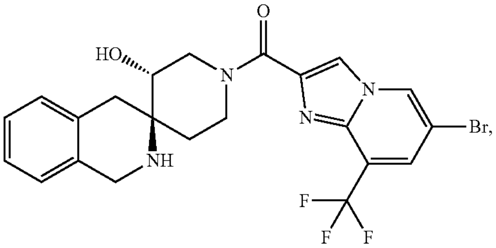
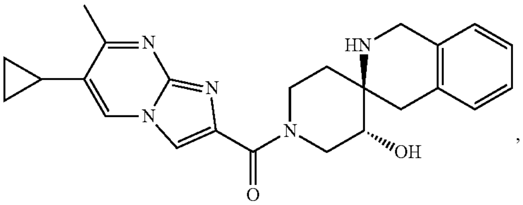,
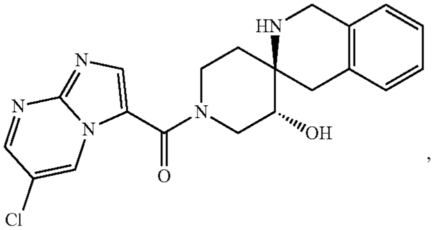,
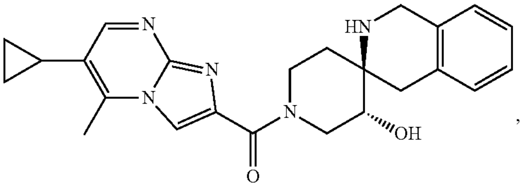,
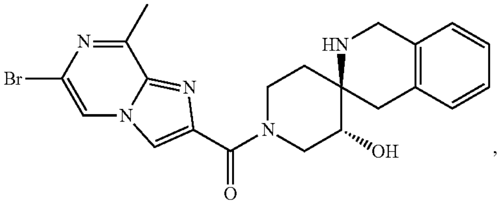, -continued
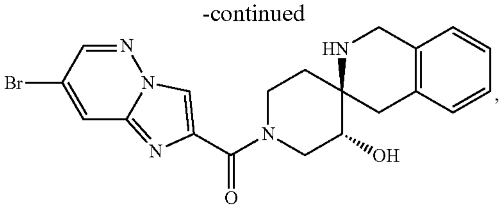
,
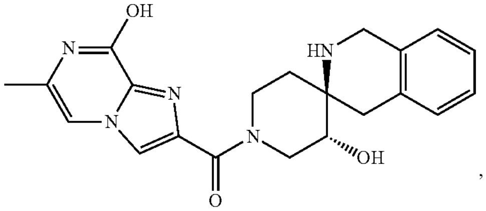
,
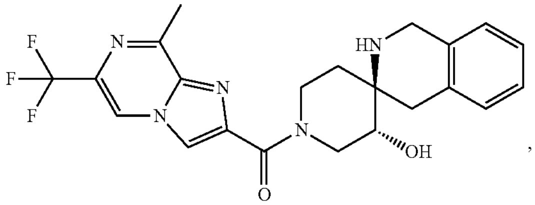
,
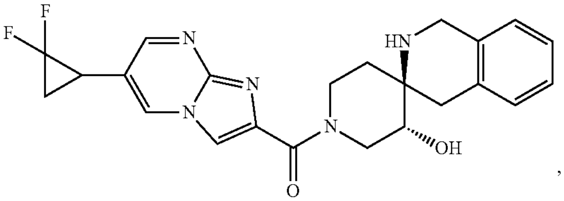
,
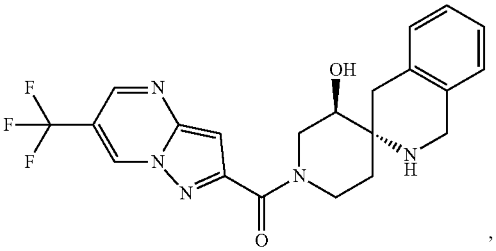
,
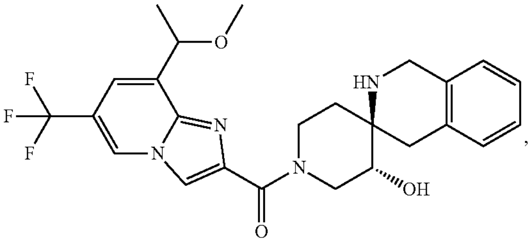
,
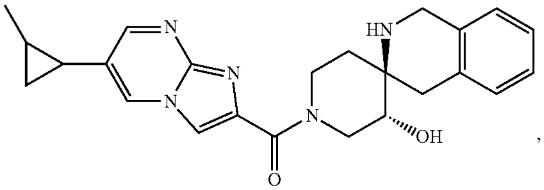
,
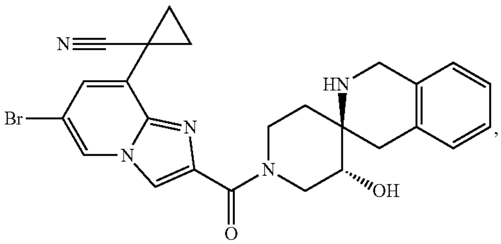
,
-continued
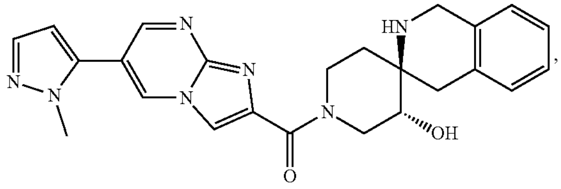
,
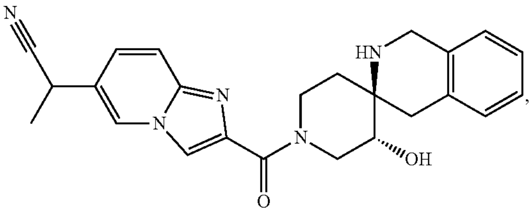
,
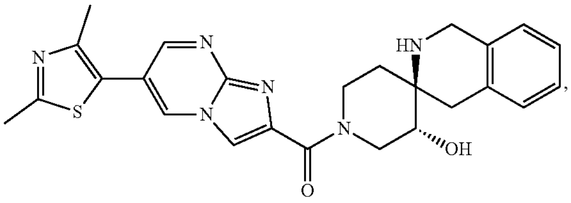
,
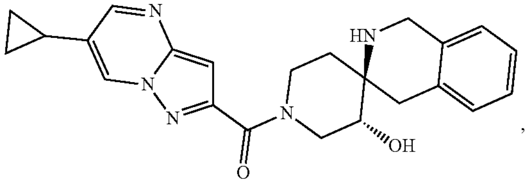
,
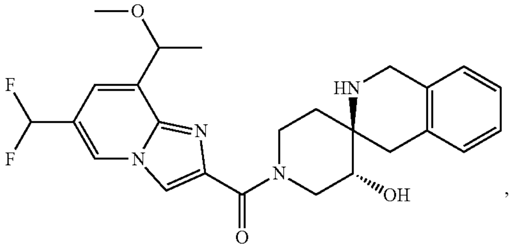
,
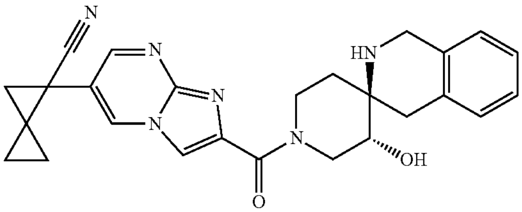
,
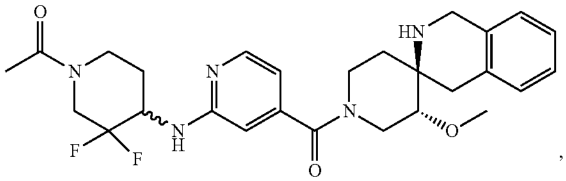
,
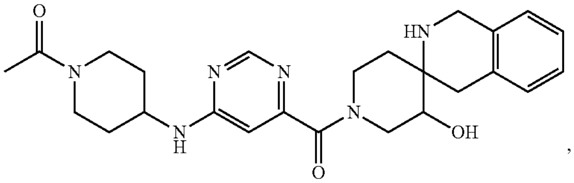
, -continued
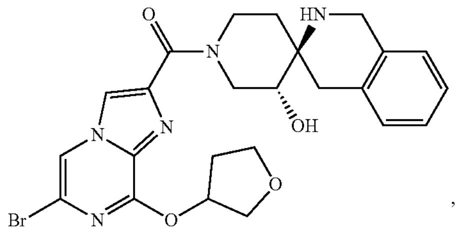
,
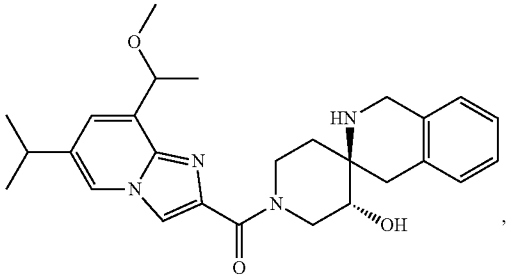
,
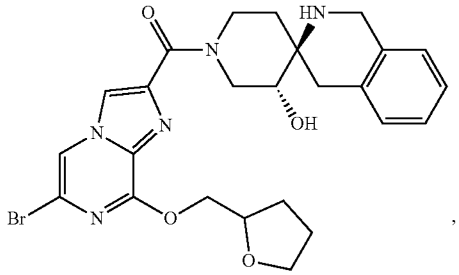
,
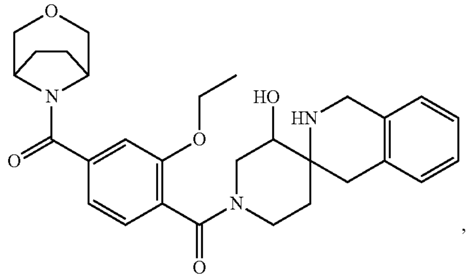
,
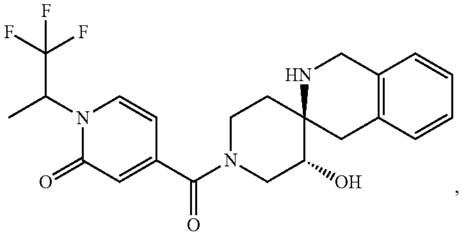
,
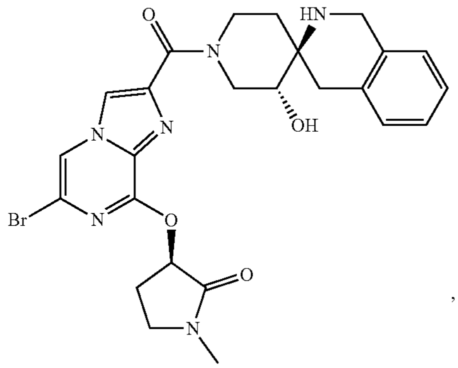
,
-continued
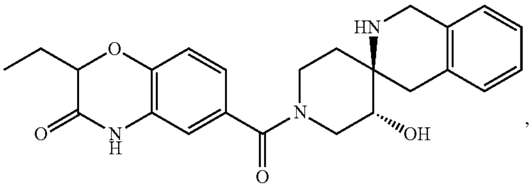
,
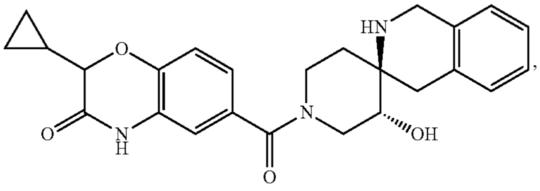
,
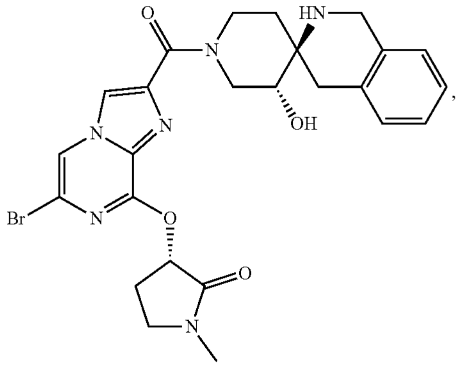
,
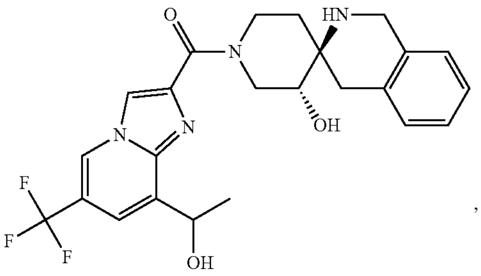
,
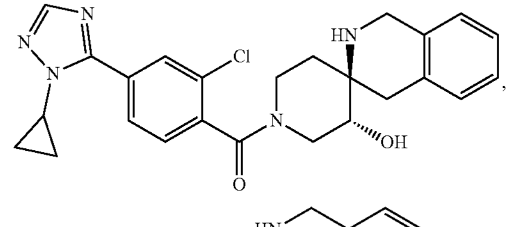
,
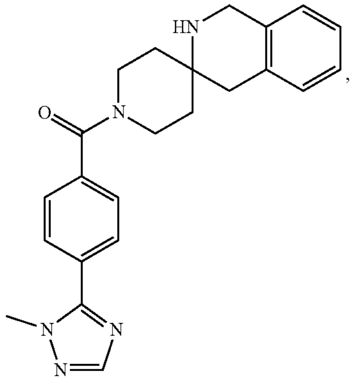
, -continued
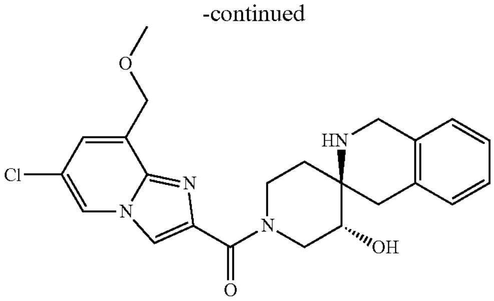
,
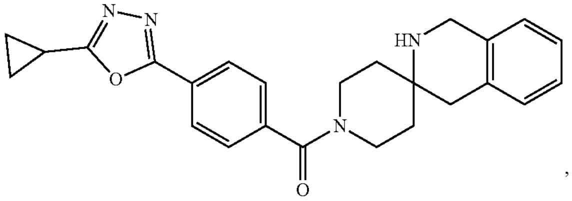
,
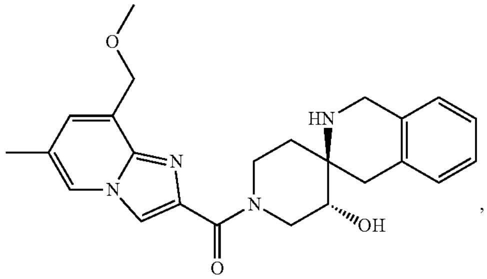
,
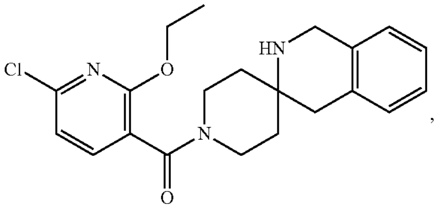
,
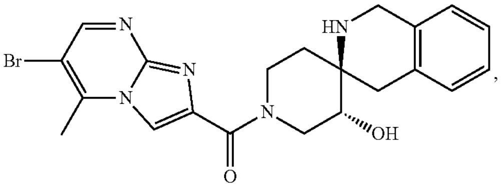
,
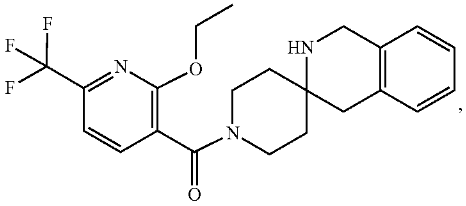
,
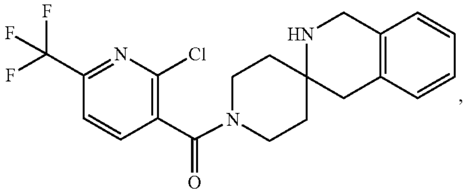
,
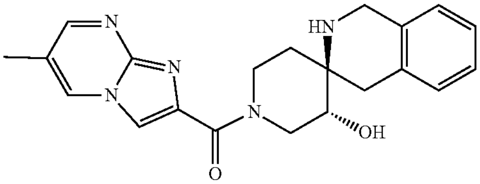
,
-continued
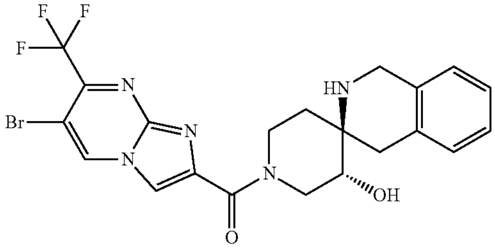
,
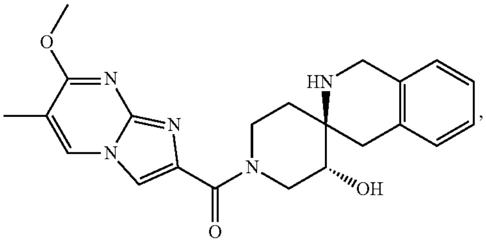
,
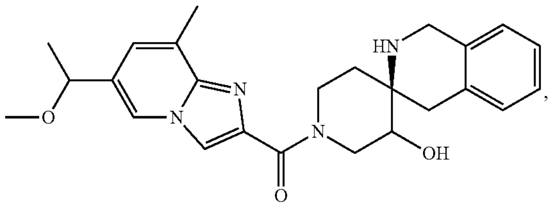
,
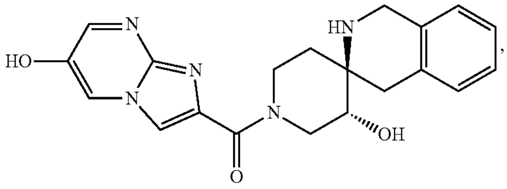
,
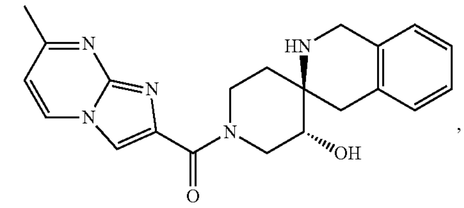
,
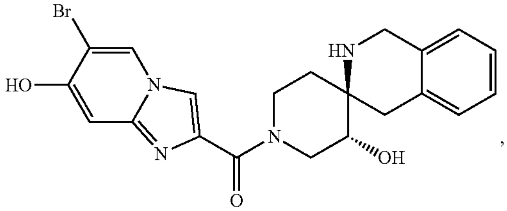
,
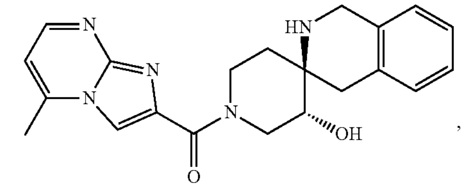
,
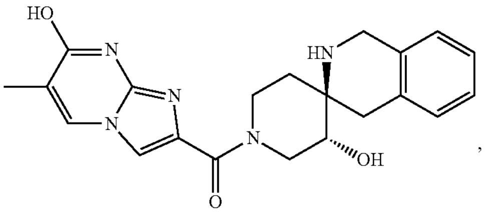
, -continued
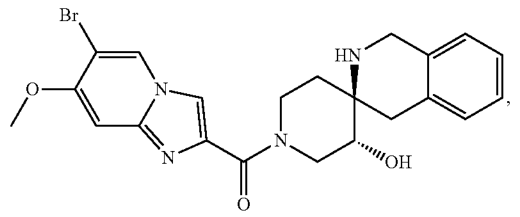
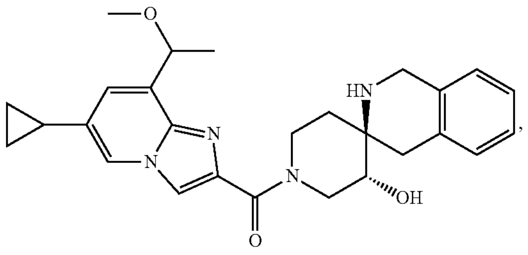
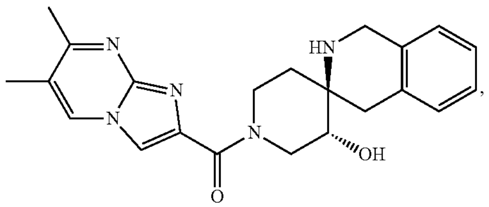
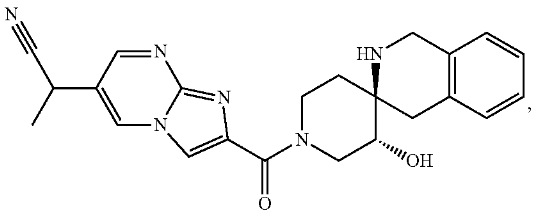
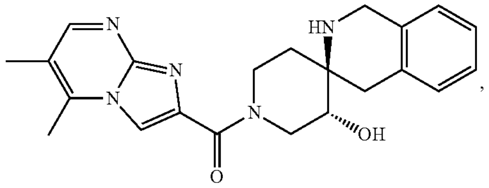
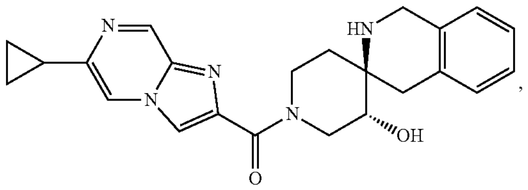
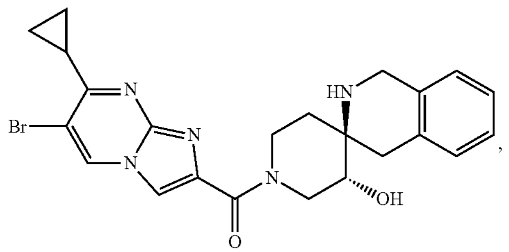
-continued
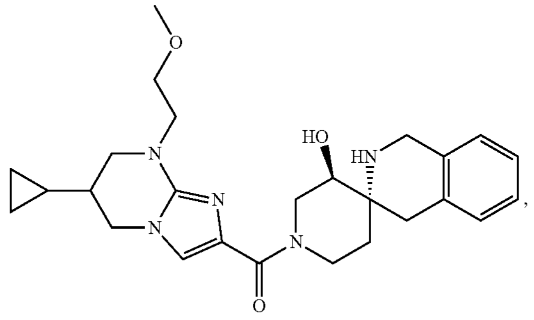
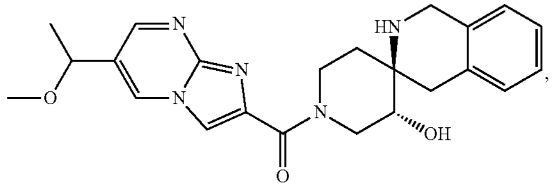
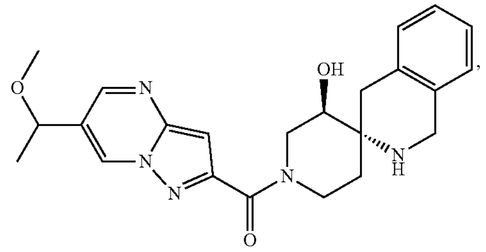
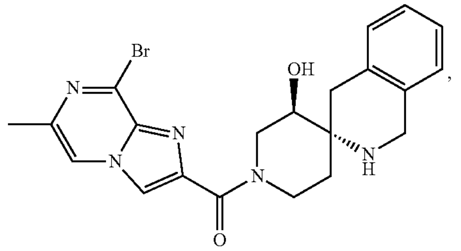
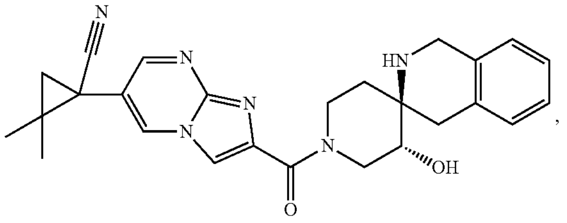
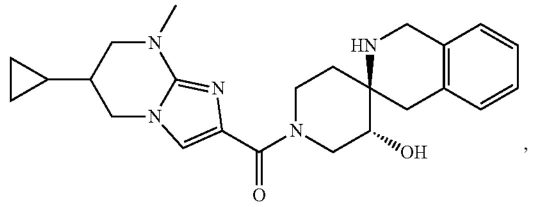
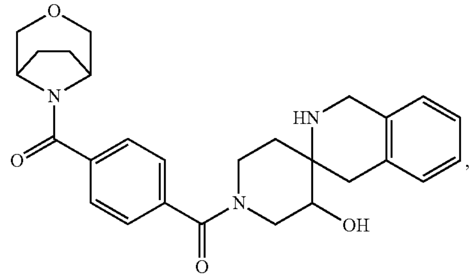

-continued
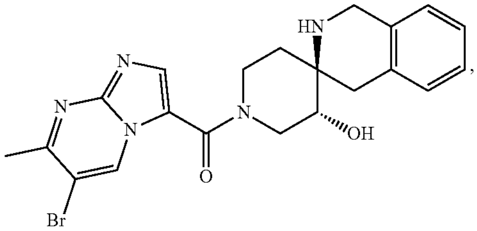
,
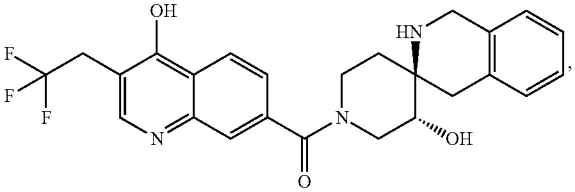
,
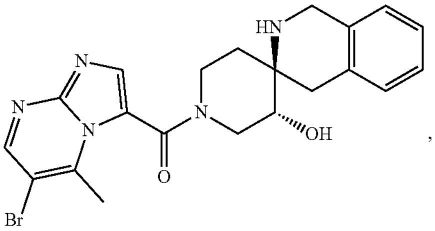
,
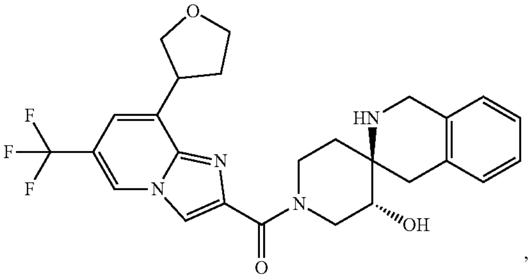
,
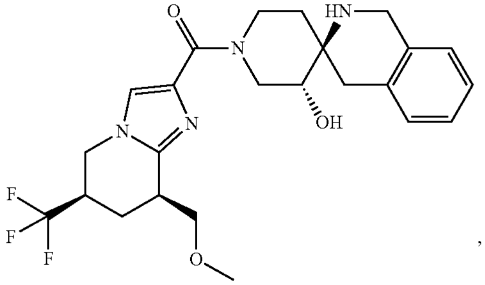
,
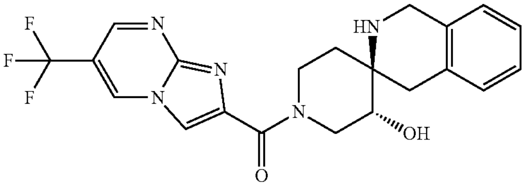
,
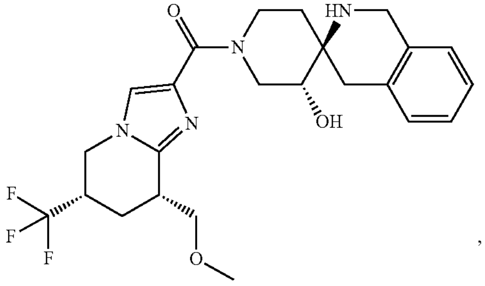
,
-continued
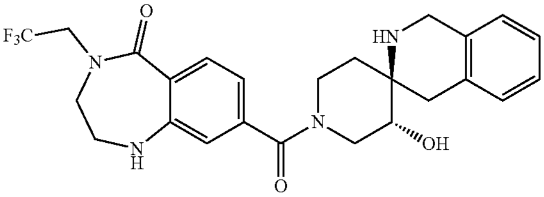
,
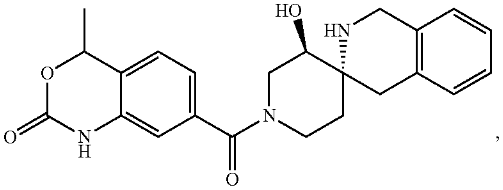
,
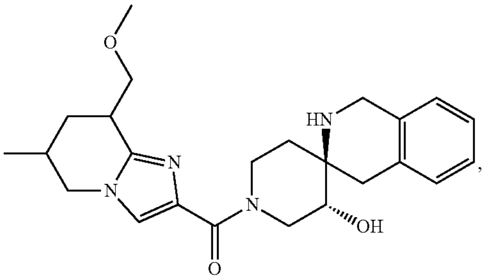
,
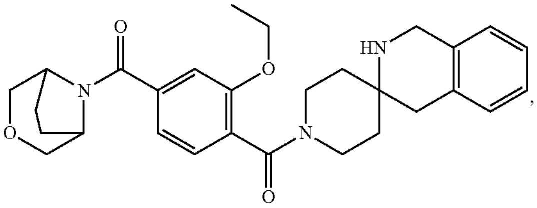
,
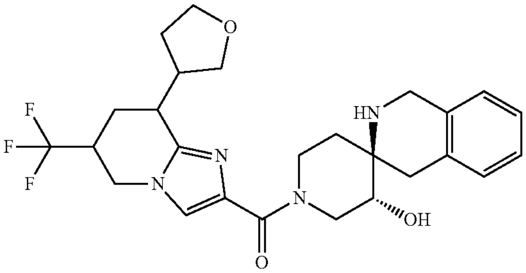
,
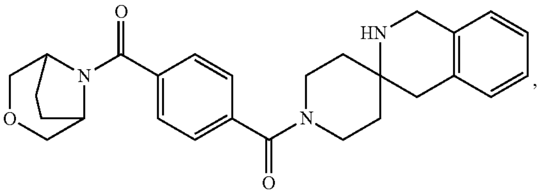
,
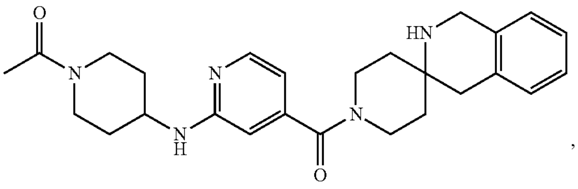
, -continued
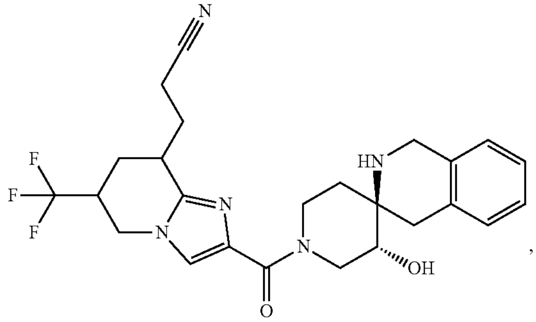
,
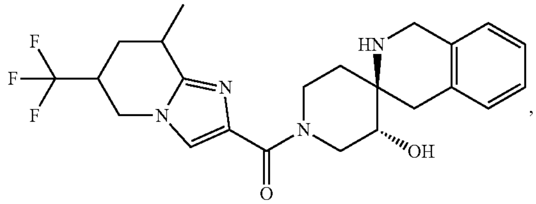
,
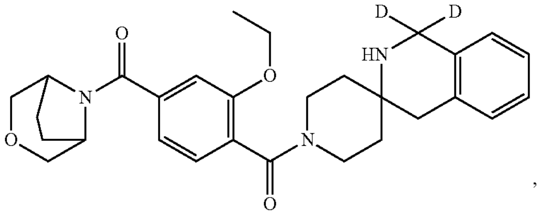
,
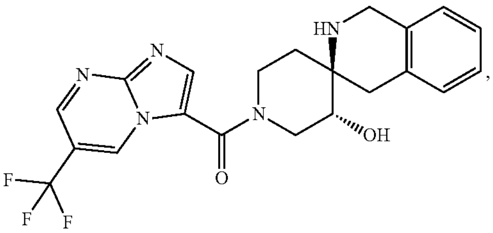
,
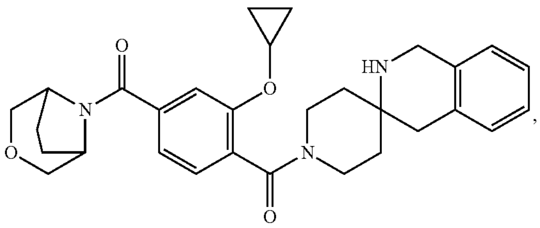
,
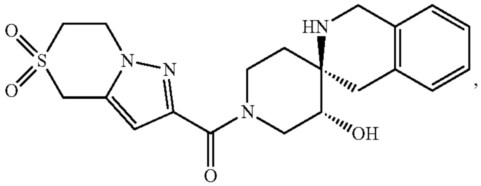
,
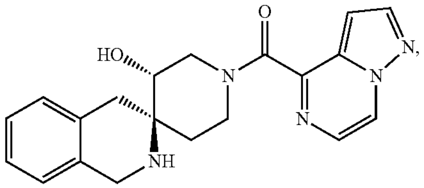
-continued
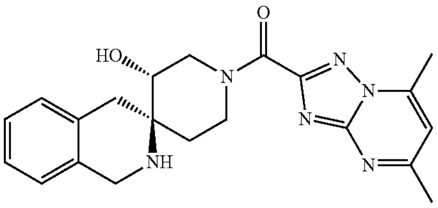
,
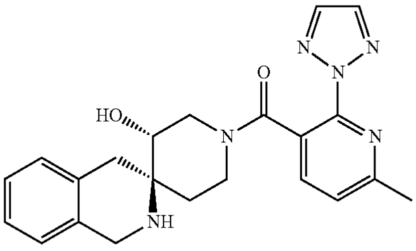
,
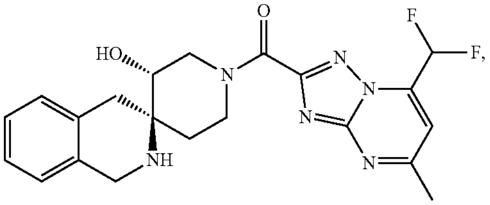
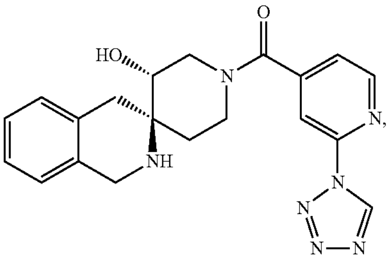
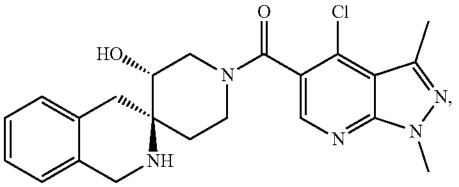
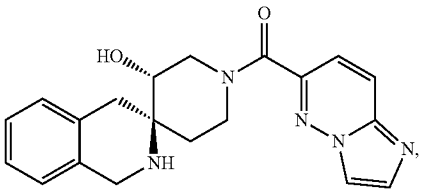
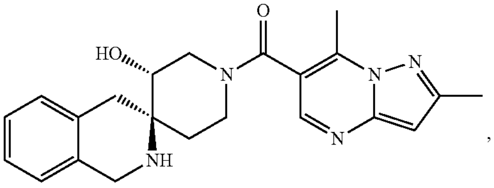
,
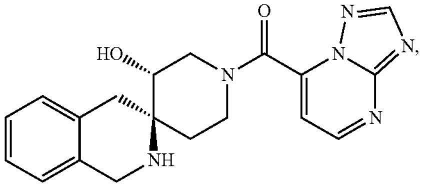

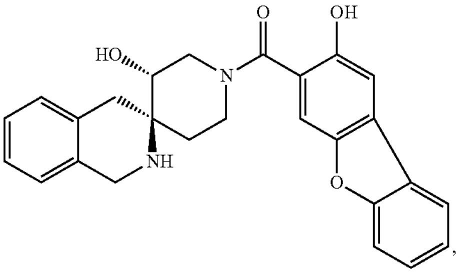
,
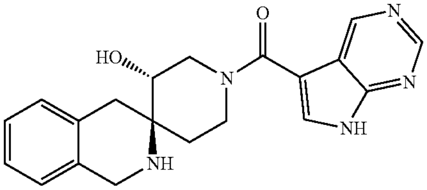
,
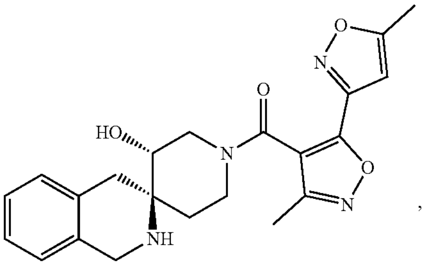
,
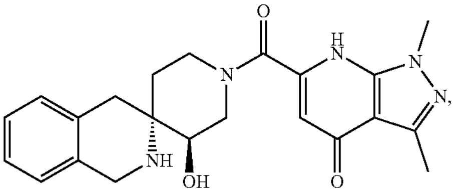
,
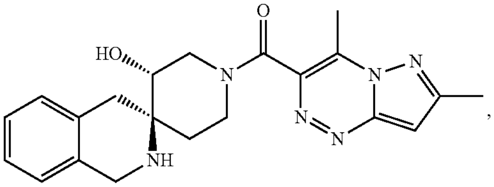
,
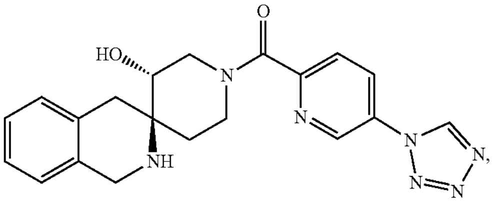
,
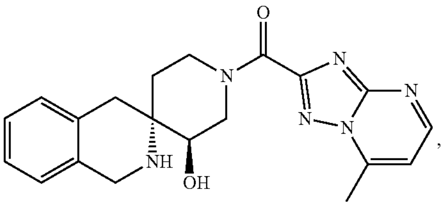
,
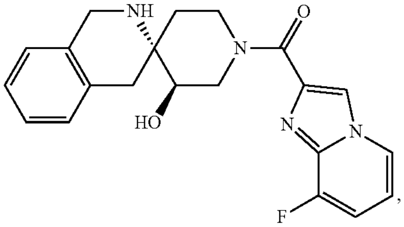
,
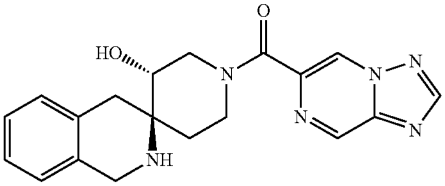
,
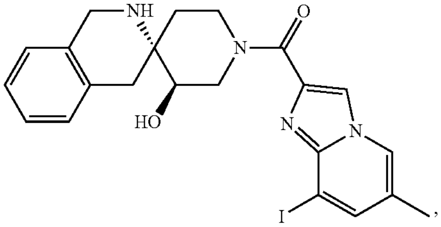
,
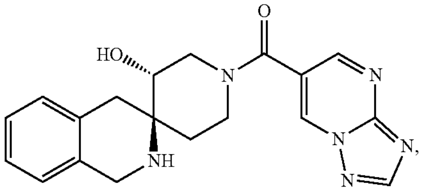
,
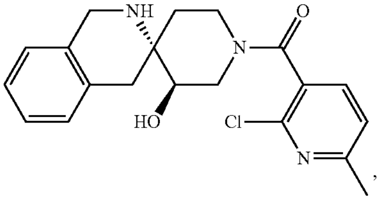
,
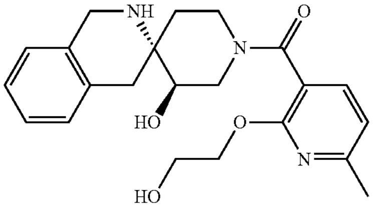
,
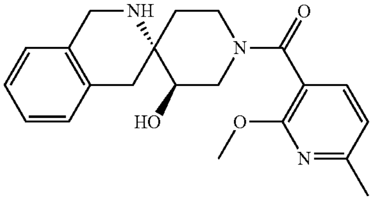
,
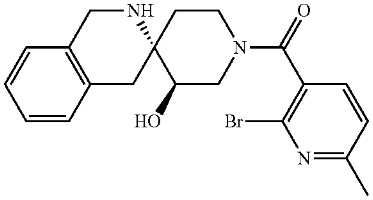
, -continued
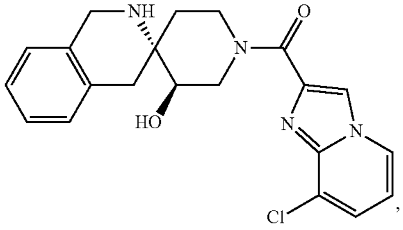
,
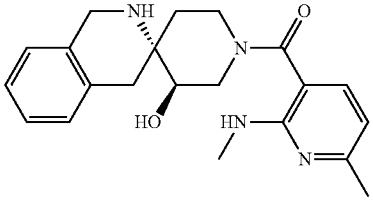
,
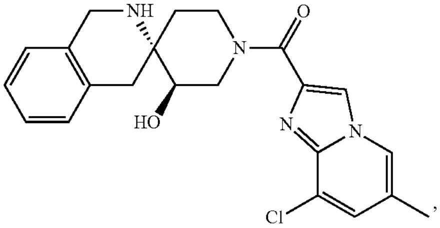
,
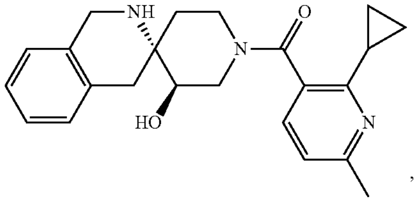
,
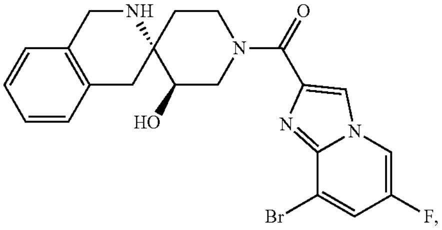
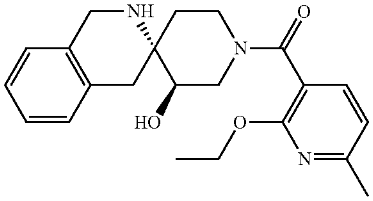
,
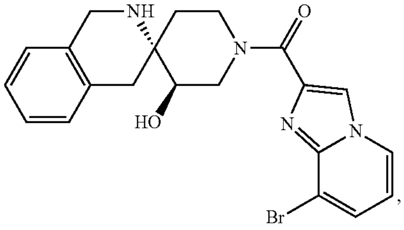
,
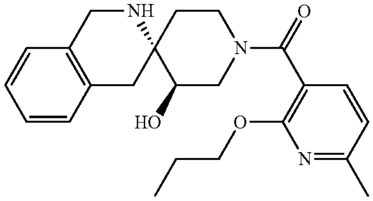
,
-continued
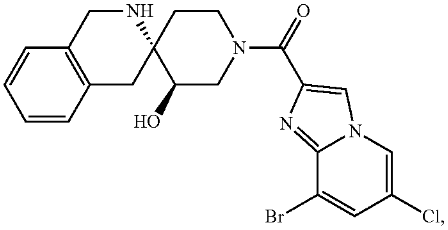
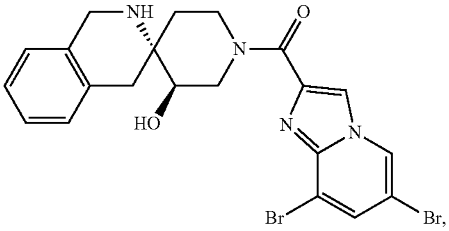
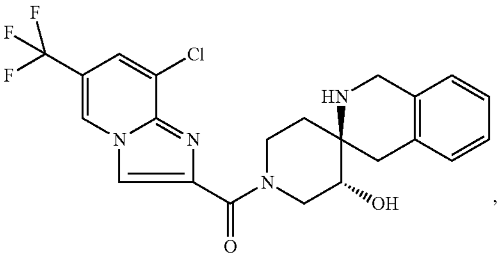
,
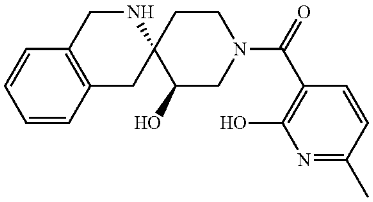
,
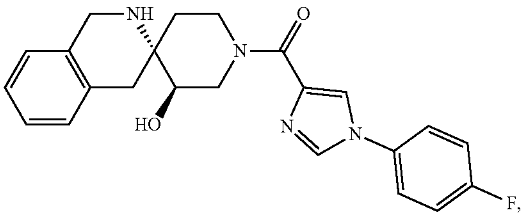
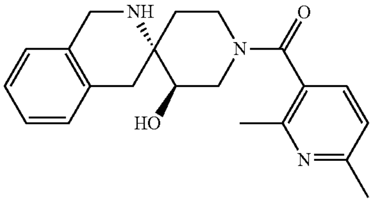
,
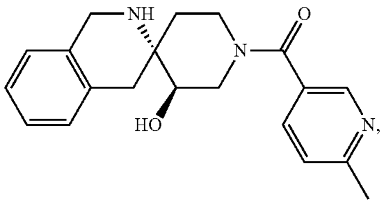

-continued
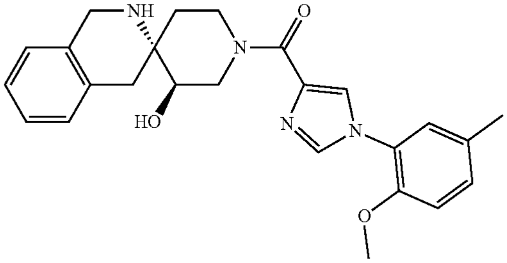
,
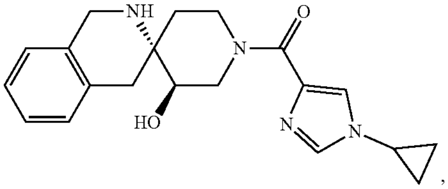
,
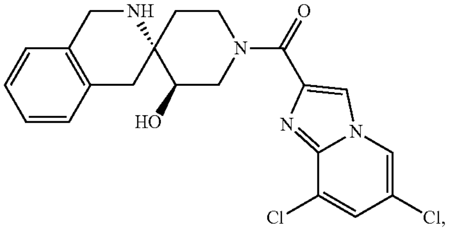
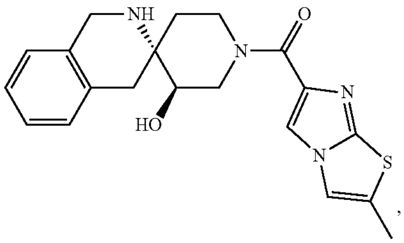
,
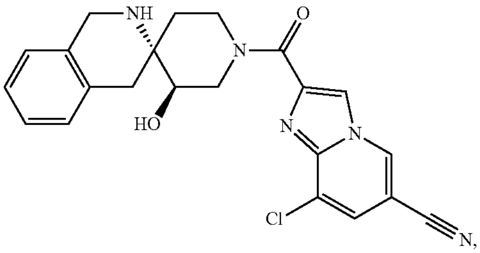
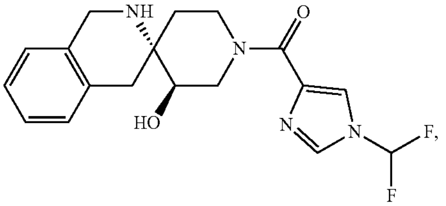
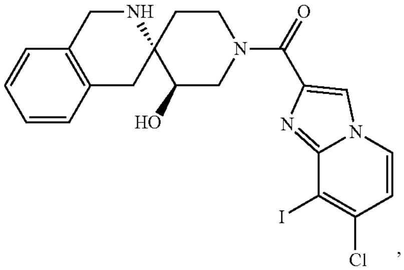
,
-continued
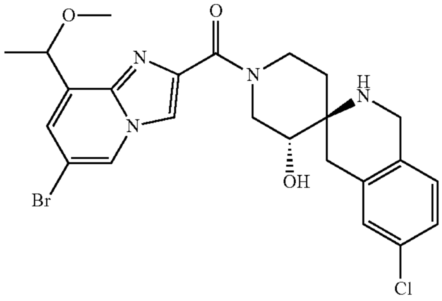
,
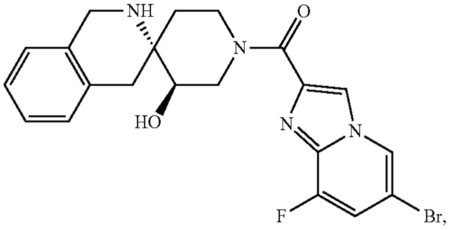
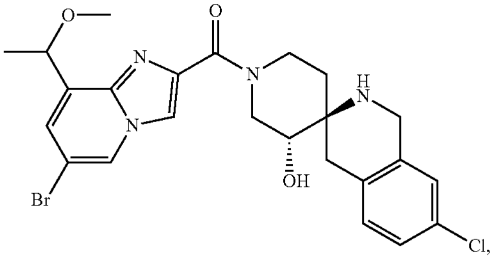
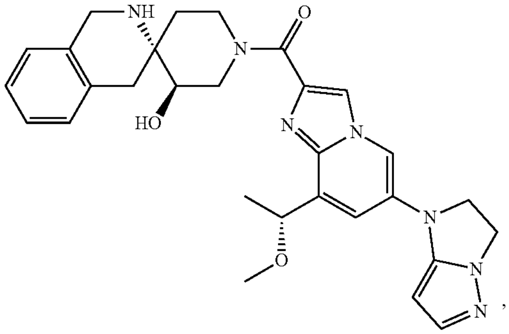
,
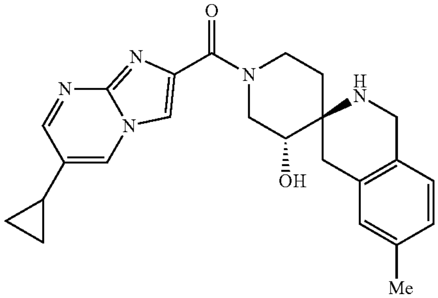
, -continued
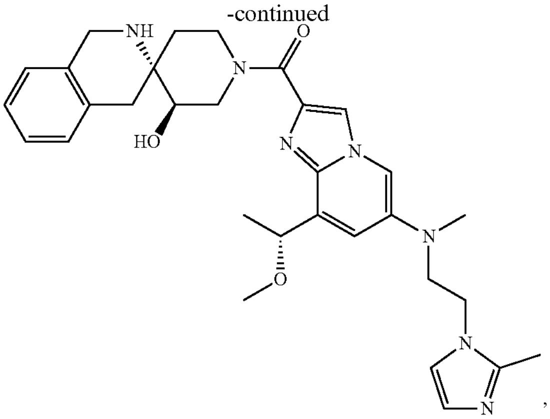,
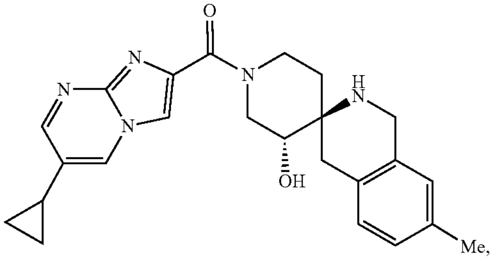,
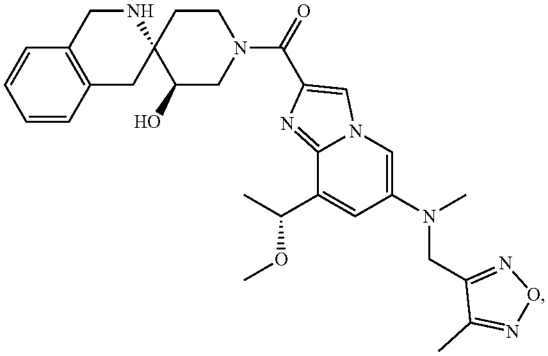,
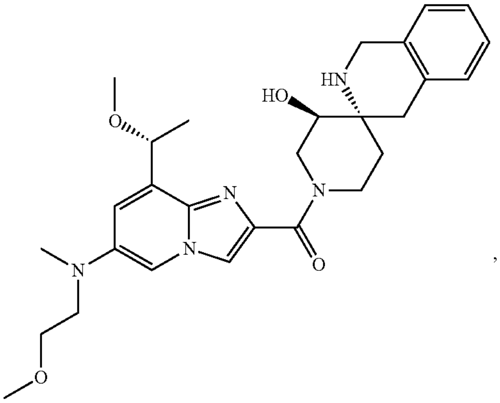,
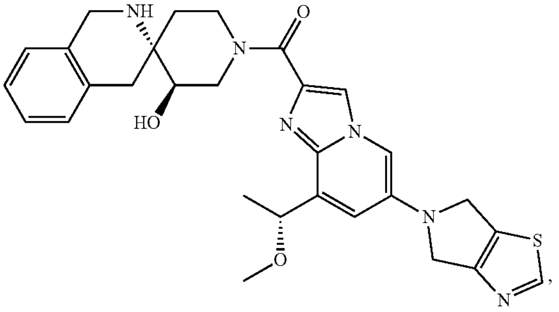,
-continued
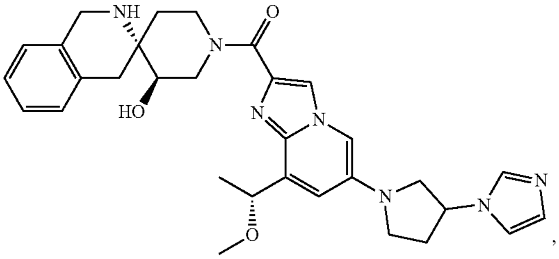,
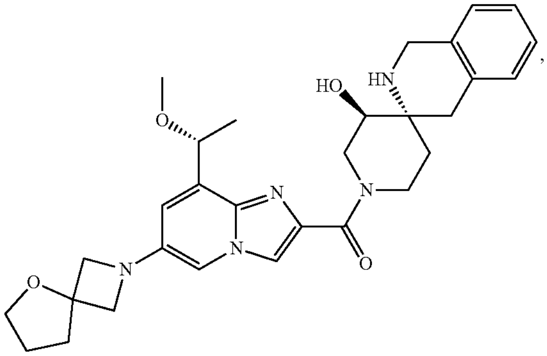,
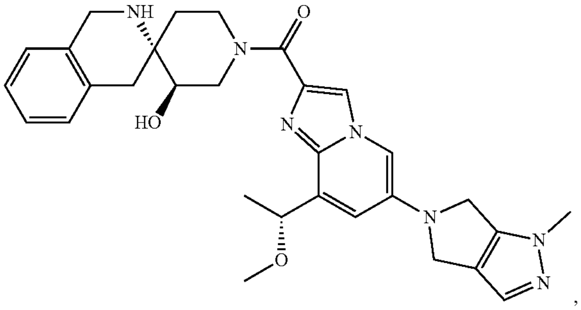,
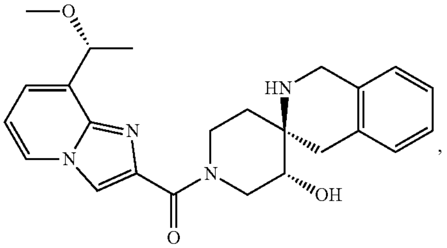,
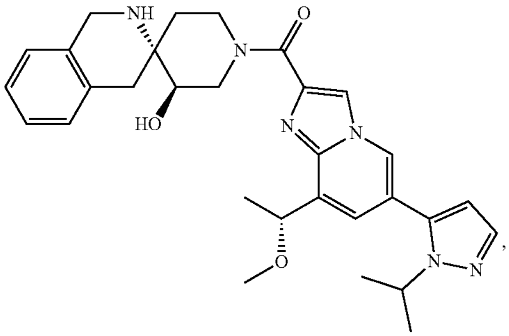, -continued
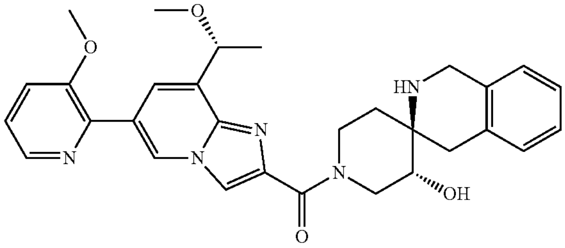
,
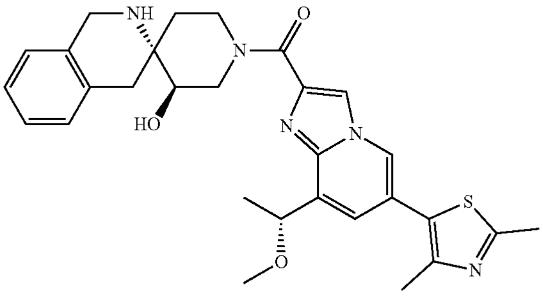
,
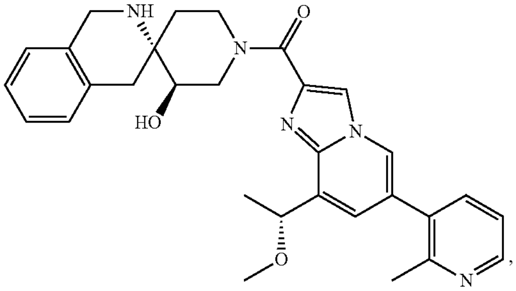
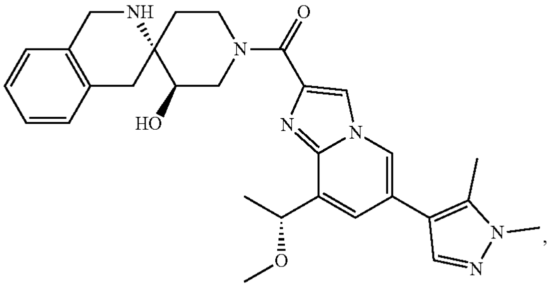
,
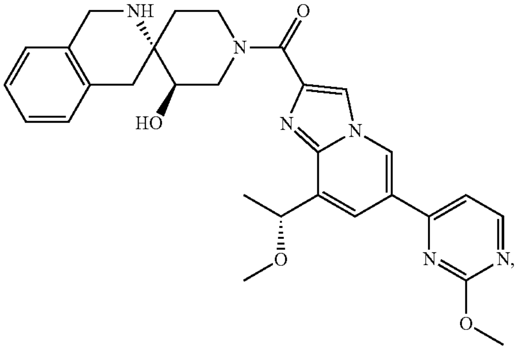
-continued
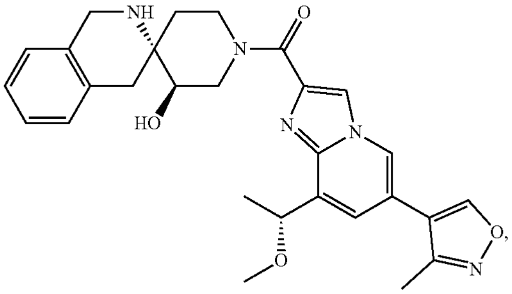
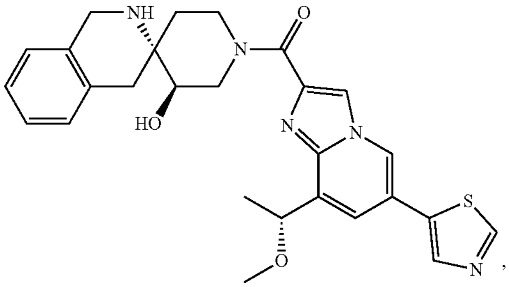
,
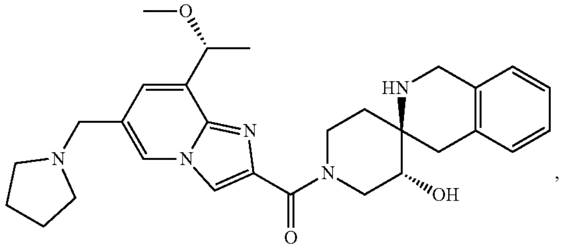
,
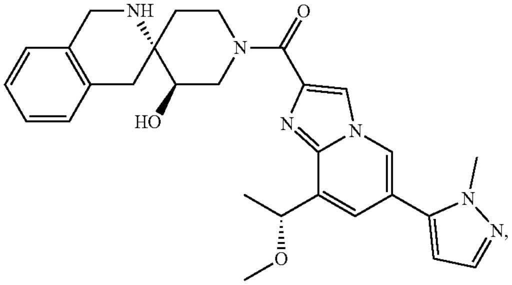
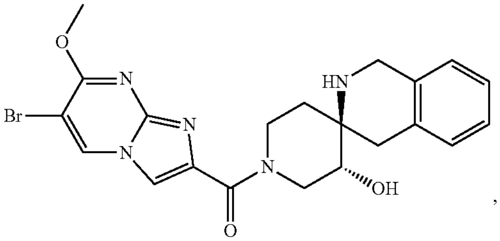
,
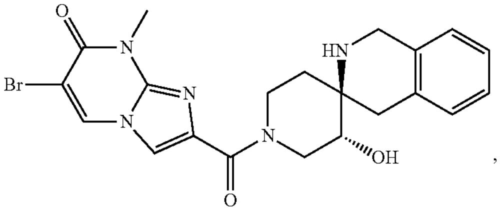
, -continued
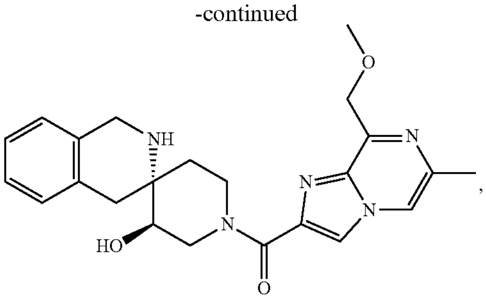
,
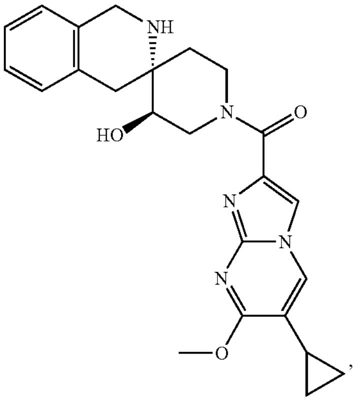
,
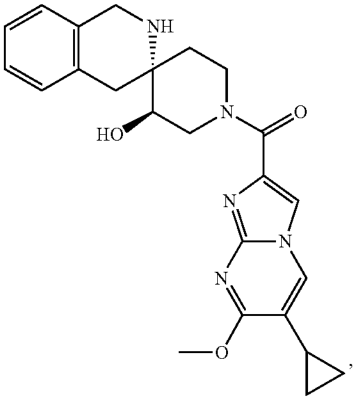
,
-continued
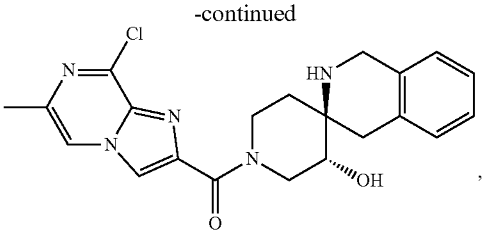
,
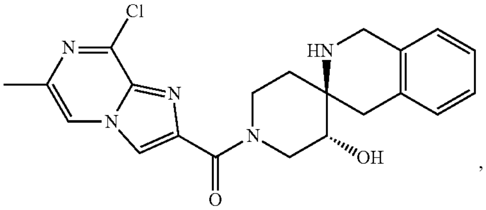
,
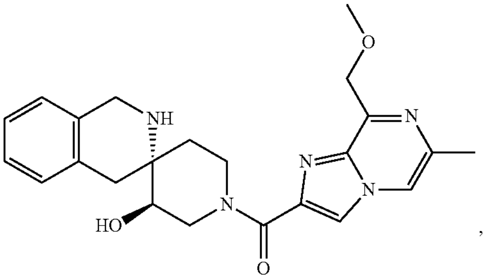
,
or a pharmaceutically acceptable salt thereof.
13. A composition comprising a compound of claim 1, or a pharmaceutically acceptable salt thereof, and a pharmaceutically acceptable carrier.
14. A method for treating cancer comprising administering to a patient in need there of a compound of claim 1, or a pharmaceutically acceptable salt thereof.
* * * * *